United States Patent
Li et al.

(10) Patent No.: US 12,421,233 B2
(45) Date of Patent: *Sep. 23, 2025

(54) WRN INHIBITORS

(71) Applicant: Nimbus Wadjet, Inc., Boston, MA (US)

(72) Inventors: Derun Li, Boston, MA (US); Angela V. West, Franklin, MA (US); Justin Caravella, Cambridge, MA (US); Nathan E. Genung, Boston, MA (US); Florian Bartels, Berlin (DE); Robert Lee Dow, Groton, CT (US); Silvana Marcel Leit de Moradei, Burlington, MA (US); Nikolay Sitnikov, Berlin (DE)

(73) Assignee: Nimbus Wadjet, Inc., Boston, MA (US)

( * ) Notice: Subject to any disclaimer, the term of this patent is extended or adjusted under 35 U.S.C. 154(b) by 16 days.

This patent is subject to a terminal disclaimer.

(21) Appl. No.: 19/038,543

(22) Filed: Jan. 27, 2025

(65) Prior Publication Data

US 2025/0171442 A1     May 29, 2025

Related U.S. Application Data

(63) Continuation of application No. 18/738,470, filed on Jun. 10, 2024.

(60) Provisional application No. 63/639,457, filed on Apr. 26, 2024, provisional application No. 63/566,038, filed on Mar. 15, 2024, provisional application No. 63/613,647, filed on Dec. 21, 2023, provisional application No. 63/586,952, filed on Sep. 29, 2023, provisional application No. 63/519,746, filed on Aug. 15, 2023, provisional application No. 63/507,014, filed on Jun. 8, 2023.

(51) Int. Cl.

| | |
|---|---|
| *C07D 471/04* | (2006.01) |
| *A61K 31/4985* | (2006.01) |
| *A61K 31/501* | (2006.01) |
| *A61K 31/506* | (2006.01) |
| *A61K 31/53* | (2006.01) |
| *A61K 31/5377* | (2006.01) |
| *A61K 31/551* | (2006.01) |
| *C07D 471/14* | (2006.01) |
| *C07D 491/147* | (2006.01) |
| *C07D 495/14* | (2006.01) |
| *C07D 513/14* | (2006.01) |
| *C07D 519/00* | (2006.01) |

(52) U.S. Cl.
CPC ........ *C07D 471/04* (2013.01); *A61K 31/4985* (2013.01); *A61K 31/501* (2013.01); *A61K 31/506* (2013.01); *A61K 31/53* (2013.01); *A61K 31/5377* (2013.01); *A61K 31/551* (2013.01); *C07D 471/14* (2013.01); *C07D 491/147* (2013.01); *C07D 495/14* (2013.01); *C07D 513/14* (2013.01); *C07D 519/00* (2013.01)

(58) Field of Classification Search
CPC .............. A61K 31/4985; A61K 31/501; A61K 31/506; A61K 31/53; A61K 31/5377; C07D 471/04; C07D 471/14; C07D 491/147; C07D 495/14; C07D 513/14; C07D 519/00; A61P 35/00
See application file for complete search history.

(56) References Cited

U.S. PATENT DOCUMENTS

| | | | |
|---|---|---|---|
| 11,530,413 | B2 | 12/2022 | Billy et al. |
| 11,878,973 | B2 | 1/2024 | Bordas et al. |
| 2005/0234091 | A1 | 10/2005 | Regan et al. |
| 2006/0131761 | A1 | 6/2006 | Chauhan et al. |
| 2010/0093716 | A1 | 4/2010 | Gilchrest et al. |
| 2010/0137279 | A1 | 6/2010 | Cheng et al. |
| 2014/0206679 | A1 | 7/2014 | Cheng et al. |
| 2021/0163423 | A1 | 6/2021 | Qian et al. |
| 2022/0133693 | A1 | 5/2022 | Vazquez et al. |
| 2023/0046859 | A1 | 2/2023 | Bordas et al. |
| 2024/0140954 | A1 | 5/2024 | Zhuo et al. |
| 2024/0245694 | A1 | 7/2024 | Bordas et al. |

FOREIGN PATENT DOCUMENTS

| | | |
|---|---|---|
| CN | 117964558 A | 5/2024 |
| CN | 118459466 A | 8/2024 |
| CN | 118684677 A | 9/2024 |

(Continued)

OTHER PUBLICATIONS

Heuser et al., "Challenges for the Discovery of Non-Covalent WRN Helicase Inhibitors," ChemMedChem. Apr. 16, 2024;19(8):e202300613.

(Continued)

*Primary Examiner* — Kortney L. Klinkel
*Assistant Examiner* — Padmaja S Rao
(74) *Attorney, Agent, or Firm* — Dechert LLP; Andrea L. C. Reid; Joseph W. Arico

(57) ABSTRACT

The present disclosure is directed to compounds of Formula I:

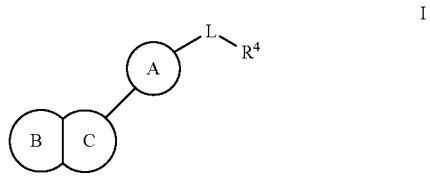

and pharmaceutically acceptable salts thereof, and compositions thereof, as well as methods of treatment of cancers such as those involving WRN protein.

20 Claims, No Drawings
Specification includes a Sequence Listing.

(56) References Cited

FOREIGN PATENT DOCUMENTS

| | | |
|---|---|---|
| CN | 118684678 A | 9/2024 |
| CN | 118994204 A | 11/2024 |
| CN | 119019407 A | 11/2024 |
| CN | 119161363 A | 12/2024 |
| WO | WO-2018229683 A1 | 12/2018 |
| WO | WO-2019016772 A2 | 1/2019 |
| WO | WO-2021178920 A1 | 9/2021 |
| WO | WO-2022249060 A1 | 12/2022 |
| WO | 2023208092 A1 | 11/2023 |
| WO | WO-2024079623 A1 | 4/2024 |
| WO | WO-2024105553 A1 | 5/2024 |
| WO | WO-2024105610 A1 | 5/2024 |
| WO | WO-2024110853 A1 | 5/2024 |
| WO | WO-2024120378 A2 | 6/2024 |
| WO | WO-2024140597 A1 | 7/2024 |
| WO | WO-2024140714 A1 | 7/2024 |
| WO | WO-2024153155 A1 | 7/2024 |
| WO | WO-2024153244 A1 | 7/2024 |
| WO | WO-2024155884 A1 | 7/2024 |
| WO | WO-2024187049 A1 | 9/2024 |
| WO | WO-2024193683 A1 | 9/2024 |
| WO | WO-2024193716 A1 | 9/2024 |
| WO | WO-2024199108 A1 | 10/2024 |
| WO | WO-2024199109 A1 | 10/2024 |
| WO | WO-2024220887 A1 | 10/2024 |
| WO | WO-2024222677 A1 | 10/2024 |
| WO | WO-2024230828 A1 | 11/2024 |
| WO | WO-2024235292 A1 | 11/2024 |
| WO | WO-2024246862 A1 | 12/2024 |
| WO | WO-2024246863 A1 | 12/2024 |
| WO | WO-2024254511 A2 | 12/2024 |
| WO | WO-2024254602 A1 | 12/2024 |
| WO | WO-2024255765 A1 | 12/2024 |
| WO | WO-2024255790 A1 | 12/2024 |
| WO | WO-2024259048 A2 | 12/2024 |
| WO | 2025002413 A1 | 1/2025 |
| WO | 2025014846 A1 | 1/2025 |
| WO | 2025014877 A2 | 1/2025 |
| WO | 2025021148 A1 | 1/2025 |
| WO | 2025026382 A1 | 2/2025 |
| WO | 2025045145 A1 | 3/2025 |
| WO | 2025049746 A1 | 3/2025 |
| WO | 2025087274 A1 | 5/2025 |

OTHER PUBLICATIONS

Picco et al., "Novel WRN Helicase Inhibitors Selectively Target Microsatellite-Unstable Cancer Cells," Cancer Discov. Aug. 2, 2024;14(8):1457-1475.

Ferretti et al., "Discovery of WRN inhibitor HRO761 with synthetic lethality in MSI cancers," Nature. May 2024;629(8011):443-449.

PCT International Search Report and Written Opinion from PCT/US2024/033090, dated Sep. 6, 2024.

PCT International Search Report and Written Opinion from PCT/US2024/025525, dated Aug. 13, 2024.

McDonald et al., "Project Drive: A Compendium of Cancer Dependencies and Synthetic Lethal Relationships Uncovered by Large-Scale, Deep RNAi Screening. Cell," Jul. 27, 2017;170(3):577-592.

U.S. Appl. No. 18/766,189, filed Jul. 8, 2024.

National Center for Biotechnology Information. "3-(2-Methoxypyridin-4-yl)-5,6,7,8-tetrahydro [1,2,4]triazolo[4,3-a]pyrimidIne: Pubchem CID 136034193" Pubchem entry (online), pp. 1-9, Jan. 21, 2019; URL: https://pubchem.ncbl.nlm.nih.gov/compound/136034193.

Pubchem, SID 248767314, Modify Date: Jan. 25, 2017 Retrieved from the Internet <URL: https://pubchem.ncbi.nlm.nih.gov/substance/248767314>.

PCT International Search Report and Written Opinion from PCT/US2024/033732, dated Sep. 17, 2024.

PCT International Search Report and Written Opinion from PCT/US2024/033276, dated Sep. 26, 2024.

Rico et al., "WRN Helicase Target Review: The Next Synthetic Lethality Drug Approval?" Drug Hunter, Mar. 5, 2025.

Pubchem, SID 438301, Modify Date: Dec. 19, 2011, Retrieved from the Internet <URL: https://pubchem.ncbi.nlm.nih.gov/substance/438301>.

Pubchem, SID 396355792, Modify Date: Dec. 6, 2019, Retrieved from the Internet <URL: https://pubchem.ncbi.nlm.nih.gov/substance/396355792>.

Boiko et al., "Preclinical Characterization of NTX-452, a Potent, Selective and Highly Efficacious WRN Inhibitor for the Treatment of MSI-H Tumors," Presented at the 2024 EORTC-NCI-AACR Symposium on Molecular Targets and Cancer Terapeutics, Barcelona, Spain, Oct. 23-25, 2024.

PCT International Search Report and Written Opinion from PCT/US2024/037061, dated Feb. 3, 2025.

PCT International Search Report and Written Opinion from PCT/US2024/061505, dated Apr. 24, 2025.

WRN INHIBITORS

CROSS-REFERENCE TO RELATED APPLICATIONS

This application is a continuation of U.S. patent application Ser. No. 18/738,470, filed Jun. 10, 2024; which claims the benefit of priority to U.S. Provisional Appl. No. 63/507,014, filed Jun. 8, 2023; U.S. Provisional Appl. No. 63/519,746, filed Aug. 15, 2023; U.S. Provisional Appl. No. 63/586,952, filed Sep. 29, 2023; U.S. Provisional Appl. No. 63/613,647, filed Dec. 21, 2023; U.S. Provisional Appl. No. 63/566,038, filed Mar. 15, 2024; and U.S. Provisional Appl. No. 63/639,457, filed Apr. 26, 2024; the entirety of each of which is herein incorporated by reference.

FIELD OF INVENTION

The invention provides bicyclic compounds and compositions, the use thereof and methods using the compounds, for inhibiting Werner Syndrome RecQ DNA helicase (WRN) and methods of treating disease using said compounds, in particular the use in treating cancer, and in particular the treatment of cancer characterized as microsatellite instability-high (MSI-H) or mismatch repair deficient (dMMR), including colorectal, gastric and endometrial cancer. The invention also provides the use of said compounds as research chemicals, intermediate compounds, combinations, processes and formulations.

SEQUENCE LISTING

This application contains a Sequence Listing which has been submitted in .xml format via EFS and is hereby incorporated by reference. The ST.26 copy, created on Jun. 8, 2023, is named 407274-78WRP5_ST26.xml and is 8,751 bytes in size.

BACKGROUND

Loss of DNA mismatch repair is a common initiating event in cancer development occurring in 10-30% of colorectal, endometrial, ovarian and gastric cancers (Aaltonen, L. A. et al. Clues to the pathogenesis of familial colorectal cancer, Science 260, 812-816 (1993), Bonneville R et al., Landscape of Microsatellite Instability Across 39 Cancer Types. JCO Precis Oncol. 1: PO.17.00073 (2017)). Cancers that are deficient in mismatch repair (dMMR) have a high mutational burden, and frequent deletion and insertion events in repetitive DNA tracts, a phenotype known as microsatellite instability (MSI). While progress has been made in the treatment of microsatellite instability high (MSI-H) cancers, and the demonstration that pembrolizumab (anti-PD1) treatment led to significantly longer progression-free survival than chemotherapy when received as first-line therapy for MSI-H-dMMR metastatic colorectal cancer (CRC) which resulted in the recent approval of pembrolizumab as first-line treatment of these cancers, there is still a significant unmet medical need in CRC and other MSI-H indications (André T., et al. Pembrolizumab in Microsatellite-Instability-High Advanced Colorectal Cancer. N Engl J Med 383(23):22072218 (2020)). Several large-scale functional genomics screens across large panels of cell lines, including Novartis with 398 cell lines from the Cancer Cell Line Encyclopedia (CCLE) (McDonald E. R. et al., Project DRIVE: A Compendium of Cancer Dependencies and Synthetic Lethal Relationships Uncovered by Large-Scale, Deep RNAi Screening. Cell 170(3):577-592 (2017)), have identified the Werner Syndrome RecQ helicase (WRN) as being selectively required for the survival of cell lines with defective mismatch repair that have become MSI-H (Behan, F. M. et al. Prioritization of cancer therapeutic targets using CRISPR-Cas9 screens. Nature 568, 511-516 (2019), Chan, E. M. et al. WRN helicase is a synthetic lethal target in microsatellite unstable cancers. Nature 568, 551-556 (2019). Kategaya, L., Perumal, S. K., Hager, J. H. & Belmont, L. D. Werner syndrome helicase is required for the survival of cancer cells with microsatellite instability. iScience 13, 488-497 (2019), Lieb, S. et al. Werner syndrome helicase is a selective vulnerability of microsatellite instability-high tumor cells. eLife 8, e43333 (2019)). WRN is synthetically lethal with MSI cancers. Depletion of WRN leads to anti-proliferative effects and results in activation of multiple DNA damage signaling markers, induction of cell cycle arrest and apoptosis in MSI-H cancer models but not cancer cells with an intact MMR pathway (otherwise known as microsatellite stable or MSS). The anti-proliferative effects of WRN depletion could not be rescued with a helicase deficient WRN construct, demonstrating that helicase activity of WRN is required for MSI-H viability. These findings indicate that WRN helicase provides a DNA repair and maintenance function that is essential for cell survival in MSI cancers. Recently, the mechanism of WRN dependence has been elucidated. It has been shown that dinucleotide TA repeats are selectively unstable in MSI cells and undergo large scale expansions. These expanded TA repeats form secondary DNA structures that require the WRN helicase for unwinding (van Wietmarschen, N. et al. Repeat expansions confer WRN dependence in microsatellite-unstable cancers. Nature 586, 292-298, 2020). In the absence of WRN (or upon WRN helicase inhibition), expanded TA repeats in MSI cells are subject to nuclease cleavage and chromosome breakage. Thus, inhibiting the WRN helicase is an attractive strategy for the treatment of MSI-H cancers.

SUMMARY

There remains a need for new treatments and therapies for the treatment of cancer, and in particular cancers characterized as microsatellite instability-high (MSI-H) or mismatch repair deficient (dMMR), including colorectal, gastric or endometrial cancer. The invention provides compounds, pharmaceutically acceptable salts thereof, pharmaceutical compositions thereof and combinations thereof, said compounds being inhibitors of Werner Syndrome RecQ DNA Helicase (WRN). The invention further provides methods of treating, preventing, or ameliorating a disease or condition, comprising administering to a subject in need thereof an effective amount of a WRN inhibitor. The invention also provides compounds, pharmaceutically acceptable salts thereof, pharmaceutical compositions thereof and combinations thereof, said compounds being useful for the treatment of cancer, in particular cancers characterized as microsatellite instability-high (MSI-H) or mismatch repair deficient (dMMR). Also provided are compounds that bind to, and/or inhibit WRN, and are therefore useful as research chemicals, e.g., as a chemical probe, and as tool compounds. Various embodiments of the invention are described herein.

In one aspect, the disclosure provides a compound of Formula I, or a pharmaceutically acceptable salt thereof:

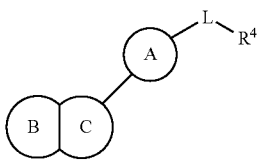

wherein bicyclic Ring BC, linker L, R⁴, and Ring A are as described and defined herein.

In another aspect, the invention provides a pharmaceutical composition comprising a compound of Formula I of the present invention and one or more pharmaceutically acceptable carriers.

In another aspect, the invention provides a combination, in particular a pharmaceutical combination, comprising a compound of Formula I of the present invention and one or more therapeutically active agents.

In another aspect, the invention provides a compound of Formula I of the present invention for use as a medicament, in particular for the treatment of a disorder or disease which can be treated by WRN inhibition.

In another aspect, the invention provides a compound of Formula I of the present invention for use in the treatment of cancer, particularly wherein the cancer is characterized as microsatellite instability-high (MSI-H) or mismatch repair deficient (dMMR).

In another aspect, the invention provides a method of treating a disorder or disease which can be treated by WRN inhibition in a subject, comprising administering to the subject a therapeutically effective amount of a compound of Formula I of the present invention.

In another aspect, the invention provides a method of treating cancer in a subject, more particularly wherein the cancer is characterized as microsatellite instability-high (MSI-H) or mismatch repair deficient (dMMR), comprising administering to the subject a therapeutically effective amount of a compound of Formula I of the present invention.

In another aspect, the invention provides the use of a compound of Formula I of the present invention in the manufacture of a medicament for the treatment of a disorder or disease which can be treated by WRN inhibition.

In another aspect, the invention provides a compound of Formula I of the present invention for use as a research chemical, for example as a chemical probe or as a tool compound.

In another aspect, the invention provides a solid form, process or intermediate as described herein.

DETAILED DESCRIPTION

1. General Description of Certain Embodiments of the Invention

In one aspect, the disclosure provides a compound of Formula I, or a pharmaceutically acceptable salt thereof.

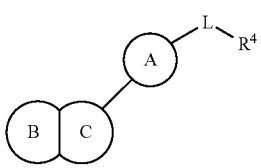

wherein bicyclic Ring BC is selected from one of the following:

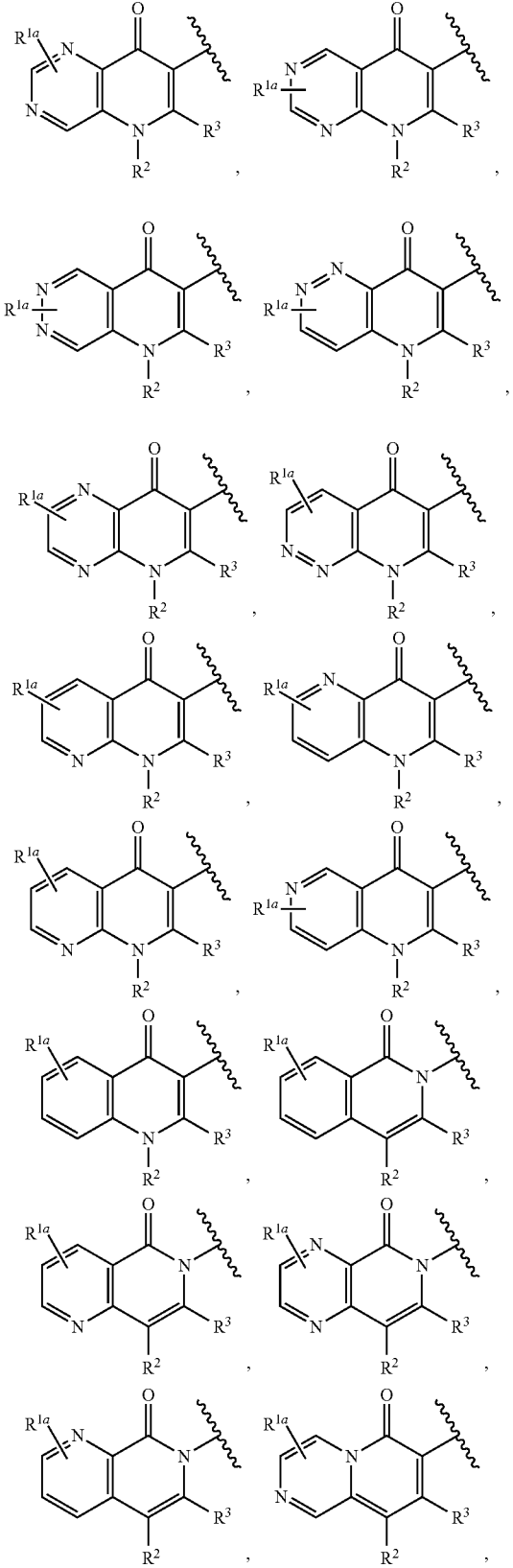

-continued

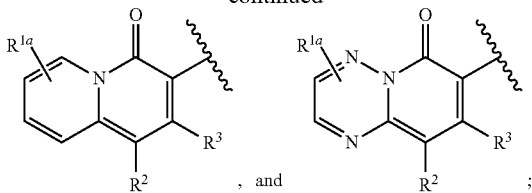

wherein ⁓ denotes the point of attachment to Ring A;
and wherein Ring B may be further optionally substituted with 1 or 2 Rib groups independently selected from H, halogen, CN, OH, $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy, wherein said $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy are each independently and optionally substituted with 1-5 halogen, OH, CN, $C_1$-$C_6$ alkyl, or $C_3$-$C_6$ cycloalkyl groups;

Ring A is:
a 4-7 membered saturated or partially unsaturated bivalent monocyclic carbocyclylene or 4-7 membered saturated or partially unsaturated bivalent heterocyclylene ring (having 1-4 heteroatoms independently selected from nitrogen, oxygen, and sulfur, and 0 or 1 nitrogen atoms in addition to the 1-4 heteroatoms); or
a 4-12 membered saturated or partially unsaturated bivalent bicyclic ring system that is fused, bridged, or spirocyclic selected from carbocyclylene or heterocyclylene (having 1-4 heteroatoms independently selected from nitrogen, oxygen, and sulfur);
wherein Ring A is substituted with 0-4 independently selected $R^B$ substituents;

-L- is a linker selected from —C(O)—, —S(O)—, —S(O)$_2$—, and

$R^{1a}$ is selected from:
a 5-6 membered heteroaryl (having 1-4 heteroatoms independently selected from nitrogen, oxygen, and sulfur) optionally substituted with 1-3 groups independently selected from halogen, $C_1$-$C_6$ aliphatic, $C_3$-$C_6$ cycloalkyl, halo$C_1$-$C_6$ alkyl, $C_1$-$C_6$ alkoxy, and $C_3$-$C_6$ cycloalkoxy, wherein said 5-6 membered heteroaryl is further substituted with 0-3 independently selected $R^B$;
a 4-7 membered saturated or partially unsaturated heterocyclyl (having 1-2 heteroatoms independently selected from nitrogen, oxygen, and sulfur), optionally substituted with 1 or 2 groups independently selected from $C_1$-$C_6$ aliphatic, $C_3$-$C_6$ cycloalkyl, $C_1$-$C_6$ alkoxy, $C_3$-$C_6$ cycloalkoxy, and —OR, wherein said 4-7 membered saturated or partially unsaturated heterocyclyl is further substituted with 0-3 independently selected $R^B$;
a 4-12 membered saturated or partially unsaturated bicyclic ring system that is fused, bridged, or spirocyclic selected from carbocyclyl or heterocyclyl (having 1-4 heteroatoms independently selected from nitrogen, oxygen, and sulfur), wherein said carbocyclyl or heterocyclyl is substituted with 0-3 independently selected $R^B$; and H, halogen, $C_1$-$C_6$ aliphatic, $C_3$-$C_7$ cycloalkyl, $C_1$-$C_6$ alkylene-O—$C_1$-$C_6$ alkyl, CN, —OR, —OR$^{10}$, —NR$^{10}$R$^{11}$, —C(O)NR$^{10}$R$^{11}$, —CH$_2$NR$^{10}$R$^{11}$, or —SO$_2$R$^{12}$, wherein said $C_1$-$C_6$ aliphatic, $C_3$-$C_7$ cycloalkyl, or $C_1$-$C_6$ alkylene-O—$C_1$-$C_6$ alkyl is substituted with 0-5 independently selected $R^B$;

or $R^{1a}$ and one $R^{1b}$ on adjacent atoms of Ring B, taken together with the adjacent Ring B atoms to which they are attached, form a cyclic group fused to Ring B selected from phenyl, a 5-6 membered heteroaryl (having 1-3 heteroatoms independently selected from nitrogen, oxygen and sulfur), a 4-7 membered saturated or partially unsaturated carbocyclyl, or a 4-7 membered saturated or partially unsaturated heterocyclyl (having 1-3 heteroatoms independently selected from nitrogen, oxygen and sulfur), wherein said cyclic group fused to Ring B is substituted with 0-3 independently selected $R^B$;

$R^2$ is C(R$^C$)$_2$C(O)N(R)R$^{2A}$;

$R^{2A}$ is phenyl or pyridyl, each of which is optionally substituted with 1, 2, or 3 substituents independently selected from halogen, $C_1$-$C_4$ aliphatic, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, and —SF$_5$, and wherein two substituents on adjacent atoms of the phenyl or pyridyl, together with said adjacent atoms, form a 4-7 membered carbocyclyl fused to the phenyl or pyridyl, and wherein two substituents on adjacent atoms of the phenyl or pyridyl together with said adjacent atoms form a 4-7 membered heterocyclyl (having 1-4 heteroatoms independently selected from nitrogen, oxygen, and sulfur) fused to the phenyl or pyridyl, wherein said fused 4-7 membered carbocyclyl or fused 4-7 membered heterocyclyl is substituted with 0-5 independently selected halogen; or $R^{2A}$ is 2-benzimidazolyl, 2-naphthyl, or 3-quinolinyl, each of which is optionally substituted with 1, 2 or 3 substituents independently selected from halogen, $C_{1-4}$ alkyl, and —OH;

$R^3$ is hydrogen, $C_1$-$C_4$ aliphatic, $C_3$-$C_5$ cycloalkyl, $C_1$-$C_4$ alkoxy, —NHR$^{3A}$, —N(R$^{3A}$)$_2$, or $C_1$-$C_4$ alkylthio, each of which, besides hydrogen, is optionally substituted with —OH, 1-5 independently selected halogen, OR, —C(O)NR$^{10}$R$^{11}$, or N(R)C(O)R;

each $R^{3A}$ is independently selected from $C_1$-$C_4$ alkyl;

$R^4$ is phenyl or a first 5-6 membered heteroaryl (having 1-4 heteroatoms independently selected from nitrogen, oxygen, and sulfur) wherein said phenyl or first 5-6 membered heteroaryl is substituted with 0-5 $R^B$; and optionally two adjacent atoms of said phenyl or first 5-6 membered heteroaryl have two substituents that together with said adjacent atoms form a cyclic group fused to the phenyl or first 5-6 membered heteroaryl selected from a 4-7 membered carbocyclyl, a 4-7 membered heterocyclyl (having 1-4 heteroatoms independently selected from nitrogen, oxygen, and sulfur), or second a 5-6 membered heteroaryl (having 1-4 heteroatoms independently selected from nitrogen, oxygen, and sulfur); wherein said fused cyclic group is substituted with 0-3 independently selected $R^B$; or $R^4$ is a $C_1$-$C_4$ aliphatic, $C_1$-$C_4$ alkoxy, or $C_3$-$C_6$ cycloalkyl, each of which is substituted with 0-3 groups independently selected from halogen, —CN, —OH, $C_1$-$C_4$ alkyl, $C_1$-$C_4$ alkoxy, optionally substituted 5-6 membered heterocyclyl, and optionally substituted 5-6 membered heterocyclyloxy;

$R^{10}$ is H, $C_1$-$C_6$ aliphatic, halo$C_1$-$C_6$ alkyl, $C_3$-$C_6$ cycloalkyl, halo$C_3$-$C_6$ cycloalkyl, —C(O)$C_1$-$C_6$ alkyl, or a 5-6 membered heteroaryl (having 1-4 heteroatoms independently selected from nitrogen, oxygen, and sulfur); each $R^{10}$ except H being optionally substituted with 1 or 2 independently selected $R^B$;

$R^{11}$ is H, $C_1$-$C_6$ aliphatic, or $C_3$-$C_6$ cycloalkyl, or $R^{10}$ and $R^{11}$ are taken together with the nitrogen atom to which they are attached to form a 5-6 membered ring optionally substituted with 1, 2, or 3 substituents independently selected from halogen, —OH, —CN, $C_1$-$C_4$ alkoxy, and halo$C_1$-$C_4$ alkoxy;

$R^{12}$ is $C_1$-$C_6$ aliphatic, $C_3$-$C_6$ cycloalkyl, or a 5-6 membered heteroaryl (having 1-4 heteroatoms independently selected from nitrogen, oxygen, and sulfur); each $R^{12}$ optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy;

$R^B$ is independently selected at each occurrence from the group consisting of optionally substituted phenyl, optionally substituted 5-6 membered heteroaryl (having 1-4 heteroatoms independently selected from nitrogen, oxygen, and sulfur), optionally substituted 4-7 membered saturated or partially unsaturated heterocyclyl (having 1-2 heteroatoms independently selected from nitrogen, oxygen, and sulfur), halogen, optionally substituted $C_1$-$C_6$ aliphatic, halo$C_1$-$C_6$ alkyl, $C_3$-$C_6$ cycloalkyl, halo$C_3$-$C_6$ cycloalkyl, $C_1$-$C_6$ alkoxy, halo$C_1$-$C_6$ alkoxy, $C_3$-$C_6$ cycloalkoxy, halo$C_3$-$C_6$ cycloalkoxy, $C_1$-$C_6$ alkylene-O—$C_1$-$C_6$ alkyl, —CN, —NO$_2$, oxo, —OR, —SR, NR$_2$, S(O)$_2$R, S(O)$_2$NR$_2$, S(O)R, S(O)NR$_2$, C(O)R, C(O)OR, —C(O)NR$_2$, C(O)N(R)OR, OC(O)R, OC(O)NR$_2$, —N(R)C(O)OR, N(R)C(O)R, N(R)C(O)NR$_2$, N(R)C(NR)NR$_2$, N(R)S(O)$_2$NR$_2$, and —N(R)S(O)$_2$R;

$R^C$ is independently selected at each occurrence from hydrogen, —CH$_3$, or —CH$_2$CH$_3$, or two $R^C$ taken together with the carbon to which they are attached form a cyclopropyl ring;

each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same atom are taken together with the same atom to form a cyclic group selected from an optionally substituted 4-7 membered saturated ring, a 4-7 membered partially unsaturated ring, or a 5-6 membered heteroaryl ring (having 1-4 heteroatoms independently selected from nitrogen, oxygen, and sulfur); wherein said cyclic group has 0-3 heteroatoms independently selected from nitrogen, oxygen, and sulfur).

In another aspect, the invention provides a method of treating a disorder or disease which can be treated by WRN inhibition in a subject, comprising administering to the subject a therapeutically effective amount of a compound of Formula I of the present invention, or a pharmaceutically acceptable salt thereof.

In one aspect, the disclosure provides a compound of Formula I', or a pharmaceutically acceptable salt thereof:

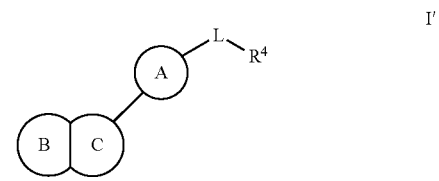

wherein bicyclic Ring BC is selected from one of the following:

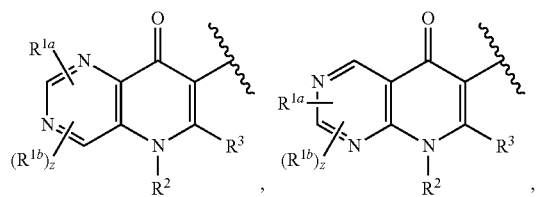

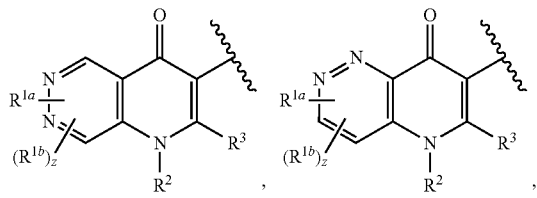

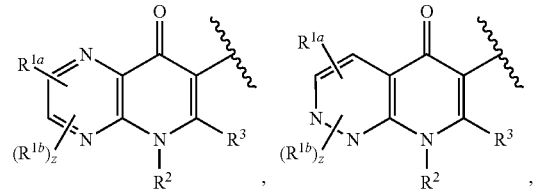

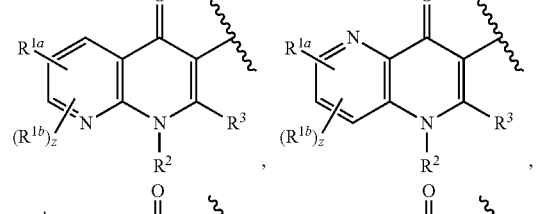

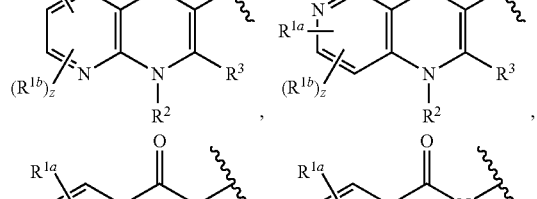

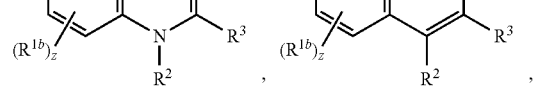

-continued

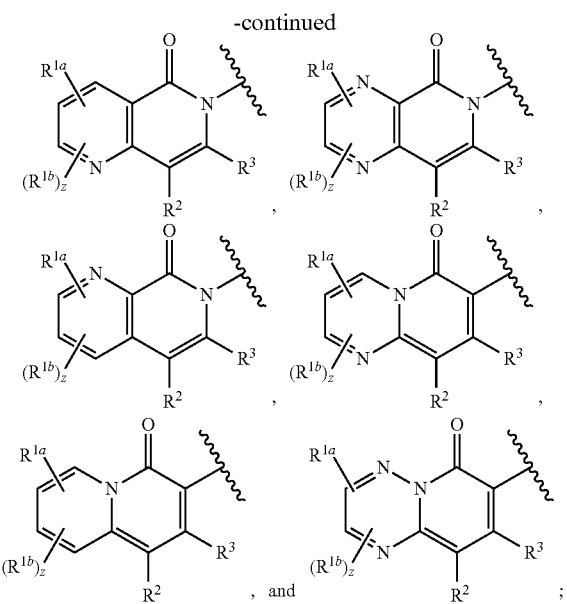

wherein ⌇⌇ denotes the point of attachment to Ring A; and each $R^{1b}$ group is independently selected from H, halogen, CN, OH, $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy, wherein said $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy are each independently and optionally substituted with 1-5 halogen, OH, CN, $C_1$-$C_6$ alkyl, or $C_3$-$C_6$ cycloalkyl groups;

wherein z is 0, 1, or 2;

Ring A is:
a 4-7 membered saturated or partially unsaturated bivalent monocyclic carbocyclylene or 4-7 membered saturated or partially unsaturated bivalent heterocyclylene ring (having 1-4 heteroatoms independently selected from nitrogen, oxygen, and sulfur, and 0 or 1 nitrogen atoms in addition to the 1-4 heteroatoms); or a 4-12 membered saturated or partially unsaturated bivalent bicyclic ring system that is fused, bridged, or spirocyclic selected from carbocyclylene or heterocyclylene (having 1-4 heteroatoms independently selected from nitrogen, oxygen, and sulfur);

wherein Ring A is substituted with 0-4 independently selected $R^B$ substituents;

-L- is a linker selected from —C(O)—, —S(O)—, —S(O)$_2$—, and

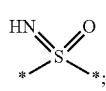

$R^{1a}$ is selected from:
a 5-6 membered heteroaryl (having 1-4 heteroatoms independently selected from nitrogen, oxygen, and sulfur) optionally substituted with 1-3 groups independently selected from halogen, $C_1$-$C_6$ aliphatic, $C_3$-$C_6$ cycloalkyl, halo$C_1$-$C_6$ alkyl, $C_1$-$C_6$ alkoxy, and $C_3$-$C_6$ cycloalkoxy, wherein said 5-6 membered heteroaryl is further substituted with 0-3 independently selected $R^B$;

a 4-7 membered saturated or partially unsaturated heterocyclyl (having 1-2 heteroatoms independently selected from nitrogen, oxygen, and sulfur), optionally substituted with 1 or 2 groups independently selected from $C_1$-$C_6$ aliphatic, $C_3$-$C_6$ cycloalkyl, $C_1$-$C_6$ alkoxy, $C_3$-$C_6$ cycloalkoxy, and —OR, wherein said 4-7 membered saturated or partially unsaturated heterocyclyl is further substituted with 0-3 independently selected $R^B$;

a 4-12 membered saturated or partially unsaturated bicyclic ring system that is fused, bridged, or spirocyclic selected from carbocyclyl or heterocyclyl (having 1-4 heteroatoms independently selected from nitrogen, oxygen, and sulfur), wherein said carbocyclyl or heterocyclyl is substituted with 0-3 independently selected $R^B$; and H, halogen, $C_1$-$C_6$ aliphatic, $C_3$-$C_7$ cycloalkyl, $C_1$-$C_6$ alkylene-O—$C_1$-$C_6$ alkyl, CN, —OR, —OR$^{10}$, —NR$^{10}$R$^{11}$, —C(O)NR$^{10}$R$^{11}$, —CH$_2$NR$^{10}$R$^{11}$, or —SO$_2$R$^{12}$, wherein said $C_1$-$C_6$ aliphatic, $C_3$-$C_7$ cycloalkyl, or $C_1$-$C_6$ alkylene-O—$C_1$-$C_6$ alkyl is substituted with 0-5 independently selected $R^B$;

or $R^{11}$ and one $R^{1b}$ on adjacent atoms of Ring B, taken together with the adjacent Ring B atoms to which they are attached, form a cyclic group fused to Ring B selected from phenyl, a 5-6 membered heteroaryl (having 1-3 heteroatoms independently selected from nitrogen, oxygen and sulfur), a 4-7 membered saturated or partially unsaturated carbocyclyl, or a 4-7 membered saturated or partially unsaturated heterocyclyl (having 1-3 heteroatoms independently selected from nitrogen, oxygen and sulfur), wherein said cyclic group fused to Ring B is substituted with 0-3 independently selected $R^B$;

$R^2$ is selected from C(R$^C$)$_2$C(O)N(R)R$^{2A}$, C(R$^C$)$_2$C(R$^C$)$_2$C(O)N(R)R$^{2A}$, C(R$^C$)$_2$C(R$^C$)$_2$N(R)C(O) N(R)R$^{2A}$, and C(R$^C$)$_2$C(R$^C$)$_2$N(R)C(O)R$^{2A}$;

$R^{2A}$ is phenyl, pyridyl, cubanyl, a saturated or partially unsaturated 4-8 membered monocyclic ring, a saturated or partially unsaturated bridged, fused, or spirocyclic 5-, 6-, 7-, 8-, 9-, 10-, 11-, or 12-membered ring, wherein said saturated or partially unsaturated monocyclic ring, or saturated or partially unsaturated bridged, fused, or spirocyclic ring contains 0, 1, 2, 3, or 4 heteroatoms independently selected from nitrogen, oxygen, and sulfur; and wherein said phenyl, pyridyl, cubanyl, saturated or partially unsaturated monocyclic ring, or saturated or partially unsaturated bridged, fused, or spirocyclic ring are each optionally substituted with 1, 2, or 3 substituents independently selected from halogen, $C_1$-$C_4$ aliphatic, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$-cycloalkoxy and —SF$_5$, and wherein two substituents on adjacent atoms of the phenyl or pyridyl, together with said adjacent atoms, optionally form a 4-7 membered carbocyclyl fused to the phenyl or pyridyl, and wherein two substituents on adjacent atoms of the phenyl or pyridyl together with said adjacent atoms optionally form a 4-7 membered heterocyclyl (having 1-4 heteroatoms independently selected from nitrogen, oxygen, and sulfur) fused to the phenyl or pyridyl, wherein said fused 4-7 membered carbocyclyl or fused 4-7 membered heterocyclyl is substituted with 0-5 independently selected halogen, and wherein two substituents on the same atom of said saturated or partially unsaturated monocyclic ring, or saturated or partially unsaturated bridged, fused, or spirocyclic ring optionally form a cyclic group selected from:
an optionally substituted 3-7 membered saturated or partially unsaturated carbocyclyl, and
an optionally substituted 4-7 membered saturated or partially unsaturated heterocyclyl having 1-3 heteroatoms independently selected from nitrogen, oxygen, and sulfur, or $R^{2A}$ is 2-benzimidazolyl, 2-naphthyl, or 3-quinolinyl, each of which is optionally substituted with 1, 2 or 3 substituents independently selected from halogen, $C_{1-4}$ alkyl, and —OH; $R^3$ is hydrogen, $C_1$-$C_4$ aliphatic, $C_3$-$C_5$ cycloalkyl, $C_1$-$C_4$ alkoxy, —NHR$^{3A}$, —N(R$^{3A}$)$_2$, or $C_1$-$C_4$ alkylthio, each of which, besides hydrogen, is optionally substituted with —OH, 1-5 independently selected halogen, OR, —C(O)NR$^{10}$R$^{11}$, or N(R)C(O)R;

each $R^{3A}$ is independently selected from $C_1$-$C_4$ alkyl;

$R^4$ is phenyl or a first 5-6 membered heteroaryl (having 1-4 heteroatoms independently selected from nitrogen, oxygen, and sulfur) wherein said phenyl or first 5-6 membered heteroaryl is substituted with 0-5 $R^B$; and optionally two adjacent atoms of said phenyl or first 5-6 membered heteroaryl have two substituents that together with said adjacent atoms form a cyclic group fused to the phenyl or first 5-6 membered heteroaryl selected from a 4-7 membered carbocyclyl, a 4-7 membered heterocyclyl (having 1-4 heteroatoms independently selected from nitrogen, oxygen, and sulfur), or a second 5-6 membered heteroaryl (having 1-4 heteroatoms independently selected from nitrogen, oxygen, and sulfur); wherein said fused cyclic group is substituted with 0-3 independently selected $R^B$; or $R^4$ is a $C_1$-$C_4$ aliphatic, $C_1$-$C_4$ alkoxy, or $C_3$-$C_6$ cycloalkyl, each of which is substituted with 0-3 groups independently selected from halogen, —CN, —OH, $C_1$-$C_4$ alkyl, $C_1$-$C_4$ alkoxy, optionally substituted 5-6 membered heterocyclyl, and optionally substituted 5-6 membered heterocyclyloxy;

$R^{10}$ is H, $C_1$-$C_6$ aliphatic, halo$C_1$-$C_6$ alkyl, $C_3$-$C_6$ cycloalkyl, halo$C_3$-$C_6$ cycloalkyl, —C(O)$C_1$-$C_6$ alkyl, or a 5-6 membered heteroaryl (having 1-4 heteroatoms independently selected from nitrogen, oxygen, and sulfur); each $R^{10}$ except H being optionally substituted with 1 or 2 independently selected $R^B$;

$R^{11}$ is H, $C_1$-$C_6$ aliphatic, or $C_3$-$C_6$ cycloalkyl, or $R^{10}$ and $R^{11}$ are taken together with the nitrogen atom to which they are attached to form a 5-6 membered ring optionally substituted with 1, 2, or 3 substituents independently selected from halogen, —OH, —CN, $C_1$-$C_4$ alkoxy, and halo$C_1$-$C_4$ alkoxy;

$R^{11}$ is $C_1$-$C_6$ aliphatic, $C_3$-$C_6$ cycloalkyl, or a 5-6 membered heteroaryl (having 1-4 heteroatoms independently selected from nitrogen, oxygen, and sulfur); each $R^{12}$ optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy;

$R^B$ is independently selected at each occurrence from the group consisting of optionally substituted phenyl, optionally substituted 5-6 membered heteroaryl (having 1-4 heteroatoms independently selected from nitrogen, oxygen, and sulfur), optionally substituted 4-7 membered saturated or partially unsaturated heterocyclyl (having 1-2 heteroatoms independently selected from nitrogen, oxygen, and sulfur), halogen, optionally substituted $C_1$-$C_6$ aliphatic, halo$C_1$-$C_6$ alkyl, $C_3$-$C_6$ cycloalkyl, halo$C_3$-$C_6$ cycloalkyl, $C_1$-$C_6$ alkoxy, halo$C_1$-$C_6$ alkoxy, $C_3$-$C_6$ cycloalkoxy, halo$C_3$-$C_6$ cycloalkoxy, $C_1$-$C_6$ alkylene-O—$C_1$-$C_6$ alkyl, —CN, —NO$_2$, oxo, —OR, —SR, NR$_2$, S(O)$_2$R, S(O)$_2$NR$_2$, S(O)R, S(O)NR$_2$, C(O)R, C(O)OR, —C(O)NR$_2$, C(O)N(R)OR, OC(O)R, OC(O)NR$_2$, —N(R)C(O)OR, N(R)C(O)R, N(R)C(O)NR$_2$, N(R)C(NR)NR$_2$, N(R)S(O)$_2$NR$_2$, and —N(R)S(O)$_2$R;

$R^C$ is independently selected at each occurrence from hydrogen, —CH$_3$, or —CH$_2$CH$_3$, or two $R^C$ taken together with the carbon to which they are attached form a cyclopropyl ring;

each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same atom are taken together with the same atom to form a cyclic group selected from an optionally substituted 4-7 membered saturated ring, a 4-7 membered partially unsaturated ring, or a 5-6 membered heteroaryl ring (having 1-4 heteroatoms independently selected from nitrogen, oxygen, and sulfur); wherein said cyclic group has 0-3 heteroatoms independently selected from nitrogen, oxygen, and sulfur).

In another aspect, the invention provides a method of treating a disorder or disease which can be treated by WRN inhibition in a subject, comprising administering to the subject a therapeutically effective amount of a compound of Formula I' of the present invention, or a pharmaceutically acceptable salt thereof.

In one aspect, the disclosure provides a compound of Formula I", or a pharmaceutically acceptable salt thereof:

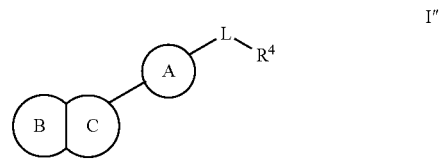

I"

wherein bicyclic Ring BC is selected from one of the following:

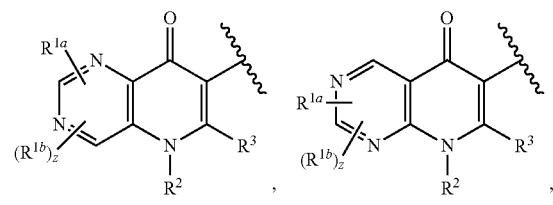

-continued

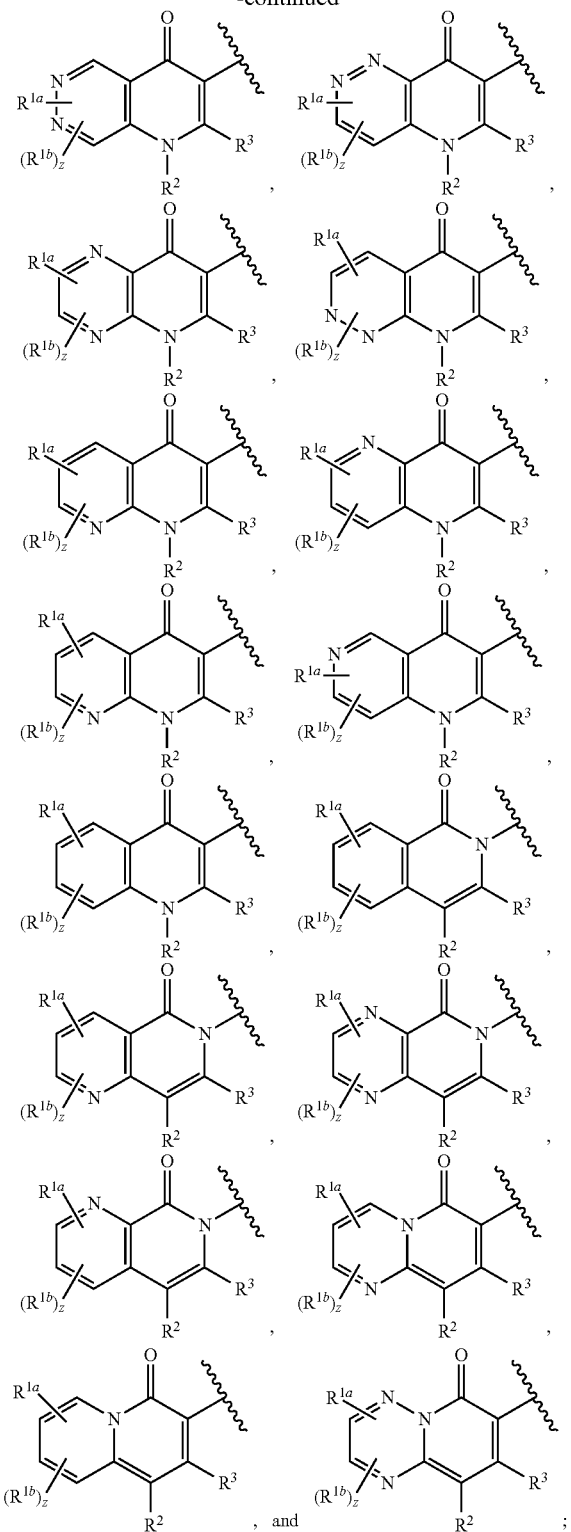

, and ;

wherein ⁓ denotes the point of attachment to Ring A;
and each $R^{1b}$ group is independently selected from H, halogen, CN, OH, $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy, wherein said $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy are each independently and optionally substituted with 1-5 halogen, OH, CN, $C_1$-$C_6$ alkyl, or $C_3$-$C_6$ cycloalkyl groups; wherein z is 0, 1, or 2;

Ring A is:
a 4-7 membered saturated or partially unsaturated bivalent monocyclic carbocyclylene or 4-7 membered saturated or partially unsaturated bivalent heterocyclylene ring (having 1-4 heteroatoms independently selected from nitrogen, oxygen, and sulfur, and 0 or 1 nitrogen atoms in addition to the 1-4 heteroatoms); or
a 4-12 membered saturated or partially unsaturated bivalent bicyclic ring system that is fused, bridged, or spirocyclic selected from carbocyclylene or heterocyclylene (having 1-4 heteroatoms independently selected from nitrogen, oxygen, and sulfur);
wherein Ring A is substituted with 0-4 independently selected $R^B$ substituents;
-L- is a linker selected from —C(O)—, —S(O)—, —S(O)$_2$—, and

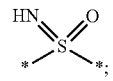

$R^{1a}$ is selected from:
a 5-6 membered heteroaryl (having 1-4 heteroatoms independently selected from nitrogen, oxygen, and sulfur) optionally substituted with 1-3 groups independently selected from halogen, $C_1$-$C_6$ aliphatic, $C_3$-$C_6$ cycloalkyl, halo$C_1$-$C_6$ alkyl, $C_1$-$C_6$ alkoxy, and $C_3$-$C_6$ cycloalkoxy, wherein said 5-6 membered heteroaryl is further substituted with 0-3 independently selected $R^B$;
a 4-7 membered saturated or partially unsaturated heterocyclyl (having 1-2 heteroatoms independently selected from nitrogen, oxygen, and sulfur), optionally substituted with 1 or 2 groups independently selected from $C_1$-$C_6$ aliphatic, $C_3$-$C_6$ cycloalkyl, $C_1$-$C_6$ alkoxy, $C_3$-$C_6$ cycloalkoxy, and —OR, wherein said 4-7 membered saturated or partially unsaturated heterocyclyl is further substituted with 0-3 independently selected $R^B$;
a 4-12 membered saturated or partially unsaturated bicyclic ring system that is fused, bridged, or spirocyclic selected from carbocyclyl or heterocyclyl (having 1-4 heteroatoms independently selected from nitrogen, oxygen, and sulfur), wherein said carbocyclyl or heterocyclyl is substituted with 0-3 independently selected $R^B$; and
H, halogen, $C_1$-$C_6$ aliphatic, $C_3$-$C_7$ cycloalkyl, $C_1$-$C_6$ alkylene-O—$C_1$-$C_6$ alkyl, CN, —OR, —OR$^{10}$, —NR$^{10}$R$^{11}$, —C(O)NR$^{10}$R$^{11}$, —CH$_2$NR$^{10}$R$^{11}$, or —SO$_2$R$^{12}$, wherein said $C_1$-$C_6$ aliphatic, $C_3$-$C_7$ cycloalkyl, or $C_1$-$C_6$ alkylene-O—$C_1$-$C_6$ alkyl is substituted with 0-5 independently selected $R^B$;
or $R^{1a}$ and one $R^{1b}$ on adjacent atoms of Ring B, taken together with the adjacent Ring B atoms to which they are attached, form a cyclic group fused to Ring B selected from phenyl, a 5-6 membered heteroaryl (having 1-3 heteroatoms independently selected from nitrogen, oxygen and sulfur), a 4-7 membered saturated or partially unsaturated carbocyclyl, or a 4-7 membered saturated or partially unsaturated heterocyclyl (having 1-3 heteroatoms independently selected from nitrogen, oxygen and sulfur), wherein said cyclic group fused to Ring B is substituted with 0-3 independently selected $R^B$;

$R^2$ is selected from $C(R^C)_2C(O)N(R)R^{2A}$, $C(R^C)_2C(R^C)_2C(O)N(R)R^{2A}$, $C(R^C)_2C(R^C)_2N(R)C(O)N(R)R^{2A}$, and $C(R^C)_2C(R^C)_2N(R)C(O)R^{2A}$;

$R^{2A}$ is phenyl, pyridyl, cubanyl, a saturated or partially unsaturated 4-8 membered monocyclic ring, a saturated or partially unsaturated bridged, fused, or spirocyclic 5-, 6-, 7-, 8-, 9-, 10-, 11-, or 12-membered ring, wherein said saturated or partially unsaturated monocyclic ring, or saturated or partially unsaturated bridged, fused, or spirocyclic ring contains 0, 1, 2, 3, or 4 heteroatoms independently selected from nitrogen, oxygen, and sulfur; and wherein said phenyl, pyridyl, cubanyl, saturated or partially unsaturated monocyclic ring, or saturated or partially unsaturated bridged, fused, or spirocyclic ring are each optionally substituted with 1, 2, or 3 substituents independently selected from halogen, $C_1$-$C_4$ aliphatic, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$-cycloalkoxy and —SF$_5$, and wherein two substituents on adjacent atoms of the phenyl or pyridyl, together with said adjacent atoms, optionally form a 4-7 membered carbocyclyl fused to the phenyl or pyridyl, and wherein two substituents on adjacent atoms of the phenyl or pyridyl together with said adjacent atoms optionally form a 4-7 membered heterocyclyl (having 1-4 heteroatoms independently selected from nitrogen, oxygen, and sulfur) fused to the phenyl or pyridyl, wherein said fused 4-7 membered carbocyclyl or fused 4-7 membered heterocyclyl is substituted with 0-5 independently selected halogen, and wherein two substituents on the same atom of said saturated or partially unsaturated monocyclic ring, or saturated or partially unsaturated bridged, fused, or spirocyclic ring optionally form a cyclic group selected from:
  an optionally substituted 3-7 membered saturated or partially unsaturated carbocyclyl, and
  an optionally substituted 4-7 membered saturated or partially unsaturated heterocyclyl having 1-3 heteroatoms independently selected from nitrogen, oxygen, and sulfur, or $R^{2A}$ is 2-benzimidazolyl, 2-naphthyl, or 3-quinolinyl, each of which is optionally substituted with 1, 2 or 3 substituents independently selected from halogen, $C_{1-4}$ alkyl, and —OH;

$R^3$ is hydrogen, $C_1$-$C_4$ aliphatic, $C_3$-$C_5$ cycloalkyl, $C_1$-$C_4$ alkoxy, —NHR$^{3A}$, —N(R$^{3A}$)$_2$, or $C_1$-$C_4$ alkylthio, each of which, besides hydrogen, is optionally substituted with —OH, 1-5 independently selected halogen, OR, —C(O)NR$^{10}$R$^{11}$, or N(R)C(O)R;

each $R^{3A}$ is independently selected from $C_1$-$C_4$ alkyl; $R^4$ is phenyl or a first 5-6 membered heteroaryl (having 1-4 heteroatoms independently selected from nitrogen, oxygen, and sulfur) wherein said phenyl or first 5-6 membered heteroaryl is substituted with 0-5 $R^B$; and optionally two adjacent atoms of said phenyl or first 5-6 membered heteroaryl have two substituents that together with said adjacent atoms form a cyclic group fused to the phenyl or first 5-6 membered heteroaryl selected from a 4-7 membered carbocyclyl, a 4-7 membered heterocyclyl (having 1-4 heteroatoms independently selected from nitrogen, oxygen, and sulfur), or a second 5-6 membered heteroaryl (having 1-4 heteroatoms independently selected from nitrogen, oxygen, and sulfur); wherein said fused cyclic group is substituted with 0-3 independently selected $R^B$; or $R^4$ is a $C_1$-$C_4$ aliphatic, $C_1$-$C_4$ alkoxy, or $C_3$-$C_6$ cycloalkyl, each of which is substituted with 0-3 groups independently selected from halogen, —CN, —OH, $C_1$-$C_4$ alkyl, $C_1$-$C_4$ alkoxy, optionally substituted 5-6 membered heterocyclyl, and optionally substituted 5-6 membered heterocyclyloxy;

$R^{10}$ is H, $C_1$-$C_6$ aliphatic, halo$C_1$-$C_6$ alkyl, $C_3$-$C_6$ cycloalkyl, halo$C_3$-$C_6$ cycloalkyl, —C(O)$C_1$-$C_6$ alkyl, or a 5-6 membered heteroaryl (having 1-4 heteroatoms independently selected from nitrogen, oxygen, and sulfur); each $R^{10}$ except H being optionally substituted with 1 or 2 independently selected $R^B$.

$R^{11}$ is H, $C_1$-$C_6$ aliphatic, or $C_3$-$C_6$ cycloalkyl, or $R^{10}$ and $R^{11}$ are taken together with the nitrogen atom to which they are attached to form a 5-6 membered ring optionally substituted with 1, 2, or 3 substituents independently selected from halogen, —OH, —CN, $C_1$-$C_4$ alkoxy, and halo$C_1$-$C_4$ alkoxy;

$R^{12}$ is $C_1$-$C_6$ aliphatic, $C_3$-$C_6$ cycloalkyl, or a 5-6 membered heteroaryl (having 1-4 heteroatoms independently selected from nitrogen, oxygen, and sulfur); each $R^{12}$ optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy;

$R^B$ is independently selected at each occurrence from the group consisting of optionally substituted phenyl, optionally substituted 5-6 membered heteroaryl (having 1-4 heteroatoms independently selected from nitrogen, oxygen, and sulfur), optionally substituted 4-7 membered saturated or partially unsaturated heterocyclyl (having 1-2 heteroatoms independently selected from nitrogen, oxygen, and sulfur), halogen, optionally substituted $C_1$-$C_6$ aliphatic, halo$C_1$-$C_6$ alkyl, $C_3$-$C_6$ cycloalkyl, halo$C_3$-$C_6$ cycloalkyl, $C_1$-$C_6$ alkoxy, halo$C_1$-$C_6$ alkoxy, $C_3$-$C_6$ cycloalkoxy, halo$C_3$-$C_6$ cycloalkoxy, $C_1$-$C_6$ alkylene-O—$C_1$-$C_6$ alkyl, —CN, —NO$_2$, oxo, —OR, —SR, NR$_2$, S(O)$_2$R, S(O)$_2$NR$_2$, S(O)R, S(O)NR$_2$, C(O)R, C(O)OR, —C(O)NR$_2$, C(O)N(R)OR, OC(O)R, OC(O)NR$_2$, —N(R)C(O)OR, N(R)C(O)R, N(R)C(O)NR$_2$, N(R)C(NR)NR$_2$, N(R)S(O)$_2$NR$_2$, and —N(R)S(O)$_2$R;

$R^C$ is independently selected at each occurrence from hydrogen, —CH$_3$, or —CH$_2$CH$_3$, or two $R^C$ taken together with the carbon to which they are attached form a cyclopropyl ring;

each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same atom are taken together with the same atom to form a cyclic group selected from an optionally substituted 4-7 membered saturated ring, a 4-7 membered partially unsaturated ring, or a 5-6 membered heteroaryl ring (having 1-4 heteroatoms independently selected from nitrogen, oxygen, and sulfur); wherein said cyclic group has 0-3 heteroatoms independently selected from nitrogen, oxygen, and sulfur).

In another aspect, the invention provides a method of treating a disorder or disease which can be treated by WRN inhibition in a subject, comprising administering to the subject a therapeutically effective amount of a compound of Formula I″ of the present invention, or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001.

Compound structures shown throughout the present specification and in the examples or claims contain designations at certain stereocenters which indicate the following: "or1" and is intended to cover stereochemically pure compounds wherein the stereochemistry at the stereocenter marked with "or1" is either the stereochemistry shown in the diagram or wherein the marked stereocenter has a configuration opposite to what is shown in the diagram. In structures with stereocenters with the same label such as "or1" the relative stereochemistry between two stereocenters with said label is as drawn, as in Example I-39 and I-40.

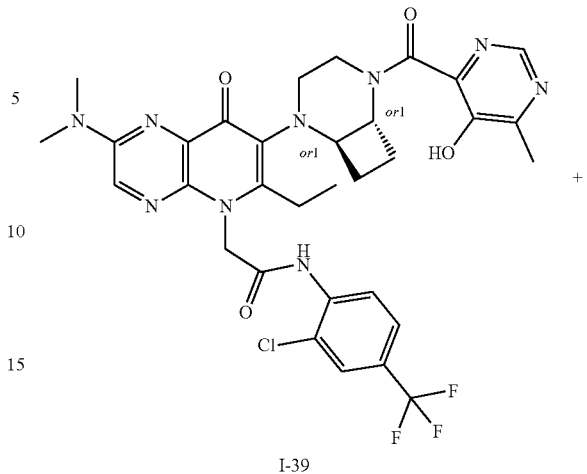

I-39

I-40

Stereocenters marked with "abs" intend to cover material wherein the marked stereocenter is of the stereochemistry shown in the diagram. Stereocenters marked with "& 1" or "and 1" indicate that the compound material has a mixture of R and S-configured stereoisomers with respect to the marked stereocenter and is in the same relative configuration to each other if they share the same label such as "and 1" or "&1" as in Example I-34.

Compound structures shown throughout the present specification and in the examples or claims which contain designations at certain stereocenters which indicate "or1" and contain other designations at certain stereocenters which are absolute and indicate "S" is intended to cover mixtures of stereochemically pure compounds wherein the stereochemistry at the stereocenter marked with "or1" is either the stereochemistry shown in the diagram or wherein the marked "or1" stereocenter has a configuration opposite to what is shown in the diagram and the stereocenters marked "S" are absolute and are as indicated as in Example (I-122): 2-(2-((1R*,5S*)-2-azabicyclo[3.1.0]hexan-2-yl)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-fluoro-4-(trifluoromethyl)phenyl)acetamide.

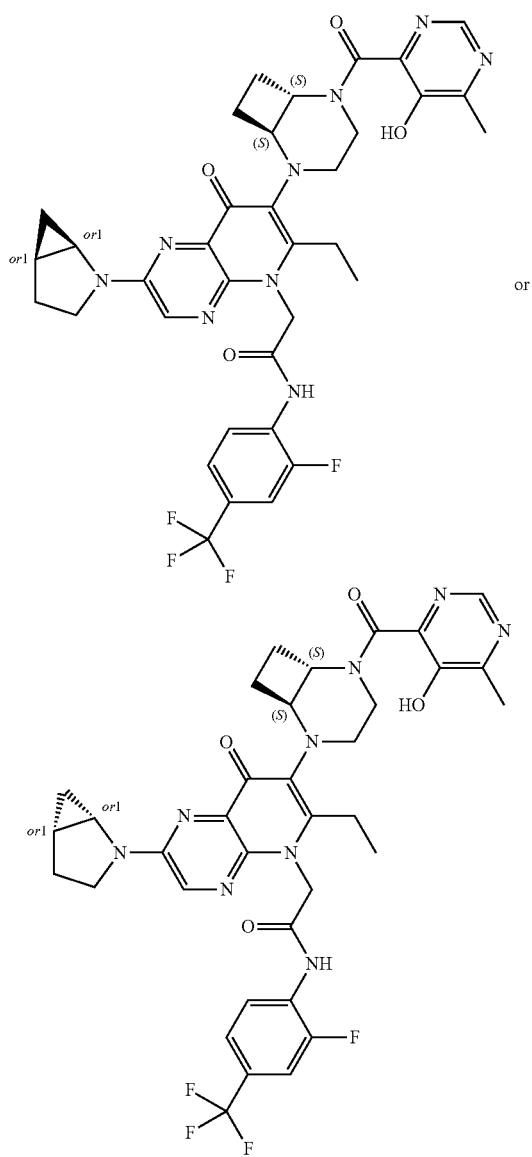

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 5-12 ring members and 0-4 heteroatoms independently selected from nitrogen, oxygen, or sulfur unless otherwise specified, a bridged bicyclic group is optionally substituted with one or more substituents as set forth for aliphatic groups. Additionally or alternatively, any substitutable nitrogen of a bridged bicyclic group is optionally substituted. The term "alkyl" refers to a $C_{1-12}$ straight or branched saturated aliphatic group. In certain instances, alkyl refers to a $C_{1-8}$ straight or branched saturated aliphatic group or a $C_{1-6}$ straight or branched saturated aliphatic group. The term "lower alkyl" refers to a $C_{1-4}$ straight or branched alkyl group.

Exemplary lower alkyl groups are methyl (—$CH_3$), ethyl (—$CH_2CH_3$), propyl, isopropyl (also referred to interchangeably herein as 2-propyl, iPr, $^i$Pr and i-Pr), butyl, isobutyl (also referred to interchangeably herein as 2-butyl, iBu, $^i$Bu and i-Bu) and tert-butyl (also referred to interchangeably herein as 2-methyl-2-butyl, tBu, $^t$Bu and t-Bu).

The term "alkenyl" refers to a $C_{2-12}$ straight or branched partially unsaturated aliphatic group comprising at least one unsaturated carbon double bond. In certain instances, alkenyl refers to a $C_{2-8}$ or a $C_{2-6}$ straight or branched partially unsaturated aliphatic group comprising at least one unsaturated carbon double bond. The term "lower alkenyl" refers to a $C_{2-4}$ straight or branched partially unsaturated aliphatic group comprising at least one unsaturated carbon carbon double bond. Alkenyl groups include both cis (Z) and trans (E) regioisomers. Exemplary lower alkenyl groups are vinyl, allyl, 2-propenyl, and butenyl isomers (—$CH_2CH_2CH$=$CH_2$, —$CH_2CH$=$CHCH_3$, and —$CH$=$CHCH_2CH_3$).

The term "alkynyl" refers to a $C_{2-12}$ straight or branched partially unsaturated aliphatic group comprising at least one unsaturated carbon triple bond. In certain instances, alkynyl refers to a $C_{2-8}$ or a $C_{2-6}$ straight or branched partially unsaturated aliphatic group comprising at least one unsaturated carbon triple bond. The term "lower alkynyl" refers to a $C_{2-4}$ straight or branched partially unsaturated aliphatic group comprising at least one unsaturated carbon carbon triple bond. Exemplary lower alkynyl groups are ethynyl, 1-propynyl, 2-propynyl, 1-butynyl, 2-butynyl, and 3-butynyl.

The term "haloalkyl" refers to a straight or branched alkyl group that is substituted with one or more halogen atoms. The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "cubanyl" refers to a substituent of cubane as shown below.

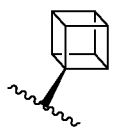

The substituent -Me, as used herein refers to a methyl group, —$CH_3$.

-continued

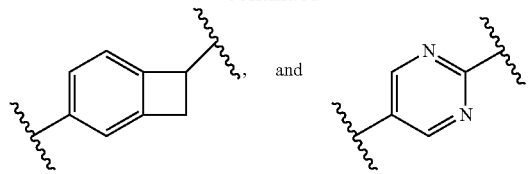

"Carbocyclylene" as used herein refers to a carbocyclic or cycloalkyl moiety that is bivalent as described above (i.e., attached at two different points to the rest of the compound). Non-limiting examples include cyclopropylene, cyclobutylene, cyclopentylene, or cyclohexylene as shown below.

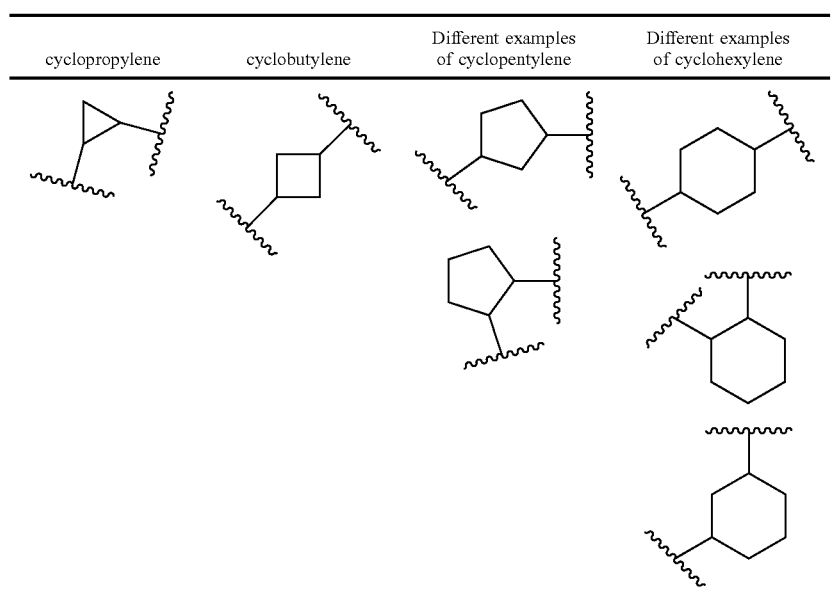

| cyclopropylene | cyclobutylene | Different examples of cyclopentylene | Different examples of cyclohexylene |
|---|---|---|---|

As used herein, the term "bivalent $C_{1-8}$ (or $C_{1-6}$ i.e., $C_1$-$C_6$) saturated or unsaturated, straight or branched, hydrocarbon chain," refers to bivalent alkylene, alkenylene, and alkynylene chains that are straight or branched as defined herein.

As used herein, the term "bivalent," to describe a cyclic (and noncyclic) group refers to, for example, bivalent carbocyclylene, phenylene, heterocyclylene, and heteroarylene that are bivalent moieties of carbocycles, phenyls, heterocycles, and heteroaryls described herein. Non-limiting examples include

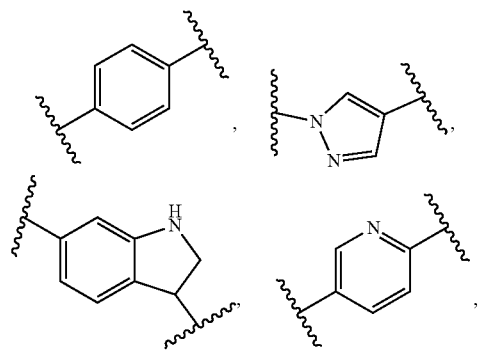

A carbocyclylene may be saturated as in the examples shown above or partially unsaturated as in the examples shown below.

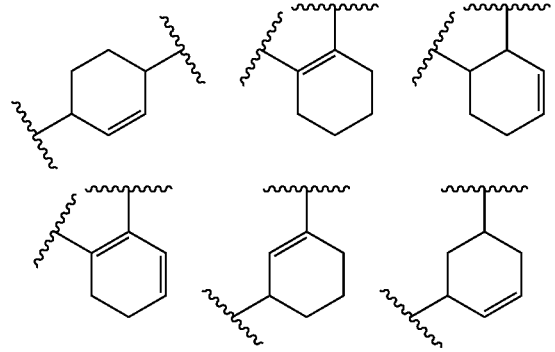

-continued

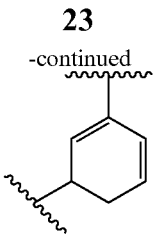

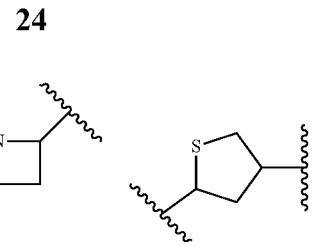

A carbocyclylene may be multi-cyclic, for example, bicyclic or tricyclic. Such multi-cyclic carbocyclylene systems may be saturated or partially unsaturated (while one ring of the bicyclic system may be aromatic it is to be understood that multi-cyclic ring systems that are not in their entirety aromatic may also fall under the definition of carbocyclylene). The rings may form bridged, fused, or spiro systems. Non-limiting examples are shown below.

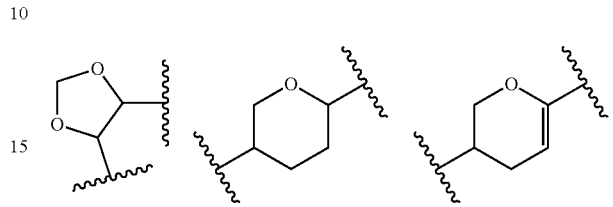

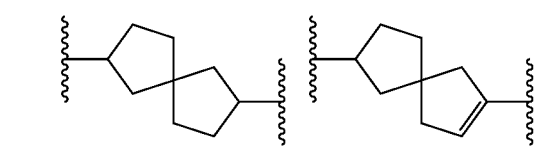

spirocyclic bicyclic carbocyclylenes

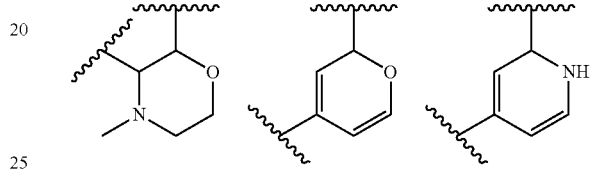

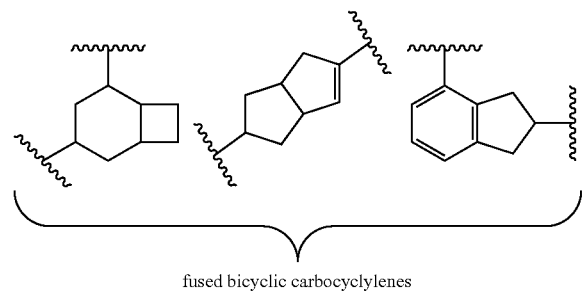

fused bicyclic carbocyclylenes

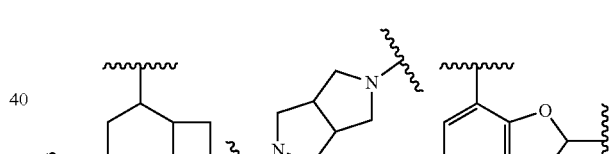

spirocyclic bicyclic carbocyclylenes

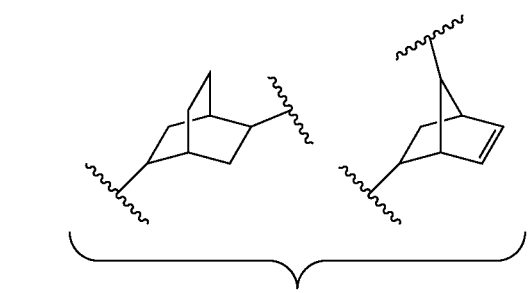

bridged bicyclic carbocyclylenes

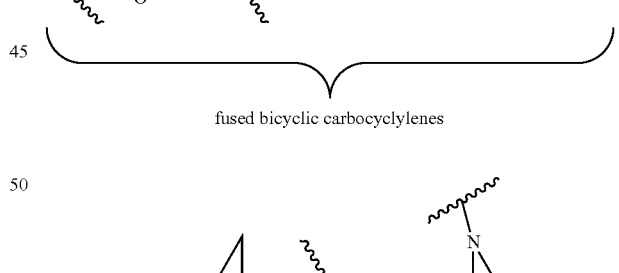

fused bicyclic carbocyclylenes

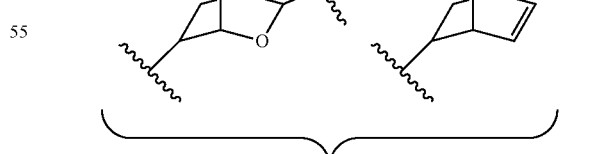

bridged bicyclic carbocyclylenes

"Heterocyclylene" as used herein refers to a heterocyclic or heterocyclyl moiety that is bivalent as described above (i.e., attached at two different points to the rest of the compound) and may also be saturated or partially unsaturated. Non-limiting examples include those shown below. Heterocyclylene is understood to include bicyclic heterocyclylene systems. Non-limiting examples of bicyclic heterocyclylene moieties are also shown below and said bicyclic systems may be spirocyclic, fused, or bridged and may be saturated or partially unsaturated.

"Phenylene" as used herein refers to a phenyl moiety that is bivalent as described above (i.e., attached at two different points to the rest of the compound). Examples are shown below.

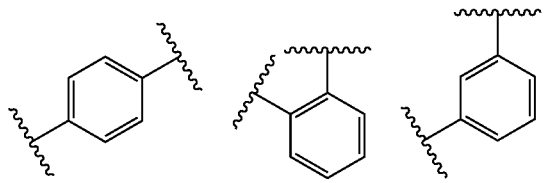 [SMILES: *c1ccc(*)cc1 ; *c1ccccc1* ; *c1cccc(*)c1]

"Arylene" as used herein refers to a mono or multi-cyclic aryl (i.e., phenyl or a multi-cyclic aryl) moiety that is bivalent as described above (i.e., attached at two different points to the rest of the compound), wherein the arylene group contains no heteroatoms. Examples are shown below.

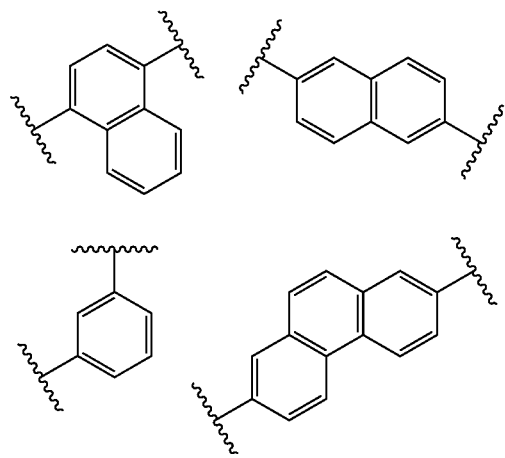

"Heteroarylene," as used herein refers to a mono or multi-cyclic aryl ring system that contains at least one heteroatom wherein the ring system is bivalent as described above (i.e., attached at two different points to the rest of the compound). Examples are shown below.

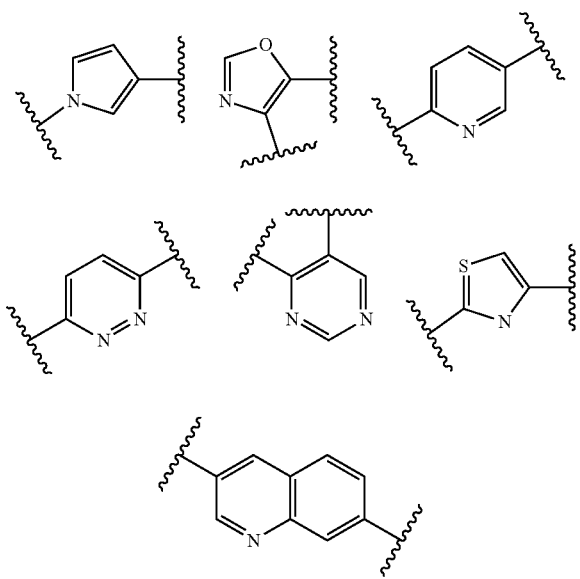

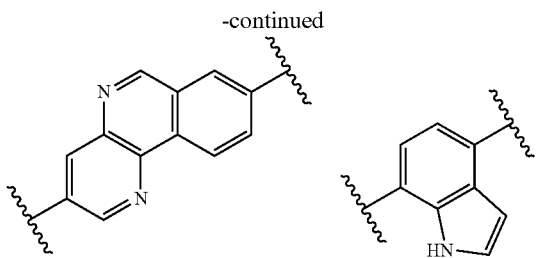

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

"Carbocyclyl (or heterocyclyl, aryl, phenyl, or heteroaryl) fused to" another phenyl, aryl, heteroaryl, carbocyclyl, or heterocyclyl, for example, a "phenyl or pyridyl" as used herein, may be referred to as "partially unsaturated" without said "carbocyclyl (or heterocyclyl, aryl, phenyl, or heteroaryl) fused to" the other ring requiring further unsaturation besides the carbon carbon bond which it shares with the ring to which it is fused (i.e., the "phenyl or pyridyl"). This is illustrated below.

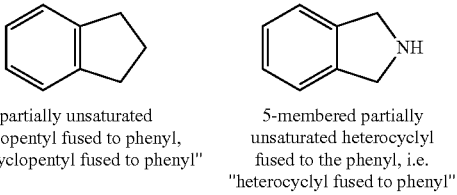

partially unsaturated cyclopentyl fused to phenyl, i.e., "cyclopentyl fused to phenyl"

5-membered partially unsaturated heterocyclyl fused to the phenyl, i.e. "heterocyclyl fused to phenyl"

A further example below shows a carbocyclyl moiety fused to a Ring E as defined in the embodiments herein. Said carbocyclyl does not explicitly require a descriptor of "partially unsaturated" to describe said carbocyclyl because it shares two carbons with the aromatic pyridine to which it is fused. Such language is used herein to describe such systems, for example, "$R^{4A}$ and $R^{4B}$, along with their intervening atoms, join to form 4-7 membered carbocyclyl that is fused to Ring E" as shown in the image below. As such, "Ring E" may refer to a monocyclic ring (i.e., the pyridine shown below and its substituents which do not form a fused ring), without any further fused rings created by its substituents (i.e., $R^{4A}$ and $R^{4B}$). Any further fused ring created by the substituents of Ring E is described as being "fused to Ring E." Likewise, $R^{4A}$ and $R^{4B}$, along with their intervening atoms, join to form 4-7 membered carbocyclyl or heterocyclyl (having 1-4 heteroatoms independently selected from nitrogen, oxygen, and sulfur) that is fused to Ring E (not pictured), is subject to the same interpretation.

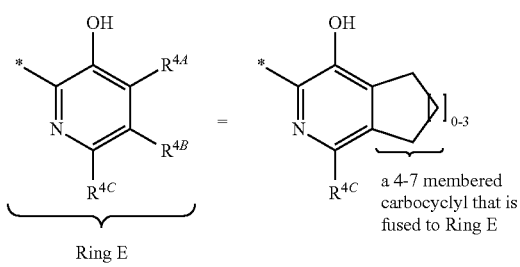

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, 9 or 10 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, pyrazinyl, pyrazolyl, pyridazinyl, pyridyl, pyrimidinyl, triazinyl, thienyl, furanyl, pyrrolyl, imidazolyl, pyrazolyl, triazolyl (i.e., 1,2,3-triazolyl), 1,2,4-triazolyl, 1,2,5-triazolyl, 1,3,4-triazolyl, tetrazolyl, oxazolyl, isoxazolyl, oxadiazolyl, 1,2,3-oxadiazolyl, 1,2,4-oxadiazolyl, 1,2,5-oxadiazolyl, 1,3,4-oxadiazolyl, thiazolyl, isothiazolyl, thiadiazolyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, indolizinyl, isoindolin-1-only, 1,2-dihydro-3H-pyrrolo[3,4-c]pyridin-3-onyl, 2,3-dihydro-1H-pyrrolo[3,4-c]pyridin-1-onyl, imidazo[1,2-a]pyridyl, imidazo[1,5-a]pyridyl, pyrazolo[1,5-a]pyridyl, pyrrolo[1,2-b]pyridazinyl, pyrrolo[1,2-a]pyrimidinyl, imidazo[1,2-b]pyridazinyl, imidazo[1,2-a]pyrimidinyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. Said 7-10-membered bicyclic heterocyclic moiety that is partially unsaturated may include an aryl or heteroaryl ring fused to a non-aromatic ring. For example, said 7-10-membered bicyclic heterocyclic moiety may include a bicyclic heterocyclyl as shown below:

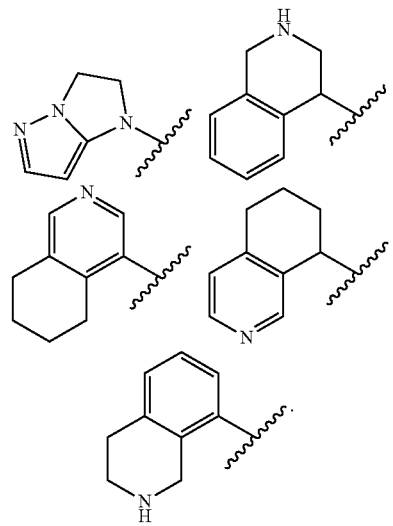

When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, oxetanyl, azetidinyl, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

"Arylene" or "heteroarylene," as used herein (i.e., phenylene), refers to any bivalent aryl or heterocyclyl described herein, that is a biradical substituted at each of two substitutable positions of the ring system as described in detail supra.

"Heterocyclyloxy," as used herein, refers to an —OR group wherein the R is a heterocyclyl. Nonlimiting examples are shown below.

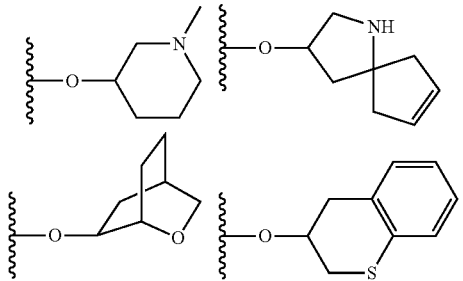

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$B(OR$^\circ$)$_2$; —(CH$_2$)$_{0-4}$R$^\circ$; —(CH$_2$)$_{0-4}$OR$^\circ$; —O(CH$_2$)$_{0-4}$R$^\circ$; —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —N(R$^\circ$)C(NR$^\circ$)N(R$^\circ$)$_2$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O) OSiR$^\circ_3$; —(CH$_2$)$_{0-4}$OC(O)R$^\circ$; —OC(O)(CH$_2$)$_{0-4}$SR$^\circ$; —(CH$_2$)$_{0-4}$SC(O)R$^\circ$; —(CH$_2$)$_{0-4}$C(O)NR$^\circ_2$; —C(S)NR$^\circ_2$; —C(S)SR$^\circ$; —SC(S)SR$^\circ$; —(CH$_2$)$_{0-4}$OC(O)NR$^\circ_2$; —C(O) N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —(CH$_2$)$_{0-4}$P(O)$_2$R$^\circ$; —(CH$_2$)$_{0-4}$P(O)R$^\circ_2$; —(CH$_2$)$_{0-4}$OP(O)R$^\circ_2$; —(CH$_2$)$_{0-4}$OP (O)(OR$^\circ$)$_2$; —SiR$^\circ_3$; —(C$_{1-4}$ straight or branched alkylene) O—N(R$^\circ$)$_2$; or —(C$_{1-4}$ straight or branched alkylene)C(O) O—N(R$^\circ$)$_2$, wherein each R$^\circ$ may be substituted as defined below and is independently hydrogen, C$_{1-6}$ aliphatic, —SO$_2$—C$_{1-4}$ aliphatic (i.e., —SO$_2$CH$_3$)—CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$,-(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group, which includes instances of R$^\circ$ (or the ring formed by taking two independent occurrences of R$^\circ$ together with their intervening atoms), include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, Z and E conformational isomers and R$_a$ (or M) and S$_a$ (or P) atropisomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, Ring A of a provided compound may be substituted with one or more deuterium atoms.

The structures as drawn represent relative configurations, unless labeled as absolute configurations. The invention contemplates individual enantiomers and racemic mixtures.

3. DESCRIPTION OF EXEMPLARY EMBODIMENTS

In one aspect, the disclosure provides a compound of Formula I, or a pharmaceutically acceptable salt thereof:

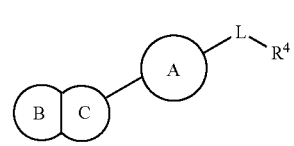

I wherein bicyclic Ring BC is selected from one of the following:

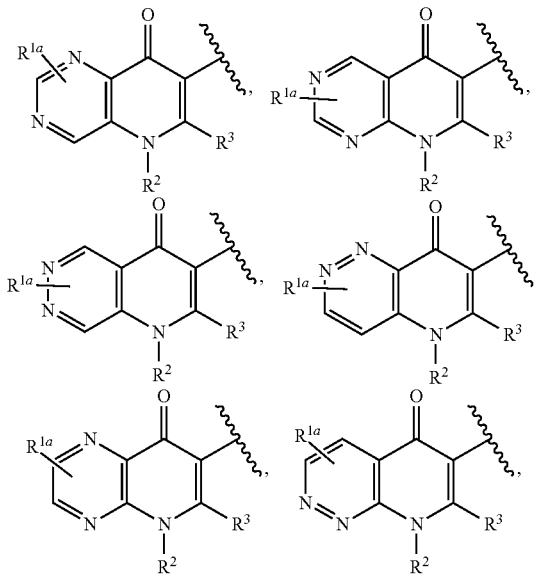

-continued

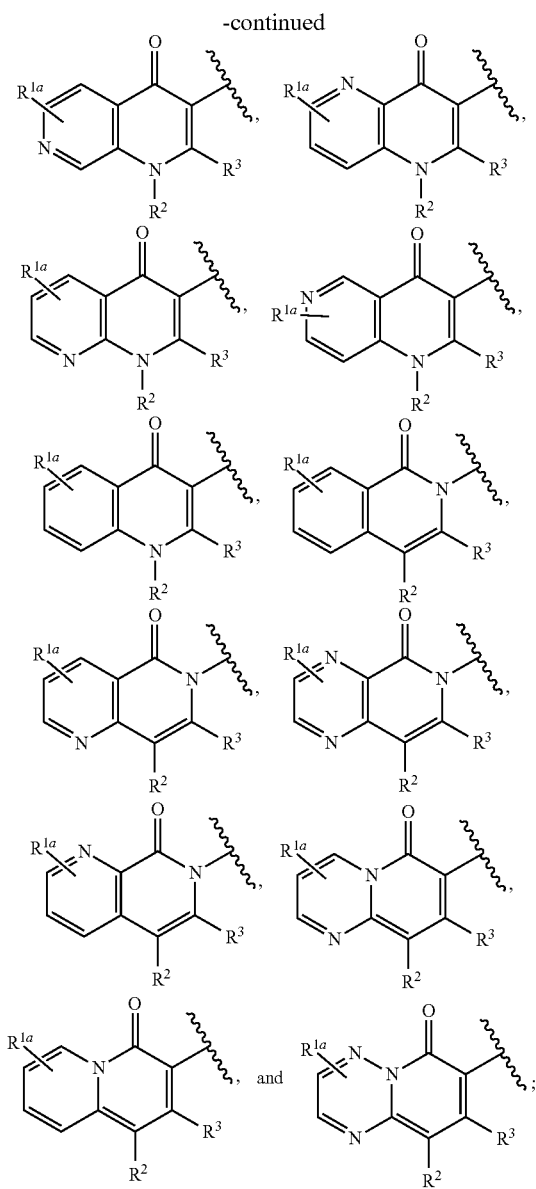

wherein ⁓ denotes the point of attachment to Ring A;
and wherein Ring B may be further optionally substituted with 1 or 2 $R^{1b}$ groups independently selected from H, halogen, CN, OH, $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy, wherein said $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy are each independently and optionally substituted with 1-5 halogen, OH, CN, $C_1$-$C_6$ alkyl, or $C_3$-$C_6$ cycloalkyl groups;
Ring A is:
 a 4-7 membered saturated or partially unsaturated bivalent monocyclic carbocyclylene or 4-7 membered saturated or partially unsaturated bivalent heterocyclylene ring (having 1-4 heteroatoms independently selected from nitrogen, oxygen, and sulfur, and 0 or 1 nitrogen atoms in addition to the 1-4 heteroatoms); or
 a 4-12 membered saturated or partially unsaturated bivalent bicyclic ring system that is fused, bridged, or spirocyclic selected from carbocyclylene or heterocyclylene (having 1-4 heteroatoms independently selected from nitrogen, oxygen, and sulfur);
wherein Ring A is substituted with 0-4 independently selected $R^B$ substituents;
-L- is a linker selected from —C(O)—, —S(O)—, —S(O)$_2$—, and

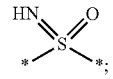

$R^{1a}$ is selected from:
 a 5-6 membered heteroaryl (having 1-4 heteroatoms independently selected from nitrogen, oxygen, and sulfur) optionally substituted with 1-3 groups independently selected from halogen, $C_1$-$C_6$ aliphatic, $C_3$-$C_6$ cycloalkyl, halo$C_1$-$C_6$ alkyl, $C_1$-$C_6$ alkoxy, and $C_3$-$C_6$ cycloalkoxy, wherein said 5-6 membered heteroaryl is further substituted with 0-3 independently selected $R^B$;
 a 4-7 membered saturated or partially unsaturated heterocyclyl (having 1-2 heteroatoms independently selected from nitrogen, oxygen, and sulfur), optionally substituted with 1 or 2 groups independently selected from $C_1$-$C_6$ aliphatic, $C_3$-$C_6$ cycloalkyl, $C_1$-$C_6$ alkoxy, $C_3$-$C_6$ cycloalkoxy, and —OR, wherein said 4-7 membered saturated or partially unsaturated heterocyclyl is further substituted with 0-3 independently selected $R^B$;
 a 4-12 membered saturated or partially unsaturated bicyclic ring system that is fused, bridged, or spirocyclic selected from carbocyclyl or heterocyclyl (having 1-4 heteroatoms independently selected from nitrogen, oxygen, and sulfur), wherein said carbocyclyl or heterocyclyl is substituted with 0-3 independently selected $R^B$; and
 H, halogen, $C_1$-$C_6$ aliphatic, $C_3$-$C_7$ cycloalkyl, $C_1$-$C_6$ alkylene-O—$C_1$-$C_6$ alkyl, CN, —OR, —OR$^{10}$, —NR$^{10}$R$^{11}$, —C(O)NR$^{10}$R$^{11}$, —CH$_2$NR$^{10}$R$^{11}$, or —SO$_2$R$^{12}$, wherein said $C_1$-$C_6$ aliphatic, $C_3$-$C_7$ cycloalkyl, or $C_1$-$C_6$ alkylene-O—$C_1$-$C_6$ alkyl is substituted with 0-5 independently selected $R^B$;
or $R^{1a}$ and one $R^{1b}$ on adjacent atoms of Ring B, taken together with the adjacent Ring B atoms to which they are attached, form a cyclic group fused to Ring B selected from phenyl, a 5-6 membered heteroaryl (having 1-3 heteroatoms independently selected from nitrogen, oxygen and sulfur), a 4-7 membered saturated or partially unsaturated carbocyclyl, or a 4-7 membered saturated or partially unsaturated heterocyclyl (having 1-3 heteroatoms independently selected from nitrogen, oxygen and sulfur), wherein said cyclic group fused to Ring B is substituted with 0-3 independently selected $R^B$;

$R^2$ is C(R$^C$)$_2$C(O)N(R)R$^{24}$;

$R^{24}$ is phenyl or pyridyl, each of which is optionally substituted with 1, 2, or 3 substituents independently selected from halogen, $C_1$-$C_4$ aliphatic, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, and —SF$_5$, and wherein two substituents on adjacent atoms of the phenyl or pyridyl, together with said adjacent atoms, form a 4-7 membered carbocyclyl fused to the phenyl or pyridyl, and wherein two substituents on adjacent atoms of the phenyl or pyridyl together with said adjacent atoms form a 4-7 membered heterocyclyl (having 1-4 heteroatoms independently selected from nitrogen, oxygen, and sulfur) fused to the phenyl or pyridyl, wherein said fused 4-7 membered carbocyclyl or fused 4-7 membered heterocyclyl is substituted with 0-5 independently selected halogen; or $R^{2A}$ is 2-benzimidazolyl, 2-naphthyl, or 3-quinolinyl, each of which is optionally substituted with 1, 2 or 3 substituents independently selected from halogen, $C_{1-4}$ alkyl, and —OH;

$R^3$ is hydrogen, $C_1$-$C_4$ aliphatic, $C_3$-$C_5$ cycloalkyl, $C_1$-$C_4$ alkoxy, —NHR$^{3A}$, —N(R$^{3A}$)$_2$, or $C_1$-$C_4$ alkylthio, each of which, besides hydrogen, is optionally substituted with —OH, 1-5 independently selected halogen, OR, —C(O)NR$^{10}$R$^{11}$, or N(R)C(O)R;

each $R^{3A}$ is independently selected from $C_1$-$C_4$ alkyl;

$R^4$ is phenyl or a first 5-6 membered heteroaryl (having 1-4 heteroatoms independently selected from nitrogen, oxygen, and sulfur) wherein said phenyl or first 5-6 membered heteroaryl is substituted with 0-5 $R^B$; and optionally two adjacent atoms of said phenyl or first 5-6 membered heteroaryl have two substituents that together with said adjacent atoms form a cyclic group fused to the phenyl or first 5-6 membered heteroaryl selected from a 4-7 membered carbocyclyl, a 4-7 membered heterocyclyl (having 1-4 heteroatoms independently selected from nitrogen, oxygen, and sulfur), or a second 5-6 membered heteroaryl (having 1-4 heteroatoms independently selected from nitrogen, oxygen, and sulfur); wherein said fused cyclic group is substituted with 0-3 independently selected $R^B$; or $R^4$ is a $C_1$-$C_4$ aliphatic, $C_1$-$C_4$ alkoxy, or $C_3$-$C_6$ cycloalkyl, each of which is substituted with 0-3 groups independently selected from halogen, —CN, —OH, $C_1$-$C_4$ alkyl, $C_1$-$C_4$ alkoxy, optionally substituted 5-6 membered heterocyclyl, and optionally substituted 5-6 membered heterocyclyloxy;

$R^{10}$ is H, $C_1$-$C_6$ aliphatic, halo$C_1$-$C_6$ alkyl, $C_3$-$C_6$ cycloalkyl, halo$C_3$-$C_6$ cycloalkyl, —C(O)$C_1$-$C_6$ alkyl, or a 5-6 membered heteroaryl (having 1-4 heteroatoms independently selected from nitrogen, oxygen, and sulfur); each $R^{10}$ except H being optionally substituted with 1 or 2 independently selected $R^B$.

$R^{11}$ is H, $C_1$-$C_6$ aliphatic, or $C_3$-$C_6$ cycloalkyl, or $R^{10}$ and $R^{11}$ are taken together with the nitrogen atom to which they are attached to form a 5-6 membered ring optionally substituted with 1, 2, or 3 substituents independently selected from halogen, —OH, —CN, $C_1$-$C_4$ alkoxy, and halo$C_1$-$C_4$ alkyl;

$R^{12}$ is $C_1$-$C_6$ aliphatic, $C_3$-$C_6$ cycloalkyl, or a 5-6 membered heteroaryl (having 1-4 heteroatoms independently selected from nitrogen, oxygen, and sulfur); each $R^{12}$ optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy;

$R^B$ is independently selected at each occurrence from the group consisting of optionally substituted phenyl, optionally substituted 5-6 membered heteroaryl (having 1-4 heteroatoms independently selected from nitrogen, oxygen, and sulfur), optionally substituted 4-7 membered saturated or partially unsaturated heterocyclyl (having 1-2 heteroatoms independently selected from nitrogen, oxygen, and sulfur), halogen, optionally substituted $C_1$-$C_6$ aliphatic, halo$C_1$-$C_6$ alkyl, $C_3$-$C_6$ cycloalkyl, halo$C_3$-$C_6$ cycloalkyl, $C_1$-$C_6$ alkoxy, halo$C_1$-$C_6$ alkoxy, $C_3$-$C_6$ cycloalkoxy, halo$C_3$-$C_6$ cycloalkoxy, $C_1$-$C_6$ alkylene-O—$C_1$-$C_6$ alkyl, —CN, —NO$_2$, oxo, —OR, —SR, NR$_2$, S(O)$_2$R, S(O)$_2$NR$_2$, S(O)R, S(O)NR$_2$, C(O)R, C(O)OR, —C(O)NR$_2$, C(O)N(R)OR, OC(O)R, OC(O)NR$_2$, —N(R)C(O)OR, N(R)C(O)R, N(R)C(O)NR$_2$, N(R)C(NR)NR$_2$, N(R)S(O)$_2$NR$_2$, and —N(R)S(O)$_2$R;

$R^C$ is independently selected at each occurrence from hydrogen, —CH$_3$, or —CH$_2$CH$_3$, or two $R^C$ taken together with the carbon to which they are attached form a cyclopropyl ring;

each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same atom are taken together with the same atom to form a cyclic group selected from an optionally substituted 4-7 membered saturated ring, a 4-7 membered partially unsaturated ring, or a 5-6 membered heteroaryl ring (having 1-4 heteroatoms independently selected from nitrogen, oxygen, and sulfur); wherein said cyclic group has 0-3 heteroatoms independently selected from nitrogen, oxygen, and sulfur).

In one aspect, the disclosure provides a compound of Formula I', or a pharmaceutically acceptable salt thereof:

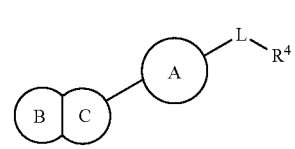

wherein bicyclic Ring BC is selected from one of the following:

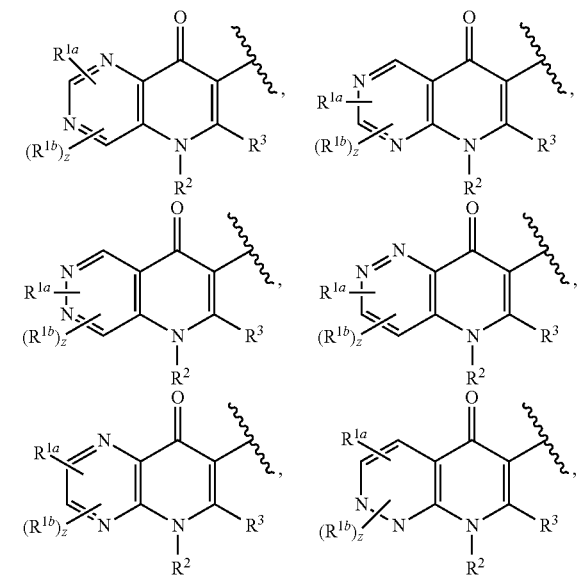

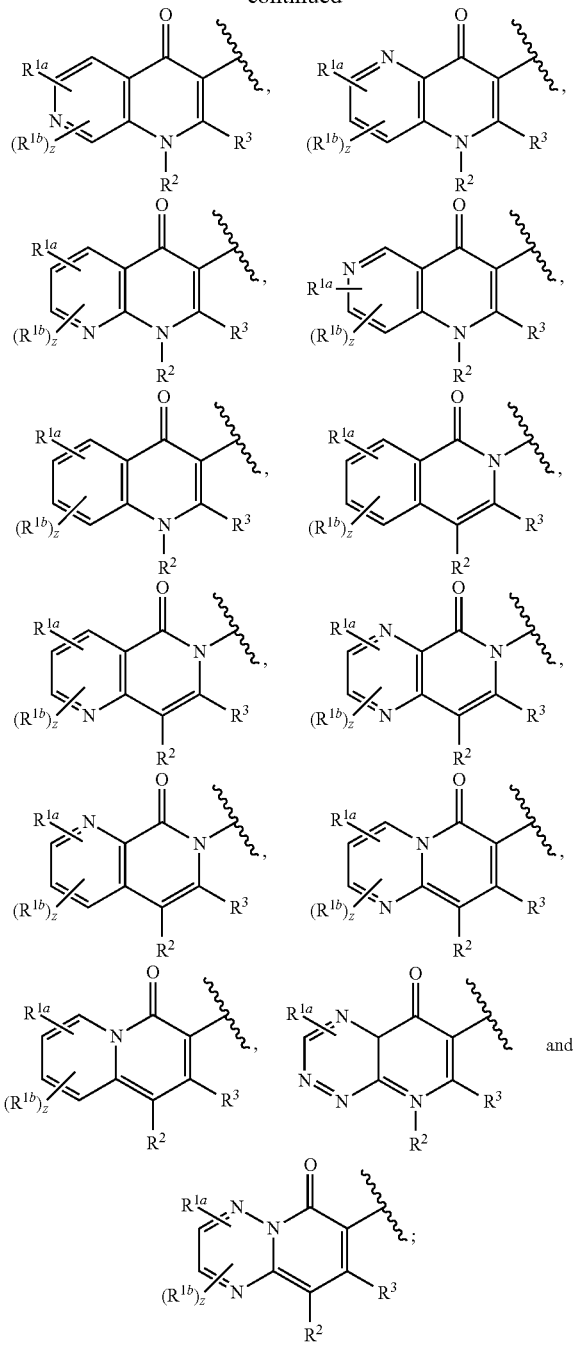

wherein ⁓ denotes the point of attachment to Ring A;
and wherein each $R^{1b}$ group is independently selected from H, halogen, CN, OH, $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy, wherein said $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy are each independently and optionally substituted with 1-5 halogen, OH, CN, $C_1$-$C_6$ alkyl, or $C_3$-$C_6$ cycloalkyl groups; wherein z is 0, 1, or 2;

Ring A is:
a 4-7 membered saturated or partially unsaturated bivalent monocyclic carbocyclylene or 4-7 membered saturated or partially unsaturated bivalent heterocyclylene ring (having 1-4 heteroatoms independently selected from nitrogen, oxygen, and sulfur, and 0 or 1 nitrogen atoms in addition to the 1-4 heteroatoms); or
a 4-12 membered saturated or partially unsaturated bivalent bicyclic ring system that is fused, bridged, or spirocyclic selected from carbocyclylene or heterocyclylene (having 1-4 heteroatoms independently selected from nitrogen, oxygen, and sulfur);
wherein Ring A is substituted with 0-4 independently selected $R^B$ substituents;
-L- is a linker selected from —C(O)—, —S(O)—, —S(O)$_2$—, and

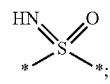

$R^{1a}$ is selected from:
a 5-6 membered heteroaryl (having 1-4 heteroatoms independently selected from nitrogen, oxygen, and sulfur) optionally substituted with 1-3 groups independently selected from halogen, $C_1$-$C_6$ aliphatic, $C_3$-$C_6$ cycloalkyl, halo$C_1$-$C_6$ alkyl, $C_1$-$C_6$ alkoxy, and $C_3$-$C_6$ cycloalkoxy, wherein said 5-6 membered heteroaryl is further substituted with 0-3 independently selected $R^B$;
a 4-7 membered saturated or partially unsaturated heterocyclyl (having 1-2 heteroatoms independently selected from nitrogen, oxygen, and sulfur), optionally substituted with 1 or 2 groups independently selected from $C_1$-$C_6$ aliphatic, $C_3$-$C_6$ cycloalkyl, $C_1$-$C_6$ alkoxy, $C_3$-$C_6$ cycloalkoxy, and —OR, wherein said 4-7 membered saturated or partially unsaturated heterocyclyl is further substituted with 0-3 independently selected $R^B$;
a 4-12 membered saturated or partially unsaturated bicyclic ring system that is fused, bridged, or spirocyclic selected from carbocyclyl or heterocyclyl (having 1-4 heteroatoms independently selected from nitrogen, oxygen, and sulfur), wherein said carbocyclyl or heterocyclyl is substituted with 0-3 independently selected $R^B$; and
H, halogen, $C_1$-$C_6$ aliphatic, $C_3$-$C_7$ cycloalkyl, $C_1$-$C_6$ alkylene-O—$C_1$-$C_6$ alkyl, CN, —OR, —OR$^{10}$, —NR$^{10}$R$^{11}$, —C(O)NR$^{10}$R$^{11}$, —CH$_2$NR$^{10}$R$^{11}$, —SO$_2$R$^{12}$, wherein said $C_1$-$C_6$ aliphatic, $C_3$-$C_7$ cycloalkyl, or $C_1$-$C_6$ alkylene-O—$C_1$-$C_6$ alkyl is substituted with 0-5 independently selected $R^B$;
or $R^{1a}$ and one $R^{1b}$ on adjacent atoms of Ring B, taken together with the adjacent Ring B atoms to which they are attached, form a cyclic group fused to Ring B selected from phenyl, a 5-6 membered heteroaryl (having 1-3 heteroatoms independently selected from nitrogen, oxygen and sulfur), a 4-7 membered saturated or partially unsaturated carbocyclyl, or a 4-7 membered saturated or partially unsaturated heterocyclyl (having 1-3 heteroatoms independently selected from nitrogen, oxygen and sulfur), wherein said cyclic group fused to Ring B is substituted with 0-3 independently selected $R^B$;

$R^2$ is selected from C(R$^C$)$_2$C(O)N(R)R$^{2A}$, C(R$^C$)$_2$C(R$^C$)$_2$C(O)N(R)R$^{2A}$, C(R$^C$)$_2$C(R$^C$)$_2$N(R)C(O) N(R)R$^{2A}$, and C(R$^C$)$_2$C(R$^C$)$_2$N(R)C(O)R$^{2A}$;

$R^{2A}$ is phenyl, pyridyl, cubanyl, a saturated or partially unsaturated 4-8 membered monocyclic ring, a saturated or partially unsaturated bridged, fused, or spirocyclic 5-, 6-, 7-, 8-, 9-, 10-, 11-, or 12-membered ring, wherein said saturated or partially unsaturated monocyclic ring, or saturated or partially unsaturated bridged, fused, or spirocyclic ring contains 0, 1, 2, 3, or 4 heteroatoms independently selected from nitrogen, oxygen, and sulfur; and wherein said phenyl, pyridyl, cubanyl, saturated or partially unsaturated monocyclic ring, or saturated or partially unsaturated bridged, fused, or spirocyclic ring are each optionally substituted with 1, 2, or 3 substituents independently selected from halogen, $C_1$-$C_4$ aliphatic, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$-cycloalkoxy and —SF$_5$, and wherein two substituents on adjacent atoms of the phenyl or pyridyl, together with said adjacent atoms, optionally form a 4-7 membered carbocyclyl fused to the phenyl or pyridyl, and wherein two substituents on adjacent atoms of the phenyl or pyridyl together with said adjacent atoms optionally form a 4-7 membered heterocyclyl (having 1-4 heteroatoms independently selected from nitrogen, oxygen, and sulfur) fused to the phenyl or pyridyl, wherein said fused 4-7 membered carbocyclyl or fused 4-7 membered heterocyclyl is substituted with 0-5 independently selected halogen, and wherein two substituents on the same atom of said saturated or partially unsaturated monocyclic ring, or saturated or partially unsaturated bridged, fused, or spirocyclic ring optionally form a cyclic group selected from:
  an optionally substituted 3-7 membered saturated or partially unsaturated carbocyclyl, and
  an optionally substituted 4-7 membered saturated or partially unsaturated heterocyclyl having 1-3 heteroatoms independently selected from nitrogen, oxygen, and sulfur, or $R^{2A}$ is 2-benzimidazolyl, 2-naphthyl, or 3-quinolinyl, each of which is optionally substituted with 1, 2 or 3 substituents independently selected from halogen, $C_{1-4}$ alkyl, and —OH;

$R^3$ is hydrogen, $C_1$-$C_4$ aliphatic, $C_3$-$C_5$ cycloalkyl, $C_1$-$C_4$ alkoxy, —NHR$^{3A}$, —N(R$^{3A}$)$_2$, or $C_1$-$C_4$ alkylthio, each of which, besides hydrogen, is optionally substituted with —OH, 1-5 independently selected halogen, OR, —C(O)NR$^{10}$R$^{11}$, or N(R)C(O)R;

each $R^{3A}$ is independently selected from $C_1$-$C_4$ alkyl;

$R^4$ is phenyl or a first 5-6 membered heteroaryl (having 1-4 heteroatoms independently selected from nitrogen, oxygen, and sulfur) wherein said phenyl or first 5-6 membered heteroaryl is substituted with 0-5 R$^B$; and optionally two adjacent atoms of said phenyl or first 5-6 membered heteroaryl have two substituents that together with said adjacent atoms form a cyclic group fused to the phenyl or first 5-6 membered heteroaryl selected from a 4-7 membered carbocyclyl, a 4-7 membered heterocyclyl (having 1-4 heteroatoms independently selected from nitrogen, oxygen, and sulfur), or a second 5-6 membered heteroaryl (having 1-4 heteroatoms independently selected from nitrogen, oxygen, and sulfur); wherein said fused cyclic group is substituted with 0-3 independently selected R$^B$; or $R^4$ is a $C_1$-$C_4$ aliphatic, $C_1$-$C_4$ alkoxy, or $C_3$-$C_6$ cycloalkyl, each of which is substituted with 0-3 groups independently selected from halogen, —CN, —OH, $C_1$-$C_4$ alkyl, $C_1$-$C_4$ alkoxy, optionally substituted 5-6 membered heterocyclyl, and optionally substituted 5-6 membered heterocyclyloxy;

$R^{10}$ is H, $C_1$-$C_6$ aliphatic, halo$C_1$-$C_6$ alkyl, $C_3$-$C_6$ cycloalkyl, halo$C_3$-$C_6$ cycloalkyl, —C(O)$C_1$-$C_6$ alkyl, or a 5-6 membered heteroaryl (having 1-4 heteroatoms independently selected from nitrogen, oxygen, and sulfur); each $R^{10}$ except H being optionally substituted with 1 or 2 independently selected R$^B$;

$R^{11}$ is H, $C_1$-$C_6$ aliphatic, or $C_3$-$C_6$ cycloalkyl, or R$^{10}$ and R$^{11}$ are taken together with the nitrogen atom to which they are attached to form a 5-6 membered ring optionally substituted with 1, 2, or 3 substituents independently selected from halogen, —OH, —CN, $C_1$-$C_4$ alkoxy, and halo$C_1$-$C_4$ alkoxy;

$R^{12}$ is $C_1$-$C_6$ aliphatic, $C_3$-$C_6$ cycloalkyl, or a 5-6 membered heteroaryl (having 1-4 heteroatoms independently selected from nitrogen, oxygen, and sulfur); each $R^{12}$ optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy;

$R^B$ is independently selected at each occurrence from the group consisting of optionally substituted phenyl, optionally substituted 5-6 membered heteroaryl (having 1-4 heteroatoms independently selected from nitrogen, oxygen, and sulfur), optionally substituted 4-7 membered saturated or partially unsaturated heterocyclyl (having 1-2 heteroatoms independently selected from nitrogen, oxygen, and sulfur), halogen, optionally substituted $C_1$-$C_6$ aliphatic, halo$C_1$-$C_6$ alkyl, $C_3$-$C_6$ cycloalkyl, halo$C_3$-$C_6$ cycloalkyl, $C_1$-$C_6$ alkoxy, halo$C_1$-$C_6$ alkoxy, $C_3$-$C_6$ cycloalkoxy, halo$C_3$-$C_6$ cycloalkoxy, $C_1$-$C_6$ alkylene-O—$C_1$-$C_6$ alkyl, —CN, —NO$_2$, oxo, —OR, —SR, NR$_2$, S(O)$_2$R, S(O)$_2$NR$_2$, S(O)R, S(O)NR$_2$, C(O)R, C(O)OR, —C(O)NR$_2$, C(O)N(R)OR, OC(O)R, OC(O)NR$_2$, —N(R)C(O)OR, —N(R)C(O)R, N(R)C(O)NR$_2$, N(R)C(NR)NR$_2$, N(R)S(O)$_2$NR$_2$, and —N(R)S(O)$_2$R;

$R^C$ is independently selected at each occurrence from hydrogen, —CH$_3$, or —CH$_2$CH$_3$, or two R$^C$ taken together with the carbon to which they are attached form a cyclopropyl ring;

each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same atom are taken together with the same atom to form a cyclic group selected from an optionally substituted 4-7 membered saturated ring, a 4-7 membered partially unsaturated ring, or a 5-6 membered heteroaryl ring (having 1-4 heteroatoms independently selected from nitrogen, oxygen, and sulfur); wherein said cyclic group has 0-3 heteroatoms independently selected from nitrogen, oxygen, and sulfur).

In some embodiments, Ring A is a 4-7 membered saturated or partially unsaturated bivalent monocyclic carbocyclylene or 4-7 membered saturated or partially unsaturated bivalent heterocyclylene ring (having 1-4 heteroatoms independently selected from nitrogen, oxygen, and sulfur, and 0 or 1 nitrogen atoms in addition to the 1-4 heteroatoms). In some embodiments, Ring A is a 4-7 membered saturated or partially unsaturated bivalent monocyclic carbocyclylene, wherein Ring A is substituted with 0-4 independently selected R$^B$ substituents. In some embodiments, Ring A is a 4-7 membered saturated or partially unsaturated bivalent monocyclic heterocyclylene (having 1-4 heteroatoms independently selected from nitrogen, oxygen, and sulfur, and 0 or 1 nitrogen atoms in addition to the 1-4 heteroatoms), wherein Ring A is substituted with 0-4 independently selected R$^B$ substituents.

In some embodiments, Ring A is a 4-12 membered saturated or partially unsaturated bivalent bicyclic ring system that is fused, bridged, or spirocyclic selected from carbocyclylene or heterocyclylene (having 1-4 heteroatoms independently selected from nitrogen, oxygen, and sulfur). In some embodiments, Ring A is a 4-12 membered saturated or partially unsaturated bivalent bicyclic ring system that is fused, bridged, or spirocyclic and is a carbocyclylene, wherein Ring A is substituted with 0-4 independently selected R$^B$ substituents. In some embodiments, Ring A is a 4-12 membered saturated or partially unsaturated bivalent bicyclic ring system that is fused, bridged, or spirocyclic and is a heterocyclylene (having 1-4 heteroatoms independently selected from nitrogen, oxygen, and sulfur), wherein Ring A is substituted with 0-4 independently selected R$^B$ substituents.

In some embodiments, Ring A is a 4-12 membered saturated or partially unsaturated bivalent bicyclic ring system comprising 2 fused rings. In some embodiments, Ring A is a 4-12 membered saturated or partially unsaturated bivalent bicyclic ring system comprising a spirocyclic ring system. In some embodiments, Ring A is a 4-12 membered saturated or partially unsaturated bivalent bicyclic ring system comprising a bridged ring system.

In some embodiments, Ring A is

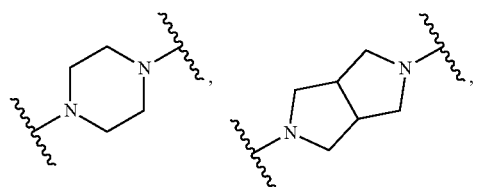

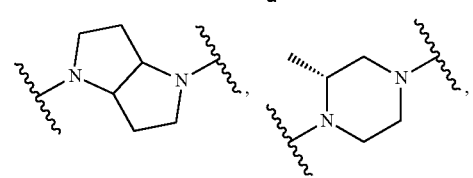

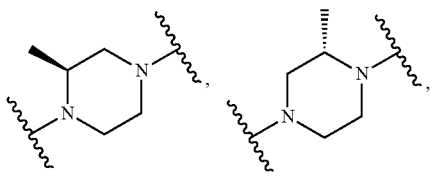

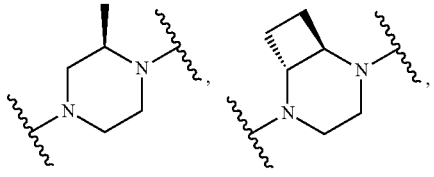

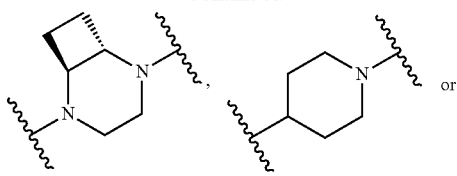

In some embodiments, Ring A is

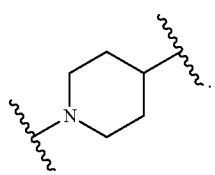

In some embodiments, Ring A is

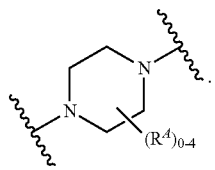

In some embodiments, Ring A is

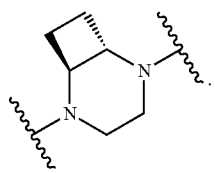 [SMILES: *N1CCN(*)[C@H]2CC[C@@H]21]

In some embodiments, Ring A is as selected from one of the substituents of Table 1 or Table 1a.

As described generally above, L is a linker selected from —C(O)—, —S(O)—, —S(O)$_2$—, and

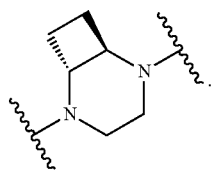 [SMILES: *N1CCN(*)[C@@H]2CC[C@H]21]

In some embodiments, linker L is —C(O)—.
In some embodiments, linker L is —S(O)—.
In some embodiments, linker L is —S(O)$_2$—.

In some embodiments, linker L is

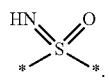

In some embodiments, linker L is as selected from one of the substituents of Table 1 or Table 1a.

As described generally above, $R^{1a}$ is selected from:
a) a 5-6 membered heteroaryl (having 1-4 heteroatoms independently selected from nitrogen, oxygen, and sulfur) optionally substituted with 1-3 groups independently selected from halogen, $C_1$-$C_6$ aliphatic, $C_3$-$C_6$ cycloalkyl, halo$C_1$-$C_6$ alkyl, $C_1$-$C_6$ alkoxy, and $C_3$-$C_6$ cycloalkoxy, wherein said 5-6 membered heteroaryl is further substituted with 0-3 independently selected $R^B$;
a 4-7 membered saturated or partially unsaturated heterocyclyl (having 1-2 heteroatoms independently selected from nitrogen, oxygen, and sulfur), optionally substituted with 1 or 2 groups independently selected from $C_1$-$C_6$ aliphatic, $C_3$-$C_6$ cycloalkyl, $C_1$-$C_6$ alkoxy, $C_3$-$C_6$ cycloalkoxy, and —OR, wherein said 4-7 membered saturated or partially unsaturated heterocyclyl is further substituted with 0-3 independently selected $R^B$;
a 4-12 membered saturated or partially unsaturated bicyclic ring system that is fused, bridged, or spirocyclic selected from carbocyclyl or heterocyclyl (having 1-4 heteroatoms independently selected from nitrogen, oxygen, and sulfur), wherein said carbocyclyl or heterocyclyl is substituted with 0-3 independently selected $R^B$; and H, halogen, $C_1$-$C_6$ aliphatic, $C_3$-$C_7$ cycloalkyl, $C_1$-$C_6$ alkylene-O—$C_1$-$C_6$ alkyl, CN, —OR, —OR$^{10}$, —NR$^{10}$R$^{11}$, —C(O)NR$^{10}$R$^{11}$, —CH$_2$NR$^{10}$R$^{11}$, —SO$_2$R$^{12}$, wherein said $C_1$-$C_6$ aliphatic, $C_3$-$C_7$ cycloalkyl, or $C_1$-$C_6$ alkylene-O—$C_1$-$C_6$ alkyl is substituted with 0-5 independently selected $R^B$;
or $R^{1a}$ and one $R^{1b}$ on adjacent atoms of Ring B, taken together with the adjacent Ring B atoms to which they are attached, form a cyclic group fused to Ring B selected from phenyl, a 5-6 membered heteroaryl (having 1-3 heteroatoms independently selected from nitrogen, oxygen and sulfur), a 4-7 membered saturated or partially unsaturated carbocyclyl, or a 4-7 membered saturated or partially unsaturated heterocyclyl (having 1-3 heteroatoms independently selected from nitrogen, oxygen and sulfur), wherein said cyclic group fused to Ring B is substituted with 0-3 independently selected $R^B$.

In some embodiments, $R^{1a}$ is a 5-6 membered heteroaryl (having 1-4 heteroatoms independently selected from nitrogen, oxygen, and sulfur) optionally substituted with 1 or 2 groups independently selected from $C_1$-$C_6$ alkyl, $C_1$-$C_6$ alkoxy, $C_3$-$C_6$ cycloalkyl, and $C_3$-$C_6$ cycloalkoxy, wherein said 5-6 membered heteroaryl is further substituted with 0-3 independently selected $R^B$. In some embodiments, $R^{1a}$ is a 4-6 membered saturated or partially unsaturated heterocyclyl (having 1-2 heteroatoms independently selected from nitrogen, oxygen, and sulfur), said heterocyclyl substituted with 0-2 $R^B$ groups independently selected from halogen, oxo, —NR$_2$, optionally substituted $C_{1-4}$ aliphatic, —OR, azetidinyl optionally substituted with 1 or 2 independently selected halogen, and pyrrolidinyl optionally substituted with 1 or 2 independently selected halogen. In some embodiments, $R^{1a}$ is a 6-8 membered saturated or partially unsaturated bridged bicyclic heterocyclyl (having 1-4 heteroatoms independently selected from nitrogen, oxygen, and sulfur), said heterocyclyl substituted with 0-2 $R^B$ groups independently selected from halogen, oxo, —NR$_2$, optionally substituted $C_{1-4}$ aliphatic, —OR, azetidinyl optionally substituted with 1 or 2 independently selected halogen, and pyrrolidinyl optionally substituted with 1 or 2 independently selected halogen. In some embodiments, $R^{1a}$ is a 3-7 membered optionally substituted carbocyclyl. In some embodiments, $R^{1a}$ is an optionally substituted $C_2$-$C_4$ alkenyl. In some embodiments, $R^{1a}$ is cyclopropyl substituted $C_2$-$C_4$ alkenyl. In some embodiments, $R^{1a}$ is methyl substituted $C_2$-$C_4$ alkenyl.

In some embodiments, $R^{1a}$ is a 6-membered partially unsaturated heterocyclyl (having 1 oxygen atom). In some embodiments, $R^{1a}$ is a 4-membered saturated heterocyclyl (having 1 oxygen atom). In some embodiments, $R^{1a}$ is a 6-membered heteroaryl (having 1 nitrogen atom), said heteroaryl may be optionally substituted with 1 or 2 groups independently selected from $C_1$-$C_6$ alkyl, $C_1$-$C_6$ alkoxy, $C_3$-$C_6$ cycloalkyl, and $C_3$-$C_6$ cycloalkoxy, wherein said heteroaryl is further substituted with 0-1 $R^B$, wherein $R^B$ is an optionally substituted $C_{1-6}$ aliphatic group. In some embodiments, $R^{1a}$ is a 6-membered heteroaryl (having 2 nitrogen atoms), said heteroaryl may be optionally substituted with 1 or 2 groups independently selected from $C_1$-$C_6$ alkyl, $C_1$-$C_6$ alkoxy, $C_3$-$C_6$ cycloalkyl, and $C_3$-$C_6$ cycloalkoxy, wherein said heteroaryl is further substituted with 0-1 $R^B$, wherein $R^B$ is an optionally substituted $C_{1-6}$ aliphatic group. In some embodiments, $R^{1a}$ is —NR$^{10}$R$^{11}$ wherein $R^{10}$ is a 5-6 membered heteroaryl (having 1 or 2 nitrogen atoms) optionally substituted with 1 or 2 groups independently selected from halogen, CH$_3$, OCH$_3$, $C_3$-$C_6$ cycloalkyl, and $C_3$-$C_6$ cycloalkoxy and wherein $R^{11}$ is H or CH$_3$. In some embodiments, $R^{1a}$ is —CH$_2$NR$^{10}$R$^{11}$ wherein $R^{10}$ is a 5-6 membered heteroaryl (having 1 or 2 nitrogen atoms) optionally substituted with 1 or 2 groups independently selected from halogen, CH$_3$, OCH$_3$, $C_3$-$C_6$ cycloalkyl, and $C_3$-$C_6$ cycloalkoxy and wherein $R^{11}$ is H or CH$_3$. In some embodiments, $R^{1a}$ is $C_2$-$C_4$alkene wherein said alkene is optionally substituted with OCH$_3$ or 1, 2, or 3 fluorine. In some embodiments, $R^{1a}$ is $C_2$-$C_4$alkyne wherein said alkyne is optionally substituted with OCH$_3$ or 1, 2, or 3 fluorine. In some embodiments, $R^{1a}$ is —SO$_2$R$^{12}$ wherein $R^{12}$ is selected from CH$_3$ or a 5-6 membered heteroaryl having 1-2 nitrogen heteroatoms optionally substituted with 1 or 2 groups independently selected from halogen and CH$_3$. In some embodiments, $R^{1a}$ is cyclopropyl optionally substituted with 1-2 fluorine. In some embodiments, $R^{1a}$ is $C_1$-$C_6$ alkyl optionally substituted with OH or 1-2 fluorine. In some embodiments, $R^{1a}$ is —C(O)NR$^{10}$R$^{11}$ wherein $R^{10}$ is H or CH$_3$ and wherein $R^{11}$ is H or CH$_3$.

In some embodiments, $R^{1a}$ is a 5-membered heteroaryl (having 1-3 heteroatoms independently selected from nitrogen, oxygen, and sulfur) optionally substituted with 1 or 2 groups independently selected from $C_1$-$C_6$ alkyl, $C_1$-$C_6$ alkoxy, $C_3$-$C_6$ cycloalkyl, and $C_3$-$C_6$ cycloalkoxy, wherein said 5-membered heteroaryl is optionally further substituted with 0-3 independently selected $R^B$. In some embodiments, $R^{1a}$ is a 5-membered heteroaryl (having 1-3 heteroatoms independently selected from nitrogen, oxygen, and sulfur) optionally substituted with 1 or 2 groups independently selected from $C_1$-$C_6$ alkyl, $C_1$-$C_6$ alkoxy, $C_3$-$C_6$ cycloalkyl, and $C_3$-$C_6$ cycloalkoxy. In some embodiments, $R^{1a}$ is a 5-membered heteroaryl (having 2 nitrogen atoms) optionally substituted with 1 or 2 groups independently selected from $C_1$-$C_6$ alkyl, $C_1$-$C_6$ alkoxy, $C_3$—$C_6$ cycloalkyl, and $C_3$-$C_6$ cycloalkoxy, wherein said 5-membered heteroaryl is optionally further substituted with 0-1 $R^B$, wherein $R^B$ is hydroxyl substituted $C_1$-$C_4$ alkyl.

In some embodiments, $R^{1a}$ is a 5-6 membered heteroaryl (having 1-4 heteroatoms independently selected from nitrogen, oxygen, and sulfur) optionally substituted with one group of $C_1$-$C_6$ alkoxy or $C_3$-$C_6$ cycloalkyl, wherein said 5-6 membered heteroaryl is optionally further substituted with 0-3 independently selected $R^B$.

In some embodiments, $R^{1a}$ is pyridyl substituted with $C_1$-$C_4$ alkoxy and further substituted with 0-2 $R^B$.

In some embodiments, $R^{1a}$ is 5-membered heteroaryl (having 1 heteroatom independently selected from nitrogen, oxygen, and sulfur, and 0 or 1 additional ring nitrogen atoms), wherein said 5-membered heteroaryl is optionally substituted with $C_1$-$C_6$ alkyl, or $C_3$-$C_5$ cycloalkyl and further substituted with 0-2 $R^B$.

In some embodiments, $R^{1a}$ is selected from groups a-d:
a) a 5-6 membered heteroaryl (having 1-4 heteroatoms independently selected from nitrogen, oxygen, and sulfur) optionally substituted with 1 or 2 groups independently selected from $C_1$-$C_6$ alkyl, $C_3$-$C_6$ cycloalkyl, $C_1$-$C_6$ alkoxy, and $C_3$-$C_6$ cycloalkoxy, wherein said 5-6 membered heteroaryl is further substituted with 0-3 independently selected $R^B$;
a 4-7 membered saturated or partially unsaturated heterocyclyl (having 1-2 heteroatoms independently selected from nitrogen, oxygen, and sulfur), optionally substituted with 1 or 2 groups independently selected from $C_1$-$C_6$ alkyl, $C_3$-$C_6$ cycloalkyl, $C_1$-$C_6$ alkoxy, $C_3$-$C_6$ cycloalkoxy, and —OR, wherein said 4-7 membered saturated or partially unsaturated heterocyclyl is further substituted with 0-3 independently selected $R^B$;
a 4-12 membered saturated or partially unsaturated bivalent bicyclic ring system that is fused, bridged, or spirocyclic selected from carbocyclylene or heterocyclylene (having 1-4 heteroatoms independently selected from nitrogen, oxygen, and sulfur), said carbocyclylene or heterocyclylene is substituted with 0-3 independently selected $R^B$; and H, halogen, $C_1$-$C_6$ alkyl, $C_2$-$C_4$ alkenyl, $C_2$-$C_4$ alkynyl, $C_3$-$C_7$ cycloalkyl, $C_1$-$C_6$ alkyl-O—$C_1$-$C_6$ alkyl, CN, —OR, —$NR^{10}R^{11}$, —C(O)$NR^{10}R^{11}$, —$CH_2NR^{10}R^{11}$, —$SO_2R^{12}$, wherein $C_1$-$C_6$ alkyl, $C_2$-$C_4$ alkenyl, $C_2$-$C_4$ alkynyl, $C_3$-$C_7$ cycloalkyl, or $C_1$-$C_6$ alkylene-O—$C_1$-$C_6$ alkyl may be substituted with 0-5 independently selected $R^B$.

In some embodiments, $R^{1a}$ is a 4-7 membered saturated or partially unsaturated heterocyclyl (having 1-2 heteroatoms independently selected from nitrogen, oxygen, and sulfur), optionally substituted with 1 or 2 groups independently selected from $C_1$-$C_6$ alkyl, $C_3$-$C_6$ cycloalkyl, $C_1$-$C_6$ alkoxy, and $C_3$-$C_6$ cycloalkoxy, and —OR, wherein said 4-7 membered saturated or partially unsaturated heterocyclyl is further substituted with 0-3 independently selected $R^B$.

In some embodiments, $R^{1a}$ is a 5-6 membered heteroaryl (having 1-4 heteroatoms independently selected from nitrogen, oxygen, and sulfur) optionally substituted with 1 or 2 groups independently selected from $C_1$-$C_6$ alkyl, $C_3$-$C_6$ cycloalkyl, $C_1$-$C_6$ alkoxy, and $C_3$-$C_6$ cycloalkoxy, wherein said 5-6 membered heteroaryl is further substituted with 0-3 independently selected $R^B$.

In some embodiments, $R^{1a}$ is selected from the group consisting of:

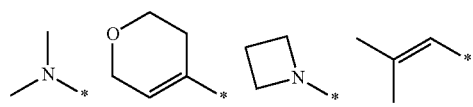

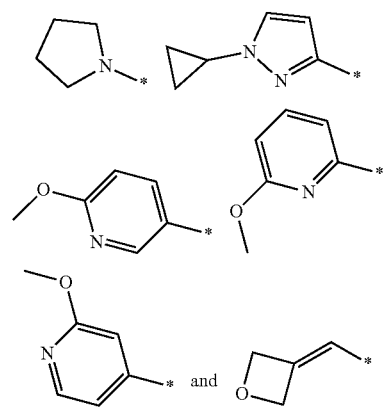

wherein * is the point of attachment to Ring B.

In some embodiments, $R^{1a}$ is

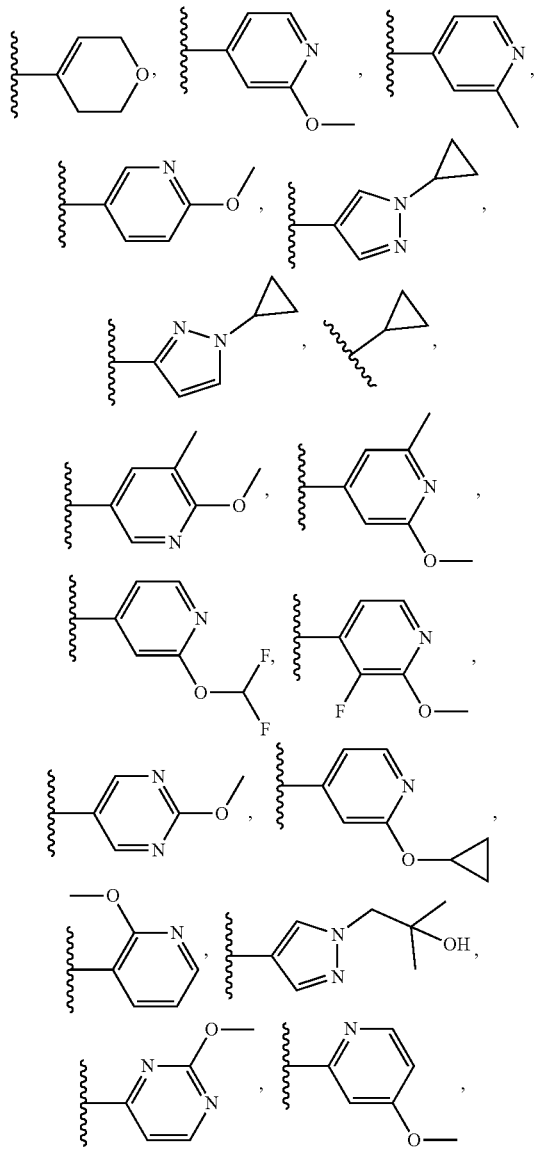

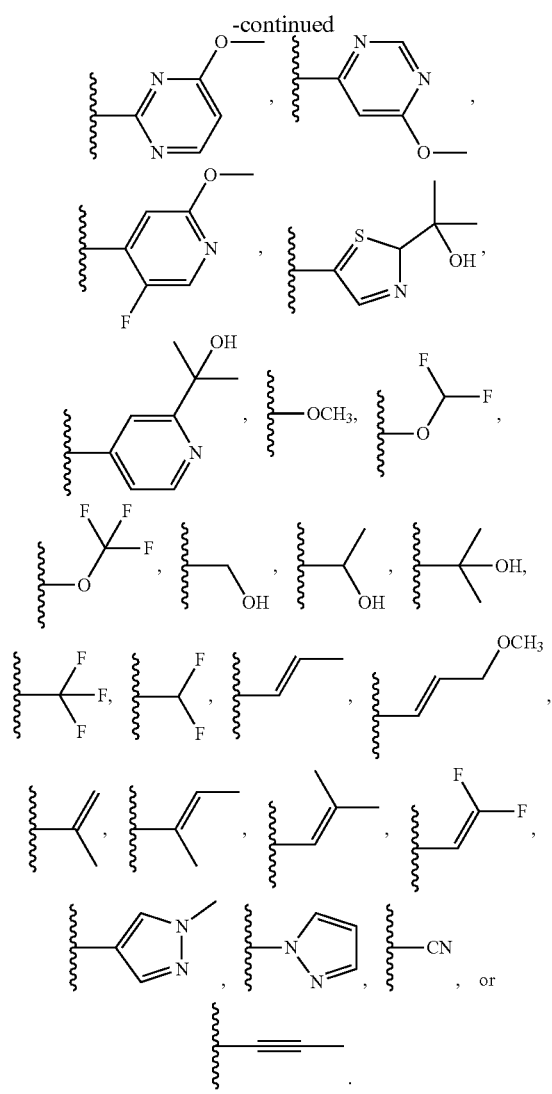
In some embodiments, R[1a] is
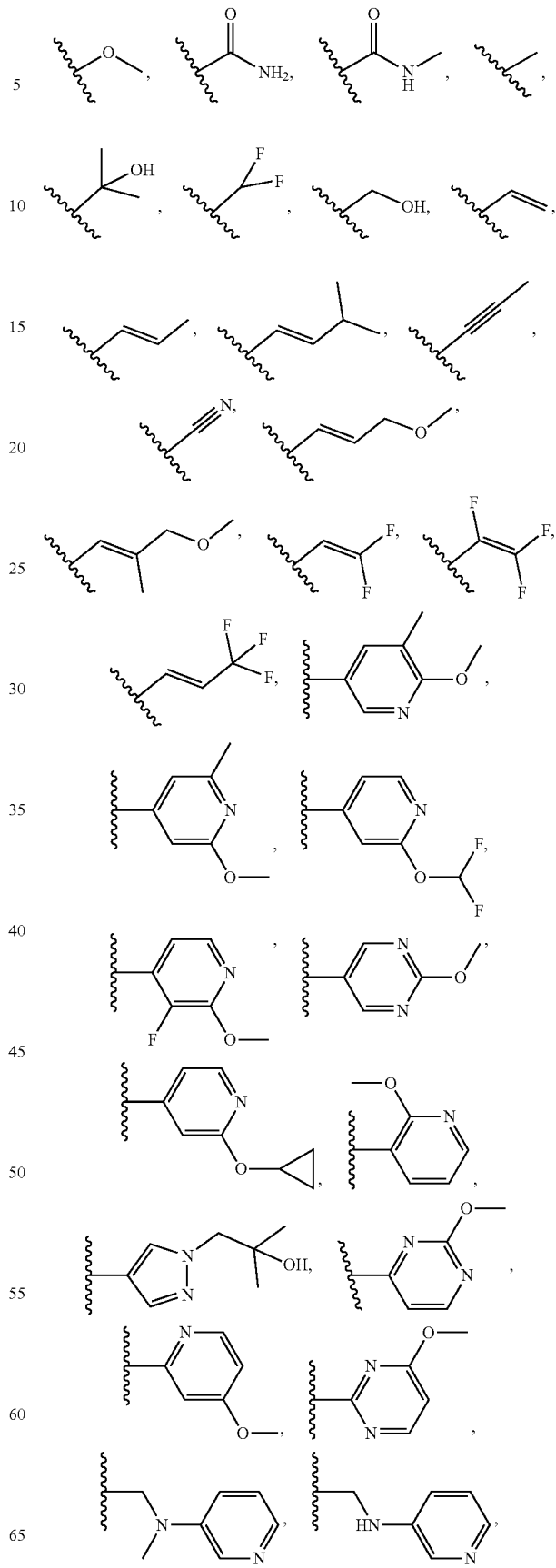

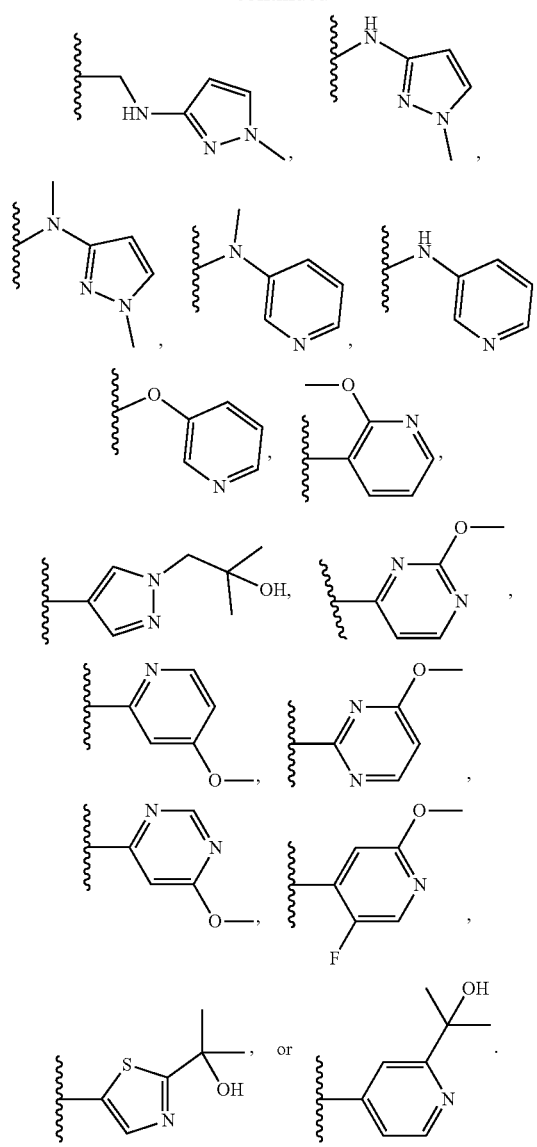
In some embodiments, $R^{1a}$ is
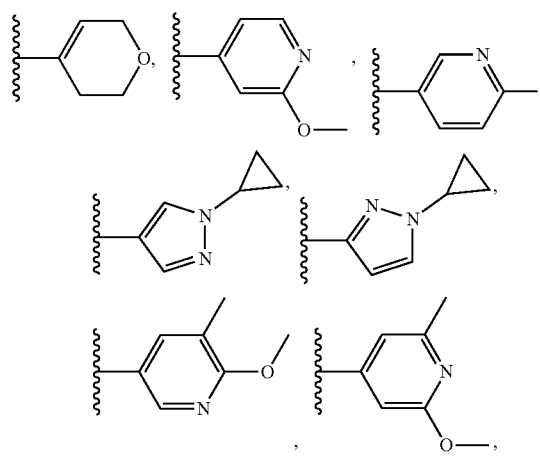
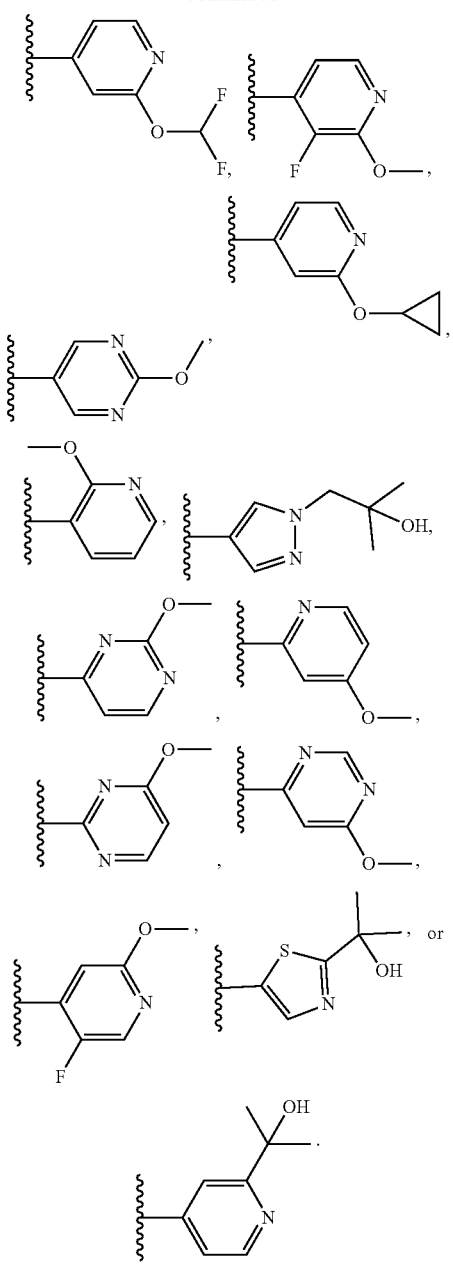
In some embodiments, $R^{1a}$ is
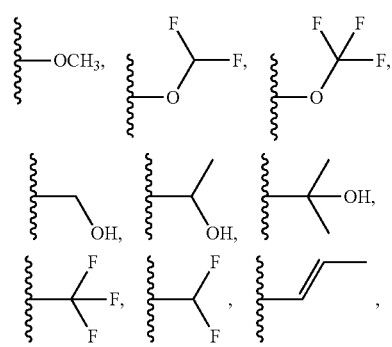

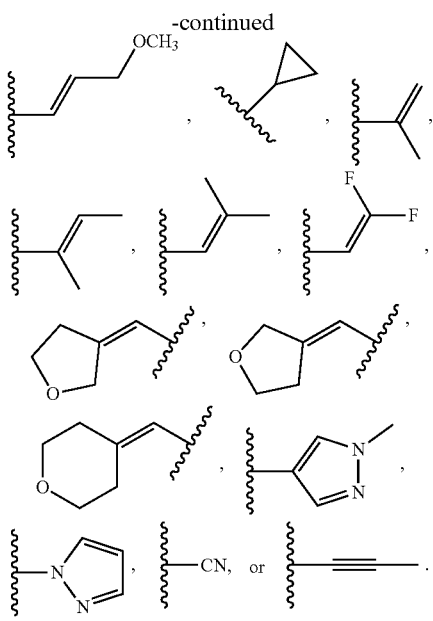

In some embodiments, $R^{1a}$ is as selected from one of the substituents of Table 1 or Table 1a.

In some embodiments, $R^{1a}$ is

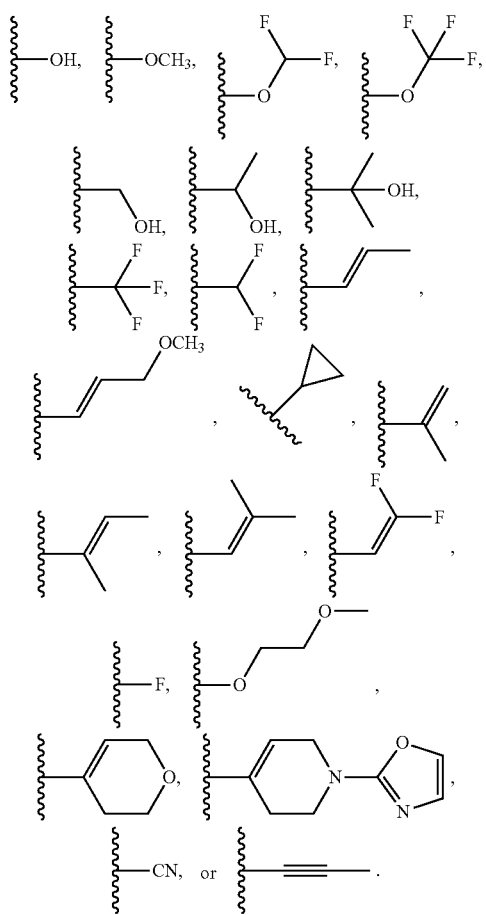

As described generally above, each $R^{1b}$ is independently selected from H, halogen, CN, OH, $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy, wherein said $C_1$-$C_6$ aliphatic, $C_1$-$C_6$ alkoxy, $C_3$-$C_6$ cycloalkyl, $C_1$-$C_6$ alkylene-O—$C_1$-$C_6$ alkyl, halo$C_1$-$C_6$ alkyl, halo$C_1$-$C_6$ alkoxy, and $C_3$-$C_6$ cycloalkoxy are each independently and optionally substituted with 1-5 halogen, OH, CN, $C_1$-$C_6$ alkyl, or $C_3$-$C_6$ cycloalkyl groups.

In some embodiments, $R^{1a}$ and one $R^{1b}$ on adjacent atoms of Ring B, taken together with the adjacent Ring B atoms to which they are attached, form a cyclic group fused to Ring B selected from phenyl, a 5-6 membered heteroaryl (having 1-3 heteroatoms independently selected from nitrogen, oxygen and sulfur), a 4-7 membered saturated or partially unsaturated carbocyclyl, or a 4-7 membered saturated or partially unsaturated heterocyclyl (having 1-3 heteroatoms independently selected from nitrogen, oxygen and sulfur), wherein said cyclic group fused to Ring B is substituted with 0-3 independently selected $R^B$.

In some embodiments, $R^{1a}$ and one $R^{1b}$ on adjacent atoms of Ring B, taken together with the adjacent Ring B atoms to which they are attached, form a cyclic group fused to Ring B of phenyl, wherein said cyclic group fused to Ring B is substituted with 0-3 independently selected $R^B$. In some embodiments, $R^{1a}$ and one $R^{1b}$ on adjacent atoms of Ring B, taken together with the adjacent Ring B atoms to which they are attached, form a cyclic group fused to Ring B of a 5-6 membered heteroaryl (having 1-3 heteroatoms independently selected from nitrogen, oxygen and sulfur), wherein said cyclic group fused to Ring B is substituted with 0-3 independently selected $R^B$. In some embodiments, $R^{1a}$ and one $R^{1b}$ on adjacent atoms of Ring B, taken together with the adjacent Ring B atoms to which they are attached, form a cyclic group fused to Ring B of a 4-7 membered saturated or partially unsaturated carbocyclyl, wherein said cyclic group fused to Ring B is substituted with 0-3 independently selected $R^B$. In some embodiments, $R^{1a}$ and one $R^{1b}$ on adjacent atoms of Ring B, taken together with the adjacent Ring B atoms to which they are attached, form a cyclic group fused to Ring B of a 4-7 membered saturated or partially unsaturated heterocyclyl (having 1-3 heteroatoms independently selected from nitrogen, oxygen and sulfur), wherein said cyclic group fused to Ring B is substituted with 0-3 independently selected $R^B$.

As described generally above, $R^2$ is $C(R^C)_2C(O)N(R)R^{2A}$. In some embodiments, $R^2$ is $C(R^C)_2C(R^C)_2C(O)N(R)R^{2A}$. In some embodiments, $R^2$ is $C(R^C)_2C(R^C)_2N(R)C(O)N(R)R^{2A}$. In some embodiments, $R^2$ is $C(R^C)_2C(R^C)_2N(R)C(O)R^{2A}$. In some embodiments, $R^2$ is $CH_2C(O)N(H)R^{2A}$. In some embodiments, $R^2$ is $CH_2CH_2C(O)N(H)R^{2A}$. In some embodiments, $R^2$ is $CH_2CH_2N(R)C(O)N(R)R^{2A}$. In some embodiments, $R^2$ is $CH_2CH_2N(H)C(O)R^{2A}$. In some embodiments, $R^2$ is $C(R^C)_2C(O)N(H)R^{2A}$, wherein $R^{2A}$ is phenyl or bicyclo[1.1.1]pentyl optionally substituted with 1, 2, or 3 substituents independently selected from halogen, $C_1$-$C_4$ alkyl, or halo$C_1$-$C_4$ alkyl. In some embodiments, $R^2$ is $C(R^C)_2C(O)N(H)R^{2A}$, wherein $R^{2A}$ is phenyl optionally substituted with 1, 2, or 3 substituents independently selected from halogen, $C_1$-$C_4$ alkyl, or halo$C_1$-$C_4$ alkyl. In some embodiments, $R^2$ is $C(R^C)_2C(O)N(H)R^{2A}$, wherein $R^{2A}$ is bicyclo[1.1.1]pentyl optionally substituted with 1, 2, or 3 substituents independently selected from halogen, $C_1$-$C_4$ alkyl, or halo$C_1$-$C_4$ alkyl.

In some embodiments, $R^2$ is
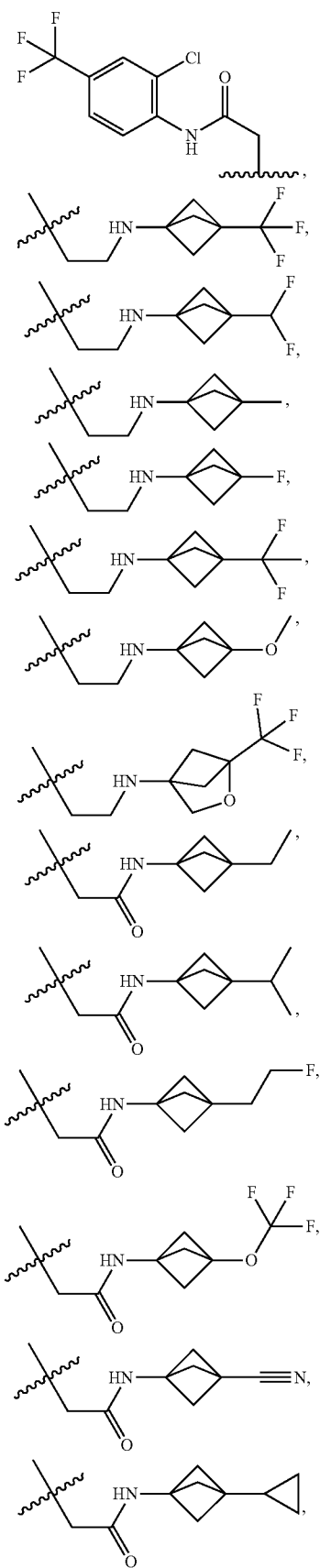
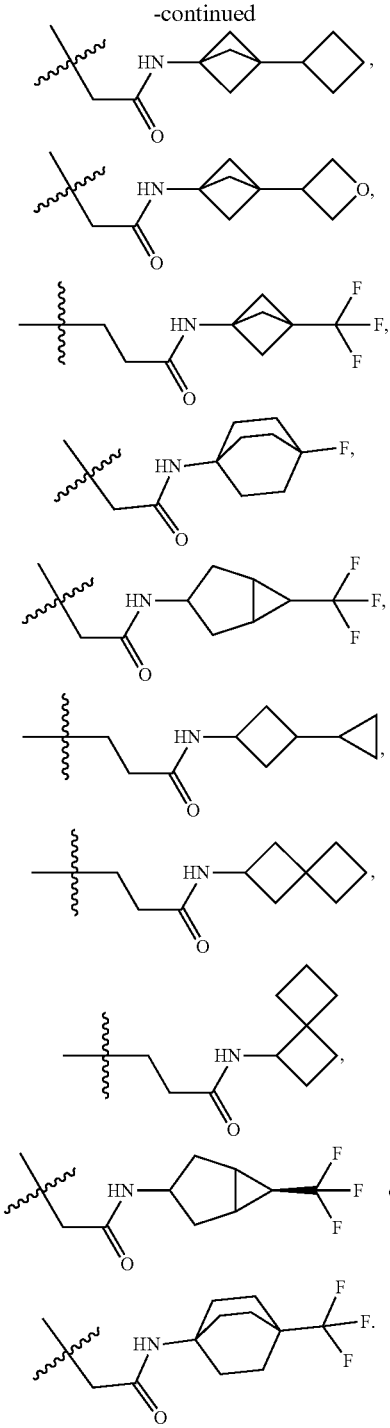
In some embodiments $R^2$ is
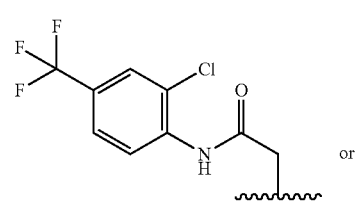

-continued

In some embodiments $R^2$ is

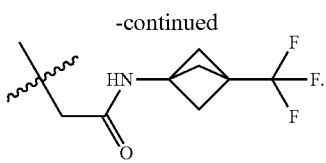

In some embodiments $R^2$ is

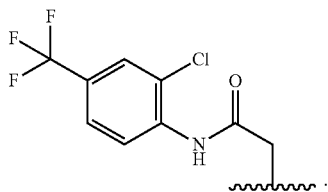 [SMILES: *CC(=O)Nc1ccc(C(F)(F)F)cc1Cl]

In some embodiments $R^2$ is

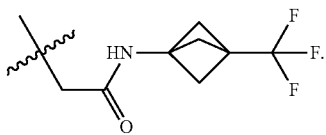 [SMILES: *CC(=O)NC12CC(C(F)(F)F)(C1)C2]

In some embodiments, $R^2$ is as selected from one of the substituents of Table 1 or Table 1a.

As described generally above, $R^{1A}$ is phenyl, pyridyl, cubanyl, a saturated or partially unsaturated 4-8 membered monocyclic ring, a saturated or partially unsaturated bridged, fused, or spirocyclic 5-, 6-, 7-, 8-, 9-, 10-, 11-, or 12-membered ring, wherein said saturated or partially unsaturated monocyclic ring, or saturated or partially unsaturated bridged, fused, or spirocyclic ring contains 0, 1, 2, 3, or 4 heteroatoms independently selected from nitrogen, oxygen, and sulfur; and wherein said phenyl, pyridyl, cubanyl, saturated or partially unsaturated monocyclic ring, or saturated or partially unsaturated bridged, fused, or spirocyclic ring are each optionally substituted with 1, 2 or 3 substituents independently selected from halogen, $C_1$-$C_4$ aliphatic, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$-cycloalkoxy, halo$C_3$-$C_6$ cycloalkoxy and —$SF_5$, and wherein two substituents on adjacent atoms of the phenyl or pyridyl, together with said adjacent atoms, optionally form a 4-7 membered carbocyclyl fused to the phenyl or pyridyl, and wherein two substituents on adjacent atoms of the phenyl or pyridyl together with said adjacent atoms optionally form a 4-7 membered heterocyclyl (having 1-4 heteroatoms independently selected from nitrogen, oxygen, and sulfur) fused to the phenyl or pyridyl, wherein said fused 4-7 membered carbocyclyl or fused 4-7 membered heterocyclyl is substituted with 0-5 independently selected halogen, and wherein two substituents on the same atom of said saturated or partially unsaturated monocyclic ring, or saturated or partially unsaturated bridged, fused, or spirocyclic ring optionally form a cyclic group selected from:
an optionally substituted 3-7 membered saturated or partially unsaturated carbocyclyl, and
an optionally substituted 4-7 membered saturated or partially unsaturated heterocyclyl having 1-3 heteroatoms independently selected from nitrogen, oxygen, and sulfur, or $R^{2A}$ is 2-benzimidazolyl, 2-naphthyl, or 3-quinolinyl, each of which is optionally substituted with 1, 2 or 3 substituents independently selected from halogen, $C_{1-4}$ alkyl, and —OH.

In some embodiments, there are 1-6 respective instances of wherein 2 substituents on the same $1^{st}$, $2^{nd}$, $3^{rd}$, $4^{th}$, $5^{th}$, or $6^{th}$ atom of said saturated or partially unsaturated monocyclic ring, or said saturated or partially unsaturated bridged, fused, or spirocyclic ring form 1-6 of said cyclic groups. In some embodiments, there is one instance wherein 2 substituents on the same atom of said saturated or partially unsaturated monocyclic ring, or said saturated or partially unsaturated bridged, fused, or spirocyclic ring form one of said cyclic groups. In some embodiments, there 2 respective instances of wherein 2 substituents on the same $1^{st}$ and $2^{nd}$ atoms of said saturated or partially unsaturated monocyclic ring, or said saturated or partially unsaturated bridged, fused, or spirocyclic ring form both of said cyclic groups. In some embodiments, there are 3 respective instances of wherein 2 substituents on the same $1^{st}$, $2^{nd}$ and $3^{rd}$, atoms of said saturated or partially unsaturated monocyclic ring, or said saturated or partially unsaturated bridged, fused, or spirocyclic ring form the three of said cyclic groups. In some embodiments, there are 4 respective instances of wherein 2 substituents on the same $1^{st}$, $2^{nd}$, $3^{rd}$ and $4^{th}$ atoms of said saturated or partially unsaturated monocyclic ring, or said saturated or partially unsaturated bridged, fused, or spirocyclic ring form the four of said cyclic groups. In some embodiments, there are 5 respective instances of wherein 2 substituents on the same $1^{st}$, $2^{nd}$, $3^{rd}$, $4^{th}$ and $5^{th}$ atoms of said saturated or partially unsaturated monocyclic ring, or said saturated or partially unsaturated bridged, fused, or spirocyclic ring form the five of said cyclic groups. In some embodiments, there 6 respective instances of wherein 2 substituents on the same $1^{st}$, $2^{nd}$, $3^{rd}$, $4^{th}$, $5^{th}$, and $6^{th}$ atoms of said saturated or partially unsaturated monocyclic ring, or said saturated or partially unsaturated bridged, fused, or spirocyclic ring form the six of said cyclic groups.

In some embodiments, $R^{2A}$ is phenyl optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$-cycloalkyl, —OH, —CN, $C_1$-$C_4$ alkoxy, halo$C_1$-$C_4$ alkoxy, —$SF_5$, two optional substituents on adjacent atoms of the phenyl together with their intervening atoms form a 4-7 membered carbocyclyl fused to the phenyl, and two optional substituents on adjacent atoms of the phenyl together with their intervening atoms form a 4-7 membered heterocyclyl (having 1-4 heteroatoms independently selected from nitrogen, oxygen, and sulfur) fused to the phenyl.

In some embodiments, $R^{2A}$ is phenyl optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$-cycloalkyl, —OH, —CN, $C_1$-$C_4$ alkoxy, halo$C_1$-$C_4$ alkoxy, and —$SF_5$. In some embodiments, $R^{2A}$ is phenyl optionally substituted with 1, 2, or 3 substituents independently selected from halogen, $C_1$-$C_4$ alkyl, and halo$C_1$-$C_4$ alkyl. In some embodiments, $R^{2A}$ is phenyl optionally substituted with a halogen, $C_1$-$C_4$ alkyl, and halo$C_1$-$C_4$ alkyl. In some embodiments, $R^{2A}$ is phenyl optionally substituted with two substituents independently selected from halogen, $C_1$-$C_4$ alkyl, and halo$C_1$—$C_4$ alkyl. In some embodiments, $R^{2A}$ is phenyl optionally substituted with three substituents independently selected from halogen, $C_1$-$C_4$ alkyl, and halo$C_1$-$C_4$ alkyl.

In some embodiments, $R^{2A}$ is pyridyl optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$-cycloalkyl, —OH, —CN, $C_1$-$C_4$ alkoxy, halo$C_1$-$C_4$ alkoxy, and —SF$_5$, two optional substituents on adjacent atoms of the pyridyl together with their intervening atoms form a 4-7 membered carbocyclyl fused to the pyridyl, and two optional substituents on adjacent atoms of the pyridyl together with their intervening atoms form a 4-7 membered heterocyclyl (having 1-4 heteroatoms independently selected from nitrogen, oxygen, and sulfur) fused to the pyridyl.

In some embodiments, $R^{2A}$ is pyridyl optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$-cycloalkyl, —OH, —CN, $C_1$-$C_4$ alkoxy, halo$C_1$-$C_4$ alkoxy, and —SF$_5$. In some embodiments, $R^{2A}$ is pyridyl optionally substituted with 1, 2, or 3 substituents independently selected from halogen, $C_1$-$C_4$ alkyl, and halo$C_1$-$C_4$ alkyl. In some embodiments, $R^{2A}$ is pyridyl optionally substituted with a halogen, $C_1$-$C_4$ alkyl, or halo$C_1$-$C_4$ alkyl. In some embodiments, $R^{2A}$ is pyridyl optionally substituted with 2 substituents independently selected from halogen, $C_1$-$C_4$ alkyl, and halo$C_1$-$C_4$ alkyl. In some embodiments, $R^{2A}$ is pyridyl optionally substituted with 3 substituents independently selected from halogen, $C_1$-$C_4$ alkyl, and halo$C_1$-$C_4$ alkyl.

In some embodiments, $R^{2A}$ is cubanyl, a saturated or partially unsaturated 4-8 membered monocyclic ring, a saturated or partially unsaturated bridged, fused, or spirocyclic 5-, 6-, 7-, 8-, 9-, 10-, 11-, or 12-membered ring, wherein said saturated or partially unsaturated monocyclic ring, or saturated or partially unsaturated bridged, fused, or spirocyclic ring contains 0, 1, 2, 3, or 4 heteroatoms independently selected from nitrogen, oxygen, and sulfur; and wherein said cubanyl, partially unsaturated monocyclic ring, or saturated or partially unsaturated bridged, fused, or spirocyclic ring are each optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$ cycloalkoxy and —SF$_5$. In some embodiments, $R^{2A}$ is bicyclo[1.1.1]pentyl optionally substituted with 1, 2, or 3 substituents independently selected from halogen, $C_1$-$C_4$ alkyl, and halo$C_1$-$C_4$ alkyl.

In some embodiments, $R^{2A}$ is a saturated or partially unsaturated bridged ring, 5-, 6-, 7-, 8-, 9-, 10-, 11-, or 12-membered ring, which contains 0, 1, 2, 3, or 4 heteroatoms independently selected from nitrogen, oxygen, and sulfur; and wherein said bridged ring is optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$ cycloalkoxy and —SF$_5$.

In some embodiments, $R^{2A}$ is a saturated or partially unsaturated fused ring, 5-, 6-, 7-, 8-, 9-, 10-, 11-, or 12-membered ring, which contains 0, 1, 2, 3, or 4 heteroatoms independently selected from nitrogen, oxygen, and sulfur; and wherein said fused ring is optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$ cycloalkoxy and —SF$_5$.

In some embodiments, $R^{2A}$ is a saturated or partially unsaturated spirocyclic 5-, 6-, 7-, 8-, 9-, 10-, 11-, or 12-membered ring, which contains 0, 1, 2, 3, or 4 heteroatoms independently selected from nitrogen, oxygen, and sulfur; and wherein said spirocyclic ring is optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$-cycloalkoxy, halo$C_3$-$C_6$ cycloalkoxy and —SF$_5$.

In some embodiments, $R^{2A}$ is bicyclo[1.1.1]pentyl optionally substituted with 1, 2, or 3 substituents independently selected from halogen, $C_1$-$C_4$ alkyl, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$-cycloalkoxy and —SF$_5$. In some embodiments, $R^{2A}$ is bicyclo[1.1.1]pentyl optionally substituted with 1, 2, or 3 substituents independently selected from halogen, $C_1$-$C_4$ alkyl, and halo$C_1$-$C_4$ alkyl. In some embodiments, $R^{2A}$ is bicyclo[1.1.1]pentyl optionally substituted with a halogen, $C_1$-$C_4$ alkyl, or halo$C_1$-$C_4$ alkyl. In some embodiments, $R^{2A}$ is bicyclo[1.1.1]pentyl optionally substituted with 2 substituents independently selected from halogen, $C_1$-$C_4$ alkyl, and halo$C_1$-$C_4$ alkyl. In some embodiments, $R^{2A}$ is bicyclo[1.1.1]pentyl optionally substituted with 3 substituents independently selected from halogen, $C_1$-$C_4$ alkyl, and halo$C_1$-$C_4$ alkyl.

In some embodiments, $R^{2A}$ is Ring F selected from the group consisting of:

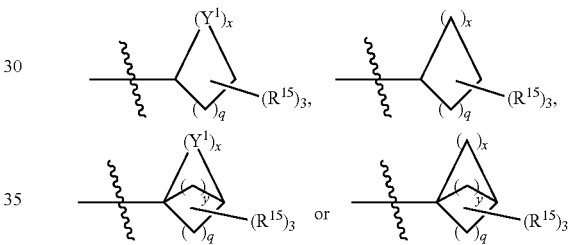

wherein x, y, and q are independently selected from 1, 2 or 3, $Y^1$ is independently selected from O, NR$^{15}$, CHR$^{15}$ or CR$^{15}$R$^{15}$, wherein R$^{15}$ is independently selected from H, halogen, $C_1$-$C_4$ aliphatic, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$ cycloalkoxy and —SF$_5$.

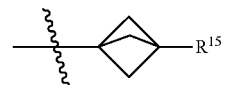

In some embodiments, $R^{2A}$ is Ring F of the following structure wherein R$^{15}$ is selected from halogen, $C_1$-$C_4$ aliphatic, halo$C_1$-$C_4$ alkyl, $C_3$-$C_6$ cycloalkyl, halo$C_3$-$C_6$ cycloalkyl, —OH, —CN, $C_1$-$C_4$ alkoxy, halo$C_1$-$C_4$ alkoxy, $C_3$-$C_6$ cycloalkoxy, halo$C_3$-$C_6$ cycloalkoxy and —SF$_5$.

In some embodiments, $R^{2A}$ is 2-benzimidazolyl, 2-naphthyl, or 3-quinolinyl, each of which is optionally substituted with 1, 2, or 3 substituents independently selected from halogen, $C_{1-4}$ alkyl and, —OH. In some embodiments, $R^{2A}$ is 2-benzimidazolyl optionally substituted with 1, 2, or 3 substituents independently selected from halogen, $C_{1-4}$ alkyl and, —OH. In some embodiments, $R^{2A}$ is 2-naphthyl optionally substituted with 1, 2, or 3 substituents independently selected from halogen, $C_{1-4}$ alkyl and, —OH. In some embodiments, $R^{2A}$ is 3-quinolinyl optionally substituted with 1, 2, or 3 substituents independently selected from halogen, $C_{1-4}$ alkyl and, —OH.

In some embodiments, $R^{2A}$ is phenyl comprising a —$CF_3$ substituent or pyridyl comprising a —$CF_3$ substituent.

In some embodiments, $R^{2A}$ is bicyclo[1.1.1]pentyl comprising a —$CF_3$ substituent or bicyclo[1.1.1]pentyl comprising a —$CHF_2$ substituent.

In some embodiments, $R^{2A}$ is as selected from one of the substituents of Table 1 or Table 1a.

As described generally above, $R^3$ is hydrogen, $C_1$-$C_4$ alkyl, $C_3$-$C_5$ cycloalkyl, $C_1$-$C_4$ alkoxy, —$NHR^{3A}$, —$N(R^{3A})_2$ or $C_1$-$C_4$ alkylthio each of which, besides hydrogen, is optionally substituted with —OH, 1-5 independently selected halogen, —OR, —$C(O)NR^{10}R^{11}$, or $N(R)C(O)R$.

In some embodiments, $R^3$ is hydrogen. In some embodiments, $R^3$ is $C_1$-$C_4$ alkyl optionally substituted with —OH, 1-5 independently selected halogen, or $C_1$-$C_4$ alkoxy. In some embodiments, $R^3$ is $C_1$-$C_4$ alkyl. In some embodiments, $R^3$ is —$CH_2CH_3$. In some embodiments, $R^3$ is —$CH_3$. In some embodiments, $R^3$ is $C_3$-$C_5$ cycloalkyl, $C_1$-$C_4$ alkoxy, —$NHR^{3A}$, —$N(R^{3A})_2$ or $C_1$-$C_4$ alkylthio optionally substituted with —OH, 1-5 independently selected halogen, or $C_1$-$C_4$ alkoxy. In some embodiments, $R^3$ is $C_3$-$C_5$ cycloalkyl optionally substituted with —OH, 1-5 independently selected halogen, or $C_1$-$C_4$ alkoxy. In some embodiments, $R^3$ is $C_1$-$C_4$ alkoxy optionally substituted with —OH, 1-5 independently selected halogen, or $C_1$-$C_4$ alkoxy. In some embodiments, $R^3$ is —$NHR^{3A}$ optionally substituted with —OH, 1-5 independently selected halogen, or $C_1$-$C_4$ alkoxy. In some embodiments, $R^3$ is —$N(R^{3A})_2$ optionally substituted with —OH, 1-5 independently selected halogen, or $C_1$-$C_4$ alkoxy. In some embodiments, $R^3$ is $C_1$-$C_4$ alkylthio optionally substituted with —OH, 1-5 independently selected halogen, or $C_1$-$C_4$ alkoxy. In some embodiments, $R^3$ is selected from the group consisting of $C_1$-$C_4$ alkyl and $C_3$-$C_5$ cycloalkyl.

In some embodiments, $R^3$ is as selected from one of the substituents of Table 1 or Table 1a.

As described generally above, each $R^{3A}$ is independently selected at each occurrence from $C_1$-$C_4$ alkyl. In some embodiments, $R^{3A}$ is —$CH_3$. In some embodiments, $R^{3A}$ is —$CH_2CH_3$. In some embodiments, $R^{3A}$ is propyl. In some embodiments, $R^{3A}$ is butyl.

In some embodiments, $R^{3A}$ is as selected from one of the substituents of Table 1 or Table 1a.

In some embodiments, $R^4$ is selected from one of a), b), and c):

a) $R^4$ is a Ring E that is selected from the group consisting of:

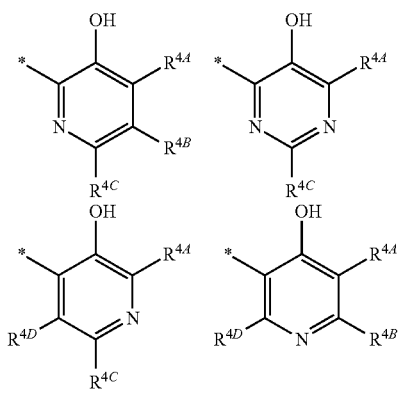

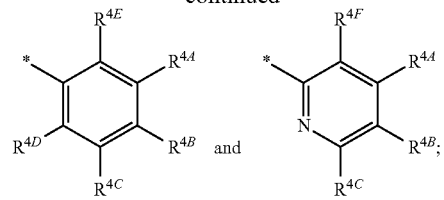

wherein * is a point of attachment to L; and any substituents that are present on Ring E selected from $R^{4A}$, $R^{4B}$, $R^{4C}$, $R^{4D}$, $R^{4E}$ and $R^{4F}$ are each independently selected from hydrogen; halogen; —CN; $C_1$-$C_4$ alkyl; $C_2$-$C_4$ alkenyl; $C_2$-$C_4$ alkynyl; $C_1$-$C_4$ alkoxy; halo$C_1$-$C_4$ alkyl; $C_1$-$C_3$ alkyl substituted with —OH, —$OCH_3$, or —$OCH_2CH_3$; halo$C_1$-$C_4$ alkoxy; $C_3$-$C_6$ cycloalkyl; $C_3$-$C_6$ cycloalkoxy; and $NR^{13}R^{14}$; or $R^{4A}$ and $R^{4B}$, along with their intervening atoms, join to form 4-7 membered carbocyclyl substituted with 0-3 independently selected $R^B$, a 4-7 membered heterocyclyl substituted with 0-3 independently selected $R^B$, or a 5-6 membered heteroaryl (having 1-4 heteroatoms independently selected from nitrogen, oxygen, and sulfur) substituted with 0-3 independently selected $R^B$; that is fused to Ring E; and any substituents that are present on Ring E selected from $R^{4C}$, $R^{4D}$, $R^{4E}$ and $R^{4F}$ are each independently selected from hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —$OCH_3$, or —$OCH_2CH_3$; halo$C_1$-$C_4$ alkoxy; $C_3$-$C_6$ cycloalkyl; $C_3$-$C_6$ cycloalkoxy; and $NR^{13}R^{14}$; or $R^{4B}$ and $R^{4C}$, along with their intervening atoms, join to form a 4-7 membered carbocyclyl substituted with 0-3 independently selected $R^B$, a 4-7 membered heterocyclyl substituted with 0-3 independently selected $R^B$, or a 5-6 membered heteroaryl (having 1-4 heteroatoms independently selected from nitrogen, oxygen, and sulfur) substituted with 0-3 independently selected $R^B$; that is fused to Ring E; and any substituents that are present on Ring E selected from $R^{4A}$, $R^{4D}$, $R^{4E}$, and $R^{4F}$ are each independently selected from hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —$OCH_3$, or —$OCH_2CH_3$; halo$C_1$-$C_4$ alkoxy; $C_3$-$C_6$ cycloalkyl; $C_3$-$C_6$ cycloalkoxy; and $NR^{13}R^{14}$; or $R^{4C}$ and $R^{4D}$, along with their intervening atoms, join to form a 4-7 membered carbocyclyl substituted with 0-3 independently selected $R^B$, a 4-7 membered heterocyclyl substituted with 0-3 independently selected $R^B$, or a 5-6 membered heteroaryl (having 1-4 heteroatoms independently selected from nitrogen, oxygen, and sulfur) substituted with 0-3 independently selected $R^B$; that is fused to Ring E;

and any substituents that are present on Ring E selected from $R^{4A}$, $R^{4B}$, $R^{4E}$ and $R^{4F}$ are each independently selected from hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —$OCH_3$, or —$OCH_2CH_3$; halo$C_1$-$C_4$ alkoxy; $C_3$-$C_6$ cycloalkyl; $C_3$-$C_6$ cycloalkoxy; and $NR^{13}R^{14}$; or $R^{4E}$ is halogen or —OH, and $R^{4A}$, $R^{4B}$, $R^{4C}$, and $R^{4D}$ are each independently selected from hydrogen; halogen; —CN; $C_1$-$C_4$ alkyl; $C_2$-$C_4$ alkenyl; $C_2$-$C_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$; or R$^{4E}$ and R$^{4A}$, along with their intervening atoms, join to form a 5-6 membered optionally substituted heteroaryl (having 1-4 heteroatoms independently selected from nitrogen, oxygen, and sulfur) substituted with 0-3 independently selected R$^B$; that is fused to Ring E; and R$^{4B}$, R$^{4C}$, and R$^{4D}$ are each independently selected from hydrogen; halogen; —CN; C$_1$-C$_4$ alkyl; C$_2$-C$_4$ alkenyl; C$_2$-C$_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$; or R$^{4E}$ and R$^{4A}$, along with their intervening atoms, join to form a 5-6 membered heteroaryl (having 1-4 heteroatoms independently selected from nitrogen, oxygen, and sulfur) substituted with 0-3 independently selected R$^B$; that is fused to Ring E; and R$^{4B}$ and R$^{4C}$ are each independently selected from hydrogen; halogen; —CN; C$_1$—C$_4$ alkyl; C$_2$-C$_4$ alkenyl; C$_2$-C$_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$;

R$^{13}$ is independently selected at each occurrence from hydrogen and C$_1$-C$_4$ alkyl optionally substituted with —OH, —OCH$_3$, or —OCH$_2$CH$_3$; and R$^{14}$ is hydrogen, or R$^{13}$ and R$^{14}$ combine with the nitrogen atom to which they are attached to form a heterocyclic ring selected from azetidinyl, pyrrolidinyl, or piperidinyl, said heterocyclic ring optionally substituted with —CH$_3$; or R$^4$ is a 5-membered heteroaryl (having 1 heteroatom independently selected from nitrogen, oxygen, and sulfur and 0, 1, 2, or 3 additional ring nitrogen atoms), wherein said heteroaryl is substituted with 0-4 groups independently selected from halogen, —OH, —CN, C$_1$-C$_4$ alkyl, haloC$_1$-C$_4$ alkyl, C$_3$-C$_6$ cycloalkyl, and C$_1$-C$_4$ alkoxy; and R$^4$ is a C$_1$-C$_4$ alkyl, C$_1$-C$_4$ alkoxy, or C$_3$-C$_6$ cycloalkyl, each of which is substituted with 0-3 groups independently selected from halogen, —CN, —OH, C$_1$-C$_4$ alkyl, C$_1$-C$_4$ alkoxy, optionally substituted 5-6 membered heterocyclyl, and optionally substituted 5-6 membered heterocyclyloxy.

In some embodiments, R$^4$ is Ring E of the following structure:

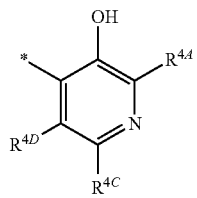

wherein * is a point of attachment to linker L that is bonded to Ring A in Formula I, I', or I"; and wherein:
R$^{4A}$, R$^{4C}$, and R$^{4D}$ are each independently selected from hydrogen; halogen; —CN; C$_1$-C$_4$ alkyl; C$_2$-C$_4$ alkenyl; C$_2$-C$_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$; or R$^{4C}$ and R$^{4D}$, along with their intervening atoms, join to form 4-7 membered carbocyclyl) substituted with 0-3 independently selected R$^B$, a 4-7 membered heterocyclyl substituted with 0-3 independently selected R$^B$, or 5-6 membered heteroaryl (having 1-4 heteroatoms independently selected from nitrogen, oxygen, and sulfur) substituted with 0-3 independently selected R$^B$, that is fused to Ring E; and R$^{4A}$ is hydrogen; halogen; —CN; C$_1$-C$_4$ alkyl; C$_2$-C$_4$ alkenyl; C$_2$-C$_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$; and R$^{13}$ is independently selected at each occurrence from hydrogen and C$_1$-C$_4$ alkyl optionally substituted with —OH, —OCH$_3$, or —OCH$_2$CH$_3$; and NR$^{13}$R$^{14}$, taken in combination form a heterocyclic ring selected from azetidinyl, pyrrolidinyl, or piperidinyl, said heterocyclic ring optionally substituted with —CH$_3$.

R$^{14}$ is hydrogen, or R$^{13}$ and R$^{14}$ combine with the nitrogen atom to which they are attached to form a heterocyclic ring selected from azetidinyl, pyrrolidinyl, or piperidinyl, said heterocyclic ring optionally substituted with —CH$_3$.

In some embodiments, R$^4$ is Ring E of the following structure:

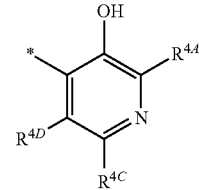

wherein * is a point of attachment to linker L that is bonded to Ring A in Formula I, I', or I"; and wherein:
R$^{4A}$ is —OCH$_3$, —OCH$_2$CH$_3$, or —OCHF$_2$;
R$^{4C}$ and R$^{4D}$ are each independently selected from hydrogen; —CN; C$_1$-C$_4$ alkyl; C$_2$-C$_4$ alkenyl; C$_2$-C$_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$; and R$^{13}$ is independently selected at each occurrence from hydrogen or C$_1$-C$_4$ alkyl optionally substituted with —OH, —OCH$_3$, or —OCH$_2$CH$_3$; or NR$^{13}$R$^{14}$, taken in combination form a heterocyclic ring selected from azetidinyl, pyrrolidinyl, or piperidinyl, said heterocyclic ring optionally substituted with —CH$_3$;

R$^{14}$ is hydrogen, or R$^{13}$ and R$^{14}$ combine with the nitrogen atom to which they are attached to form a heterocyclic ring selected from azetidinyl, pyrrolidinyl, or piperidinyl, said heterocyclic ring optionally substituted with —CH$_3$. or R$^4$ is a 5-membered heteroaryl (having 1 heteroatom independently selected from nitrogen, oxygen, and sulfur and 0, 1, 2, or 3 additional ring nitrogen atoms), wherein said heteroaryl is substituted with 0-4 substituents independently selected from halogen, —OH, —CN, C$_1$-C$_4$ alkyl, haloC$_1$-C$_4$ alkyl, C$_3$-C$_6$ cycloalkyl, and C$_1$-C$_4$ alkoxy.

In some embodiments, $R^4$ is Ring E of the following structure:

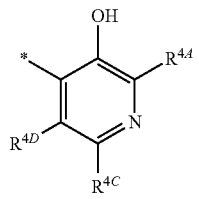

wherein * is a point of attachment to linker L that is bonded to Ring A in Formula I, I', or I''; and wherein:
$R^{4A}$ is —OCH$_3$, —OCH$_2$CH$_3$, or —OCHF$_2$;
$R^{4C}$ and $R^{4D}$ are each independently selected from hydrogen; —CN; C$_1$-C$_4$ alkyl; C$_2$-C$_4$ alkenyl; C$_2$-C$_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$; and
$R^{13}$ is independently selected at each occurrence from hydrogen or C$_1$-C$_4$ alkyl optionally substituted with —OH, —OCH$_3$, or —OCH$_2$CH$_3$; or NR$^{13}$R$^{14}$, taken in combination form a heterocyclic ring selected from azetidinyl, pyrrolidinyl, or piperidinyl, said heterocyclic ring optionally substituted with —CH$_3$; and
$R^{14}$ is hydrogen.

In some embodiments, $R^4$ is Ring E of the following structure:

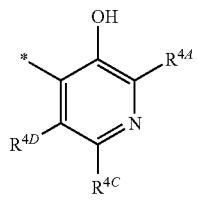

wherein * is a point of attachment to linker L that is bonded to Ring A in Formula I, I', or I''; and wherein:
$R^{4A}$, $R^{4C}$, and $R^{4D}$ are each independently selected from hydrogen; halogen; and C$_1$-C$_4$ alkyl.

In some embodiments, $R^4$ is Ring E of the following structure:

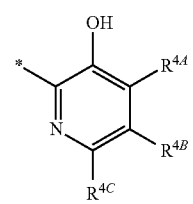

wherein * is a point of attachment to linker L that is bonded to Ring A in Formula I, I', or I''; and wherein:
$R^{4A}$, $R^{4B}$, and $R^{4C}$ are each independently selected from hydrogen; halogen; —CN; C$_1$-C$_4$ alkyl; C$_2$-C$_4$ alkenyl; C$_2$-C$_4$ alkynyl; C$_1$-C$_4$ alkoxy; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$; or $R^{4A}$ and $R^{4B}$, along with their intervening atoms, join to form 4-7 membered carbocyclyl or heterocyclyl or 5-6 membered heteroaryl (having 1-4 heteroatoms independently selected from nitrogen, oxygen, and sulfur) that is fused to Ring E; and $R^{4C}$ is hydrogen; halogen; —CN; C$_1$-C$_4$ alkyl; C$_2$-C$_4$ alkenyl; C$_2$-C$_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; or NR$^{13}$R$^{14}$; or $R^{4B}$ and $R^{4C}$, along with their intervening atoms, join to form a 4-7 membered carbocyclyl substituted with 0-3 independently selected R$^B$, a 4-7 membered heterocyclyl substituted with 0-3 independently selected R$^B$, or a 5-6 membered heteroaryl (having 1-4 heteroatoms independently selected from nitrogen, oxygen, and sulfur) substituted with 0-3 independently selected R$^B$; that is fused to Ring E; and $R^{4A}$ is selected from hydrogen; halogen; —CN; C$_1$-C$_4$ alkyl; C$_2$-C$_4$ alkenyl; C$_2$-C$_4$ alkynyl; haloC$_1$-C$_4$ alkyl; C$_1$-C$_3$ alkyl substituted with —OH, —OCH$_3$, or —OCH$_2$CH$_3$; haloC$_1$-C$_4$ alkoxy; C$_3$-C$_6$ cycloalkyl; C$_3$-C$_6$ cycloalkoxy; and NR$^{13}$R$^{14}$; and $R^{13}$ is independently selected at each occurrence from hydrogen or C$_1$-C$_4$ alkyl optionally substituted with —OH, —OCH$_3$, or —OCH$_2$CH$_3$; or NR$^{13}$R$^{14}$, taken in combination form a heterocyclic ring selected from azetidinyl, pyrrolidinyl, or piperidinyl, said heterocyclic ring optionally substituted with —CH$_3$; and
$R^{14}$ is hydrogen.

In some embodiments, $R^4$ is Ring E of the following structure:

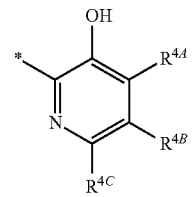

wherein * is a point of attachment to linker L that is bonded to Ring A in Formula I, I', or I''; and wherein:
$R^{4A}$ and $R^{4B}$, along with their intervening atoms, join to form 4-7 membered carbocyclyl, 4-7 membered heterocyclyl, or 5-6 membered heteroaryl (having 1-4 heteroatoms independently selected from nitrogen, oxygen, and sulfur) that is fused to Ring E; and
$R^{4C}$ is hydrogen.

In some embodiments, $R^4$ is Ring E of the following structure:

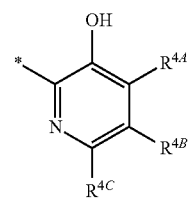

wherein * is a point of attachment to linker L that is bonded to Ring A in Formula I, I', or I''; and wherein:

$R^{4A}$ and $R^{4B}$, along with their intervening atoms, join to form 5-membered heterocyclyl (having 1 oxygen atom) that is fused to Ring E; and $R^{4C}$ is hydrogen.

In some embodiments, $R^4$ is Ring E of the following structure:

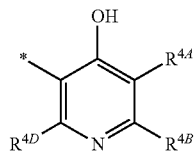

wherein * is a point of attachment linker L that is bonded to Ring A in Formula I, I', or I"; and wherein:

$R^{4A}$, $R^{4B}$, and $R^{4D}$ are each independently selected from hydrogen; halogen; —CN; $C_1$-$C_4$ alkyl; $C_2$-$C_4$ alkenyl; $C_2$-$C_4$ alkynyl; $C_1$-$C_4$ alkoxy; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; and $NR^{13}R^{14}$; or $R^{4A}$ and $R^{4B}$, along with their intervening atoms, join to form a 4-7 membered carbocyclyl, a 4-7 membered heterocyclyl, a 5-6 membered heteroaryl (having 1-4 heteroatoms independently selected from nitrogen, oxygen, and sulfur) that is fused to Ring E; and $R^{4D}$ is hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; or $NR^{13}R^{14}$; and $R^{13}$ is independently selected at each occurrence from hydrogen or $C_1$-$C_4$ alkyl optionally substituted with —OH, —OCH$_3$, or —OCH$_2$CH$_3$; or $NR^{13}R^{14}$, taken in combination form a heterocyclic ring selected from azetidinyl, pyrrolidinyl, or piperidinyl, said heterocyclic ring optionally substituted with —CH$_3$; and $R^{14}$ is H.

In some embodiments, $R^4$ is Ring E of the following structure:

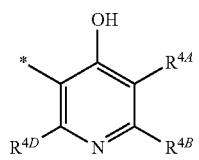

wherein * is a point of attachment to linker L that is bonded to Ring A in Formula I, I', or I"; and wherein:

$R^{4A}$ and $R^{4D}$ are each hydrogen; and $R^{4B}$ is $C_1$-$C_4$ alkyl.

In some embodiments, $R^4$ is Ring E of the following structure:

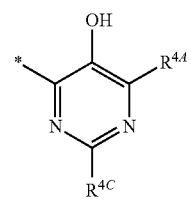

wherein * is a point of attachment linker L that is bonded to Ring A in Formula I, I', or I"; and wherein:

$R^{4A}$ and $R^{4C}$ are each independently selected from hydrogen; halogen; —CN; $C_1$-$C_4$ alkyl; $C_2$-$C_4$ alkenyl; $C_2$-$C_4$ alkynyl; $C_1$-$C_4$ alkoxy; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; and $NR^{13}R^{14}$; and $R^{13}$ is independently selected at each occurrence from hydrogen or $C_1$-$C_4$ alkyl optionally substituted with —OH, —OCH$_3$, or —OCH$_2$CH$_3$; or $NR^{13}R^{14}$, taken in combination form a heterocyclic ring selected from azetidinyl, pyrrolidinyl, or piperidinyl, said heterocyclic ring optionally substituted with —CH$_3$; and $R^{14}$ is H.

In some embodiments, $R^4$ is Ring E of the following structure:

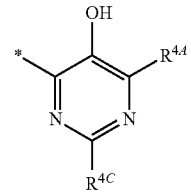

wherein * is a point of attachment to linker L that is bonded to Ring A in Formula I, I', or I"; and wherein:

$R^{4A}$ and $R^{4C}$ are each independently selected from hydrogen and $C_1$-$C_4$ alkyl.

In some embodiments, $R^4$ is Ring E of the following structure:

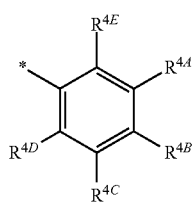

wherein * is a point of attachment to linker L that is bonded to Ring A in Formula I, I', or I"; and wherein:

$R^{4A}$, $R^{4B}$, $R^{4C}$, $R^{4D}$, and $R^{4E}$ are each independently selected from hydrogen; halogen; —CN; $C_1$-$C_4$ alkyl; $C_2$-$C_4$ alkenyl; $C_2$-$C_4$ alkynyl; $C_1$-$C_4$ alkoxy; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; and $NR^{13}R^{14}$; or $R^{4A}$ and $R^{4B}$, along with their intervening atoms, join to form 4-7 membered carbocyclyl, 4-7 membered heterocyclyl, or 5-6 membered heteroaryl (having 1-4 heteroatoms independently selected from nitrogen, oxygen, and sulfur) that is fused to Ring E; and $R^{4C}$, $R^{4D}$, and $R^{4E}$ are each independently selected from hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; and NR$^{13}$R$^{14}$; or $R^{4C}$ and $R^{4D}$, along with their intervening atoms, join to form 4-7 membered carbocyclyl, 4-7 membered heterocyclyl, 5-6 membered heteroaryl (having 1-4 heteroatoms independently selected from nitrogen, oxygen, and sulfur) that is fused to Ring E; and $R^{4A}$, $R^{4B}$, and $R^{4E}$ are each independently selected from hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; and NR$^{13}$R$^{14}$; or $R^{4E}$ is halogen or —OH, and $R^{4A}$, $R^{4B}$, $R^{4C}$, and $R^{4D}$ are each independently selected from hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; and NR$^{13}$R$^{14}$; or $R^{4E}$ and $R^{4A}$, along with their intervening atoms, join to form 5-6 membered heteroaryl (having 1-4 heteroatoms independently selected from nitrogen, oxygen, and sulfur) fused to Ring E; and $R^{4B}$, $R^{4C}$, and $R^{4D}$ are each independently selected from hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; and NR$^{13}$R$^{14}$; and $R^{13}$ is independently selected at each occurrence from hydrogen or $C_1$-$C_4$ alkyl optionally substituted with —OH, —OCH$_3$, or —OCH$_2$CH$_3$; or NR$^{13}$R$^{14}$, taken in combination form a heterocyclic ring selected from azetidinyl, pyrrolidinyl, or piperidinyl, said heterocyclic ring optionally substituted with —CH$_3$; and $R^{14}$ is H.

In some embodiments, $R^4$ is Ring E of the following structure:

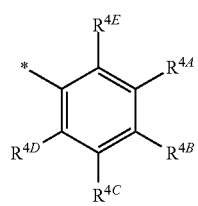

wherein * is a point of attachment to linker L that is bonded to Ring A in Formula I, I', or I"; and wherein: $R^{4A}$, $R^{4B}$, $R^{4C}$, $R^{4D}$, and $R^{4E}$ are each independently selected from hydrogen; halogen; $C_1$-$C_4$ alkyl; and $C_1$-$C_4$ alkoxy; or $R^{4C}$ and $R^{4D}$, along with their intervening atoms, join to form a 4-7 membered heterocyclyl (having 1-3 nitrogen atoms) fused to Ring E; and $R^{4A}$, $R^{4B}$, and $R^{4E}$ are each hydrogen.

In some embodiments, $R^4$ is Ring E of the following structure:

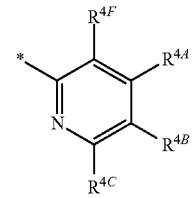

wherein * is a point of attachment to linker L that is bonded to Ring A in Formula I, I', or I"; and wherein: $R^{4F}$ and $R^{4A}$, along with their intervening atoms, join to form 5-6 membered heteroaryl (having 1-4 heteroatoms independently selected from nitrogen, oxygen, and sulfur) fused to Ring E; and $R^{4B}$ and $R^{4C}$ are each independently selected from hydrogen; halogen; —CN; $C_1$-$C_4$ alkyl; $C_2$-$C_4$ alkenyl; $C_2$-$C_4$ alkynyl; halo$C_1$-$C_4$ alkyl; $C_1$-$C_3$ alkyl substituted with —OH, —OCH$_3$, or —OCH$_2$CH$_3$; halo$C_1$-$C_4$ alkoxy; $C_3$-$C_6$ cycloalkyl; $C_3$-$C_6$ cycloalkoxy; and NR$^{13}$R$^{14}$;

$R^{13}$ is independently selected at each occurrence from hydrogen or $C_1$-$C_4$ alkyl optionally substituted with —OH, —OCH$_3$, or —OCH$_2$CH$_3$; or NR$^{13}$R$^{14}$, taken in combination form a heterocyclic ring selected from azetidinyl, pyrrolidinyl, or piperidinyl, said heterocyclic ring optionally substituted with —CH$_3$; and $R^{14}$ is H.

In some embodiments, $R^4$ is Ring E of the following structure:

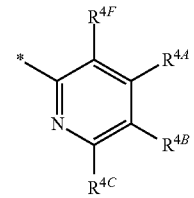

wherein * is a point of attachment to linker L that is bonded to Ring A in Formula I, I', or I"; and wherein: $R^{4F}$ and $R^{4A}$, along with their intervening atoms, join to form 5-6 membered heteroaryl (having 1-2 nitrogen atoms) fused to Ring E; and $R^{4B}$ and $R^{4C}$ are each hydrogen.

In some embodiments, $R^4$ is a 5-membered heteroaryl (having 1 heteroatom independently selected from nitrogen, oxygen, and sulfur and 0, 1, 2, or 3 additional ring nitrogen atoms), wherein said heteroaryl is substituted with 0-4 groups independently selected from halogen, —OH, —CN, $C_1$-$C_4$ alkyl, halo$C_1$-$C_4$ alkyl, $C_3$-$C_6$ cycloalkyl, and $C_1$-$C_4$ alkoxy.

In some embodiments, $R^4$ is a 5-membered heteroaryl (having 1 heteroatom independently selected from nitrogen, oxygen, and sulfur and 0, 1, 2, or 3 additional ring nitrogen atoms), wherein said heteroaryl is substituted with 0-4 groups independently selected from OH, —CH$_3$, —CHF$_2$, cyclopropyl, and —OCH$_3$.

In some embodiments, $R^4$ is a $C_1$-$C_4$ alkyl, $C_1$-$C_4$ alkoxy, or $C_3$-$C_6$ cycloalkyl, each of which is substituted with 0-3 groups independently selected from halogen, —CN, —OH, $C_1$-$C_4$ alkyl, $C_1$-$C_4$ alkoxy, optionally substituted 5-6 membered heterocyclyl, and optionally substituted 5-6 membered heterocyclyloxy. In some embodiments, $R^4$ is a $C_1$-$C_4$ alkyl, substituted with 0-3 independently selected halogen, —CN, —OH, $C_1$-$C_4$ alkyl, and $C_1$-$C_4$ alkoxy. In some embodiments, $R^4$ is a $C_1$-$C_4$ alkoxy, substituted with 0-3 independently selected halogen, —CN, —OH, $C_1$-$C_4$ alkyl, and $C_1$-$C_4$ alkoxy. In some embodiments, $R^4$ is a $C_3$-$C_6$ cycloalkyl, substituted with 0-3 independently selected halogen, —CN, —OH, $C_1$-$C_4$ alkyl, and $C_1$-$C_4$ alkoxy.

In some embodiments, $R^4$ is an isoxazolyl substituted with —OH or $C_1$-$C_4$ alkyl.

In some embodiments, $R^4$ is a 5-membered heteroaryl (having 1 heteroatom independently selected from nitrogen, oxygen, and sulfur and 0, 1, 2, or 3 additional ring nitrogen atoms) selected from the group consisting of thiophenyl, imidazolyl, pyrazolyl, tetrazolyl, thiazolyl, isothiazolyl, 1,2,5-thiadiazolyl, 1,3,4-thiadiazolyl, oxazolyl, isoxazolyl, 1,2,4-oxadiazolyl, 1,2,3-triazolyl, 1,2,4-triazolyl, wherein said heteroaryl is substituted with 0-4 groups independently selected from halogen, —OH, —CN, $C_1$-$C_4$ alkyl, halo$C_1$-$C_4$ alkyl, $C_3$-$C_6$ cycloalkyl, and $C_1$-$C_4$ alkoxy.

In some embodiments, $R^4$ is selected from the group consisting of:

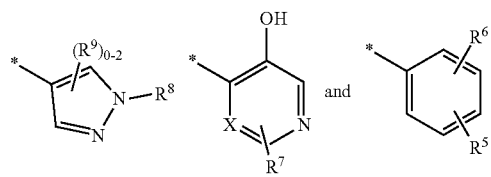

wherein * indicated the point of attachment to L, and $R^{1a}$, $R^{1b}$, $R^2$, and $R^3$, are as defined herein, both singly and in combination, and wherein:

X is CH, $CR^7$, or N;
$R^5$ is —OH or halogen;
$R^6$ is halogen, $C_{1-4}$ alkyl, or $C_{1-4}$ alkoxy;
each $R^7$ is independently hydrogen, halogen, $C_{1-4}$ alkyl, or $C_{1-4}$ alkoxy;
$R^8$ is $C_{1-4}$ alkyl;
each of the 0-2 instances of $R^9$ is independently a hydrogen or $C_{1-4}$ alkyl.

In Some Embodiments:
X is CH or N;
$R^5$ is —OH or fluoro;
$R^6$ is fluoro, —$CH_3$, or —$OCH_3$;
each $R^7$ is independently hydrogen, fluoro, —$CH_3$, or —$OCH_3$;
$R^8$ is —$CH_3$;
each instance of $R^9$ is independently a hydrogen or —$CH_3$.

In Some Embodiments, $R^4$ is

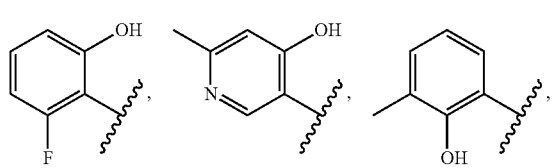

-continued

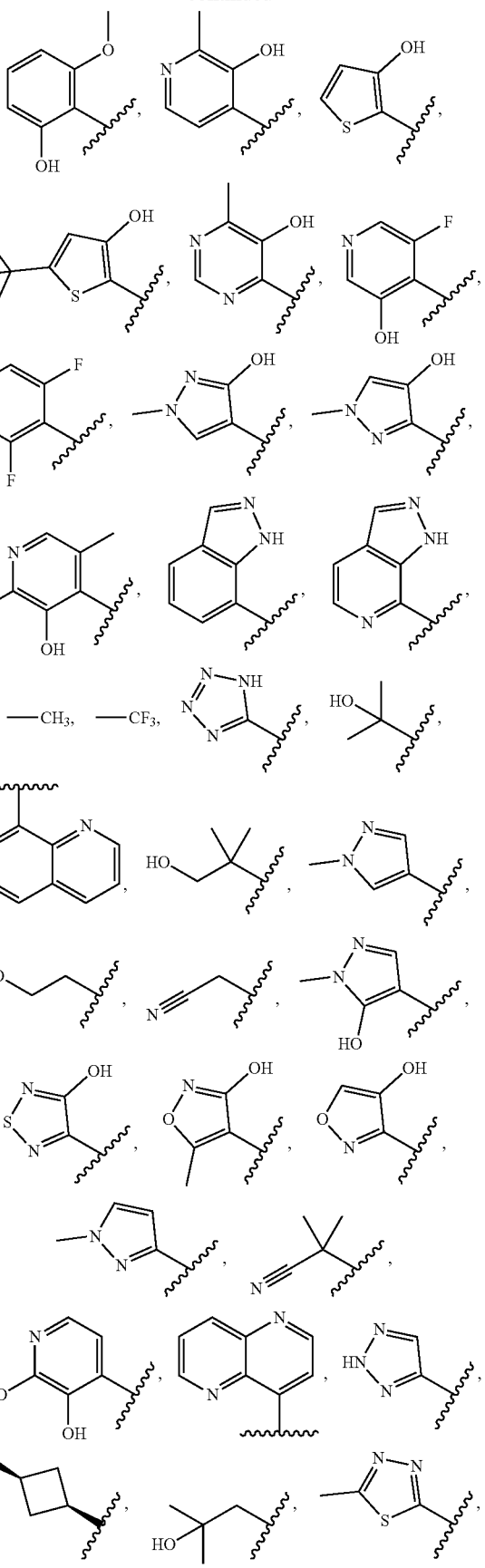

-continued
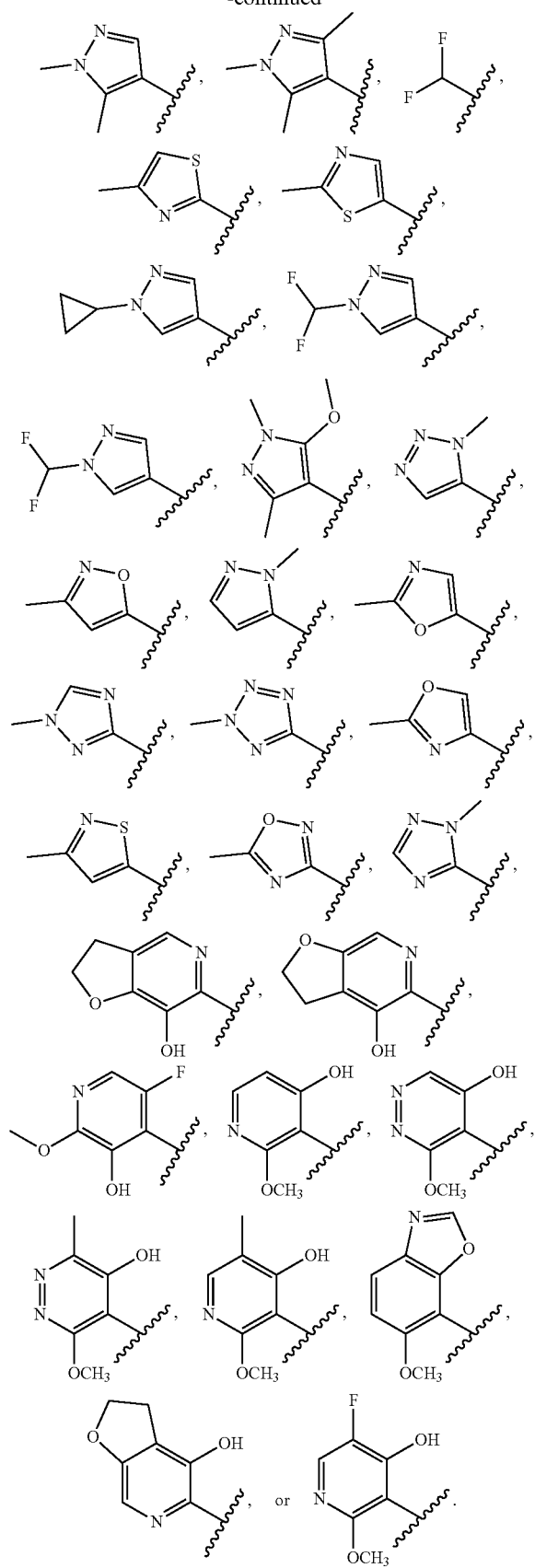
In Some Embodiments, R⁴ is
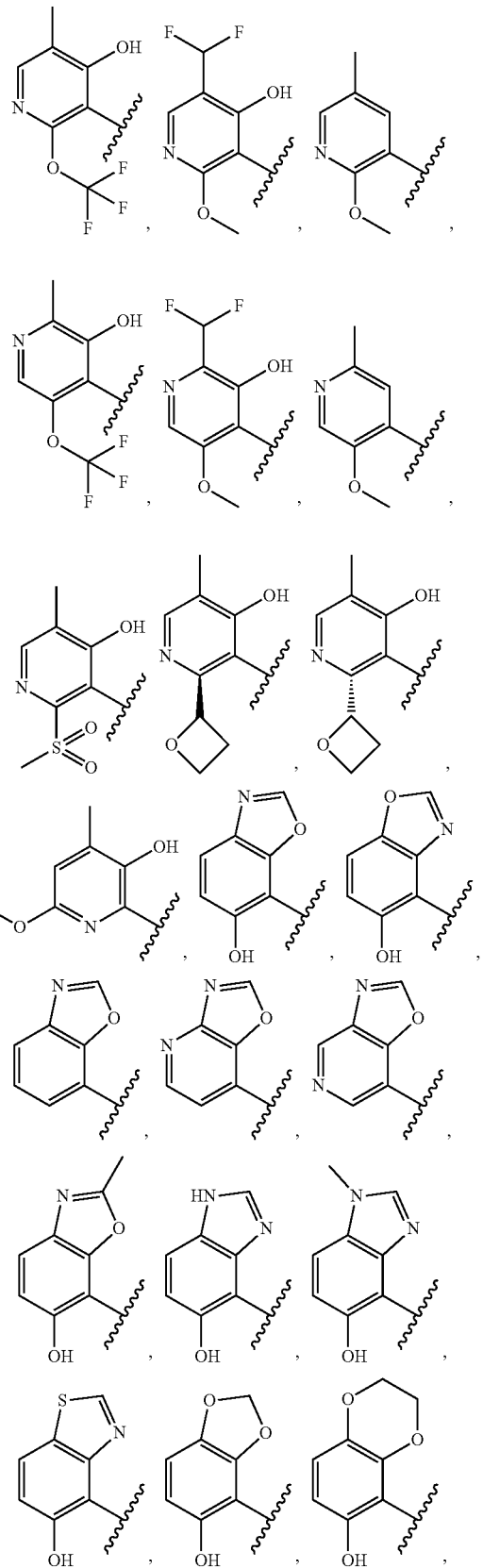

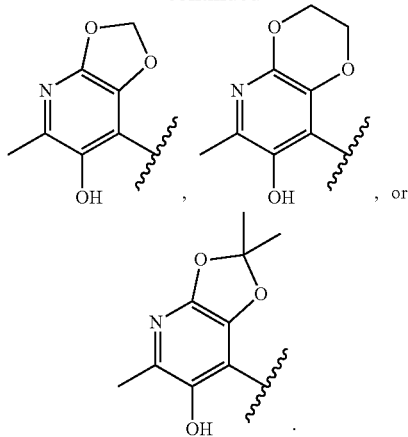

In some embodiments, R⁴ is as shown in a substituent of Table 1 or Table 1a.

As described generally above, $R^{10}$ is H, $C_1$-$C_6$ aliphatic, halo$C_1$-$C_6$ alkyl, $C_3$-$C_6$ cycloalkyl, halo$C_3$-$C_6$ cycloalkyl, —C(O)$C_1$-$C_6$ alkyl, or a 5-6 membered heteroaryl (having 1-4 heteroatoms independently selected from nitrogen, oxygen, and sulfur); each $R^{10}$ except H being optionally substituted with 1 or 2 independently selected $R^B$.

In some embodiments, $R^{10}$ is H. In some embodiments, $R^{10}$ is $C_1$-$C_6$ aliphatic, halo$C_1$-$C_6$ alkyl, $C_3$-$C_6$ cycloalkyl, halo$C_3$-$C_6$ cycloalkyl, —C(O)$C_1$-$C_6$ alkyl, or a 5-6 membered heteroaryl (having 1-4 heteroatoms independently selected from nitrogen, oxygen, and sulfur); each $R^{10}$ being optionally substituted with 1 or 2 independently selected $R^B$. In some embodiments, $R^{10}$ is $C_1$-$C_6$ aliphatic, halo$C_1$-$C_6$ alkyl, $C_3$-$C_6$ cycloalkyl, halo$C_3$-$C_6$ cycloalkyl, or —C(O)$C_1$-$C_6$ alkyl; each $R^{10}$ being optionally substituted with 1 or 2 independently selected $R^B$. In some embodiments, $R^{10}$ is a 5-6 membered heteroaryl (having 1-4 heteroatoms independently selected from nitrogen, oxygen, and sulfur); $R^{10}$ being optionally substituted with 1 or 2 independently selected $R^B$.

In some embodiments, $R^{10}$ is as shown in a substituent of Table 1 or Table 1a.

As described generally above, $R^{11}$ is H, $C_1$-$C_6$ aliphatic, or $C_3$-$C_6$ cycloalkyl, or $R^{10}$ and $R^{11}$ are taken together with the nitrogen atom to which they are attached to form a 5-6 membered ring optionally substituted with 1, 2, or 3 substituents independently selected from halogen, —OH, —CN, $C_1$-$C_4$ alkoxy, and halo$C_1$-$C_4$ alkoxy.

In some embodiments, $R^{11}$ is H, $C_1$-$C_6$ aliphatic, or $C_3$-$C_6$ cycloalkyl. In some embodiments, $R^{11}$ is H. In some embodiments, $R^{11}$ is $C_1$-$C_6$ aliphatic. In some embodiments, $R^{11}$ is $C_3$-$C_6$ cycloalkyl. In some embodiments, $R^{10}$ and $R^{11}$ are taken together with the nitrogen atom to which they are attached to form a 5-6 membered ring optionally substituted with 1, 2, or 3 substituents independently selected from halogen, —OH, —CN, $C_1$-$C_4$ alkoxy, and halo$C_1$-$C_4$ alkoxy.

In some embodiments, $R^{11}$ is as shown in a substituent of Table 1 or Table 1a.

As described generally above, $R^{12}$ is $C_1$-$C_6$ aliphatic, $C_3$-$C_6$ cycloalkyl, or a 5-6 membered heteroaryl (having 1-4 heteroatoms independently selected from nitrogen, oxygen, and sulfur); each $R^{12}$ optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy.

In some embodiments, $R^{12}$ is $C_1$-$C_6$ aliphatic optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy. In some embodiments, $R^{12}$ is $C_1$-$C_6$ aliphatic optionally substituted with 1 or 2 groups independently selected from halogen, $C_1$-$C_6$ aliphatic, halo$C_1$—$C_6$ alkyl, $C_1$-$C_6$ alkoxy, $C_3$-$C_6$ cycloalkyl, and $C_3$-$C_6$ cycloalkoxy. In some embodiments, $R^{12}$ is $C_3$-$C_6$ cycloalkyl optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy. In some embodiments, $R^{12}$ is a 5-6 membered heteroaryl (having 1-4 heteroatoms independently selected from nitrogen, oxygen, and sulfur) optionally substituted with 1 or 2 groups independently selected from halogen, $C_1$-$C_6$ aliphatic, halo$C_1$-$C_6$ alkyl, $C_1$-$C_6$ alkoxy, $C_3$-$C_6$ cycloalkyl, and $C_3$-$C_6$ cycloalkoxy.

As described generally above, $R^B$ is independently selected at each occurrence from the group consisting of optionally substituted phenyl, optionally substituted 5-6 membered heteroaryl (having 1-4 heteroatoms independently selected from nitrogen, oxygen, and sulfur), optionally substituted 4-7 membered saturated or partially unsaturated heterocyclyl (having 1-2 heteroatoms independently selected from nitrogen, oxygen, and sulfur), halogen, optionally substituted $C_1$-$C_6$ aliphatic, halo$C_1$-$C_6$ alkyl, $C_3$-$C_6$ cycloalkyl, halo-$C_3$-$C_6$ cycloalkyl, $C_1$-$C_6$ alkoxy, halo-$C_1$-$C_6$ alkoxy, $C_3$-$C_6$ cycloalkoxy, halo-$C_3$-$C_6$ cycloalkoxy, $C_1$-$C_6$ alkylene-O—$C_1$-$C_6$ alkyl, —CN, —NO₂, oxo, —OR, —SR, NR₂, S(O)₂R, S(O)₂NR₂, S(O)R, S(O)NR₂, C(O)R, C(O)OR, —C(O)NR₂, C(O)N(R)OR, OC(O)R, OC(O)NR₂, —N(R)C(O)OR, N(R)C(O)R, N(R)C(O)NR₂, N(R)C(NR)NR₂, N(R)S(O)₂NR₂, and —N(R)S(O)₂R.

In some embodiments, $R^B$ is independently selected at each occurrence from the group consisting of halogen, —OR, or an optionally substituted $C_{1-6}$ aliphatic group. In some embodiments, $R^B$ is independently selected at each occurrence from a halogen. In some embodiments, $R^B$ is independently selected at each occurrence from —OR. In some embodiments, $R^B$ is independently selected at each occurrence from an optionally substituted $C_{1-6}$ aliphatic group.

In some embodiments, $R^B$ is as selected from one of the substituents of Table 1 or Table 1a.

As described generally above, $R^C$ is independently selected at each occurrence from hydrogen, —CH₃, and —CH₂CH₃, or two $R^C$ taken together with the carbon to which they are attached form a cyclopropyl ring. In some embodiments, $R^C$ is independently selected at each occurrence from hydrogen, —CH₃, and —CH₂CH₃. In some embodiments, $R^C$ is hydrogen. In some embodiments, one $R^C$ is —CH₃, and the other $R^C$ is hydrogen. In some embodiments, two $R^C$ taken together with the carbon to which they are attached form a cyclopropyl ring.

In some embodiments, $R^C$ is as selected from one of the substituents of Table 1 or Table 1a.

As described generally above, each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same atom are taken together with the same atom to form a cyclic group selected from an optionally substituted 4-7 membered saturated ring, a 4-7 membered partially unsaturated ring, or a 5-6 membered heteroaryl ring (having 1-4 heteroatoms independently selected from nitrogen, oxygen, and sulfur); wherein said cyclic group has 0-3 heteroatoms independently selected from nitrogen, oxygen, and sulfur).

In some embodiments, each R is hydrogen. In some embodiments, each R is independently an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur).

In some embodiments, two R groups on the same atom are taken together with the same atom to form a cyclic group selected from an optionally substituted 4-7 membered saturated ring, a 4-7 membered partially unsaturated ring, or a 5-6 membered heteroaryl ring (having 1-4 heteroatoms independently selected from nitrogen, oxygen, and sulfur); wherein said cyclic group has 0-3 heteroatoms independently selected from nitrogen, oxygen, and sulfur). In some embodiments, each R is independently hydrogen or a $C_{1-6}$ alkyl.

In some embodiments, each R is as selected from one or more of the substituents of Table 1 or Table 1a.

In some embodiments, the compound of Formula I is a compound of Formula IIa-Formula IIs:

II-a

II-b

II-c

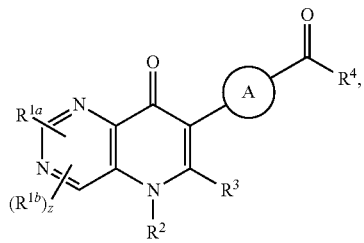

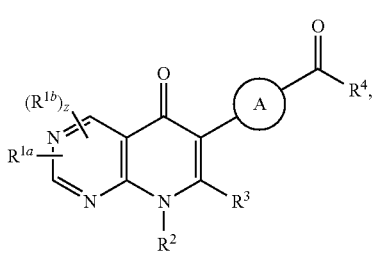

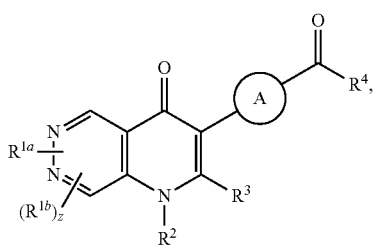

-continued

II-d

II-e

II-f

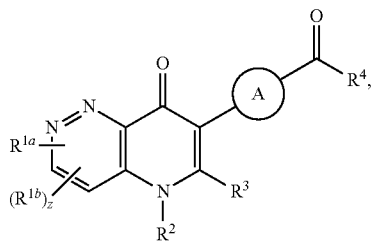

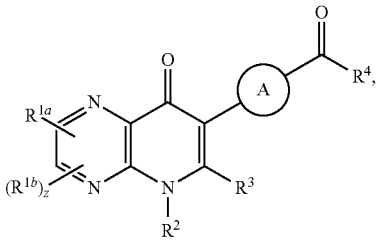

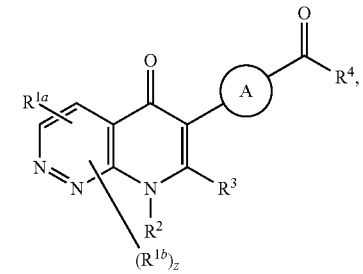

II-g

II-h

II-i

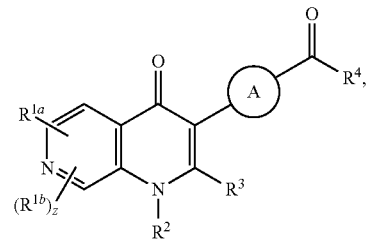

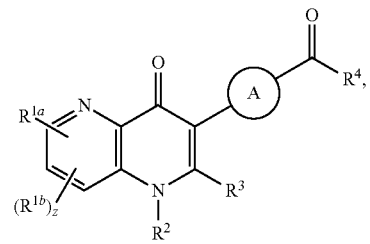

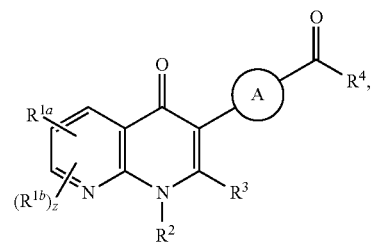

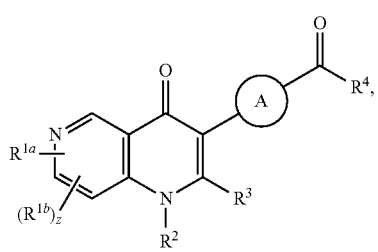
II-j
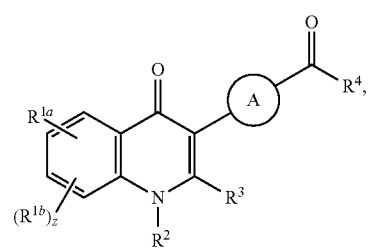
II-k
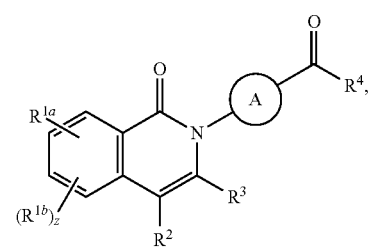
II-l
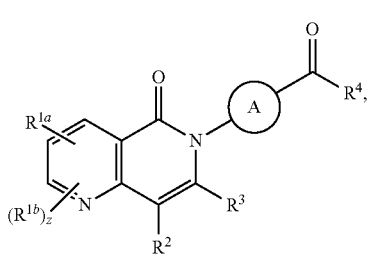
II-m
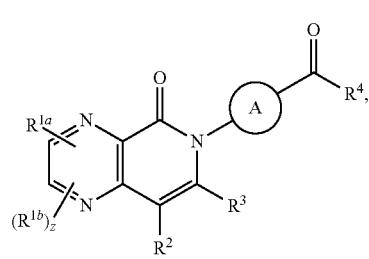
II-n
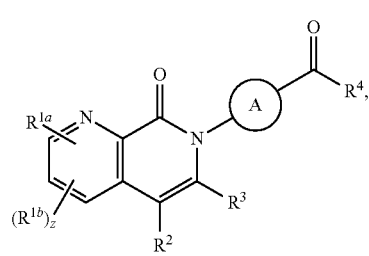
II-o
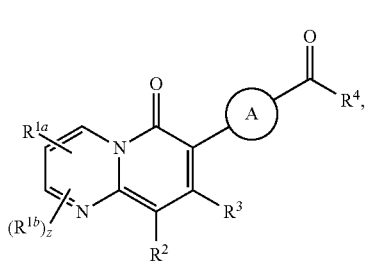
II-p
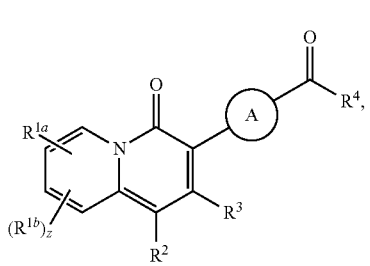
II-q
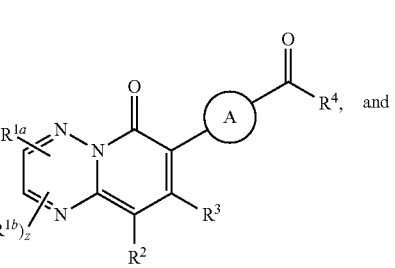
II-r
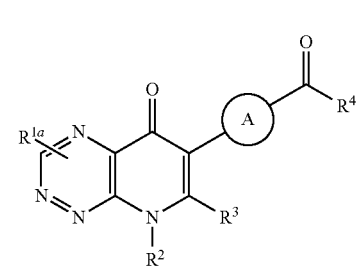
II-s
or a pharmaceutically acceptable salt thereof;
wherein $R^{1a}$, $R^{1b}$, z, Ring A, $R^2$, $R^3$, and $R^4$, are as defined herein, both singly and in combination.
In some embodiments, the compound of Formula I is a compound of Formula IIa'-Formula IIs':
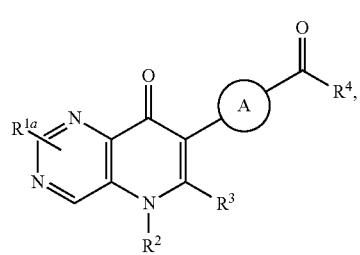
II-a'

-continued
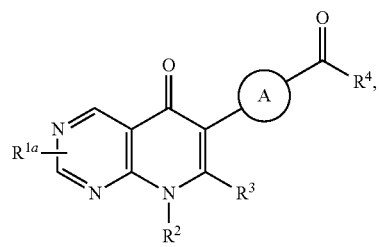
II-b′
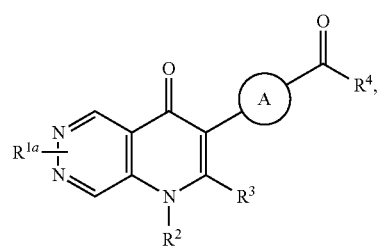
II-c′
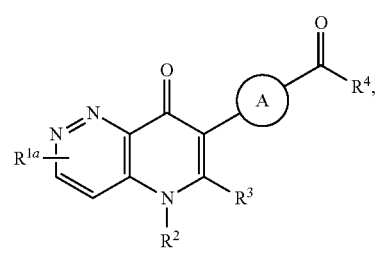
II-d′
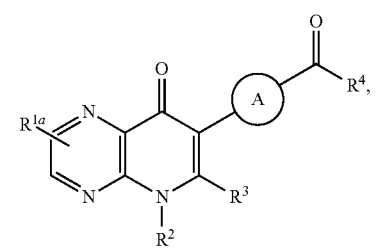
II-e′
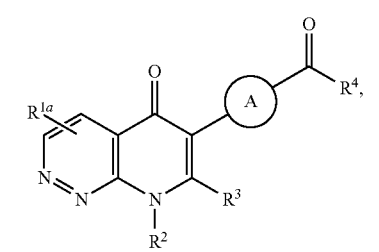
II-f′
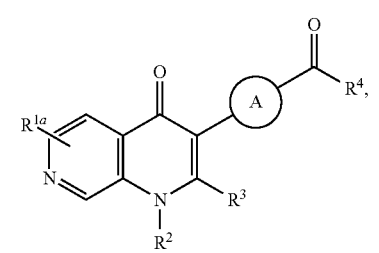
II-g′
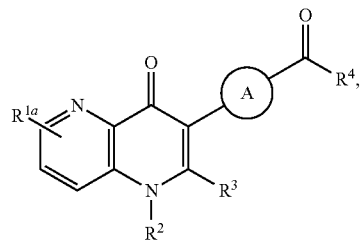
II-h′
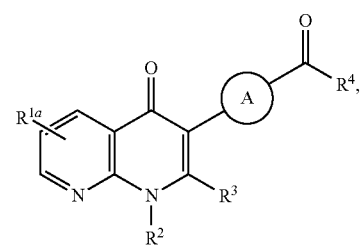
II-i′
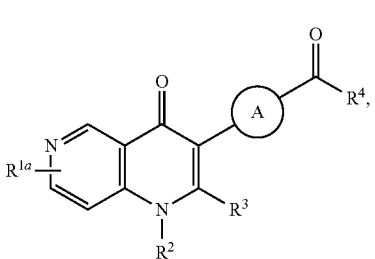
II-j′
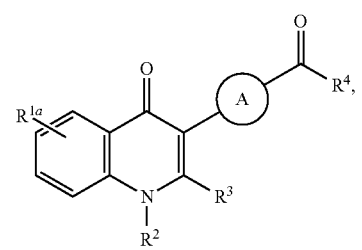
II-k′
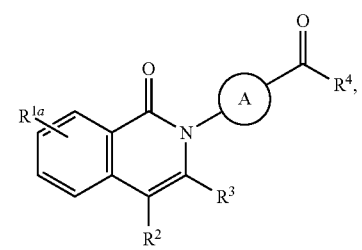
II-l′
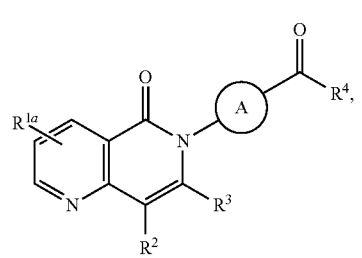
II-m′

-continued
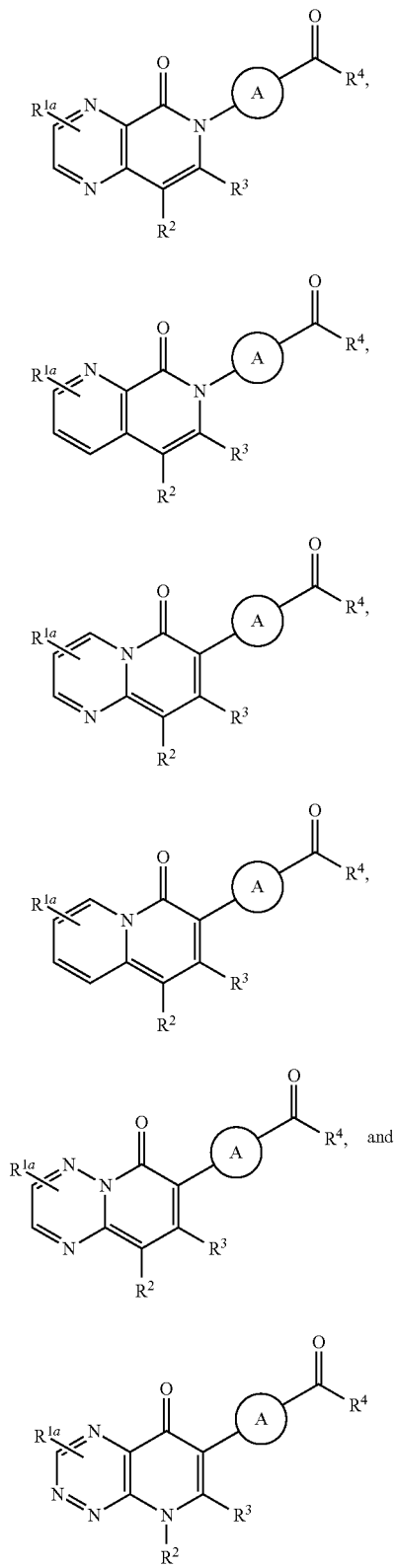
or a pharmaceutically acceptable salt thereof;
wherein $R^{1a}$, Ring A, $R^2$, $R^3$, and $R^4$, are as defined herein, both singly and in combination.
In some embodiments, the compound of Formula I is a compound of Formula IIa -Formula IIs:
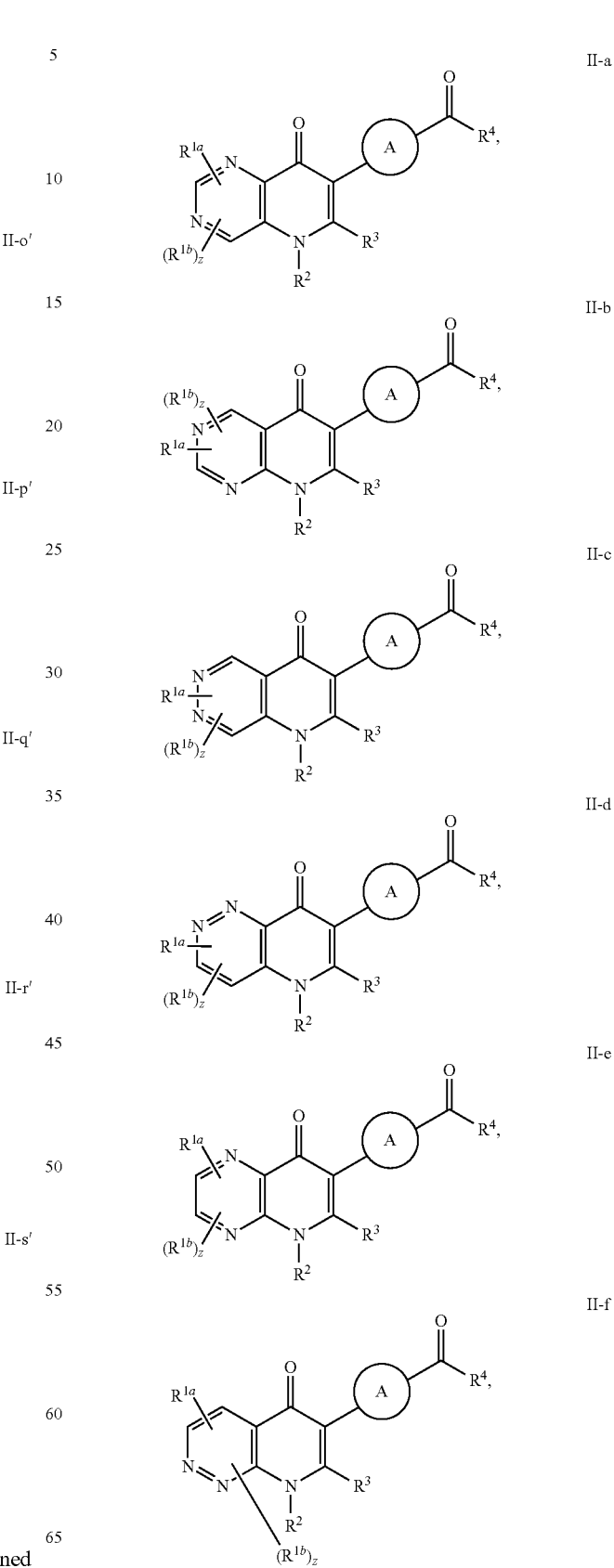

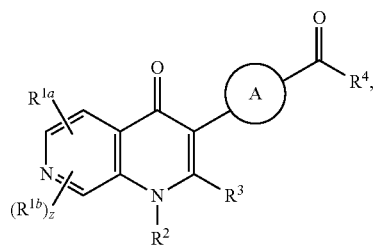
II-g
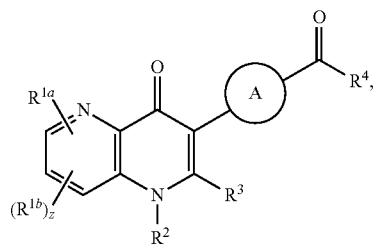
II-h
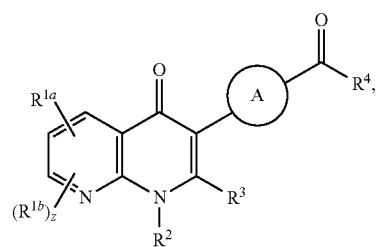
II-i
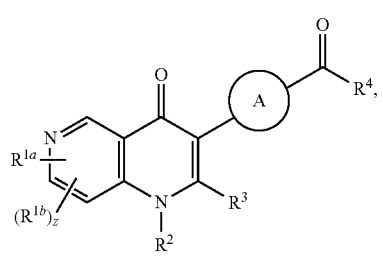
II-j
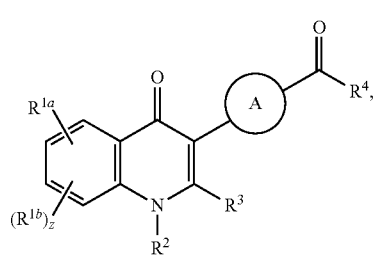
II-k
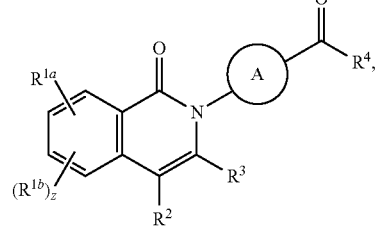
II-l
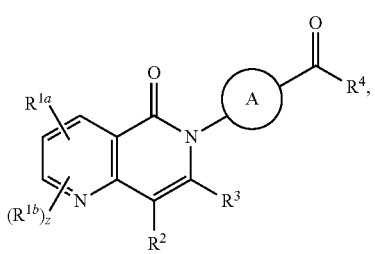
II-m
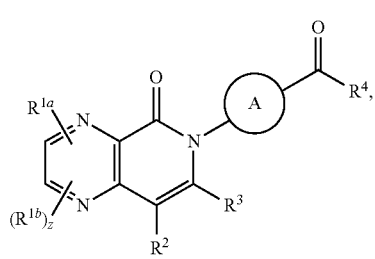
II-n
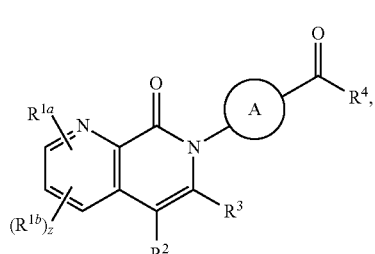
II-o
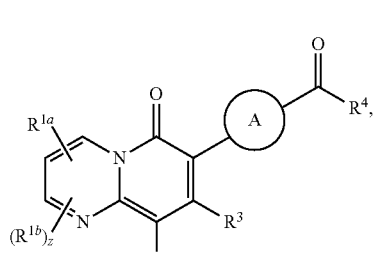
II-p
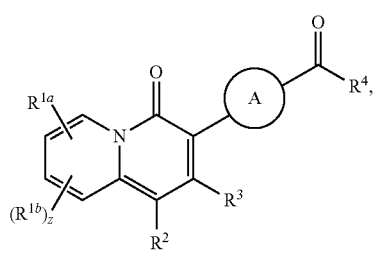
II-q
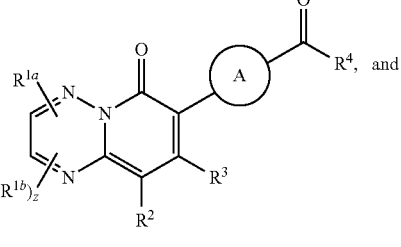
II-r II-s
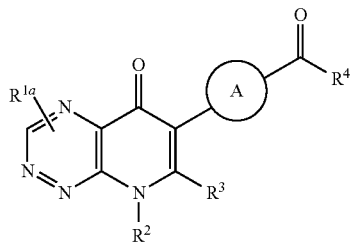
or a pharmaceutically acceptable salt thereof;
wherein $R^{1a}$, $R^{1b}$, z, Ring A, $R^2$, $R^3$, and $R^4$, are as defined herein, both singly and in combination and $R^{2a}$ is selected from
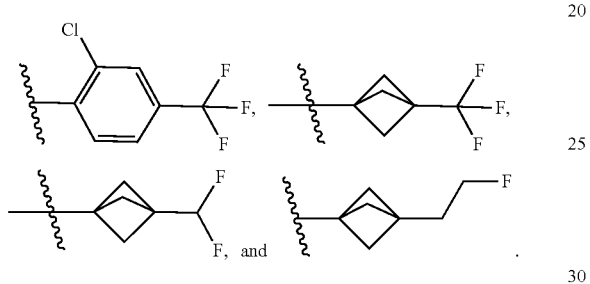
In some embodiments, the compound of Formula I is a compound of Formula IIa'-Formula IIs':
II-a'
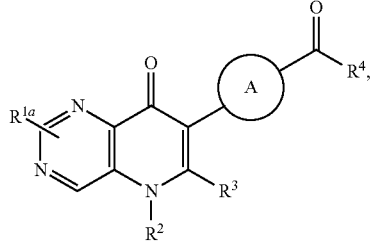
II-b'
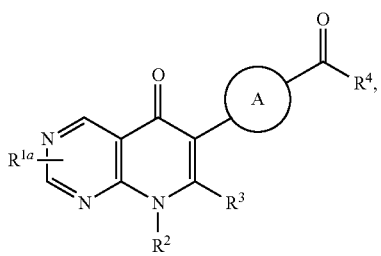
II-c'
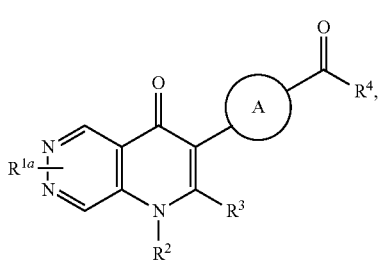
II-d'
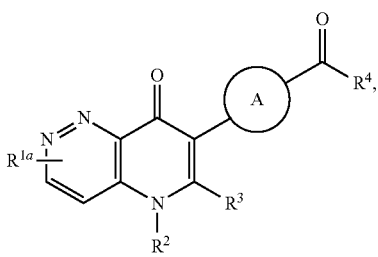
II-e'
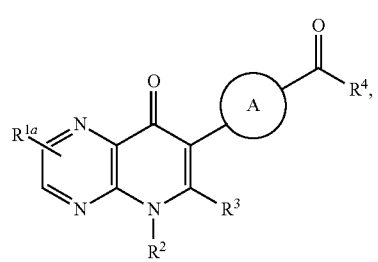
II-f'
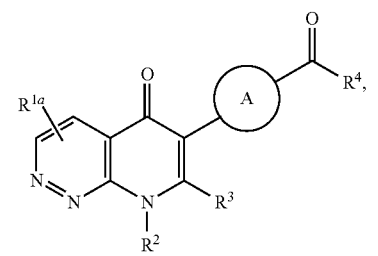
II-g'
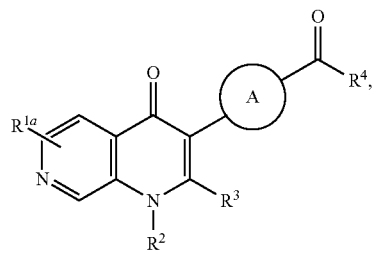
II-h'
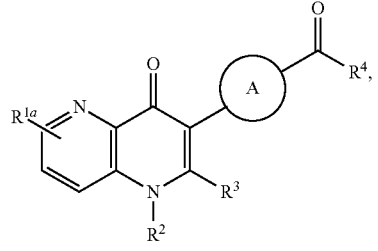
II-i'
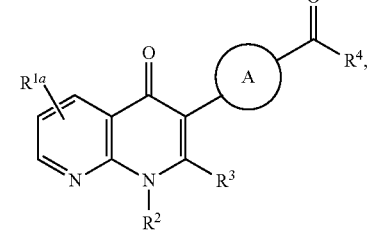

II-j'
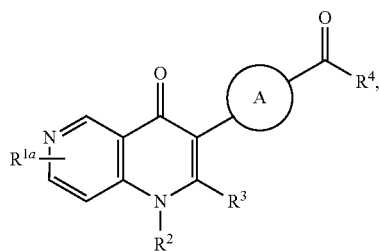
II-k'
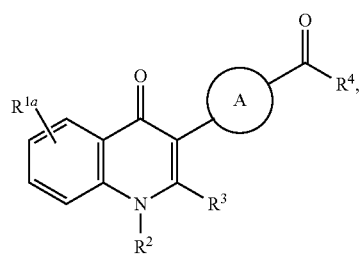
II-l'
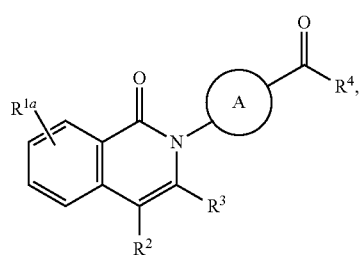
II-m'
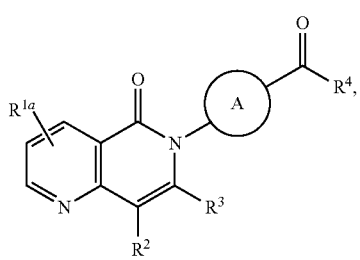
II-n'
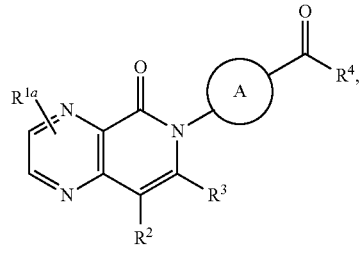
II-o'
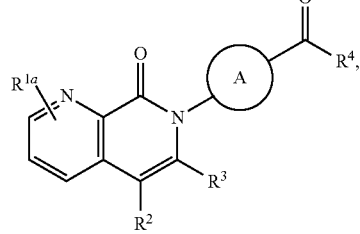
II-p'
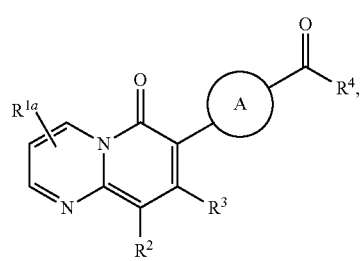
II-q'
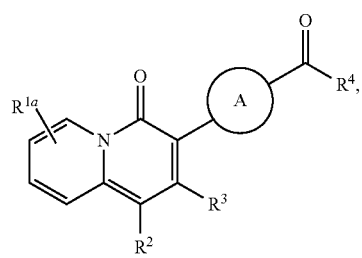
II-r'
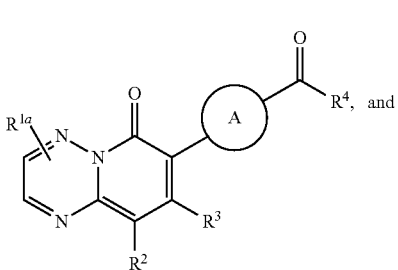
II-s'
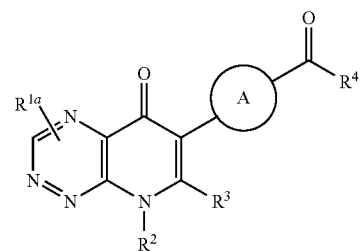
or a pharmaceutically acceptable salt thereof;
wherein $R^{1a}$, $R^{1b}$, Ring A, $R^2$, $R^3$, and $R^4$, are as defined herein, both singly and in combination and $R^{2a}$ is selected from
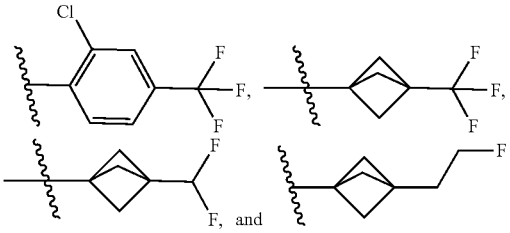
In some embodiments, the compound of Formula I is a compound of Formula IIa - Formula IIs:

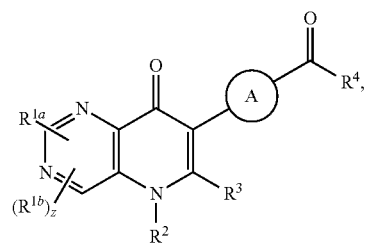
II-a
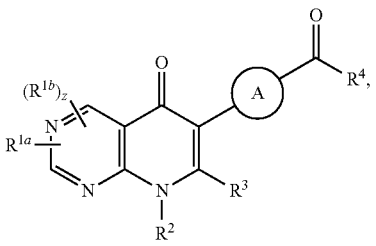
II-b
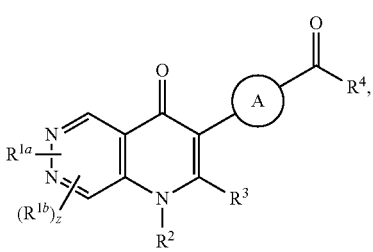
II-c
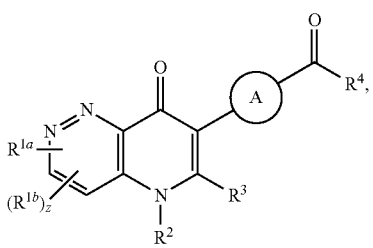
II-d
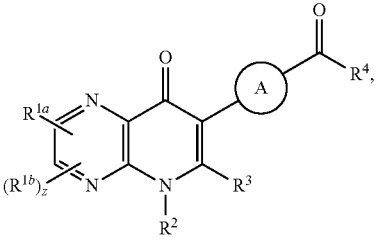
II-e
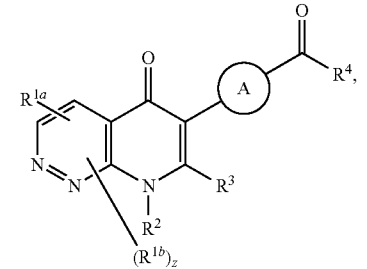
II-f
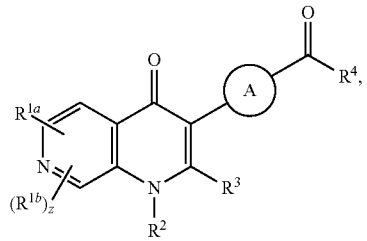
II-g
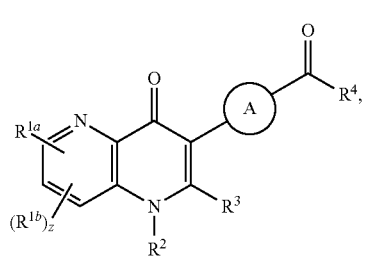
II-h
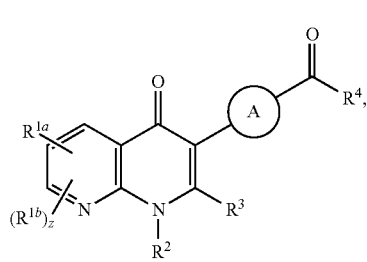
II-i
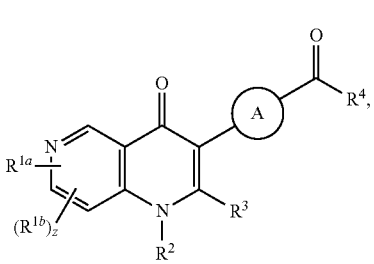
II-j
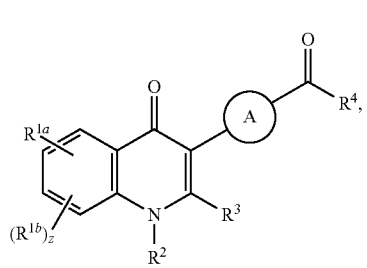
II-k
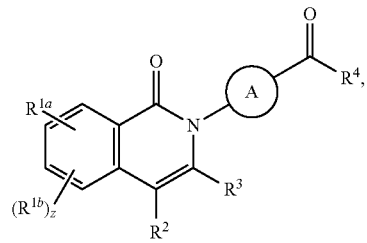
II-l

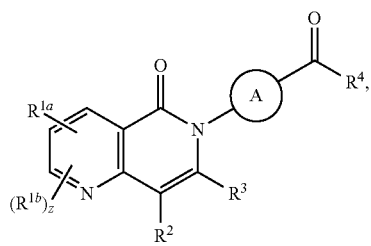
II-m
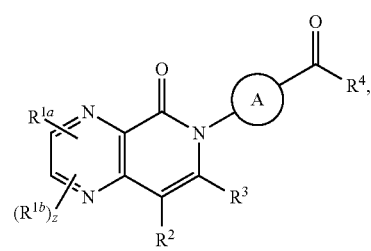
II-n
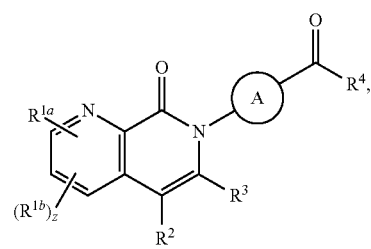
II-o
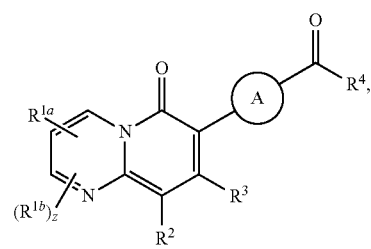
II-p
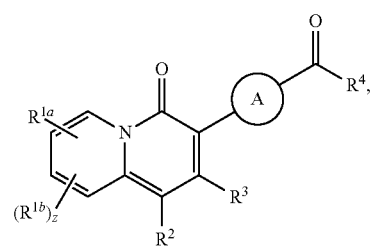
II-q
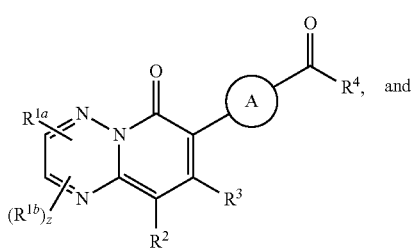
II-r, and
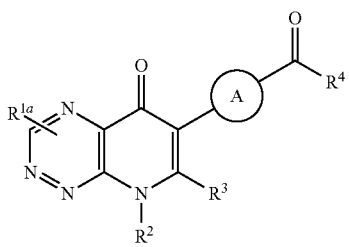
II-s
or a pharmaceutically acceptable salt thereof;
wherein $R^{1a}$, $R^{1b}$, z, $R^2$, $R^3$, and $R^4$, are as defined herein, both singly and in combination, Ring A is selected from
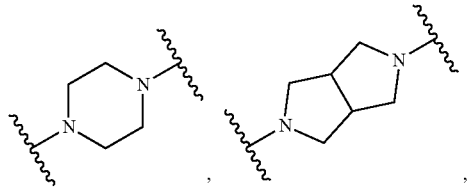
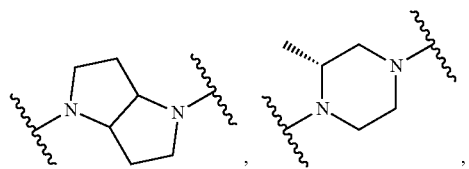
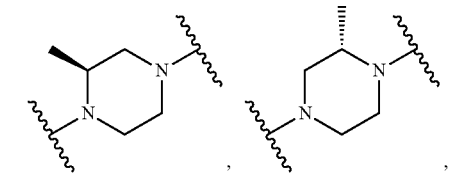
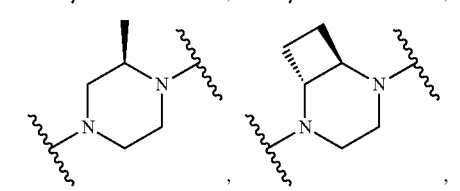
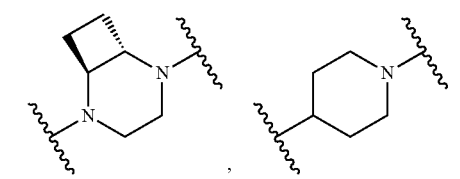
and $R^{2a}$ is selected from
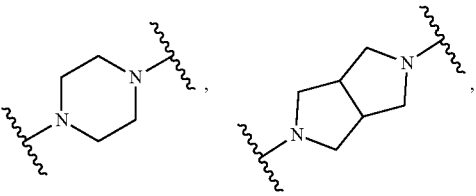

-continued
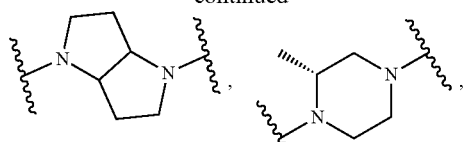
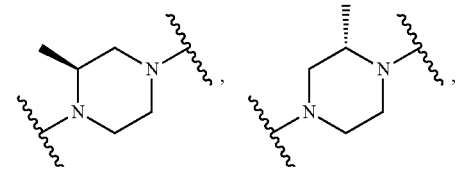
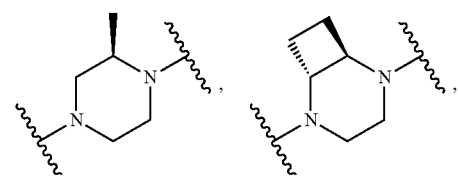
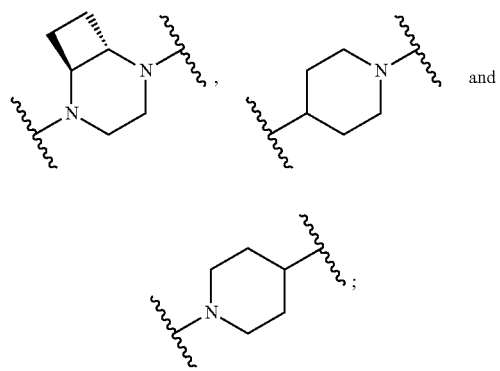
In some embodiments, the compound of Formula I is a compound of Formula IIa'-Formula IIs':
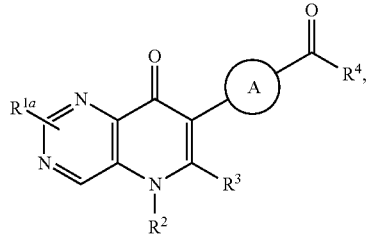
II-a'
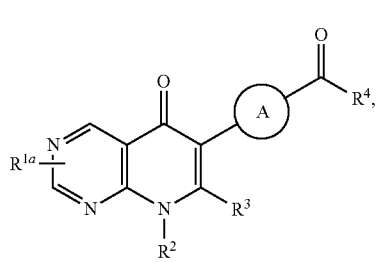
II-b'
-continued
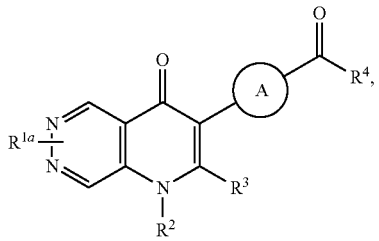
II-c'
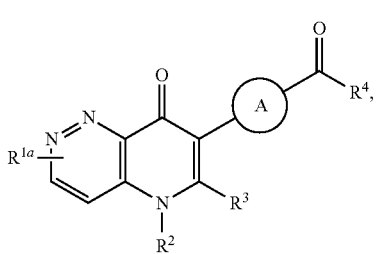
II-d'
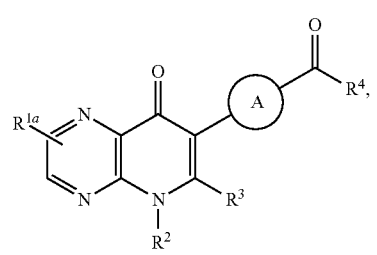
II-e'
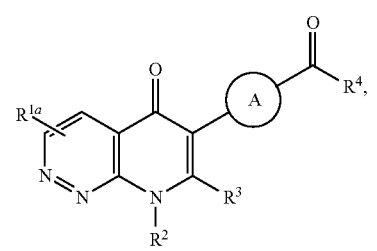
II-f'
II-g'
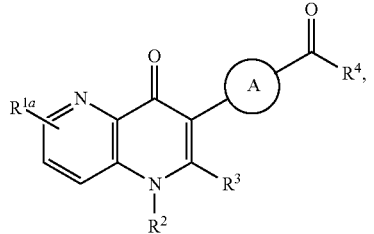
II-h'

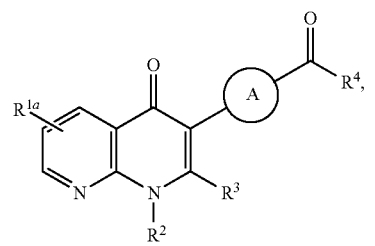
II-I′
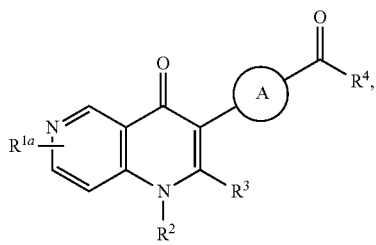
II-j′
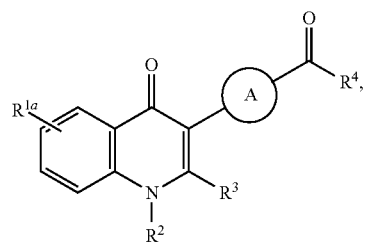
II-k′
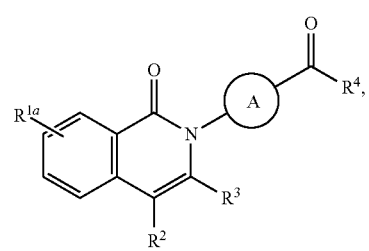
II-l′
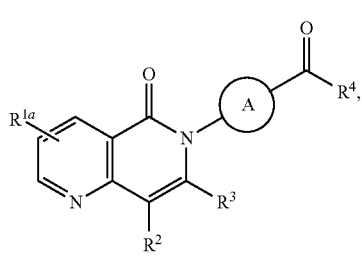
II-m′
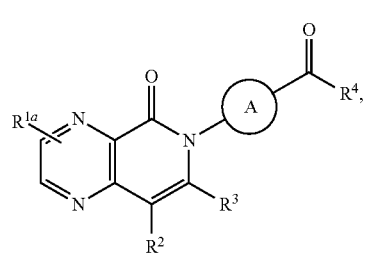
II-n′
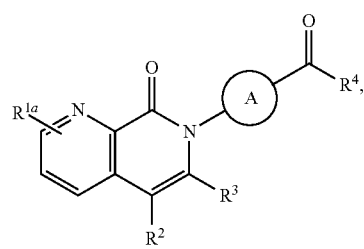
II-o′
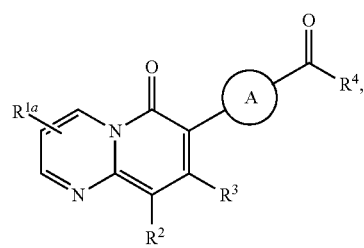
II-p′
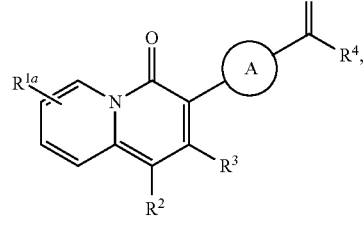
II-q′
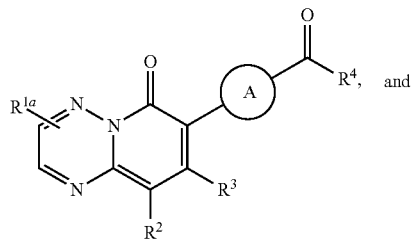
II-r′, and
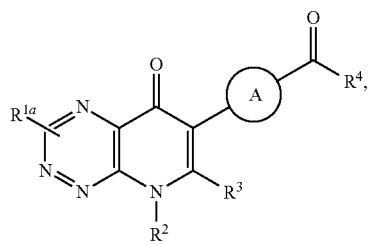
II-s′
or a pharmaceutically acceptable salt thereof;
wherein $R^{1a}$, $R^2$, $R^3$, and $R^4$, are as defined herein, both singly and in combination, Ring A is selected from
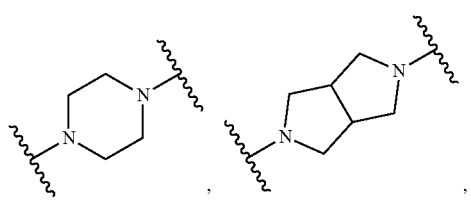

-continued

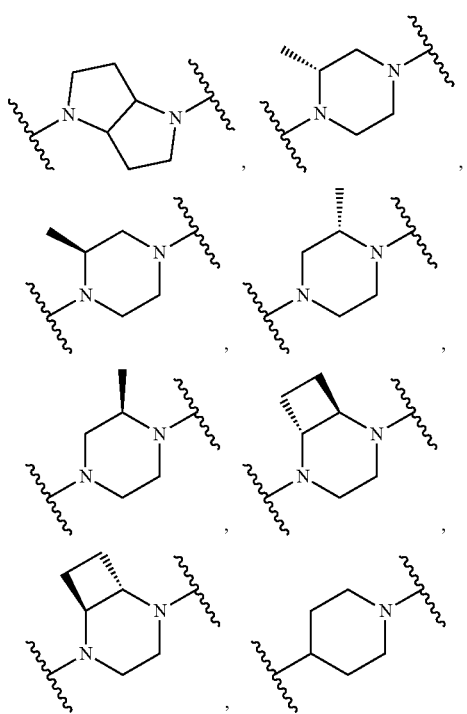

and $R^{2a}$ is selected from

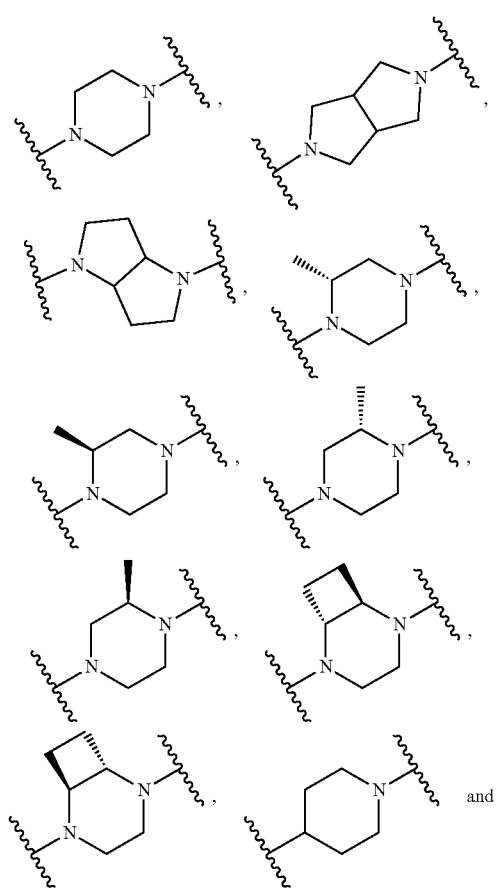

-continued

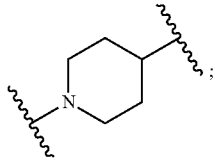

In some embodiments, the compound of Formula I, I', or I" is a compound of Formula

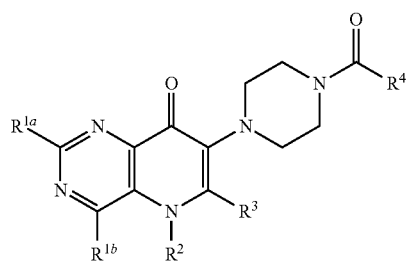

III-a or a pharmaceutically acceptable salt thereof;
wherein $R^{1a}$, $R^{1b}$, $R^2$, $R^3$, and $R^4$, are as defined herein, both singly and in combination.

In some embodiments, the compound of Formula I, I', or I" is a compound of Formula

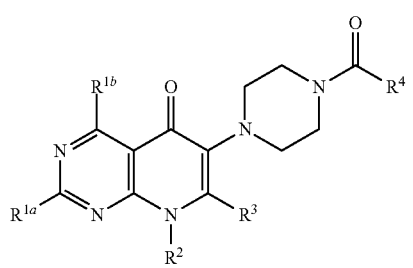

III-b or a pharmaceutically acceptable salt thereof;
wherein $R^{1a}$, $R^{1b}$, $R^2$, $R^3$, and $R^4$, are as defined herein, both singly and in combination.

In some embodiments, the compound of Formula I, I', or I" is a compound of III-c:

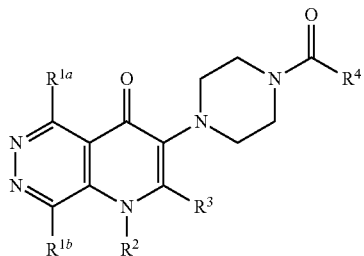

III-c or a pharmaceutically acceptable salt thereof;
wherein $R^{1a}$, $R^{1b}$, $R^2$, $R^3$, and $R^4$, are as defined herein, both singly and in combination.

In some embodiments, the compound of Formula I, I', or I" is a compound of Formula III-d:

III-d or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-e or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-f:

III-f or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-g or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-h or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-i:

III-i or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula

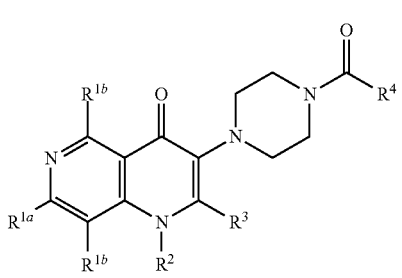

III-j or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-k:

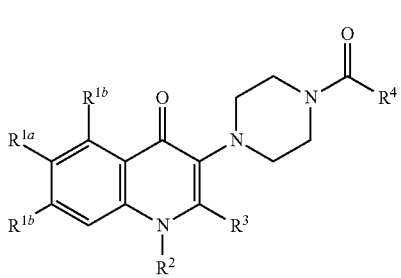

III-k or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-l:

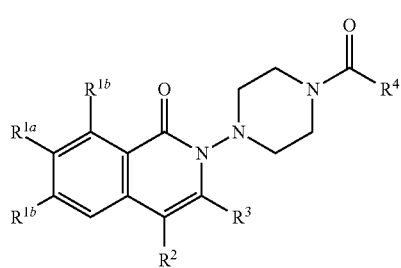

III-l or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-m:

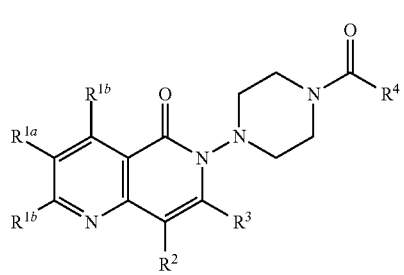

III-m or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-n:

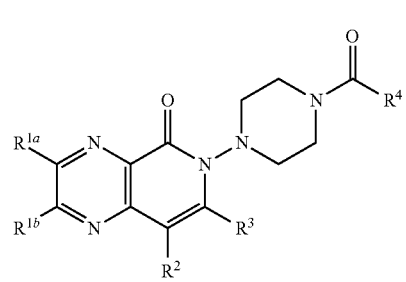

III-n or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-o:

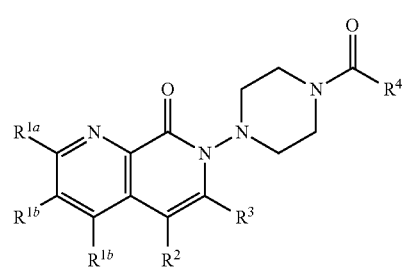

III-o or a pharmaceutically acceptable salt thereof;

wherein $R^{1a}$, $R^{1b}$, $R^2$, $R^3$, and $R^4$, are as defined herein, both singly and in combination.

In some embodiments, the compound of Formula I, I', or I" is a compound of Formula III-p:

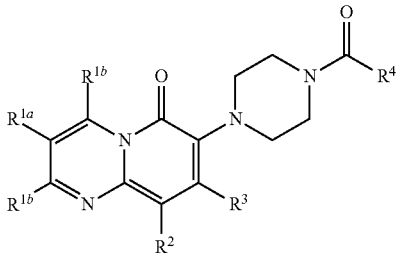

III-p or a pharmaceutically acceptable salt thereof;
wherein $R^{1a}$, $R^{1b}$, $R^2$, $R^3$, and $R^4$, are as defined herein, both singly and in combination.

In some embodiments, the compound of Formula I, I', or I" is a compound of Formula III-q:

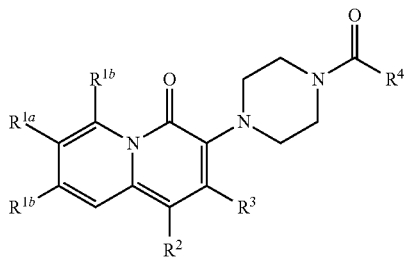

III-q or a pharmaceutically acceptable salt thereof;
wherein $R^{1a}$, $R^{1b}$, $R^2$, $R^3$, and $R^4$, are as defined herein, both singly and in combination.

In some embodiments, the compound of Formula I, I', or I" is a compound of Formula III-r:

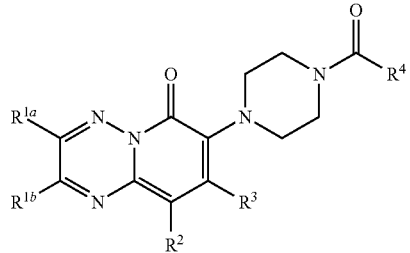

III-r or a pharmaceutically acceptable salt thereof;
wherein $R^{1a}$, $R^{1b}$, $R^2$, $R^3$, and $R^4$, are as defined herein, both singly and in combination.

In some embodiments, the compound of Formula I, I', or I" is a compound of Formula III-s:

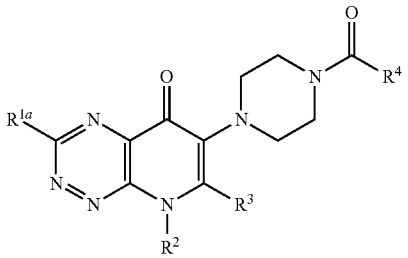

III-s or a pharmaceutically acceptable salt thereof;
wherein $R^{1a}$, $R^2$, $R^3$, and $R^4$, are as defined herein, both singly and in combination.

In some embodiments, the compound of Formula I, I', or I" is a compound of Formula III-a:

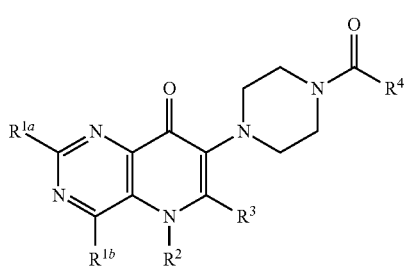

III-a or a pharmaceutically acceptable salt thereof;
wherein $R^{1a}$, $R^{1b}$, $R^2$, $R^3$, and $R^4$, are as defined herein, both singly and in combination and $R^{2a}$ is selected from

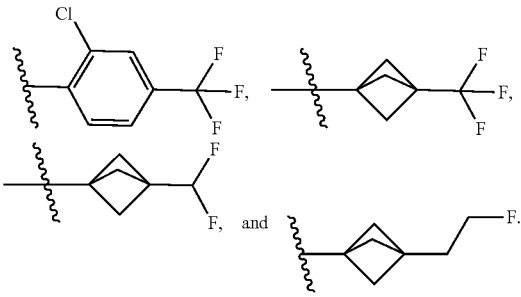

In some embodiments, the compound of Formula I, I', or I" is a compound of Formula III-b:

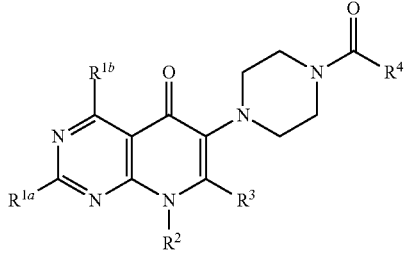

III-b or a pharmaceutically acceptable salt thereof;

wherein $R^{1a}$, $R^{1b}$, $R^2$, $R^3$, and $R^4$, are as defined herein, both singly and in combination and $R^{2a}$ is selected from

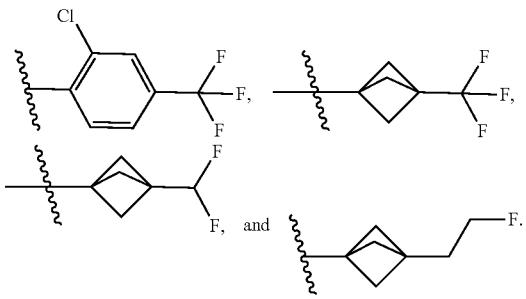

In some embodiments, the compound of Formula I, I', or I" is a compound of III-c:

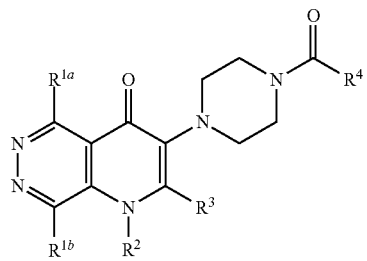

or a pharmaceutically acceptable salt thereof;
wherein $R^{1a}$, $R^{1b}$, $R^2$, $R^3$, and $R^4$, are as defined herein, both singly and in combination and $R^{2a}$ is selected from

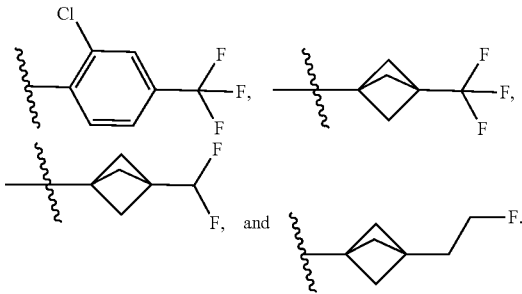

In some embodiments, the compound of Formula I, I', or I" is a compound of Formula III-d:

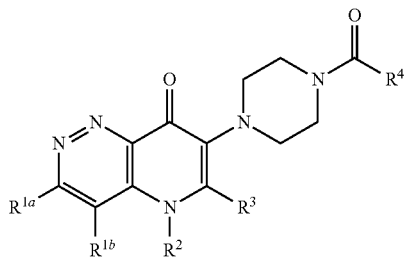

or a pharmaceutically acceptable salt thereof;

wherein $R^{1a}$, $R^{1b}$, $R^2$, $R^3$, and $R^4$, are as defined herein, both singly and in combination and $R^{2a}$ is selected from

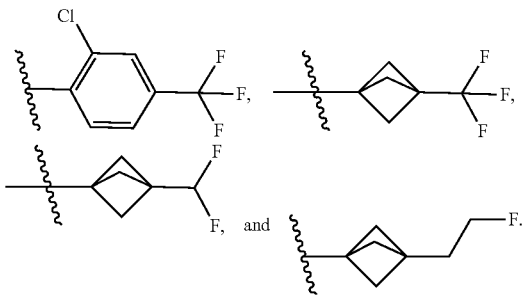

In some embodiments, the compound of Formula I, I', or I" is a compound of Formula III-e:

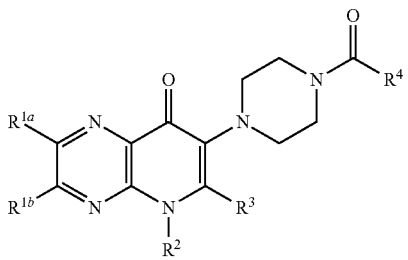

or a pharmaceutically acceptable salt thereof;
wherein $R^{1a}$, $R^{1b}$, $R^2$, $R^3$, and $R^4$, are as defined herein, both singly and in combination and $R^{2a}$ is selected from

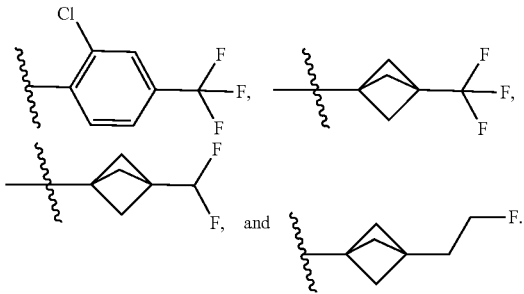

In some embodiments, the compound of Formula I, I', or I" is a compound of Formula III-f:

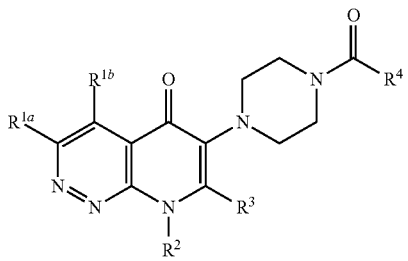

or a pharmaceutically acceptable salt thereof;

wherein $R^{1a}$, $R^{1b}$, $R^2$, $R^3$, and $R^4$, are as defined herein, both singly and in combination and $R^{2a}$ is selected from

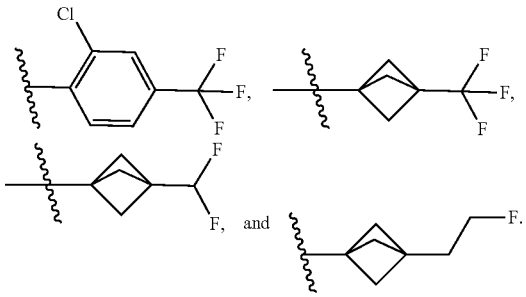

In some embodiments, the compound of Formula I, I', or I" is a compound of Formula III-g:

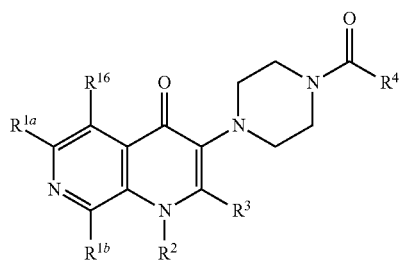

III-g or a pharmaceutically acceptable salt thereof;
wherein $R^{1a}$, $R^{1b}$, $R^2$, $R^3$, and $R^4$, are as defined herein, both singly and in combination and $R^{2a}$ is selected from

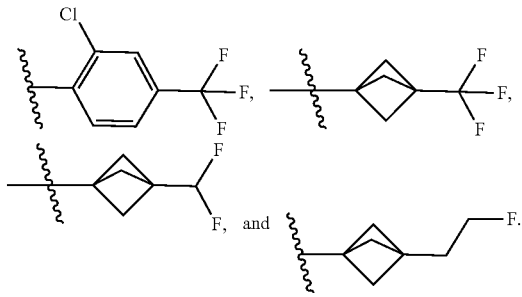

In some embodiments, the compound of Formula I, I', or I" is a compound of Formula III-h:

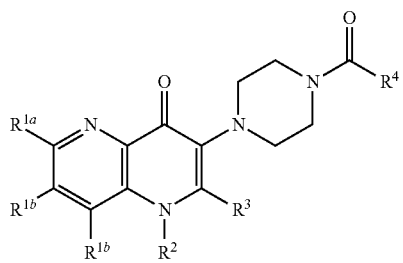

III-h or a pharmaceutically acceptable salt thereof;

wherein $R^{1a}$, $R^{1b}$, $R^2$, $R^3$, and $R^4$, are as defined herein, both singly and in combination and $R^{2a}$ is selected from

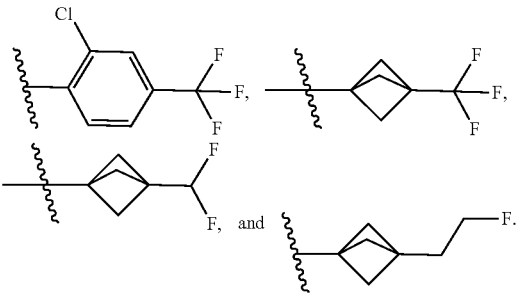

In some embodiments, the compound of Formula I, I', or I" is a compound of Formula III-i:

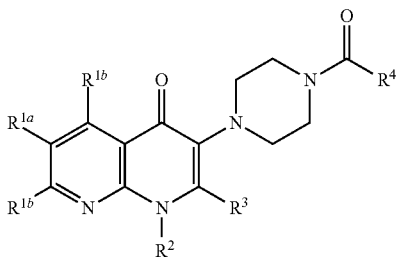

III-i or a pharmaceutically acceptable salt thereof;
wherein $R^{1a}$, $R^{1b}$, $R^2$, $R^3$, and $R^4$, are as defined herein, both singly and in combination and $R^{2a}$ is selected from

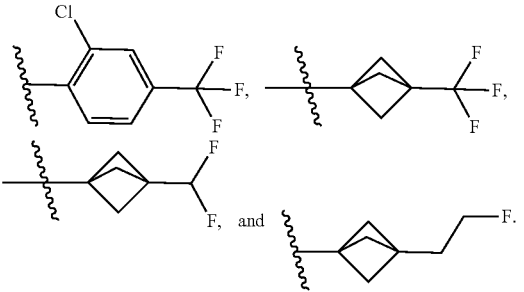

In some embodiments, the compound of Formula I, I', or I" is a compound of Formula III-j:

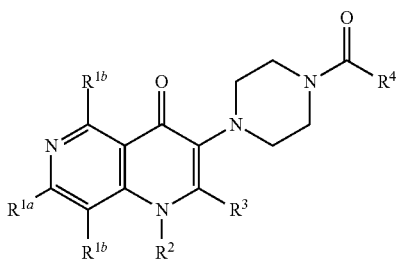

III-j or a pharmaceutically acceptable salt thereof;

wherein $R^{1a}$, $R^{1b}$, $R^2$, $R^3$, and $R^4$, are as defined herein, both singly and in combination and $R^{2a}$ is selected from

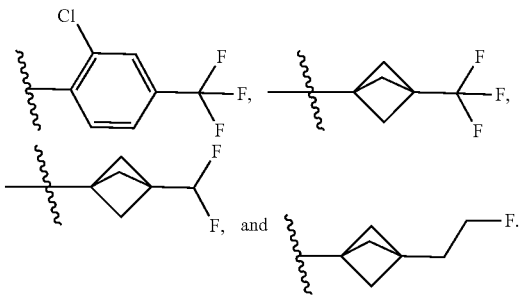

In some embodiments, the compound of Formula I, I', or I" is a compound of Formula III-k:

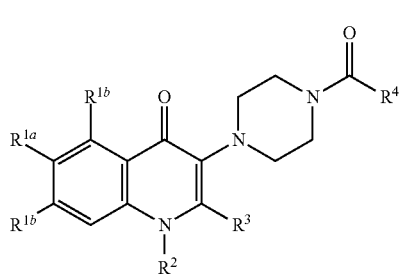

III-k or a pharmaceutically acceptable salt thereof;
wherein $R^{1a}$, $R^{1b}$, $R^2$, $R^3$, and $R^4$, are as defined herein, both singly and in combination and $R^{2a}$ is selected from

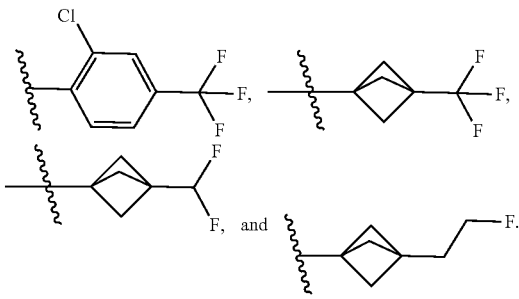

In some embodiments, the compound of Formula I, I', or I" is a compound of Formula III-p:

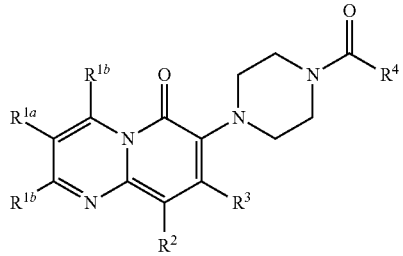

III-p or a pharmaceutically acceptable salt thereof;

wherein $R^{1a}$, $R^{1b}$, $R^2$, $R^3$, and $R^4$, are as defined herein, both singly and in combination and $R^{2a}$ is selected from

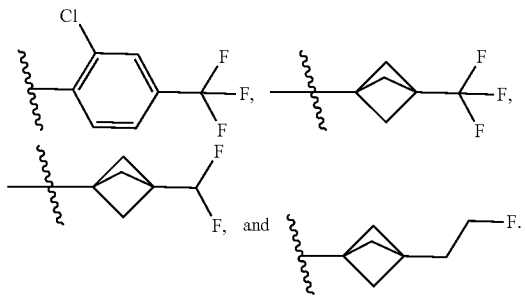

In some embodiments, the compound of Formula I, I', or I" is a compound of Formula III-q:

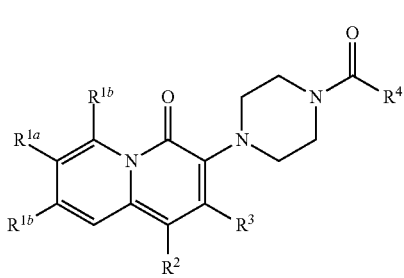

III-q or a pharmaceutically acceptable salt thereof;
wherein $R^{1a}$, $R^{1b}$, $R^2$, $R^3$, and $R^4$, are as defined herein, both singly and in combination and $R^{2a}$ is selected from

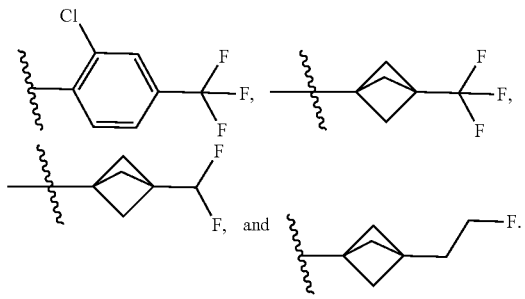

In some embodiments, the compound of Formula I, I', or I" is a compound of Formula III-r:

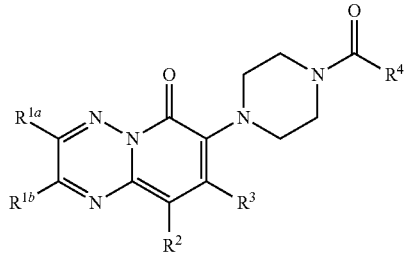

III-r or a pharmaceutically acceptable salt thereof;

wherein $R^{1a}$, $R^{1b}$, $R^2$, $R^3$, and $R^4$, are as defined herein, both singly and in combination and $R^{2a}$ is selected from

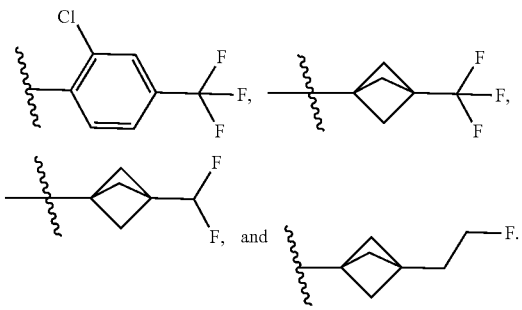

In some embodiments, the compound of Formula I, I', or I" is a compound of Formula III-s:

III-s

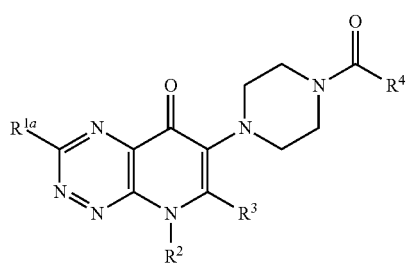

or a pharmaceutically acceptable salt thereof;
wherein $R^{1a}$, $R^{1b}$, $R^2$, $R^3$, and $R^4$, are as defined herein, both singly and in combination and $R^{2a}$ is selected from

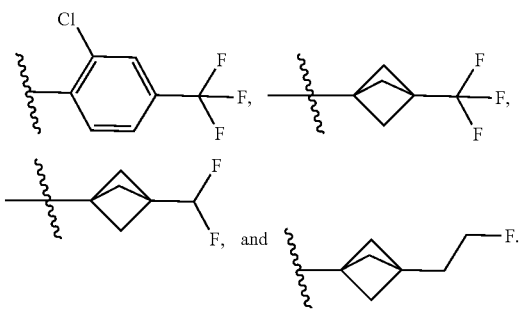

In some embodiments, the compound of Formula I, I', or I" is a compound of Formula IV-a-IV-h:

IV-a

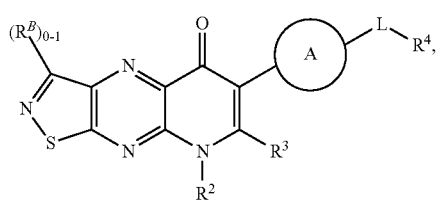

IV-b

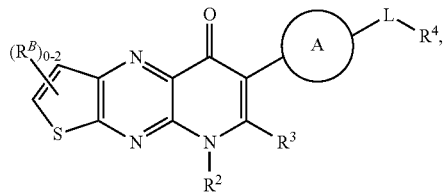

IV-c

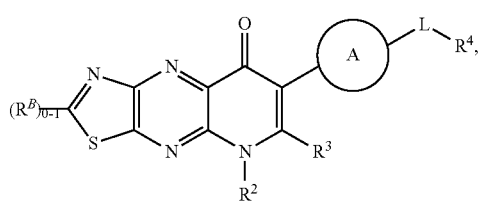

IV-d

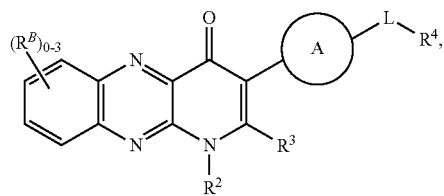

IV-e

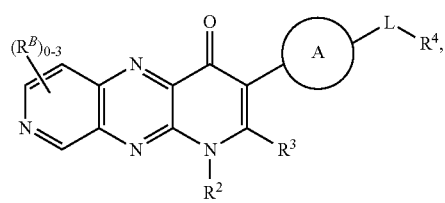

IV-f

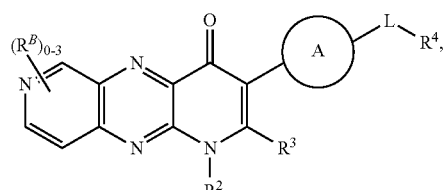

IV-g

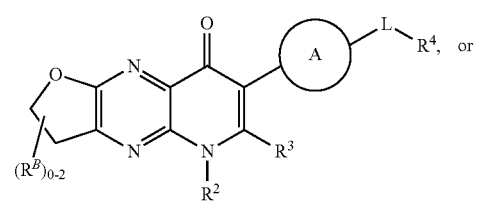

IV-h

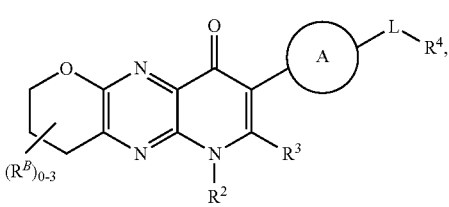

or a pharmaceutically acceptable salt thereof;
wherein $R^B$, $R^2$, $R^3$, Ring A, linker L and $R^4$, are as defined herein, both singly and in combination.

In some embodiments, the compound of Formula I, I', or I" is a compound of Formula V-a:

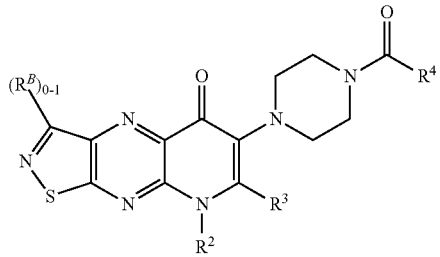

V-a or a pharmaceutically acceptable salt thereof;
wherein $R^B$, $R^2$, $R^3$, and $R^4$, are as defined herein, both singly and in combination.

In some embodiments, the compound of Formula I, I', or I" is a compound of Formula V-b:

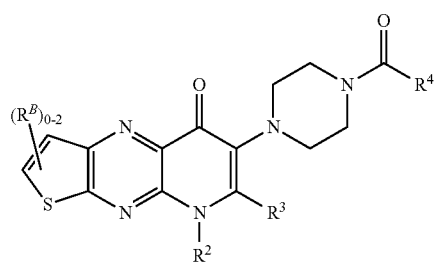

V-b or a pharmaceutically acceptable salt thereof;
wherein $R^B$, $R^2$, $R^3$, and $R^4$, are as defined herein, both singly and in combination.

In some embodiments, the compound of Formula I, I', or I" is a compound of Formula V-c:

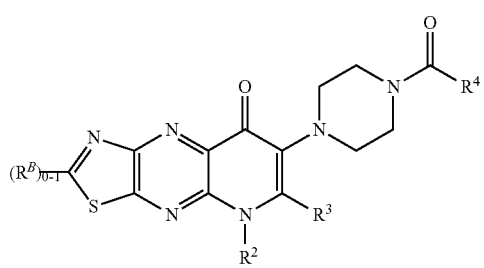

V-c or a pharmaceutically acceptable salt thereof;
wherein $R^B$, $R^2$, $R^3$, and $R^4$, are as defined herein, both singly and in combination.

In some embodiments, the compound of Formula I, I', or I" is a compound of Formula V-d:

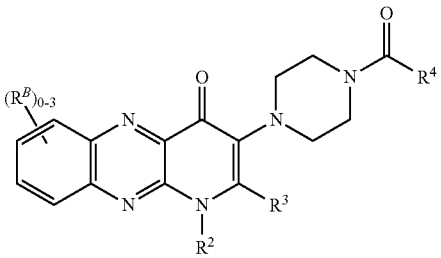

V-d or a pharmaceutically acceptable salt thereof;
wherein $R^B$, $R^2$, $R^3$, and $R^4$, are as defined herein, both singly and in combination.

In some embodiments, the compound of Formula I, I', or I" is a compound of Formula V-e:

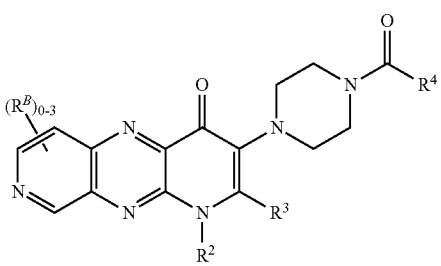

V-e or a pharmaceutically acceptable salt thereof;
wherein $R^B$, $R^2$, $R^3$, and $R^4$, are as defined herein, both singly and in combination.

In some embodiments, the compound of Formula I, I', or I" is a compound of Formula V-f:

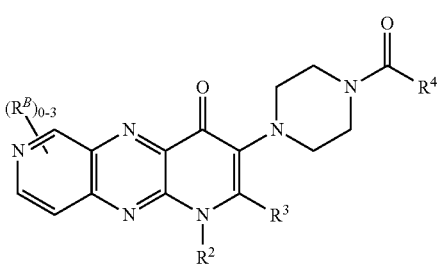

V-f or a pharmaceutically acceptable salt thereof;
wherein $R^B$, $R^2$, $R^3$, and $R^4$, are as defined herein, both singly and in combination.

In some embodiments, the compound of Formula I, I', or I" is a compound of Formula V-g:

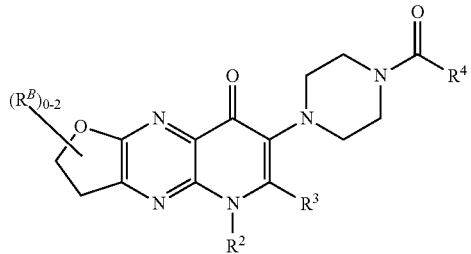

V-g or a pharmaceutically acceptable salt thereof;
wherein $R^B$, $R^2$, $R^3$, and $R^4$, are as defined herein, both singly and in combination.

In some embodiments, the compound of Formula I, I', or I" is a compound of Formula V-h:

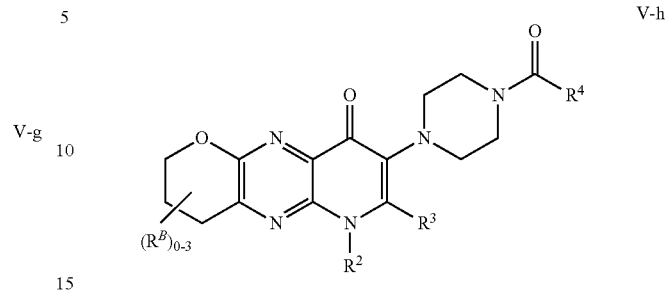

V-h or a pharmaceutically acceptable salt thereof;
wherein $R^B$, $R^2$, $R^3$, and $R^4$, are as defined herein, both singly and in combination.

In some embodiments, the compound of Formula I, I', or I" is selected from one of those depicted in Table 1 or Table 1a, or a pharmaceutically acceptable salt thereof. Table 1 or Table 1a, identifies compounds by their IUPAC name and Table 2 or Table 2a lists the same compounds and shows their chemical structure. In the event of any discrepancy between Table 1's or Table 1a's name for a compound and Table 2's or Table 2a's structure for that same compound, Table 2's or Table 2a's compound structures will dominate and identify the compound corresponding to each respective compound number (I—#) in Table 1 or 1a.

TABLE 1

| Compound No. | IUPAC Name |
|---|---|
| I-1 | N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxopyrido[2,3-b]pyrazin-5(8H)-yl)acetamide |
| I-2 | N-(2-chloro-4-(trifluoromethyl)phenyl)-2-(6-ethyl-3-methyl-7-(4-(1-methyl-1H-pyrazole-4-carbonyl)piperazin-1-yl)-8-oxopyrido[2,3-b]pyrazin-5(8H)-yl)acetamide |
| I-3 | N-(2-chloro-4-(trifluoromethyl)phenyl)-2-(6-ethyl-7-(4-(3-hydroxypicolinoyl)piperazin-1-yl)-3-methyl-8-oxopyrido[2,3-b]pyrazin-5(8H)-yl)acetamide |
| I-4 | N-(2-chloro-4-(trifluoromethyl)phenyl)-2-(6-ethyl-7-(4-(3-hydroxy-2-methoxyisonicotinoyl)piperazin-1-yl)-3-methyl-8-oxopyrido[2,3-b]pyrazin-5(8H)-yl)acetamide |
| I-5 | 2-(7-(4-acetylpiperazin-1-yl)-6-ethyl-3-methyl-8-oxopyrido[2,3-b]pyrazin-5(8H)-yl)-N-(2-chloro-4-(trifluoromethyl)phenyl)acetamide |
| I-6 | N-(2-chloro-4-(trifluoromethyl)phenyl)-2-(6-ethyl-7-(4-(4-hydroxy-2-methoxynicotinoyl)piperazin-1-yl)-3-methyl-8-oxopyrido[2,3-b]pyrazin-5(8H)-yl)acetamide |
| I-7 | N-(2-chloro-4-(trifluoromethyl)phenyl)-2-(6-ethyl-7-(4-(5-hydroxy-6-methylpyrimidine-4-carbonyl)piperazin-1-yl)-2-(2-methoxypyridin-4-yl)-8-oxopyrido[2,3-b]pyrazin-5(8H)-yl)acetamide |
| I-8 | (E)-N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(prop-1-en-1-yl)pyrido[2,3-b]pyrazin-5(8H)-yl)acetamide |
| I-9 | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(prop-1-en-2-yl)pyrido[2,3-b]pyrazin-5(8H)-yl)acetamide |
| I-10 | N-(2-chloro-4-(trifluoromethyl)phenyl)-2-(2-cyclopropyl-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-11 | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(prop-1-yn-1-yl)pyrido[2,3-b]pyrazin-5(8H)-yl)acetamide |
| I-12 | N-(2-chloro-4-(trifluoromethyl)phenyl)-2-(6-ethyl-7-(4-(5-hydroxy-6-methylpyrimidine-4-carbonyl)piperazin-1-yl)-2-methoxy-3-methyl-8-oxopyrido[2,3-b]pyrazin-5(8H)-yl)acetamide |
| I-13 | N-(2-chloro-4-(trifluoromethyl)phenyl)-2-(2-(difluoromethyl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-14 | N-(2-chloro-4-(trifluoromethyl)phenyl)-2-(2-(dimethylamino)-6-ethyl-7-(4-(5-hydroxy-6-methylpyrimidine-4-carbonyl)piperazin-1-yl)-8-oxopyrido[2,3-b]pyrazin-5(8H)-yl)acetamide |

TABLE 1-continued

| Compound No. | IUPAC Name |
|---|---|
| I-15 | (E)-N-(2-chloro-4-(trifluoromethyl)phenyl)-2-(2-(2-ethoxyvinyl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-16 | rac-N-(2-chloro-4-(trifluoromethyl)phenyl)-2-(6-ethyl-7-(5-(5-hydroxy-6-methylpyrimidine-4-carbonyl)-2,5-diazabicyclo[4.2.0]octan-2-yl)-2-methoxy-3-methyl-8-oxopyrido[2,3-b]pyrazin-5(8H)-yl)acetamide (racemic mixture, trans) |
| I-17 | N-(2-chloro-4-(trifluoromethyl)phenyl)-2-(2-cyclopropyl-6-ethyl-7-(4-(5-hydroxy-6-methylpyrimidine-4-carbonyl)piperazin-1-yl)-3-methyl-8-oxopyrido[2,3-b]pyrazin-5(8H)-yl)acetamide |
| I-18 | N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-vinylpyrido[2,3-b]pyrazin-5(8H)-yl)acetamide |
| I-19 | N-(2-chloro-4-(trifluoromethyl)phenyl)-2-(2-chloro-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-20 | N-(2-chloro-4-(trifluoromethyl)phenyl)-2-(6-ethyl-7-(4-(5-hydroxy-6-methylpyrimidine-4-carbonyl)piperazin-1-yl)-2-(methylamino)-8-oxopyrido[2,3-b]pyrazin-5(8H)-yl)acetamide |
| I-21 | (E)-N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(prop-1-en-1-yl)pyrido[2,3-b]pyrazin-5(8H)-yl)acetamide |
| I-22 | N-(2-chloro-4-(trifluoromethyl)phenyl)-2-(6-ethyl-7-(4-(5-hydroxy-6-methylpyrimidine-4-carbonyl)piperazin-1-yl)-2-(2-hydroxypropan-2-yl)-3-methyl-8-oxopyrido[2,3-b]pyrazin-5(8H)-yl)acetamide |
| I-23 | N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(prop-1-en-2-yl)pyrido[2,3-b]pyrazin-5(8H)-yl)acetamide |
| I-24 | N-(2-chloro-4-(trifluoromethyl)phenyl)-2-(6-ethyl-2-hydroxy-7-(4-(5-hydroxy-6-methylpyrimidine-4-carbonyl)piperazin-1-yl)-8-oxopyrido[2,3-b]pyrazin-5(8H)-yl)acetamide |
| I-25 | N-(2-chloro-4-(trifluoromethyl)phenyl)-2-(6-ethyl-7-(4-(5-hydroxy-6-methylpyrimidine-4-carbonyl)piperazin-1-yl)-2-(hydroxymethyl)-8-oxopyrido[2,3-b]pyrazin-5(8H)-yl)acetamide |
| I-26 | N-(2-chloro-4-(trifluoromethyl)phenyl)-2-(2-(difluoromethoxy)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-27 | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(2-oxopyrrolidin-1-yl)pyrido[2,3-b]pyrazin-5(8H)-yl)acetamide |
| I-28 | N-(2-chloro-4-(trifluoromethyl)phenyl)-2-(2-(difluoromethyl)-6-ethyl-7-(4-(5-hydroxy-6-methylpyrimidine-4-carbonyl)piperazin-1-yl)-3-methyl-8-oxopyrido[2,3-b]pyrazin-5(8H)-yl)acetamide |
| I-29 | N-(2-chloro-4-(trifluoromethyl)phenyl)-2-(2-(dimethylamino)-6-ethyl-7-(4-(5-hydroxy-6-methylpyrimidine-4-carbonyl)piperazin-1-yl)-3-methyl-8-oxopyrido[2,3-b]pyrazin-5(8H)-yl)acetamide |
| I-30 | N-(2-chloro-4-(trifluoromethyl)phenyl)-2-(6-ethyl-7-(4-(5-hydroxy-6-methylpyrimidine-4-carbonyl)piperazin-1-yl)-2-(N-methylacetamido)-8-oxopyrido[2,3-b]pyrazin-5(8H)-yl)acetamide |
| I-31 | 2-(2-acetamido-6-ethyl-7-(4-(5-hydroxy-6-methylpyrimidine-4-carbonyl)piperazin-1-yl)-8-oxopyrido[2,3-b]pyrazin-5(8H)-yl)-N-(2-chloro-4-(trifluoromethyl)phenyl)acetamide |
| I-32 | N-(2-chloro-4-(trifluoromethyl)phenyl)-2-(6-ethyl-7-(4-(4-hydroxy-3-methyl-1H-pyrazole-5-carbonyl)piperazin-1-yl)-3-methyl-8-oxopyrido[2,3-b]pyrazin-5(8H)-yl)acetamide |
| I-33 | N-(2-chloro-4-(trifluoromethyl)phenyl)-2-(6-ethyl-7-(4-(7-hydroxy-1H-indazole-6-carbonyl)piperazin-1-yl)-3-methyl-8-oxopyrido[2,3-b]pyrazin-5(8H)-yl)acetamide |
| I-34 | rac-N-(2-chloro-4-(trifluoromethyl)phenyl)-2-(2-(dimethylamino)-6-ethyl-7-(-5-(5-hydroxy-6-methylpyrimidine-4-carbonyl)-2,5-diazabicyclo[4.2.0]octan-2-yl)-8-oxopyrido[2,3-b]pyrazin-5(8H)-yl)acetamide (racemic mixture, trans) |
| I-35 | N-(2-chloro-4-(trifluoromethyl)phenyl)-2-(2-((dihydrofuran-3(2H)-ylidene)methyl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-36 | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-((tetrahydro-4H-pyran-4-ylidene)methyl)pyrido[2,3-b]pyrazin-5(8H)-yl)acetamide |

TABLE 1-continued

| Compound No. | IUPAC Name |
|---|---|
| I-37 | N-(2-chloro-4-(trifluoromethyl)phenyl)-2-(6-ethyl-7-(4-(5-hydroxy-6-methylpyrimidine-4-carbonyl)piperazin-1-yl)-2-(2-methylprop-1-en-1-yl)-8-oxopyrido[2,3-b]pyrazin-5(8H)-yl)acetamide |
| I-38 | N-(2-chloro-4-(trifluoromethyl)phenyl)-2-(2-(cyclobutylidenemethyl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-39 | N-(2-chloro-4-(trifluoromethyl)phenyl)-2-(2-(dimethylamino)-6-ethyl-7-(-5-(5-hydroxy-6-methylpyrimidine-4-carbonyl)-2,5-diazabicyclo[4.2.0]octan-2-yl)-8-oxopyrido[2,3-b]pyrazin-5(8H)-yl)acetamide (single stereoisomer, first eluting compound as stereoisomer 1, trans) |
| I-40 | N-(2-chloro-4-(trifluoromethyl)phenyl)-2-(2-(dimethylamino)-6-ethyl-7-(-5-(5-hydroxy-6-methylpyrimidine-4-carbonyl)-2,5-diazabicyclo[4.2.0]octan-2-yl)-8-oxopyrido[2,3-b]pyrazin-5(8H)-yl)acetamide (single stereoisomer, second eluting compound as stereoisomer 2, trans) |
| I-41 | N-(2-chloro-4-(trifluoromethyl)phenyl)-2-(6-ethyl-7-(4-(5-hydroxy-6-methylpyrimidine-4-carbonyl)piperazin-1-yl)-2-(2-hydroxyethyl)-8-oxopyrido[2,3-b]pyrazin-5(8H)-yl)acetamide |
| I-42 | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(piperidin-1-yl)pyrido[2,3-b]pyrazin-5(8H)-yl)acetamide |
| I-43 | N-(2-chloro-4-(trifluoromethyl)phenyl)-2-(3-chloro-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-44 | N-(2-chloro-4-(trifluoromethyl)phenyl)-2-(6-ethyl-2-(3-hydroxy-3-methylazetidin-1-yl)-7-(4-(5-hydroxy-6-methylpyrimidine-4-carbonyl)piperazin-1-yl)-8-oxopyrido[2,3-b]pyrazin-5(8H)-yl)acetamide |
| I-45 | N-(2-chloro-4-(trifluoromethyl)phenyl)-2-(6-ethyl-7-(4-(5-hydroxy-6-methylpyrimidine-4-carbonyl)piperazin-1-yl)-2-(3-hydroxyazetidin-1-yl)-8-oxopyrido[2,3-b]pyrazin-5(8H)-yl)acetamide |
| I-46 | N-(2-chloro-4-(trifluoromethyl)phenyl)-2-(6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-47 | N-(2-chloro-4-(trifluoromethyl)phenyl)-2-(6-ethyl-2-(3-hydroxy-3-methylpyrrolidin-1-yl)-7-(4-(5-hydroxy-6-methylpyrimidine-4-carbonyl)piperazin-1-yl)-8-oxopyrido[2,3-b]pyrazin-5(8H)-yl)acetamide |
| I-48 | 5-(2-((2-chloro-4-(trifluoromethyl)phenyl)amino)-2-oxoethyl)-6-ethyl-7-(4-(5-hydroxy-6-methylpyrimidine-4-carbonyl)piperazin-1-yl)-N,N-dimethyl-8-oxo-5,8-dihydropyrido[2,3-b]pyrazine-2-carboxamide |
| I-49 | N-(2-chloro-4-(trifluoromethyl)phenyl)-2-(6-ethyl-7-(4-(5-hydroxy-6-methylpyrimidine-4-carbonyl)piperazin-1-yl)-2-(morpholinomethyl)-8-oxopyrido[2,3-b]pyrazin-5(8H)-yl)acetamide |
| I-50 | 5-(2-((2-chloro-4-(trifluoromethyl)phenyl)amino)-2-oxoethyl)-6-ethyl-7-(4-(5-hydroxy-6-methylpyrimidine-4-carbonyl)piperazin-1-yl)-8-oxo-5,8-dihydropyrido[2,3-b]pyrazine-2-carboxamide |
| I-51 | N-(2-chloro-4-(trifluoromethyl)phenyl)-2-(2-(dimethylamino)-6-ethyl-7-(4-(4-hydroxy-2-methoxynicotinoyl)piperazin-1-yl)-8-oxopyrido[2,3-b]pyrazin-5(8H)-yl)acetamide |
| I-52 | N-(2-chloro-4-(trifluoromethyl)phenyl)-2-(6-ethyl-7-(4-(5-hydroxy-6-methylpyrimidine-4-carbonyl)piperazin-1-yl)-2-morpholino-8-oxopyrido[2,3-b]pyrazin-5(8H)-yl)acetamide |
| I-53 | 2-(2-(azetidin-1-yl)-6-ethyl-7-(4-(5-hydroxy-6-methylpyrimidine-4-carbonyl)piperazin-1-yl)-8-oxopyrido[2,3-b]pyrazin-5(8H)-yl)-N-(2-chloro-4-(trifluoromethyl)phenyl)acetamide |
| I-54 | 5-(2-((2-chloro-4-(trifluoromethyl)phenyl)amino)-2-oxoethyl)-6-ethyl-7-(4-(5-hydroxy-6-methylpyrimidine-4-carbonyl)piperazin-1-yl)-N-methyl-8-oxo-5,8-dihydropyrido[2,3-b]pyrazine-2-carboxamide |
| I-55 | (E)-N-(2-chloro-4-(trifluoromethyl)phenyl)-2-(6-ethyl-7-(4-(5-hydroxy-6-methylpyrimidine-4-carbonyl)piperazin-1-yl)-2-(3-methoxyprop-1-en-1-yl)-8-oxopyrido[2,3-b]pyrazin-5(8H)-yl)acetamide |
| I-56 | (R)-N-(2-chloro-4-(trifluoromethyl)phenyl)-2-(6-ethyl-7-(4-(5-hydroxy-6-methylpyrimidine-4-carbonyl)piperazin-1-yl)-2-(3-hydroxypyrrolidin-1-yl)-8-oxopyrido[2,3-b]pyrazin-5(8H)-yl)acetamide |
| I-57 | (R)-N-(2-chloro-4-(trifluoromethyl)phenyl)-2-(2-(dimethylamino)-6-ethyl-7-(4-(5-hydroxy-6-methylpyrimidine-4-carbonyl)-3-methylpiperazin-1-yl)-8-oxopyrido[2,3-b]pyrazin-5(8H)-yl)acetamide |
| I-58 | N-(2-chloro-4-(trifluoromethyl)phenyl)-2-(2-(cyclopropyl(methyl)amino)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-59 | N-(2-chloro-4-(trifluoromethyl)phenyl)-2-(6-ethyl-2-((3-hydroxy-3-methylcyclobutyl)(methyl)amino)-7-(4-(5-hydroxy-6-methylpyrimidine-4-carbonyl)piperazin-1-yl)-8-oxopyrido[2,3-b]pyrazin-5(8H)-yl)acetamide |

TABLE 1-continued

| Compound No. | IUPAC Name |
| --- | --- |
| I-60 | N-(2-chloro-4-(trifluoromethyl)phenyl)-2-(6-ethyl-7-(4-(5-hydroxy-6-methylpyrimidine-4-carbonyl)piperazin-1-yl)-2-((3-methoxycyclobutyl)(methyl)amino)-8-oxopyrido[2,3-b]pyrazin-5(8H)-yl)acetamide |
| I-61 | N-(2-chloro-4-(trifluoromethyl)phenyl)-2-(7-ethyl-6-(4-(5-hydroxy-6-methylpyrimidine-4-carbonyl)piperazin-1-yl)-2-methyl-5-oxopyrido[2,3-b]thieno[3,2-e]pyrazin-8(5H)-yl)acetamide |
| I-62 | N-(2-chloro-4-(trifluoromethyl)phenyl)-2-(6-ethyl-7-(4-(5-fluoro-3-hydroxy-2-methoxyisonicotinoyl)piperazin-1-yl)-3-methyl-8-oxopyrido[2,3-b]pyrazin-5(8H)-yl)acetamide |
| I-63 | N-(2-chloro-4-(trifluoromethyl)phenyl)-2-(6-ethyl-7-(4-(5-hydroxy-6-methylpyrimidine-4-carbonyl)piperazin-1-yl)-3-methyl-2-(1-methyl-1H-pyrazol-4-yl)-8-oxopyrido[2,3-b]pyrazin-5(8H)-yl)acetamide |
| I-64 | N-(2-chloro-4-(trifluoromethyl)phenyl)-2-(6-ethyl-7-(4-(5-hydroxy-6-methylpyrimidine-4-carbonyl)piperazin-1-yl)-2,3-dimethyl-8-oxopyrido[2,3-b]pyrazin-5(8H)-yl)acetamide |
| I-65 | N-(2-chloro-4-(trifluoromethyl)phenyl)-2-(6-ethyl-7-(4-(5-hydroxy-6-methylpyrimidine-4-carbonyl)piperazin-1-yl)-2-(2-methoxypyridin-4-yl)-3-methyl-8-oxopyrido[2,3-b]pyrazin-5(8H)-yl)acetamide |
| I-66 | N-(2-chloro-4-(trifluoromethyl)phenyl)-2-(6-ethyl-7-(4-(5-hydroxy-6-methylpyrimidine-4-carbonyl)piperazin-1-yl)-2-(3-methoxyazetidin-1-yl)-8-oxopyrido[2,3-b]pyrazin-5(8H)-yl)acetamide |
| I-67 | N-(2-chloro-4-(trifluoromethyl)phenyl)-2-(7-(4-(2,6-dihydroxybenzoyl)piperazin-1-yl)-6-ethyl-3-methyl-8-oxopyrido[2,3-b]pyrazin-5(8H)-yl)acetamide |
| I-68 | N-(2-chloro-4-(trifluoromethyl)phenyl)-2-(6-ethyl-7-(4-(7-hydroxy-2,3-dihydrofuro[3,2-c]pyridine-6-carbonyl)piperazin-1-yl)-3-methyl-8-oxopyrido[2,3-b]pyrazin-5(8H)-yl)acetamide |
| I-69 | N-(2-chloro-4-(trifluoromethyl)phenyl)-2-(6-ethyl-7-(4-(4-hydroxy-2,3-dihydrofuro[2,3-c]pyridine-5-carbonyl)piperazin-1-yl)-3-methyl-8-oxopyrido[2,3-b]pyrazin-5(8H)-yl)acetamide |
| I-70 | N-(2-chloro-4-(trifluoromethyl)phenyl)-2-(6-ethyl-3-methyl-8-oxo-7-(4-(2-oxo-2,3-dihydrobenzo[d]oxazole-4-carbonyl)piperazin-1-yl)pyrido[2,3-b]pyrazin-5(8H)-yl)acetamide |
| I-71 | N-(2-chloro-4-(trifluoromethyl)phenyl)-2-(6-ethyl-7-(4-(6-hydroxy-1H-benzo[d]imidazole-7-carbonyl)piperazin-1-yl)-3-methyl-8-oxopyrido[2,3-b]pyrazin-5(8H)-yl)acetamide |
| I-72 | N-(2-chloro-4-(trifluoromethyl)phenyl)-2-(6-ethyl-7-(4-(5-hydroxy-6-methylpyrimidine-4-carbonyl)piperazin-1-yl)-2-((2-methoxyethyl)(methyl)amino)-8-oxopyrido[2,3-b]pyrazin-5(8H)-yl)acetamide |
| I-73 | N-(2-chloro-4-(trifluoromethyl)phenyl)-2-(6-ethyl-7-(4-(5-hydroxy-6-methylpyrimidine-4-carbonyl)piperazin-1-yl)-2-((2-hydroxyethyl)(methyl)amino)-8-oxopyrido[2,3-b]pyrazin-5(8H)-yl)acetamide |
| I-74 | N-(2-chloro-4-(trifluoromethyl)phenyl)-2-(6-ethyl-2-(ethyl(methyl)amino)-7-(4-(5-hydroxy-6-methylpyrimidine-4-carbonyl)piperazin-1-yl)-8-oxopyrido[2,3-b]pyrazin-5(8H)-yl)acetamide |
| I-75 | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(pyrrolidin-1-yl)pyrido[2,3-b]pyrazin-5(8H)-yl)acetamide |
| I-76 | N-(2-chloro-4-(trifluoromethyl)phenyl)-2-(6-ethyl-7-(4-(5-hydroxy-1H-indazole-4-carbonyl)piperazin-1-yl)-3-methyl-8-oxopyrido[2,3-b]pyrazin-5(8H)-yl)acetamide |
| I-77 | N-(2-chloro-4-(trifluoromethyl)phenyl)-2-(6-ethyl-7-(4-(4-hydroxyisoxazole-3-carbonyl)piperazin-1-yl)-3-methyl-8-oxopyrido[2,3-b]pyrazin-5(8H)-yl)acetamide |
| I-79 | N-(2-chloro-4-(trifluoromethyl)phenyl)-2-(6-ethyl-7-(4-(5-hydroxy-6-methylpyrimidine-4-carbonyl)piperazin-1-yl)-2-(1-methyl-1H-pyrazol-4-yl)-8-oxopyrido[2,3-b]pyrazin-5(8H)-yl)acetamide |
| I-80 | N-(2-chloro-4-(trifluoromethyl)phenyl)-2-(6-ethyl-7-(4-(5-hydroxy-6-methylpyrimidine-4-carbonyl)piperazin-1-yl)-2-methyl-8-oxopyrido[2,3-b]pyrazin-5(8H)-yl)acetamide |
| I-81 | N-(2-chloro-4-(trifluoromethyl)phenyl)-2-(6-ethyl-7-(4-(5-hydroxy-6-methylpyrimidine-4-carbonyl)piperazin-1-yl)-2-methoxy-8-oxopyrido[2,3-b]pyrazin-5(8H)-yl)acetamide |
| I-82 | N-(2-chloro-4-(trifluoromethyl)phenyl)-2-(2-(3,6-dihydro-2H-pyran-4-yl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-83 | N-(2-chloro-4-(trifluoromethyl)phenyl)-2-(2-cyano-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-84 | N-(2-chloro-4-(trifluoromethyl)phenyl)-2-(6-ethyl-7-(4-(5-hydroxy-6-methylpyrimidine-4-carbonyl)piperazin-1-yl)-2-(2-hydroxypropan-2-yl)-8-oxopyrido[2,3-b]pyrazin-5(8H)-yl)acetamide |

TABLE 1-continued

| Compound No. | IUPAC Name |
| --- | --- |
| I-86 | 2-(2-bromo-6-ethyl-7-(4-(5-hydroxy-6-methylpyrimidine-4-carbonyl)piperazin-1-yl)-8-oxopyrido[2,3-b]pyrazin-5(8H)-yl)-N-(2-chloro-4-(trifluoromethyl)phenyl)acetamide |
| I-87 | N-(2-chloro-4-(trifluoromethyl)phenyl)-2-(2-(dimethylamino)-6-ethyl-7-(4-(5-hydroxy-6-methylpyrimidine-4-carbonyl)-3,3-dimethylpiperazin-1-yl)-8-oxopyrido[2,3-b]pyrazin-5(8H)-yl)acetamide |
| I-88 | (S)-N-(2-chloro-4-(trifluoromethyl)phenyl)-2-(6-ethyl-7-(4-(5-hydroxy-6-methylpyrimidine-4-carbonyl)piperazin-1-yl)-2-(3-hydroxypyrrolidin-1-yl)-8-oxopyrido[2,3-b]pyrazin-5(8H)-yl)acetamide |
| I-89 | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(piperazin-1-yl)pyrido[2,3-b]pyrazin-5(8H)-yl)acetamide |
| I-90 | N-(2-chloro-4-(trifluoromethyl)phenyl)-2-(2-(2,5-dihydrofuran-3-yl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-91 | N-(2-chloro-4-(trifluoromethyl)phenyl)-2-(2-(2,3-dihydro-1H-imidazo[1,2-b]pyrazol-1-yl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-92 | N-(2-chloro-4-(trifluoromethyl)phenyl)-2-(6-ethyl-7-(4-(5-hydroxy-6-methylpyrimidine-4-carbonyl)piperazin-1-yl)-2-(((1r,3r)-3-methoxycyclobutyl)(methyl)amino)-8-oxopyrido[2,3-b]pyrazin-5(8H)-yl)acetamide |
| I-93 | 2-(2-(2-azabicyclo[3.1.0]hexan-2-yl)-6-ethyl-7-(4-(5-hydroxy-6-methylpyrimidine-4-carbonyl)piperazin-1-yl)-8-oxopyrido[2,3-b]pyrazin-5(8H)-yl)-N-(2-chloro-4-(trifluoromethyl)phenyl)acetamide |
| I-94 | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(1H-pyrazol-4-yl)pyrido[2,3-b]pyrazin-5(8H)-yl)acetamide |
| I-95 | N-(2-chloro-4-(trifluoromethyl)phenyl)-2-(6-ethyl-7-(4-(5-hydroxy-6-methylpyrimidine-4-carbonyl)piperazin-1-yl)-2-methyl-8-oxopyrido[2,3-b]thiazolo[4,5-e]pyrazin-5(8H)-yl)acetamide |
| I-96 | N-(2-chloro-4-(trifluoromethyl)phenyl)-2-(2-(dimethylamino)-6-ethyl-7-(4-(5-hydroxy-6-methylpyrimidine-4-carbonyl)-3-(methoxymethyl)piperazin-1-yl)-8-oxopyrido[2,3-b]pyrazin-5(8H)-yl)acetamide (single stereoisomer, second eluting compound as stereoisomer 2) |
| I-97 | rac-N-(2-chloro-4-(trifluoromethyl)phenyl)-2-(6-ethyl-7-(-5-(5-hydroxy-6-methylpyrimidine-4-carbonyl)-2,5-diazabicyclo[4.2.0]octan-2-yl)-2-(methylamino)-8-oxopyrido[2,3-b]pyrazin-5(8H)-yl)acetamide (racemic mixture, trans) |
| I-98 | (S)-N-(2-chloro-4-(trifluoromethyl)phenyl)-2-(2-(dimethylamino)-6-ethyl-7-(4-(5-hydroxy-6-methylpyrimidine-4-carbonyl)-2-methylpiperazin-1-yl)-8-oxopyrido[2,3-b]pyrazin-5(8H)-yl)acetamide |
| I-99 | (R)-N-(2-chloro-4-(trifluoromethyl)phenyl)-2-(2-(dimethylamino)-6-ethyl-7-(4-(5-hydroxy-6-methylpyrimidine-4-carbonyl)-2-methylpiperazin-1-yl)-8-oxopyrido[2,3-b]pyrazin-5(8H)-yl)acetamide |
| I-100 | N-(2-chloro-4-(trifluoromethyl)phenyl)-2-(2-cyclopropyl-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)acetamide |
| I-101 | 2-(2-(bis(methyl-d3)amino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(2-chloro-4-(trifluoromethyl)phenyl)acetamide |
| I-102 | N-(2-chloro-4-(trifluoromethyl)phenyl)-2-(2-cyclopropoxy-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)acetamide |
| I-103 | 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(2-methyl-4-(trifluoromethyl)phenyl)acetamide |
| I-104 | 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(4-(trifluoromethyl)phenyl)acetamide |
| I-105 | N-(2-chloro-4-(trifluoromethyl)phenyl)-2-(6-ethyl-7-((1S,6S)-5-(5-hydroxy-6-methylpyrimidine-4-carbonyl)-2,5-diazabicyclo[4.2.0]octan-2-yl)-8-oxo-2-(pyrrolidin-1-yl)pyrido[2,3-b]pyrazin-5(8H)-yl)acetamide |
| I-106 | rac-N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5(8H)-yl)acetamide (racemic mixture, cis) |

TABLE 1-continued

| Compound No. | IUPAC Name |
| --- | --- |
| I-107 | N-(2-chloro-4-(trifluoromethyl)phenyl)-2-(2-(dimethylamino)-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5(8H)-yl)acetamide |
| I-108 | 2-(2-(dimethylamino)-6-ethyl-7-(4-(5-hydroxy-6-methylpyrimidine-4-carbonyl)piperazin-1-yl)-8-oxopyrido[2,3-b]pyrazin-5(8H)-yl)-N-(3-(trifluoromethyl)bicyclo[1.1.1]pentan-1-yl)acetamide |
| I-109 | N-(2-chloro-4-(trifluoromethyl)phenyl)-2-(6-(dimethylamino)-2-ethyl-7-fluoro-3-(4-(5-hydroxy-6-methylpyrimidine-4-carbonyl)piperazin-1-yl)-4-oxo-1,5-naphthyridin-1(4H)-yl)acetamide |
| I-110 | 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(3-(trifluoromethyl)bicyclo[1.1.1]pentan-1-yl)acetamide |
| I-111 | N-(2-chloro-4-(trifluoromethyl)phenyl)-2-(7-ethyl-6-((1S,6S)-5-(5-hydroxy-6-methylpyrimidine-4-carbonyl)-2,5-diazabicyclo[4.2.0]octan-2-yl)-3-(2-methylprop-1-en-1-yl)-5-oxopyrido[3,2-e][1,2,4]triazin-8(5H)-yl)acetamide |
| I-112 | N-(2-chloro-4-(trifluoromethyl)phenyl)-2-(7-ethyl-6-(4-(5-hydroxy-6-methylpyrimidine-4-carbonyl)piperazin-1-yl)-2-methyl-5-oxofuro[2,3-b]pyrido[3,2-e]pyrazin-8(5H)-yl)acetamide |
| I-113 | N-(2-chloro-4-(trifluoromethyl)phenyl)-2-(6-ethyl-7-(4-(5-hydroxy-6-methylpyrimidine-4-carbonyl)piperazin-1-yl)-2-methyl-8-oxopyrido[2,3-b]thieno[2,3-e]pyrazin-5(8H)-yl)acetamide |
| I-114 | N-(2-chloro-4-(trifluoromethyl)phenyl)-2-(6-ethyl-7-((1S,6S)-5-(5-hydroxy-6-methylpyrimidine-4-carbonyl)-2,5-diazabicyclo[4.2.0]octan-2-yl)-2-methyl-8-oxopyrido[2,3-b]thiazolo[4,5-e]pyrazin-5(8H)-yl)acetamide |
| I-115 | 2-(7-ethyl-6-(4-(5-hydroxy-6-methylpyrimidine-4-carbonyl)piperazin-1-yl)-2-methyl-5-oxopyrido[2,3-b]thieno[3,2-e]pyrazin-8(5H)-yl)-N-(3-(trifluoromethyl)bicyclo[1.1.1]pentan-1-yl)acetamide |
| I-116 | N-(2-chloro-4-(trifluoromethyl)phenyl)-2-(6-ethyl-7-(4-(5-hydroxy-6-methylpyrimidine-4-carbonyl)piperazin-1-yl)-1-methyl-8-oxo-1,2,3,8-tetrahydro-5H-pyrido[2,3-b]pyrrolo[2,3-e]pyrazin-5-yl)acetamide |
| I-117 | N-(2-chloro-4-(trifluoromethyl)phenyl)-2-(6-ethyl-7-(4-(5-hydroxy-6-methylpyrimidine-4-carbonyl)piperazin-1-yl)-2-((3-methoxycyclobutylidene)methyl)-8-oxopyrido[2,3-b]pyrazin-5(8H)-yl)acetamide |
| I-118 | (S)-N-(2-chloro-4-(trifluoromethyl)phenyl)-2-(3-(dimethylamino)-7-ethyl-6-(4-(5-hydroxy-6-methylpyrimidine-4-carbonyl)-2-methylpiperazin-1-yl)-5-oxopyrido[3,2-e][1,2,4]triazin-8(5H)-yl)acetamide |
| I-119 | N-(2-chloro-4-(trifluoromethyl)phenyl)-2-(2-(cyclopropyl(methyl)amino)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5(8H)-yl)acetamide (single stereoisomer, trans) |
| I-120 | 2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]-N-[4-(trifluoromethoxy)phenyl]acetamide |
| I-121 | 2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]-N-[2-fluoro-4-(trifluoromethyl)phenyl]acetamide |
| I-122 | 2-(2-((1R*,5S*)-2-azabicyclo[3.1.0]hexan-2-yl)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(2-fluoro-4-(trifluoromethyl)phenyl)acetamide |
| I-123 | 2-{11-[(4aS,7aS)-4-(5-hydroxy-6-methylpyrimidine-4-carbonyl)-octahydro-1H-cyclopenta[b]pyrazin-1-yl]-12-ethyl-5-methyl-10-oxo-4-oxa-2,8,13-triazatricyclo[7.4.0.0^{3,7}]trideca-1,3(7),5,8,11-pentaen-13-yl}-N-[2-chloro-4-(trifluoromethyl)phenyl]acetamide |
| I-124 | N-[2-chloro-4-(trifluoromethyl)phenyl]-2-[6-(dimethylamino)-2-ethyl-3-[(1S,6S)-5-(5-hydroxy-6-methylpyrimidine-4-carbonyl)-2,5-diazabicyclo[4.2.0]octan-2-yl]-4-oxo-1,4-dihydro-1,8-naphthyridin-1-yl]acetamide |
| I-125 | 2-{2-cyclopropyl-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl}-N-[2-fluoro-4-(trifluoromethyl)phenyl]acetamide |
| I-126 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2,3-dimethyl-8-oxo-5H,8H-pyrido[2,3-b]pyrazin-5-yl}acetamide |

TABLE 1-continued

| Compound No. | IUPAC Name |
|---|---|
| I-127 | N-[2-chloro-4-(trifluoromethyl)phenyl]-2-{6-ethyl-7-[(1S,6S)-5-(4-hydroxy-2-methoxy-5-methylpyridine-3-carbonyl)-2,5-diazabicyclo[4.2.0]octan-2-yl]-2,3-dimethyl-8-oxo-5H,8H-pyrido[2,3-b]pyrazin-5-yl}acetamide |
| I-128 | 2-(6-ethyl-7-((1S,6S)-5-(5-hydroxy-6-methylpyrimidine-4-carbonyl)-2,5-diazabicyclo[4.2.0]octan-2-yl)-2,3-dimethyl-8-oxopyrido[2,3-b]pyrazin-5(8H)-yl)-N-(2-fluoro-4-(trifluoromethyl)phenyl)acetamide |
| I-129 | 2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-3-methyl-8-oxo-5H,8H-pyrido[2,3-b]pyrazin-5-yl]-N-[2-fluoro-4-(trifluoromethyl)phenyl]acetamide |
| I-130 | 2-{7-[(4aS,7aS)-4-(5-hydroxy-6-methylpyrimidine-4-carbonyl)-octahydro-1H-cyclopenta[b]pyrazin-1-yl]-2-(dimethylamino)-6-ethyl-8-oxo-5H,8H-pyrido[2,3-b]pyrazin-5-yl}-N-[2-chloro-4-(trifluoromethyl)phenyl]acetamide |
| I-131 | N-[2-chloro-4-(trifluoromethyl)phenyl]-2-{2-[cyclobutyl(methyl)amino]-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide |
| I-132 | N-[2-chloro-4-(pentafluoro-lambda6-sulfanyl)phenyl]-2-[2-(dimethylamino)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-133 | N-[2-chloro-6-fluoro-4-(trifluoromethyl)phenyl]-2-[2-(dimethylamino)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-134 | (2E)-3-[5-({[2-chloro-4-(trifluoromethyl)phenyl]carbamoyl}methyl)-6-ethyl-7-[4-(5-hydroxy-6-methylpyrimidine-4-carbonyl)piperazin-1-yl]-8-oxo-5H,8H-pyrido[2,3-b]pyrazin-2-yl]-N,N-dimethylprop-2-enamide |
| I-135 | rac-N-[2-chloro-4-(trifluoromethyl)phenyl]-2-(2-(2-ethoxyvinyl)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5(8H)-yl)acetamide (racemic mixture, trans) |
| I-136 | rac-N-[2-chloro-4-(trifluoromethyl)phenyl]-2-{2-[(1E)-2-ethoxyethenyl]-6-ethyl-7-[-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl}acetamide (racemic mixture, trans) |
| I-137 | N-[2-chloro-4-(trifluoromethyl)phenyl]-2-{6-ethyl-7-[4-(5-hydroxy-6-methylpyrimidine-4-carbonyl)piperazin-1-yl]-2-(1-methyl-1H-pyrazol-5-yl)-8-oxo-5H,8H-pyrido[2,3-b]pyrazin-5-yl}acetamide |
| I-138 | N-[2-chloro-4-(trifluoromethyl)phenyl]-2-{6-ethyl-2-[(1E)-3-hydroxy-3-methylbut-1-en-1-yl]-7-[4-(5-hydroxy-6-methylpyrimidine-4-carbonyl)piperazin-1-yl]-8-oxo-5H,8H-pyrido[2,3-b]pyrazin-5-yl}acetamide |
| I-139 | rac-N-[2-chloro-4-(trifluoromethyl)phenyl]-2-[2-(dimethylamino)-6-ethyl-7-[-5-(4-hydroxy-2-methoxypyridine-3-carbonyl)-2,5-diazabicyclo[4.2.0]octan-2-yl]-8-oxo-5H,8H-pyrido[2,3-b]pyrazin-5-yl]acetamide (racemic mixture, trans) |
| I-140 | N-[2-chloro-4-(trifluoromethyl)phenyl]-2-{6-ethyl-7-[4-(5-hydroxy-6-methylpyrimidine-4-carbonyl)piperazin-1-yl]-2-(oxetan-3-yloxy)-8-oxo-5H,8H-pyrido[2,3-b]pyrazin-5-yl}acetamide |
| I-141 | N-[2-chloro-4-(trifluoromethyl)phenyl]-2-{2-cyclobutoxy-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide |
| I-142 | N-[2-chloro-4-(trifluoromethyl)phenyl]-2-{6-ethyl-7-[4-(5-hydroxy-6-methylpyrimidine-4-carbonyl)piperazin-1-yl]-2-[(2-methylcyclobutylidene)methyl]-8-oxo-5H,8H-pyrido[2,3-b]pyrazin-5-yl}acetamide |
| I-143 | rac-N-(2-chloro-4-(trifluoromethyl)phenyl)-2-(6-ethyl-7-(4-(5-hydroxy-6-methylpyrimidine-4-carbonyl)piperazin-1-yl)-2-((2-methoxycyclobutyl)(methyl)amino)-8-oxopyrido[2,3-b]pyrazin-5(8H)-yl)acetamide (racemic mixture, trans) |
| I-144 | N-[2-chloro-4-(trifluoromethyl)phenyl]-2-{2-[(1E)-2-cyclobutylethenyl]-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide |
| I-145 | N-[2-chloro-4-(trifluoromethyl)phenyl]-2-{7-[4-(5-cyano-3-hydroxy-2-methylpyridine-4-carbonyl)piperazin-1-yl]-6-ethyl-3-methyl-8-oxo-5H,8H-pyrido[2,3-b]pyrazin-5-yl}acetamide |
| I-146 | rac-N-(2-chloro-4-(trifluoromethyl)phenyl)-2-(6-ethyl-7-(4-(5-hydroxy-6-methylpyrimidine-4-carbonyl)piperazin-1-yl)-2-((2-methoxycyclobutyl)(methyl)amino)-8-oxopyrido[2,3-b]pyrazin-5(8H)-yl)acetamide (racemic mixture, cis) |
| I-147 | N-[2-chloro-4-(trifluoromethyl)phenyl]-2-[2-(dimethylamino)-6-ethyl-7-[4-(5-hydroxy-6-methylpyrimidine-4-carbonyl)-1,4-diazepan-1-yl]-8-oxo-5H,8H-pyrido[2,3-b]pyrazin-5-yl]acetamide |

TABLE 1-continued

| Compound No. | IUPAC Name |
| --- | --- |
| I-148 | N-[2,6-difluoro-4-(trifluoromethyl)phenyl]-2-[2-(dimethylamino)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-149 | N-[2-chloro-4-(trifluoromethyl)phenyl]-2-{6-ethyl-7-[4-(5-hydroxy-6-methylpyrimidine-4-carbonyl)piperazin-1-yl]-2-[(2S)-2-methylpyrrolidin-1-yl]-8-oxo-5H,8H-pyrido[2,3-b]pyrazin-5-yl}acetamide |
| I-150 | N-[2-chloro-4-(trifluoromethyl)phenyl]-2-{6-ethyl-7-[4-(5-hydroxy-6-methylpyrimidine-4-carbonyl)piperazin-1-yl]-2-[(2R)-2-methylpyrrolidin-1-yl]-8-oxo-5H,8H-pyrido[2,3-b]pyrazin-5-yl}acetamide |
| I-151 | 2-(2-{6-azaspiro[3.4]octan-6-yl}-6-ethyl-7-[4-(5-hydroxy-6-methylpyrimidine-4-carbonyl)piperazin-1-yl]-8-oxo-5H,8H-pyrido[2,3-b]pyrazin-5-yl)-N-[2-chloro-4-(trifluoromethyl)phenyl]acetamide |
| I-152 | N-[2-chloro-4-(trifluoromethyl)phenyl]-2-{6-ethyl-7-[4-(5-hydroxy-6-methylpyrimidine-4-carbonyl)piperazin-1-yl]-2-[2-(2-hydroxypropan-2-yl)pyrrolidin-1-yl]-8-oxo-5H,8H-pyrido[2,3-b]pyrazin-5-yl}acetamide |
| I-153 | N-[2-chloro-4-(trifluoromethyl)phenyl]-2-{6-ethyl-7-[4-(5-hydroxy-6-methylpyrimidine-4-carbonyl)piperazin-1-yl]-2-[(2S)-2-(2-hydroxypropan-2-yl)pyrrolidin-1-yl]-8-oxo-5H,8H-pyrido[2,3-b]pyrazin-5-yl}acetamide |
| I-154 | N-[2-chloro-4-(trifluoromethyl)phenyl]-2-(2-{[2-(dimethylamino)ethyl](methyl)amino}-6-ethyl-7-[4-(5-hydroxy-6-methylpyrimidine-4-carbonyl)piperazin-1-yl]-8-oxo-5H,8H-pyrido[2,3-b]pyrazin-5-yl)acetamide |
| I-155 | N-[2-chloro-4-(trifluoromethyl)phenyl]-2-{2-[(1R,5S,6S)-6-(dimethylamino)-3-azabicyclo[3.1.0]hexan-3-yl]-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide |
| I-156 | 2-(2-{3-azabicyclo[3.1.0]hexan-3-yl}-6-ethyl-7-[4-(5-hydroxy-6-methylpyrimidine-4-carbonyl)piperazin-1-yl]-8-oxo-5H,8H-pyrido[2,3-b]pyrazin-5-yl)-N-[2-chloro-4-(trifluoromethyl)phenyl]acetamide |
| I-157 | N-[2-chloro-4-(trifluoromethyl)phenyl]-2-[6-ethyl-2-(1-fluoroethenyl)-7-[4-(5-hydroxy-6-methylpyrimidine-4-carbonyl)piperazin-1-yl]-8-oxo-5H,8H-pyrido[2,3-b]pyrazin-5-yl]acetamide |
| I-158 | N-[2-chloro-4-(trifluoromethyl)phenyl]-2-{7-[4-(5-cyano-3-hydroxy-2-methylpyridine-4-carbonyl)piperazin-1-yl]-6-ethyl-2-methyl-8-oxo-5H,8H-pyrido[2,3-b]pyrazin-5-yl}acetamide |
| I-159 | methyl 3-[5-({[2-chloro-4-(trifluoromethyl)phenyl]carbamoyl}methyl)-6-ethyl-7-[4-(5-hydroxy-6-methylpyrimidine-4-carbonyl)piperazin-1-yl]-8-oxo-5H,8H-pyrido[2,3-b]pyrazin-2-yl]-2,5-dihydro-1H-pyrrole-1-carboxylate |
| I-160 | N-[2-chloro-4-(trifluoromethyl)phenyl]-2-[2-(3,3-difluoroazetidin-1-yl)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-161 | N-[2-chloro-4-(trifluoromethyl)phenyl]-2-[2-(cyclobutylamino)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-162 | 2-(2-{5-azaspiro[2.3]hexan-5-yl}-6-ethyl-7-[4-(5-hydroxy-6-methylpyrimidine-4-carbonyl)piperazin-1-yl]-8-oxo-5H,8H-pyrido[2,3-b]pyrazin-5-yl)-N-[2-chloro-4-(trifluoromethyl)phenyl]acetamide |
| I-163 | N-[2-chloro-4-(trifluoromethyl)phenyl]-2-{6-ethyl-7-[4-(5-hydroxy-6-methylpyrimidine-4-carbonyl)piperazin-1-yl]-2-{2-oxa-6-azaspiro[3.4]octan-6-yl}-8-oxo-5H,8H-pyrido[2,3-b]pyrazin-5-yl}acetamide |
| I-164 | N-[2-chloro-4-(trifluoromethyl)phenyl]-2-[6-ethyl-2-(3-fluoroazetidin-1-yl)-7-[4-(5-hydroxy-6-methylpyrimidine-4-carbonyl)piperazin-1-yl]-8-oxo-5H,8H-pyrido[2,3-b]pyrazin-5-yl]acetamide |
| I-165 | N-[2-chloro-4-(trifluoromethyl)phenyl]-2-[2-(cyclopropylamino)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-166 | N-[2-chloro-4-(trifluoromethyl)phenyl]-2-[2-(cyclopentylidenemethyl)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-167 | N-[2-chloro-4-(trifluoromethyl)phenyl]-2-{2-[(2,2-difluoroethyl)(methyl)amino]-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide |
| I-168 | N-[2-chloro-4-(trifluoromethyl)phenyl]-2-[2-(dimethylamino)-6-ethyl-7-[9-(5-hydroxy-6-methylpyrimidine-4-carbonyl)-3-oxa-7,9-diazabicyclo[3.3.1]nonan-7-yl]-8-oxo-5H,8H-pyrido[2,3-b]pyrazin-5-yl]acetamide |
| I-169 | N-[2-chloro-4-(trifluoromethyl)phenyl]-2-{2-[cyclopropyl(methyl)amino]-6-ethyl-7-[-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl}acetamide (single stereoisomer, first eluting compound as stereoisomer 1, trans) |

TABLE 1-continued

| Compound No. | IUPAC Name |
|---|---|
| I-170 | 2-(2-{1-azaspiro[3.3]heptan-1-yl}-6-ethyl-7-[4-(5-hydroxy-6-methylpyrimidine-4-carbonyl)piperazin-1-yl]-8-oxo-5H,8H-pyrido[2,3-b]pyrazin-5-yl)-N-[2-chloro-4-(trifluoromethyl)phenyl]acetamide |
| I-171 | N-(2-chloro-4-(trifluoromethyl)phenyl)-2-(6-ethyl-7-(5-(5-hydroxy-6-methylpyrimidine-4-carbonyl)-2,5-diazabicyclo[4.2.0]octan-2-yl)-2-(methylamino)-8-oxopyrido[2,3-b]pyrazin-5(8H)-yl)acetamide (single stereoisomer, first eluting compound as stereoisomer 1, trans) |
| I-172 | N-(2-chloro-4-(trifluoromethyl)phenyl)-2-(6-ethyl-7-(5-(5-hydroxy-6-methylpyrimidine-4-carbonyl)-2,5-diazabicyclo[4.2.0]octan-2-yl)-2-(methylamino)-8-oxopyrido[2,3-b]pyrazin-5(8H)-yl)acetamide (single stereoisomer, second eluting compound as stereoisomer 2, trans) |
| I-173 | N-[2-chloro-4-(trifluoromethyl)phenyl]-2-[2-(dimethylamino)-6-ethyl-7-[(3S)-4-(5-hydroxy-6-methylpyrimidine-4-carbonyl)-3-methylpiperazin-1-yl]-8-oxo-5H,8H-pyrido[2,3-b]pyrazin-5-yl]acetamide |
| I-174 | N-[2-chloro-4-(trifluoromethyl)phenyl]-2-[6-ethyl-2-(2-fluoropropan-2-yl)-7-[4-(5-hydroxy-6-methylpyrimidine-4-carbonyl)piperazin-1-yl]-8-oxo-5H,8H-pyrido[2,3-b]pyrazin-5-yl]acetamide |
| I-175 | N-[2-chloro-4-(trifluoromethyl)phenyl]-2-{6-ethyl-7-[4-(5-hydroxy-6-methylpyrimidine-4-carbonyl)piperazin-1-yl]-2-[methyl(propan-2-yl)amino]-8-oxo-5H,8H-pyrido[2,3-b]pyrazin-5-yl}acetamide |
| I-176 | N-[2-chloro-4-(trifluoromethyl)phenyl]-2-[2-(dimethylamino)-6-ethyl-7-[4-(5-hydroxy-6-methylpyrimidine-4-carbonyl)-4,7-diazaspiro[2.5]octan-7-yl]-8-oxo-5H,8H-pyrido[2,3-b]pyrazin-5-yl]acetamide |
| I-177 | N-[2-chloro-4-(trifluoromethyl)phenyl]-2-[2-(3,3-difluoropyrrolidin-1-yl)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-178 | N-[2-chloro-4-(trifluoromethyl)phenyl]-2-[2-(dimethylamino)-6-ethyl-7-[4-(5-hydroxy-6-methylpyrimidine-4-carbonyl)-3-(hydroxymethyl)piperazin-1-yl]-8-oxo-5H,8H-pyrido[2,3-b]pyrazin-5-yl]acetamide |
| I-179 | N-[2-chloro-4-(trifluoromethyl)phenyl]-2-[2-(dicyclopropylamino)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-180 | N-[2-chloro-4-(trifluoromethyl)phenyl]-2-{6-ethyl-2-[(3-hydroxy-3-methylcyclobutylidene)methyl]-7-[4-(5-hydroxy-6-methylpyrimidine-4-carbonyl)piperazin-1-yl]-8-oxo-5H,8H-pyrido[2,3-b]pyrazin-5-yl}acetamide |
| I-181 | N-[2-chloro-4-(trifluoromethyl)phenyl]-2-{2-cyclobutoxy-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl}acetamide |
| I-182 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-methoxy-8-oxo-5H,8H-pyrido[2,3-b]pyrazin-5-yl}acetamide |
| I-183 | N-[2-chloro-4-(trifluoromethyl)phenyl]-2-[2-(dimethylamino)-6-ethyl-7-[(1S,6S)-5-(5-hydroxy-3-methoxypyridazine-4-carbonyl)-2,5-diazabicyclo[4.2.0]octan-2-yl]-8-oxo-5H,8H-pyrido[2,3-b]pyrazin-5-yl]acetamide |
| I-184 | N-[2-chloro-4-(trifluoromethyl)phenyl]-2-[2-(dimethylamino)-6-ethyl-7-[(1S,6S)-5-(1-methyl-1H-pyrazole-4-carbonyl)-2,5-diazabicyclo[4.2.0]octan-2-yl]-8-oxo-5H,8H-pyrido[2,3-b]pyrazin-5-yl]acetamide |
| I-185 | N-[2-chloro-4-(pentafluoro-lambda6-sulfanyl)phenyl]-2-[2-(dimethylamino)-6-ethyl-7-[(2S)-4-(5-hydroxy-6-methylpyrimidine-4-carbonyl)-2-methylpiperazin-1-yl]-8-oxo-5H,8H-pyrido[2,3-b]pyrazin-5-yl]acetamide |
| I-186 | N-[2-chloro-4-(trifluoromethyl)phenyl]-2-{2-[(cyclopropylmethyl)amino]-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide |
| I-187 | 2-[2-(azetidin-1-yl)-6-ethyl-7-[(2S)-4-(5-hydroxy-6-methylpyrimidine-4-carbonyl)-2-methylpiperazin-1-yl]-8-oxo-5H,8H-pyrido[2,3-b]pyrazin-5-yl]-N-[2-chloro-4-(trifluoromethyl)phenyl]acetamide |
| I-188 | N-[2-chloro-4-(trifluoromethyl)phenyl]-2-{6-ethyl-7-[(2S)-4-(5-hydroxy-6-methylpyrimidine-4-carbonyl)-2-methylpiperazin-1-yl]-2-[(2S)-2-(methoxymethyl)azetidin-1-yl]-8-oxo-5H,8H-pyrido[2,3-b]pyrazin-5-yl}acetamide |
| I-189 | N-[2-chloro-4-(trifluoromethyl)phenyl]-2-{6-ethyl-7-[(2S)-4-(5-hydroxy-6-methylpyrimidine-4-carbonyl)-2-methylpiperazin-1-yl]-2-[(2R)-2-(methoxymethyl)azetidin-1-yl]-8-oxo-5H,8H-pyrido[2,3-b]pyrazin-5-yl}acetamide |
| I-190 | 2-[2-(azetidin-1-yl)-6-ethyl-7-[(2S)-4-(5-hydroxy-6-methylpyrimidine-4-carbonyl)-2-methylpiperazin-1-yl]-8-oxo-5H,8H-pyrido[2,3-b]pyrazin-5-yl]-N-[2-chloro-4-(pentafluoro-lambda6-sulfanyl)phenyl]acetamide |

TABLE 1-continued

| Compound No. | IUPAC Name |
| --- | --- |
| I-191 | N-[2-chloro-4-(trifluoromethyl)phenyl]-2-[2-(dimethylamino)-6-ethyl-7-[(2S)-2-ethyl-4-(5-hydroxy-6-methylpyrimidine-4-carbonyl)piperazin-1-yl]-8-oxo-5H,8H-pyrido[2,3-b]pyrazin-5-yl]acetamide |
| I-192 | 2-(2-(2-azabicyclo[3.1.0]hexan-2-yl)-6-ethyl-7-((S)-4-(5-hydroxy-6-methylpyrimidine-4-carbonyl)-2-methylpiperazin-1-yl)-8-oxopyrido[2,3-b]pyrazin-5(8H)-yl)-N-(2-chloro-4-(trifluoromethyl)phenyl)acetamide (single stereoisomer, first eluting compound as stereoisomer 1, cis) |
| I-193 | 2-(2-(2-azabicyclo[3.1.0]hexan-2-yl)-6-ethyl-7-((S)-4-(5-hydroxy-6-methylpyrimidine-4-carbonyl)-2-methylpiperazin-1-yl)-8-oxopyrido[2,3-b]pyrazin-5(8H)-yl)-N-(2-chloro-4-(trifluoromethyl)phenyl)acetamide (single stereoisomer, second eluting compound as stereoisomer 2, cis) |
| I-194 | N-[2-chloro-4-(trifluoromethyl)phenyl]-2-{2-[cyclopropyl(methyl)amino]-6-ethyl-7-(4-{4-hydroxy-2H,3H-furo[2,3-c]pyridine-5-carbonyl}piperazin-1-yl)-8-oxo-5H,8H-pyrido[2,3-b]pyrazin-5-yl}acetamide |
| I-195 | N-[2-chloro-4-(trifluoromethyl)phenyl]-2-{2-cyclopropoxy-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide |
| I-196 | N-(2-chloro-4-(trifluoromethyl)phenyl)-2-(2-(dimethylamino)-6-ethyl-7-(4-(5-hydroxy-6-methylpyrimidine-4-carbonyl)-2,3-dimethylpiperazin-1-yl)-8-oxopyrido[2,3-b]pyrazin-5(8H)-yl)acetamide (single stereoisomer, first eluting compound as stereoisomer 1, cis) |
| I-197 | N-[2-chloro-4-(trifluoromethyl)phenyl]-2-{7-[(3R)-3-(difluoromethyl)-4-(5-hydroxy-6-methylpyrimidine-4-carbonyl)piperazin-1-yl]-2-(dimethylamino)-6-ethyl-8-oxo-5H,8H-pyrido[2,3-b]pyrazin-5-yl}acetamide |
| I-198 | N-(2-chloro-4-(trifluoromethyl)phenyl)-2-(2-(dimethylamino)-6-ethyl-7-(4-(5-hydroxy-6-methylpyrimidine-4-carbonyl)-2,3-dimethylpiperazin-1-yl)-8-oxopyrido[2,3-b]pyrazin-5(8H)-yl)acetamide (single stereoisomer, second eluting compound as stereoisomer 2, cis) |
| I-199 | N-[2-chloro-4-(trifluoromethoxy)phenyl]-2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]acetamide |
| I-200 | N-[2-chloro-4-(pentafluoro-lambda6-sulfanyl)phenyl]-2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]acetamide |
| I-201 | N-[2-chloro-4-(trifluoromethyl)phenyl]-2-{6-ethyl-7-[4-(5-hydroxy-6-methylpyrimidine-4-carbonyl)piperazin-1-yl]-8-oxo-2-(1H-pyrazol-1-yl)-5H,8H-pyrido[2,3-b]pyrazin-5-yl}acetamide |
| I-203 | N-[2-chloro-4-(trifluoromethyl)phenyl]-2-{2-[cyclopropyl(methyl)amino]-6-ethyl-7-(4-{7-hydroxy-2H,3H-furo[3,2-c]pyridine-6-carbonyl}piperazin-1-yl)-8-oxo-5H,8H-pyrido[2,3-b]pyrazin-5-yl}acetamide |
| I-204 | N-[2-chloro-4-(trifluoromethyl)phenyl]-2-[2-(dimethylamino)-6-ethyl-7-[4-(4-hydroxy-2-methoxy-5-methylpyridine-3-carbonyl)piperazin-1-yl]-8-oxo-5H,8H-pyrido[2,3-b]pyrazin-5-yl]acetamide |
| I-205 | N-[2-chloro-4-(trifluoromethyl)phenyl]-2-{6-ethyl-7-[4-(5-hydroxy-6-methylpyrimidine-4-carbonyl)piperazin-1-yl]-2-[methyl(1-methylcyclopropyl)amino]-8-oxo-5H,8H-pyrido[2,3-b]pyrazin-5-yl}acetamide |
| I-206 | N-[2-chloro-4-(trifluoromethyl)phenyl]-2-[2-(dimethylamino)-6-ethyl-7-[(1R,5S)-8-(5-hydroxy-6-methylpyrimidine-4-carbonyl)-3,8-diazabicyclo[3.2.1]octan-3-yl]-8-oxo-5H,8H-pyrido[2,3-b]pyrazin-5-yl]acetamide |
| I-207 | N-[2-chloro-4-(trifluoromethyl)phenyl]-2-{6-ethyl-7-[4-(5-hydroxy-6-methylpyrimidine-4-carbonyl)piperazin-1-yl]-2-{6-oxa-1-azaspiro[3.3]heptan-1-yl}-8-oxo-5H,8H-pyrido[2,3-b]pyrazin-5-yl}acetamide |
| I-208 | N-(2-chloro-4-(trifluoromethyl)phenyl)-2-(2-(dimethylamino)-6-ethyl-7-(4-(5-hydroxy-6-methylpyrimidine-4-carbonyl)octahydro-1H-cyclopenta[b]pyrazin-1-yl)-8-oxopyrido[2,3-b]pyrazin-5(8H)-yl)acetamide (single stereoisomer, first eluting compound as stereoisomer 1, cis) |
| I-209 | N-(2-chloro-4-(trifluoromethyl)phenyl)-2-(2-(dimethylamino)-6-ethyl-7-(4-(5-hydroxy-6-methylpyrimidine-4-carbonyl)octahydro-1H-cyclopenta[b]pyrazin-1-yl)-8-oxopyrido[2,3-b]pyrazin-5(8H)-yl)acetamide (single stereoisomer, second eluting compound as stereoisomer 2, cis) |
| I-210 | 2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]-N-[2-fluoro-4-(trifluoromethoxy)phenyl]acetamide |

TABLE 1-continued

| Compound No. | IUPAC Name |
| --- | --- |
| I-211 | 2-{2-[bis(methyl-d3)amino]-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl}-N-[2-fluoro-4-(trifluoromethyl)phenyl]acetamide |
| I-212 | N-[2-chloro-4-(trifluoromethyl)phenyl]-2-[2-(dimethylamino)-6-ethyl-7-[4-(4-fluoro-3-hydroxypyridine-2-carbonyl)piperazin-1-yl]-8-oxo-5H,8H-pyrido[2,3-b]pyrazin-5-yl]acetamide |
| I-213 | N-[2-chloro-4-(trifluoromethyl)phenyl]-2-[2-(dimethylamino)-6-ethyl-7-[1-(5-hydroxy-6-methylpyrimidine-4-carbonyl)-1,2,3,6-tetrahydropyridin-4-yl]-8-oxo-5H,8H-pyrido[2,3-b]pyrazin-5-yl]acetamide |
| I-214 | 2-{2-[di(2H3)methylamino]-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl}-N-[2-fluoro-4-(trifluoromethyl)phenyl]acetamide |
| I-215 | 2-{7-[(4aR,7aR)-4-(5-hydroxy-6-methylpyrimidine-4-carbonyl)-octahydro-1H-cyclopenta[b]pyrazin-1-yl]-2-(dimethylamino)-6-ethyl-8-oxo-5H,8H-pyrido[2,3-b]pyrazin-5-yl}-N-[2-chloro-4-(trifluoromethyl)phenyl]acetamide |
| I-216 | N-[2-chloro-4-(trifluoromethyl)phenyl]-2-[2-(dimethylamino)-6-ethyl-7-[5-(5-hydroxy-6-methylpyrimidine-4-carbonyl)-5,8-diazaspiro[3.5]nonan-8-yl]-8-oxo-5H,8H-pyrido[2,3-b]pyrazin-5-yl]acetamide |
| I-217 | N-[2-chloro-4-(trifluoromethyl)phenyl]-2-{6-ethyl-7-[4-(5-hydroxy-6-methylpyrimidine-4-carbonyl)piperazin-1-yl]-2-(N-methylmethanesulfonamido)-8-oxo-5H,8H-pyrido[2,3-b]pyrazin-5-yl}acetamide |
| I-218 | 2-{7-[4-(4-chloro-3-hydroxypyridine-2-carbonyl)piperazin-1-yl]-2-(dimethylamino)-6-ethyl-8-oxo-5H,8H-pyrido[2,3-b]pyrazin-5-yl}-N-[2-chloro-4-(trifluoromethyl)phenyl]acetamide |
| I-219 | 2-(2-(2-azabicyclo[3.1.0]hexan-2-yl)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(2-chloro-4-(trifluoromethyl)phenyl)acetamide (single stereoisomer, first eluting compound as stereoisomer 1, cis) |
| I-220 | 2-(2-(2-azabicyclo[3.1.0]hexan-2-yl)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(2-chloro-4-(trifluoromethyl)phenyl)acetamide (single stereoisomer, second eluting compound as stereoisomer 2, cis) |
| I-221 | N-[2-chloro-4-(trifluoromethyl)phenyl]-2-[2-(dimethylamino)-6-ethyl-7-[1-(5-hydroxy-6-methylpyrimidine-4-carbonyl)piperidin-4-yl]-8-oxo-5H,8H-pyrido[2,3-b]pyrazin-5-yl]acetamide |
| I-222 | N-[2-chloro-6-(trifluoromethyl)pyridin-3-yl]-2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]acetamide |
| I-223 | N-[2-chloro-4-(trifluoromethyl)phenyl]-2-{2-cyclobutyl-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide |
| I-224 | 2-(2-{4-azaspiro[2.4]heptan-4-yl}-6-ethyl-7-[4-(5-hydroxy-6-methylpyrimidine-4-carbonyl)piperazin-1-yl]-8-oxo-5H,8H-pyrido[2,3-b]pyrazin-5-yl)-N-[2-chloro-4-(trifluoromethyl)phenyl]acetamide |
| I-225 | N-[2-chloro-4-(trifluoromethyl)phenyl]-2-{2-cyclopropyl-6-ethyl-7-[(2S)-4-(4-hydroxy-2-methoxy-5-methylpyridine-3-carbonyl)-2-methylpiperazin-1-yl]-8-oxo-5H,8H-pyrido[2,3-b]pyrazin-5-yl}acetamide |
| I-226 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-[(methyl-d3)amino]-8-oxo-5H,8H-pyrido[2,3-b]pyrazin-5-yl}acetamide |
| I-227 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-(methylamino)-8-oxo-5H,8H-pyrido[2,3-b]pyrazin-5-yl}acetamide |
| I-228 | N-[2-chloro-4-(trifluoromethyl)phenyl]-2-[2-(dimethylamino)-6-ethyl-7-[(2S)-4-(4-hydroxy-2-methoxy-5-methylpyridine-3-carbonyl)-2-methylpiperazin-1-yl]-8-oxo-5H,8H-pyrido[2,3-b]pyrazin-5-yl]acetamide |
| I-229 | N-[2-chloro-4-(trifluoromethyl)phenyl]-2-[2-(dimethylamino)-6-ethyl-7-[3-(5-hydroxy-6-methylpyrimidine-4-carbonyl)-3-azabicyclo[4.1.0]heptan-6-yl]-8-oxo-5H,8H-pyrido[2,3-b]pyrazin-5-yl]acetamide |
| I-230 | rac-2-(2-(2-azabicyclo[3.2.0]heptan-2-yl)-6-ethyl-7-(4-(5-hydroxy-6-methylpyrimidine-4-carbonyl)piperazin-1-yl)-8-oxopyrido[2,3-b]pyrazin-5(8H)-yl)-N-(2-chloro-4-(trifluoromethyl)phenyl)acetamide (racemic mixture, cis) |

TABLE 1-continued

| Compound No. | IUPAC Name |
| --- | --- |
| I-231 | 2-(2-(2-azabicyclo[3.1.0]hexan-2-yl)-6-ethyl-7-((S)-4-(4-hydroxy-2-methoxy-5-methylnicotinoyl)-2-methylpiperazin-1-yl)-8-oxopyrido[2,3-b]pyrazin-5(8H)-yl)-N-(2-chloro-4-(trifluoromethyl)phenyl)acetamide (single stereoisomer, first eluting compound as stereoisomer 1, trans) |
| I-232 | 2-(2-(2-azabicyclo[3.1.0]hexan-2-yl)-6-ethyl-7-((S)-4-(4-hydroxy-2-methoxy-5-methylnicotinoyl)-2-methylpiperazin-1-yl)-8-oxopyrido[2,3-b]pyrazin-5(8H)-yl)-N-(2-chloro-4-(trifluoromethyl)phenyl)acetamide (single stereoisomer, second eluting compound as stereoisomer 2, trans) |
| I-233 | N-(2-chloro-4-(trifluoromethyl)phenyl)-2-(2-(dimethylamino)-6-ethyl-7-(4-(5-hydroxy-6-methylpyrimidine-4-carbonyl)-2,3-dimethylpiperazin-1-yl)-8-oxopyrido[2,3-b]pyrazin-5(8H)-yl)acetamide (single stereoisomer, first eluting compound as stereoisomer 1, trans) |
| I-234 | N-(2-chloro-4-(trifluoromethyl)phenyl)-2-(2-(dimethylamino)-6-ethyl-7-(4-(5-hydroxy-6-methylpyrimidine-4-carbonyl)-2,3-dimethylpiperazin-1-yl)-8-oxopyrido[2,3-b]pyrazin-5(8H)-yl)acetamide (single stereoisomer, second eluting compound as stereoisomer 2, trans) |
| I-236 | 2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]-N-[5-fluoro-2-methyl-4-(trifluoromethyl)phenyl]acetamide |
| I-237 | N-[2-chloro-4-(trifluoromethyl)phenyl]-2-{2-[(1R)-2,2-difluorocyclopropyl]-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide (single stereoisomer, first eluting compound as stereoisomer 1) |
| I-238 | N-[2-chloro-4-(trifluoromethyl)phenyl]-2-{2-[(1R)-2,2-difluorocyclopropyl]-6-ethyl-7-[4-(5-hydroxy-6-methylpyrimidine-4-carbonyl)piperazin-1-yl]-8-oxo-5H,8H-pyrido[2,3-b]pyrazin-5-yl}acetamide (single stereoisomer, second eluting compound as stereoisomer 2) |
| I-239 | N-[2-chloro-4-(trifluoromethyl)phenyl]-2-{2-cyclopropyl-6-ethyl-7-[4-(4-hydroxy-2-methoxy-5-methylpyridine-3-carbonyl)piperazin-1-yl]-8-oxo-5H,8H-pyrido[2,3-b]pyrazin-5-yl} acetamide |
| I-240 | N-[2-chloro-4-(difluoromethyl)phenyl]-2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]acetamide |
| I-241 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-(1-methyl-1H-pyrazol-5-yl)-8-oxo-5H,8H-pyrido[2,3-b]pyrazin-5-yl}acetamide |
| I-242 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-(3-methoxyazetidin-1-yl)-8-oxo-5H,8H-pyrido[2,3-b]pyrazin-5-yl}acetamide |
| I-243 | 2-{7-[(4aS,7aS)-4-(4-hydroxy-2-methoxy-5-methylpyridine-3-carbonyl)-octahydro-1H-cyclopenta[b]pyrazin-1-yl]-2-(dimethylamino)-6-ethyl-8-oxo-5H,8H-pyrido[2,3-b]pyrazin-5-yl}-N-[2-chloro-4-(trifluoromethyl)phenyl]acetamide |
| I-244 | N-[2-chloro-4-(trifluoromethyl)phenyl]-2-[2-(dimethylamino)-6-ethyl-7-[(2R)-4-(5-hydroxy-6-methylpyrimidine-4-carbonyl)-2-(hydroxymethyl)piperazin-1-yl]-8-oxo-5H,8H-pyrido[2,3-b]pyrazin-5-yl]acetamide |
| I-245 | N-[2-chloro-4-(trifluoromethyl)phenyl]-2-[2-(3,3-difluoroazetidin-1-yl)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]acetamide |
| I-246 | N-[2-chloro-4-(trifluoromethyl)phenyl]-2-[6-ethyl-2-(3-hydroxy-3-methylazetidin-1-yl)-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]acetamide |
| I-247 | N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[2.2.2]octan-2-yl)-8-oxopyrido[2,3-b]pyrazin-5(8H)-yl)acetamide (single stereoisomer, first eluting compound as stereoisomer 1) |
| I-248 | N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[2.2.2]octan-2-yl)-8-oxopyrido[2,3-b]pyrazin-5(8H)-yl)acetamide (single stereoisomer, second eluting compound as stereoisomer 2) |
| I-249 | N-[2-chloro-4-(trifluoromethyl)phenyl]-2-[2-(dimethylamino)-6-ethyl-7-[4-(5-hydroxy-6-methylpyrimidine-4-carbonyl)-2,2-dimethylpiperazin-1-yl]-8-oxo-5H,8H-pyrido[2,3-b]pyrazin-5-yl]acetamide |

TABLE 1-continued

| Compound No. | IUPAC Name |
| --- | --- |
| I-250 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-(morpholin-4-yl)-8-oxo-5H,8H-pyrido[2,3-b]pyrazin-5-yl}acetamide |
| I-251 | N-(2-chloro-4-(trifluoromethyl)phenyl)-2-(2-(dimethylamino)-6-ethyl-7-(4-(4-hydroxy-2-methoxy-5-methylnicotinoyl)octahydro-1H-cyclopenta[b]pyrazin-1-yl)-8-oxopyrido[2,3-b]pyrazin-5(8H)-yl)acetamide (single stereoisomer, first eluting compound as stereoisomer 1, cis) |
| I-252 | N-(2-chloro-4-(trifluoromethyl)phenyl)-2-(2-(dimethylamino)-6-ethyl-7-(4-(4-hydroxy-2-methoxy-5-methylnicotinoyl)octahydro-1H-cyclopenta[b]pyrazin-1-yl)-8-oxopyrido[2,3-b]pyrazin-5(8H)-yl)acetamide (single stereoisomer, second eluting compound as stereoisomer 2, cis) |
| I-253 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-8-oxo-2-(2-oxopyrrolidin-1-yl)-5H,8H-pyrido[2,3-b]pyrazin-5-yl}acetamide |
| I-254 | N-[2-chloro-4-(trifluoromethyl)phenyl]-2-[2-(1-cyanocyclopropyl)-6-ethyl-7-[4-(5-hydroxy-6-methylpyrimidine-4-carbonyl)piperazin-1-yl]-8-oxo-5H,8H-pyrido[2,3-b]pyrazin-5-yl]acetamide |
| I-255 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-[(2-methoxyethyl)(methyl)amino]-8-oxo-5H,8H-pyrido[2,3-b]pyrazin-5-yl}acetamide |
| I-256 | rel-N-(2-chloro-4-(trifluoromethyl)phenyl)-2-(2-(dimethylamino)-6-ethyl-7-((1R,4R)-5-(5-hydroxy-6-methylpyrimidine-4-carbonyl)-2,5-diazabicyclo[2.2.1]heptan-2-yl)-8-oxopyrido[2,3-b]pyrazin-5(8H)-yl)acetamide (single stereoisomer, second eluting compound as stereoisomer 2) |
| I-257 | rel-N-(2-chloro-4-(trifluoromethyl)phenyl)-2-(2-(dimethylamino)-6-ethyl-7-((1R,4R)-5-(5-hydroxy-6-methylpyrimidine-4-carbonyl)-2,5-diazabicyclo[2.2.1]heptan-2-yl)-8-oxopyrido[2,3-b]pyrazin-5(8H)-yl)acetamide (single stereoisomer, first eluting compound as stereoisomer 1) |
| I-258 | N-[2-chloro-4-(trifluoromethyl)phenyl]-2-[2-(dimethylamino)-6-ethyl-7-[5-(5-hydroxy-6-methylpyrimidine-4-carbonyl)-2,5-diazabicyclo[2.2.1]heptan-2-yl]-8-oxo-5H,8H-pyrido[2,3-b]pyrazin-5-yl]acetamide |
| I-259 | N-[2-chloro-4-(trifluoromethyl)phenyl]-2-[2-(dimethylamino)-6-ethyl-7-[(1S,6S)-5-(2-methoxy-5-methylpyridine-3-carbonyl)-2,5-diazabicyclo[4.2.0]octan-2-yl]-8-oxo-5H,8H-pyrido[2,3-b]pyrazin-5-yl]acetamide |
| I-260 | N-[2-chloro-4-(trifluoromethyl)phenyl]-2-[2-(dimethylamino)-6-ethyl-7-[(2S)-2-ethynyl-4-(5-hydroxy-6-methylpyrimidine-4-carbonyl)piperazin-1-yl]-8-oxo-5H,8H-pyrido[2,3-b]pyrazin-5-yl]acetamide |
| I-261 | N-[2-chloro-4-(trifluoromethyl)phenyl]-2-[2-(dimethylamino)-6-ethyl-7-[(1S,6S)-5-(4-hydroxy-2-methoxy-5-methylpyridine-3-carbonyl)-2,5-diazabicyclo[4.2.0]octan-2-yl]-8-oxo-5H,8H-pyrido[2,3-b]pyrazin-5-yl]acetamide |
| I-262 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-methyl-8-oxo-5H,8H-pyrido[2,3-b]pyrazin-5-yl}acetamide |
| I-263 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-8-oxo-2-(piperazin-1-yl)-5H,8H-pyrido[2,3-b]pyrazin-5-yl}acetamide |
| I-264 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-[(2-hydroxyethyl)(methyl)amino]-8-oxo-5H,8H-pyrido[2,3-b]pyrazin-5-yl}acetamide |
| I-265 | 2-{7-[(1S,6S)-5-(1,3-benzoxazole-7-carbonyl)-2,5-diazabicyclo[4.2.0]octan-2-yl]-2-(dimethylamino)-6-ethyl-8-oxo-5H,8H-pyrido[2,3-b]pyrazin-5-yl}-N-[2-chloro-4-(trifluoromethyl)phenyl]acetamide |
| I-266 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-{[(2R,3S)-3-hydroxybutan-2-yl]amino}-8-oxo-5H,8H-pyrido[2,3-b]pyrazin-5-yl}acetamide |
| I-267 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-{methyl[(1r,3r)-3-methoxycyclobutyl]amino}-8-oxo-5H,8H-pyrido[2,3-b]pyrazin-5-yl}acetamide |

TABLE 1-continued

| Compound No. | IUPAC Name |
| --- | --- |
| I-268 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-8-oxo-2-(1H-pyrazol-4-yl)-5H,8H-pyrido[2,3-b]pyrazin-5-yl}acetamide |
| I-269 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-{[(2S)-2-methoxypropyl](methyl)amino}-8-oxo-5H,8H-pyrido[2,3-b]pyrazin-5-yl}acetamide |
| I-270 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-[(3R)-3-hydroxypyrrolidin-1-yl]-8-oxo-5H,8H-pyrido[2,3-b]pyrazin-5-yl}acetamide |
| I-271 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-[(3S)-3-hydroxypyrrolidin-1-yl]-8-oxo-5H,8H-pyrido[2,3-b]pyrazin-5-yl}acetamide |
| I-272 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-8-oxo-2-(1,3-thiazol-5-yl)-5H,8H-pyrido[2,3-b]pyrazin-5-yl}acetamide |
| I-273 | N-[2-chloro-4-(trifluoromethyl)phenyl]-2-[2-(dimethylamino)-6-ethyl-7-[(1S,6S)-5-{4-hydroxy-5-methyl-2-[(1-methyl-1H-pyrazol-4-yl)oxy]pyridine-3-carbonyl}-2,5-diazabicyclo[4.2.0]octan-2-yl]-8-oxo-5H,8H-pyrido[2,3-b]pyrazin-5-yl]acetamide |
| I-274 | N-[2-chloro-4-(trifluoromethyl)phenyl]-2-[2-(dimethylamino)-6-ethyl-7-[(1S,6S)-5-(4-hydroxy-2,5-dimethoxypyridine-3-carbonyl)-2,5-diazabicyclo[4.2.0]octan-2-yl]-8-oxo-5H,8H-pyrido[2,3-b]pyrazin-5-yl]acetamide |
| I-275 | N-[2-chloro-4-(trifluoromethyl)phenyl]-2-[2-(dimethylamino)-7-[(1S,6S)-5-(2-ethoxy-4-hydroxy-5-methylpyridine-3-carbonyl)-2,5-diazabicyclo[4.2.0]octan-2-yl]-6-ethyl-8-oxo-5H,8H-pyrido[2,3-b]pyrazin-5-yl]acetamide |
| I-276 | N-(2-chloro-4-(trifluoromethyl)phenyl)-2-(2-(dimethylamino)-6-ethyl-7-(3-(5-hydroxy-6-methylpyrimidine-4-carbonyl)-3-azabicyclo[4.1.0]heptan-6-yl)-8-oxopyrido[2,3-b]pyrazin-5(8H)-yl)acetamide (single stereoisomer, first eluting compound as stereoisomer 1, trans) |
| I-277 | N-(2-chloro-4-(trifluoromethyl)phenyl)-2-(2-(dimethylamino)-6-ethyl-7-(3-(5-hydroxy-6-methylpyrimidine-4-carbonyl)-3-azabicyclo[4.1.0]heptan-6-yl)-8-oxopyrido[2,3-b]pyrazin-5(8H)-yl)acetamide (single stereoisomer, second eluting compound as stereoisomer 2, trans) |
| I-278 | N-(2-chloro-4-(trifluoromethyl)phenyl)-2-(2-(dimethylamino)-6-ethyl-7-(4-(5-hydroxy-6-methylpyrimidine-4-carbonyl)hexahydrofuro[3,4-b]pyrazin-1(2H)-yl)-8-oxopyrido[2,3-b]pyrazin-5(8H)-yl)acetamide (single stereoisomer, first eluting compound as stereoisomer 1, trans) |
| I-279 | N-(2-chloro-4-(trifluoromethyl)phenyl)-2-(2-(dimethylamino)-6-ethyl-7-(4-(5-hydroxy-6-methylpyrimidine-4-carbonyl)hexahydrofuro[3,4-b]pyrazin-1(2H)-yl)-8-oxopyrido[2,3-b]pyrazin-5(8H)-yl)acetamide (single stereoisomer, second eluting compound as stereoisomer 2, trans) |
| I-280 | N-[2-chloro-4-(trifluoromethyl)phenyl]-2-{7-[(1S,6S)-5-[5-(difluoromethyl)-4-hydroxy-2-methoxypyridine-3-carbonyl]-2,5-diazabicyclo[4.2.0]octan-2-yl]-2-(dimethylamino)-6-ethyl-8-oxo-5H,8H-pyrido[2,3-b]pyrazin-5-yl}acetamide |
| I-281 | N-[2-chloro-4-(trifluoromethyl)phenyl]-2-{7-[(1S,6S)-5-[2-(difluoromethoxy)-4-hydroxy-5-methylpyridine-3-carbonyl]-2,5-diazabicyclo[4.2.0]octan-2-yl]-2-(dimethylamino)-6-ethyl-8-oxo-5H,8H-pyrido[2,3-b]pyrazin-5-yl}acetamide |
| I-282 | N-[2-chloro-4-(trifluoromethyl)phenyl]-2-[2-(dimethylamino)-6-ethyl-7-[(1S,6S)-5-[4-hydroxy-2-(2-methoxyethoxy)-5-methylpyridine-3-carbonyl]-2,5-diazabicyclo[4.2.0]octan-2-yl]-8-oxo-5H,8H-pyrido[2,3-b]pyrazin-5-yl]acetamide |
| I-283 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-(2-methoxypyridin-4-yl)-8-oxo-5H,8H-pyrido[2,3-b]pyrazin-5-yl}acetamide |
| I-284 | N-[2-chloro-4-(trifluoromethyl)phenyl]-2-[2-(3,6-dihydro-2H-pyran-4-yl)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]acetamide |
| I-285 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-[(morpholin-4-yl)methyl]-8-oxo-5H,8H-pyrido[2,3-b]pyrazin-5-yl}acetamide |

TABLE 1-continued

| Compound No. | IUPAC Name |
|---|---|
| I-286 | N-[2-chloro-4-(trifluoromethyl)phenyl]-2-{7-[(1S,6S)-5-(5-cyclopropyl-4-hydroxy-2-methoxypyridine-3-carbonyl)-2,5-diazabicyclo[4.2.0]octan-2-yl]-2-(dimethylamino)-6-ethyl-8-oxo-5H,8H-pyrido[2,3-b]pyrazin-5-yl}acetamide |
| I-287 | N-[2-chloro-4-(trifluoromethyl)phenyl]-2-[2-(dimethylamino)-6-ethyl-7-[(1S,6S)-5-[4-hydroxy-2-methoxy-5-(oxolan-3-yl)pyridine-3-carbonyl]-2,5-diazabicyclo[4.2.0]octan-2-yl]-8-oxo-5H,8H-pyrido[2,3-b]pyrazin-5-yl]acetamide |
| I-288 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-[(3-hydroxycyclopentyl)(methyl)amino]-8-oxo-5H,8H-pyrido[2,3-b]pyrazin-5-yl}acetamide |
| I-289 | N-(2-chloro-4-methoxyphenyl)-2-[2-(dimethylamino)-6-ethyl-7-[(1S,6S)-5-(5-hydroxy-6-methylpyrimidine-4-carbonyl)-2,5-diazabicyclo[4.2.0]octan-2-yl]-8-oxo-5H,8H-pyrido[2,3-b]pyrazin-5-yl]acetamide |
| I-290 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-{2-oxa-6-azaspiro[3.4]octan-6-yl}-8-oxo-5H,8H-pyrido[2,3-b]pyrazin-5-yl}acetamide |
| I-291 | rac-N-(2-chloro-4-(trifluoromethyl)phenyl)-2-(7-(6,6-difluoro-4-(5-hydroxy-6-methylpyrimidine-4-carbonyl)octahydro-1H-cyclopenta[b]pyrazin-1-yl)-2-(dimethylamino)-6-ethyl-8-oxopyrido[2,3-b]pyrazin-5(8H)-yl)acetamide (racemic mixture, trans) |
| I-292 | N-[2-chloro-4-(trifluoromethyl)phenyl]-2-[2-(dimethylamino)-6-ethyl-7-[(1S,6S)-5-[4-hydroxy-2-methoxy-5-(methoxymethyl)pyridine-3-carbonyl]-2,5-diazabicyclo[4.2.0]octan-2-yl]-8-oxo-5H,8H-pyrido[2,3-b]pyrazin-5-yl]acetamide |
| I-293 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-[(2-hydroxycyclobutyl)(methyl)amino]-8-oxo-5H,8H-pyrido[2,3-b]pyrazin-5-yl}acetamide |
| I-294 | N-(2-chloro-4-(trifluoromethyl)phenyl)-2-(2-(dimethylamino)-6-ethyl-7-(4-(5-hydroxy-6-methylpyrimidine-4-carbonyl)hexahydrofuro[3,4-b]pyrazin-1(2H)-yl)-8-oxopyrido[2,3-b]pyrazin-5(8H)-yl)acetamide (single stereoisomer, first eluting compound as stereoisomer 1, cis) |
| I-295 | N-(2-chloro-4-(trifluoromethyl)phenyl)-2-(2-(dimethylamino)-6-ethyl-7-(4-(5-hydroxy-6-methylpyrimidine-4-carbonyl)hexahydrofuro[3,4-b]pyrazin-1(2H)-yl)-8-oxopyrido[2,3-b]pyrazin-5(8H)-yl)acetamide (single stereoisomer, second eluting compound as stereoisomer 2, cis) |
| I-296 | N-(2-chloro-4-(trifluoromethyl)phenyl)-2-(7-(6,6-difluoro-4-(5-hydroxy-6-methylpyrimidine-4-carbonyl)octahydro-1H-cyclopenta[b]pyrazin-1-yl)-2-(dimethylamino)-6-ethyl-8-oxopyrido[2,3-b]pyrazin-5(8H)-yl)acetamide (single stereoisomer, first eluting compound as stereoisomer 1, trans) |
| I-297 | N-(2-chloro-4-(trifluoromethyl)phenyl)-2-(7-(6,6-difluoro-4-(5-hydroxy-6-methylpyrimidine-4-carbonyl)octahydro-1H-cyclopenta[b]pyrazin-1-yl)-2-(dimethylamino)-6-ethyl-8-oxopyrido[2,3-b]pyrazin-5(8H)-yl)acetamide (single stereoisomer, second eluting compound as stereoisomer 2, trans) |
| I-299 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-{[(1S,3S)-3-hydroxycyclopentyl](methyl)amino}-8-oxo-5H,8H-pyrido[2,3-b]pyrazin-5-yl}acetamide |
| I-300 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-{[(1R,3S)-3-hydroxycyclopentyl](methyl)amino}-8-oxo-5H,8H-pyrido[2,3-b]pyrazin-5-yl}acetamide |
| I-301 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-{[(1R,3R)-3-hydroxycyclopentyl](methyl)amino}-8-oxo-5H,8H-pyrido[2,3-b]pyrazin-5-yl}acetamide |
| I-302 | N-[2-chloro-4-(trifluoromethyl)phenyl]-2-{6-ethyl-7-[(1S,6S)-5-(5-hydroxy-6-methylpyrimidine-4-carbonyl)-2,5-diazabicyclo[4.2.0]octan-2-yl]-2-{[(1S,3R)-3-hydroxycyclopentyl](methyl)amino}-8-oxo-5H,8H-pyrido[2,3-b]pyrazin-5-yl}acetamide |
| I-303 | N-(2-chloro-4-(trifluoromethyl)phenyl)-2-(2-(dimethylamino)-6-ethyl-7-(4-(5-hydroxy-6-methylpyrimidine-4-carbonyl)-3-(methoxymethyl)piperazin-1-yl)-8-oxopyrido[2,3-b]pyrazin-5(8H)-yl)acetamide (single stereoisomer, first eluting compound as stereoisomer 1) |

TABLE 1a

| No. | IUPAC Name |
|---|---|
| I-3a | N-(2-chloro-4-(trifluoromethyl)phenyl)-2-(7-ethyl-8-(4-(5-hydroxy-6-methylpyrimidine-4-carbonyl)piperazin-1-yl)-9-oxo-2,3,4,9-tetrahydro-6H-pyrano[2,3-b]pyrido[2,3-e]pyrazin-6-yl)acetamide |
| I-4a | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(pyridin-4-yl)pyrido[2,3-b]pyrazin-5(8H)-yl)acetamide |
| I-5a | 2-(7-chloro-2-ethyl-3-(4-(5-hydroxy-6-methylpyrimidine-4-carbonyl)piperazin-1-yl)-4-oxo-1,5-naphthyridin-1(4H)-yl)-N-(2-chloro-4-(trifluoromethyl)phenyl)acetamide |
| I-14a | N-(2-chloro-4-(trifluoromethyl)phenyl)-2-(2-ethyl-3-(4-(5-hydroxy-6-methylpyrimidine-4-carbonyl)piperazin-1-yl)-4-oxopyrido[2,3-b]quinoxalin-1(4H)-yl)acetamide |
| I-15a | N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(1H-pyrazol-1-yl)pyrido[2,3-b]pyrazin-5(8H)-yl)acetamide |
| I-16a | N-(2-chloro-4-(trifluoromethyl)phenyl)-2-(3,6-diethyl-7-(4-(5-hydroxy-6-methylpyrimidine-4-carbonyl)piperazin-1-yl)-8-oxopyrido[2,3-b]pyrazin-5(8H)-yl)acetamide |
| I-17a | N-(2-chloro-4-(trifluoromethyl)phenyl)-2-(3,6-diethyl-7-(4-(5-hydroxy-6-methylpyrimidine-4-carbonyl)piperazin-1-yl)-2-methyl-8-oxopyrido[2,3-b]pyrazin-5(8H)-yl)acetamide |
| I-18a | N-(2-chloro-4-(trifluoromethyl)phenyl)-2-(6-ethyl-7-(4-(5-hydroxy-6-methylpyrimidine-4-carbonyl)piperazin-1-yl)-2-(hydroxymethyl)-3-methyl-8-oxopyrido[2,3-b]pyrazin-5(8H)-yl)acetamide |
| I-23a | N-(2-chloro-4-(trifluoromethyl)phenyl)-2-(6-ethyl-7-(4-(5-hydroxy-6-methylpyrimidine-4-carbonyl)piperazin-1-yl)-8-oxo-[1,3]dioxolo[4,5-b]pyrido[2,3-e]pyrazin-5(8H)-yl)acetamide |
| I-24a | N-(2-chloro-4-(trifluoromethyl)phenyl)-2-(6-ethyl-7-(4-(5-hydroxy-6-methylpyrimidine-4-carbonyl)piperazin-1-yl)-8-oxo-3,8-dihydrofuro[2,3-b]pyrido[2,3-e]pyrazin-5(2H)-yl)acetamide |
| I-25a | N-(2-chloro-4-(trifluoromethyl)phenyl)-2-(7-ethyl-6-(4-(5-hydroxy-6-methylpyrimidine-4-carbonyl)piperazin-1-yl)-5-oxo-2,3-dihydrofuro[2,3-b]pyrido[3,2-e]pyrazin-8(5H)-yl)acetamide |
| I-28a | N-(2-chloro-4-(trifluoromethyl)phenyl)-2-(2-ethyl-3-(4-(5-hydroxy-6-methylpyrimidine-4-carbonyl)piperazin-1-yl)-4-oxodipyrido[2,3-b:4',3'-e]pyrazin-1(4H)-yl)acetamide |
| I-29a | N-(2-chloro-4-(trifluoromethyl)phenyl)-2-(2-ethyl-3-(4-(5-hydroxy-6-methylpyrimidine-4-carbonyl)piperazin-1-yl)-4-oxodipyrido[2,3-b:3',4'-e]pyrazin-1(4H)-yl)acetamide |
| I-31a | N-(2-chloro-4-(trifluoromethyl)phenyl)-2-(6-ethyl-7-(4-(5-hydroxy-6-methylpyrimidine-4-carbonyl)piperazin-1-yl)-2-(oxetan-3-yl)-8-oxopyrido[2,3-b]pyrazin-5(8H)-yl)acetamide |
| I-32a | N-(2-chloro-4-(trifluoromethyl)phenyl)-2-(6-ethyl-7-(4-(5-hydroxy-6-methylpyrimidine-4-carbonyl)piperazin-1-yl)-3-methyl-2-(oxetan-3-yl)-8-oxopyrido[2,3-b]pyrazin-5(8H)-yl)acetamide |
| I-33a | N-(2-chloro-4-(trifluoromethyl)phenyl)-2-(2-ethyl-3-(4-(5-hydroxy-6-methylpyrimidine-4-carbonyl)piperazin-1-yl)-4-oxo-6,8-dihydrofuro[3,4-b]pyrido[2,3-e]pyrazin-1(4H)-yl)acetamide |
| I-34a | N-(2-chloro-4-(trifluoromethyl)phenyl)-2-(6-ethyl-7-(4-(5-hydroxy-6-methylpyrimidine-4-carbonyl)piperazin-1-yl)-2-((methyl(pyridin-3-yl)amino)methyl)-8-oxopyrido[2,3-b]pyrazin-5(8H)-yl)acetamide |
| I-35a | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-((pyridin-3-ylamino)methyl)pyrido[2,3-b]pyrazin-5(8H)-yl)acetamide |
| I-36a | N-(2-chloro-4-(trifluoromethyl)phenyl)-2-(6-ethyl-7-(4-(5-hydroxy-6-methylpyrimidine-4-carbonyl)piperazin-1-yl)-2-(((1-methyl-1H-pyrazol-3-yl)amino)methyl)-8-oxopyrido[2,3-b]pyrazin-5(8H)-yl)acetamide |
| I-37a | N-(2-chloro-4-(trifluoromethyl)phenyl)-2-(6-ethyl-7-(4-(5-hydroxy-6-methylpyrimidine-4-carbonyl)piperazin-1-yl)-2-((1-methyl-1H-pyrazol-3-yl)amino)-8-oxopyrido[2,3-b]pyrazin-5(8H)-yl)acetamide |
| I-38a | N-(2-chloro-4-(trifluoromethyl)phenyl)-2-(6-ethyl-7-(4-(5-hydroxy-6-methylpyrimidine-4-carbonyl)piperazin-1-yl)-2-(methyl(1-methyl-1H-pyrazol-3-yl)amino)-8-oxopyrido[2,3-b]pyrazin-5(8H)-yl)acetamide |
| I-39a | N-(2-chloro-4-(trifluoromethyl)phenyl)-2-(6-ethyl-7-(4-(5-hydroxy-6-methylpyrimidine-4-carbonyl)piperazin-1-yl)-2-(methyl(pyridin-3-yl)amino)-8-oxopyrido[2,3-b]pyrazin-5(8H)-yl)acetamide |
| I-40a | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(pyridin-3-ylamino)pyrido[2,3-b]pyrazin-5(8H)-yl)acetamide |
| I-41a | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(pyridin-3-yloxy)pyrido[2,3-b]pyrazin-5(8H)-yl)acetamide |
| I-42a | N-(2-chloro-4-(trifluoromethyl)phenyl)-2-(6-ethyl-7-(4-(5-hydroxy-6-methylpyrimidine-4-carbonyl)piperazin-1-yl)-3-(methylsulfonyl)-8-oxopyrido[2,3-b]pyrazin-5(8H)-yl)acetamide |
| I-43a | N-(2-chloro-4-(trifluoromethyl)phenyl)-2-(6-ethyl-7-(4-(5-hydroxy-6-methylpyrimidine-4-carbonyl)piperazin-1-yl)-3-((1-methyl-1H-pyrazol-3-yl)sulfonyl)-8-oxopyrido[2,3-b]pyrazin-5(8H)-yl)acetamide |

TABLE 1a-continued

| No. | IUPAC Name |
|---|---|
| I-44a | 2-(3-acetamido-6-ethyl-7-(4-(5-hydroxy-6-methylpyrimidine-4-carbonyl)piperazin-1-yl)-8-oxopyrido[2,3-b]pyrazin-5(8H)-yl)-N-(2-chloro-4-(trifluoromethyl)phenyl)acetamide |
| I-45a | N-(2-chloro-4-(trifluoromethyl)phenyl)-2-(2-ethyl-3-(4-(5-hydroxy-6-methylpyrimidine-4-carbonyl)piperazin-1-yl)-4,8-dioxo-4,6,7,8-tetrahydro-1H-pyrido[2,3-b]pyrrolo[3,4-e]pyrazin-1-yl)acetamide |
| I-46a | N-(2-chloro-4-(trifluoromethyl)phenyl)-2-(2-ethyl-3-(4-(5-hydroxy-6-methylpyrimidine-4-carbonyl)piperazin-1-yl)-7-(2-methoxypyridin-4-yl)-4,8-dioxo-4,6,7,8-tetrahydro-1H-pyrido[2,3-b]pyrrolo[3,4-e]pyrazin-1-yl)acetamide |
| I-47a | N-(2-chloro-4-(trifluoromethyl)phenyl)-2-(2-ethyl-3-(4-(5-hydroxy-6-methylpyrimidine-4-carbonyl)piperazin-1-yl)-7-(2-methoxypyridin-4-yl)-4,6-dioxo-4,6,7,8-tetrahydro-1H-pyrido[2,3-b]pyrrolo[3,4-e]pyrazin-1-yl)acetamide |
| I-48a | N-(2-chloro-4-(trifluoromethyl)phenyl)-2-(2-ethyl-3-(4-(5-hydroxy-6-methylpyrimidine-4-carbonyl)piperazin-1-yl)-4,6-dioxo-4,6,7,8-tetrahydro-1H-pyrido[2,3-b]pyrrolo[3,4-e]pyrazin-1-yl)acetamide |
| I-49a | 5-(2-((2-chloro-4-(trifluoromethyl)phenyl)amino)-2-oxoethyl)-6-ethyl-7-(4-(5-hydroxy-6-methylpyrimidine-4-carbonyl)piperazin-1-yl)-N-methyl-8-oxo-5,8-dihydropyrido[2,3-b]pyrazine-3-carboxamide |
| I-50a | N-(2-chloro-4-(trifluoromethyl)phenyl)-2-(6-ethyl-7-(4-(5-hydroxy-6-methylpyrimidine-4-carbonyl)piperazin-1-yl)-8-oxo-3-(pyrrolidine-1-carbonyl)pyrido[2,3-b]pyrazin-5(8H)-yl)acetamide |
| I-55a | N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(prop-1-yn-1-yl)pyrido[2,3-b]pyrazin-5(8H)-yl)acetamide |
| I-56a | N-(2-chloro-4-(trifluoromethyl)phenyl)-2-(6-ethyl-7-(4-(5-hydroxy-6-methylpyrimidine-4-carbonyl)piperazin-1-yl)-3-methyl-2-(2-methylprop-1-en-1-yl)-8-oxopyrido[2,3-b]pyrazin-5(8H)-yl)acetamide |
| I-58a | N-(2-chloro-4-(trifluoromethyl)phenyl)-2-(2-cyano-6-ethyl-7-(4-(5-hydroxy-6-methylpyrimidine-4-carbonyl)piperazin-1-yl)-3-methyl-8-oxopyrido[2,3-b]pyrazin-5(8H)-yl)acetamide |
| I-59a | N-(2-chloro-4-(trifluoromethyl)phenyl)-2-(6-ethyl-2,2-difluoro-7-(4-(5-hydroxy-6-methylpyrimidine-4-carbonyl)piperazin-1-yl)-8-oxo-[1,3]dioxolo[4,5-b]pyrido[2,3-e]pyrazin-5(8H)-yl)acetamide |
| I-60a | (Z)-N-(2-chloro-4-(trifluoromethyl)phenyl)-2-(6-ethyl-7-(4-(5-hydroxy-6-methylpyrimidine-4-carbonyl)piperazin-1-yl)-2-(3-methoxyprop-1-en-1-yl)-8-oxopyrido[2,3-b]pyrazin-5(8H)-yl)acetamide |
| I-61a | (E)-N-(2-chloro-4-(trifluoromethyl)phenyl)-2-(6-ethyl-7-(4-(5-hydroxy-6-methylpyrimidine-4-carbonyl)piperazin-1-yl)-3-(3-methoxyprop-1-en-1-yl)-8-oxopyrido[2,3-b]pyrazin-5(8H)-yl)acetamide |
| I-62a | (Z)-N-(2-chloro-4-(trifluoromethyl)phenyl)-2-(6-ethyl-7-(4-(5-hydroxy-6-methylpyrimidine-4-carbonyl)piperazin-1-yl)-3-(3-methoxyprop-1-en-1-yl)-8-oxopyrido[2,3-b]pyrazin-5(8H)-yl)acetamide |
| I-64a | N-(2-chloro-4-(trifluoromethyl)phenyl)-2-(2-(2,2-difluorovinyl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-65a | N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(1,2,2-trifluorovinyl)pyrido[2,3-b]pyrazin-5(8H)-yl)acetamide |
| I-66a | N-(2-chloro-4-(trifluoromethyl)phenyl)-2-(3-(2,2-difluorovinyl)-6-ethyl-7-(4-(5-hydroxy-6-methylpyrimidine-4-carbonyl)piperazin-1-yl)-8-oxopyrido[2,3-b]pyrazin-5(8H)-yl)acetamide |
| I-67a | N-(2-chloro-4-(trifluoromethyl)phenyl)-2-(6-ethyl-7-(4-(5-hydroxy-6-methylpyrimidine-4-carbonyl)piperazin-1-yl)-8-oxo-3-(1,2,2-trifluorovinyl)pyrido[2,3-b]pyrazin-5(8H)-yl)acetamide |
| I-68a | (E)-N-(2-chloro-4-(trifluoromethyl)phenyl)-2-(6-ethyl-7-(4-(5-hydroxy-6-methylpyrimidine-4-carbonyl)piperazin-1-yl)-2-(3-methoxy-2-methylprop-1-en-1-yl)-8-oxopyrido[2,3-b]pyrazin-5(8H)-yl)acetamide |
| I-69a | (E)-N-(2-chloro-4-(trifluoromethyl)phenyl)-2-(6-ethyl-7-(4-(5-hydroxy-6-methylpyrimidine-4-carbonyl)piperazin-1-yl)-3-(3-methoxy-2-methylprop-1-en-1-yl)-8-oxopyrido[2,3-b]pyrazin-5(8H)-yl)acetamide |
| I-70a | (E)-N-(2-chloro-4-(trifluoromethyl)phenyl)-2-(6-ethyl-7-(4-(5-hydroxy-6-methylpyrimidine-4-carbonyl)piperazin-1-yl)-8-oxo-3-(3,3,3-trifluoroprop-1-en-1-yl)pyrido[2,3-b]pyrazin-5(8H)-yl)acetamide |
| I-71a | (E)-N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(3,3,3-trifluoroprop-1-en-1-yl)pyrido[2,3-b]pyrazin-5(8H)-yl)acetamide |
| I-72a | rac-2-(2-(cyclopropyl(methyl)amino)-6-ethyl-7-(-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(3-(trifluoromethyl)bicyclo[1.1.1]pentan-1-yl)acetamide (racemic mixture, trans) |
| I-73a | rac-2-(2-(cyclopropylamino)-6-ethyl-7-(-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(3-(trifluoromethyl)bicyclo[1.1.1]pentan-1-yl)acetamide (racemic mixture, trans) |
| I-74a | rac-2-(2-(azetidin-1-yl)-6-ethyl-7-(-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(3-(trifluoromethyl)bicyclo[1.1.1]pentan-1-yl)acetamide (racemic mixture, trans) |

TABLE 1a-continued

| No. | IUPAC Name |
|---|---|
| I-75a | rac-2-(6-ethyl-7-(-5-(5-hydroxy-6-methylpyrimidine-4-carbonyl)-2,5-diazabicyclo[4.2.0]octan-2-yl)-2-(methylamino)-8-oxopyrido[2,3-b]pyrazin-5(8H)-yl)-N-(3-(trifluoromethyl)bicyclo[1.1.1]pentan-1-yl)acetamide (racemic mixture, trans) |
| I-76a | rac-2-(2-(bis(methyl-d3)amino)-6-ethyl-7-(-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(3-(trifluoromethyl)bicyclo[1.1.1]pentan-1-yl)acetamide (racemic mixture, trans) |
| I-77a | rac-2-(2-(cyclobutylidenemethyl)-6-ethyl-7-(-5-(5-hydroxy-6-methylpyrimidine-4-carbonyl)-2,5-diazabicyclo[4.2.0]octan-2-yl)-8-oxopyrido[2,3-b]pyrazin-5(8H)-yl)-N-(3-(trifluoromethyl)bicyclo[1.1.1]pentan-1-yl)acetamide (racemic mixture, trans) |
| I-78a | rac-2-(6-ethyl-7-(-5-(5-hydroxy-6-methylpyrimidine-4-carbonyl)-2,5-diazabicyclo[4.2.0]octan-2-yl)-2-methoxy-3-methyl-8-oxopyrido[2,3-b]pyrazin-5(8H)-yl)-N-(3-(trifluoromethyl)bicyclo[1.1.1]pentan-1-yl)acetamide (racemic mixture, trans) |
| I-79a | rac-2-(2-cyclopropyl-6-ethyl-7-(-5-(5-hydroxy-6-methylpyrimidine-4-carbonyl)-2,5-diazabicyclo[4.2.0]octan-2-yl)-3-methyl-8-oxopyrido[2,3-b]pyrazin-5(8H)-yl)-N-(3-(trifluoromethyl)bicyclo[1.1.1]pentan-1-yl)acetamide (racemic mixture, trans) |
| I-80a | rac-2-(6-ethyl-7-(-5-(5-hydroxy-6-methylpyrimidine-4-carbonyl)-2,5-diazabicyclo[4.2.0]octan-2-yl)-2-(((1r,3R)-3-methoxycyclobutyl)(methyl)amino)-3-methyl-8-oxopyrido[2,3-b]pyrazin-5(8H)-yl)-N-(3-(trifluoromethyl)bicyclo[1.1.1]pentan-1-yl)acetamide (racemic mixture, trans) |
| I-81a | rac-2-(6-ethyl-7-(-5-(5-hydroxy-6-methylpyrimidine-4-carbonyl)-2,5-diazabicyclo[4.2.0]octan-2-yl)-8-oxo-2-(pyrrolidin-1-yl)pyrido[2,3-b]pyrazin-5(8H)-yl)-N-(3-(trifluoromethyl)bicyclo[1.1.1]pentan-1-yl)acetamide (racemic mixture, trans) |
| I-82a | rac-2-(7-ethyl-6-(-5-(5-hydroxy-6-methylpyrimidine-4-carbonyl)-2,5-diazabicyclo[4.2.0]octan-2-yl)-2-methyl-5-oxopyrido[2,3-b]thieno[3,2-e]pyrazin-8(5H)-yl)-N-(3-(trifluoromethyl)bicyclo[1.1.1]pentan-1-yl)acetamide (racemic mixture, trans) |
| I-83a | rac-2-(6-ethyl-7-(-5-(5-hydroxy-6-methylpyrimidine-4-carbonyl)-2,5-diazabicyclo[4.2.0]octan-2-yl)-2-methyl-8-oxopyrido[2,3-b]thiazolo[4,5-e]pyrazin-5(8H)-yl)-N-(3-(trifluoromethyl)bicyclo[1.1.1]pentan-1-yl)acetamide (racemic mixture, trans) |
| I-84a | rac-2-(6-ethyl-7-(-5-(5-hydroxy-6-methylpyrimidine-4-carbonyl)-2,5-diazabicyclo[4.2.0]octan-2-yl)-1-methyl-8-oxo-1,2,3,8-tetrahydro-5H-pyrido[2,3-b]pyrrolo[2,3-e]pyrazin-5-yl)-N-(3-(trifluoromethyl)bicyclo[1.1.1]pentan-1-yl)acetamide (racemic mixture, trans) |
| I-85a | rac-2-(2-(dimethylamino)-6-ethyl-7-(-5-(5-hydroxy-6-methylpyrimidine-4-carbonyl)-2,5-diazabicyclo[4.2.0]octan-2-yl)-3-methyl-8-oxopyrido[2,3-b]pyrazin-5(8H)-yl)-N-(3-(trifluoromethyl)bicyclo[1.1.1]pentan-1-yl)acetamide (racemic mixture, trans) |
| I-86a | N-(2-chloro-4-(trifluoromethyl)phenyl)-2-(3-(dimethylamino)-7-ethyl-6-(4-(5-hydroxy-6-methylpyrimidine-4-carbonyl)piperazin-1-yl)-5-oxopyrido[3,2-e][1,2,4]triazin-8(5H)-yl)acetamide |
| I-87a | rac-N-(2-chloro-4-(trifluoromethyl)phenyl)-2-(3-(dimethylamino)-7-ethyl-6-(-5-(5-hydroxy-6-methylpyrimidine-4-carbonyl)-2,5-diazabicyclo[4.2.0]octan-2-yl)-5-oxopyrido[3,2-e][1,2,4]triazin-8(5H)-yl)acetamide (racemic mixture, trans) |
| I-89a | N-(2-chloro-4-(trifluoromethyl)phenyl)-2-(3-(cyclobutylidenemethyl)-7-ethyl-6-((1S,6S)-5-(5-hydroxy-6-methylpyrimidine-4-carbonyl)-2,5-diazabicyclo[4.2.0]octan-2-yl)-5-oxopyrido[3,2-e][1,2,4]triazin-8(5H)-yl)acetamide |
| I-91a | 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5(8H)-yl)-N-(2-fluoro-4-(trifluoromethyl)phenyl)acetamide |
| I-95a | N-(2-chloro-4-(trifluoromethyl)phenyl)-2-(6-ethyl-7-((1S,6S)-5-(5-hydroxy-6-methylpyrimidine-4-carbonyl)-2,5-diazabicyclo[4.2.0]octan-2-yl)-2-(methyl(methyl-d3)amino)-8-oxopyrido[2,3-b]pyrazin-5(8H)-yl)acetamide |

4. Pharmaceutical Compositions, Methods of Treatment and Uses of Compounds

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration, in particular oral administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethylene glycol; for tablets also
  c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and
e) absorbents, colorants, flavors and sweeteners.

Typical approaches to solubilize compounds for parenteral administration are the optimization of the pH or the use of co-solvents (e.g. PEG300, PEG400, propylene glycol, or ethanol). If these approaches are, for any reason, not feasible, the use of surfactants may be considered (e.g. Tween® 80 or Cremophor EL®). Cyclodextrins are established as safe solubilizing agents. Compounds with a high solubility in natural oils may be solubilized in parenteral fat emulsions.

There is also provided a pharmaceutical composition comprising a compound of Formula I, I', or I" as described herein, or a pharmaceutically acceptable salt thereof, and one or more pharmaceutically acceptable carriers.

Uses

The compounds of Formula I, I', or I" of the present invention in free form or in pharmaceutically acceptable salt form, exhibit valuable pharmacological properties, e.g. WRN inhibiting properties, e.g. as indicated in vitro tests as provided in the next sections, and are therefore indicated for therapy, or for use as research chemicals, e.g. as a chemical probe, and as tool compounds.

Also provided is a compound of Formula I, I', or I", as described herein. Said compound can be used as a research chemical, a compound herein comprising an added biotin moiety, for example a tool compound or chemical probe, in particular for research on WRN. In another embodiment there is provided the use of a compound of Formula I, I', or I", as described herein, as a research chemical, for example tool compound or chemical probe, in particular for research on WRN.

There is also provided a compound of Formula I, I', or I" as described herein, or a pharmaceutically acceptable salt thereof, for use in the treatment of cancer. Cancers that may be treated by WRN inhibition include cancers that are characterized as microsatellite instability-high (MSI-H) or mismatch repair deficient (dMMR). In particular, a compound of Formula I, I', or I" as described herein, or a pharmaceutically acceptable salt thereof, may be useful in the treatment of a cancer that is characterized as microsatellite instability-high (MSI-H) or mismatch repair deficient (dMMR).

There is also provided a compound of Formula I, I', or I" as described herein, or a pharmaceutically acceptable salt thereof, for use as a medicament. In particular, said use is:
  for the treatment of a disease that is treated by WRN inhibition,
  for the treatment of cancer,
  for the treatment of cancer that is characterized as microsatellite instability-high (MSI-H) or mismatch repair deficient (dMMR),
  for the treatment of cancer that is characterized as microsatellite instability-high (MSI-H) or mismatch repair deficient (dMMR), such as colorectal, gastric, prostate, endometrial, adrenocortical, uterine, cervical, esophageal, breast, kidney and ovarian cancer,
  for the treatment of cancer that is characterized as microsatellite instability-high (MSI-H) or mismatch repair deficient (dMMR) is selected from colorectal, gastric, prostate and endometrial cancer, or
  for the treatment of cancer wherein the cancer characterized as microsatellite instability-high (MSI-H) or mismatch repair deficient (dMMR) is selected from uterine corpus endometrial carcinoma, colon adenocarcinoma, stomach adenocarcinoma, rectal adenocarcinoma, adrenocortical carcinoma, uterine carcinosarcoma, cervical squamous cell carcinoma, endocervical adenocarcinoma, esophageal carcinoma, breast carcinoma, kidney renal clear cell carcinoma, prostate cancer and ovarian serous cystadenocarcinoma.

There is Also Provided a Method of:
  modulating WRN activity in a subject, wherein the method comprises administering to the subject a therapeutically effective amount of the compound of Formula I, I', or I" as described herein, or a pharmaceutically acceptable salt thereof,
  inhibiting WRN in a subject, wherein the method comprises administering to the subject a therapeutically effective amount of the compound of Formula I, I', or I" as described herein, or a pharmaceutically acceptable salt thereof,
  treating a disorder or disease which can be treated by WRN inhibition in a subject, comprising administering to the subject a therapeutically effective amount of the compound of Formula I, I', or I" as described herein, or a pharmaceutically acceptable salt thereof,
  treating cancer in a subject, comprising administering to the subject a therapeutically effective amount of the compound of Formula I, I', or I" as described herein, or a pharmaceutically acceptable salt thereof,
  treating cancer in a subject, comprising administering a compound of Formula I, I', or I" as described herein, wherein the cancer is characterized as microsatellite instability-high (MSI-H) or mismatch repair deficient (dMMR). In particular, the cancer characterized as microsatellite instability-high (MSI-H) or mismatch repair deficient (dMMR) is selected from colorectal, gastric, prostate, endometrial, adrenocortical, uterine, cervical, esophageal, breast, kidney and ovarian cancer. More particularly, the cancer characterized as microsatellite instability-high (MSI-H) or mismatch repair deficient (dMMR) is selected from colorectal, gastric, prostate and endometrial cancer. Examples include uterine corpus endometrial carcinoma, colon adenocarcinoma, stomach adenocarcinoma, rectal adenocarcinoma, adrenocortical carcinoma, uterine carcinosarcoma, cervical squamous cell carcinoma, endocervical adenocarcinoma, esophageal carcinoma, breast carcinoma, kidney renal clear cell carcinoma, prostate cancer and ovarian serous cystadenocarcinoma.

There is also provided the use of a compound of Formula I, I', or I" as described herein, or a pharmaceutically acceptable salt thereof:
  in therapy,
  in the manufacture of a medicament,
  in the manufacture of a medicament for the treatment of cancer. In particular, said cancer is characterized as microsatellite instability-high (MSI-H) or mismatch repair deficient (dMMR),
  in the manufacture of a medicament for treatment of a disease which may be treated by WRN inhibition,
wherein in particular, the cancer is characterized by microsatellite instability-high (MSI-H) or mismatch repair deficient (dMMR), for example colorectal, gastric, prostate, endometrial, adrenocortical, uterine, cervical, esophageal, breast, kidney and ovarian cancer, in particular, colorectal, gastric, prostate or endometrial cancer, or uterine corpus endometrial carcinoma, colon adenocarcinoma, stomach adenocarcinoma, rectal adenocarcinoma, adrenocortical carcinoma, uterine carcinosarcoma, cervical squamous cell carcinoma, endocervical adenocarcinoma, esophageal carcinoma, breast carcinoma, kidney renal clear cell carcinoma and ovarian serous cystadenocarcinoma.

In some embodiments, the subject has or is identified as having a microsatellite instable (MSI-H) cancer, e.g., in reference to a control, e.g., a normal, subject. In one embodiment, the subject has MSI-H advanced solid tumors, a colorectal cancer (CRC), endometrial, uterine, stomach or other MSI-H cancer. In some embodiments, the subject has a colorectal (CRC), endometrial or stomach cancer, which cancer has or is identified as having a microsatellite instability (MSI-H), e.g., in reference to a control, e.g., a normal, subject. Such identification techniques are known in the art.

Forms

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any formula given herein is intended to represent unlabeled forms as well as isotopically labeled forms of the compounds, in addition to the deuteration specifically claimed in Formula I, I', or I''. Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., 2H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present invention. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as 3H, 11C, 13C, 14C, 15N, 18F, 31P, 32P, 35S, 36Cl, 123I, 124I, and 125I, respectively. Accordingly it should be understood that the invention includes compounds that incorporate one or more of any of the aforementioned isotopes, including for example, radioactive isotopes, such as 3H and 14C, or those into which non-radioactive isotopes, such as 2H and 13C are present. Such isotopically labelled compounds are useful in metabolic studies (with 14C), reaction kinetic studies (with, for example 2H or 3H), detection or imaging techniques, such as positron emission tomography (PET) or single-photon emission computed tomography (SPECT) including drug or substrate tissue distribution assays, or in radioactive treatment of patients. In particular, an 18F or labeled compound may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagents in place of the non-labeled reagent previously employed.

A "compound of the present invention" or a "compound of Formula I, I', or I''" includes a zwitterion thereof, a non-zwitterion thereof (non-charged form), or a pharmaceutically acceptable salt of said zwitterionic or non-zwitterionic form thereof. "Zwitterion" or "zwitterionic form" means a compound containing both positive and negatively charged functional groups.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to colorectal, gastric, endometrial, prostate, adrenocortical, uterine, cervical, esophageal, breast, kidney, ovarian cancer and the like.

The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

"WRN inhibitor" or "WRN helicase inhibitor" as used herein means a compound that inhibits Werner Syndrome RecQ DNA helicase (WRN). The term "WRN" as used herein refers to the protein of Werner Syndrome RecQ DNA helicase. The term "WRN" includes mutants, fragments, variants, isoforms, and homologs of full-length wild-type WRN. In one embodiment, the protein is encoded by the WRN gene (Entrez gene ID 7486; Ensembl ID ENSG00000165392). Exemplary WRN sequences are available at the Uniprot database under accession number Q14191.

"Disease or condition mediated by WRN" includes a disease or condition, such as cancer, which is treated by WRN inhibition. In particular this can include cancers characterized as microsatellite instability-high (MSI-H) or mismatch repair deficient (dMMR).

"Microsatellite unstable cancer," "microsatellite instability-high cancer," "microsatellite high cancer" and "MSI-high cancer," "MSIhi" and "MSI-H" when used herein, are used interchangeably, and describe cancers that have a high number of alterations in the length of simple repetitive genomic sequences within microsatellites.

The determination of MSI-H or dMMR tumor status for patients can be performed using, e.g., polymerase chain reaction (PCR) tests for MSI-H status or immunohistochemistry (IHC) tests for dMMR. Methods for identification of MSI-H or dMMR tumor status are described, e.g., in Ryan et al. Crit Rev Oncol Hematol. 2017; 116:38-57; Dietmaier and Hofstadter. Lab Invest 2001, 81:1453-1456; and Kawakami et al. Curr Treat Options Oncol. 2015; 16(7): 30).

Microsatellite instability can be found in colorectal cancer, gastric cancer and endometrial cancer in particular, but also in adrenocortical, uterine, cervical, esophageal, breast, kidney, prostate and ovarian cancers. Examples of microsatellite high cancers include uterine corpus endometrial carcinoma, colon adenocarcinoma, stomach adenocarcinoma, rectal adenocarcinoma, adrenocortical carcinoma, uterine carcinosarcoma, cervical squamous cell carcinoma, endocervical adenocarcinoma, esophageal carcinoma, breast carcinoma, kidney renal clear cell carcinoma and ovarian serous cystadenocarcinoma.

A cancer that has "defective mismatch repair" (dMMR) or "dMMR character" includes cancer types associated with documented MLH1, PMS2, MSH2, MSH3, MSH6, MLH3, and PMS1 mutations or epigenetic silencing, microsatellite fragile sites, or other gene inactivation mechanisms, including but not limited to cancers of the lung, breast, kidney, large intestine, ovary, prostate, upper aerodigestive tract, stomach, endometrium, liver, pancreas, haematopoietic and lymphoid tissue, skin, thyroid, pleura, autonomic ganglia, central nervous system, soft tissue, pediatric rhabdoid sarcomas, melanomas and other cancers. A cell or cancer with "defective" mismatch repair has a significantly reduced (e.g., at least about 25%, 30%, 40%, 50%, 60%, 70%, 80% or 90% decrease) amount of mismatch repair. In some cases, a cell or cancer which is defective in mismatch repair will perform no mismatch repair.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22nd Ed. Pharmaceutical Press, 2013, pp. 1049-1070).

The terms "synthetic lethality," and "synthetically lethal" are used to refer to reduced cell viability and/or a reduced rate of cell proliferation caused by a combination of mutations or approaches to cause loss of function (e.g., RNA interference or protein function inhibition) in two or more genes but not by the loss of function of only one of these genes.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In some embodiments, the methods of the invention comprise administration of a therapeutically effective amount of a compound herein.

In one embodiment, the term "a therapeutically effective amount" refers to the amount of the compound of the present invention that, when administered to a subject, is effective to (1) at least partially alleviate, prevent and/or ameliorate a condition, or a disorder or a disease (i) mediated by WRN, or (ii) associated with WRN activity, or (iii) characterized by activity (normal or abnormal) of WRN; or (2) reduce or inhibit the activity of WRN.

In another embodiment, the term "a therapeutically effective amount" refers to the amount of the compound of the present invention that, when administered to a cell, or a tissue, or a non-cellular biological material, or a medium, is effective to at least partially reducing or inhibiting the activity of WRN, or reducing WRN protein levels.

As used herein, the term "subject" refers to primates (e.g., humans, male or female), dogs, rabbits, guinea pigs, pigs, rats and mice. In certain embodiments, the subject is a primate, a rat or a mouse. In yet other embodiments, the subject is a human.

As used herein, the term "inhibit," "inhibition" or "inhibiting" refers to the reduction or suppression of a given condition, symptom, or disorder, or disease, or a significant decrease in the baseline activity of a biological activity or process.

As used herein, the term "treat," "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent," "preventing" or "prevention" of any disease or disorder refers to the prophylactic treatment of the disease or disorder; or delaying the onset or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

"May join" means joins or does not join.

"May be replaced by deuterium" means is replaced by deuterium, or is not replaced by deuterium.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Isomeric Forms

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

Compounds of the invention, i.e. compounds of Formula I, I', or I" that contain groups capable of acting as donors and/or acceptors for hydrogen bonds may be capable of forming co-crystals with suitable co-crystal formers. These co-crystals may be prepared from compounds of Formula I, I', or I" by known co-crystal forming procedures. Such procedures include grinding, heating, co-subliming, co-melting, or contacting in solution compounds of Formula I, I', or I" with the co-crystal former under crystallization conditions and isolating co-crystals thereby formed. Suitable co-crystal formers include those described in WO 2004/078163. Hence the invention further provides co-crystals comprising a compound of Formula I, I', or I".

Furthermore, the compounds of the present invention, including their salts, can also be obtained in the form of their hydrates, or include other solvents used for their crystallization.

The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Dosage Forms

The pharmaceutical composition or combination of the present invention may, for example, be in unit dosage of about 1-1000 mg of active ingredient(s) for a subject of about 50-70 kg.

Combinations

"Combination" refers to either a fixed combination in one dosage unit form, or a combined administration where a compound of Formula I, I', or I", or a pharmaceutically acceptable salt thereof, and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage.

The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agents.

The combinations described herein can include a compound of Formula I, I', or I" and one or more additional therapeutic agents, e.g., one or more anti-cancer agents, cytotoxic or cytostatic agents, hormone treatment, vaccines, and/or other immunotherapies. In other embodiments, the combination is further administered or used in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the treatment.

There is also provided a combination comprising a compound of Formula I, I', or I" as described herein, or a pharmaceutically acceptable salt thereof, as described herein, and one or more additional therapeutically active agents. The additional therapeutic agent is, for example, a chemical compound, peptide, antibody, antibody fragment or nucleic acid, which is therapeutically active or enhances the therapeutic activity when administered to a patient in combination with a compound of the present disclosure. In particular, an additional therapeutically active agent is:

an anti-cancer agent,
a chemotherapy,
chemotherapy selected from anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC- Dome®), dactinomycin (Actinomycin D, Cosmegan), daunorubicin hydrochloride (Cerubidine®), daunorubicin citrate, liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEXO), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), in particular fluorouracil (5-FU) and irinotecan (Camptosar®).

a PD-1 inhibitor, an anti-PD-1 antibody molecule, a PD-1 inhibitor selected from spartalizumab (Novartis), nivolumab (Bristol-Myers Squibb), pembrolizumab (Merck & Co), pidilizumab (CureTech), MED10680 (Medimmune), cemiplimab (REGN2810, Regeneron), dostarlimab (TSR-042, Tesaro), PF-06801591 (Pfizer), tislelizumab (BGB-A317, Beigene), BGB-108 (Beigene), INCSHR1210 (Incyte), balstilimab (AGEN2035, Agenus), sintilimab (InnoVent), toripalimab (Shanghai Junshi Bioscience), camrelizumab (Jiangsu Hengrui Medicine Co.), AMP-224 (Amplimmune), penpulimab (Akeso Biopharma Inc), zimberelimab (Arcus Biosciences Inc), and prolgolimab (Biocad Ltd), spartalizumab, or tislelizumab (BGB-A317, Beigene).

In a further embodiment, the additional therapeutically active agent is the chemotherapy irinotecan (Camptosar®).

In another embodiment, the additional therapeutically active agent is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. In another embodiment, the additional therapeutically active agent is an anti-PD-1 antibody molecule.

In a further embodiment, the PD-1 inhibitor is an anti-PD-1 antibody molecule as described in US 2015/0210769, published on Jul. 30, 2015, entitled "Antibody Molecules to PD-1 and Uses Thereof"

In another embodiment, there is provided a combination of a compound of Formula I, I', or I" or a pharmaceutically acceptable salt thereof, and a chemotherapy, and a PD-1 inhibitor. In particular, the chemotherapy and PD-1 inhibitor are selected from those described above. In some embodiments, the PD-1 inhibitor is pembrolizumab, nivolumab, cemiplimab, dostarlimab, or retifanlimab.

The above-mentioned compounds, which can be used in combination with a compound of the present invention, can be prepared and administered as described in the art, such as in the documents cited above.

In one embodiment, the invention provides a product comprising a compound of the present invention and at least one other therapeutic agent as a combined preparation for simultaneous, separate or sequential use in therapy. In one embodiment, the therapy is the treatment of a disease or condition mediated by WRN. Products provided as a combined preparation include a composition comprising the compound of Formula I, I', or I" and the other therapeutic agent(s) together in the same pharmaceutical composition, or the compound of the present invention and the other therapeutic agent(s) in separate form, e.g. in the form of a kit.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

Accordingly, the invention provides the use of a compound of the present invention for treating a disease or condition mediated by WRN, wherein the medicament is prepared for administration with another therapeutic agent. The invention also provides the use of another therapeutic agent for treating a disease or condition mediated by WRN, wherein the medicament is administered with a compound of the present invention.

The invention also provides a compound of the present invention for use in treating a disease or condition mediated by WRN, wherein the compound of the present invention is prepared for administration with another therapeutic agent. The invention also provides another therapeutic agent for use in treating a disease or condition mediated by WRN, wherein the other therapeutic agent is prepared for administration with a compound of the present invention. The invention also provides a compound of the present invention for use in treating a disease or condition mediated by WRN, wherein the compound of the present invention is administered with another therapeutic agent. The invention also provides another therapeutic agent for use in a method of treating a disease or condition mediated by WRN, wherein the other therapeutic agent is administered with a compound of the present invention.

The invention also provides the use of a compound of the present invention for treating a disease or condition mediated by WRN, wherein the patient has previously (e.g. within 24 hours) been treated with another therapeutic agent. The invention also provides the use of another therapeutic agent for treating a disease or condition mediated by WRN, wherein the patient has previously (e.g. within 24 hours) been treated with compound of the present invention.

5. General Synthetic Methods of Producing Compounds of the Disclosure
Compounds of the present invention can generally be prepared by conventional techniques known to those skilled in the art or by processes analogous to those described in the accompanying synthetic schemes.
Scheme 1
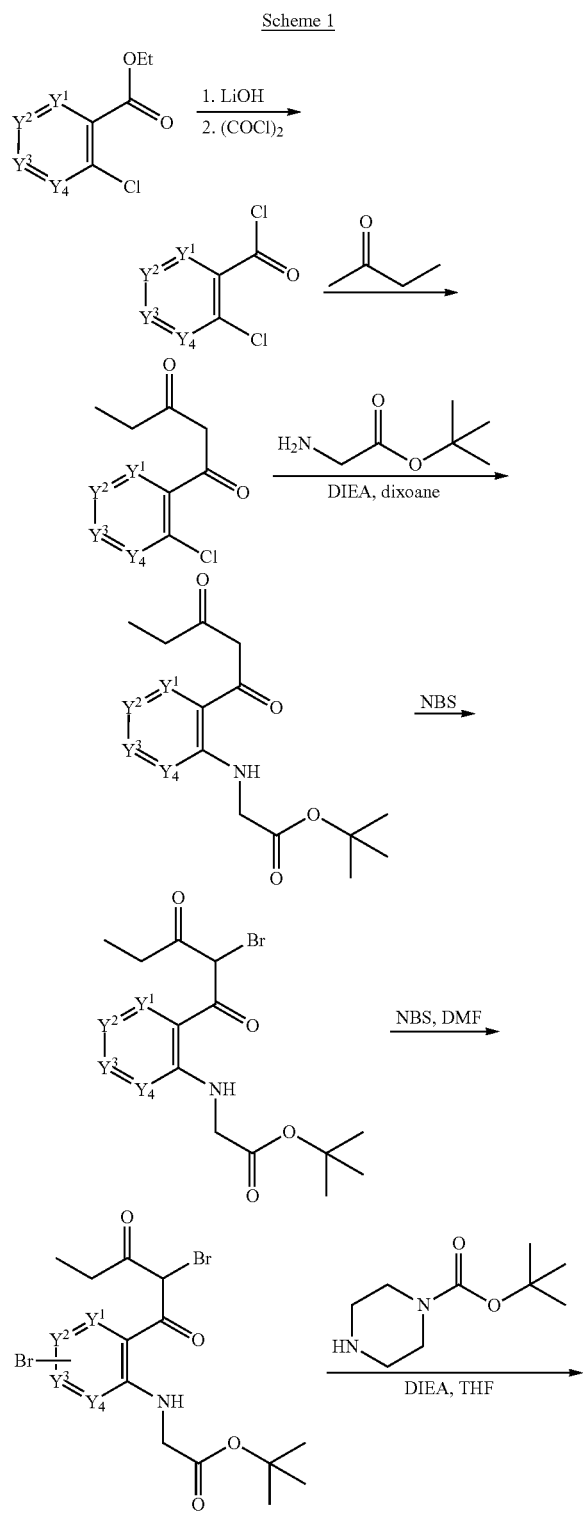
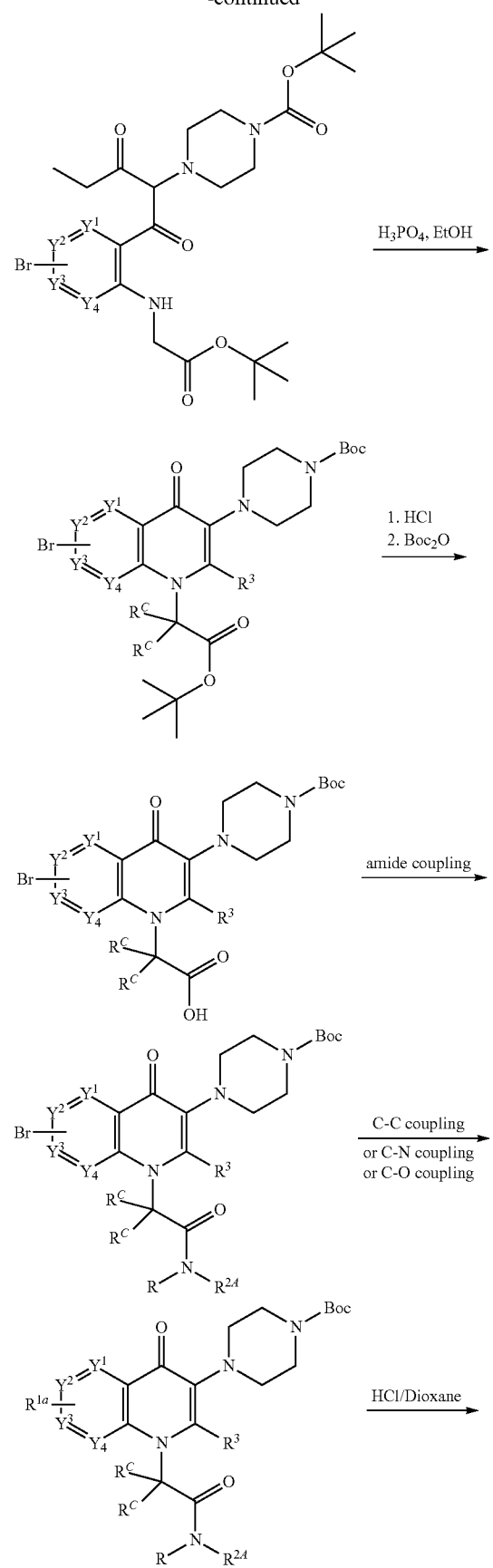

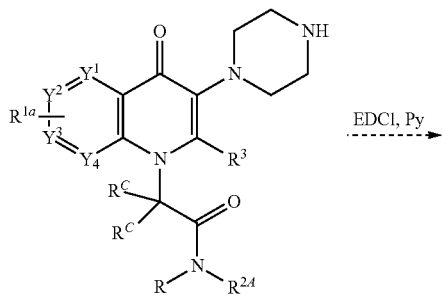
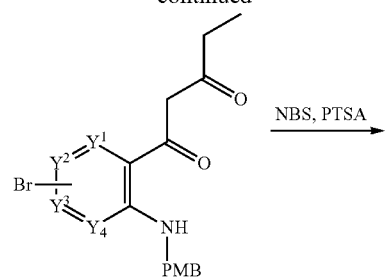
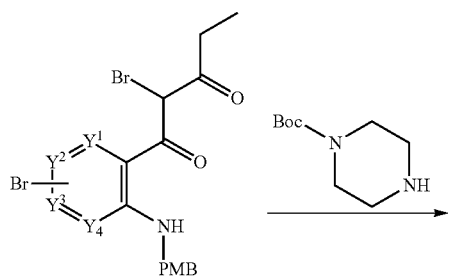
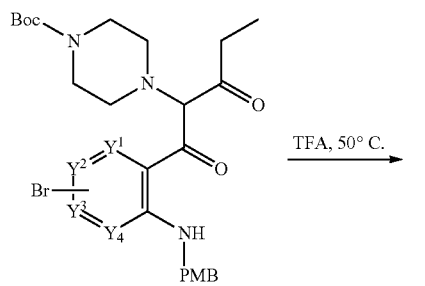
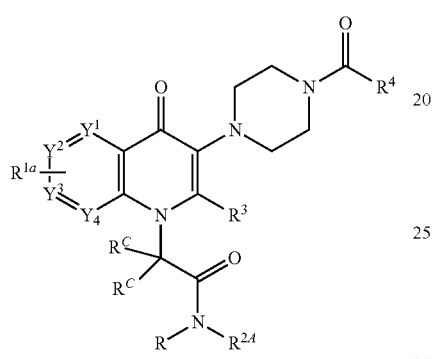
Y1, Y2, Y3, Y4 = CH or N
Scheme 2
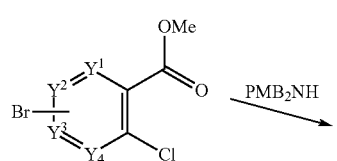
PMB₂NH →
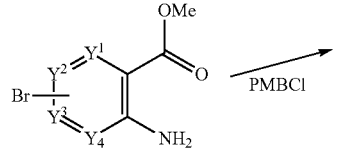
PMBCl →
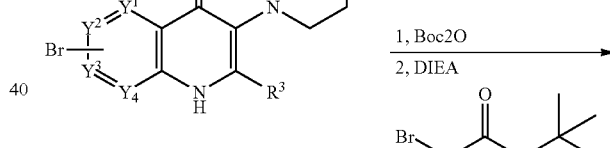
1, Boc₂O
2, DIEA →
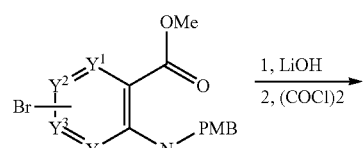
1, LiOH
2, (COCl)₂ →
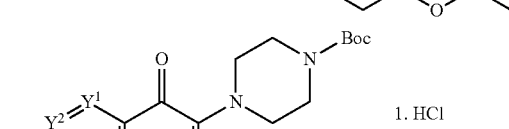
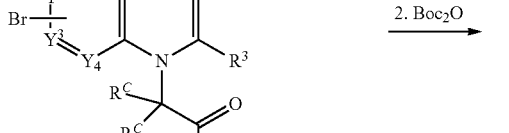
1. HCl
2. Boc₂O →
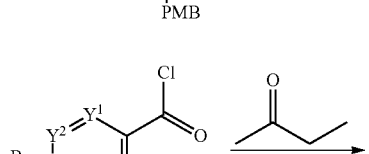
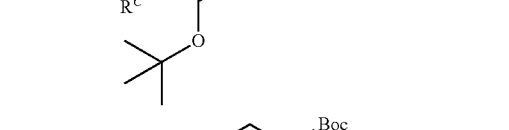
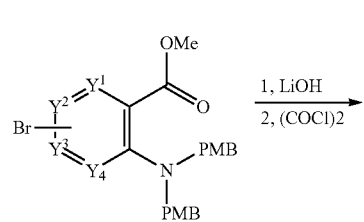
LDA →
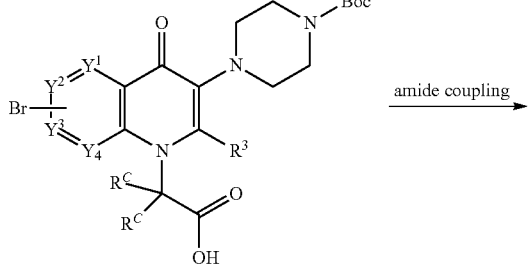
amide coupling →
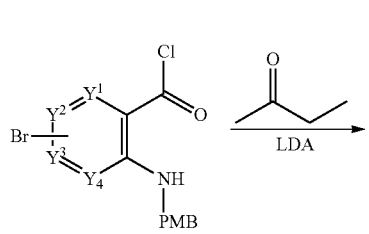

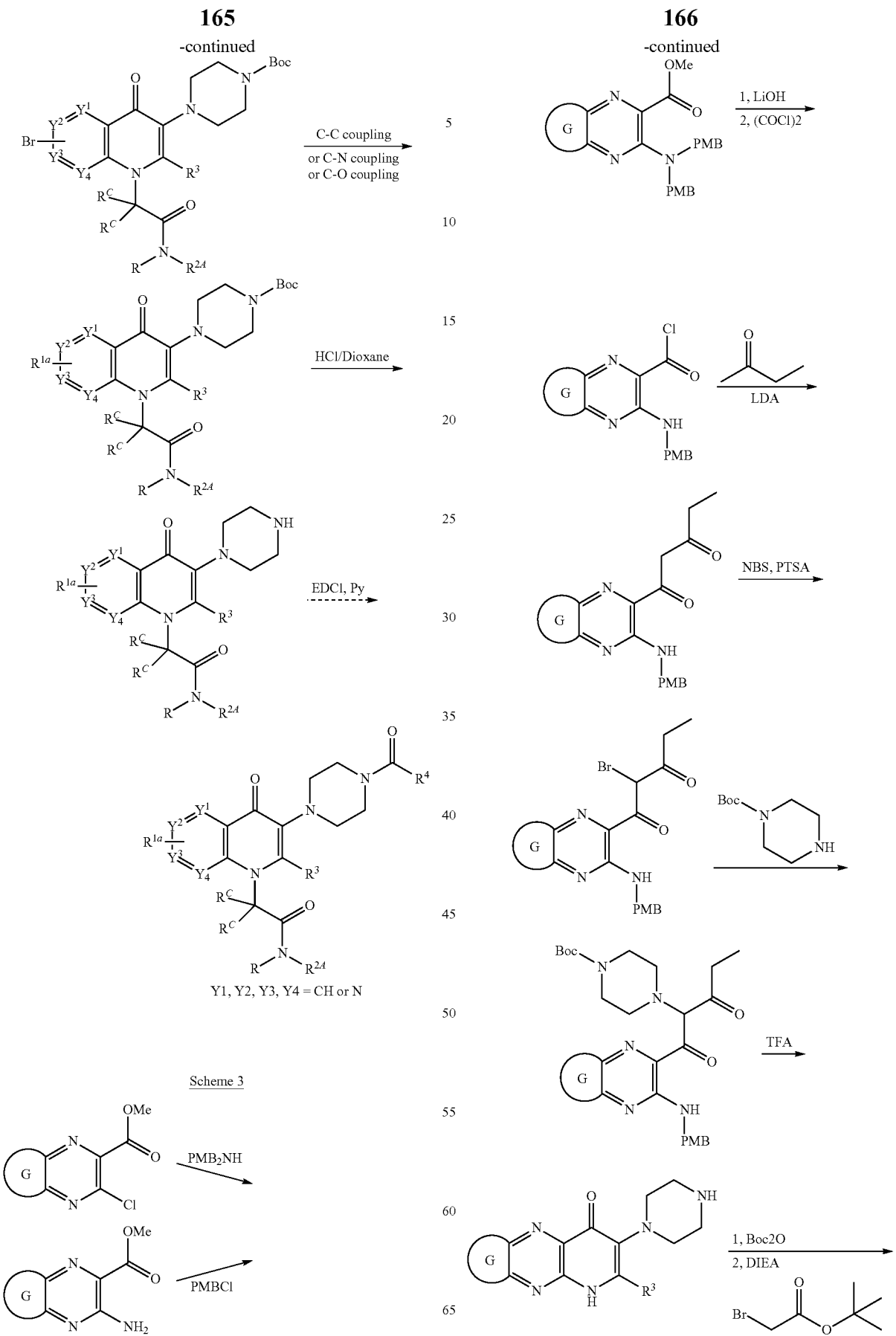

167
-continued
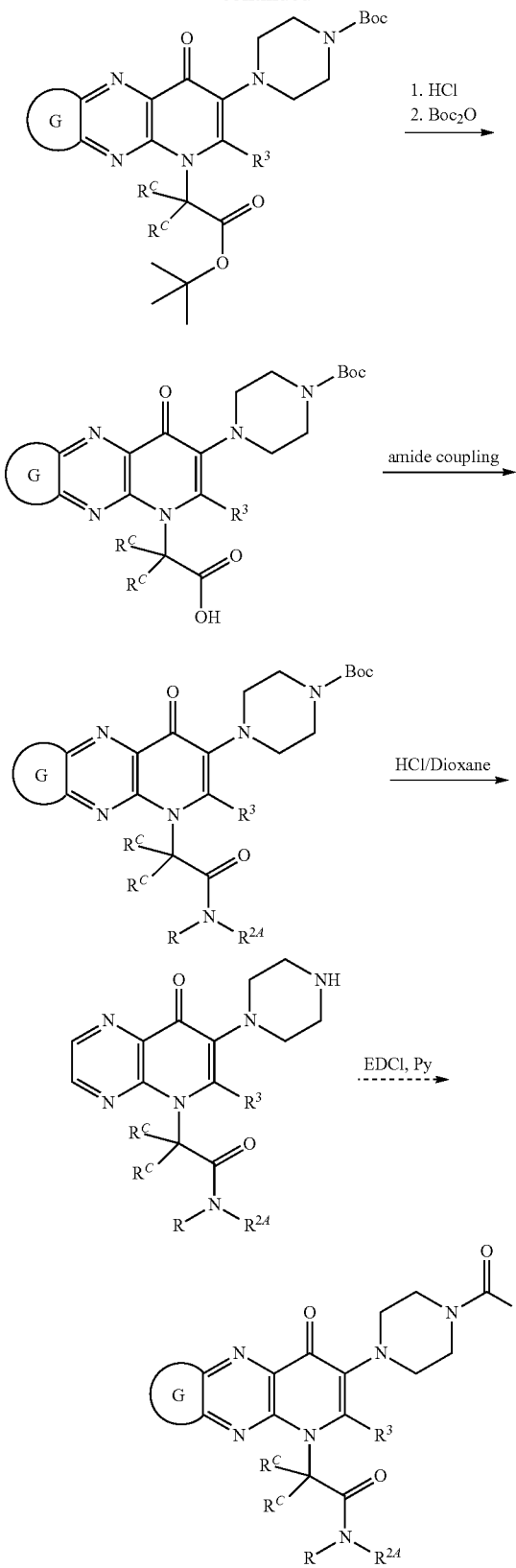
Ring G: optionally substituted phenyl, pyridyl or a 5-6 membered aromatic ring, 4-7 membered saturated or partially unsaturated carbocycle or a 4-7 membered saturated or partially unsaturated heterocycle
168
Scheme 4
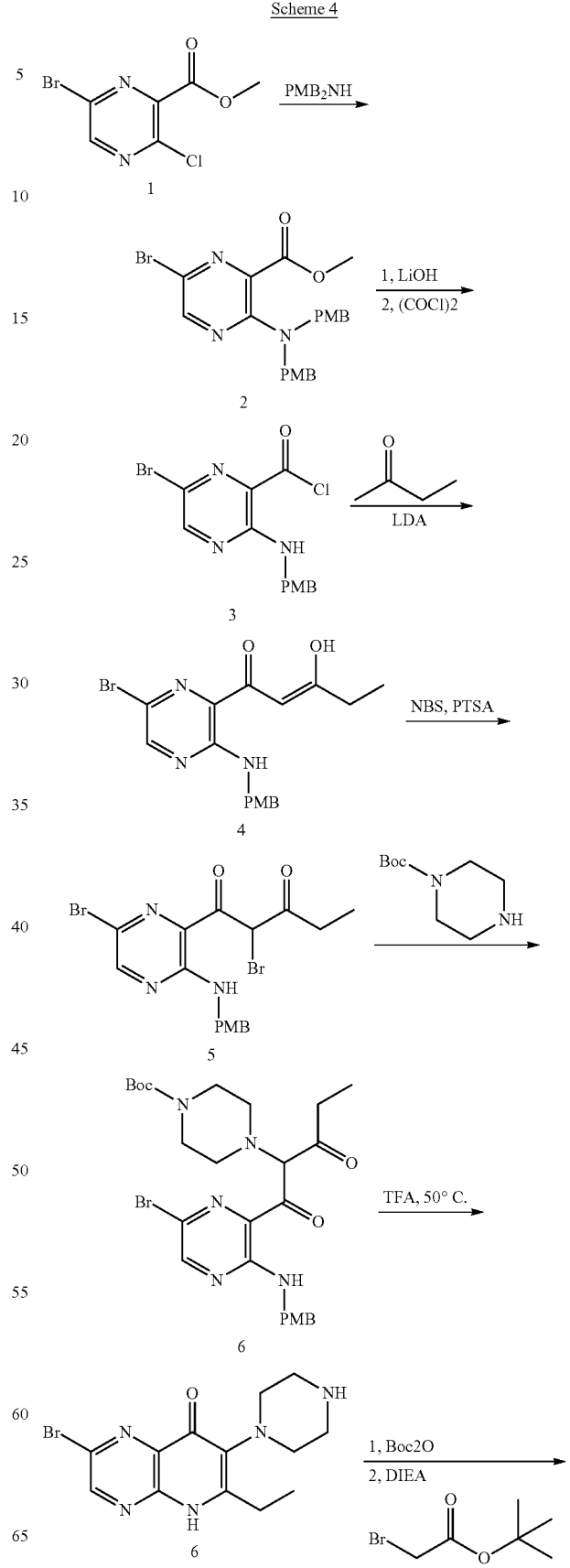

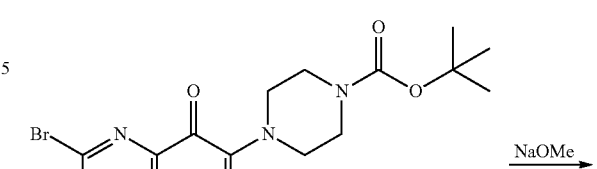
Scheme 6
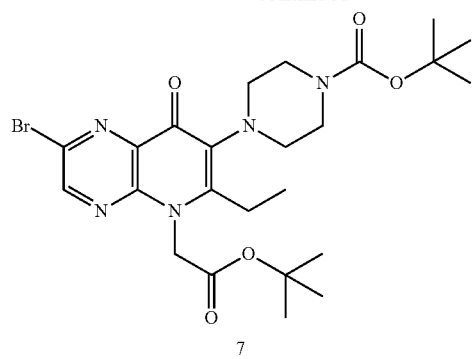
1. HCl
2. Boc₂O
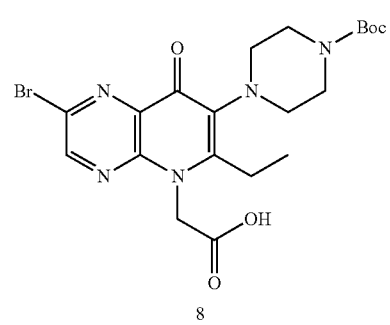
amide coupling
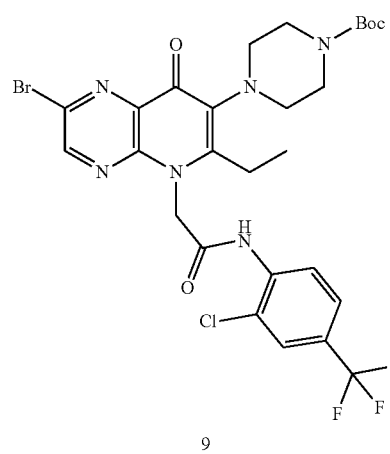
C—C coupling
C—N coupling
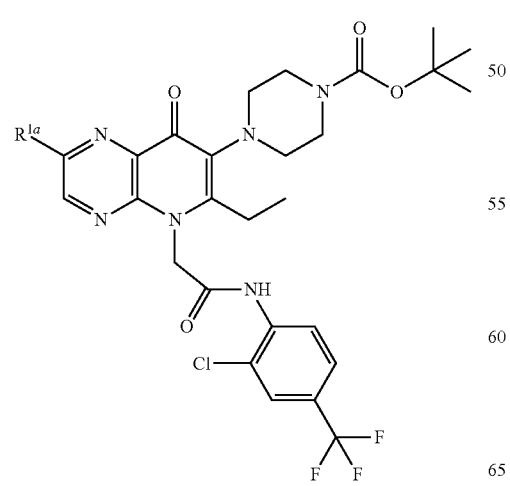
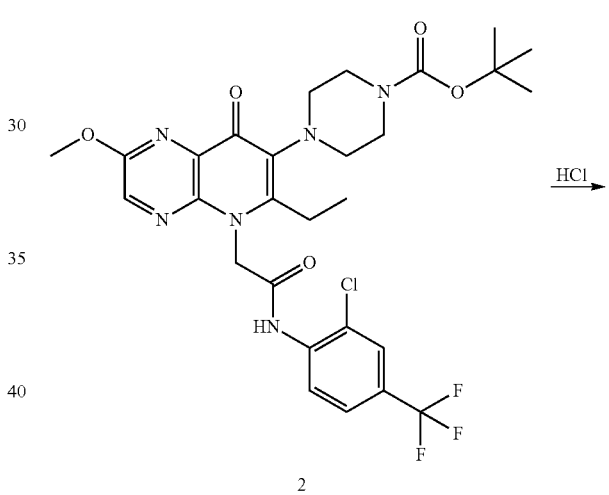
NaOMe / THF
HCl
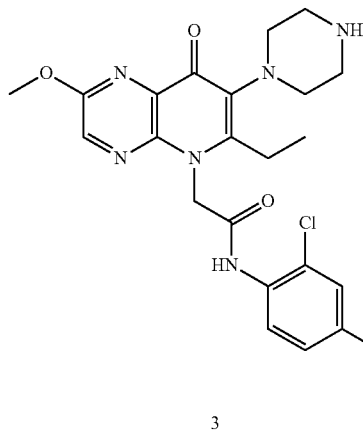
EDCl, Py

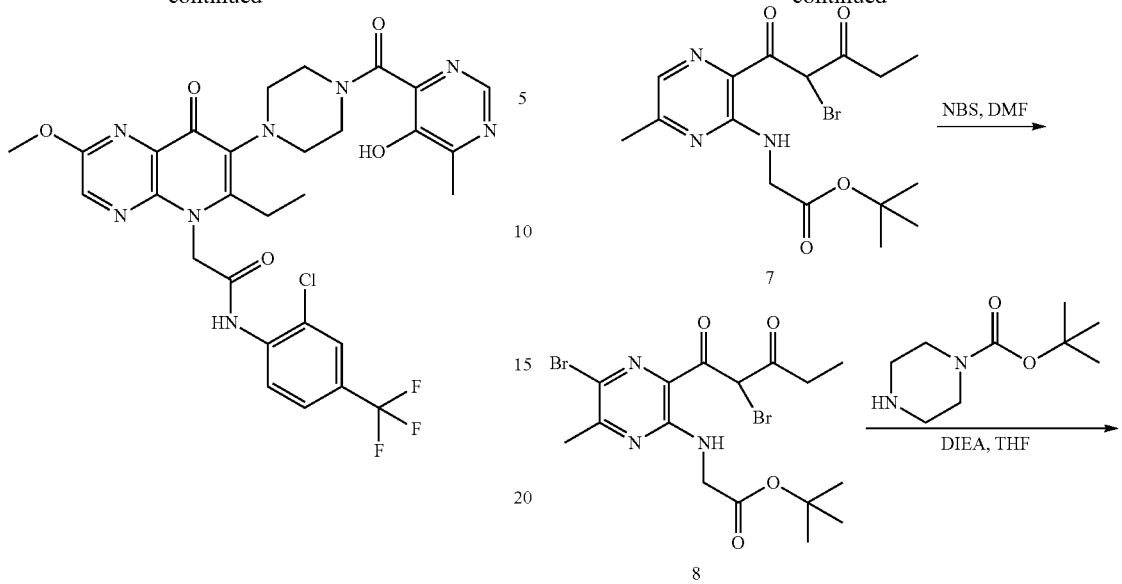
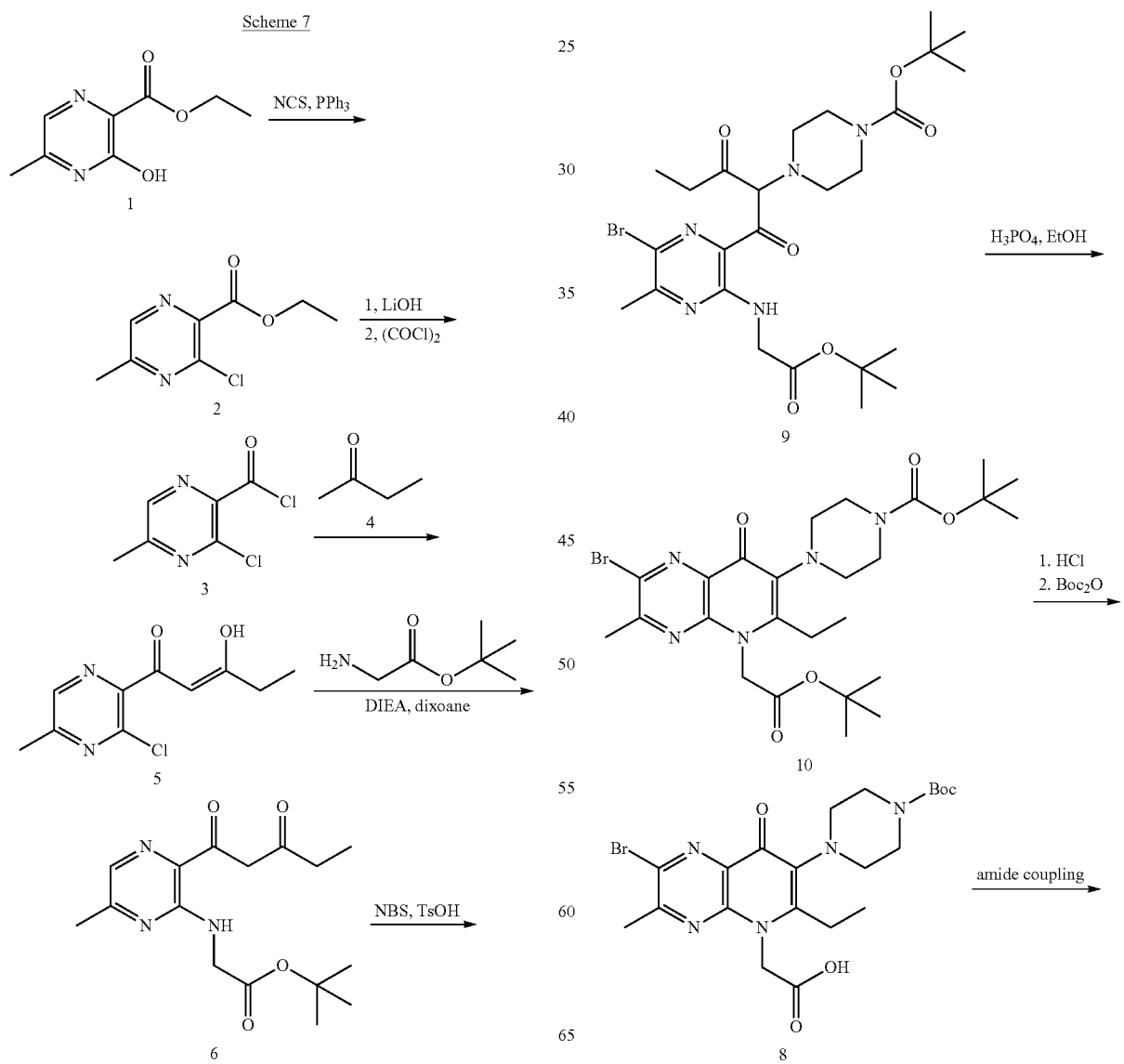
Scheme 7

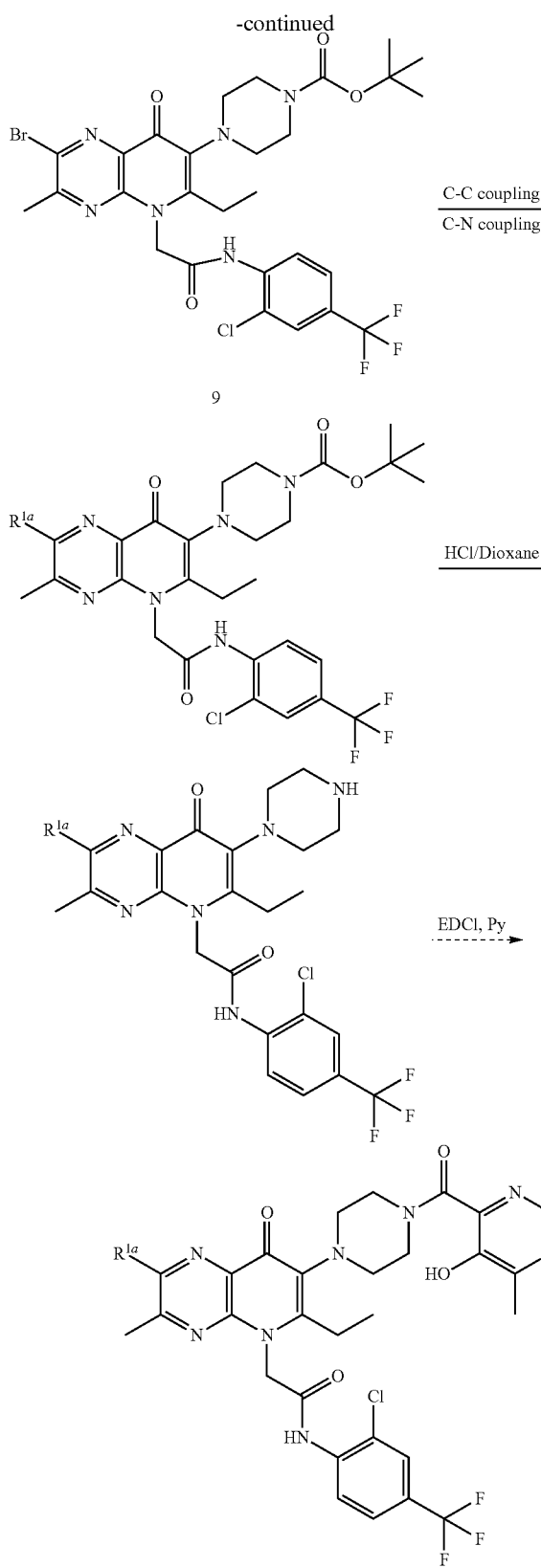

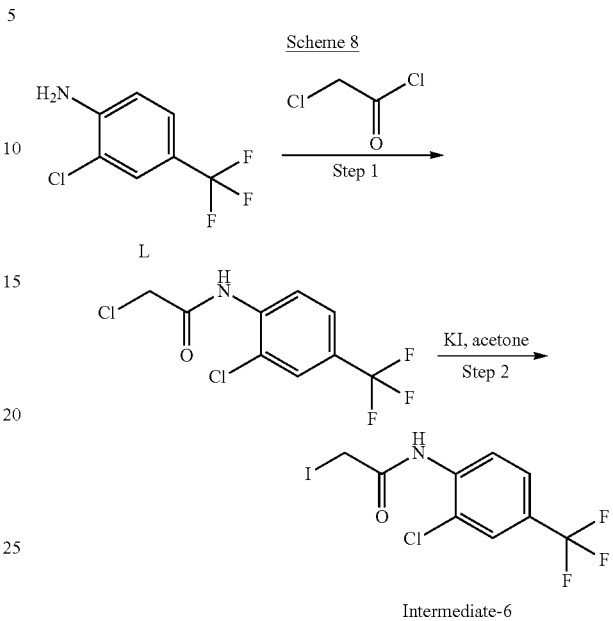

Intermediate-6

Synthesis of Intermediate-6 which is representative of R² moieties within the present genus may be prepared as shown below in Scheme 8. Substituted anilines such as L may be used in the amide coupling of the above schemes. Alternatively, L may be used to furnish Intermediate-6 as shown below to produce a substrate amenable to nucleophilic substitution to produce compounds of the disclosure.

Scheme 8

Those having ordinary skill in the art will be able to adapt such synthetic procedures to afford variably substituted compounds of Formula I, I', or I" for synthesis of the compounds of the disclosure.

Examples

As depicted in the Examples below, in certain exemplary embodiments, compounds are prepared according to the procedures provided herein. It will be appreciated that, although the methods depict the synthesis of certain compounds of the present disclosure, the methods, and other methods known to one of ordinary skill in the art, can be applied to all compounds and subclasses and species of each of these compounds, as described herein.

LIST OF ABBREVIATIONS

NCS: N-chlorosuccinimide
THF: tetrahydrofuran
LiOH—H₂O: Lithium hydroxide monohydrate
(COCl)₂: Oxalyl chloride
DIEA: N,N-diisopropylethylamine
NBS: N-bromosuccinimide
TsOH-H₂O: 4-methylbenzenesulfonic acid monohydrate
TsOH: 4-Methylbenzenesulfonic acid
H₃PO₄: phosphoric acid
EtOH: ethanol
TFA: trifluoroacetic acid
Boc₂O: Di-tert-butyl dicarbonate
POCl₃: Phosphoryl chloride
HCl: hydrochloric acid
EDCI: N-(3-dimethylaminopropyl)-N'-ethylcarbodiimide hydrochloride
ppm: parts per million
LCMS: liquid chromatography-mass spectrometry
HPLC: high-performance liquid chromatography
NMR: nuclear magnetic resonance CDCl$_3$: deuterated chloroform
H$_2$O: water
DCM: dichloromethane
MeOH: methanol
DMF: N,N-dimethyl formamide
EtOAc: ethyl acetate
PE: petroleum ether
Na$_2$SO$_4$: sodium sulfate
br: broad
s: singlet
d: doublet
t: triplet
m: multiplet
q: quartet
dq: doublet of quartets
PPh$_3$: triphenyl phosphine
LDA: Lithium diisopropylamide
ACN: acetonitrile
NH$_4$HCO$_3$: ammonium bicarbonate
eq: equivalent
N: normality
aq.: aqueous
M: molar concentration
Boc: tert-butyloxycarbonyl
FA: formic acid
Et$_3$N: triethylamine
NaOH: sodium hydroxide
N$_2$: nitrogen
Pd(dppf)Cl$_2$: bis(diphenylphosphino)ferrocene]dichloropalladium(II), complex
K$_3$PO$_4$: tripotassium phosphate
NH$_4$Cl: ammonium chloride
pH: potential of hydrogen
TLC: thin layer chromatography
CuCN: Copper(I) cyanide
DMA: Dimethylacetamide
NaIO$_4$: sodium periodate
NaHCO$_3$: Sodium hydrogen carbonate
NaBH$_4$: sodium borohydride
K$_3$PO$_4$: Tripotassium phosphate anhydrous
Cs$_2$CO$_3$: dicesium carbonate
CuI Copper(I) iodide
Pd(PPh$_3$)$_2$Cl$_2$: dichloropalladium triphenylphosphane
Rose Bengal: dipotassium 4,5,6,7-tetrachloro-2',4',5',7'-tetraiodo-3-oxospiro[2-benzofuran-1,9'-xanthene]-3',6'-diolate
Pd(PPh$_3$)$_4$: Tetrakis(triphenylphosphine)palladium(0)
NaH: Sodium Hydride
K$_2$OsO$_4$-2H$_2$O: potassium osmate (VI) dihydrate
DAST: Diethylaminosulfur trifluoride
LiOH: Lithium Hydroxide
K$_2$CO$_3$: Potassium carbonate, anhydrous
Pd(dppf)Cl$_2$—CH$_2$Cl$_2$: [1,1'-Bis(diphenylphosphino)ferrocene]dichloropalladium(II), complex with dichloromethane
O$_2$: Oxygen
DMSO: Dimethyl sulfoxide
LED: light emitting diode
br: broad
s: singlet
d: doublet
t: triplet
m: multiplet
q: quartet
h: hour
PPh$_3$: triphenyl phosphine
LDA: Lithium diisopropylamide
ACN: acetonitrile
NH$_4$HCO$_3$: ammonium bicarbonate
eq: equivalent
N: normality
aq: aqueous
M: molar concentration
Boc: tert-butyloxycarbonyl
FA: formic acid
Et$_3$N: triethylamine
NaOH: sodium hydroxide
N$_2$: nitrogen
Pd(dppf)Cl$_2$: bis(diphenylphosphino)ferrocene]dichloropalladium(II), complex
pH: potential of hydrogen
Co(acac)$_2$: Cobalt(II) acetylacetonate
Na$_2$S: sodium sulfide
NH$_3$: ammonia
CO: carbon monoxide
t-BuOK: potassium t-butoxide
NaBH(OAc)$_3$: Sodium triacetoxyborohydride
SFC: Supercritical fluid chromatography
PMB: 4-methoxybenzyl
CD$_3$OD: deuterated methanol
MeMgBr: methylmagnesium bromide
HBr: hydrobromic acid
HI: Hydriodic acid
N$_2$: nitrogen
DMSO-d$_6$: deuterated dimethyl sulfoxide
P$_2$S$_5$: phosphorus pentasulfide
DMAP: 4-dimethylaminopyridine
NMP: N-methylpyrrolidone
DEA: Diethylamine
BOP: (Benzotriazolyloxy)tris(dimethylamino)phosphonium hexafluorphosphate
KI: potassium iodide
MTBE: methyl tertiary butyl ether Example 1: Synthesis of Compounds of the Disclosure Synthesis of N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxopyrido[2,3-b]pyrazin-5 (8H)-yl)acetamide (I-1)

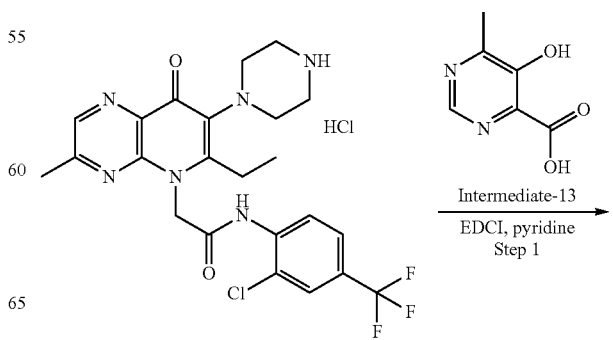

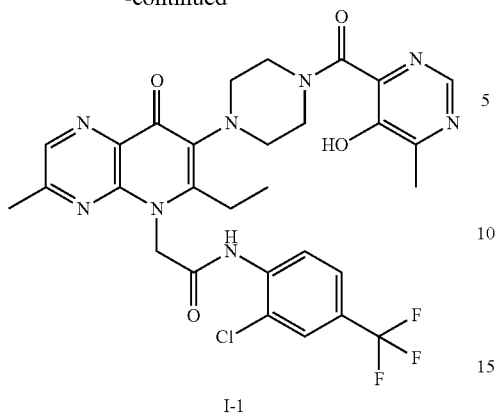

I-1

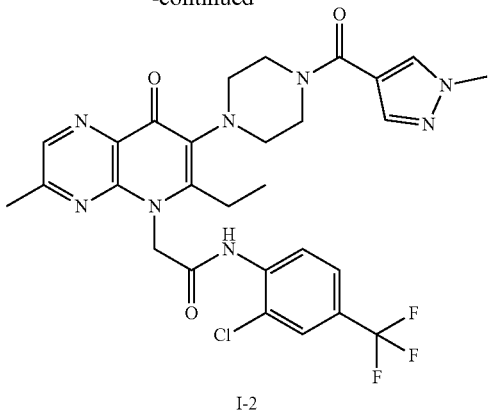

I-2

Step 1: Synthesis of N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxopyrido[2,3-b]pyrazin-5 (8H)-yl)acetamide To a solution of 5-hydroxy-6-methylpyrimidine-4-carboxylic acid (Intermediate-13) (27 mg, 0.17 mmol, 1.1 eq) in pyridine (2 mL) was added EDCI (33 mg, 0.17 mmol, 1.1 eq) and the mixture was stirred at room temperature for 0.5 h. Then N-(2-chloro-4-(trifluoromethyl)phenyl)-2-(6-ethyl-3-methyl-8-oxo-7-(piperazin-1-yl)pyrido[2,3-b]pyrazin-5 (8H)-yl)acetamide hydrochloride (Intermediate-2, prepared according to general methods of the Schemes above) (80 mg, 0.16 mmol, 1.0 eq) was added to the mixture and the mixture was stirred at room temperature overnight. The reaction mixture was concentrated under reduced pressure and then diluted with H$_2$O (10 mL). The resulting mixture was adjusted to pH 5 with aq. 1N HCl solution, extracted with DCM (10 mL*2). The combined organic layers were washed with brine (10 mL), dried over anhydrous Na$_2$SO$_4$, concentrated under reduced pressure. The residue was purified by reverse phase HPLC (C18 column, H$_2$O (10 mmol/L NH$_4$HCO$_3$)-ACN) to afford the title compound.

$^1$H NMR (400 MHz, CDCl$_3$) δ ppm 11.82 (br s, 1H), 8.65 (s, 1H), 8.59 (s, 1H), 8.49 (d, 1H), 8.42 (s, 1H), 7.64 (s, 1H), 7.55 (br d, 1H), 5.75-5.51 (m, 1H), 5.38 (br s, 2H), 4.79 (br d, 1H), 4.16-3.93 (m, 2H), 3.63-3.47 (m, 1H), 3.29 (br d, 2H), 3.10 (br d, 1H), 2.92-2.74 (m, 2H), 2.71 (s, 3H), 2.57 (s, 3H), 1.36 (t, 3H).

LCMS: 645.4 [M+H]$^+$.

Synthesis of N-(2-chloro-4-(trifluoromethyl)phenyl)-2-(6-ethyl-3-methyl-7-(4-(1-methyl-1H-pyrazole-4-carbonyl)piperazin-1-yl)-8-oxopyrido[2,3-b]pyrazin-5 (8H)-yl)acetamide (I-2)

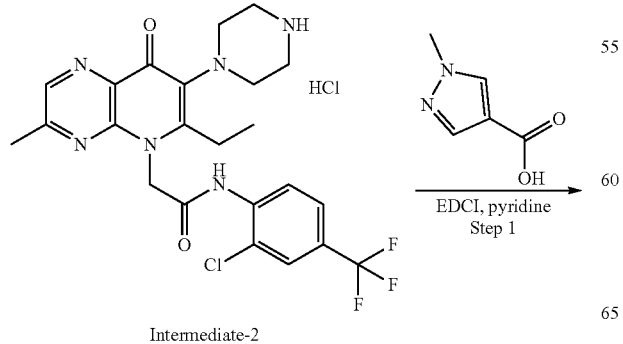

Step 1. N-(2-chloro-4-(trifluoromethyl)phenyl)-2-(6-ethyl-3-methyl-7-(4-(1-methyl-1H-pyrazole-4-carbonyl)piperazin-1-yl)-8-oxopyrido[2,3-b]pyrazin-5 (8H)-yl)acetamide A solution of 1-methyl-1H-pyrazole-4-carboxylic acid was reacted and worked up according the procedure described for I-1.

LCMS: 617.2 [M+H]$^+$.

Synthesis of N-(2-chloro-4-(trifluoromethyl)phenyl)-2-(6-ethyl-7-(4-(3-hydroxypicolinoyl)piperazin-1-yl)-3-methyl-8-oxopyrido[2,3-b]pyrazin-5 (8H)-yl)acetamide (I-3)

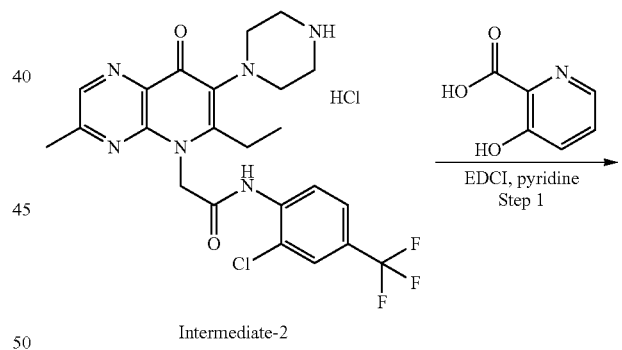

Intermediate-2

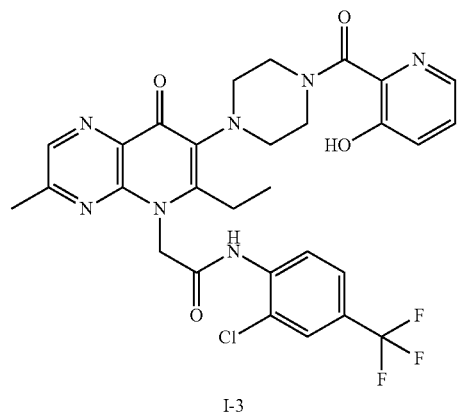

I-3

Step 1. Synthesis of N-(2-chloro-4-(trifluoromethyl)phenyl)-2-(6-ethyl-7-(4-(3-hydroxypicolinoyl)piperazin-1-yl)-3-methyl-8-oxopyrido[2,3-b]pyrazin-5(8H)-yl)acetamide A solution of 3-hydroxypicolinic acid was reacted and worked up according the procedure described for I-1.
LCMS: 630.2 [M+H]+.

Synthesis of N-(2-chloro-4-(trifluoromethyl)phenyl)-2-(6-ethyl-7-(4-(3-hydroxy-2-methoxyisonicotinoyl)piperazin-1-yl)-3-methyl-8-oxopyrido[2,3-b]pyrazin-5(8H)-yl)acetamide (I-4)

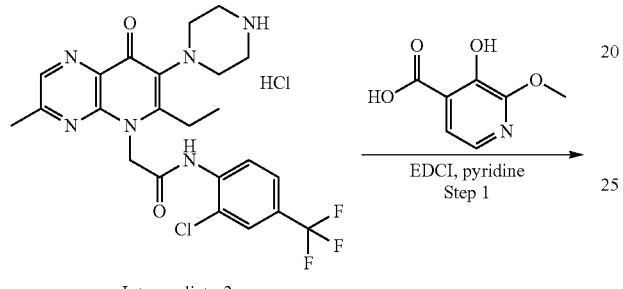

Synthesis of 2-(7-(4-acetylpiperazin-1-yl)-6-ethyl-3-methyl-8-oxopyrido[2,3-b]pyrazin-5(8H)-yl)-N-(2-chloro-4-(trifluoromethyl)phenyl)acetamide (I-5)

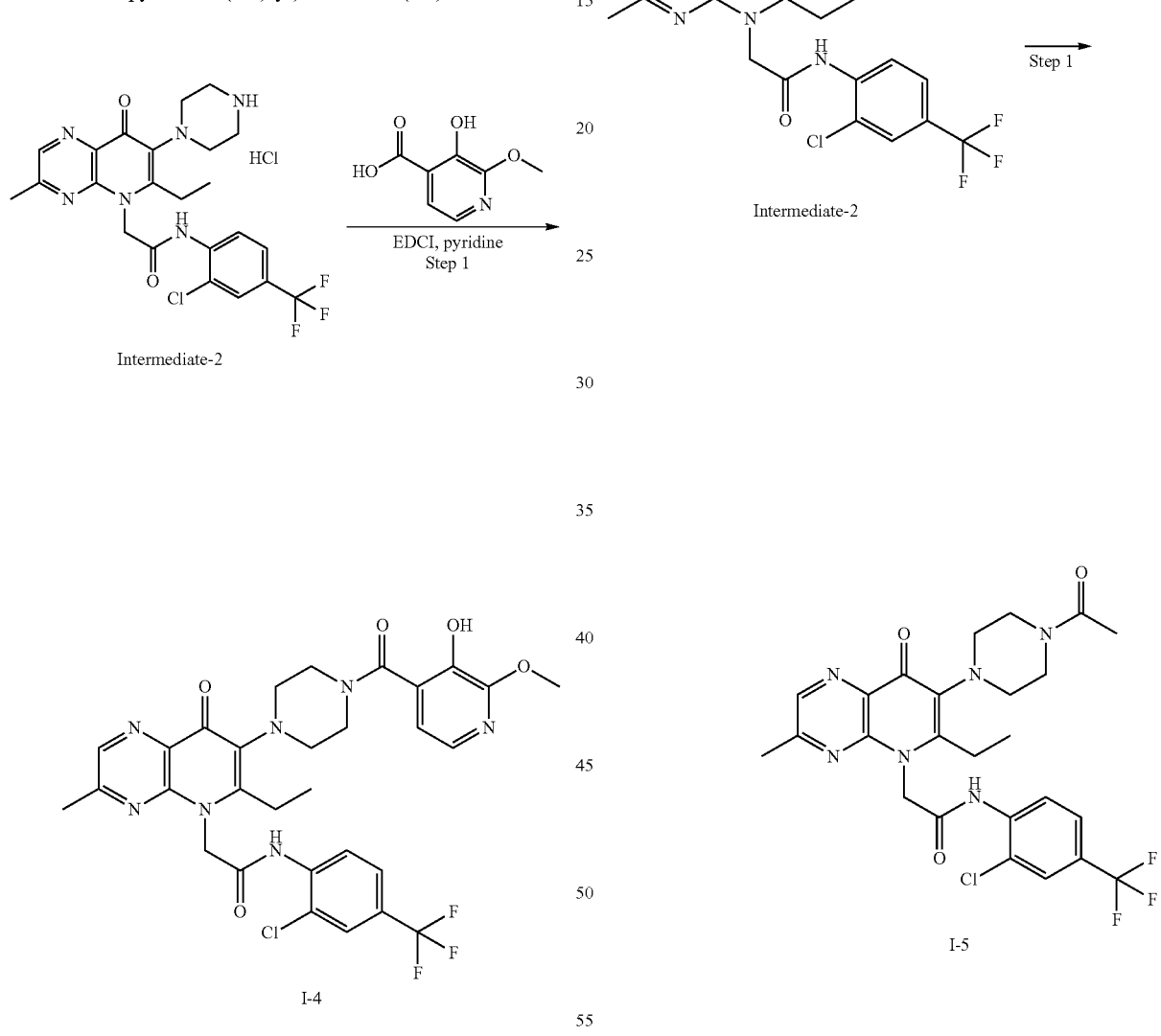

Step 1. Synthesis of N-(2-chloro-4-(trifluoromethyl)phenyl)-2-(6-ethyl-7-(4-(3-hydroxy-2-methoxyisonicotinoyl)piperazin-1-yl)-3-methyl-8-oxopyrido[2,3-b]pyrazin-5(8H)-yl)acetamide A solution of 3-hydroxy-2-methoxyisonicotinic acid was reacted and worked up according the procedure described for I-1.
LCMS: 660.4 [M+H]+.

Step 1. Synthesis of 2-(7-(4-acetylpiperazin-1-yl)-6-ethyl-3-methyl-8-oxopyrido[2,3-b]pyrazin-5(8H)-yl)-N-(2-chloro-4-(trifluoromethyl)phenyl)acetamide Acetic acid was reacted and worked up according the procedure described for I-1.
LCMS: 551.2 [M+H]+.

181

Synthesis of N-(2-chloro-4-(trifluoromethyl)phenyl)-2-(6-ethyl-7-(4-(4-hydroxy-2-methoxynicotinoyl)piperazin-1-yl)-3-methyl-8-oxopyrido[2,3-b]pyrazin-5 (8H)-yl)acetamide (I-6)

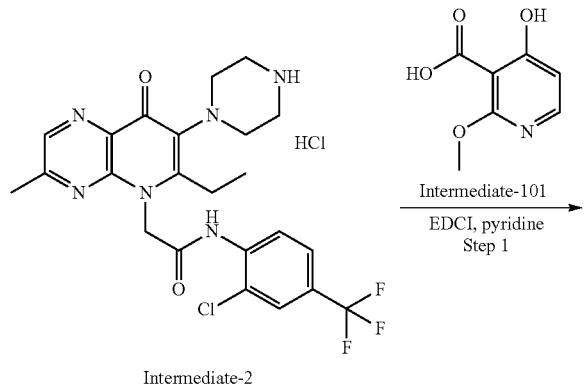

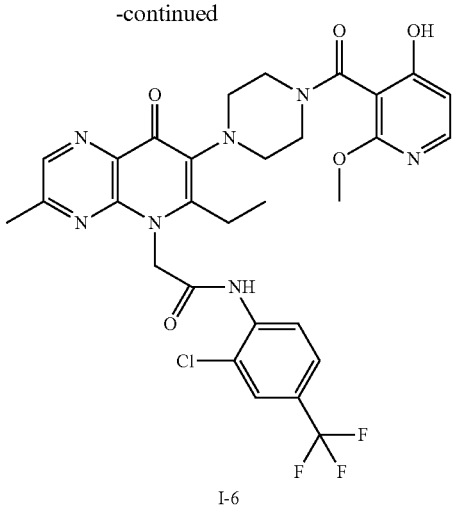

Step 1. Synthesis of N-(2-chloro-4-(trifluoromethyl)phenyl)-2-(6-ethyl-7-(4-(3-hydroxy-2-methoxyisonicotinoyl)piperazin-1-yl)-3-methyl-8-oxopyrido[2,3-b]pyrazin-5 (8H)-yl)acetamide A solution of 4-hydroxy-2-methoxy-pyridine-3-carboxylic acid (Intermediate-101) was reacted and worked up according the procedure described for I-1.
LCMS: 660.2 [M+H]⁺.

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(2-methoxypyridin-4-yl)-8-oxopyrido[2,3-b]pyrazin-5 (8H)-yl)acetamide (I-7)

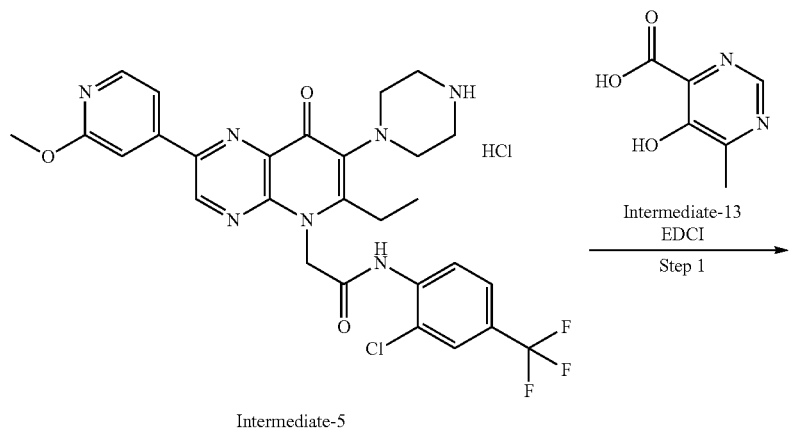

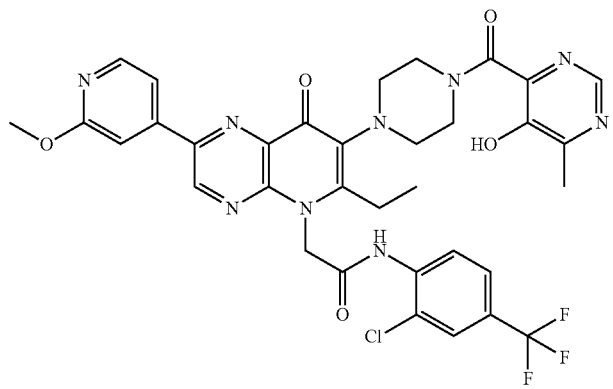

Step 1. Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(2-methoxypyridin-4-yl)-8-oxopyrido[2,3-b]pyrazin-5 (8H)-yl) acetamide To a solution of 5-hydroxy-6-methylpyrimidine-4-carboxylic acid (Intermediate-13) (44 mg, 0.29 mmol, 8.0 eq) in pyridine (0.5 mL) was added EDCI (55 mg, 0.29 mmol, 8.0 eq) and the resulting mixture was stirred at room temperature for 0.5 h. N-(2-chloro-4-(trifluoromethyl)phenyl)-2-(6-ethyl-2-(2-methoxypyridin-4-yl)-8-oxo-7-(piperazin-1-yl)pyrido[2,3-b]pyrazin-5 (8H)-yl)acetamide hydrochloride (Intermediate-5) (23 mg, 36 μmol, 1.0 eq) was added to the mixture and the reaction was stirred at room temperature for 1 h. The reaction mixture was concentrated under reduced pressure. The residue was purified by reverse phase HPLC (C18 column, water (0.1% FA)-ACN) to afford the title compound.

LCMS: 738.2 [M+H]$^+$.

$^1$H NMR (400 MHz, CDCl$_3$) δ ppm 11.79 (br s, 1H), 9.08 (s, 1H), 8.65 (s, 1H), 8.59 (s, 1H), 8.50 (d, 1H), 8.32 (d, 1H), 7.69-7.63 (m, 2H), 7.54 (br d, 1H), 7.45 (s, 1H), 5.59 (br s, 1H), 5.42 (br s, 2H), 4.79 (br s, 1H), 4.08-3.96 (m, 5H), 3.54 (br s, 1H), 3.31 (br s, 2H), 3.11 (br s, 1H), 2.84 (br d, 2H), 2.58 (s, 3H), 1.39 (br t, 3H).

Synthesis of (E)-N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(prop-1-en-1-yl)pyrido[2,3-b]pyrazin-5 (8H)-yl)acetamide (I-8): I-8 was Synthesized from Intermediate-3 According to Chemistry Outlined in Scheme 4

Synthesis of N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(prop-1-en-2-yl)pyrido[2,3-b]pyrazin-5 (8H)-yl)acetamide (I-9: I-9 was Synthesized from Intermediate-3 According to Chemistry Outlined in Scheme 4

Synthesis of N-(2-chloro-4-(trifluoromethyl)phenyl)-2-(2-cyclopropyl-6-ethyl-7-(4-(5-hydroxy-6-methylpyrimidine-4-carbonyl)piperazin-1-yl)-8-oxopyrido[2,3-b]pyrazin-5 (8H)-yl)acetamide (I-10): I-10 was Synthesized from Intermediate-3 According to Chemistry Outlined in Scheme 4

Synthesis of N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(prop-1-yn-1-yl)pyrido[2,3-b]pyrazin-5 (8H)-yl)acetamide (I-11)

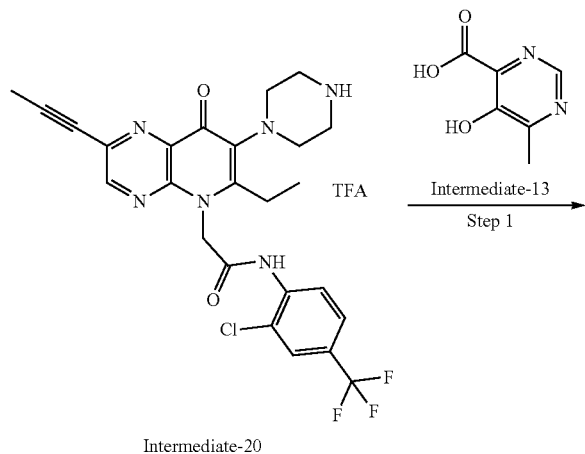

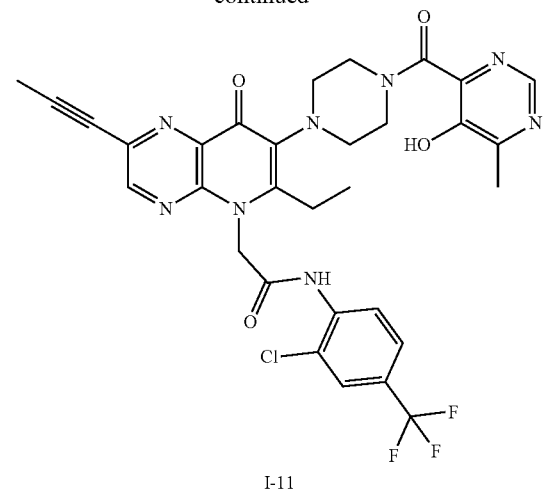

I-11

Step 1: Synthesis of N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(prop-1-yn-1-yl)pyrido[2,3-b]pyrazin-5 (8H)-yl)acetamide To a solution of N-(2-chloro-4-(trifluoromethyl)phenyl)-2-(6-ethyl-8-oxo-7-(piperazin-1-yl)-2-(prop-1-yn-1-yl) pyrido[2,3-b]pyrazin-5 (8H)-yl)acetamide trifluoroacetate (Intermediate-20) (33 mg, 62 mol, 1.0 eq) and 5-hydroxy-6-methylpyrimidine-4-carboxylic acid (Intermediate-13) (19 mg, 0.12 mmol, 2.0 eq) in pyridine (1 mL) was added EDCI (24 mg, 0.12 mmol, 2.0 eq) and then the resulting mixture was stirred at 40° C. for 15 h. The mixture was quenched with H$_2$O (10 mL) and extracted with EtOAc (20 mL*3). The combined organic layers were washed with brine (20 mL), dried over anhydrous Na$_2$SO$_4$, filtered and the filtrate was concentrated under reduced pressure. The residue was purified by reverse phase HPLC (C18 column, water (0.1% FA)-ACN) to afford the title compound.

LCMS: 669.4 [M+H]$^+$.

$^1$H NMR (400 MHz, CDCl$_3$) δ ppm 12.05 (s, 1H), 8.67-8.59 (m, 3H), 8.51 (br d, 1H), 7.67 (s, 1H), 7.56 (br d, 1H), 5.73-5.51 (m, 1H), 5.37 (br d, 2H), 4.88-4.67 (m, 1H), 4.07-3.95 (m, 2H), 3.62-3.44 (m, 1H), 3.37-3.22 (m, 2H), 3.17-3.04 (m, 1H), 2.90-2.73 (m, 2H), 2.60 (s, 3H), 2.15 (s, 3H), 1.39 (br t, 3H).

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-methoxy-3-methyl-8-oxopyrido[2,3-b]pyrazin-5 (8H)-yl)acetamide (I-12)

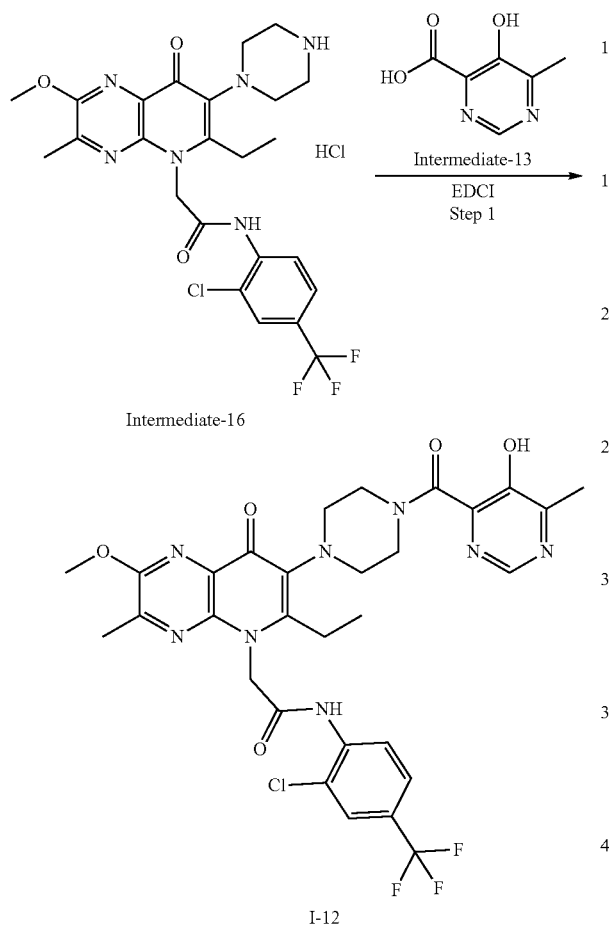

Intermediate-16

I-12

Step 1. Synthesis of N-(2-chloro-4-(trifluoromethyl)phenyl)-2-(6-ethyl-7-(4-(5-hydroxy-6-methylpyrimidine-4-carbonyl)piperazin-1-yl)-2-methoxy-3-methyl-8-oxopyrido[2,3-b]pyrazin-5 (8H)-yl)acetamide To a solution of 5-hydroxy-6-methylpyrimidine-4-carboxylic acid (Intermediate-13) (22 mg, 0.15 mmol, 3.0 eq) in pyridine (1 mL) was added EDCI (28 mg, 0.15 mmol, 3.0 eq) and it was stirred at room temperature for 0.5 h. Then a solution of N-(2-chloro-4-(trifluoromethyl)phenyl)-2-(6-ethyl-2-methoxy-3-methyl-8-oxo-7-(piperazin-1-yl)pyrido[2,3-b]pyrazin-5 (8H)-yl)acetamide hydrochloride (Intermediate-16) (26 mg, 48 mol, 1.0 eq) in pyridine (1 mL) was added, and the resulting mixture was stirred at room temperature for 3 h. The mixture was concentrated and then purified by reverse phase HPLC (C18 column, water (0.1% FA)-ACN) to afford the title compound.

LCMS: 675.0 [M+H]$^+$.

$^1$H NMR (400 MHz, CDCl$_3$) δ ppm 11.88 (s, 1H), 8.58 (s, 1H), 8.51 (d, 1H), 8.36 (s, 1H), 7.63 (s, 1H), 7.55 (br d, 1H), 5.63-5.48 (m, 1H), 5.37 (br s, 2H), 4.86-4.69 (m, 1H), 4.17 (s, 3H), 4.09-3.98 (m, 2H), 3.60-3.46 (m, 1H), 3.33-3.20 (m, 2H), 3.16-3.03 (m, 1H), 2.91-2.70 (m, 2H), 2.61 (s, 3H), 2.57 (s, 3H), 1.34 (br t, 3H).

Synthesis of N-(2-chloro-4-(trifluoromethyl)phenyl)-2-(2-(difluoromethyl)-6-ethyl-7-(4-(5-hydroxy-6-methylpyrimidine-4-carbonyl)piperazin-1-yl)-8-oxopyrido[2,3-b]pyrazin-5 (8H)-yl)acetamide (I-13)

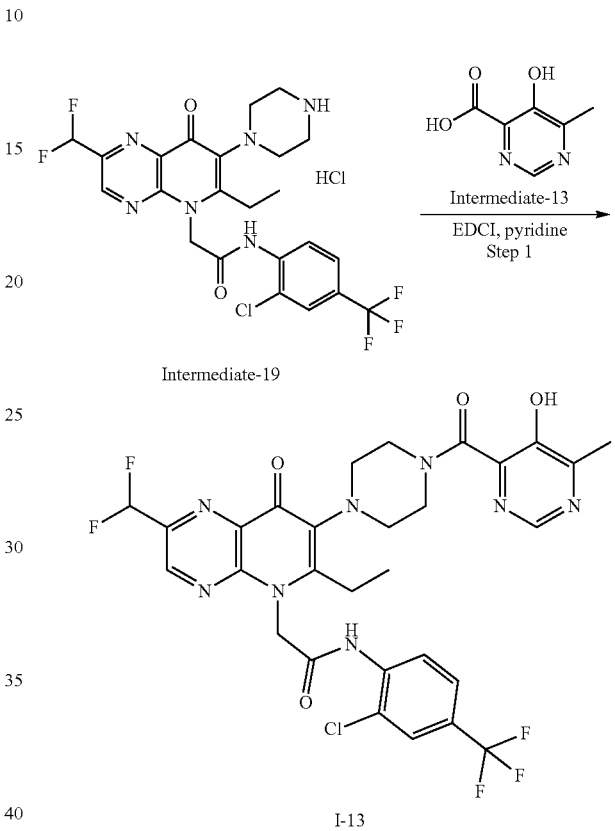

Intermediate-19

I-13

Step 1. Synthesis of N-(2-chloro-4-(trifluoromethyl)phenyl)-2-(2-(difluoromethyl)-6-ethyl-7-(4-(5-hydroxy-6-methylpyrimidine-4-carbonyl)piperazin-1-yl)-8-oxopyrido[2,3-b]pyrazin-5 (8H)-yl)acetamide To a solution of 5-hydroxy-6-methyl-pyrimidine-4-carboxylic acid (Intermediate-13) (21 mg, 134 mol, 6.0 eq) in pyridine (0.5 mL) was added EDCI (26 mg, 134 mol, 6.0 eq) and it was stirred at room temperature for 0.5 h. N-(2-chloro-4-(trifluoromethyl)phenyl)-2-(2-(difluoromethyl)-6-ethyl-8-oxo-7-(piperazin-1-yl)pyrido[2,3-b]pyrazin-5 (8H)-yl)acetamide hydrochloride (Intermediate-19) (13 mg, 22 mol, 1.0 eq) was added to the mixture and the reaction was stirred at 30° C. for 1 h. The mixture was concentrated under reduced pressure, the residue was purified by reverse phase HPLC (water (0. % FA)-ACN) to afford the title compound.

LCMS: 681.2 [M+H]$^+$.

$^1$H NMR (400 MHz, CDCl$_3$) δ ppm 11.81 (br s, 1H), 9.00 (s, 1H), 8.60 (s, 1H), 8.52-8.44 (m, 2H), 7.68 (s, 1H), 7.55 (br d, 1H), 7.08-6.77 (m, 1H), 5.62 (br d, 1H), 5.40 (br s, 2H), 4.80 (br d, 1H), 3.98 (br t, 2H), 3.53 (br s, 1H), 3.31 (br s, 2H), 3.18-2.98 (m, 1H), 2.83 (m, 2H), 2.58 (s, 3H), 1.39 (t, 3H).

187

Synthesis of N-(2-chloro-4-(trifluoromethyl)phenyl)-2-(2-(dimethylamino)-6-ethyl-7-(4-(5-hydroxy-6-methylpyrimidine-4-carbonyl)piperazin-1-yl)-8-oxopyrido[2,3-b]pyrazin-5 (8H)-yl)acetamide (I-14)

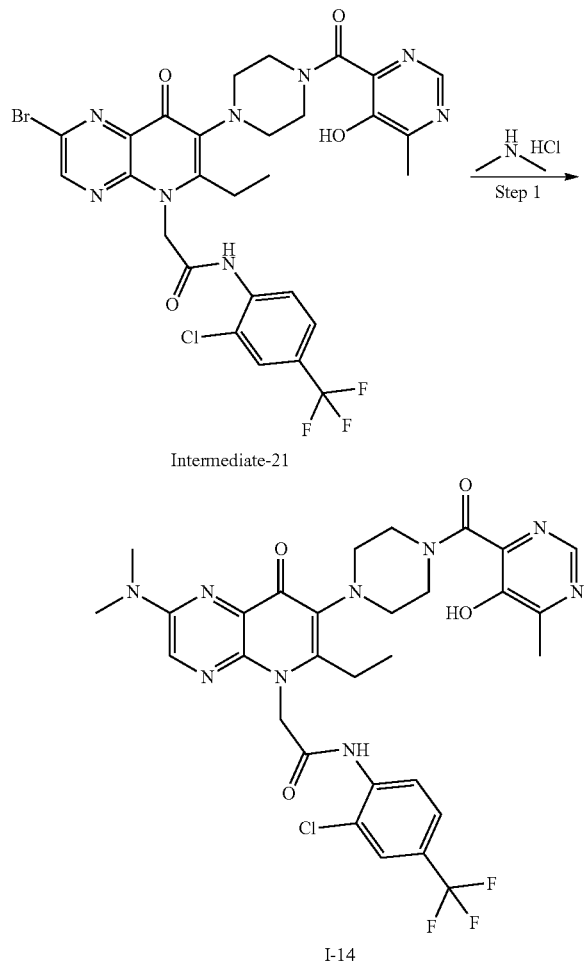

Intermediate-21

I-14

Step 1. Synthesis of N-(2-chloro-4-(trifluoromethyl)phenyl)-2-(2-(dimethylamino)-6-ethyl-7-(4-(5-hydroxy-6-methylpyrimidine-4-carbonyl)piperazin-1-yl)-8-oxopyrido[2,3-b]pyrazin-5 (8H)-yl)acetamide To a solution of 2-(2-bromo-6-ethyl-7-(4-(5-hydroxy-6-methylpyrimidine-4-carbonyl)piperazin-1-yl)-8-oxopyrido [2,3-b]pyrazin-5 (8H)-yl)-N-(2-chloro-4-(trifluoromethyl) phenyl)acetamide (Intermediate-21) (20 mg, 28 mol, 1.0 eq) in 1,4-dioxane (0.5 mL) was added dimethylamine hydrochloride (11 mg, 0.14 mmol, 5.0 eq) and DIEA (22 mg, 0.17 mmol, 6.0 eq). The resulting mixture was stirred at 100° C. for 1 h and then concentrated under reduced pressure. The residue was purified by reverse phase HPLC (C18 column, water (0.1% FA)-ACN) to afford the title compound.

LCMS: 674.4 [M+H]$^+$.

$^1$H NMR (400 MHz, CDCl$_3$) δ ppm 11.91 (s, 1H), 8.58 (s, 2H), 8.54 (d, 1H), 8.20 (s, 1H), 7.61 (d, 1H), 7.53 (dd, 1H), 5.53 (br dd, 1H), 5.31 (br s, 2H), 4.84-4.68 (m, 1H), 4.05 (dt, 2H), 3.60-3.44 (m, 1H), 3.27 (s, 6H), 3.24 (br s, 2H), 3.15-3.00 (m, 1H), 2.88-2.67 (m, 2H), 2.56 (s, 3H), 1.34 (t, 3H).

188

Synthesis of (E)-N-(2-chloro-4-(trifluoromethyl) phenyl)-2-(2-(2-ethoxyvinyl)-6-ethyl-7-(4-(5-hydroxy-6-methylpyrimidine-4-carbonyl)piperazin-1-yl)-8-oxopyrido[2,3-b]pyrazin-5 (8H)-yl)acetamide (I-15)

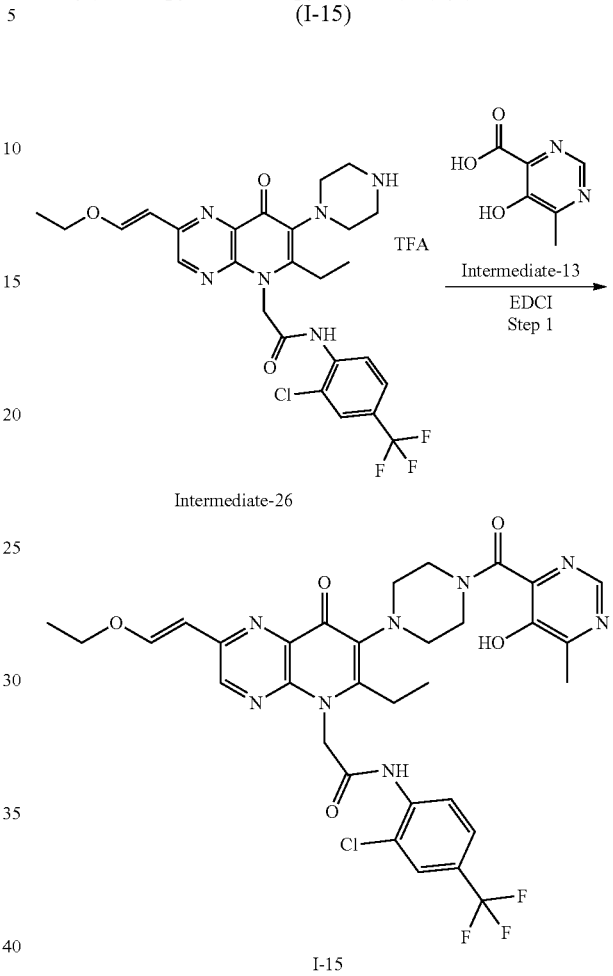

Intermediate-26

I-15

Step 1. Synthesis of (E)-N-(2-chloro-4-(trifluoromethyl)phenyl)-2-(2-(2-ethoxyvinyl)-6-ethyl-7-(4-(5-hydroxy-6-methylpyrimidine-4-carbonyl)piperazin-1-yl)-8-oxopyrido[2,3-b]pyrazin-5 (8H)-yl) acetamide To a solution of 5-hydroxy-6-methylpyrimidine-4-carboxylic acid (Intermediate-13) (22 mg, 0.14 mmol, 4.0 eq) in pyridine (0.5 mL) was added EDCI (27 mg, 0.14 mmol, 4.0 eq) and (E)-N-(2-chloro-4-(trifluoromethyl)phenyl)-2-(2-(2-ethoxyvinyl)-6-ethyl-8-oxo-7-(piperazin-1-yl)pyrido [2,3-b]pyrazin-5 (8H)-yl)acetamide trifluoroacetate (Intermediate-26) (20 mg, 35 mol, 1.0 eq). The resulting mixture was stirred at 40° C. for 1 h and then concentrated under reduced pressure. The residue was purified by reverse phase HPLC (C18 column, water (0.1% FA)-ACN) to afford the title compound.

LCMS: 701.4 [M+H]$^+$.

$^1$H NMR (400 MHz, CDCl$_3$) δ ppm 11.88 (s, 1H), 8.68 (s, 1H), 8.59 (s, 1H), 8.52 (d, 1H), 8.41 (s, 1H), 7.87 (d, 1H), 7.63 (s, 1H), 7.54 (br d, 1H), 6.02 (d, 1H), 5.64-5.50 (m, 1H), 5.42-5.23 (m, 2H), 4.84-4.72 (m, 1H), 4.08-3.94 (m, 4H), 3.59-3.45 (m, 1H), 3.33-3.23 (m, 2H), 3.16-3.03 (m, 1H), 2.89-2.72 (m, 2H), 2.57 (s, 3H), 1.36 (dt, 6H).

Synthesis of rac-N-(2-chloro-4-(trifluoromethyl)
phenyl)-2-(6-ethyl-7-(5-(5-hydroxy-6-methylpyrimi-
dine-4-carbonyl)-2,5-diazabicyclo[4.2.0]octan-2-yl)-
2-methoxy-3-methyl-8-oxopyrido[2,3-b]pyrazin-5
(8H)-yl)acetamide (Racemic Mixture, Trans (I-16))

and then purified by reverse phase HPLC (C18 column,
water (0.1% FA)-ACN) to afford the title compound.
LCMS: 701.4 [M+H]$^+$.
$^1$H NMR (400 MHz, CDCl$_3$) δ 8.61 (br s, 1H), 8.51 (d,
1H), 8.26 (br s, 1H), 7.62 (s, 1H), 7.54 (br d, 1H), 5.42-5.28
(m, 3H), 5.03-4.24 (m, 2H), 4.20 (s, 3H), 4.05-3.57 (m, 2H),
3.37 (br d, 2H), 3.25-3.13 (m, 1H), 2.62 (s, 3H), 2.55 (s, 3H),
2.38-1.94 (m, 2H), 1.52-1.39 (m, 2H), 1.34 (br t, 3H).

Synthesis of N-(2-chloro-4-(trifluoromethyl)phe-
nyl)-2-(2-cyclopropyl-6-ethyl-7-(4-(5-hydroxy-6-
methylpyrimidine-4-carbonyl)piperazin-1-yl)-3-
methyl-8-oxopyrido[2,3-b]pyrazin-5 (8H)-yl)
acetamide (I-17)

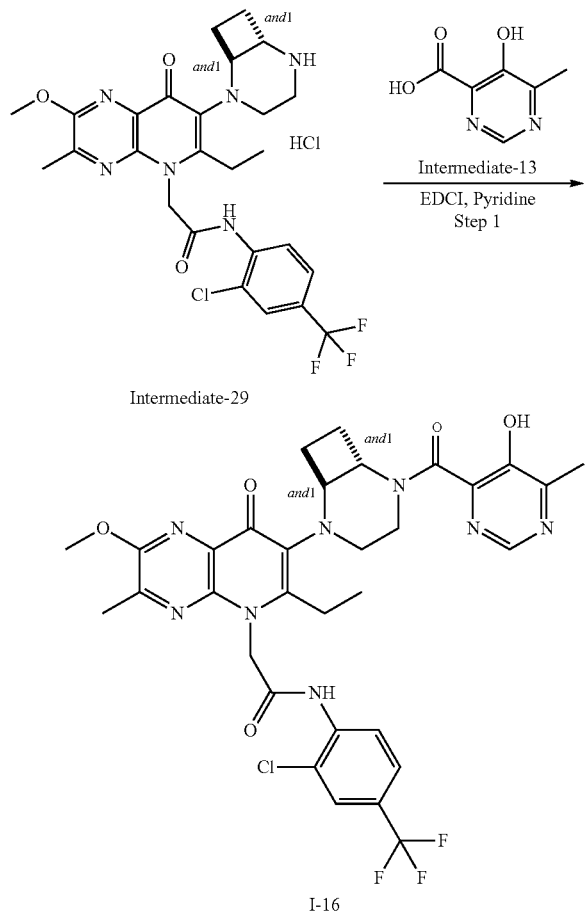

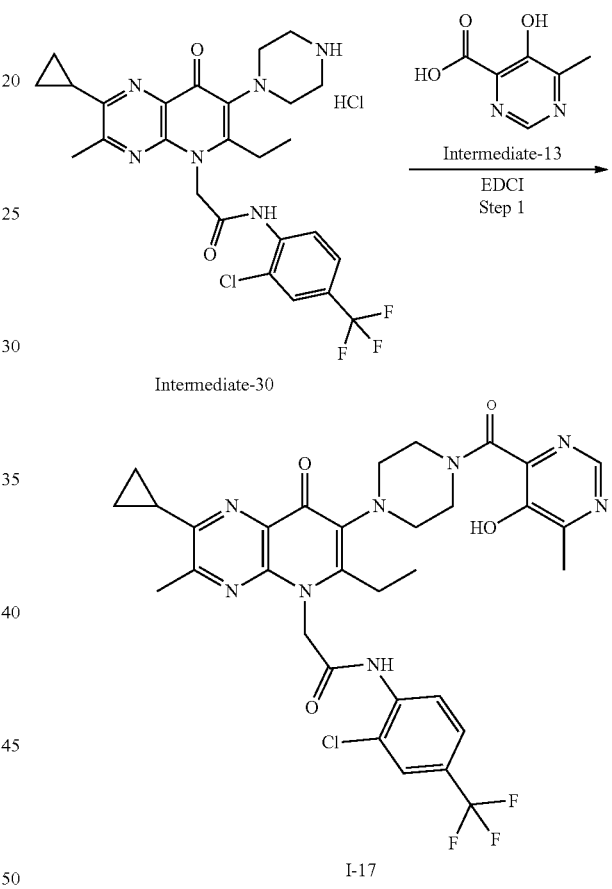

Step 1. Synthesis of rac-N-(2-chloro-4-(trifluorom-
ethyl)phenyl)-2-(6-ethyl-7-(5-(5-hydroxy-6-meth-
ylpyrimidine-4-carbonyl)-2,5-diazabicyclo[4.2.0]
octan-2-yl)-2-methoxy-3-methyl-8-oxopyrido[2,3-b]
pyrazin-5 (8H)-yl)acetamide (Racemic Mixture,
Trans)

To a solution of rac-2-(7-(2,5-diazabicyclo[4.2.0]octan-2-
yl)-6-ethyl-2-methoxy-3-methyl-8-oxopyrido[2,3-b]
pyrazin-5 (8H)-yl)-N-(2-chloro-4-(trifluoromethyl)phenyl)
acetamide hydrochloride (racemic mixture, trans)
(Intermediate-29) (45 mg, 80 mol, 1.0 eq) and 5-hydroxy-
6-methylpyrimidine-4-carboxylic acid (Intermediate-13)
(15 mg, 95 mol, 1.2 eq) in pyridine (1 mL) was added EDCI
(46 mg, 0.24 mmol, 3.0 eq) and the resulting mixture was
stirred at room temperature for 15 h. The reaction mixture
was concentrated under reduced pressure. The residue was
dissolved into MeOH (0.25 mL), THF (0.25 mL) and H$_2$O
(0.5 mL). Aqueous LiOH solution (0.5 mL, 1 M) was added,
and the mixture was stirred at room temperature for 1 h. The
reaction mixture was concentrated under reduced pressure Step 1. Synthesis of N-(2-chloro-4-(trifluoromethyl)
phenyl)-2-(2-cyclopropyl-6-ethyl-7-(4-(5-hydroxy-6-
methylpyrimidine-4-carbonyl)piperazin-1-yl)-3-
methyl-8-oxopyrido[2,3-b]pyrazin-5 (8H)-yl)
acetamide To a mixture of N-[2-chloro-4-(trifluoromethyl)phenyl]-
2-(2-cyclopropyl-6-ethyl-3-methyl-8-oxo-7-piperazin-1-yl-
pyrido[2,3-b]pyrazin-5-yl)acetamide hydrochloride (Inter-
mediate-30) (37 mg, 67 mol, 1.0 eq) and 5-hydroxy-6-
methyl-pyrimidine-4-carboxylic acid (Intermediate-13) (21
mg, 0.14 mmol, 2.0 eq) in pyridine (1 mL) was added EDCI
(26 mg, 0.14 mmol, 2.0 eq), and the resulting mixture was
stirred at room temperature for 1 h. The reaction mixture was
quenched by H$_2$O (10 mL) and extracted with EtOAc (10 mL*3). The combined organic layers were washed with brine (10 mL), dried over anhydrous Na$_2$SO$_4$, filtered and concentrated under reduced pressure. The residue was purified by reverse phase HPLC (C18 column, H$_2$O (10 mmol/L NH$_4$HCO$_3$)-ACN) to afford the title compound.

LCMS: 685.2 [M+H]$^+$.

$^1$H NMR (400 MHz, CDCl$_3$) δ ppm 11.67 (br s, 1H), 8.58 (s, 1H), 8.51 (d, 1H), 8.43 (s, 1H), 7.63 (d, 1H), 7.55 (br d, 1H), 5.65-5.43 (m, 1H), 5.36 (br s, 2H), 4.76 (br dd, 1H), 4.02 (dt, 2H), 3.62-3.39 (m, 1H), 3.34-3.19 (m, 2H), 3.18-2.96 (m, 1H), 2.89-2.71 (m, 5H), 2.57 (s, 3H), 2.24-2.16 (m, 1H), 1.37-1.30 (m, 5H), 1.10 (br dd, 2H).

Synthesis of N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-vinylpyrido[2,3-b]pyrazin-5 (8H)-yl)acetamide (I-18)

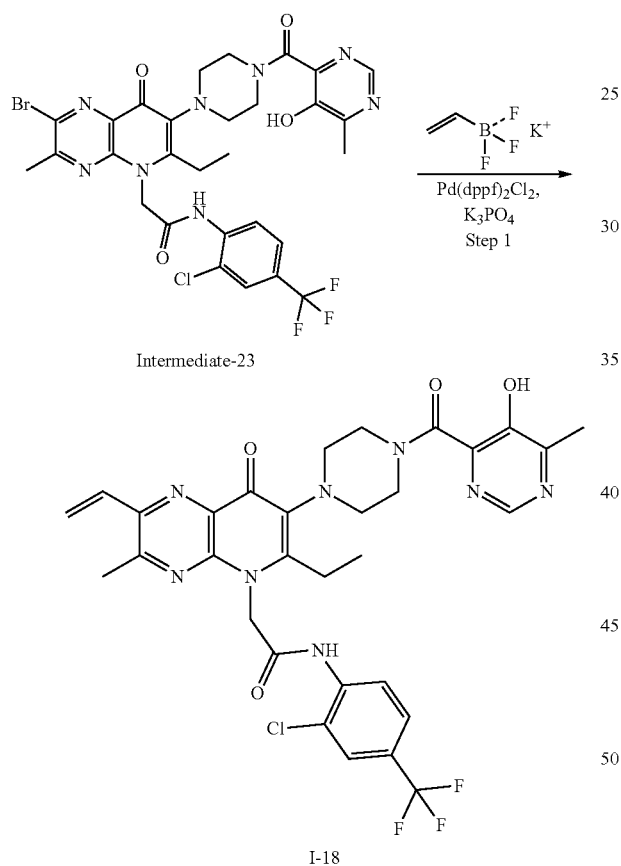

Step 1. Synthesis of N-(2-chloro-4-(trifluoromethyl) phenyl)-2-(6-ethyl-7-(4-(5-hydroxy-6-methylpyrimidine-4-carbonyl)piperazin-1-yl)-3-methyl-8-oxo-2-vinylpyrido[2,3-b]pyrazin-5 (8H)-yl)acetamide To a solution of 2-(2-bromo-6-ethyl-7-(4-(5-hydroxy-6-methylpyrimidine-4-carbonyl)piperazin-1-yl)-3-methyl-8-oxopyrido[2,3-b]pyrazin-5 (8H)-yl)-N-(2-chloro-4 (trifluoromethyl)phenyl)acetamide (Intermediate-23) (40 mg, 55 mol, 1.0 eq) and potassium trifluoro(vinyl)borate (7 mg, 55 mol, 1.0 eq) in dioxane (4 mL) and H$_2$O (0.8 mL) was added Pd(dppf)Cl$_2$ (4 mg, 6 mol, 0.1 eq) and K$_3$PO$_4$ (23 mg, 0.11 mmol, 2.0 eq). The reaction was degassed and purged with N$_2$ for 3 times, and then stirred at 80° C. for 1 h under N$_2$ atmosphere. The reaction mixture was concentrated under reduced pressure. The residue was diluted with H$_2$O (10 mL) and extracted with EtOAc (10 mL*2). The combined organic layers were washed with brine (7.5 mL*2), dried over anhydrous Na$_2$SO$_4$, filtered and the filtrate was concentrated under reduced pressure. The residue was purified by reverse phase HPLC (C18 column, water (0.1% FA)-ACN) to afford the title compound.

LCMS: 671.2 [M+H]$^+$.

$^1$H NMR (400 MHz, CDCl$_3$) δ ppm 11.81 (s, 1H), 8.59 (s, 1H), 8.51 (d, 1H), 8.39 (br s, 1H), 7.63 (s, 1H), 7.55 (br d, 1H), 7.09-6.99 (m, 1H), 6.74 (d, 1H), 5.73 (d, 1H), 5.64-5.53 (m, 1H), 5.36 (br d, 2H), 4.87-4.70 (m, 1H), 4.08-3.96 (m, 2H), 3.60-3.46 (m, 1H), 3.34-3.22 (m, 2H), 3.16-3.04 (m, 1H), 2.95-2.77 (m, 2H), 2.75 (s, 3H), 2.58 (s, 3H), 1.39-1.34 (m, 3H).

Synthesis of N-(2-chloro-4-(trifluoromethyl)phenyl)-2-(2-chloro-6-ethyl-7-(4-(5-hydroxy-6-methylpyrimidine-4-carbonyl)piperazin-1-yl)-8-oxopyrido[2,3-b]pyrazin-5 (8H)-yl)acetamide (I-19)

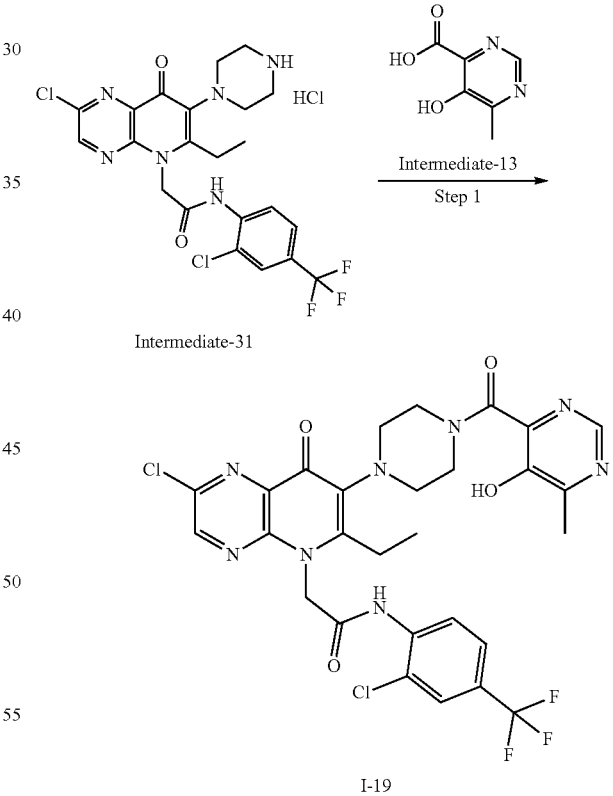

Step 1: Synthesis of N-(2-chloro-4-(trifluoromethyl) phenyl)-2-(2-chloro-6-ethyl-7-(4-(5-hydroxy-6-methylpyrimidine-4-carbonyl)piperazin-1-yl)-8-oxopyrido[2,3-b]pyrazin-5 (8H)-yl)acetamide To a solution of N-(2-chloro-4-(trifluoromethyl)phenyl)-2-(2-chloro-6-ethyl-8-oxo-7-(piperazin-1-yl)pyrido[2,3-b]

pyrazin-5 (8H)-yl)acetamide hydrochloride (Intermediate-31) (390 mg, 737 mol, 1.0 eq) and 5-hydroxy-6-methylpyrimidine-4-carboxylic acid (227 mg, 1.47 mmol, 2.0 eq) in pyridine (5 mL) was added EDCI (282 mg, 1.47 mmol, 2.0 eq), the resulting mixture was stirred at 40° C. for 15 h. The mixture was concentrated under reduced pressure and the residue was purified by reverse phase HPLC (C18 column, water (0.1% FA)-ACN) to afford the title compound.

LCMS: 665.4[M+H]+.

1H NMR (400 MHz, CDCl3) δ 11.83 (s, 1H), 8.62 (d, 2H), 8.52-8.42 (m, 2H), 7.69 (d, 1H), 7.56 (d, 1H), 5.69-5.57 (m, 1H), 5.39 (br s, 2H), 4.88-4.73 (m, 1H), 4.08-3.93 (m, 2H), 3.62-3.48 (m, 1H), 3.30 (br d, 2H), 3.17-3.04 (m, 1H), 2.91-2.72 (m, 2H), 2.59 (s, 3H), 1.39 (t, 3H).

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(methylamino)-8-oxopyrido[2,3-b]pyrazin-5 (8H)-yl)acetamide (I-20)

mol, 1.0 eq) was dissolved in TFA (0.5 mL) and then stirred at room temperature for 1 h. The mixture was concentrated under reduced pressure and the residue was purified by reverse phase HPLC (C18 column, water (0.1% FA)-ACN) to afford the title compound.

LCMS: 660.4 [M+H]+.

1H NMR (400 MHz, CDCl3) δ ppm 8.99 (s, 1H), 8.60 (s, 1H), 8.40 (br d, 1H), 8.22 (s, 1H), 7.64 (s, 1H), 7.50 (br d, 1H), 5.70-5.32 (m, 3H), 4.85-4.65 (m, 1H), 4.02-3.75 (m, 2H), 3.61-3.41 (m, 1H), 3.27 (br s, 2H), 3.13-2.97 (m, 4H), 2.87-2.72 (m, 2H), 2.58 (s, 3H), 1.35 (br t, 3H).

Synthesis of (E)N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(prop-1-en-1-yl)pyrido[2,3-b]pyrazin-5 (8H)-yl) acetamide (I-21)

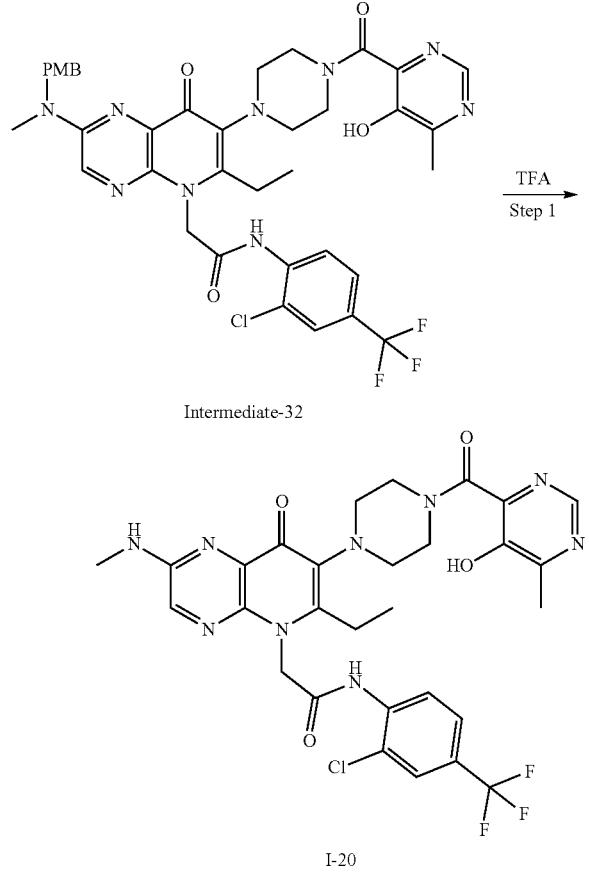

Intermediate-32

I-20

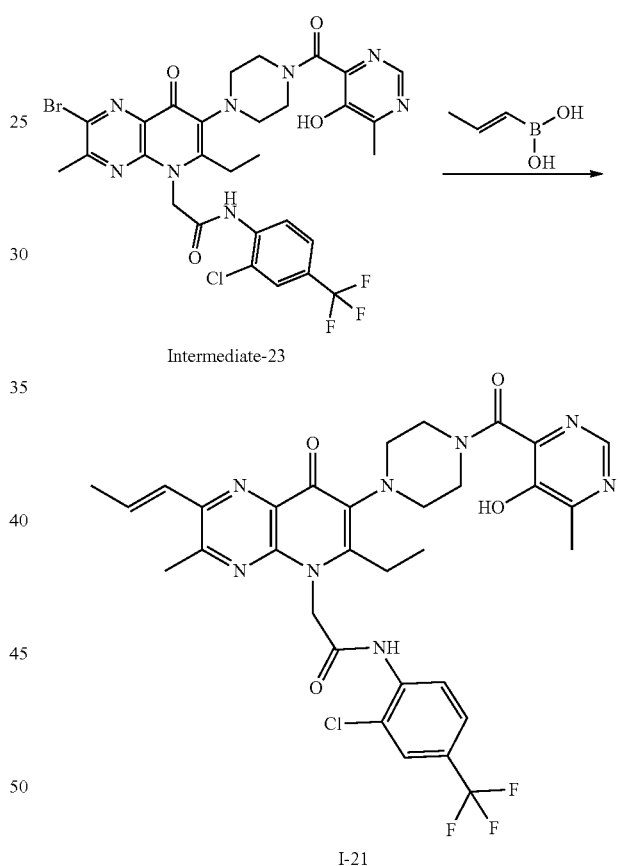

Intermediate-23

I-21

Step 1: Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(methylamino)-8-oxopyrido[2,3-b]pyrazin-5 (8H)-yl)acetamide N-(2-chloro-4-(trifluoromethyl)phenyl)-2-(6-ethyl-7-(4-(5-hydroxy-6-methylpyrimidine-4-carbonyl)piperazin-1-yl)-2-((4-methoxybenzyl)(methyl)amino)-8-oxopyrido[2,3-b]pyrazin-5 (8H)-yl)acetamide (Intermediate-32) (15 mg, 19

Step 1. Synthesis (E)-N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(prop-1-en-1-yl)pyrido[2,3-b]pyrazin-5 (8H)-yl)acetamide To a solution of 2-(2-bromo-6-ethyl-7-(4-(5-hydroxy-6-methylpyrimidine-4-carbonyl)piperazin-1-yl)-3-methyl-8-oxopyrido[2,3-b]pyrazin-5 (8H)-yl)-N-(2-chloro-4-(trifluoromethyl)phenyl)acetamide (Intermediate-23) (50 mg, 69 mol, 1.0 eq and (E)-prop-1-en-1-ylboronic acid (6 mg, 69 mol, 1.0 eq) in 1,4-dioxane (1 mL) and H2O (0.2 mL) was added Pd(dppf)Cl$_2$—CH$_2$Cl$_2$ (6 mg, 7 mol, 0.1 eq) and K$_3$PO$_4$ (29 mg, 0.14 mmol, 2.0 eq), and the resulting mixture was stirred at 80° C. for 1 h under N$_2$ atmosphere. The reaction mixture was quenched by saturated NH$_4$Cl aqueous solution (100 mL) and extracted with EtOAc (50 mL*3). The combined organic layers were washed with brine (30 mL), dried over anhydrous Na$_2$SO$_4$, filtered and concentrated under reduced pressure. The residue was purified by reverse phase HPLC (C18 column, H$_2$O (10 mmol/L NH$_4$HCO$_3$)-ACN) to afford the title compound.

LCMS: 685.2 [M+H]$^+$.

$^1$H NMR (400 MHz, CDCl$_3$) δ ppm 11.68 (br s, 1H), 8.60 (s, 1H), 8.52 (br d, 1H), 8.47 (br s, 1H), 7.63 (s, 1H), 7.56 (br d, 1H), 7.37-7.30 (m, 1H), 6.69 (br d, 1H), 5.73-5.51 (m, 1H), 5.37 (br s, 2H), 4.91-4.67 (m, 1H), 4.11-3.92 (m, 2H), 3.65-3.45 (m, 1H), 3.36-3.23 (m, 2H), 3.19-3.02 (m, 1H), 2.91-2.76 (m, 2H), 2.73 (s, 3H), 2.59 (s, 3H), 2.01 (br d, 3H), 1.37 (br t, 3H).

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(2-hydroxypropan-2-yl)-3-methyl-8-oxopyrido[2,3-b]pyrazin-5 (8H)-yl)acetamide (I-22)

Step 1. Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(2-hydroxypropan-2-yl)-3-methyl-8-oxopyrido[2,3-b]pyrazin-5 (8H)-yl)acetamide To a solution of N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(prop-1-en-2-yl)pyrido[2,3-b]pyrazin-5 (8H)-yl)acetamide (I-23) (30 mg, 44 mol, 1 eq) in THF (1 mL) was added phenylsilane (9 mg, 88 mol, 2.0 eq) and bis[(Z)-1-methyl-3-oxo-but-1-enoxy]cobalt (1 mg, 2 mol, 0.05 eq). The resulting mixture was stirred at room temperature for 16 h under O$_2$ atmosphere. The reaction mixture was concentrated under reduced pressure and then purified by reverse phase HPLC (C18 column, water (0.1% FA)-ACN) to afford the title compound

LCMS: 703.4 [M+H]$^+$.

$^1$H NMR (400 MHz, CDCl$_3$) δ ppm 8.58 (s, 1H), 8.48 (br d, 1H), 8.42-8.24 (m, 1H), 7.65 (s, 1H), 7.55 (br d, 1H), 7.49-7.28 (m, 1H), 5.75-5.50 (m, 1H), 5.48-5.13 (m, 2H), 5.12-4.84 (m, 1H), 4.83-4.59 (m, 1H), 4.32-3.76 (m, 2H), 3.62-3.39 (m, 1H), 3.38-3.18 (m, 2H), 3.18-2.98 (m, 1H), 2.97-2.82 (m, 3H), 2.81-2.70 (m, 1H), 2.57 (s, 3H), 1.70 (br s, 6H), 1.36 (br t, 3H).

Synthesis of N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(prop-1-en-2-yl)pyrido[2,3-b]pyrazin-5 (8H)-yl)acetamide (I-23)

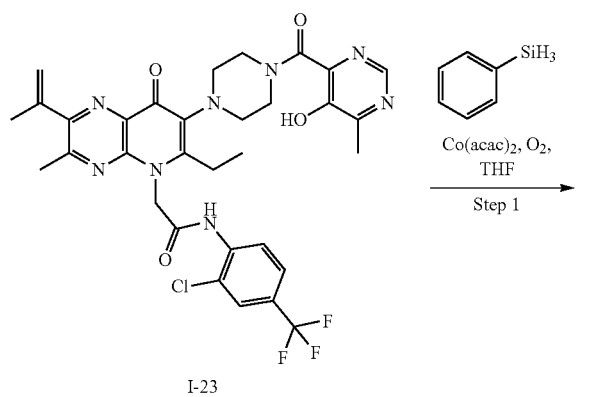

I-23

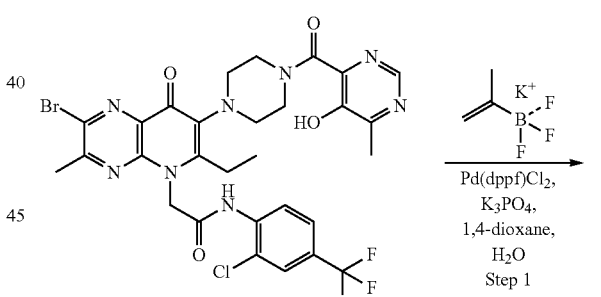

Intermediate-23

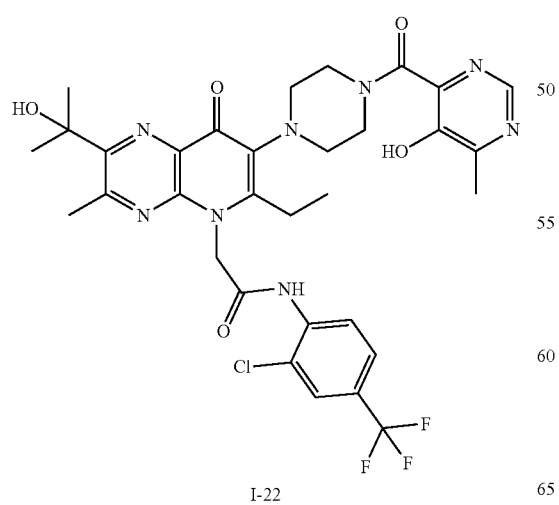

I-22

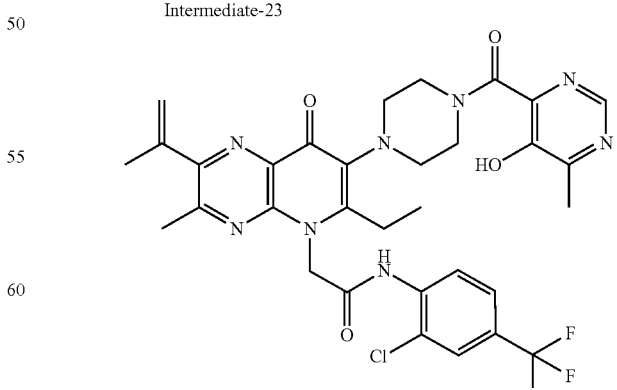

I-23

Step 1. Synthesis of N-(2-chloro-4-(trifluoromethyl)phenyl)-2-(6-ethyl-7-(4-(5-hydroxy-6-methylpyrimidine-4-carbonyl)piperazin-1-yl)-3-methyl-8-oxo-2-(prop-1-en-2-yl)pyrido[2,3-b]pyrazin-5 (8H)-yl)acetamide To a solution of 2-(2-bromo-6-ethyl-7-(4-(5-hydroxy-6-methylpyrimidine-4-carbonyl)piperazin-1-yl)-3-methyl-8-oxopyrido[2,3-b]pyrazin-5 (8H)-yl)-N-(2-chloro-4-(trifluoromethyl)phenyl)acetamide (Intermediate-23) (50 mg, 69 mol, 1.0 eq) and potassium trifluoro(prop-1-en-2-yl)borate (11 mg, 76 mol, 1.1 eq) in 1,4-dioxane (1 mL) and H$_2$O (0.2 mL) was added Pd(dppf)Cl$_2$ (5 mg, 7 mol, 0.1 eq) and K$_3$PO$_4$ (29 mg, 0.14 mmol, 2.0 eq). The resulting mixture was stirred at 80° C. for 2 h under N$_2$ atmosphere. After being cooled to room temperature, the reaction mixture was diluted with H$_2$O (10 mL) and extracted with EtOAc (5 mL*3). The combined organic layers were washed with brine (5 mL*3), dried over anhydrous Na$_2$SO$_4$, filtered and the filtrate was concentrated under reduced pressure. The residue was purified by reverse phase HPLC (C18 column, water (0.1% FA)-ACN) to afford the title compound.

LCMS: 685.4 [M+H]$^+$.

$^1$H NMR (400 MHz, CDCl$_3$) δ ppm 11.79 (br s, 1H), 8.58 (s, 1H), 8.49 (br d, 2H), 7.63 (s, 1H), 7.55 (br d 1H), 5.69-5.50 (m, 2H), 5.49-5.28 (m, 2H), 5.22 (s, 1H), 4.89-4.65 (m, 1H), 4.12-3.87 (m, 2H), 3.63-3.41 (m, 1H), 3.40-3.18 (m, 2H), 3.17-2.99 (m, 1H), 2.98-2.76 (m, 2H), 2.74 (s, 3H), 2.57 (s, 3H), 2.24 (s, 3H), 1.42-1.28 (m, 3H).

Synthesis of N-(2-chloro-4-(trifluoromethyl)phenyl)-2-(6-ethyl-2-hydroxy-7-(4-(5-hydroxy-6-methylpyrimidine-4-carbonyl)piperazin-1-yl)-8-oxopyrido[2,3-b]pyrazin-5 (8H)-yl)acetamide (I-24)

Step 1. Synthesis of N-(2-chloro-4-(trifluoromethyl)phenyl)-2-(6-ethyl-2-hydroxy-7-(4-(5-hydroxy-6-methylpyrimidine-4-carbonyl)piperazin-1-yl)-8-oxopyrido[2,3-b]pyrazin-5 (8H)-yl)acetamide To a solution of 5-hydroxy-6-methylpyrimidine-4-carboxylic acid (Intermediate-13) (29 mg, 0.16 mmol, 4.0 eq) in pyridine (0.5 mL) was added EDCI (32 mg, 0.16 mmol, 4.0 eq), and the mixture was stirred at room temperature for 0.5 h. Then N-(2-chloro-4-(trifluoromethyl)phenyl)-2-(6-ethyl-2-hydroxy-8-oxo-7-(piperazin-1-yl)pyrido[2,3-b]pyrazin-5 (8H)-yl)acetamide hydrochloride (Intermediate-34) (21 mg, 41 mol, 1.0 eq) was added at room temperature and the reaction mixture was stirred at 40° C. for 16 h. The reaction mixture was concentrated under reduced pressure and then purified by reverse phase HPLC (C18 column, water (0.1% FA)-ACN) to afford the title compound.

LCMS: 647.1 [M+H]$^+$.

$^1$H NMR (400 MHz, CHCl$_3$) δ 11.65 (br s, 1H), 8.60 (s, 1H), 8.50 (d, 1H), 8.37 (s, 1H), 8.32 (s, 1H), 7.70 (s, 1H), 7.57 (br d, 1H), 5.59-5.44 (m, 1H), 5.36 (br s, 2H), 4.90-4.73 (m, 1H), 4.01 (br t, 2H), 3.59-3.41 (m, 1H), 3.32-3.19 (m, 2H), 3.14-3.02 (m, 1H), 2.90-2.71 (m, 2H), 2.58 (s, 3H), 1.35 (br t, 3H).

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(hydroxymethyl)-8-oxopyrido[2,3-b]pyrazin-5 (8H)-yl)acetamide (I-25)

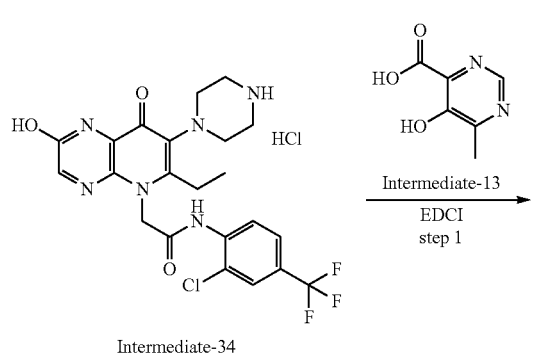

Intermediate-34

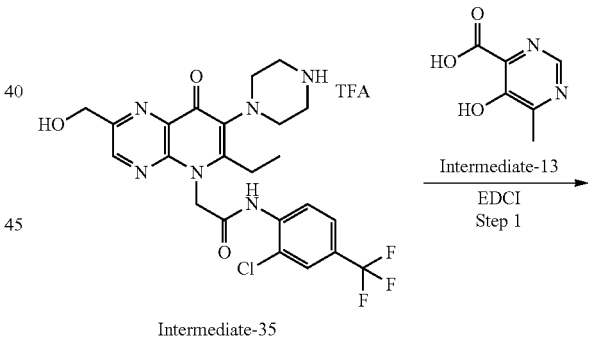

Intermediate-35

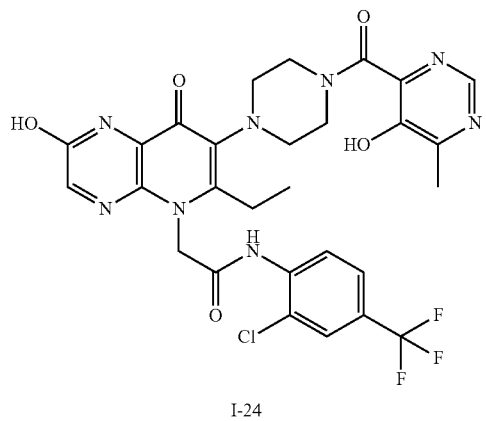

I-24

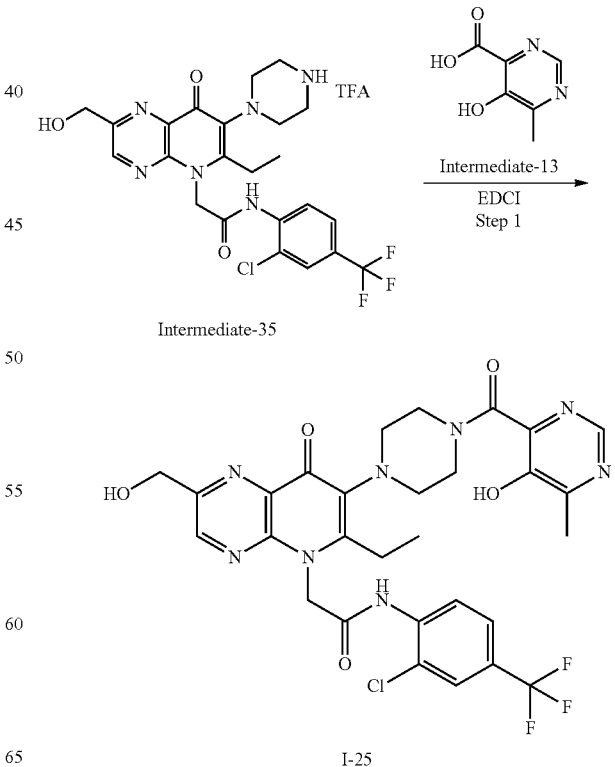

I-25

Step 1. Synthesis of N-(2-chloro-4-(trifluoromethyl) phenyl)-2-(6-ethyl-7-(4-(5-hydroxy-6-methylpyrimidine-4-carbonyl)piperazin-1-yl)-2-(hydroxymethyl)-8-oxopyrido[2,3-b]pyrazin-5 (8H)-yl)acetamide To a solution of N-(2-chloro-4-(trifluoromethyl)phenyl)-2-(6-ethyl-2-(hydroxymethyl)-8-oxo-7-(piperazin-1-yl) pyrido[2,3-b]pyrazin-5 (8H)-yl)acetamide trifluoroacetate (Intermediate-35) (40 mg, 76 mol, 1.0 eq) in pyridine (0.8 mL) was added EDCI (44 mg, 0.23 mmol, 3.0 eq) and 5-hydroxy-6-methylpyrimidine-4-carboxylic acid (Intermediate-13) (40 mg, 0.23 mmol, 3.0 eq). The mixture was stirred at 40° C. for 16 h and then concentrated under reduced pressure. The residue was purified by reverse phase HPLC (water (0.1% FA)-ACN) to afford the title compound.
LCMS: 661.1 [M+H]$^+$.
$^1$H NMR (400 MHz, CDCl$_3$) δ ppm 8.86 (br d, 1H), 8.80 (s, 1H), 8.58 (s, 1H), 8.43 (br d, 1H), 7.63 (s, 1H), 7.51 (br d, 1H), 5.55-5.39 (m, 3H), 5.00 (s, 2H), 4.77-4.70 (m, 1H), 4.04-3.92 (m, 2H), 3.55-3.46 (m, 1H), 3.29 (br s, 2H), 3.10-3.04 (m, 1H), 2.85-2.75 (m, 2H), 2.56 (s, 3H), 1.36 (br t, 3H).

Synthesis of N-(2-chloro-4-(trifluoromethyl)phenyl)-2-(2-(difluoromethoxy)-6-ethyl-7-(4-(5-hydroxy-6-methylpyrimidine-4-carbonyl)piperazin-1-yl)-8-oxopyrido[2,3-b]pyrazin-5 (8H)-yl)acetamide (I-26)

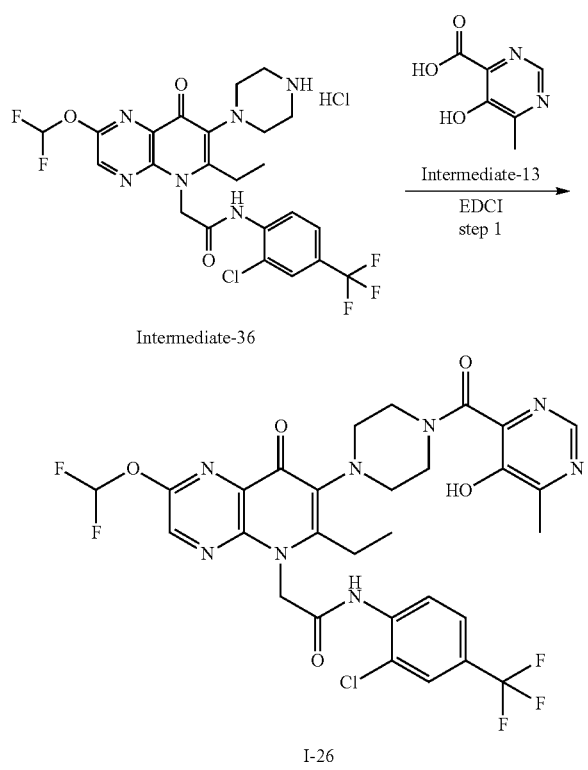

I-26

Step 1. Synthesis of N-(2-chloro-4-(trifluoromethyl) phenyl)-2-(2-(difluoromethoxy)-6-ethyl-7-(4-(5-hydroxy-6-methylpyrimidine-4-carbonyl)piperazin-1-yl)-8-oxopyrido[2,3-b]pyrazin-5 (8H)-yl) acetamide To a solution of 5-hydroxy-6-methyl-pyrimidine-4-carboxylic acid (Intermediate-13) (18 mg, 0.10 mmol, 4.0 eq) in pyridine (0.5 mL) was added EDCI (19 mg, 0.10 mmol, 4.0 eq), and the mixture was stirred at room temperature for 0.5 h. Then, N-(2-chloro-4-(trifluoromethyl)phenyl)-2-(2-(difluoromethoxy)-6-ethyl-8-oxo-7-(piperazin-1-yl)pyrido [2,3-b]pyrazin-5 (8H)-yl)acetamide hydrochloride (Intermediate-36) (14 mg, 25 mol, 1.0 eq) was added and the mixture was stirred at room temperature for 16 h. The reaction mixture was concentrated under reduced pressure, the residue was purified by reverse phase HPLC (C18 column, water (0. % FA)-ACN) to afford the title compound.
LCMS: 697.1 [M+H]$^+$.
$^1$H NMR (400 MHz, CDCl$_3$) δ ppm 11.75 (br s, 1H), 8.59 (s, 1H), 8.48 (d, 1H), 8.45 (s, 1H), 8.41 (s, 1H), 7.75 (t, 1H), 7.67 (d, 1H), 7.55 (d, 1H), 5.59 (d, 1H), 5.38 (s, 2H), 4.77 (s, 1H), 4.06-3.89 (m, 2H), 3.52 (s, 1H), 3.28 (s, 2H), 3.10 (s, 1H), 2.92-2.68 (m, 2H), 2.57 (s, 3H), 1.37 (t, 3H).

Synthesis of N-(2-chloro-4-(trifluoromethyl)phenyl)-2-(6-ethyl-7-(4-(5-hydroxy-6-methylpyrimidine-4-carbonyl)piperazin-1-yl)-8-oxo-2-(2-oxopyrrolidin-1-yl)pyrido[2,3-b]pyrazin-5 (8H)-yl) acetamide (I-27)

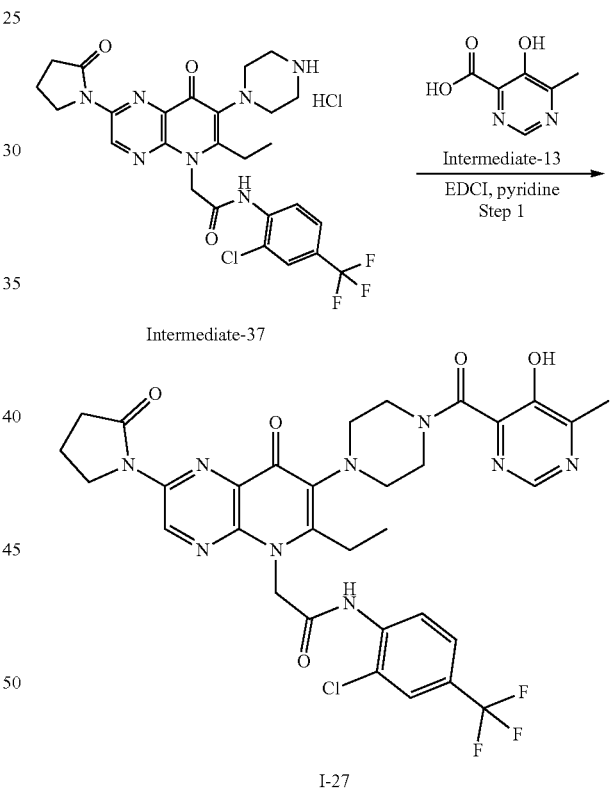

I-27

Step 1. Synthesis of N-(2-chloro-4-(trifluoromethyl) phenyl)-2-(6-ethyl-7-(4-(5-hydroxy-6-methylpyrimidine-4-carbonyl)piperazin-1-yl)-8-oxo-2-(2-oxopyrrolidin-1-yl)pyrido[2,3-b]pyrazin-5 (8H)-yl) acetamide To a solution of 5-hydroxy-6-methyl-pyrimidine-4-carboxylic acid (Intermediate-13) (34 mg, 0.22 mmol, 5.0 eq) in pyridine (0.5 mL) was added EDCI (42 mg, 0.22 mmol, 5.0 eq) and the mixture was stirred at room temperature for 0.5 h. N-(2-chloro-4-(trifluoromethyl)phenyl)-2-(6-ethyl-8- oxo-2-(2-oxopyrrolidin-1-yl)-7-(piperazin-1-yl)pyrido[2,3-b]pyrazin-5 (8H)-yl)acetamide hydrochloride (Intermediate-37) (27 mg, 44 mol, 1.0 eq) was added to the mixture and the reaction mixture was stirred at 30° C. for 1 h. The mixture was concentrated under reduced pressure, the residue was purified by reverse phase HPLC (water (0.1% FA)-ACN) to afford the title compound.

LCMS: 714.2 [M+H]$^+$.

$^1$H NMR (400 MHz, CDCl$_3$) δ ppm 11.79 (br s, 1H), 9.88 (s, 1H), 8.64 (s, 1H), 8.59 (s, 1H), 8.51 (d, 1H), 7.64 (s, 1H), 7.53 (d, 1H), 5.57 (br s, 1H), 5.37 (br s, 2H), 4.77 (br s, 1H), 4.28 (t, 2H), 4.08-3.96 (m, 2H), 3.61-3.45 (m, 1H), 3.32 (br d, 2H), 3.11 (br s, 1H), 2.82 (br d, 2H), 2.73 (t, 2H), 2.57 (s, 3H), 2.23 (m, 2H), 1.38 (t, 3H).

Synthesis of N-(2-chloro-4-(trifluoromethyl)phenyl)-2-(2-(difluoromethyl)-6-ethyl-7-(4-(5-hydroxy-6-methylpyrimidine-4-carbonyl)piperazin-1-yl)-3-methyl-8-oxopyrido[2,3-b]pyrazin-5 (8H)-yl)acetamide (I-28)

hydrochloride (Intermediate-39) (50 mg, 89 mol, 1.0 eq) was added and the resulting mixture was stirred at room temperature for 15 h. The reaction mixture was concentrated under reduced pressure and then purified by reverse phase HPLC (C18 column, water (0.1% FA)-ACN) to afford the title compound.

LCMS: 695.1 [M+H]$^+$.

$^1$H NMR (400 MHz, CDCl$_3$) δ 11.84 (s, 1H), 8.60 (s, 1H), 8.47 (d, 1H), 8.30 (s, 1H), 7.68 (d, 1H), 7.59-7.52 (m, 1H), 7.12-6.79 (m, 1H), 5.68-5.53 (m, 1H), 5.44-5.31 (m, 2H), 4.90-4.72 (m, 1H), 4.05-3.93 (m, 2H), 3.59-3.46 (m, 1H), 3.33-3.21 (m, 2H), 3.17-3.05 (m, 1H), 2.87 (s, 3H), 2.85-2.73 (m, 2H), 2.57 (s, 3H), 1.39-1.35 (m, 3H).

Synthesis of N-(2-chloro-4-(trifluoromethyl)phenyl)-2-(2-(dimethylamino)-6-ethyl-7-(4-(5-hydroxy-6-methylpyrimidine-4-carbonyl)piperazin-1-yl)-3-methyl-8-oxopyrido[2,3-b]pyrazin-5 (8H)-yl)acetamide (I-29)

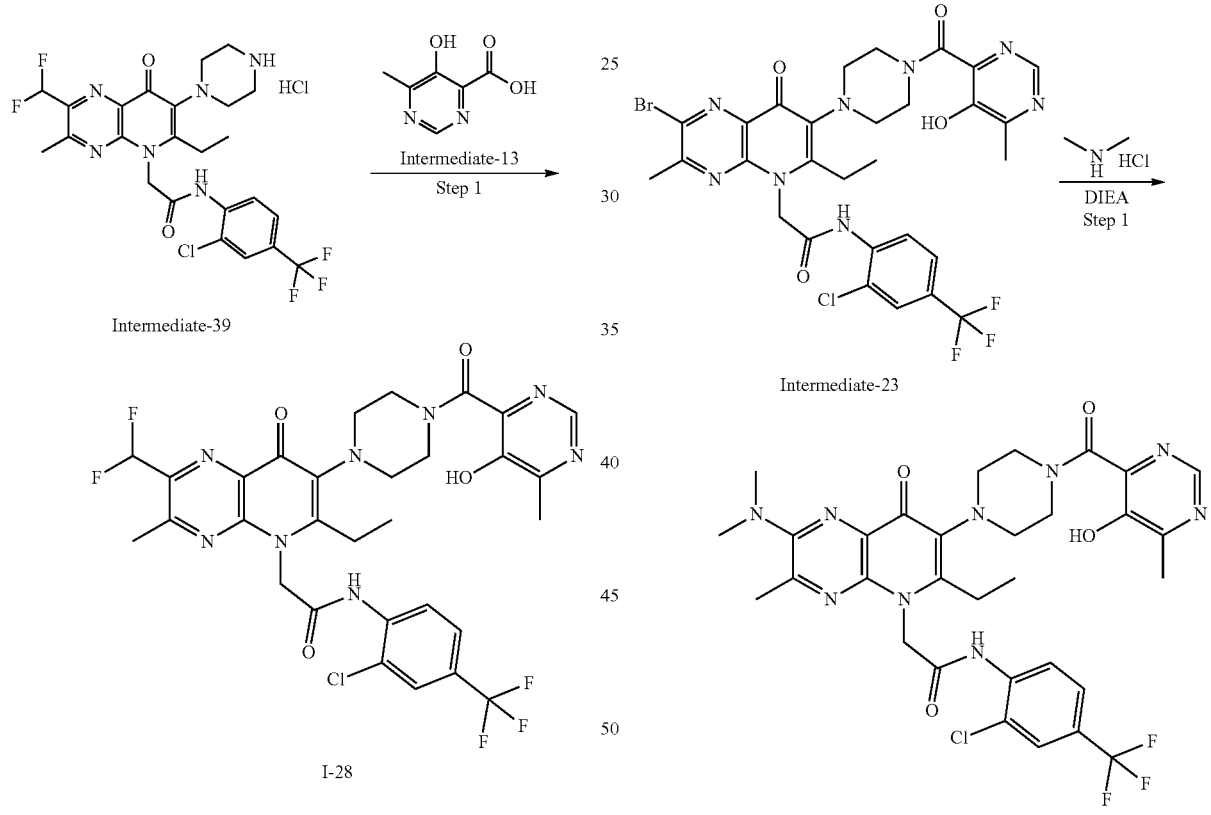

Step 1. Synthesis of N-(2-chloro-4-(trifluoromethyl)phenyl)-2-(2-(difluoromethyl)-6-ethyl-7-(4-(5-hydroxy-6-methylpyrimidine-4-carbonyl)piperazin-1-yl)-3-methyl-8-oxopyrido[2,3-b]pyrazin-5 (8H)-yl)acetamide To a solution of 5-hydroxy-6-methylpyrimidine-4-carboxylic acid (Intermediate-13) (69 mg, 0.45 mmol, 5.0 eq) in pyridine (1 mL) was added EDCI (77 mg, 0.40 mmol, 4.5 eq) and the resulting mixture was stirred at room temperature for 0.5 h. Then N-(2-chloro-4-(trifluoromethyl)phenyl)-2-(2-(difluoromethyl)-6-ethyl-3-methyl-8-oxo-7-(piperazin-1-yl)pyrido[2,3-b]pyrazin-5 (8H)-yl)acetamide Step 1. N-(2-chloro-4-(trifluoromethyl)phenyl)-2-(2-(dimethylamino)-6-ethyl-7-(4-(5-hydroxy-6-methylpyrimidine-4-carbonyl)piperazin-1-yl)-3-methyl-8-oxopyrido[2,3-b]pyrazin-5 (8H)-yl)acetamide To a solution of 2-(2-bromo-6-ethyl-7-(4-(5-hydroxy-6-methylpyrimidine-4-carbonyl)piperazin-1-yl)-3-methyl-8-oxopyrido[2,3-b]pyrazin-5 (8H)-yl)-N-(2-chloro-4-(trifluoromethyl)phenyl)acetamide (50 mg, 69 mol, 1.0 eq) and dimethylamine hydrochloride (41 mg, 0.35 mmol, 5.0 eq) in 1,4-dioxane (1 mL) was added DIEA (54 mg, 0.41 mmol, 6.0 eq) and the resulting mixture was stirred at 100° C. for 1 h. The reaction mixture was concentrated under reduced pressure and then purified by reverse phase HPLC (C18 column, water (0.1% FA)-ACN) to afford the title compound.

LCMS: 688.2 [M+H]$^+$.

$^1$H NMR (400 MHz, CDCl$_3$) δ 8.78-8.66 (m, 1H), 8.61 (s, 1H), 8.40 (br d, 1H), 7.65 (s, 1H), 7.53 (br d, 1H), 5.57 (br s, 3H), 4.86-4.73 (m, 1H), 3.97 (br t, 2H), 3.60-3.46 (m, 1H), 3.32 (br d, 2H), 3.09 (s, 7H), 2.94-2.78 (m, 2H), 2.72 (s, 3H), 2.58 (s, 3H), 1.36 (t, 3H).

Synthesis of 2-(2-acetamido-6-ethyl-7-(4-(5-hydroxy-6-methylpyrimidine-4-carbonyl)piperazin-1-yl)-8-oxopyrido[2,3-b]pyrazin-5 (8H)-yl)-N-(2-chloro-4-(trifluoromethyl)phenyl)acetamide (I-31)

centrated under reduced pressure and then purified by reverse phase HPLC (C18 column, water (0.1% FA)-ACN) to afford the title compound.

LCMS: 688.3 [M+H]$^+$.

$^1$H NMR (400 MHz, CDCl$_3$) δ ppm 9.66 (s, 1H), 9.29-9.04 (m, 1H), 8.74-8.61 (m, 1H), 8.59 (s, 1H), 8.48 (d, 1H), 7.65 (d, 1H), 7.58-7.48 (m, 1H), 5.64-5.47 (m, 1H), 5.46-5.19 (m, 2H), 4.88-4.66 (m, 1H), 4.06-3.88 (m, 2H), 3.51 (br t, 1H), 3.38-3.24 (m, 2H), 3.10 (br d, 1H), 2.87-2.73 (m, 2H), 2.56 (s, 3H), 2.26 (s, 3H), 1.37 (br t, 3H).

Synthesis of rac-N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetamide (Racemic Mixture, Trans, I-34)

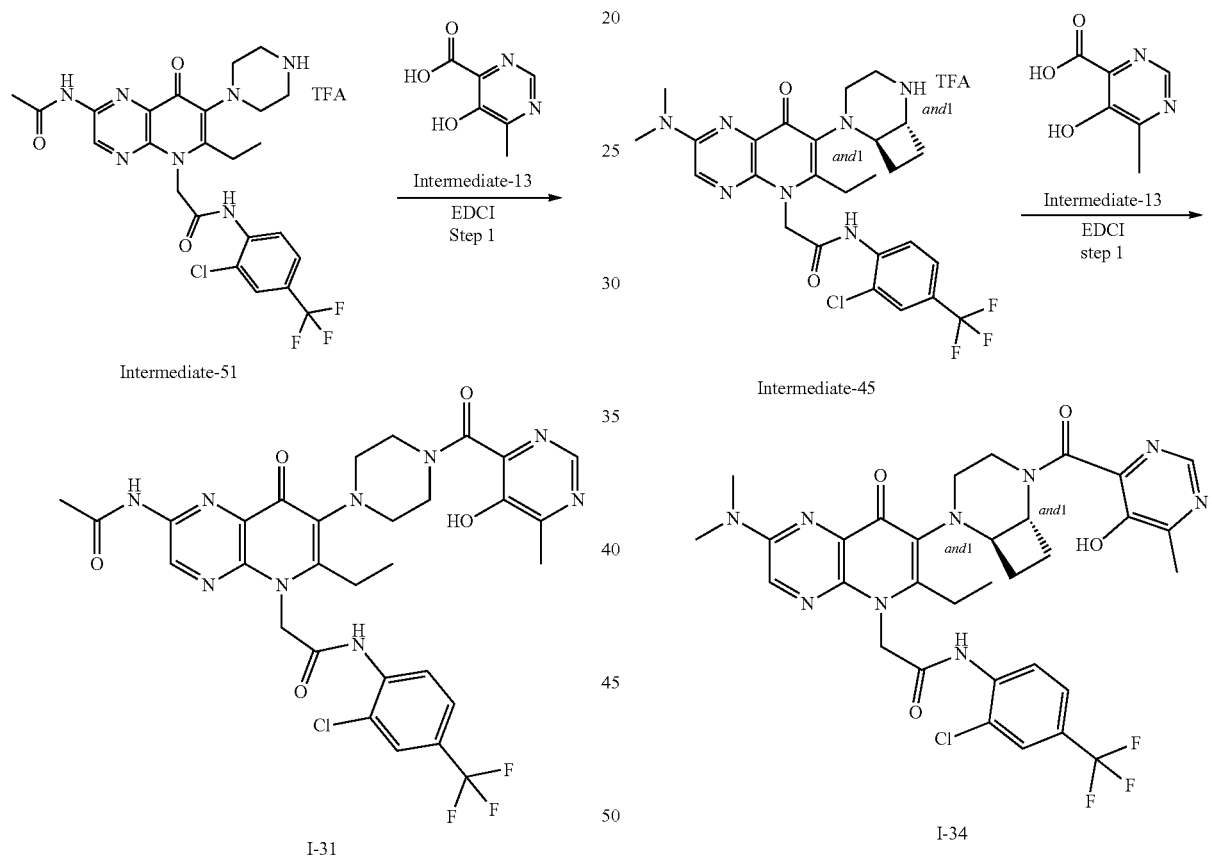

Step 1. Synthesis of 2-(2-acetamido-6-ethyl-7-(4-(5-hydroxy-6-methylpyrimidine-4-carbonyl)piperazin-1-yl)-8-oxopyrido[2,3-b]pyrazin-5 (8H)-yl)-N-(2-chloro-4-(trifluoromethyl)phenyl)acetamide To a solution of 5-hydroxy-6-methylpyrimidine-4-carboxylic acid (Intermediate-13) (45 mg, 0.29 mmol, 4.0 eq) in pyridine (1 mL) was added EDCI (56 mg, 0.29 mmol, 4.0 eq) and 2-(2-acetamido-6-ethyl-8-oxo-7-(piperazin-1-yl)pyrido[2,3-b]pyrazin-5 (8H)-yl)-N-(2-chloro-4-(trifluoromethyl)phenyl)acetamide trifluoroacetate (Intermediate-51) (40 mg, 72 mol, 1.0 eq), and the resulting mixture was stirred at 40° C. overnight. The reaction mixture was con- Step 1: Synthesis of rac-N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetamide (Racemic Mixture, Trans)

To a mixture of rac-2-(7-(2,5-diazabicyclo[4.2.0]octan-2-yl)-2-(dimethylamino)-6-ethyl-8-oxopyrido[2,3-b]pyrazin-5 (8H)-yl)-N-(2-chloro-4-(trifluoromethyl)phenyl)acetamide trifluoroacetate (racemic mixture, trans) (Intermediate-45) (80 mg, 0.14 mmol, 1.0 eq) and 5-hydroxy-6-methylpyrimidine-4-carboxylic acid (Intermediate-13) (44 mg, 0.28 mmol, 2.0 eq) in pyridine (2 mL) was added EDCI (54 mg, 0.28 mmol, 2.0 eq). The mixture was stirred at room temperature for 1 h and then quenched with H₂O (100 mL). The resulting mixture was extracted with EtOAc (50 mL*3). The combined organic layers were washed with brine (30 mL), dried over Na₂SO₄, filtered and the filtrate was concentrated in vacuo. The residue was purified by reverse phase HPLC (C18 column, water (0.1% FA)-ACN) to afford the title compound.

LCMS: 700.4 [M+H]⁺.

¹HNMR: (400 MHz, CDCl₃) δ ppm 12.71 (s, 1H), 8.61 (br s, 1H), 8.54 (d, 1H), 8.45 (s, 1H), 8.22 (s, 1H), 7.60 (s, 1H), 7.53 (br d, 1H), 5.78-4.87 (m, 3H), 4.57-4.10 (m, 2H), 4.02-3.53 (m, 2H), 3.37 (br d, 2H), 3.29 (s, 6H), 3.21-3.11 (m, 1H), 2.61-1.95 (m, 5H), 1.57-1.38 (m, 2H), 1.34 (br t, 3H).

Synthesis of N-(2-chloro-4-(trifluoromethyl)phenyl)-2-(2-(cyclobutylidenemethyl)-6-ethyl-7-(4-(5-hydroxy-6-methylpyrimidine-4-carbonyl)piperazin-1-yl)-8-oxopyrido[2,3-b]pyrazin-5 (8H)-yl) acetamide (I-38)

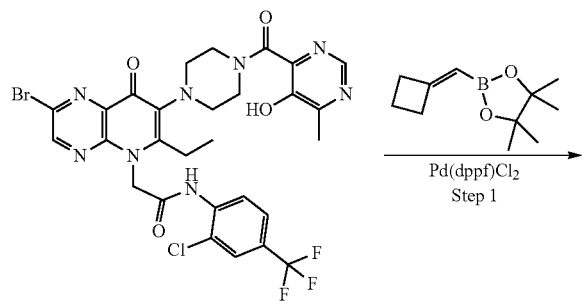

Intermediate-21

Step 1. Synthesis of N-(2-chloro-4-(trifluoromethyl) phenyl)-2-(2-(cyclobutylidenemethyl)-6-ethyl-7-(4-(5-hydroxy-6-methylpyrimidine-4-carbonyl)piperazin-1-yl)-8-oxopyrido[2,3-b]pyrazin-5 (8H)-yl) acetamide To a solution of 2-(2-bromo-6-ethyl-7-(4-(5-hydroxy-6-methylpyrimidine-4-carbonyl)piperazin-1-yl)-8-oxopyrido[2,3-b]pyrazin-5 (8H)-yl)-N-(2-chloro-4-(trifluoromethyl)phenyl)acetamide (Intermediate-21) (30 mg, 42 mol, 1.0 eq) and 2-(cyclobutylidenemethyl)-4,4,5,5-tetramethyl-1,3,2-dioxaborolane (8 mg, 42 mol, 1.0 eq) in 1,4-dioxane (0.5 mL) and H₂O (0.1 mL) was added Pd(dppf)Cl₂ (3 mg, 4 mol, 0.1 eq) and K₃PO₄ (18 mg, 85 mol, 2.0 eq). The resulting mixture was stirred at 80° C. for 1 h and then concentrated in vacuo. The residue was purified by reverse phase HPLC (C18 column, water (0.1% FA)-ACN) to afford the title compound.

LCMS: 697.2 [M+H]⁺.

¹H NMR (400 MHz, CDCl₃) δ ppm 8.70 (br s, 1H), 8.58 (s, 1H), 8.55-8.49 (m, 2H), 7.63 (d, 1H), 7.54 (br d, 1H), 6.47 (br s, 1H), 5.64-5.51 (m, 1H), 5.34 (br s, 2H), 4.86-4.72 (m, 1H), 4.11-3.96 (m, 2H), 3.60-3.44 (m, 1H), 3.38-3.20 (m, 4H), 3.17-3.05 (m, 1H), 2.98 (br t, 2H), 2.89-2.71 (m, 2H), 2.57 (s, 3H), 2.18 (q, 2H), 1.36 (br t, 3H).

Chiral separation of rac-N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetamide (Racemic Mixture, Trans, I-34) to Yield First and Second Eluting; Stereoisomer 1 and Stereoisomer 2; (I-39 and I-40)

N-(2-chloro-4-(trifluoromethyl)phenyl)-2-(2-(dimethylamino)-6-ethyl-7-(−5-(5-hydroxy-6-methylpyrimidine-4-carbonyl)-2,5-diazabicyclo[4.2.0]octan-2-yl)-8-oxopyrido[2,3-b]pyrazin-5 (8H)-yl) acetamide (Single Stereoisomer, First Eluting Compound as Stereoisomer 1, trans) (I-39); and N-(2-chloro-4-(trifluoromethyl)phenyl)-2-(2-(dimethylamino)-6-ethyl-7-(−5-(5-hydroxy-6-methylpyrimidine-4-carbonyl)-2,5-diazabicyclo[4.2.0]octan-2-yl)-8-oxopyrido[2,3-b]pyrazin-5 (8H)-yl) acetamide (Single Stereoisomer, Second Eluting Compound as Stereoisomer 2, Trans) (I-40)

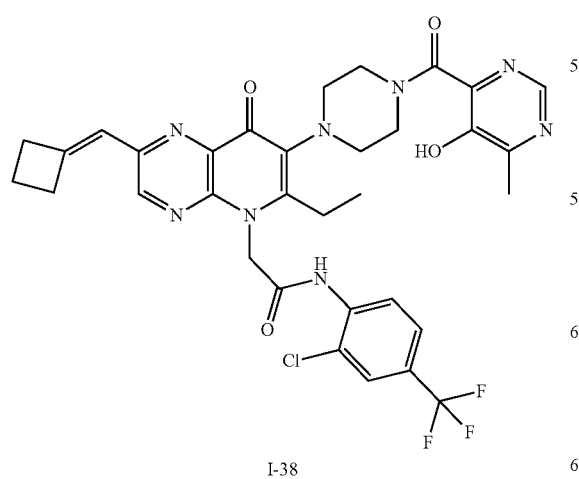

I-38

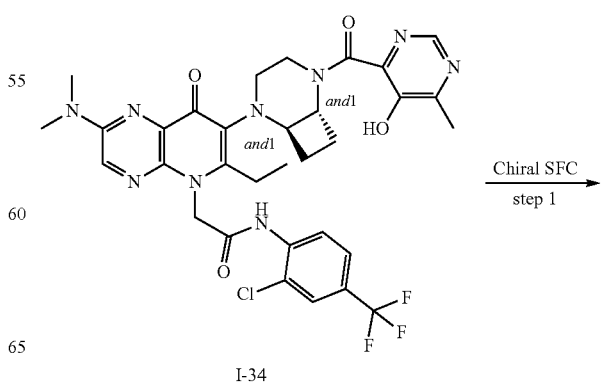

I-34

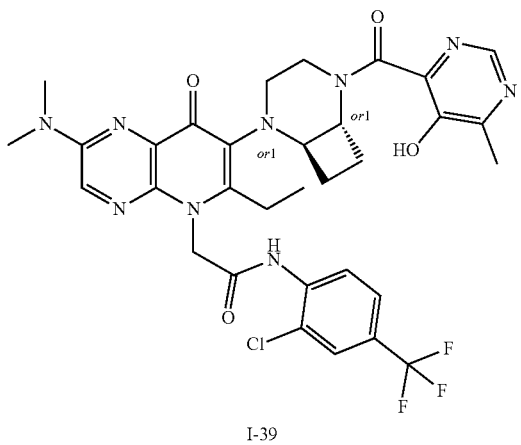

I-39

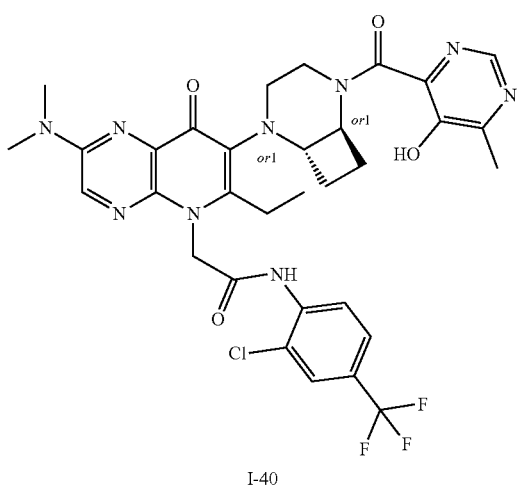

I-40 rac-N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetamide (racemic mixture, trans) was separated by chiral SFC (SFC Preparative Method: Instrument: Waters 80Q Preparative SFC system; Column: Daicel Chiralpak OD column, 250×25 mm I.D., 10 μm particle size; Mobile phase A: $CO_2$, Mobile Phase B: EtOH (0.1% saturated aqueous $NH_3$); Isocratic elution: 35% Phase B in Supercritical $CO_2$; Flow rate: 70 g/min; Retention time: Peak1: 5.40 min, Peak2: 7.86 min; Back Pressure: 100 bar to keep the $CO_2$ in Supercritical flow; Wave Length: 220 nm) to afford the title compounds.

SFC Analytical Method:

| Instrument column | SHIMADZU LC-30ADsf Chiralcel OD-3 50 × 4.6 mm I.D., particle size 3 μm | |
|---|---|---|
| Mobile Phase | Phase A for $CO_2$ | Phase B for EtOH (0.05% diethylamine) |
| Gradient | Time (min) | A(%) | B(%) |
| | 0.01 | 95 | 5 |
| | 1.80 | 60 | 40 |
| | 2.70 | 60 | 40 |
| | 2.71 | 95 | 5 |
| | 3.00 | 95 | 5 |
| Flow rate | | 3.0 mL/min | |
| Column Temp | | 35° C. | |
| Back pressure | | 100 bar | |
| UV | | 220 nm | |

N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetamide, single isomer, first eluting stereoisomer as stereoisomer 1, retention time (SFC analytical method): 2.09 minutes.

LCMS: 700.4 [M+H]$^+$.

$^1$HNMR: (400 MHz, CDCl$_3$) δ ppm 8.61 (br s, 1H), 8.55 (d, 1H), 8.43 (s, 1H), 8.22 (s, 1H), 7.60 (d, 1H), 7.54 (br d, 1H), 5.64-4.97 (m, 3H), 4.52-4.18 (m, 2H), 4.02-3.73 (m, 2H), 3.37 (br d, 2H), 3.29 (s, 6H), 3.23-3.11 (m, 1H), 2.68-1.87 (m, 5H), 1.43 (br d, 2H), 1.34 (t, 3H).

N-(2-chloro-4-(trifluoromethyl)phenyl)-2-(2-(dimethylamino)-6-ethyl-7-(5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetamide, single stereoisomer, second eluting stereoisomer as stereoisomer 2, retention time (SFC analytical method): 2.30 minutes.

LCMS: 700.4 [M+H]$^+$.

$^1$HNMR: (400 MHz, CDCl$_3$) δ ppm 8.60 (br s, 1H), 8.54 (d, 1H), 8.45 (br s, 1H), 8.22 (s, 1H), 7.60 (s, 1H), 7.53 (br d, 1H), 5.58-4.91 (m, 3H), 4.51-4.19 (m, 2H), 4.03-3.64 (m, 2H), 3.37 (br d, 2H), 3.29 (s, 6H), 3.19-3.17 (m, 1H), 2.64-2.58 (m, 1H), 2.55 (s, 3H), 2.33-2.23 (m, 1H), 1.71-1.62 (m, 1H), 1.43-1.37 (m, 1H), 1.34 (t, 3H).

Synthesis of 5-(2-((2-chloro-4-(trifluoromethyl)phenyl)amino)-2-oxoethyl)-6-ethyl-7-(4-(5-hydroxy-6-methylpyrimidine-4-carbonyl)piperazin-1-yl)-N,N-dimethyl-8-oxo-5,8-dihydropyrido[2,3-b]pyrazine-2-carboxamide (I-48)

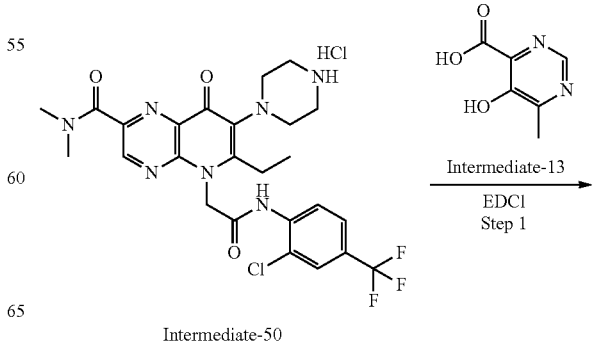

Intermediate-50

Intermediate-13

EDCl
Step 1

209

-continued

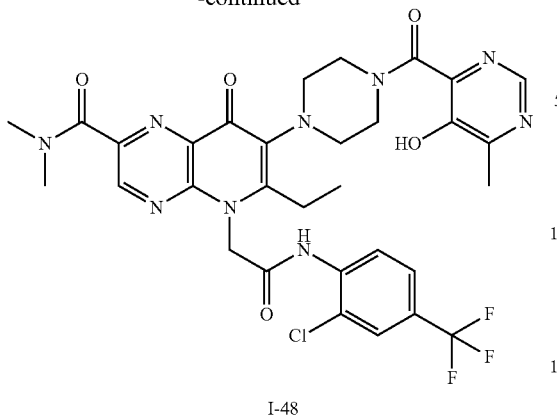

I-48

Step 1. 5-[2-[2-chloro-4-(trifluoromethyl)anilino]-2-oxo-ethyl]-6-ethyl-7-[4-(5-hydroxy-6-methyl-pyrimidine-4-carbonyl)piperazin-1-yl]-N,N-dimethyl-8-oxo-pyrido[2,3-b]pyrazine-2-carboxamide To a solution of 5-hydroxy-6-methylpyrimidine-4-carboxylic acid (Intermediate-13) (22 mg, 0.14 mol, 2.0 eq) in pyridine (1 mL) was added EDCI (27 mg, 0.14 mmol, 2.0 eq) and 5-(2-((2-chloro-4-(trifluoromethyl)phenyl)amino)-2-oxoethyl)-6-ethyl-N,N-dimethyl-8-oxo-7-(piperazin-1-yl)-5,8-dihydropyrido[2,3-b]pyrazine-2-carboxamide hydrochloride (Intermediate-50) (40 mg, 71 mol, 1.0 eq). The mixture was stirred at 40° C. for 1 h and then concentrated in vacuo. The residue was purified by reverse phase HPLC (C18 column, water (0.1% FA)-ACN) to afford the title compound.

LCMS: 702.2 [M+H]$^+$.

$^1$H NMR (400 MHz, CDCl$_3$) δ ppm 9.18 (s, 1H), 8.93-8.65 (m, 1H), 8.58 (s, 1H), 8.45 (br d, 1H), 7.67 (s, 1H), 7.53 (br d, 1H), 5.69-5.51 (m, 1H), 5.50-5.30 (m, 2H), 4.90-4.66 (m, 1H), 3.99 (br t, 2H), 3.59-3.46 (m, 1H), 3.39 (s, 3H), 3.35-3.24 (m, 2H), 3.18 (s, 3H), 3.12-3.03 (m, 1H), 2.95-2.74 (m, 2H), 2.57 (s, 3H), 1.38 (br t, 3H).

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(morpholinomethyl)-8-oxopyrido[2,3-b]pyrazin-5 (8H)-yl)acetamide (I-49)

210

-continued

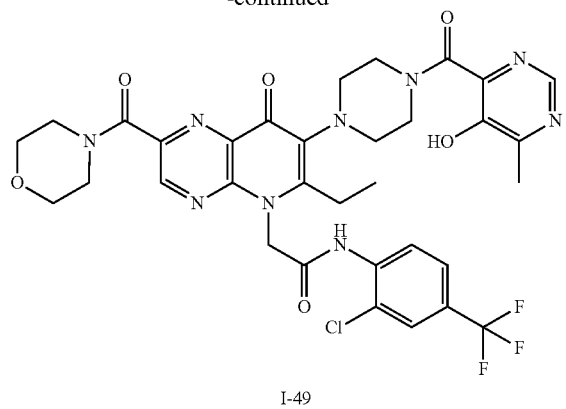

I-49

Step 1. Synthesis of N-(2-chloro-4-(trifluoromethyl)phenyl)-2-(6-ethyl-7-(4-(5-hydroxy-6-methylpyrimidine-4-carbonyl)piperazin-1-yl)-2-(morpholinomethyl)-8-oxopyrido[2,3-b]pyrazin-5 (8H)-yl)acetamide To a solution of 5-hydroxy-6-methylpyrimidine-4-carboxylic acid (Intermediate-13) (31 mg, 0.20 mol, 2.0 eq) in pyridine (1 mL) was added EDCI (39 mg, 0.20 mmol, 2.0 eq) and N-(2-chloro-4-(trifluoromethyl)phenyl)-2-(6-ethyl-2-(morpholinomethyl)-8-oxo-7-(piperazin-1-yl)pyrido[2,3-b]pyrazin-5 (8H)-yl)acetamide hydrochloride (Intermediate-49) (60 mg, 0.10 mol, 1.0 eq). The mixture was stirred at 40° C. for 1 h and then concentrated under reduced pressure. The residue was purified by reverse phase HPLC (C18 column, water (0.1% FA)-ACN) to afford the title compound.

LCMS: 730.2 [M+H]$^+$.

$^1$H NMR (400 MHz, CDCl$_3$) δ ppm 8.87 (s, 1H), 8.84 (br s, 1H), 8.58 (s, 1H), 8.48 (d, 1H), 7.64 (d, 1H), 7.53 (br d, 1H), 5.56 (br d, 1H), 5.42 (br s, 2H), 4.82-4.69 (m, 1H), 4.10-3.94 (m, 2H), 3.90 (s, 2H), 3.77-3.65 (m, 4H), 3.50 (br d, 1H), 3.30 (br d, 2H), 3.09 (br s, 1H), 2.91-2.72 (m, 2H), 2.68-2.44 (m, 7H), 1.36 (t, 3H).

Synthesis of N-(2-chloro-4-(trifluoromethyl)phenyl)-2-(7-ethyl-6-(4-(5-hydroxy-6-methylpyrimidine-4-carbonyl)piperazin-1-yl)-2-methyl-5-oxopyrido[2,3-b]thieno[3,2-e]pyrazin-8 (5H)-yl)acetamide (I-61)

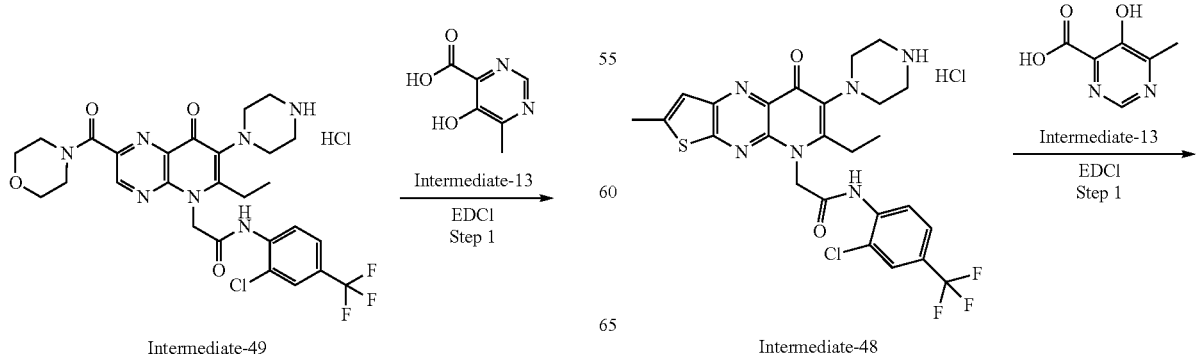

211

-continued

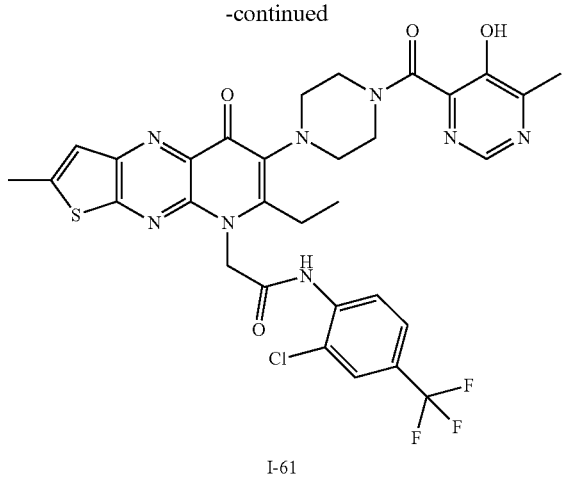

I-61

Step 1. Synthesis of tert-butyl 4-(8-(2-((2-chloro-4-(trifluoromethyl)phenyl)amino)-2-oxoethyl)-7-ethyl-2-methyl-5-oxo-5,8-dihydropyrido[2,3-b]thieno[3,2-e]pyrazin-6-yl)piperazine-1-carboxylate To a solution of N-(2-chloro-4-(trifluoromethyl)phenyl)-2-(7-ethyl-2-methyl-5-oxo-6-(piperazin-1-yl)pyrido[2,3-b]thieno[3,2-e]pyrazin-8 (5H)-yl)acetamide hydrochloride (Intermediate-48) (27 mg, 45 mol, 1 eq) and 5-hydroxy-6-methylpyrimidine-4-carboxylic acid (Intermediate-13) (27 mg, 0.14 mmol, 3 eq) in pyridine (0.5 mL) was added EDCI (26 mg, 0.14 mmol, 3 eq). The mixture was stirred at 60° C. for 1 h. The reaction mixture was concentrated under reduced pressure to give a residue. The residue was purified by Prep-TLC (SiO₂, Eluent of MeOH/DCM) and reversed-phase HPLC (C18 column, water (FA)-ACN) to afford the title compound.

¹H NMR (400 MHz, CD₃OD) δ ppm 8.57 (s, 1H), 8.09 (d, 1H), 7.83 (s, 1H), 7.61 (d, 1H), 7.39-7.31 (m, 1H), 5.68 (s, 2H), 4.82-4.68 (m, 2H), 4.64-4.57 (m, 1H), 4.19-4.07 (m, 1H), 3.97 (q, 2H), 3.54-3.42 (m, 1H), 3.23-3.12 (m, 1H), 3.01-2.89 (m, 1H), 2.86-2.77 (m, 1H), 2.74 (s, 3H), 2.55 (s, 3H), 1.40 (t, 3H).

LCMS: 701.2 [M+H]⁺.

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-methyl-8-oxopyrido[2,3-b]thiazolo[4,5-e]pyrazin-5 (8H)-yl) acetamide (I-95)

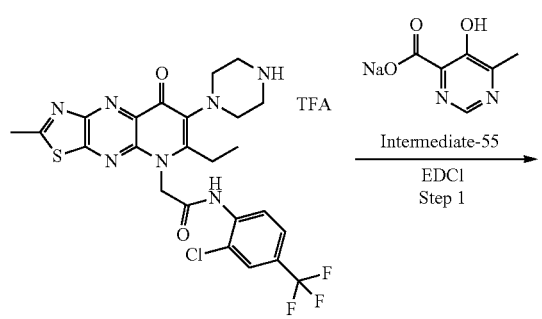

212

-continued

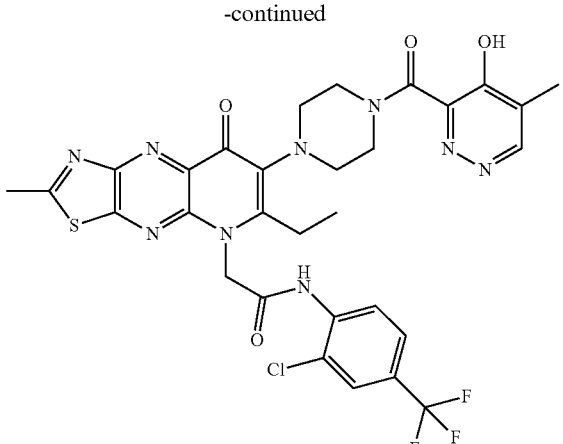

I-95

Step 15. Synthesis of N-(2-chloro-4-(trifluoromethyl)phenyl)-2-(6-ethyl-7-(4-(5-hydroxy-6-methylpyrimidine-4-carbonyl)piperazin-1-yl)-2-methyl-8-oxopyrido[2,3-b]thiazolo[4,5-e]pyrazin-5 (8H)-yl) acetamide To a solution of N-(2-chloro-4-(trifluoromethyl)phenyl)-2-(6-ethyl-2-methyl-8-oxo-7-(piperazin-1-yl)pyrido[2,3-b]thiazolo[4,5-e]pyrazin-5 (8H)-yl)acetamide trifluoroacetate (Intermediate-54) (21 mg, 31 mol, 1 eq) and sodium 5-hydroxy-6-methylpyrimidine-4-carboxylate (Intermediate-55) (25 mg, 0.13 mmol, 4 eq) in pyridine (1 mL) EDCI (24 mg, 0.13 mmol, 4 eq) was added and the mixture was stirred at 25° C. for 14 h. Then sodium 5-hydroxy-6-methylpyrimidine-4-carboxylate (6 mg, 31 mol, 1 eq) and EDCI (6 mg, 31 mol, 1 eq) were added at 60° C. and the reaction mixture was stirred for 1 h at 60° C. The addition of sodium 5-hydroxy-6-methylpyrimidine-4-carboxylate (6 mg, 31 mol, 1 eq) and EDCI (6 mg, 31 mol, 1 eq) followed by stirring for 1 h at 60° C. was repeated five times. The reaction mixture was concentrated to give a residue. The residue was purified by Prep-TLC (SiO₂, Eluent of MeOH/DCM) to afford the title compound.

¹H NMR (400 MHz, CD₃OD) δ ppm 8.54 (s, 1H), 8.07 (d, 1H), 7.80 (d, 1H), 7.58 (m, 1H), 5.69 (s, 2H), 4.12-4.09 (m, 1H), 3.96-3.90 (m, 2H), 3.54-3.40 (m, 1H), 3.36-3.32 (m, 2H), 3.21-3.11 (m, 1H), 3.01-2.85 (m, 5H), 2.82-2.73 (m, 1H), 2.52 (s, 3H), 1.38 (t, 3H).

LCMS: 702.3 [M+H]⁺.

Synthesis of N-(2-chloro-4-(trifluoromethyl)phenyl)-2-(6-(dimethylamino)-2-ethyl-7-fluoro-3-(4-(5-hydroxy-6-methylpyrimidine-4-carbonyl)piperazin-1-yl)-4-oxo-1,5-naphthyridin-1 (4H)-yl)acetamide (I-109)

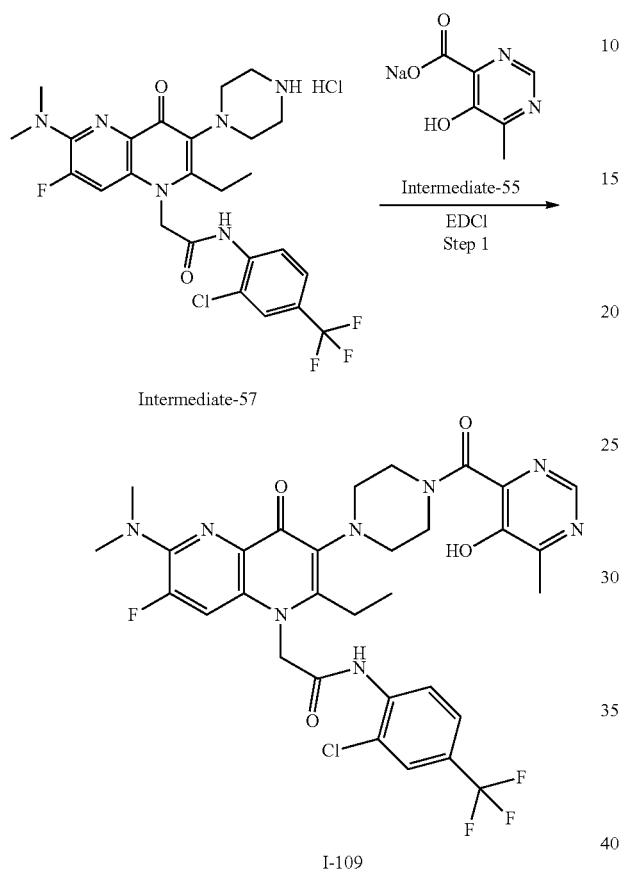

Synthesis of 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(3-(trifluoromethyl)bicyclo[1.1.1]pentan-1-yl)acetamide (I-110)

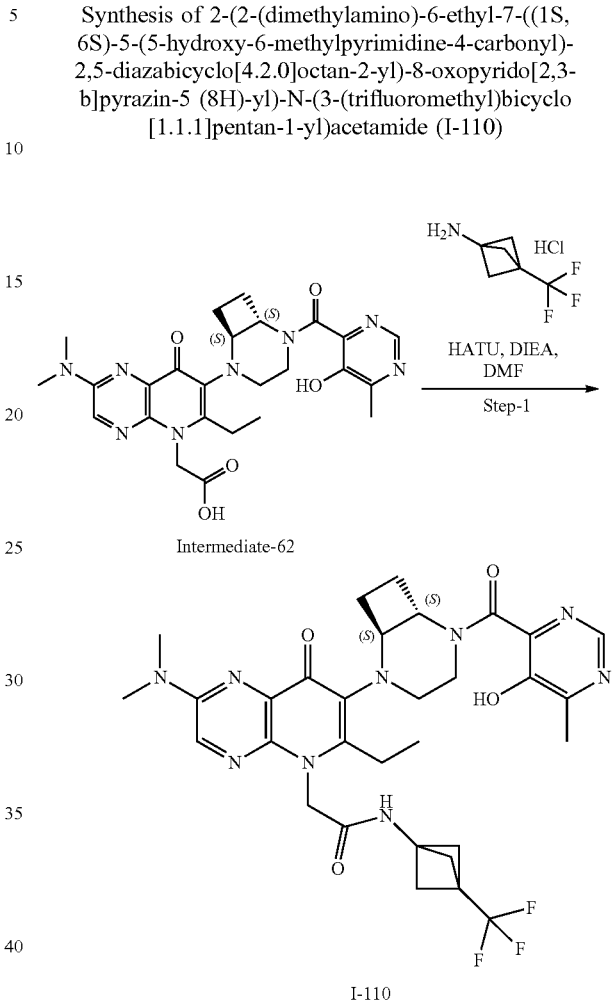

Step 1. Synthesis of N-(2-chloro-4-(trifluoromethyl)phenyl)-2-(6-(dimethylamino)-2-ethyl-7-fluoro-3-(4-(5-hydroxy-6-methylpyrimidine-4-carbonyl) piperazin-1-yl)-4-oxo-1,5-naphthyridin-1 (4H)-yl) acetamide To a solution of N-[2-chloro-4-(trifluoromethyl)phenyl]-2-[6-(dimethylamino)-2-ethyl-7-fluoro-4-oxo-3-piperazin-1-yl-1,5-naphthyridin-1-yl]acetamide hydrochloride (Intermediate-57) (14 mg, 23 mol, 1 eq) and sodium 5-hydroxy-6-methylpyrimidine-4-carboxylate (Intermediate-55) (23 mg, 118 mol, 5 eq) in pyridine (0.4 mL) was added EDCI (18 mg, 95 mol, 4 eq). The mixture was stirred at 20° C. for 2 h. To the reaction mixture was added brine (15 mL) and the mixture was extracted with EtOAc (10 mL*3). The combined organic layers were dried over anhydrous Na$_2$SO$_4$, filtered and concentrated under reduced pressure to give a residue. The residue was purified by Prep-TLC (SiO$_2$, DCM: MeOH) to afford the title compound.
$^1$H NMR (400 MHz, CDCl$_3$) δ ppm 12.30-11.04 (m, 1H), 9.02 (br s, 1H), 8.56 (s, 1H), 8.44 (d, 1H), 7.60 (s, 1H), 7.53 (d, 1H), 7.34 (d, 1H), 5.63-5.40 (m, 1H), 5.09 (s, 2H), 4.90-4.63 (m, 1H), 4.60-4.29 (m, 1H), 4.07 (q, 2H), 3.49 (s, 1H), 3.26-3.00 (m, 7H), 2.90-2.67 (m, 2H), 2.55 (s, 3H), 2.10-1.97 (m, 1H), 1.27 (t, 3H).
LCMS: 691.3 [M+H]$^+$.

Step 1. Synthesis of 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(3-(trifluoromethyl)bicyclo[1.1.1]pentan-1-yl)acetamide To a solution of 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetic acid (Intermediate-62) (17 mg, 33 mol, 1.0 eq) and 3-(trifluoromethyl)bicyclo[1.1.1]pentan-1-amine hydrochloride (12 mg, 65 mol, 2.0 eq) in DMF (1 mL) was added HATU (25 mg, 65 mol, 2.0 eq) and DIEA (13 mg, 98 mol, 3.0 eq), and the resulting mixture was stirred at room temperature for 1 h. The reaction mixture was diluted with H$_2$O (10 mL) and extracted with EtOAc (5 mL*3). The combined organic layers were washed with brine (5 mL), dried over anhydrous Na$_2$SO$_4$, filtered and the filtrate was concentrated under reduced pressure. The residue was purified by reverse phase HPLC (C18 column, water (0.1% FA)-ACN) to afford the title compound.
LCMS: 656.5 [M+H]$^+$.

¹H NMR (400 MHz, CDCl₃) δ ppm 12.60 (s, 1H), 8.74-8.49 (m, 1H), 8.32 (br s, 1H), 6.90-6.43 (m, 1H), 5.75-4.79 (m, 3H), 4.39-4.08 (m, 2H), 4.00-3.51 (m, 2H), 3.40 (br s, 1H), 3.31 (s, 6H), 3.28-3.22 (m, 1H), 3.13 (br s, 1H), 2.55 (s, 3H), 2.29 (s, 8H), 1.56-1.36 (m, 2H), 1.30 (br t, 3H).

Synthesis of 2-(2-(bis(methyl-d3)amino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-chloro-4-(trifluoromethyl)phenyl)acetamide (I-101)

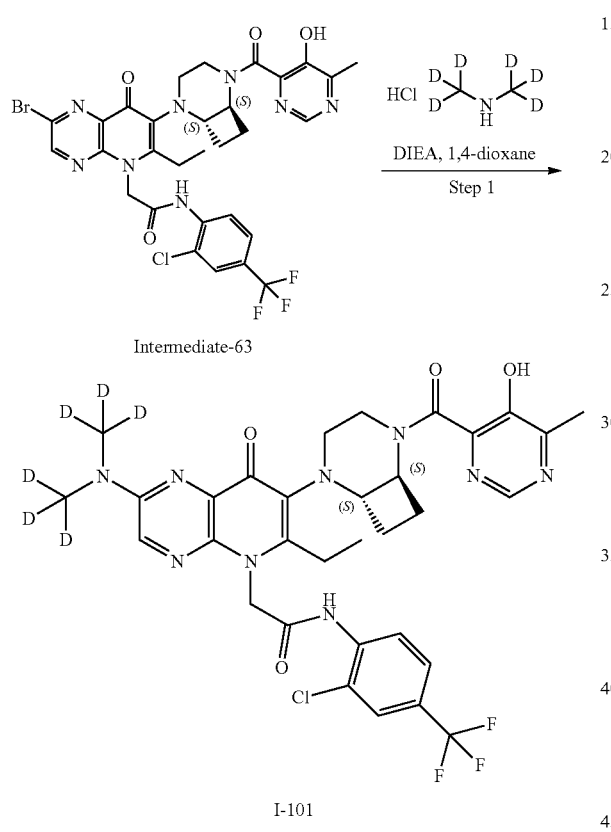

I-101

Step 1. Synthesis of 2-(2-(bis(methyl-d3)amino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-chloro-4-(trifluoromethyl)phenyl)acetamide To a solution of 2-(2-bromo-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-chloro-4-(trifluoromethyl)phenyl)acetamide (Intermediate-63) (40 mg, 54 mol, 1.0 eq) in 1,4-dioxane (1 mL) was added DIEA (42 mg, 326 mol, 6.0 eq) and bis(methyl-d3)amine hydrochloride (24 mg, 272 mol, 5.0 eq). The resulting mixture was stirred at 100° C. for 1 h and then concentrated under reduced pressure. The residue was purified by reverse phase HPLC (C18 column, water (0.1% FA)-ACN) to afford the title compound.

LCMS: 706.3 [M+H]⁺.

¹H NMR (400 MHz, CDCl₃) δ 12.68 (s, 1H), 8.61 (br s, 1H), 8.55 (d, 1H), 8.41 (s, 1H), 8.21 (s, 1H), 7.60 (s, 1H), 7.54 (d, 1H), 5.80-4.89 (m, 3H), 4.54-4.14 (m, 2H), 4.06-3.56 (m, 2H), 3.47-3.27 (m, 2H), 3.25-3.00 (m, 1H), 2.61-1.94 (m, 5H), 1.50-1.39 (m, 2H), 1.34 (t, 3H).

Synthesis of N-(2-chloro-4-(trifluoromethyl)phenyl)-2-(7-ethyl-6-((1S,6S)-5-(5-hydroxy-6-methylpyrimidine-4-carbonyl)-2,5-diazabicyclo[4.2.0]octan-2-yl)-3-(2-methylprop-1-en-1-yl)-5-oxopyrido[3,2-e][1,2,4]triazin-8 (5H)-yl)acetamide (I-111)

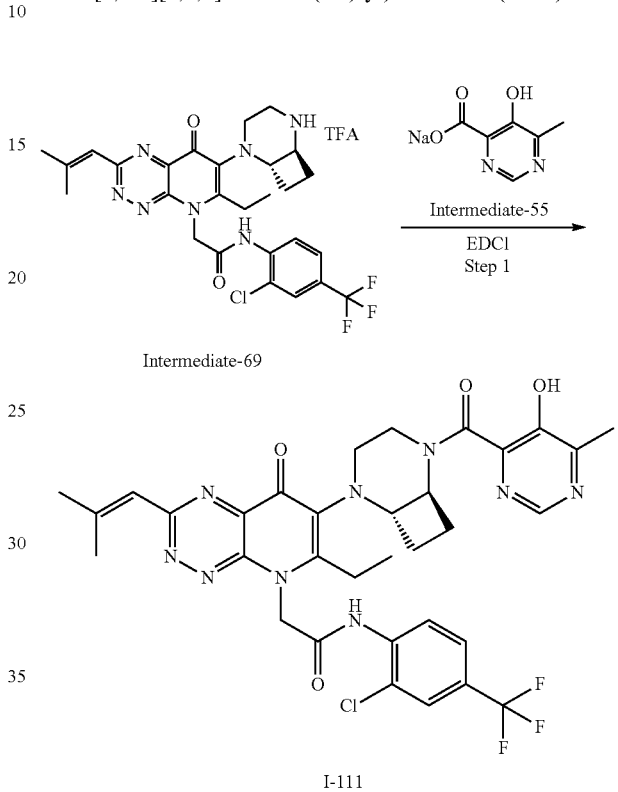

I-111

Step 1: Synthesis of N-(2-chloro-4-(trifluoromethyl)phenyl)-2-(7-ethyl-6-((1S,6S)-5-(5-hydroxy-6-methylpyrimidine-4-carbonyl)-2,5-diazabicyclo[4.2.0]octan-2-yl)-3-(2-methylprop-1-en-1-yl)-5-oxopyrido[3,2-e][1,2,4]triazin-8 (5H)-yl)acetamide To a solution of 2-(6-((1S,6S)-2,5-diazabicyclo[4.2.0]octan-2-yl)-7-ethyl-3-(2-methylprop-1-en-1-yl)-5-oxopyrido[3,2-e][1,2,4]triazin-8 (5H)-yl)-N-(2-chloro-4-(trifluoromethyl)phenyl)acetamide trifluoroacetate (Intermediate-69) (170 mg, 295 mol, 1.0 eq) and sodium 5-hydroxy-6-methylpyrimidine-4-carboxylate (Intermediate-55) (91 mg, 590 mol, 2.0 eq) in pyridine (2 mL) was added EDCI (141 mg, 738 mol, 2.5 eq), and it was stirred at room temperature overnight. The reaction mixture was diluted with saturated NH₄Cl aqueous solution (10 mL), and then extracted with EtOAc (5 mL*3). The combined organic layers were washed with brine (5 mL), dried over anhydrous Na₂SO₄, filtered and concentrated in vacuo. The residue was purified by reverse phase HPLC (C18 column, water (0.1% FA)-ACN) to afford the title compound.

LCMS: 712.2 [M+H]⁺.

¹H NMR (400 MHz, CDCl₃) δ ppm 12.48 (m, 1H), 8.74 (s, 1H), 8.53 (s, 1H), 8.34 (d, 1H), 7.56 (s, 1H), 7.42 (d, 1H), 6.73 (s, 1H), 5.58 (s, 2H), 4.80 (d, 1H), 4.15 (s, 2H), 3.96-3.45 (m, 2H), 3.41-3.01 (m, 3H), 2.47 (s, 3H), 2.37-2.16 (m, 4H), 2.03 (s, 3H), 1.97-1.72 (m, 2H), 1.39 (s, 1H), 1.31 (t, 3H).

Synthesis of N-(2-chloro-4-(trifluoromethyl)phenyl)-2-(7-ethyl-6-(4-(5-hydroxy-6-methylpyrimidine-4-carbonyl)piperazin-1-yl)-2-methyl-5-oxofuro[2,3-b]pyrido[3,2-e]pyrazin-8 (5H)-yl)acetamide (I-112)

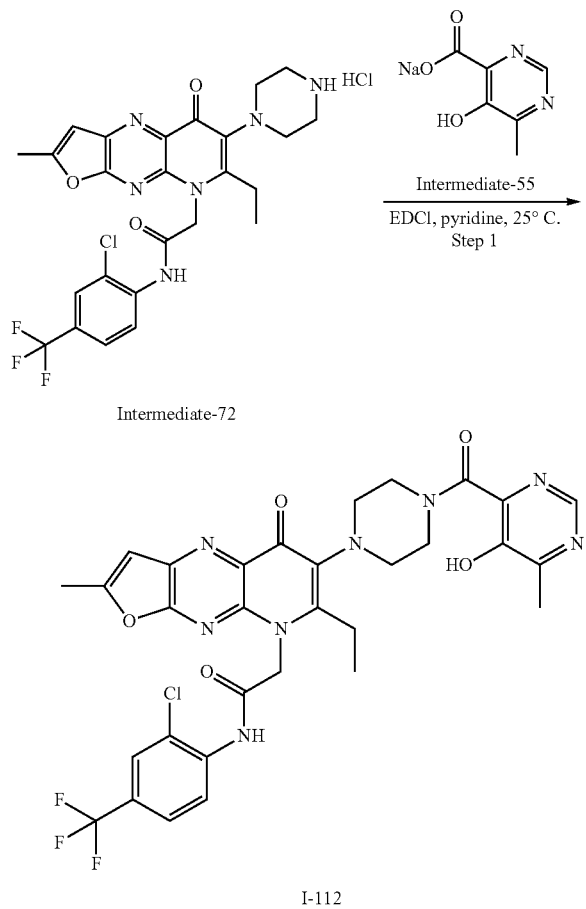

Intermediate-72

I-112

Step 1. Synthesis of N-(2-chloro-4-(trifluoromethyl)phenyl)-2-(7-ethyl-6-(4-(5-hydroxy-6-methylpyrimidine-4-carbonyl)piperazin-1-yl)-2-methyl-5-oxofuro[2,3-b]pyrido[3,2-e]pyrazin-8 (5H)-yl)acetamide To a solution of N-(2-chloro-4-(trifluoromethyl)phenyl)-2-(7-ethyl-2-methyl-5-oxo-6-(piperazin-1-yl)furo[2,3-b]pyrido[3,2-e]pyrazin-8 (5H)-yl)acetamide hydrochloride (Intermediate-72) (80 mg, 137 mol, 1 eq) in pyridine (2 mL) was added EDCI (131 mg, 685 mol, 5 eq) and sodium 5-hydroxy-6-methylpyrimidine-4-carboxylate (Intermediate-55) (120 mg, 685 mol, 5 eq). The mixture was stirred at 25° C. for 12 h. The mixture was poured into H$_2$O (20 mL) and extracted with DCM (10 mL*3). The combined organic layer was concentrated in vacuum to give a residue. The residue was purified by reverse Phase HPLC (C18 column, water (10 mmol/L FA)-ACN) to afford the title compound.

$^1$H NMR (400 MHz, CD$_3$OD) δ ppm 8.55 (s, 1H), 8.11 (d, 1H), 7.81 (d, 1H), 7.58 (d, 1H), 6.87 (s, 1H), 5.64 (s, 2H), 4.71-4.68 (m, 1H), 4.18-4.05 (m, 1H), 3.95-3.93 (m, 2H), 3.53-3.40 (m, 1H), 3.30-3.29 (m, 2H), 3.21-3.09 (m, 1H), 3.00-2.87 (m, 1H), 2.82-2.73 (m, 1H), 2.61 (s, 3H), 2.52 (s, 3H), 1.37 (t, 3H).

LCMS: 685.3 [M+H]$^+$.

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-methyl-8-oxopyrido[2,3-b]thieno[2,3-e]pyrazin-5 (8H)-yl)acetamide (I-113)

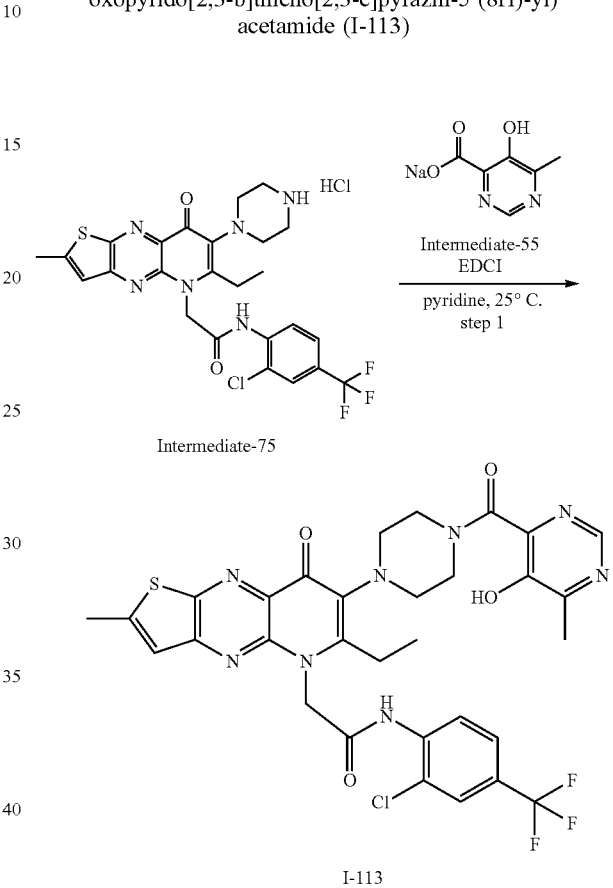

Intermediate-75

I-113

Step 1. Synthesis of N-(2-chloro-4-(trifluoromethyl)phenyl)-2-(6-ethyl-7-(4-(5-hydroxy-6-methylpyrimidine-4-carbonyl)piperazin-1-yl)-2-methyl-8-oxopyrido[2,3-b]thieno[2,3-e]pyrazin-5 (8H)-yl)acetamide To a solution of N-(2-chloro-4-(trifluoromethyl)phenyl)-2-(6-ethyl-2-methyl-8-oxo-7-(piperazin-1-yl)pyrido[2,3-b]thieno[2,3-e]pyrazin-5 (8H)-yl)acetamide hydrochloride (Intermediate-75) (22 mg, 37 mol, 1 eq) and sodium 5-hydroxy-6-methylpyrimidine-4-carboxylate (Intermediate-55) (26 mg, 148 mol, 4 eq) in pyridine (0.5 mL) was added EDCI (25 mg, 129 mol, 3.5 eq). The mixture was stirred at 25° C. for 1 h. The reaction mixture was diluted with H$_2$O (5 mL) and was extracted with DCM (5 mL*2). The combined organic phase was washed with brine (5 mL), dried over anhydrous Na$_2$SO$_4$, filtered and concentrated in vacuum to give a residue. The residue was purified by prep-TLC (SiO$_2$, Eluent: EtOAc) to afford the title compound.

$^1$H NMR (400 MHz, CDCl$_3$) δ ppm 8.73 (s, 1H), 8.60 (s, 1H), 8.52 (d, 1H), 7.61 (s, 1H), 7.54 (d, 1H), 7.18 (s, 1H), 5.60 (s, 1H), 5.42 (s, 2H), 4.82-4.79 (m, 1H), 4.06-4.01 (m, 2H), 3.58-3.50 (m, 1H), 3.36-3.35 (m, 2H), 3.19-3.06 (m, 1H), 2.89-2.80 (m, 3H), 2.77 (s, 3H), 2.58 (s, 3H), 1.39 (t, 3H).

LCMS: 701.3 [M+H]$^+$.

Synthesis of N-(2-chloro-4-(trifluoromethyl)phenyl)-2-(6-ethyl-7-((1S,6S)-5-(5-hydroxy-6-methylpyrimidine-4-carbonyl)-2,5-diazabicyclo[4.2.0]octan-2-yl)-2-methyl-8-oxopyrido[2,3-b]thiazolo[4,5-e]pyrazin-5 (8H)-yl)acetamide (I-114)

$^1$H NMR (400 MHz, CD$_3$OD) δ ppm 8.57 (s, 1H), 8.08 (d, 1H), 7.82 (s, 1H), 7.60 (d, 1H), 5.67 (s, 2H), 4.82-4.69 (m, 1H), 4.22-4.02 (m, 1H), 3.84-3.59 (m, 3H), 3.57-3.34 (m, 3H), 2.98 (s, 3H), 2.52 (s, 3H), 1.83-1.62 (m, 2H), 1.58-1.44 (m, 2H), 1.39 (t, 3H).

LCMS: 728.1 [M+H]$^+$.

Synthesis of 2-(7-ethyl-6-(4-(5-hydroxy-6-methylpyrimidine-4-carbonyl)piperazin-1-yl)-2-methyl-5-oxopyrido[2,3-b]thieno[3,2-e]pyrazin-8 (5H)-yl)-N-(3-(trifluoromethyl)bicyclo[1.1.1]pentan-1-yl)acetamide (I-115)

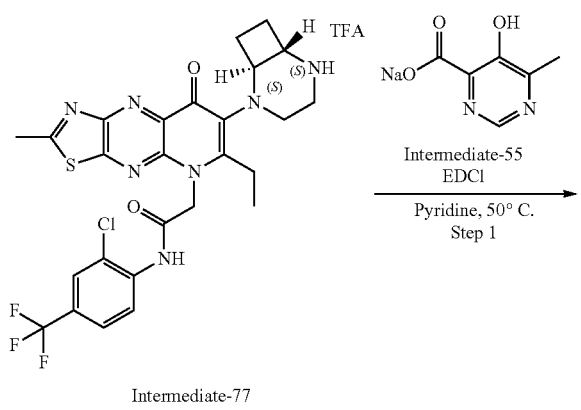

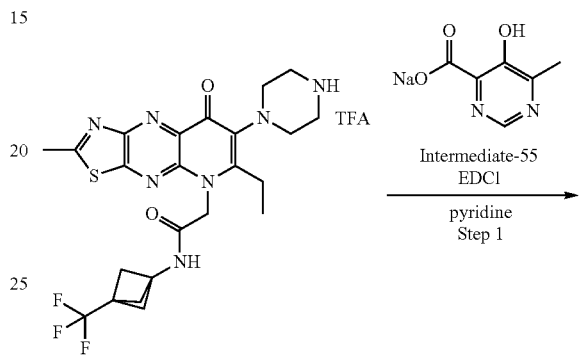

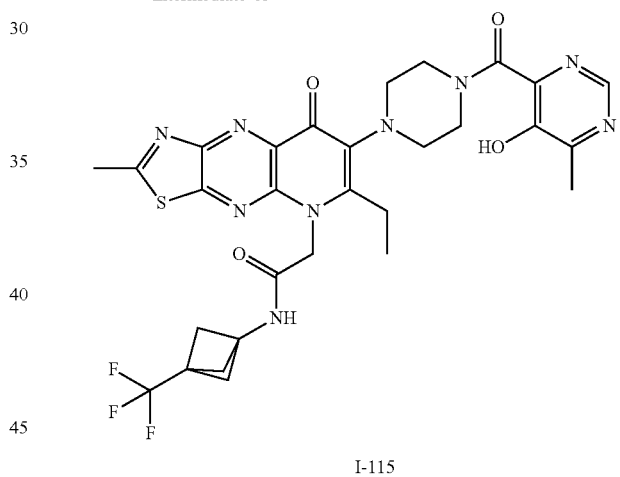

I-115

Step 1. Synthesis of N-(2-chloro-4-(trifluoromethyl)phenyl)-2-(6-ethyl-7-((1S,6S)-5-(5-hydroxy-6-methylpyrimidine-4-carbonyl)-2,5-diazabicyclo[4.2.0]octan-2-yl)-2-methyl-8-oxopyrido[2,3-b]thiazolo[4,5-e]pyrazin-5 (8H)-yl) acetamide To a solution of 2-(7-((1S,6S)-2,5-diazabicyclo[4.2.0]octan-2-yl)-6-ethyl-2-methyl-8-oxopyrido[2,3-b]thiazolo[4,5-e]pyrazin-5 (8H)-yl)-N-(2-chloro-4-(trifluoromethyl)phenyl)acetamide trifluoroacetate (Intermediate-77) (80 mg, 113 mol, 1 eq) in pyridine (2 mL) was added and sodium 5-hydroxy-6-methylpyrimidine-4-carboxylate (Intermediate-55) (112 mg, 662 mol, 5.5 eq) and EDCI (109 mg, 565 mol, 5 eq). The mixture was stirred at 50° C. for 12 hr. The mixture was concentrated in vacuum to give a residue. The residue was purified by reverse Phase HPLC (C18 column, water (10 mmol/L FA)-ACN) to afford the title compound.

Step 1. Synthesis of 2-(7-ethyl-6-(4-(5-hydroxy-6-methylpyrimidine-4-carbonyl)piperazin-1-yl)-2-methyl-5-oxopyrido[2,3-b]thieno[3,2-e]pyrazin-8 (5H)-yl)-N-(3-(trifluoromethyl)bicyclo[1.1.1]pentan-1-yl)acetamide To a solution of 2-(7-ethyl-2-methyl-5-oxo-6-(piperazin-1-yl)pyrido[2,3-b]thieno[3,2-e]pyrazin-8 (5H)-yl)-N-(3-(trifluoromethyl)bicyclo[1.1.1]pentan-1-yl)acetamide trifluoroacetate (Intermediate-83) (120 mg, 189 mol, 1 eq) and sodium 5-hydroxy-6-methylpyrimidine-4-carboxylate (Intermediate-55) (155 mg, 880 mol, 4.6 eq) in pyridine (3 mL) was added EDCI (181 mg, 946 mol, 5 eq). The mixture was stirred at 60° C. for 6 h. The mixture was concentrated in vacuum directly to give a residue. The residue was purified by silica gel chromatography (Eluent of EtOAc/PE) and reverse Phase HPLC (C18 column, water (10 mmol/L FA)-ACN) to afford the title compound.

$^1$H NMR (400 MHz, CD$_3$OD) δ ppm 8.57 (s, 1H), 7.36 (s, 1H), 5.32 (s, 2H), 4.76-4.65 (m, 1H), 4.19-3.88 (m, 3H), 3.53-3.39 (m, 1H), 3.23 (q, 2H), 3.19-3.11 (m, 1H), 2.96-2.85 (m, 1H), 2.78-2.74 (m, 4H), 2.53 (s, 3H), 2.29 (s, 6H), 1.33 (t, 3H).

LCMS: 657.3 [M+H]$^+$.

Synthesis of N-(2-chloro-4-(trifluoromethyl)phenyl)-2-(6-ethyl-7-(4-(5-hydroxy-6-methylpyrimidine-4-carbonyl)piperazin-1-yl)-1-methyl-8-oxo-1,2,3,8-tetrahydro-5H-pyrido[2,3-b]pyrrolo[2,3-e]pyrazin-5-yl)acetamide (I-116)

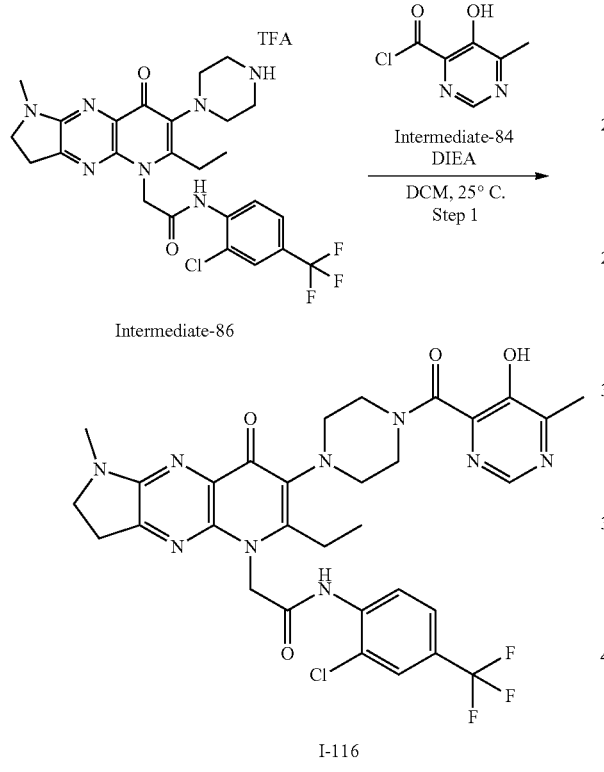

Step 1: Synthesis of N-[2-chloro-4-(trifluoromethyl)phenyl]-2-[11-ethyl-12-[4-(5-hydroxy-6-methyl-pyrimidine-4-carbonyl)piperazin-1-yl]-4-methyl-13-oxo-2,4,8,10-tetrazatricyclo[7.4.0.03,7]trideca-1 (9),2,7,11-tetraen-10-yl]acetamide To a solution of N-[2-chloro-4-(trifluoromethyl)phenyl]-2-(11-ethyl-4-methyl-13-oxo-12-piperazin-1-yl-2,4,8,10-tetrazatricyclo[7.4.0.03,7]trideca-1 (9),2,7,11-tetraen-10-yl) acetamide trifluoroacetate (Intermediate-86) (8 mg, 15 mol, 1.0 eq) in DCM (2 mL) was added DIEA (8 mg, 58 mol, 4.0 eq) and 5-hydroxy-6-methyl-pyrimidine-4-carbonyl chloride (Intermediate-84) (12 mg, 73 mol, 5.0 eq). And the resulting mixture was stirred at room temperature for 10 min. The reaction mixture was diluted with H$_2$O (10 mL), extracted with DCM (10 mL*2). The organic phase was washed with brine (10 mL), dried over anhydrous Na$_2$SO$_4$, filtered and concentrated under reduced pressure to give a residue. The residue was purified by reverse phase HPLC (C18 column, water (0.1% FA)-ACN) to afford the title compound.

$^1$H NMR (400 MHz, CDCl$_3$) δ ppm 11.79 (s, 1H), 8.58 (s, 1H), 8.54 (d, 1H), 8.29 (s, 1H), 7.61 (s, 1H), 7.55 (d, 1H), 5.50 (s, 1H), 5.29 (s, 2H), 4.76 (d, 1H), 4.13-4.00 (m, 2H), 3.74 (t, 2H), 3.50 (s, 1H), 3.23 (t, 4H), 3.15 (s, 3H), 3.08 (s, 1H), 2.87-2.67 (m, 2H), 2.57 (s, 3H), 1.32 (t, 3H).

LCMS: 686.5[M+H]$^+$.

Synthesis of (S)—N-(2-chloro-4-(trifluoromethyl)phenyl)-2-(2-(dimethylamino)-6-ethyl-7-(4-(5-hydroxy-6-methylpyrimidine-4-carbonyl)-2-methylpiperazin-1-yl)-8-oxopyrido[2,3-b]pyrazin-5 (8H)-yl)acetamide (I-98) and (R)—N-(2-chloro-4-(trifluoromethyl)phenyl)-2-(2-(dimethylamino)-6-ethyl-7-(4-(5-hydroxy-6-methylpyrimidine-4-carbonyl)-2-methylpiperazin-1-yl)-8-oxopyrido[2,3-b]pyrazin-5 (8H)-yl)acetamide (I-99)

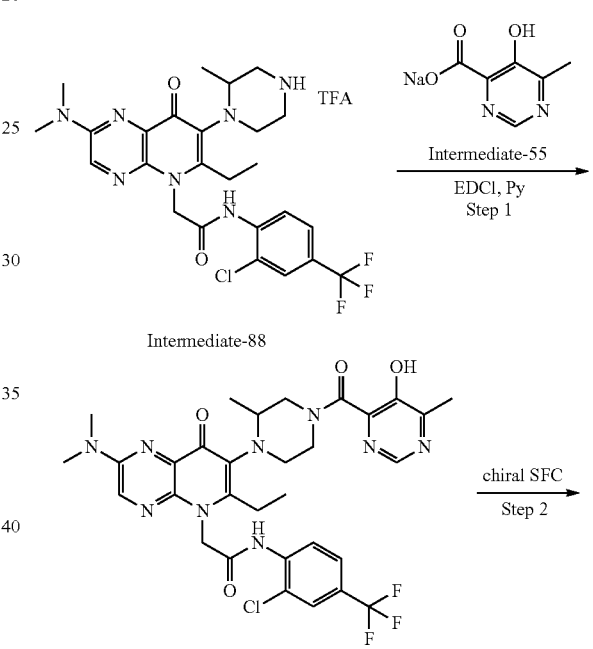

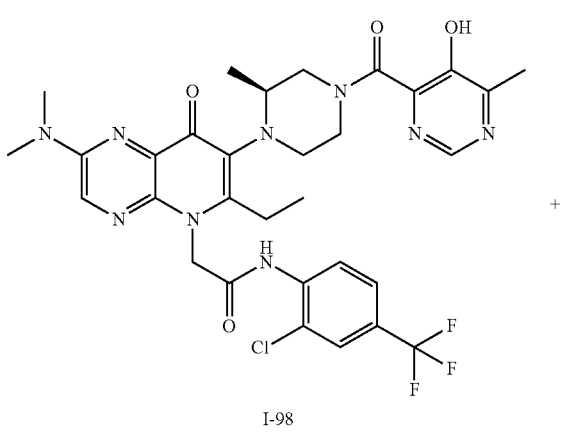

I-98
First eluting compound

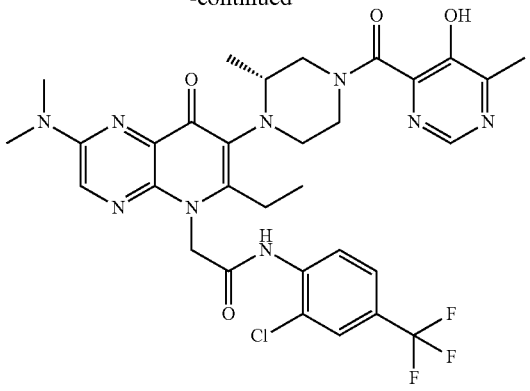

I-99

Second eluting compound

Step 1. Synthesis of N-(2-chloro-4-(trifluoromethyl)phenyl)-2-(2-(dimethylamino)-6-ethyl-7-(4-(5-hydroxy-6-methylpyrimidine-4-carbonyl)-2-methylpiperazin-1-yl)-8-oxopyrido[2,3-b]pyrazin-5 (8H)-yl) acetamide To a solution of N-(2-chloro-4-(trifluoromethyl)phenyl)-2-(2-(dimethylamino)-6-ethyl-7-(2-methylpiperazin-1-yl)-8-oxopyrido[2,3-b]pyrazin-5 (8H)-yl)acetamide (Intermediate-88) (175 mg, 317 mol, 1.0 eq) in pyridine (3 mL) was added EDCI (365 mg, 1.90 mmol, 6.0 eq) and sodium 5-hydroxy-6-methylpyrimidine-4-carboxylate (Intermediate-55) (279 mg, 1.59 mmol, 5.0 eq), and the resulting mixture was stirred at 40° C. overnight. The reaction mixture was concentrated under reduced pressure and then purified by reverse phase HPLC (water (0.1% FA-ACN) to afford the title compound.

Step 2. Synthesis of (S)—N-(2-chloro-4-(trifluoromethyl)phenyl)-2-(2-(dimethylamino)-6-ethyl-7-(4-(5-hydroxy-6-methylpyrimidine-4-carbonyl)-2-methylpiperazin-1-yl)-8-oxopyrido[2,3-b]pyrazin-5 (8H)-yl) acetamide (single stereoisomer, first eluting compound) and (R)—N-(2-chloro-4-(trifluoromethyl)phenyl)-2-(2-(dimethylamino)-6-ethyl-7-(4-(5-hydroxy-6-methylpyrimidine-4-carbonyl)-2-methylpiperazin-1-yl)-8-oxopyrido[2,3-b]pyrazin-5 (8H)-yl) acetamide (Single Stereoisomer, Second Eluting Compound)

N-(2-chloro-4-(trifluoromethyl)phenyl)-2-(2-(dimethylamino)-6-ethyl-7-(4-(5-hydroxy-6-methylpyrimidine-4-carbonyl)-2-methylpiperazin-1-yl)-8-oxopyrido[2,3-b]pyrazin-5 (8H)-yl)acetamide was separated by chiral SFC (SFC Preparative Method: Instrument: Waters 80Q Preparative SFC system; Column: DAICEL CHIRALCEL OX, 250×30 mm I.D., 10 um particle size; Mobile phase A: $CO_2$, Mobile Phase B: MeOH/ACN=7/3=100% (0.1% $NH_3$—$H_2O$); Isocratic elution: 50% Phase B in Supercritical $CO_2$; Flow rate: 80 g/min; Retention Time: Peak1: 3.23 min, Peak2: 4.59 min; Back Pressure: 100 bar to keep the $CO_2$ in Supercritical flow; Wave Length: 220 nm) to afford the title compounds.

I-98

LCMS: 688.2 [M+H]$^+$.

$^1$H NMR (400 MHz, $CDCl_3$) δ 8.58 (br s, 1H), 8.54 (d, 1H), 8.45 (br s, 1H), 8.20 (s, 1H), 7.60 (s, 1H), 7.53 (br d, 1H), 5.61-5.29 (m, 2H), 5.29-5.05 (m, 1H), 4.83-4.63 (m, 1H), 4.25-4.10 (m, 1H), 3.94 (dt, 1H), 3.60-3.50 (m, 1H), 3.26 (s, 6H), 3.07 (br dd, 2H), 2.92-2.60 (m, 2H), 2.56 (s, 3H), 1.33 (br t, 3H), 1.01-0.79 (m, 3H).

Analytical Chiral SFC Retention time: 0.919 min.

I-99

LCMS: 688.2 [M+H]$^+$.

$^1$H NMR (400 MHz, $CDCl_3$) δ 8.58 (br s, 1H), 8.54 (d, 1H), 8.42 (s, 1H), 8.20 (s, 1H), 7.60 (s, 1H), 7.53 (d, 1H), 5.62-5.33 (m, 2H), 5.30-5.11 (m, 1H), 4.82-4.68 (m, 1H), 4.24-4.11 (m, 1H), 3.94 (dt, 1H), 3.57-3.48 (m, 1H), 3.27 (s, 6H), 3.19-2.97 (m, 2H), 2.97-2.59 (m, 2H), 2.57 (s, 3H), 1.34 (br t, 3H), 0.98-0.83 (m, 3H).

Analytical Chiral SFC Retention time: 1.519 min.

Analytical SFC Method:

Instrument: SHIMADZU LC-30Adsf, Column: Cellulose-4 50×4.6 mm I.D., 3 μm; Mobile phase: Phase A for $CO_2$, and Phase B for MeOH+ACN(0.05% DEA); Isocratic elution: 40% MeOH+ACN(0.05% DEA) in $CO_2$; Flow rate: 3 mL/min; Detector: PDA; Column Temp: 35° C.; Back Pressure: 100 Bar.

Synthesis of N-(2-chloro-4-(trifluoromethyl)phenyl)-2-(6-ethyl-7-(4-(5-hydroxy-6-methylpyrimidine-4-carbonyl)piperazin-1-yl)-2-((3-methoxycyclobutylidene)methyl)-8-oxopyrido[2,3-b]pyrazin-5 (8H)-yl)acetamide (I-117)

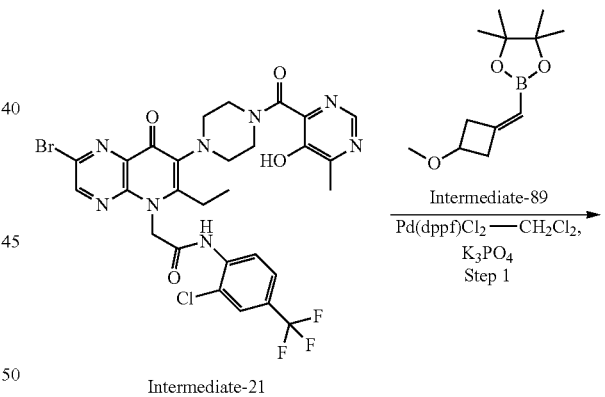

Intermediate-21    Intermediate-89

Pd(dppf)Cl$_2$—$CH_2Cl_2$, $K_3PO_4$
Step 1

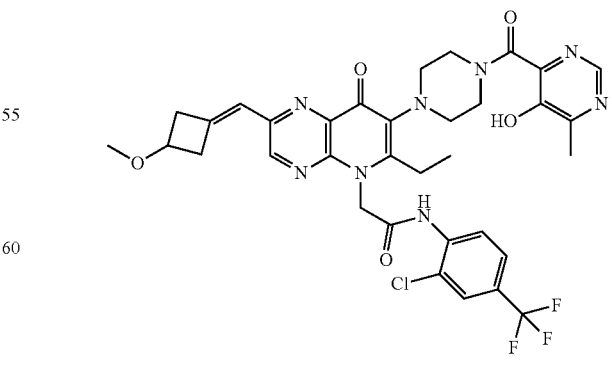

I-117

Step 1. Synthesis of N-[2-chloro-4-(trifluoromethyl)phenyl]-2-[6-ethyl-7-[4-(5-hydroxy-6-methyl-pyrimidine-4-carbonyl)piperazin-1-yl]-2-[(3-methoxycyclobutylidene)methyl]-8-oxo-pyrido[2,3-b]pyrazin-5-yl]acetamide To a mixture of 2-(2-bromo-6-ethyl-7-(4-(5-hydroxy-6-methylpyrimidine-4-carbonyl)piperazin-1-yl)-8-oxopyrido[2,3-b]pyrazin-5 (8H)-yl)-N-(2-chloro-4-(trifluoromethyl)phenyl)acetamide (Intermediate-21) (50 mg, 70 mol, 1.0 eq) and 2-((3-methoxycyclobutylidene)methyl)-4,4,5,5-tetramethyl-1,3,2-dioxaborolane (Intermediate-89) (16 mg, 70 mol, 1.0 eq) in 1,4-dioxane (1 mL) and H$_2$O (0.2 mL) was added Pd(dppf)Cl$_2$·CH$_2$Cl$_2$ (17 mg, 21 mol, 0.3 eq) and K$_3$PO$_4$ (45 mg, 211 mol, 3.0 eq), and the resulting mixture was stirred at 80° C. for 2 h under N$_2$ atmosphere. The reaction mixture was diluted with H$_2$O (10 mL) and extracted with EtOAc (5 mL*3). The combined organic layers were washed with brine (10 mL), dried over anhydrous Na$_2$SO$_4$, filtered and the filtrate was concentrated in vacuo. The residue was purified by reverse phase HPLC (water (0.1% FA)-ACN) to afford the title compound.

LCMS: 727.4 [M+H]$^+$.

$^1$H NMR (400 MHz, CDCl$_3$) δ ppm 12.28 (s, 1H), 8.72-8.61 (m, 1H), 8.58 (s, 1H), 8.52 (br d, 2H), 7.64 (s, 1H), 7.54 (br d, 1H), 6.72-6.51 (m, 1H), 5.73-5.51 (m, 1H), 5.51-5.18 (m, 2H), 4.92-4.65 (m, 1H), 4.14-3.98 (m, 3H), 3.67-3.48 (m, 2H), 3.37-3.28 (m, 5H), 3.23-3.07 (m, 3H), 3.00-2.92 (m, 1H), 2.90-2.71 (m, 2H), 2.57 (s, 3H), 1.37 (br d, 3H).

Synthesis of 2-(2-(dimethylamino)-6-ethyl-7-(4-(5-hydroxy-6-methylpyrimidine-4-carbonyl)piperazin-1-yl)-8-oxopyrido[2,3-b]pyrazin-5 (8H)-yl)-N-(3-(trifluoromethyl)bicyclo[1.1.1]pentan-1-yl)acetamide (I-108)

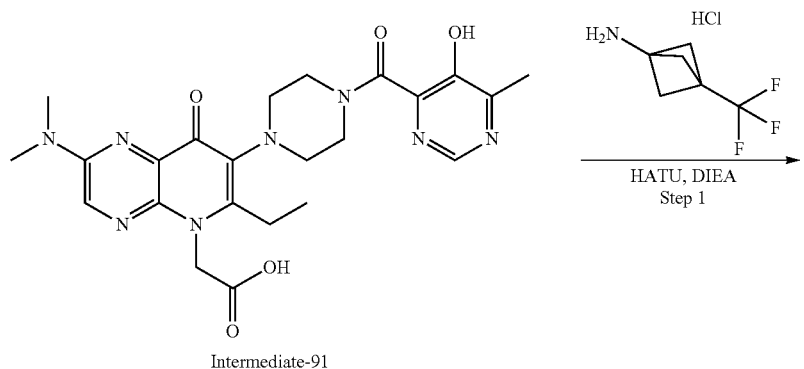

Intermediate-91

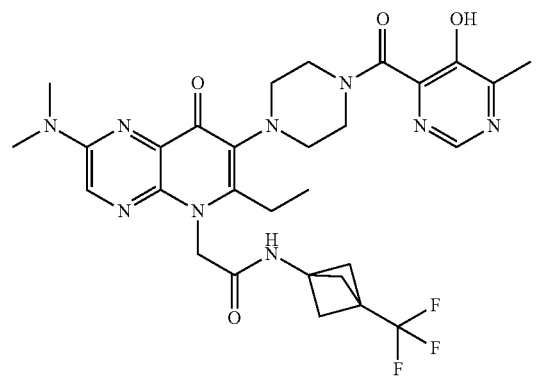

I-108

Step 1. Synthesis of 2-(2-(dimethylamino)-6-ethyl-7-(4-(5-hydroxy-6-methylpyrimidine-4-carbonyl)piperazin-1-yl)-8-oxopyrido[2,3-b]pyrazin-5 (8H)-yl)-N-(3-(trifluoromethyl)bicyclo[1.1.1]pentan-1-yl)acetamide To a mixture of 2-(2-(dimethylamino)-6-ethyl-7-(4-(5-hydroxy-6-methylpyrimidine-4-carbonyl)piperazin-1-yl)-8-oxopyrido[2,3-b]pyrazin-5 (8H)-yl)acetic acid (Intermediate-91) (20 mg, 40 mol, 1.0 eq) and 3-(trifluoromethyl)bicyclo[1.1.1]pentan-1-amine hydrochloride (15 mg, 81 mol, 2.0 eq) in DMF (1 mL) was added HATU (31 mg, 81 mol, 2.0 eq) and DIEA (16 mg, 121 mol, 3.0 eq), and the resulting mixture was stirred at room temperature for 1 h. The reaction mixture was diluted with H$_2$O (10 mL) and extracted with EtOAc (5 mL*3). The combined organic layers were washed with brine (5 mL), dried over anhydrous Na$_2$SO$_4$, filtered and the filtrate was concentrated in vacuo. The residue was purified by reverse phase HPLC (C18 column, water (0.1% FA-ACN) to afford the title compound.

LCMS: 630.3 [M+H]$^+$.

$^1$H NMR (400 MHz, CDCl$_3$) δ ppm 12.07 (s, 1H), 8.58 (s, 1H), 8.23 (s, 1H), 6.84-6.52 (m, 1H), 5.64-5.37 (m, 1H), 5.15 (br d, 2H), 4.86-4.60 (m, 1H), 4.06-3.87 (m, 2H), 3.62-3.42 (m, 1H), 3.24 (s, 6H), 3.18-3.04 (m, 3H), 2.87-2.75 (m, 2H), 2.57 (s, 3H), 2.29 (s, 6H), 1.28 (br t, 3H).

Synthesis of (S)—N-(2-chloro-4-(trifluoromethyl)phenyl)-2-(3-(dimethylamino)-7-ethyl-6-(4-(5-hydroxy-6-methylpyrimidine-4-carbonyl)-2-methylpiperazin-1-yl)-5-oxopyrido[3,2-e][1,2,4]triazin-8 (5H)-yl)acetamide (I-118)

Step 1: Synthesis of (S)—N-(2-chloro-4-(trifluoromethyl)phenyl)-2-(3-(dimethylamino)-7-ethyl-6-(4-(5-hydroxy-6-methylpyrimidine-4-carbonyl)-2-methylpiperazin-1-yl)-5-oxopyrido[3,2-e][1,2,4]triazin-8 (5H)-yl)acetamide To a solution of (S)—N-(2-chloro-4-(trifluoromethyl)phenyl)-2-(3-(dimethylamino)-7-ethyl-6-(2-methylpiperazin-1-yl)-5-oxopyrido[3,2-e][1,2,4]triazin-8 (5H)-yl)acetamide trifluoroacetate (Intermediate-95) (33 mg, 60 mol, 1.0 eq) and sodium 5-hydroxy-6-methylpyrimidine-4-carboxylate (Intermediate-55) (14 mg, 90 mol, 1.5 eq) in pyridine (1 mL) was added EDCI (23 mg, 119 mol, 2.0 eq), and the resulting mixture was stirred at room temperature overnight. The reaction mixture was poured into saturated NH$_4$Cl aqueous solution (10 mL), and then extracted with EtOAc (5 mL*3). The combined organic layers were washed with brine (5 mL), dried over anhydrous Na$_2$SO$_4$, filtered and concentrated under reduced pressure. The residue was purified by reverse phase HPLC (C18 column, water (0.1% FA)-ACN) to afford the title compound.

LCMS: 689.4 [M+H]$^+$.

$^1$H NMR (400 MHz, CDCl$_3$) δ 8.56-8.44 (m, 2H), 8.42 (d, 1H), 7.57 (d, 1H), 7.44 (br d, 1H), 5.71-5.16 (m, 3H), 4.76-4.55 (m, 1H), 4.08-3.92 (m, 1H), 3.84-3.71 (m, 1H), 3.50-3.41 (m, 1H), 3.31 (s, 6H), 3.06-2.90 (m, 2H), 2.82-2.54 (m, 2H), 2.49 (s, 3H), 1.28 (br t, 3H), 0.93-0.75 (m, 3H).

Synthesis of 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5 (8H)-yl)-N-(2-fluoro-4-(trifluoromethyl)phenyl)acetamide (I-129)

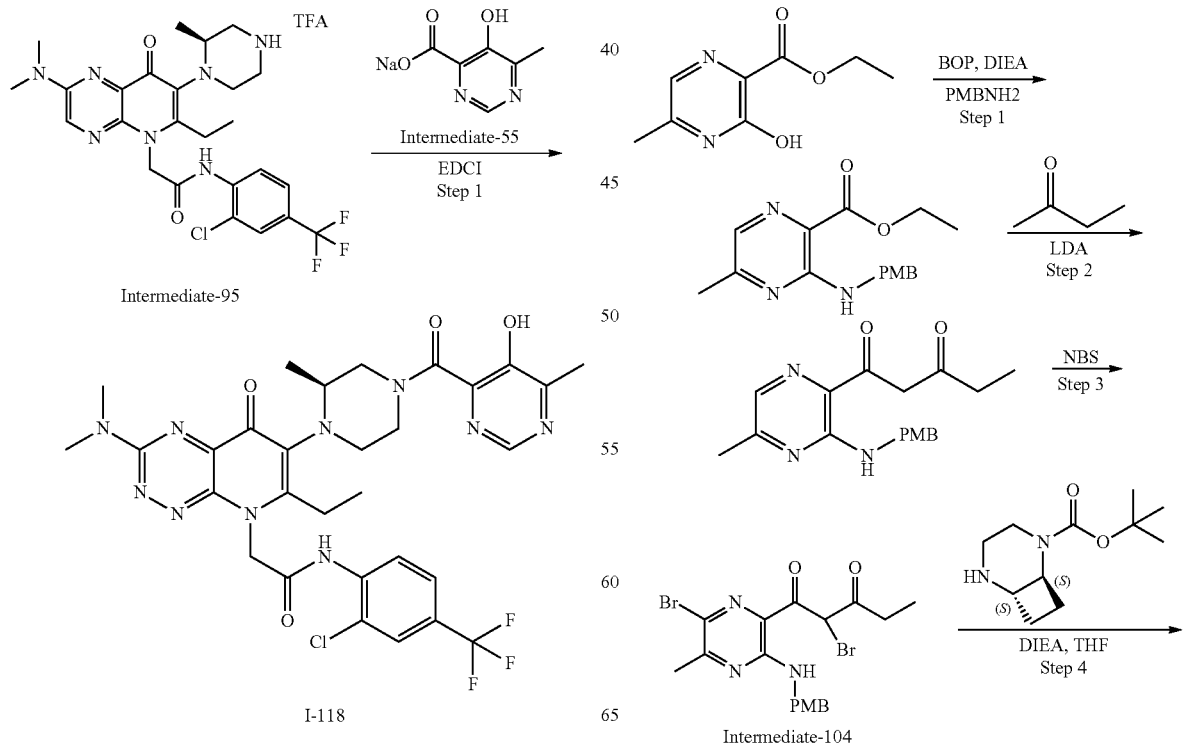

-continued

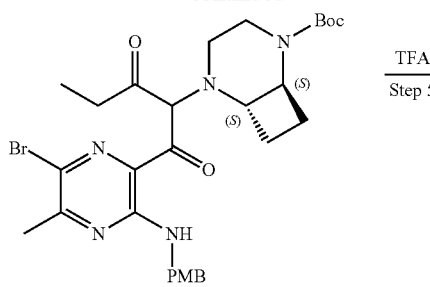

TFA
Step 5

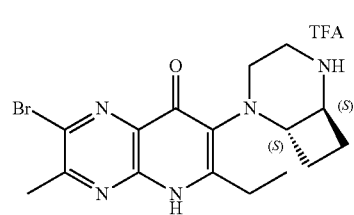

Boc₂O, DIEA
Step 6

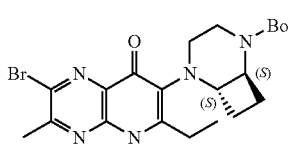

Intermediate-105

Intermediate-111
DIEA, 1,4-dioxane
Step 7

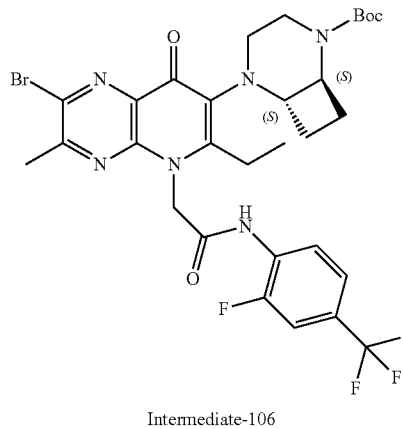

Intermediate-106

TFA
Step 8

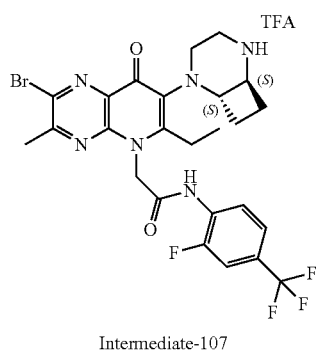

Intermediate-107

Intermediate-55
EDCI
Step 9

-continued

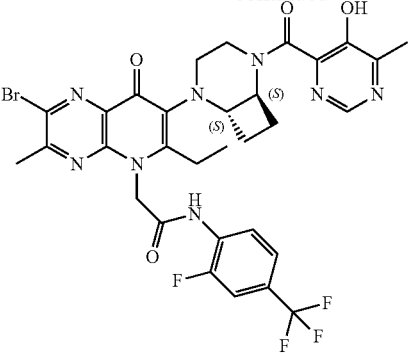

Intermediate-108

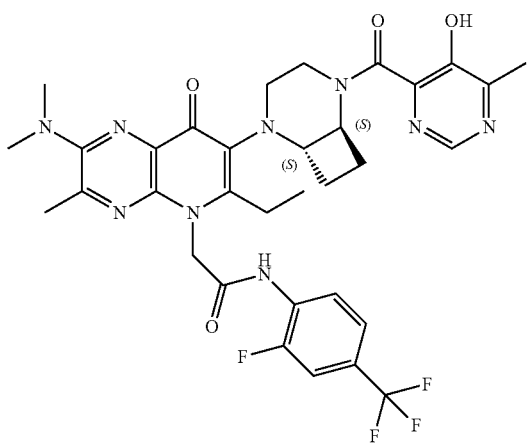

I-129

Step 10: Synthesis of 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5(8H)-yl)-N-(2-fluoro-4-(trifluoromethyl)phenyl)acetamide To a solution of 2-(2-bromo-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5(8H)-yl)-N-(2-fluoro-4-(trifluoromethyl)phenyl)acetamide (Intermediate-108) (80 mg, 109 mol, 1.0 eq) and dimethylamine hydrochloride (89 mg, 1.09 mmol, 10.0 eq) in 1,4-dioxane (1 mL) was added DIEA (211 mg, 1.64 mmol, 15.0 eq), and the resulting mixture was stirred at 100° C. for 3 h. The reaction mixture was concentrated under reduced pressure and then purified by reverse phase HPLC (C18 column, water (0.1% FA)-ACN) to afford the title compound.

LCMS: 698.3 [M+H]⁺.

¹H NMR (400 MHz, CDCl₃) δ 11.79 (br s, 1H), 8.99 (s, 1H), 8.60 (s, 1H), 8.48-8.44 (t, 1H), 7.42-7.40 (d, 1H), 7.35-7.32 (d, 1H), 5.64-5.23 (m, 3H), 4.34-4.29 (m, 2H), 3.92-3.76 (m, 2H), 3.38-3.35 (m, 2H), 3.23-3.20 (m, 1H), 3.06 (s, 6H), 2.71 (s, 3H), 2.54 (s, 3H), 2.43-2.26 (m, 1H), 1.71-1.69 (m, 1H), 1.43-1.42 (m, 1H), 1.42-1.34 (m, 2H), 1.32 (t, 3H).

Synthesis of N-(2-chloro-4-(trifluoromethyl)phenyl)-2-(6-ethyl-7-((1S,6S)-5-(5-hydroxy-6-methylpyrimidine-4-carbonyl)-2,5-diazabicyclo[4.2.0]octan-2-yl)-2,3-dimethyl-8-oxopyrido[2,3-b]pyrazin-5 (8H)-yl)acetamide (I-126)

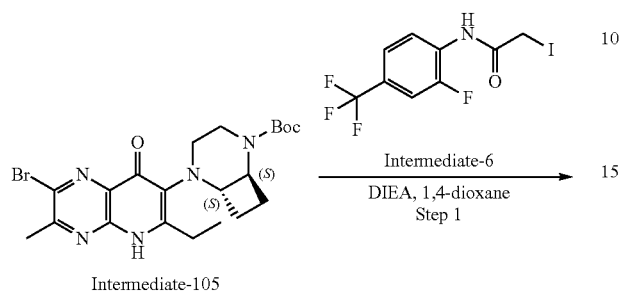

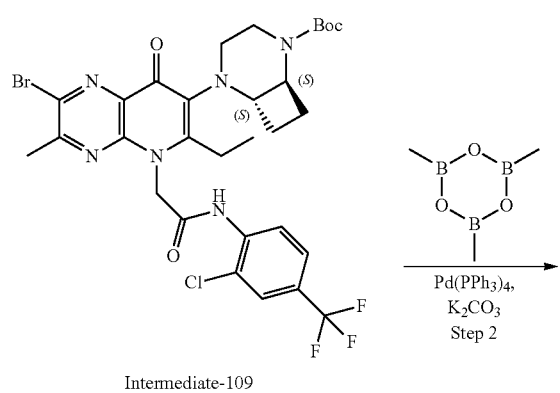

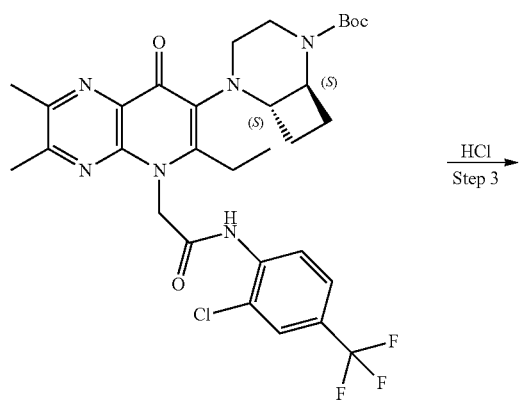

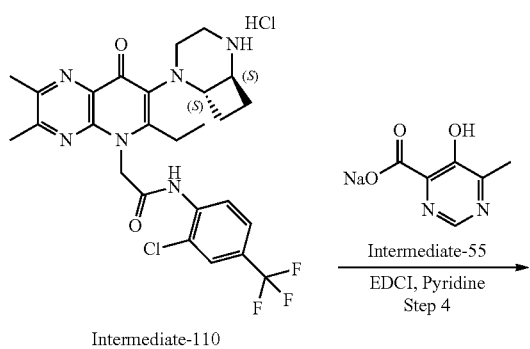

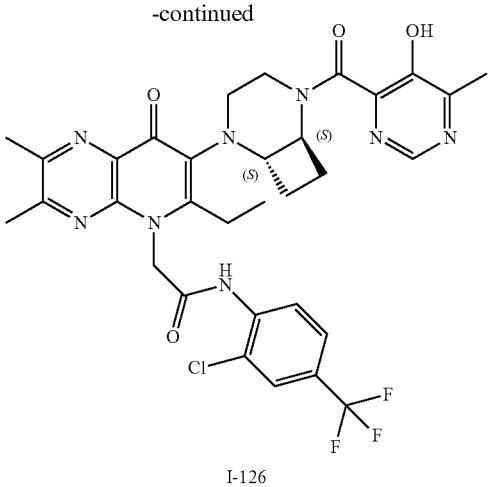

I-126

Step 4: Synthesis of N-(2-chloro-4-(trifluoromethyl)phenyl)-2-(6-ethyl-7-((1S,6S)-5-(5-hydroxy-6-methylpyrimidine-4-carbonyl)-2,5-diazabicyclo[4.2.0]octan-2-yl)-2,3-dimethyl-8-oxopyrido[2,3-b]pyrazin-5 (8H)-yl)acetamide To a solution of 2-(7-((1S,6S)-2,5-diazabicyclo[4.2.0]octan-2-yl)-6-ethyl-2,3-dimethyl-8-oxopyrido[2,3-b]pyrazin-5 (8H)-yl)-N-(2-chloro-4-(trifluoromethyl)phenyl)acetamide hydrochloride (Intermediate-110) (80 mg, 145.72 mol, 1.0 eq) and sodium 5-hydroxy-6-methylpyrimidine-4-carboxylate (Intermediate-55) (67 mg, 437 mol, 3.0 eq) in pyridine (1.0 mL) was added EDCI (140 mg, 728 μmol, 5 eq), and the resulting mixture was stirred at 30° C. for 3 h. A solution of aqueous NaOH (1 M, 1 mL) was added to the reaction mixture and stirred for 15 min. The resulting mixture was adjust to pH=6 with aqueous HCl solution (1 M) and extracted with EtOAc (10 mL*2). The combined organic layers were washed with brine (10 mL), dried over anhydrous $Na_2SO_4$, filtered and concentrated under reduced pressure. The residue was purified by reverse phase HPLC (C18 column, water (0.1% FA)-ACN) to afford the title compound.

LCMS: 685.3 $[M+H]^+$.

$^1$H NMR (400 MHz, $CDCl_3$) δ 11.72 (br s, 1H), 8.61 (s, 1H), 8.50-8.48 (d, 1H), 8.34 (s, 1H), 7.62 (s, 1H), 7.55-7.43 (d, 1H), 5.66-4.92 (m, 3H), 4.26 (s, 2H), 3.90-3.70 (m, 2H), 3.39-3.22 (m, 3H), 2.74 (s, 3H), 2.69 (s, 3H), 2.55 (s, 3H), 2.30-2.28 (m, 1H), 1.46 (br s, 2H), 1.37-1.33 (t, 3H), 1.32-1.26 (m, 1H).

Synthesis of 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-fluoro-4-(trifluoromethyl)phenyl)acetamide (I-121)

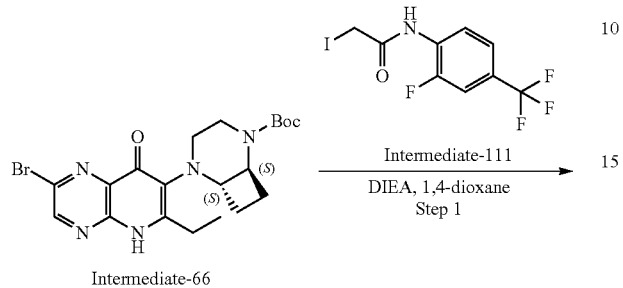

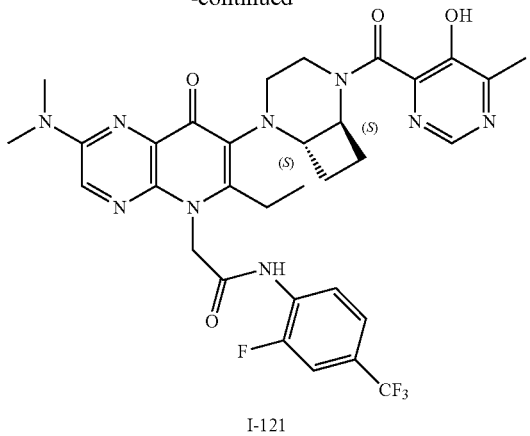

Step 4: Synthesis of 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-fluoro-4-(trifluoromethyl)phenyl)acetamide

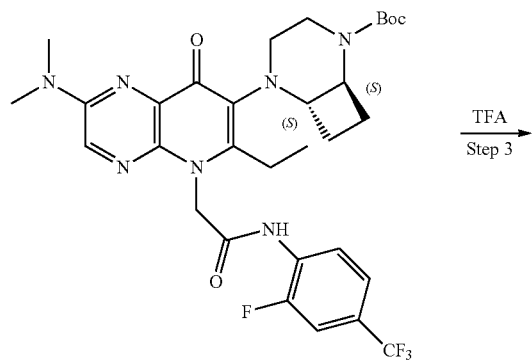

To a solution of 2-(7-((1S,6S)-2,5-diazabicyclo[4.2.0]octan-2-yl)-2-(dimethylamino)-6-ethyl-8-oxopyrido[2,3-b]pyrazin-5 (8H)-yl)-N-(2-fluoro-4-(trifluoromethyl)phenyl)acetamide trifluoroacetate (Intermediate-114) (50 mg, 91 mol, 1.0 eq) in DCM (1 mL) was added DIEA (94 mg, 731 mol, 8.0 eq) and a solution of 5-hydroxy-6-methylpyrimidine-4-carbonyl chloride (Intermediate-84) (79 mg, 457 mol, 5.0 eq) in DCM (0.5 mL), and the resulting mixture was stirred at room temperature for 15 min. The reaction mixture was quenched with $H_2O$ (10 mL), and then extracted with DCM (10 mL*3). The combined organic layers were washed with brine (5 mL), dried over anhydrous $Na_2SO_4$, filtered and concentrated under reduced pressure. The residue was purified by reverse phase HPLC (C18 column, water (0.1% FA)-ACN) to afford the title compound.

LCMS: 684.3 [M+H]$^+$.

$^1$H NMR (400 MHz, CDCl$_3$) δ 12.01 (s, 1H), 8.71 (br s, 1H), 8.61 (br s, 1H), 8.47 (t, 1H), 8.23 (s, 1H), 7.41 (br d, 1H), 7.34 (br d, 1H), 5.80-4.88 (m, 3H), 4.56-4.10 (m, 2H), 4.08-3.82 (m, 1H), 3.81-3.58 (m, 1H), 3.37 (br d, 2H), 3.29 (s, 6H), 3.25-3.14 (m, 1H), 2.55 (s, 3H), 1.45 (dt, 2H), 1.33 (br t, 4H), 1.26 (br s, 1H).

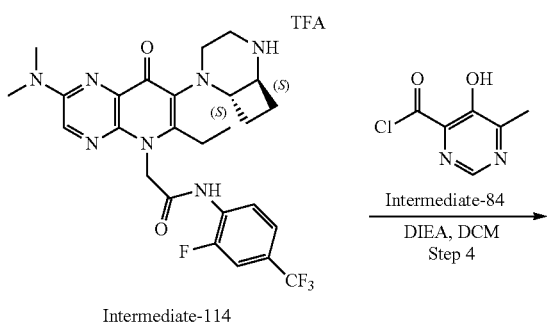

Synthesis of 2-(2-cyclopropyl-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-fluoro-4-(trifluoromethyl)phenyl)acetamide (I-125)

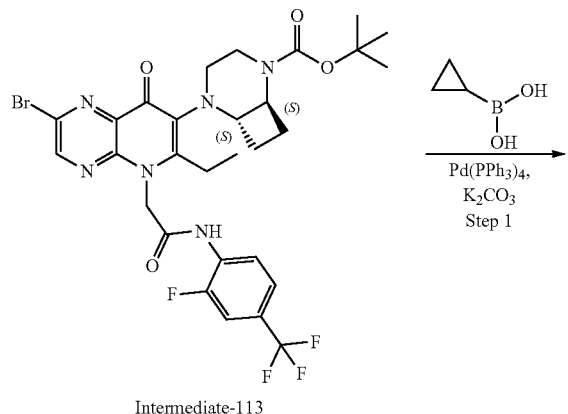

Intermediate-113

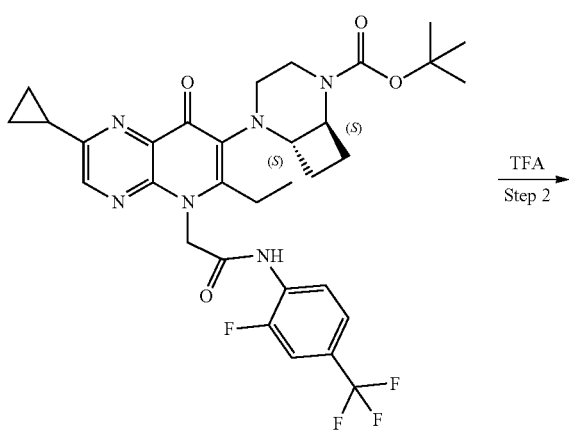

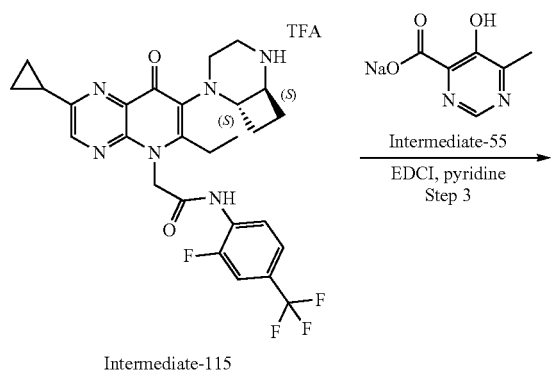

Intermediate-115

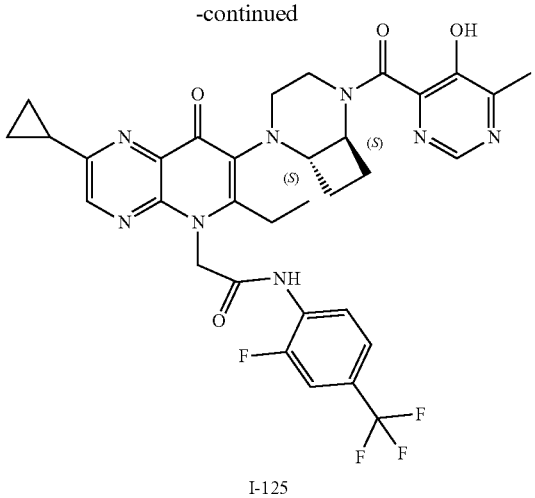

I-125

Step 3: Synthesis of 2-(2-cyclopropyl-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-fluoro-4-(trifluoromethyl)phenyl)acetamide To a solution of 2-(7-((1S,6S)-2,5-diazabicyclo[4.2.0]octan-2-yl)-2-cyclopropyl-6-ethyl-8-oxopyrido[2,3-b]pyrazin-5 (8H)-yl)-N-(2-fluoro-4-(trifluoromethyl)phenyl)acetamide trifluoroacetate (Intermediate-115) (160 mg, 294 mol, 1.0 eq) and sodium 5-hydroxy-6-methylpyrimidine-4-carboxylate (Intermediate-55) (136 mg, 881 mol, 3.0 eq) in pyridine (4 mL) was added EDCI (225 mg, 1.18 mmol, 4.0 eq), and the resulting mixture was stirred at 45° C. for 1.5 h. The mixture was diluted with $H_2O$ (20 mL) and extracted with DCM (25 mL*2). The combined organic layers were washed with brine (20 mL), dried over anhydrous $Na_2SO_4$, filtered, and concentrated under reduced pressure. The residue was purified by reverse phase HPLC (C18 column, water (0.1% FA)-ACN) to afford the title compound.

LCMS: 681.2 [M+H]$^+$.

$^1$H NMR (400 MHz, CDCl$_3$) δ 11.62 (s, 1H), 8.78 (br s, 1H), 8.61 (br s, 1H), 8.57 (s, 1H), 8.45 (t, 1H), 7.41 (br d, 1H), 7.36 (br d, 1H), 5.92-4.80 (m, 3H), 4.47-4.11 (m, 2H), 4.02-3.55 (m, 2H), 3.47-3.32 (m, 2H), 3.26-3.11 (m, 1H), 2.55 (s, 3H), 2.47-2.19 (m, 2H), 1.71 (br dd, 1H), 1.52-1.38 (m, 2H), 1.37-1.28 (m, 5H), 1.16 (dd, 2H).

Synthesis of N-(2-chloro-4-(trifluoromethyl)phenyl)-2-(2-(dimethylamino)-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5(8H)-yl)acetamide (I-107)

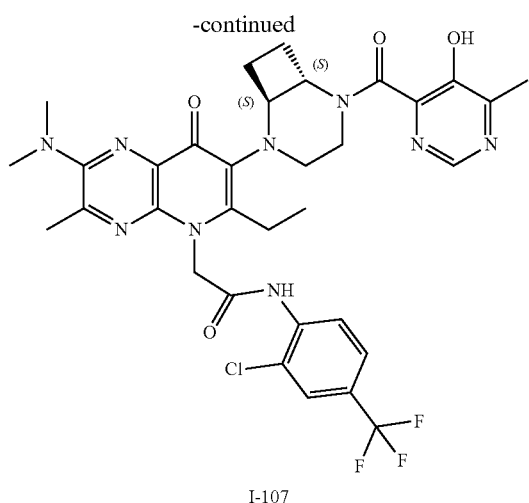

I-107

Step 7: Synthesis of N-(2-chloro-4-(trifluoromethyl) phenyl)-2-(2-(dimethylamino)-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5 (8H)-yl)acetamide To a solution of 2-(7-((1S,6S)-2,5-diazabicyclo[4.2.0]octan-2-yl)-2-(dimethylamino)-6-ethyl-3-methyl-8-oxopyrido[2,3-b]pyrazin-5 (8H)-yl)-N-(2-chloro-4-(trifluoromethyl) phenyl)acetamide trifluoroacetate (Intermediate-117) (110 mg, 190 mol, 1.0 eq) in pyridine (2 mL) was added EDCI (292 mg, 1.52 mmol, 8.0 eq) and sodium 5-hydroxy-6-methylpyrimidine-4-carboxylate (Intermediate-55) (88 mg, 571 mol, 3.0 eq), and the resulting mixture was stirred at room temperature for 2 h. The reaction mixture was concentrated and then purified by reverse phase HPLC (C18 column, water (0.1% FA)-ACN) to afford the title compound.

LCMS: 714.2 [M+H]$^+$.

$^1$H NMR (400 MHz, CDCl$_3$) δ 12.75 (s, 1H), 8.64-8.55 (m, 1H), 8.52 (d, 1H), 8.27 (s, 1H), 7.60 (s, 1H), 7.54 (d, 1H), 5.81-4.85 (m, 3H), 4.59-4.13 (m, 2H), 4.07-3.50 (m, 2H), 3.45-3.27 (m, 2H), 3.23-2.90 (m, 7H), 2.68 (s, 3H), 2.54 (s, 3H), 2.38-2.17 (m, 1H), 1.73-1.38 (m, 3H), 1.32 (t, 3H).

Synthesis of Intermediates of the Disclosure

Intermediate-1: tert-butyl 4-(5-(2-(tert-butoxy)-2-oxoethyl)-6-ethyl-3-methyl-8-oxo-5,8-dihydropyrido [2,3-b]pyrazin-7-yl)piperazine-1-carboxylate

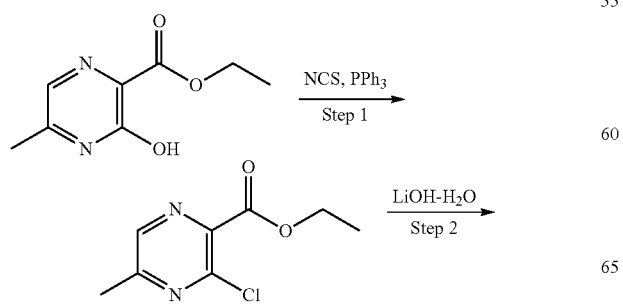

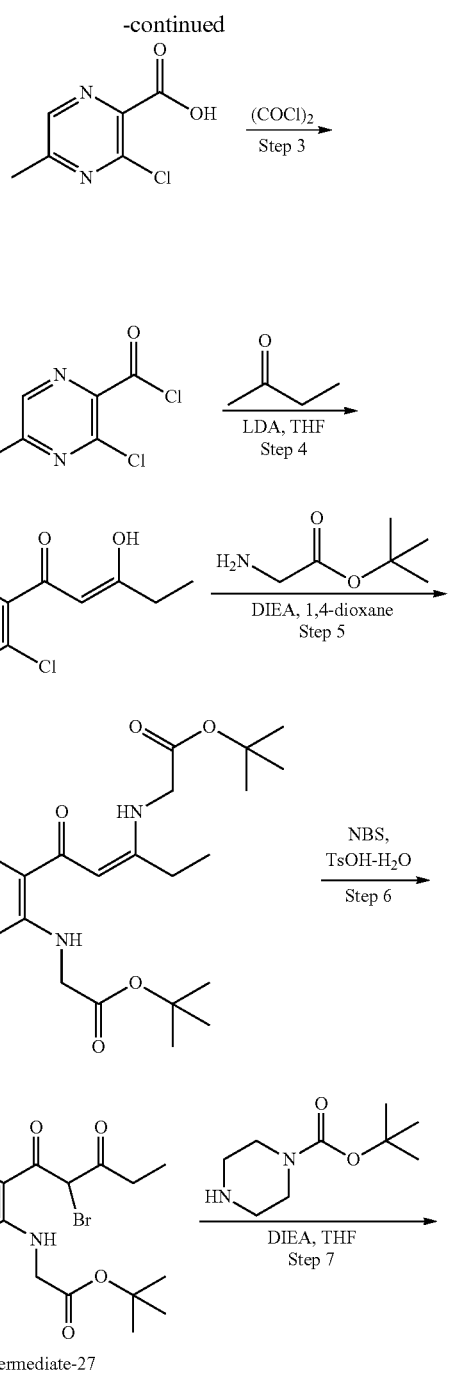

Intermediate-27

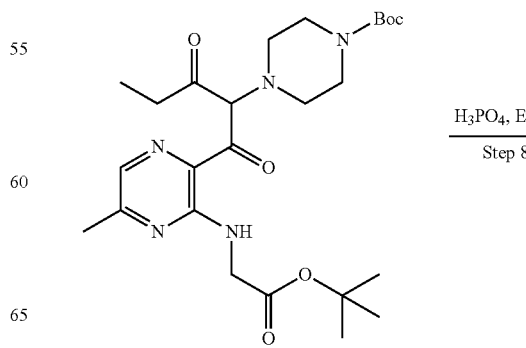

-continued

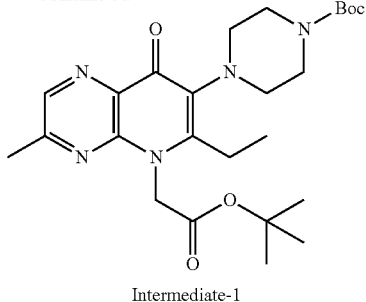

Intermediate-1

Step 1: Synthesis of ethyl 3-chloro-5-methylpyrazine-2-carboxylate

To a solution of $PPh_3$ (64.79 g, 247.0 mmol, 3.0 eq) in 1,4-dioxane (200 mL) was added NCS (33.53 g, 251.1 mmol, 3.05 eq) and the mixture was stirred at 10° C. for 1 h. Then ethyl 3-hydroxy-5-methylpyrazine-2-carboxylate (15.00 g, 82.34 mmol, 1.0 eq) was added and the resulting mixture was stirred at 100° C. overnight. The reaction mixture was concentrated under reduced pressure to remove solvent. The residue was purified by flash silica gel chromatography (Eluent of EtOAc/PE) to afford the title compound. LCMS: 201.1 $[M+H]^+$.

Step 2: Synthesis of 3-chloro-5-methylpyrazine-2-carboxylic Acid

To a solution of ethyl 3-chloro-5-methylpyrazine-2-carboxylate (11.70 g, 58.32 mmol, 1.0 eq) in MeOH (40 mL) and $H_2O$ (40 mL) was added LiOH—$H_2O$ (3.92 g, 93.3 mmol, 1.6 eq) and the reaction was stirred at 5° C. for 20 mins. The reaction mixture was diluted with $H_2O$ (40 mL), and then adjusted to pH 3 with aq. 1N HCl solution. The resulting mixture was extracted with DCM (50 mL*2). The combined organic phase was washed with brine (40 mL), dried over anhydrous $Na_2SO_4$, concentrated under reduced pressure to afford the title compound, which was used into the next step without further purification.

Step 3: Synthesis of 3-chloro-5-methylpyrazine-2-carbonyl Chloride

To a solution of 3-chloro-5-methylpyrazine-2-carboxylic acid (10.00 g, 57.95 mmol, 1 eq) in DCM (80 mL) was added $(COCl)_2$ (11.03 g, 86.92 mmol, 1.5 eq) and DMF (85 mg, 1.2 mmol, 0.02 eq). The reaction was stirred at room temperature for 2 h under $N_2$ atmosphere. The resulting mixture was concentrated under reduced pressure to afford the title compound, it was used into next step without further purification.

Step 4: Synthesis of 1-(3-chloro-5-methylpyrazin-2-yl)-3-hydroxypent-2-en-1-one To a solution of butan-2-one (6.23 g, 86.4 mmol, 1.5 eq) in THF (40 mL) was added LDA (2 M in THF, 43.2 mL, 86.4 mmol, 1.5 eq) at −65° C. The reaction mixture was stirred for 5 mins, 3-chloro-5-methylpyrazine-2-carbonyl chloride (11.0 g, 57.6 mmol, 1.0 eq) in THF (40 mL) was added dropwise to the mixture at −65° C. The resulting mixture was warmed to room temperature and stirred at room temperature for 1 h. The reaction was quenched with water (10 mL), adjusted to pH 4 with aq. 1N HCl solution, and then extracted with EtOAc (50 mL*2). The organic phase was washed with brine (50 mL), dried over anhydrous $Na_2SO_4$, concentrated under reduced pressure. The residue was purified by flash silica gel chromatography (Eluent of EtOAc/PE) to afford the title compound.
$^1$H NMR (400 MHz, $CDCl_3$) δ ppm 15.45 (br s, 1H), 8.42 (s, 1H), 6.39 (s, 1H), 2.63 (s, 3H), 2.49 (q, 2H), 1.23 (t, 3H).

Step 5: Synthesis of tert-butyl (1-(3-((2-(tert-butoxy)-2-oxoethyl)amino)-5-methylpyrazin-2-yl)-1-oxopent-2-en-3-yl)glycinate To a solution of 1-(3-chloro-5-methylpyrazin-2-yl)-3-hydroxypent-2-en-1-one (3.00 g, 13.2 mmol, 1.0 eq) in 1,4-dioxane (30 mL) was added DIEA (2.57 g, 19.9 mmol, 1.5 eq) and tert-butyl 2-aminoacetate (1.74 g, 13.2 mmol, 1.0 eq). The reaction was stirred at 100° C. for 2 h. The mixture was diluted with $H_2O$ (40 mL), extracted with EtOAc (20 mL*2). The organic phase was washed with brine (10 mL), dried over anhydrous $Na_2SO_4$, and concentrated under reduced pressure. The residue was purified by flash silica gel chromatography (Eluent of EtOAc/PE) to afford the title compound.
$^1$H NMR (400 MHz, $CDCl_3$) δ ppm 11.23 (br s, 1H), 9.57 (br s, 1H), 7.68 (s, 1H), 6.47 (s, 1H), 4.17 (br d, 2H), 4.02 (d, 2H), 2.39 (s, 3H), 2.33 (q, 2H), 1.51 (s, 9H), 1.48 (s, 9H), 1.23 (t, 3H).

Step 6: Synthesis of tert-butyl (3-(2-bromo-3-oxopentanoyl)-6-methylpyrazin-2-yl)glycinate To a solution of tert-butyl (1-(3-((2-(tert-butoxy)-2-oxoethyl)amino)-5-methylpyrazin-2-yl)-1-oxopent-2-en-3-yl)glycinate (1.70 g, 3.91 mmol, 1.0 eq) in DCM (15 mL) was added TsOH-$H_2O$ (135 mg, 710 μmol, 0.18 eq) and NBS (627 mg, 3.52 mmol, 0.9 eq). The mixture was stirred at room temperature for 0.5 h. The reaction mixture was diluted with $H_2O$ (10 mL) and then extracted with DCM (30 mL*2). The organic phase was washed with brine (10 mL), dried over anhydrous $Na_2SO_4$, concentrated under reduced pressure to afford the title compound, which was used in the next step without further purification. LCMS: 400.2 $[M+H]^+$.

Step 7: Synthesis of tert-butyl 4-(1-(3-((2-(tert-butoxy)-2-oxoethyl)amino)-5-methylpyrazin-2-yl)-1,3-dioxopentan-2-yl)piperazine-1-carboxylate To a solution of tert-butyl (3-(2-bromo-3-oxopentanoyl)-6-methylpyrazin-2-yl)glycinate (Intermediate-27) (1.50 g, 3.75 mmol, 1.0 eq) in THF (9 mL) was added tert-butyl piperazine-1-carboxylate (698 mg, 3.75 mmol, 1.0 eq) and DIEA (969 mg, 7.50 mmol, 2.0 eq) and the mixture was stirred at room temperature for 0.5 h. The reaction mixture was diluted with $H_2O$ (10 mL) and then extracted with EtOAc (10 mL*2). The organic phase was washed with brine (10 mL), dried over anhydrous $Na_2SO_4$, concentrated under reduced pressure. The residue was purified by flash silica gel chromatography (Eluent of EtOAc/PE) to afford the title compound, which was used in the next step without further purification. LCMS: 506.3 $[M+H]^+$.

Step 8: Synthesis of tert-butyl 4-(5-(2-(tert-butoxy)-2-oxoethyl)-6-ethyl-3-methyl-8-oxo-5,8-dihydropyrido[2,3-b]pyrazin-7-yl)piperazine-1-carboxylate To a solution of tert-butyl 4-(1-(3-((2-(tert-butoxy)-2-oxoethyl)amino)-5-methylpyrazin-2-yl)-1,3-dioxopentan-2- yl)piperazine-1-carboxylate (1.20 g, 2.37 mmol, 1.0 eq) in EtOH (10 mL) was added $H_3PO_4$ (465 mg, 4.75 mmol, 2.0 eq) and the resulting mixture was stirred at 60° C. overnight. The reaction mixture was concentrated under reduced pressure. The residue was diluted with $H_2O$ (10 mL) and then extracted with EtOAc (10 mL*2). The organic phase was washed with brine (10 mL), dried over anhydrous $Na_2SO_4$, concentrated under reduced pressure. The residue was purified by flash silica gel chromatography (Eluent of EtOAc/PE) to afford the title compound. LCMS: 488.3 $[M+H]^+$.

Intermediate-2: N-(2-chloro-4-(trifluoromethyl)phenyl)-2-(6-ethyl-3-methyl-8-oxo-7-(piperazin-1-yl)pyrido[2,3-b]pyrazin-5 (8H)-yl)acetamide Hydrochloride

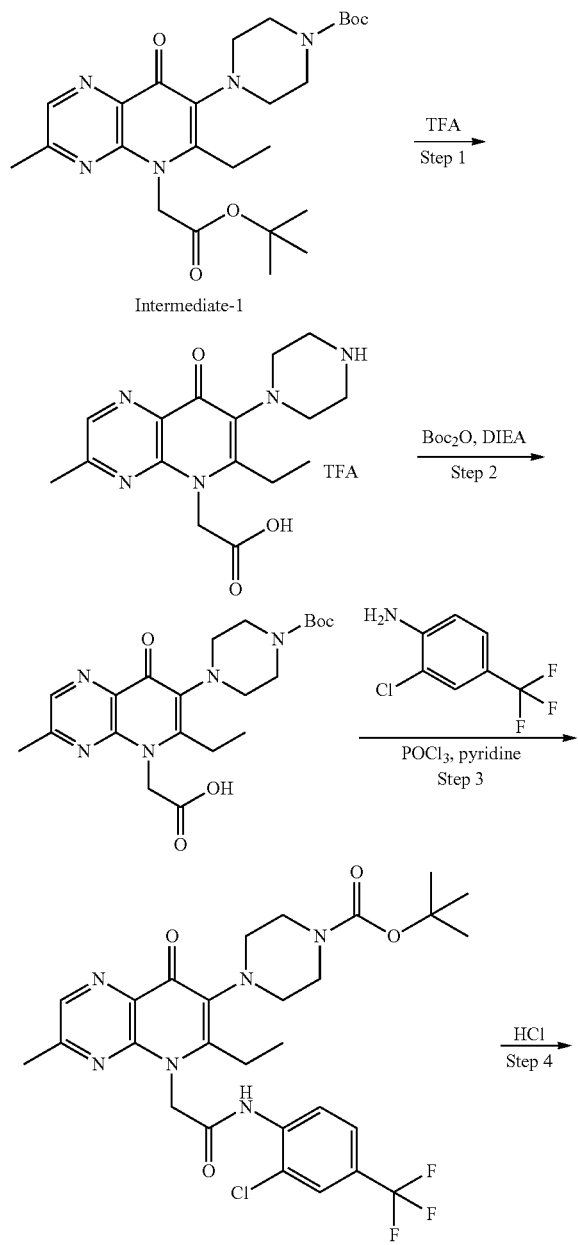

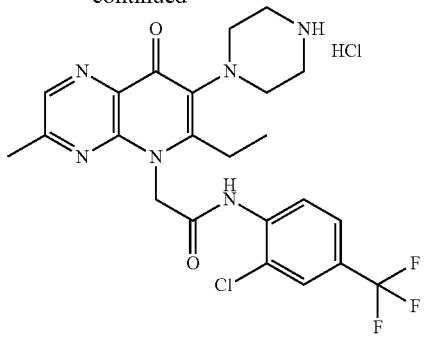

Intermediate-2

Step 1: Synthesis of 2-(6-ethyl-3-methyl-8-oxo-7-(piperazin-1-yl)pyrido[2,3-b]pyrazin-5 (8H)-yl)acetic Acid Trifluoroacetate To a solution of tert-butyl 4-(5-(2-(tert-butoxy)-2-oxoethyl)-6-ethyl-3-methyl-8-oxo-5,8-dihydropyrido[2,3-b]pyrazin-7-yl)piperazine-1-carboxylate (Intermediate-1) (550 mg, 1.13 mmol, 1.0 eq) in DCM (1 mL) was added TFA (5 mL) and the mixture was stirred at room temperature for 1 h. The reaction mixture was concentrated under reduced pressure to afford the title compound, which was used in the next step without further purification.
LCMS: 332.2 $[M+H]^+$.

Step 2: Synthesis of 2-(7-(4-(tert-butoxycarbonyl)piperazin-1-yl)-6-ethyl-3-methyl-8-oxopyrido[2,3-b]pyrazin-5 (8H)-yl)acetic Acid To a solution of 2-(6-ethyl-3-methyl-8-oxo-7-(piperazin-1-yl)pyrido[2,3-b]pyrazin-5 (8H)-yl)acetic acid trifluoroacetate (500 mg, 1.12 mmol, 1.0 eq) in DCM (8 mL) was added DIEA (725 mg, 5.61 mmol, 5.0 eq) and $Boc_2O$ (245 mg, 1.12 mmol, 1.0 eq). The mixture was stirred at room temperature for 1 h. The reaction mixture was poured into $H_2O$ (10 mL) and extracted with DCM (10 mL*2). The organic phase was washed with brine (10 mL), dried over anhydrous $Na_2SO_4$, concentrated under reduced pressure to afford the title compound, which was used in the next step without further purification.
LCMS: 432.2 $[M+H]^+$.

Step 3: Synthesis of tert-butyl 4-(5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)piperazine-1-carboxylate To a solution of 2-(7-(4-(tert-butoxycarbonyl)piperazin-1-yl)-6-ethyl-3-methyl-8-oxopyrido[2,3-b]pyrazin-5 (8H)-yl)acetic acid (100 mg, 231 μmol, 1.0 eq) and 2-chloro-4-(trifluoromethyl) aniline (68 mg, 0.35 mmol, 1.5 eq) in pyridine (1 mL) and DCM (1 mL) was added $POCl_3$ (53 mg, 0.35 μmol, 1.5 eq) dropwise at −10° C. The reaction mixture was stirred at −10° C. for 1 h and then poured into $H_2O$ (10 mL). The resulting solution was extracted with EtOAc (10 mL*2), the organic phase was washed with brine (10 mL), dried over anhydrous $Na_2SO_4$, concentrated under reduced pressure to afford the title compound, which was used in the next step without further purification.
LCMS: 609.2 $[M+H]^+$.

Step 4: Synthesis of N-(2-chloro-4-(trifluoromethyl)phenyl)-2-(6-ethyl-3-methyl-8-oxo-7-(piperazin-1-yl)pyrido[2,3-b]pyrazin-5 (8H)-yl)acetamide Hydrochloride tert-butyl 4-(5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)piperazine-1-carboxylate (130 mg, 213 µmol, 1.0 eq) was added to a 4 M solution of HCl in 1,4-dioxane (2 mL) and then stirred at room temperature for 1 h. The reaction mixture was concentrated under reduced pressure to afford the title compound, which was used in the next step without further purification.

LCMS: 509.2 [M+H]+.

Intermediate-3: tert-butyl 4-(2-bromo-5-(2-(tert-butoxy)-2-oxoethyl)-6-ethyl-8-oxo-5,8-dihydropyrido[2,3-b]pyrazin-7-yl)piperazine-1-carboxylate

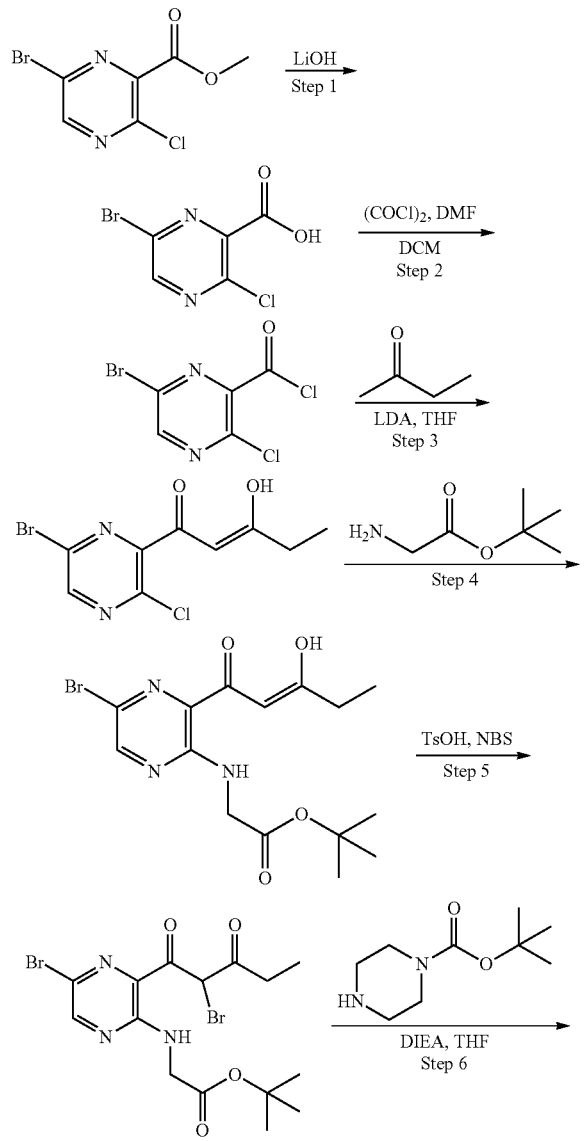

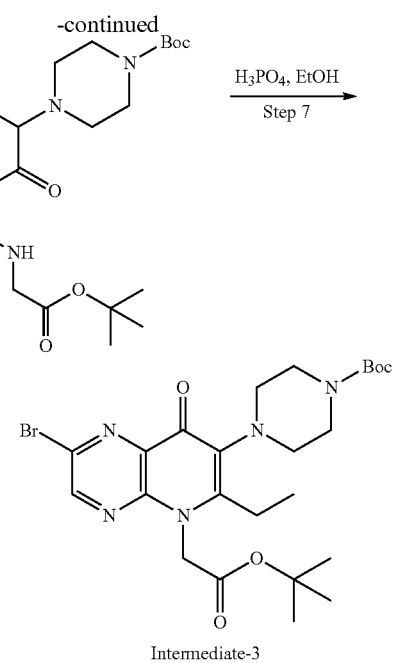

Intermediate-3

Step 1. Synthesis of 6-bromo-3-chloropyrazine-2-carboxylic Acid

To a solution of methyl 6-bromo-3-chloropyrazine-2-carboxylate (21.45 g, 85.30 mmol, 1.0 eq) in THF (30 mL) was added MeOH (60 mL), $H_2O$ (60 mL) and LiOH—$H_2O$ (7.16 g, 171 mmol, 2.0 eq) at 0° C. and the resulting mixture was stirred at 0° C. for 1 h. The reaction mixture was diluted with $H_2O$ (100 mL) and then adjusted pH 2~3 with aq. 6N HCl solution. The resulting mixture was extracted with DCM (100 mL*3). The combined organic layers were washed with brine (50 mL*3), dried over anhydrous $Na_2SO_4$, filtered and the filtrate was concentrated under reduced pressure to afford the title compound, which was used into the next step without further purification.

Step 2. Synthesis of 6-bromo-3-chloropyrazine-2-carbonyl Chloride

To a solution of 6-bromo-3-chloropyrazine-2-carboxylic acid (9.50 g, 40.0 mmol, 1.0 eq) in DCM (95 mL) was added $(COCl)_2$ (7.62 g, 60.0 mmol, 5.25 mL, 1.5 eq) and DMF (58 mg, 0.80 mmol, 0.02 eq) and the mixture was stirred at room temperature for 1 h. The reaction mixture was concentrated under reduced pressure to afford the title compound, which was used in the next step without further purification.

Step 3. Synthesis of (Z)-1-(6-bromo-3-chloropyrazin-2-yl)-3-hydroxypent-2-en-1-one To a solution of butan-2-one (3.95 g, 54.7 mmol, 2.0 eq) in THF (70 mL) was added a 2 M solution of LDA (27.4 mL, 54.7 µmol, 2.0 eq) in THF at −65° C. and the reaction mixture was stirred at −65° C. for 0.5 h. 6-bromo-3-chloropyrazine-2-carbonyl chloride (7.00 g, 27.4 mmol, 1.0 eq) was added at −65° C. and the mixture was stirred at −65° C. for 1 h. The reaction mixture was quenched by addition of saturated aq. $NH_4Cl$ solution (20 mL) at −65° C. and allowed to warm to room temperature slowly. The resulting mixture was diluted with H$_2$O (100 mL) and extracted with EtOAc (100 mL*2). The organic layer was dried over Na$_2$SO$_4$, filtered, and concentrated under reduced pressure. The residue was purified by silica gel chromatography (EtOAc/PE) to afford the title compound.

$^1$H NMR (400 MHz, CDCl$_3$) δ ppm 15.32 (s, 1H), 8.56 (s, 1H), 6.36 (s, 1H), 2.51 (q, 2H), 1.23 (br t, 3H).

Step 4. Synthesis of tert-butyl (Z)-(5-bromo-3-(3-hydroxypent-2-enoyl)pyrazin-2-yl)glycinate To a solution of tert-butyl glycinate (450 mg, 3.43 mmol, 2.0 eq) in 1,4-dioxane (10 mL) was added (Z)-1-(6-bromo-3-chloropyrazin-2-yl)-3-hydroxypent-2-en-1-one (1.00 g, 1.72 mmol, 1.0 eq) in 1,4-dioxane (10 mL) dropwise over 10 min at 100° C. The mixture was stirred at 100° C. for 10 min after addition. The reaction mixture was concentrated under reduced pressure. The residue was purified by silica gel chromatography (EtOAc/PE) to afford the title compound.

LCMS: 330.2 [M-55]$^+$.

Step 5. Synthesis of tert-butyl (5-bromo-3-(2-bromo-3-oxopentanoyl)pyrazin-2-yl)glycinate To a solution of tert-butyl (Z)-(5-bromo-3-(3-hydroxypent-2-enoyl)pyrazin-2-yl)glycinate (330 mg, 854 mol, 1.0 eq) in DCM (5 mL) was added TsOH-H$_2$O (15 mg, 85 µmol, 0.1 eq), NBS (152 mg, 854 mol, 1.0 eq) at 0° C. and it was stirred at 0° C. for 0.5 h. The reaction mixture was quenched with H$_2$O (10 mL) and extracted with DCM (10 mL*2). The combined organic layers were washed with brine (10 mL), dried over anhydrous Na$_2$SO$_4$, filtered and the filtrate was concentrated under reduced pressure to afford the title compound, which was used into the next step without further purification.

LCMS: 410.0 [M-55]$^+$.

Step 6. Synthesis of tert-butyl 4-(1-(6-bromo-3-((2-(tert-butoxy)-2-oxoethyl)amino)pyrazin-2-yl)-1,3-dioxopentan-2-yl)piperazine-1-carboxylate To a solution of tert-butyl (5-bromo-3-(2-bromo-3-oxopentanoyl)pyrazin-2-yl)glycinate (397 mg, 853 mol, 1.0 eq) in THF (5 mL) was added tert-butyl piperazine-1-carboxylate (238 mg, 1.28 mmol, 1.5 eq), DIEA (110 mg, 853 mol, 1.0 eq) and the mixture was stirred at room temperature for 5 h. The reaction mixture was diluted with H$_2$O (10 mL) and extracted with DCM (10 mL*2). The combined organic layers were washed with brine (10 mL), dried over anhydrous Na$_2$SO$_4$, filtered and the filtrate was concentrated under reduced pressure. The residue was purified by silica gel chromatography (EtOAc/PE) to afford the title compound.

LCMS: 572.2 [M+H]$^+$.

Step 7. Synthesis of tert-butyl 4-(2-bromo-5-(2-(tert-butoxy)-2-oxoethyl)-6-ethyl-8-oxo-5,8-dihydropyrido[2,3-b]pyrazin-7-yl)piperazine-1-carboxylate To a solution of tert-butyl 4-(1-(6-bromo-3-((2-(tert-butoxy)-2-oxoethyl)amino)pyrazin-2-yl)-1,3-dioxopentan-2-yl)piperazine-1-carboxylate (350 mg, 613 µmol, 1.0 eq) in EtOH (4 mL) was added H$_3$PO$_4$ (120 mg, 1.23 mmol, 2.0 eq) and the resulting mixture was stirred at 60° C. for 12 h. The reaction mixture was diluted with H$_2$O (10 mL) and then basified with 1N aq. NaOH solution to pH 8. The resulting mixture was extracted with EtOAc (10 mL*2). The combined organic layers were washed with brine (10 mL), dried over anhydrous Na$_2$SO$_4$, filtered and the filtrate was concentrated under reduced pressure. The residue was purified by silica gel chromatography (EtOAc/PE) to afford the title compound.

LCMS: 554.1 [M+H]$^+$.

Intermediate-4: tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate

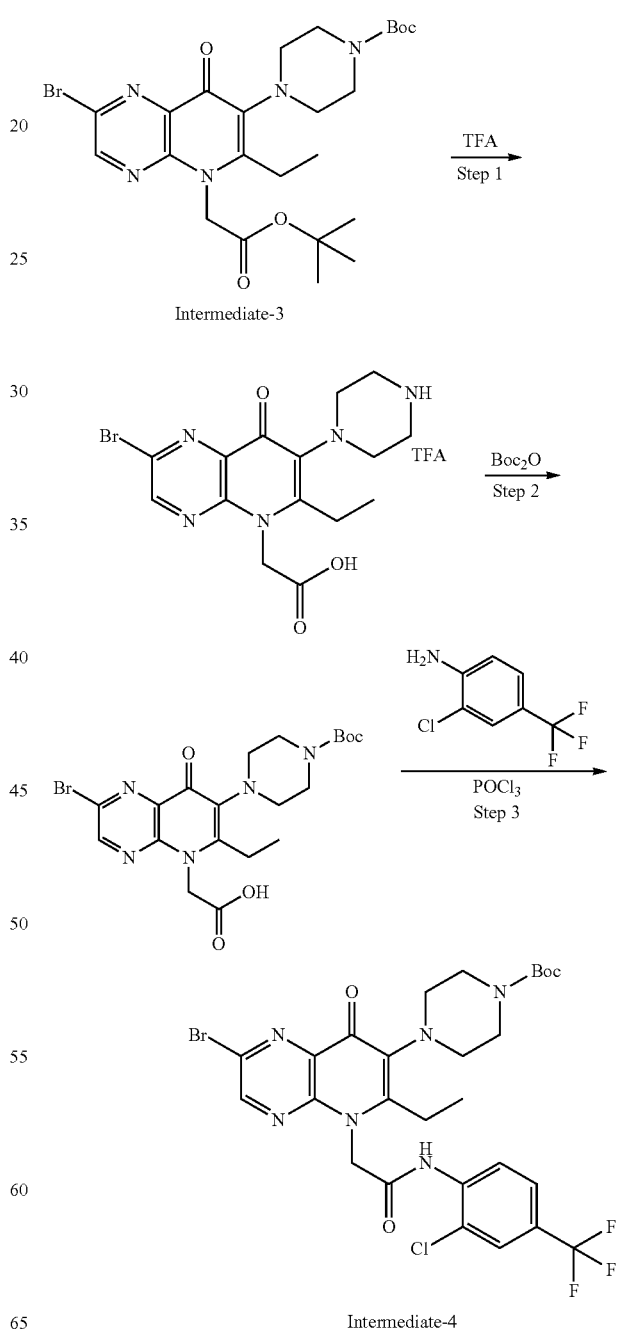

Intermediate-4

249

Step 1. Synthesis of 2-(2-bromo-6-ethyl-8-oxo-7-(piperazin-1-yl)pyrido[2,3-b]pyrazin-5 (8H)-yl)acetic Acid Trifluoroacetate The solution of tert-butyl 4-(2-bromo-5-(2-(tert-butoxy)-2-oxoethyl)-6-ethyl-8-oxo-5,8-dihydropyrido[2,3-b]pyrazin-7-yl)piperazine-1-carboxylate (Intermediate-3) (100 mg, 181 μmol, 1.0 eq) in DCM (1 mL) was added TFA (3 mL), and it was stirred at room temperature for 1 h. The mixture was concentrated under reduced pressure to afford the title compound, which was used into the next step without further purification.

LCMS: 396.0 [M+H]+.

Step 2. Synthesis of 2-(2-bromo-7-(4-(tert-butoxycarbonyl)piperazin-1-yl)-6-ethyl-8-oxopyrido[2,3-b]pyrazin-5 (8H)-yl)acetic Acid To a solution of 2-(2-bromo-6-ethyl-8-oxo-7-(piperazin-1-yl)pyrido[2,3-b]pyrazin-5 (8H)-yl)acetic acid trifluoroacetate (92 mg, 0.18 mmol, 1.0 eq) in DCM (2 mL) was added Et₃N (182 mg, 1.80 mmol, 10.0 eq) and Boc₂O (39 mg, 0.18 mmol, 1.0 eq). The reaction was stirred at room temperature for 0.5 h. The reaction mixture was diluted with H₂O (10 mL) and basified with 1N aq. NaOH solution to pH 9. The resulting mixture was extracted with DCM (10 mL*2). The DCM phase was discarded. The aq. phase was adjusted to pH 6 with 1N aq. HCl solution and then extracted with DCM (10 mL*2), the organic phase was washed with brine (20 mL), dried over anhydrous Na₂SO₄, filtered and the filtrate was concentrated under vacuum to afford the title compound, which was used into the next step without further purification.

LCMS: 496.1 [M+H]+.

Step 3. Synthesis of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate To a solution of 2-(2-bromo-7-(4-(tert-butoxycarbonyl)piperazin-1-yl)-6-ethyl-8-oxopyrido[2,3-b]pyrazin-5 (8H)-yl)acetic acid (96 mg, 0.19 mmol, 1.0 eq) and 2-chloro-4-(trifluoromethyl)aniline (57 mg, 0.29 mmol, 1.5 eq) in pyridine (1 mL) and DCM (1 mL) was added POCl₃ (44 mg, 0.29 mmol, 1.5 eq) at −10° C., and the resulting mixture was stirred at −10° C. for 1 h under N₂ atmosphere. The reaction mixture was quenched with H₂O (10 mL) and extracted with DCM (10 mL*2). The combined organic layers were washed with brine (10 mL), dried over anhydrous Na₂SO₄, filtered and the filtrate was concentrated under reduced pressure. The residue was purified by silica gel chromatography (EtOAc/PE) to afford the title compound.

LCMS: 673.1 [M+H]+.

250

Intermediate-5: N-(2-chloro-4-(trifluoromethyl)phenyl)-2-(6-ethyl-2-(2-methoxypyridin-4-yl)-8-oxo-7-(piperazin-1-yl)pyrido[2,3-b]pyrazin-5 (8H)-yl)acetamide Hydrochloride

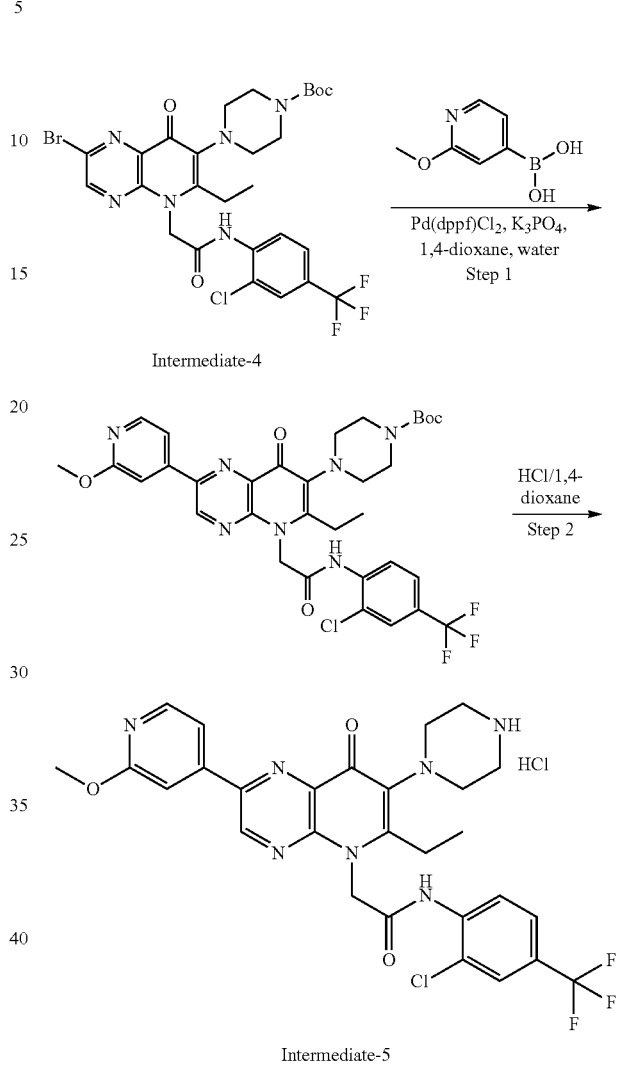

Intermediate-5

Step 1. Synthesis of tert-butyl 4-(5-(2-((2-chloro-4-(trifluoromethyl)phenyl)amino)-2-oxoethyl)-6-ethyl-2-(2-methoxypyridin-4-yl)-8-oxo-5,8-dihydropyrido[2,3-b]pyrazin-7-yl)piperazine-1-carboxylate To a solution of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (Intermediate-4) (40 mg, 59 μmol, 1.0 eq) and (2-methoxypyridin-4-yl)boronic acid (9 mg, 0.06 mmol, 1.0 eq) in 1,4-dioxane (1 mL) and H₂O (0.2 mL) was added Pd(dppf)Cl₂ (4 mg, 6 μmol, 0.1 eq) and K₃PO₄ (25 mg, 0.12 mmol, 2.0 eq), the resulting mixture was stirred at 80° C. for 1 h under N₂ atmosphere. The reaction mixture was concentrated under reduced pressure and then purified by silica gel chromatography (EtOAc/PE) to afford the title compound.

LCMS: 702.2 [M+H]+.

Step 2. Synthesis of N-(2-chloro-4-(trifluoromethyl)phenyl)-2-(6-ethyl-2-(2-methoxypyridin-4-yl)-8-oxo-7-(piperazin-1-yl)pyrido[2,3-b]pyrazin-5 (8H)-yl)acetamide Hydrochloride To a solution of 4 M HCl in 1,4-dioxane (2 mL) was added tert-butyl 4-(5-(2-((2-chloro-4-(trifluoromethyl)phenyl)amino)-2-oxoethyl)-6-ethyl-2-(2-methoxypyridin-4-yl)-8-oxo-5,8-dihydropyrido[2,3-b]pyrazin-7-yl)piperazine-1-carboxylate (31 mg, 44 μmol, 1.0 eq), and it was stirred at room temperature for 0.5 h. The resulting mixture was concentrated under reduced pressure to afford the title compound, which was used into the next step without further purification.

LCMS: 602.2 [M+H]$^+$.

Intermediate-6: N-(2-chloro-4-(trifluoromethyl)phenyl)-2-iodoacetamide

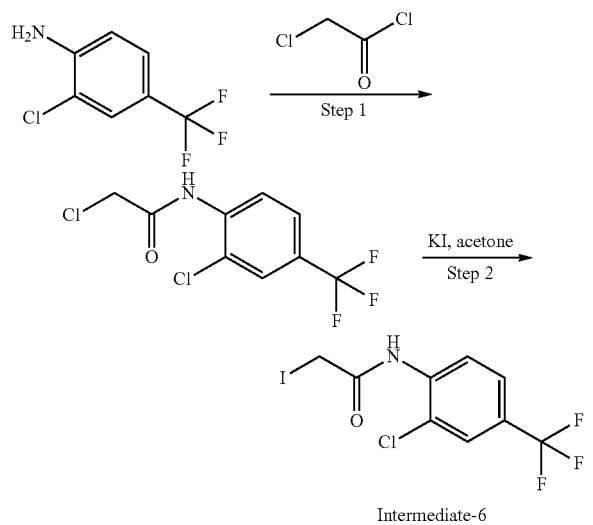

Intermediate-6

Step 1. Synthesis of 2-chloro-N-(2-chloro-4-(trifluoromethyl)phenyl)acetamide To a solution of 2-chloro-4-(trifluoromethyl)aniline (19.1 g, 97.7 mmol, 1.0 eq) and TEA (19.76 g, 195.3 mmol, 2.0 eq) in DCM (200 mL) was added dropwise a solution of 2-chloroacetyl chloride (11.03 g, 97.7 mmol, 1.0 eq) in DCM (50 mL) at 0° C. After addition, the resulting mixture was warmed to room temperature and stirred at room temperature overnight. The reaction mixture was purified by column chromatography on silica gel (eluent of EtOAc/PE) to afford the title compound.

LCMS: 273.9 [M+H]$^+$.

Step 2. Synthesis of N-(2-chloro-4-(trifluoromethyl)phenyl)-2-iodoacetamide

To a solution of 2-chloro-N-(2-chloro-4-(trifluoromethyl)phenyl)acetamide (7.70 g, 28.3 mmol, 1.0 eq) in acetone (60 mL) was added KI (5.17 g, 31.1 mmol, 1.1 eq), the resulting mixture was stirred at 60° C. for 2 h. The mixture was cooled to room temperature, filtered and the filtrate was concentrated in vacuum to afford the title compound, which was used in the next step without further purification.

LCMS: 363.9 [M+H]$^+$.

Intermediate-8: N-(2-chloro-4-(pentafluoro-λ$^6$-sulfanyl)phenyl)-2-iodoacetamide

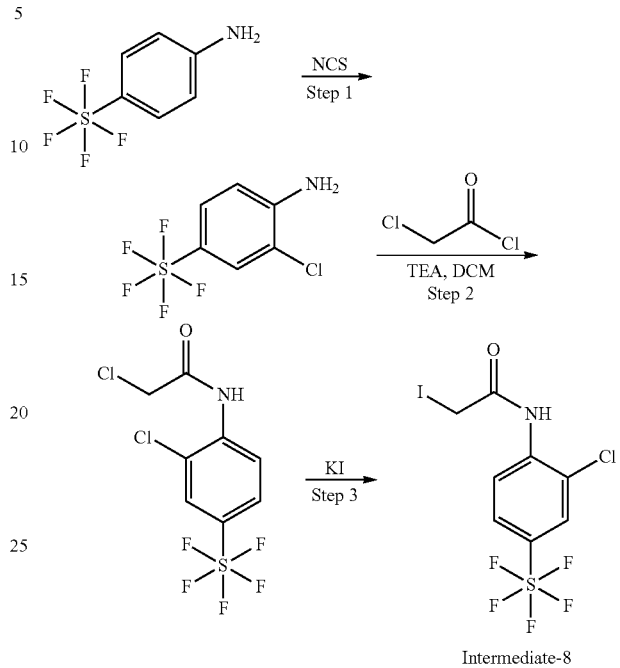

Intermediate-8

Step 1. Synthesis of 2-chloro-4-(pentafluoro-λ$^6$-sulfanyl)aniline

To a solution of 4-(pentafluoro-λ$^6$-sulfanyl)aniline (5.00 g, 22.8 mmol, 1.0 eq) in ACN (50 mL) was added NCS (3.35 g, 25.1 mmol, 1.1 eq). The resulting mixture was stirred at 60° C. for 0.5 h and then purified by silica gel chromatography (EtOAc/PE) to afford the title compound.

LCMS: 254.2 [M+H]$^+$.

Step 2. Synthesis of 2-chloro-N-(2-chloro-4-(pentafluoro-λ$^6$-sulfanyl)phenyl)acetamide To a solution of 2-chloro-4-(pentafluoro-λ$^6$-sulfanyl)aniline (1.00 g, 3.94 mmol, 1.0 eq) in DCM (10 mL) was added 2-chloroacetyl chloride (534 mg, 4.73 mmol, 1.2 eq) and TEA (798 mg, 7.89 mmol, 2.0 eq). The resulting mixture was stirred at room temperature for 2 h. The reaction mixture was diluted with H$_2$O (20 mL) and extracted with DCM (20 mL*2). The combined organic layers were dried over anhydrous Na$_2$SO$_4$, filtered and the filtrate was concentrated under reduced pressure. The residue was purified by silica gel chromatography (EtOAc/PE) to afford the title compound.

LCMS: 330.0 [M+H]$^+$.

Step 3. Synthesis of N-(2-chloro-4-(pentafluoro-λ$^6$-sulfanyl)phenyl)-2-iodoacetamide To a solution of 2-chloro-N-(2-chloro-4-(pentafluoro-λ$^6$-sulfanyl)phenyl)acetamide (1.00 g, 3.03 mmol, 1.0 eq) in acetone (10 mL) was added KI (835 mg, 5.03 mmol, 1.66 eq). The resulting mixture was stirred at 80° C. for 2 h. The reaction was diluted with H$_2$O (30 mL) and extracted with EtOAc (20 mL*3). The combined organic layers were dried over Na$_2$SO$_4$, filtered and the filtrate was concentrated under reduced pressure to afford the title compound, which was used in the next step without further purification.

LCMS: 421.9 [M+H]$^+$.

Intermediate-11: 7-hydroxy-2,3-dihydrofuro[3,2-c]pyridine-6-carboxylic Acid

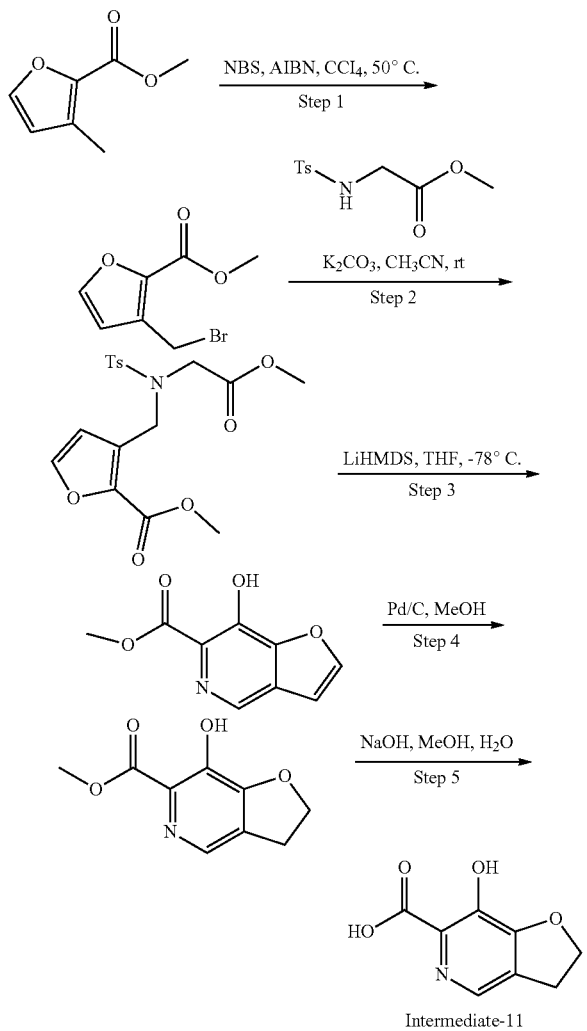

Intermediate-11

Step 1. Synthesis of methyl 3-(bromomethyl)furan-2-carboxylate

To a solution of methyl 3-methylfuran-2-carboxylate (5.00 g, 35.7 mmol, 1.00 eq) in CCl$_4$ (50.0 mL) were added NBS (6.68 g, 37.5 mmol, 1.05 eq) and AIBN (2.35 g, 14.3 mmol, 0.40 eq) at room temperature. The mixture was degassed three times with N$_2$ and stirred at 50° C. for 16 h. The resulting mixture was concentrated under reduced pressure. The residue was purified by flash silica gel chromatography (eluent of EtOAc/PE) to afford the title compound.

LCMS: 219/221 [M+H]$^+$.

Step 2. Synthesis of methyl 3-(((N-(2-methoxy-2-oxoethyl)-4-methylphenyl)sulfonamido)methyl)furan-2-carboxylate To a solution of methyl 3-(bromomethyl)furan-2-carboxylate (4.70 g, 21.5 mmol, 1.00 eq) and K$_2$CO$_3$ (5.93 g, 43.0 mmol, 2.00 eq) in ACN (47.0 mL) was added methyl 2-(4-methylbenzenesulfonamido)acetate (5.23 g, 21.5 mmol, 1.00 eq) and the mixture was stirred at room temperature for 16 h. The reaction was filtered, and the filtrate was concentrated in vacuum. The residue was purified by column chromatography on silica (Eluent of EtOAc/PE) to afford the title compound.

LCMS: 382 [M+H]$^+$.

Step 3. Synthesis of methyl 7-hydroxyfuro[3,2-c]pyridine-6-carboxylate

To a solution of methyl 3-(((N-(2-methoxy-2-oxoethyl)-4-methylphenyl)sulfonamido)methyl)furan-2-carboxylate (1.80 g, 4.72 mmol, 1.00 eq) in THF (18.0 mL) was added a 1 M solution of LiHMDS (14.2 mL, 14.2 mmol, 3.00 eq) in THF dropwise at −78° C. under N$_2$ atmosphere. After addition, the reaction mixture was allowed to warm to 0° C. and stirred for 5 h under N$_2$ atmosphere. A saturated NH$_4$Cl (aq.) solution was added to the reaction mixture and the aq. phase was extracted with EtOAc. The organic layer was dried over anhydrous Na$_2$SO$_4$, filtered and concentrated under reduced pressure. The residue was purified by flash silica gel chromatography (Eluent of EtOAc/PE) to afford the title compound.

LCMS: 194 [M+H]$^+$.

Step 4. Synthesis of methyl 7-hydroxy-2,3-dihydrofuro[3,2-c]pyridine-6-carboxylate To a mixture of methyl 7-hydroxyfuro[3,2-c]pyridine-6-carboxylate (760 mg, 3.93 mmol, 1.00 eq) in MeOH (10.0 mL) was added Pd/C (152 mg, 20%). The mixture was degassed and purged with H$_2$ gas (40 psi). Then it was stirred at 50° C. for 16 h. The mixture was filtered, and the filtrate was concentrated under reduced pressure. The residue was purified by flash silica gel chromatography (Eluent of DCM/MeOH) to afford the title compound.

LCMS: 196 [M+H]$^+$.

Step 5. Synthesis of 7-hydroxy-2,3-dihydrofuro[3,2-c]pyridine-6-carboxylic Acid

To a mixture of methyl 7-hydroxy-2,3-dihydrofuro[3,2-c]pyridine-6-carboxylate (680 mg, 3.48 mmol, 1.00 eq) in H$_2$O (3.00 mL) and MeOH (3.00 mL) was added NaOH (557 mg, 13.9 mmol, 4.00 eq) at room temperature and the resulting mixture was stirred at 60° C. for 16 h. After completion, the reaction mixture was concentrated under reduced pressure. The residue was diluted with H$_2$O and acidified by 3N HCl. The precipitated solids were collected by filtration and dried to afford the title compound, which was used in the next step directly without further purification.

LCMS: 182 [M+H]$^+$.

Intermediate-12: 4-hydroxy-2,3-dihydrofuro[2,3-c]pyridine-5-carboxylic Acid

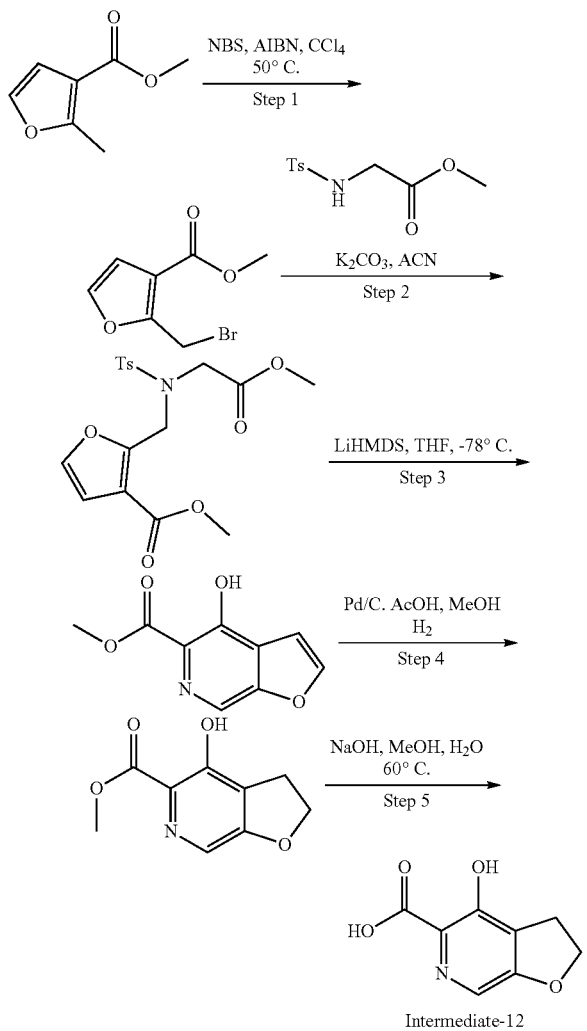

Intermediate-12

Step 1. Synthesis of methyl 2-(bromomethyl)furan-3-carboxylate

To a stirred solution of methyl 2-methylfuran-3-carboxylate (10.0 g, 71.4 mmol, 1.00 eq) in CCl$_4$ (55.0 mL) were added NBS (15.2 g, 85.6 mmol, 1.20 eq) and AIBN (586 mg, 3.57 mmol, 0.05 eq) at room temperature. The resulting mixture was degassed three times with N$_2$ and stirred overnight at 50° C. under N$_2$. The reaction mixture was concentrated under reduced pressure. The residue was purified by flash silica gel chromatography (eluent of EtOAc/PE) to afford the title compound.

$^1$H NMR (400 MHz, DMSO-d$_6$) δ ppm 7.86 (d, 1H), 6.80 (d, 1H), 4.95 (s, 2H), 3.82 (s, 3H).

Step 2. Synthesis of methyl 2-(((N-(2-methoxy-2-oxoethyl)-4-methylphenyl)sulfonamido)methyl)furan-3-carboxylate To a stirred solution of methyl 2-(bromomethyl)furan-3-carboxylate (12.0 g, 54.8 mmol, 1.00 eq) and methyl 2-(4-methylbenzenesulfonamido)acetate (13.3 g, 54.8 mmol, 1.00 eq) in ACN (100 mL) was added K$_2$CO$_3$ (15.1 g, 110 mmol, 2.00 eq) at room temperature. The resulting mixture was degassed three times with N$_2$ and then stirred overnight at room temperature. The reaction mixture was filtered, and the filtrate was concentrated under reduced pressure. The residue was purified by flash silica gel chromatography (eluent of EtOAc/PE) to afford the title compound.

LCMS: 382.1 [M+H]$^+$.

Step 3. Synthesis of methyl 4-hydroxyfuro[2,3-c]pyridine-5-carboxylate

To a stirred solution of methyl 2-([N-(2-methoxy-2-oxoethyl)4-methylbenzenesulfonamido]methylfuran-3-carboxylate (9.00 g, 23.6 mmol, 1.00 eq) in THF (50.0 mL) was added a 1 M solution of LiHMDS (70.0 mL, 70.0 mmol, 3.00 eq) in THF at −78° C. under N$_2$. The resulting mixture was stirred for 1 h at room temperature under N$_2$. The reaction mixture was quenched with saturated NH$_4$Cl solution at 0° C. and diluted with H$_2$O (200 mL). The resulting mixture was extracted with EtOAc (2×200 mL). The combined organic layers were washed with brine (3×100 mL), dried over anhydrous Na$_2$SO$_4$. After filtration, the filtrate was concentrated under reduced pressure. The residue was purified by flash silica gel chromatography (eluent of EtOAc/PE) to afford a crude product, which was purified by trituration with PE (250 mL) to afford the title compound.

LCMS: 194.0 [M+H]$^+$.

Step 4. Synthesis of methyl 4-hydroxy-2,3-dihydrofuro[2,3-c]pyridine-5-carboxylate To a solution of methyl 4-hydroxyfuro[2,3-c]pyridine-5-carboxylate (1.00 g, 5.18 mmol, 1.00 eq) in AcOH (1.00 mL) and MeOH (10.0 mL) was added Pd/C (1.65 g, 10%). The mixture was degassed three times with H$_2$, and then stirred at room temperature for 1 h under H$_2$. The reaction mixture was filtered, and the filter cake was washed with MeOH. The filtrate was concentrated under reduced pressure and the residue was purified by reverse phase HPLC (C18 column, H$_2$O (10 mmol/L NH$_4$HCO$_3$)-ACN) to afford the title compound.

LCMS: 195.9 [M+H]$^+$.

Step 5. Synthesis of 4-hydroxy-2,3-dihydrofuro[2,3-c]pyridine-5-carboxylic Acid To a stirred solution of methyl 4-hydroxy-2H,3H-furo[2,3-c]pyridine-5-carboxylate (300 mg, 1.54 mmol, 1.00 eq) in MeOH (3.00 mL) were added NaOH (246 mg, 6.15 mmol, 4.00 eq) and H$_2$O (3.00 mL) at room temperature. The reaction mixture was stirred overnight at 60° C. The mixture was acidified to pH=3 with 1N HCl. The resulting mixture was extracted with EtOAc (3×15 mL). The combined organic layers were washed with brine (2×20 mL), dried over anhydrous Na$_2$SO$_4$. After filtration, the filtrate was concentrated under reduced pressure to afford the title compound, which was used in the next step directly without further purification.

LCMS: 181.9 [M+H]$^+$.

Intermediate-13: 5-hydroxy-6-methylpyrimidine-4-carboxylic acid; and Intermediate-56: methyl 5-methoxy-6-methylpyrimidine-4-carboxylate

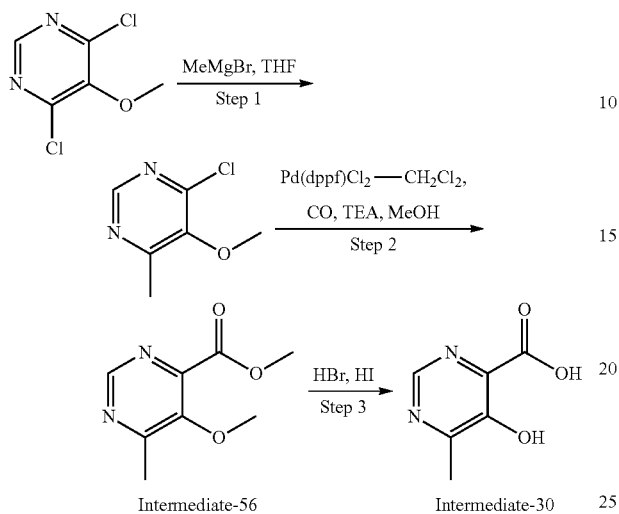

Step 1: Synthesis of 4-chloro-5-methoxy-6-methylpyrimidine

To a mixture of 4,6-dichloro-5-methoxypyrimidine (30.00 g, 167.6 mmol, 1.0 eq) in THF (300 mL) was added a 3 M solution of MeMgBr (61.45 mL, 184.4 mmol, 1.1 eq) in diethyl ether dropwise at 0° C. and then the mixture was stirred at 5° C. for 1 h. The resulting mixture was poured into H$_2$O (200 mL) and extracted with EtOAc (100 mL*3). The combined organic phase was washed with brine (100 mL), dried over anhydrous Na$_2$SO$_4$, filtered and the filtrate was concentrated in vacuum. The residue was purified by flash silica gel chromatography (eluent of EtOAc/PE) to afford the title compound.
LCMS: 159.1 [M+H]$^+$.

Step 2: Synthesis of methyl 5-methoxy-6-methylpyrimidine-4-carboxylate

To a mixture of 4-chloro-5-methoxy-6-methylpyrimidine (22.00 g, 138.7 mmol, 1.0 eq) in MeOH (250 mL) was added Pd(dppf)Cl$_2$—CH$_2$Cl$_2$ (6.80 g, 8.32 mmol, 0.06 eq) and TEA (28.1 g, 278 mmol, 2.0 eq). The reaction was purged with CO (50 psi) and stirred at 50° C. overnight. The resulting mixture was filtered, and the filtrate was concentrated under reduced pressure. The residue was purified by flash silica gel chromatography (eluent of EtOAc/PE) to afford the title compound.
LCMS: 183.1 [M+H]$^+$.

Step 3: Synthesis of 5-hydroxy-6-methylpyrimidine-4-carboxylic Acid

A mixture of methyl 5-methoxy-6-methylpyrimidine-4-carboxylate (Intermediate-56) (16.00 g, 87.83 mmol, 1.0 eq) in HBr solution (aq.) (68.5 mL, 68%) was stirred at 50° C. overnight. Then HI solution (aq.) (67.2 mL, 56%) was added and stirred at 50° C. for 6 h. The reaction mixture was cooled to room temperature and basified with 50% NaOH solution (aq.) to pH 9 at 0° C., then adjusted to pH 7 with 2 M HCl solution (aq.) at 0° C. The mixture was filtered, the filter cake was dried in vacuum to afford the title compound, which was used in the next step without further purification.
LCMS: 155.1 [M+H]$^+$. $^1$H NMR (400 MHz, DMSO-d$_6$) δ ppm 15.46 (br s, 1H), 8.37 (s, 1H), 2.34 (s, 3H).

Alternative Synthesis of Intermediate-4

Intermediate-4: tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate Intermediate-40: 2-bromo-1-(6-bromo-3-((4-methoxybenzyl)amino)pyrazin-2-yl)pentane-1,3-dione Intermediate-41: tert-butyl 4-(2-bromo-6-ethyl-8-oxo-5,8-dihydropyrido[2,3-b]pyrazin-7-yl)piperazine-1-carboxylate

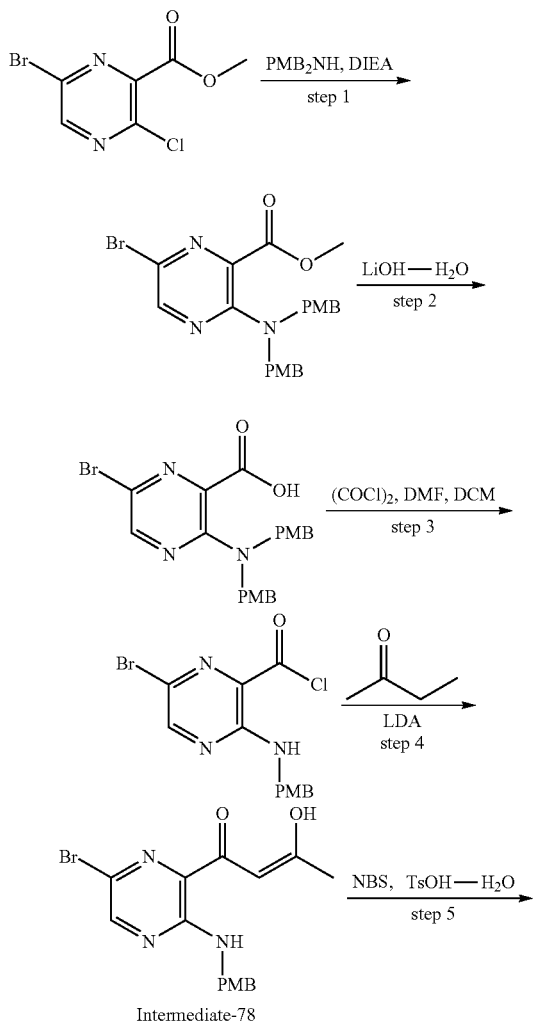

Intermediate-78

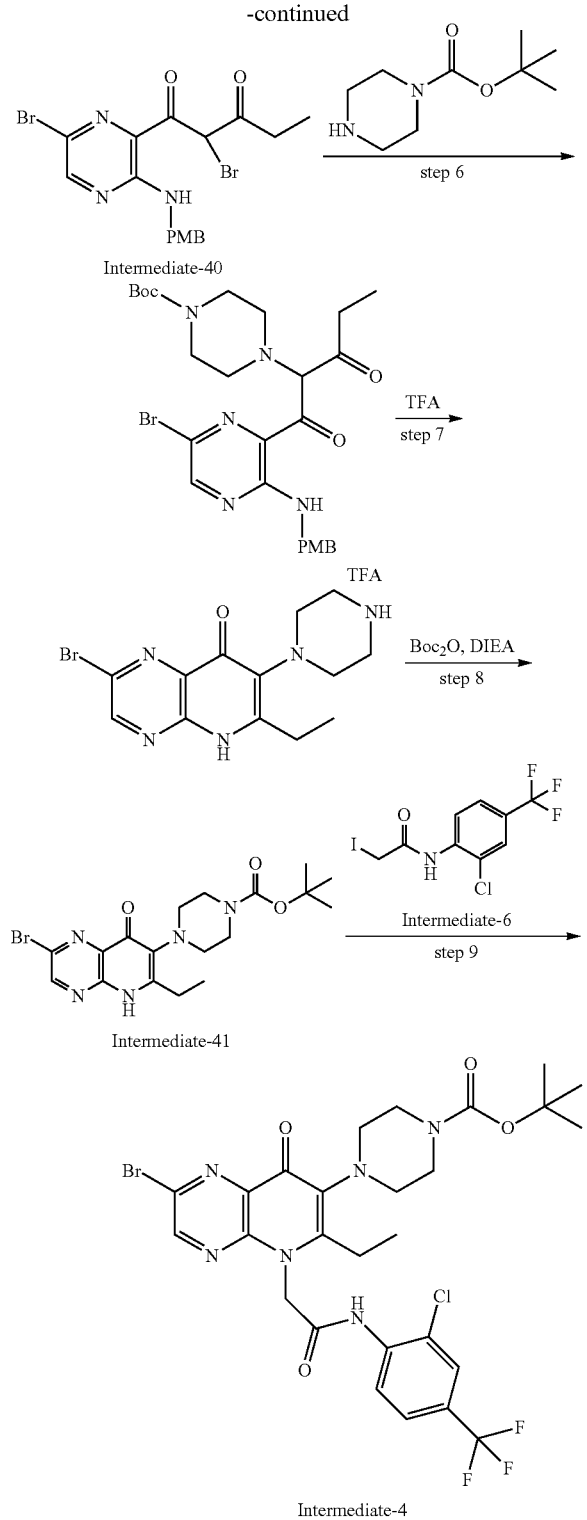

Step 1: Synthesis of methyl 3-(bis(4-methoxybenzyl)amino)-6-bromopyrazine-2-carboxylate To a solution of methyl 6-bromo-3-chloropyrazine-2-carboxylate (100.00 g, 397.67 mmol, 1.0 eq) in 1,4-dioxane (1000 mL) was added DIEA (77.09 g, 596.5 mmol, 1.5 eq) and bis(4-methoxybenzyl)amine (112.56 g, 437.44 mmol, 1.1 eq), the resulting mixture was stirred at 100° C. for 16 h. The reaction mixture was diluted with H₂O (800 mL) and extracted with EtOAc (400 mL*3). The combined organic layers were washed with brine (200 mL*2), dried over anhydrous Na₂SO₄, filtered and concentrated under reduced pressure. The residue was purified by silica gel chromatography (EtOAc/PE) to afford the title compound.

¹H NMR (400 MHz, CDCl₃) δ ppm 8.26 (s, 1H), 7.05 (d, 4H), 6.83 (d, 4H), 4.55 (s, 4H), 3.84 (s, 3H), 3.82-3.74 (m, 6H).

Step 2: Synthesis of 3-(bis(4-methoxybenzyl)amino)-6-bromopyrazine-2-carboxylic Acid To a solution of methyl 3-(bis(4-methoxybenzyl)amino)-6-bromopyrazine-2-carboxylate (161 g, 340 mmol, 1.0 eq) in MeOH (1500 mL), THF (1500 mL) and H₂O (1500 mL) was added LiOH—H₂O (57.2 g, 1.36 mol, 4.0 eq), the resulting mixture was stirred at room temperature overnight. To the mixture was added H₂O (1600 mL) and the pH adjusted to 2-3 with 1N HCl. The reaction mixture was concentrated under reduced pressure to remove organic solvent, the aqueous solution was extracted with DCM (600 mL*3). The combined organic layers were washed with brine (500 mL), dried over anhydrous Na₂SO₄, filtered and concentrated under reduced pressure to afford the title compound, which was used into the next step without further purification.

¹H NMR (400 MHz, CDCl₃) δ ppm 8.26 (s, 1H), 7.05 (d, 4H), 6.83 (d, 4H), 4.55 (s, 4H), 3.84 (s, 3H), 3.82-3.74 (m, 6H).

Step 3: Synthesis of 6-bromo-3-((4-methoxybenzyl)amino)pyrazine-2-carbonyl Chloride To a solution of 3-(bis(4-methoxybenzyl)amino)-6-bromopyrazine-2-carboxylic acid (140.00 g, 305.47 mmol, 1.0 eq) and DMF (233 mg, 3.05 mmol, 0.01 eq) in DCM (1400 mL) was added oxalyl dichloride (46.50 g, 366.6 mmol, 1.2 eq) dropwise at room temperature and the resulting mixture was stirred at room temperature for 2 h. The reaction mixture was concentrated under reduced pressure to afford the title compound, which was used directly in the next step without further purification.

Step 4: Synthesis of 1-(6-bromo-3-((4-methoxybenzyl)amino)pyrazin-2-yl)-3-hydroxypent-2-en-1-one To a solution of butan-2-one (44.49 g, 616.9 mmol, 2.2 eq) in THF (160 mL) was added LDA (2 M in THF, 308.5 mL, 616.9 mmol, 2.2 eq) at −65° C. and it was stirred at −65° C. for 0.5 h. Then 6-bromo-3-((4-methoxybenzyl)amino)pyrazine-2-carbonyl chloride (100.00 g, 280.42 mmol, 1.0 eq) in THF (1000 mL) was added dropwise to the mixture at −65° C. and the resulting mixture was stirred at −65° C. for 1 h. The reaction mixture was slowly poured into aqueous HCl solution (1 M, 1 L), and extracted with EtOAc (50 mL*3). The combined organic layers were washed with brine (50 mL*2), dried over anhydrous Na₂SO₄, filtered and concentrated under reduced pressure. The residue was purified by silica gel chromatography (EtOAc/PE) to afford the title compound.

¹H NMR (400 MHz, CDCl₃) δ ppm 15.01 (s, 1H), 8.96 (br s, 1H), 8.27 (s, 1H), 7.33-7.28 (m, 1H), 6.93-6.85 (m, 3H), 6.78 (s, 1H), 4.65 (d, 2H), 3.81 (s, 3H), 2.40 (q, 2H), 1.23 (t, 3H).

Step 5: Synthesis of 2-bromo-1-(6-bromo-3-((4-methoxybenzyl)amino)pyrazin-2-yl)pentane-1,3-dione To a solution of 1-(6-bromo-3-((4-methoxybenzyl)amino)pyrazin-2-yl)-3-hydroxypent-2-en-1-one (Intermediate-78) (19.00 g, 48.44 mmol, 1.0 eq) in DCM (200 mL) was added TsOH-H₂O (1.70 g, 39.7 mmol, 0.2 eq) and NBS (8.61 g, 48.4 mmol, 1.0 eq) at 0° C. and the resulting mixture was stirred at 0° C. for 1 h. The reaction mixture was diluted with H₂O (300 mL) and extracted with EtOAc (100 mL*3). The combined organic layers were washed with brine (50 mL*3), dried over anhydrous Na₂SO₄, filtered and concentrated under reduced pressure to afford the title compound, which was used in the next step without further purification.

LCMS: 472.0 [M+H]⁺.

Step 6: Synthesis of tert-butyl 4-(1-(6-bromo-3-((4-methoxybenzyl)amino)pyrazin-2-yl)-1,3-dioxopentan-2-yl)piperazine-1-carboxylate To a solution of 2-bromo-1-(6-bromo-3-((4-methoxybenzyl)amino)pyrazin-2-yl)pentane-1,3-dione (Intermediate-40) (23.00 g, 48.82 mmol, 1.0 eq) in THF (250 mL) was added DIEA (12.61 g, 50.93 mmol, 2.0 eq) and tert-butyl piperazine-1-carboxylate (9.09 g, 48.8 mmol, 1.0 eq) and the resulting mixture was stirred at room temperature for 1 h. The reaction mixture was diluted with H₂O (200 mL) and extracted with EtOAc (100 mL*3). The combined organic layers were washed with brine (50 mL*3), dried over Na₂SO₄, filtered and concentrated under reduced pressure. The residue was purified by silica gel chromatography (EtOAc/PE) to afford the title compound.

$^1$H NMR (400 MHz, CDCl₃) δ ppm 8.80 (br t, 1H), 8.30 (s, 1H), 7.25 (s, 1H), 6.88 (d, 2H), 5.32 (s, 1H), 4.63 (dq, 2H), 3.81 (s, 3H), 3.53-3.35 (m, 4H), 3.02-2.83 (m, 3H), 2.72-2.59 (m, 2H), 1.59 (s, 2H), 1.46 (s, 9H), 1.14 (t, 3H).

Step 7: Synthesis of 2-bromo-6-ethyl-7-(piperazin-1-yl)pyrido[2,3-b]pyrazin-8 (5H)-one trifluoroacetate tert-butyl 4-(1-(6-bromo-3-((4-methoxybenzyl)amino)pyrazin-2-yl)-1,3-dioxopentan-2-yl)piperazine-1-carboxylate (21.00 g, 36.43 mmol, 1.0 eq) was dissolved into TFA (40 mL) and then it was stirred at 50° C. for 1 h. The reaction mixture was concentrated under reduced pressure to afford the title compound, which was used in the next step without further purification.

LCMS: 338.1 [M+H]⁺.

Step 8: Synthesis of tert-butyl 4-(2-bromo-6-ethyl-8-oxo-5,8-dihydropyrido[2,3-b]pyrazin-7-yl)piperazine-1-carboxylate To a solution of 2-bromo-6-ethyl-7-(piperazin-1-yl)pyrido[2,3-b]pyrazin-8 (5H)-one trifluoroacetate (12.00 g, 35.48 mmol, 1.0 eq) in DCM (150 mL) was added DIEA (22.92 g, 177.4 mmol, 5.0 eq) and Boc₂O (7.68 g, 35.5 mmol, 1.0 eq), and then the resulting mixture was stirred at room temperature for 1 h. The reaction mixture was diluted with H₂O (200 mL) and extracted with DCM (50 mL*3). The combined organic layers were washed with brine (50 mL*3), dried over anhydrous Na₂SO₄, filtered and concentrated under reduced pressure. The residue was triturated in a mixed solvent of DCM/PE (DCM:PE=2:1, 30 mL) at room temperature for 10 mins and then filtered. The filter cake was dried under reduced pressure to afford the title compound, which was used in the next step without further purification.

LCMS: 440.1 [M+H]⁺.

Step 9: Synthesis of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate To a solution of tert-butyl 4-(2-bromo-6-ethyl-8-oxo-5,8-dihydropyrido[2,3-b]pyrazin-7-yl)piperazine-1-carboxylate (Intermediate-41) (13.00 g, 29.66 mmol, 1.0 eq) in DMF (600 mL) was added K₂CO₃ (4.10 g, 29.66 mmol, 1.0 eq) and N-(2-chloro-4-(trifluoromethyl)phenyl)-2-iodoacetamide (Intermediate-6) (10.78 g, 29.66 mmol, 1.0 eq) and the mixture was stirred at room temperature for 1.5 h. Then the second batch of N-(2-chloro-4-(trifluoromethyl)phenyl)-2-iodoacetamide (Intermediate-6) (2.16 g, 5.93 mmol, 0.2 eq) and K₂CO₃ (819 mg, 5.93 mmol, 0.2 eq) was added, and the reaction was stirred at room temperature for another 2 h. The reaction mixture was poured into H₂O (300 mL), the resulting suspension was filtered and the filter cake was dried under reduced pressure. The resulting crude product was purified by silica gel chromatography (EtOAc/PE) to afford the title compound.

LCMS: 675.2 [M+H]⁺.

Intermediate-15: tert-butyl 4-(1-(6-bromo-3-((2-(tert-butoxy)-2-oxoethyl)amino)-5-methylpyrazin-2-yl)-1,3-dioxopentan-2-yl)piperazine-1-carboxylate Intermediate-22: 2-(2-bromo-6-ethyl-3-methyl-8-oxo-7-(piperazin-1-yl)pyrido[2,3-b]pyrazin-5 (8H)-yl)-N-(2-chloro-4-(trifluoromethyl)phenyl)acetamide trifluoroacetate Intermediate-23: 2-(2-bromo-6-ethyl-7-(4-(5-hydroxy-6-methylpyrimidine-4-carbonyl)piperazin-1-yl)-3-methyl-8-oxopyrido[2,3-b]pyrazin-5 (8H)-yl)-N-(2-chloro-4-(trifluoromethyl)phenyl)acetamide Intermediate-42: tert-butyl 4-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)piperazine-1-carboxylate Intermediate-25: 2-(2-bromo-7-(4-(tert-butoxycarbonyl)piperazin-1-yl)-6-ethyl-3-methyl-8-oxopyrido[2,3-b]pyrazin-5 (8H)-yl)acetic Acid

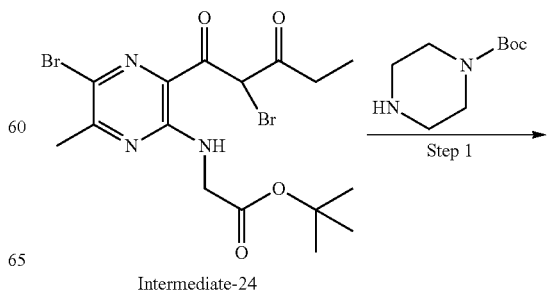

Intermediate-24

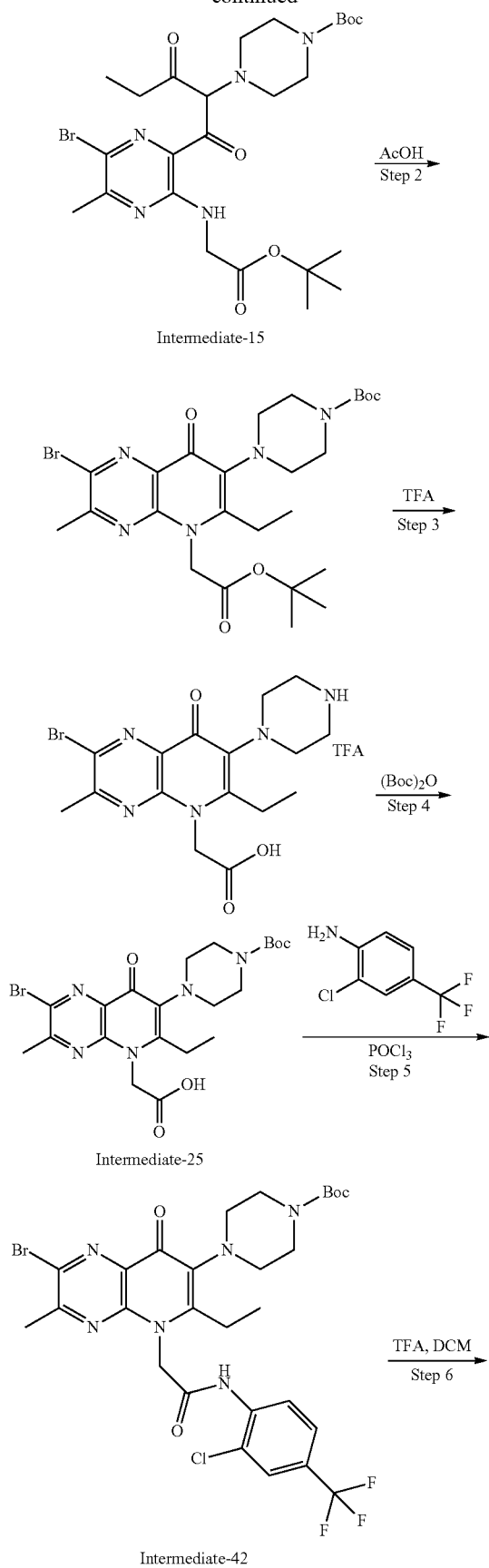

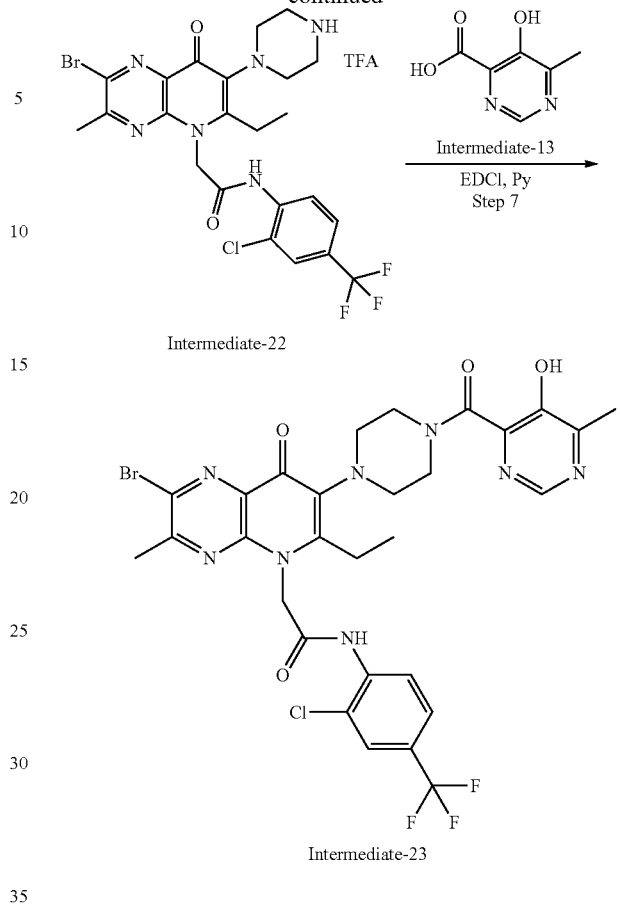

Step 1. Synthesis of tert-butyl 4-(1-(6-bromo-3-((2-(tert-butoxy)-2-oxoethyl)amino)-5-methylpyrazin-2-yl)-1,3-dioxopentan-2-yl)piperazine-1-carboxylate To a solution of tert-butyl (5-bromo-3-(2-bromo-3-oxopentanoyl)-6-methylpyrazin-2-yl)glycinate (Intermediate-24) (19.00 g, 27.76 mmol, 1.0 eq) in THF (200 mL) was added DIEA (7.17 g, 55.5 mmol, 2.0 eq) and tert-butyl piperazine-1-carboxylate (7.75 g, 41.6 mmol, 1.5 eq), the resulting mixture was stirred at room temperature for 1 h. The reaction mixture was quenched by H$_2$O (100 mL) and extracted with EtOAc (50 mL*3). The combined organic layers were washed with brine (30 mL), dried over anhydrous Na$_2$SO$_4$, filtered and concentrated under reduced pressure. The residue was purified by silica gel chromatography (EtOAc/PE) to afford the title compound.
LCMS: 586.3 [M+H]$^+$.

Step 2. Synthesis of tert-butyl 4-(2-bromo-5-(2-(tert-butoxy)-2-oxoethyl)-6-ethyl-3-methyl-8-oxo-5,8-dihydropyrido[2,3-b]pyrazin-7-yl)piperazine-1-carboxylate A solution of tert-butyl 4-(1-(6-bromo-3-((2-(tert-butoxy)-2-oxoethyl)amino)-5-methylpyrazin-2-yl)-1,3-dioxopentan-2-yl)piperazine-1-carboxylate (Intermediate-15) (9.60 g, 16.4 mmol, 1.0 eq) in AcOH (100 mL) was stirred at 60° C. for 12 h. The reaction mixture was quenched by saturated NaHCO$_3$ aqueous solution (100 mL) and extracted with EtOAc (50 mL*3). The combined organic layers were washed with brine (30 mL), dried over anhydrous Na$_2$SO$_4$, filtered and concentrated under reduced pressure. The residue was purified by silica gel chromatography (EtOAc/PE) to afford the title compound.
LCMS: 566.2 [M+H]$^+$.

Step 3. Synthesis of 2-(2-bromo-6-ethyl-3-methyl-8-oxo-7-(piperazin-1-yl)pyrido[2,3-b]pyrazin-5 (8H)-yl)acetic Acid Trifluoroacetate To a solution of tert-butyl 4-(2-bromo-5-(2-(tert-butoxy)-2-oxoethyl)-6-ethyl-3-methyl-8-oxo-5,8-dihydropyrido[2,3-b]pyrazin-7-yl)piperazine-1-carboxylate (3.50 g, 6.18 mmol, 1.0 eq) in DCM (10 mL) was added TFA (50 mL) and the resulting mixture was stirred at 30° C. for 1 h. The reaction mixture was concentrated under reduced pressure to afford the title compound, which was used into the next step without further purification.
LCMS: 466.2 [M+H]$^+$.

Step 4. Synthesis of 2-(2-bromo-7-(4-(tert-butoxycarbonyl)piperazin-1-yl)-6-ethyl-3-methyl-8-oxopyrido[2,3-b]pyrazin-5 (8H)-yl)acetic Acid To a solution of 2-(2-bromo-6-ethyl-3-methyl-8-oxo-7-piperazin-1-yl-pyrido[2,3-b]pyrazin-5-yl)acetic acid trifluoroacetate (2.50 g, 6.09 mmol, 1.0 eq) in DCM (20 mL) was added (Boc)$_2$O (1.33 g, 6.09 mmol, 1.0 eq) and DIEA (3.94 g, 30.5 mmol, 5.0 eq), and the resulting mixture was stirred at 30° C. for 1 h. The reaction mixture was diluted with H$_2$O (100 mL) and extracted with EtOAc (50 mL*3). The combined organic layers were washed with brine (30 mL), dried over anhydrous Na$_2$SO$_4$, filtered and concentrated under reduced pressure. The residue was purified by reverse phase HPLC (C18 column, water (0.1% FA)-ACN) to afford the title compound.
LCMS: 510.1 [M+H]$^+$.

Step 5. Synthesis of tert-butyl 4-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)piperazine-1-carboxylate To a solution of 2-(2-bromo-7-(4-(tert-butoxycarbonyl)piperazin-1-yl)-6-ethyl-3-methyl-8-oxopyrido[2,3-b]pyrazin-5 (8H)-yl)acetic acid (Intermediate-25) (2.00 g, 3.92 mmol, 1.0 eq) and 2-chloro-4-(trifluoromethyl)aniline (766 mg, 3.92 mmol, 1.0 eq) in pyridine (5 mL) and DCM (5 mL) was added POCl$_3$ (901 mg, 5.88 mmol, 1.5 eq) at −10° C., and it was stirred at −10° C. for 1 h. The reaction mixture was quenched by H$_2$O (100 mL) and extracted with EtOAc (50 mL*3). The combined organic layers were washed with brine (30 mL), dried over anhydrous Na$_2$SO$_4$, filtered and concentrated under reduced pressure. The residue was purified by flash silica gel chromatography (Eluent of EtOAc/PE) to afford the title compound.
LCMS: 689.3 [M+H]$^+$.

Step 6. Synthesis of 2-(2-bromo-6-ethyl-3-methyl-8-oxo-7-(piperazin-1-yl)pyrido[2,3-b]pyrazin-5 (8H)-yl)-N-(2-chloro-4-(trifluoromethyl)phenyl) acetamide Trifluoroacetate To a solution of tert-butyl 4-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)piperazine-1-carboxylate (1.00 g, 1.45 mmol, 1.0 eq) in DCM (40 mL) was added TFA (10 mL), and it was stirred at room temperature for 1 h. The reaction mixture was concentrated under reduced pressure to afford the title compound, which was used into the next step without further purification.
LCMS: 589.0 [M+H]$^+$.

Step 7. Synthesis of 2-(2-bromo-6-ethyl-7-(4-(5-hydroxy-6-methylpyrimidine-4-carbonyl)piperazin-1-yl)-3-methyl-8-oxopyrido[2,3-b]pyrazin-5 (8H)-yl)-N-(2-chloro-4-(trifluoromethyl)phenyl)acetamide To a mixture of 2-(2-bromo-6-ethyl-3-methyl-8-oxo-7-piperazin-1-yl-pyrido[2,3-b]pyrazin-5-yl)-N-[2-chloro-4-(trifluoromethyl)phenyl]acetamide trifluoroacetate (Intermediate-22) (1.00 g, 1.70 mmol, 1.0 eq) and 5-hydroxy-6-methyl-pyrimidine-4-carboxylic acid (524 mg, 3.40 mmol, 2.0 eq) in pyridine (10 mL) were added EDCI (652 mg, 3.40 mmol, 2.0 eq), and then the resulting mixture was stirred at room temperature for 1 h. The reaction mixture was quenched by saturated NH$_4$Cl aqueous solution (100 mL) and extracted with EtOAc (50 mL*3). The combined organic layers were washed with brine (30 mL), dried over anhydrous Na$_2$SO$_4$, filtered and concentrated under reduced pressure. The residue was purified by reverse phase HPLC (C18 column, water (0.1% FA)-ACN) to afford the title compound.
LCMS: 725.1 [M+H]$^+$.

$^1$H NMR (400 MHz, CDCl3) δ ppm 12.05 (br s, 1H), 8.77 (s, 1H), 8.58 (s, 1H), 8.42 (d, 1H), 7.64 (d, 1H), 7.53 (br d, 1H), 5.58 (br d, 1H), 5.47 (br s, 2H), 4.86-4.70 (m, 1H), 3.99 (br t, 2H), 3.58-3.42 (m, 1H), 3.26 (br d, 2H), 3.16-3.02 (m, 1H), 2.93-2.77 (m, 2H), 2.77 (s, 3H), 2.57 (s, 3H), 1.34 (t, 3H).

Intermediate-16: N-(2-chloro-4-(trifluoromethyl)phenyl)-2-(6-ethyl-2-methoxy-3-methyl-8-oxo-7-(piperazin-1-yl)pyrido[2,3-b]pyrazin-5 (8H)-yl)acetamide Hydrochloride

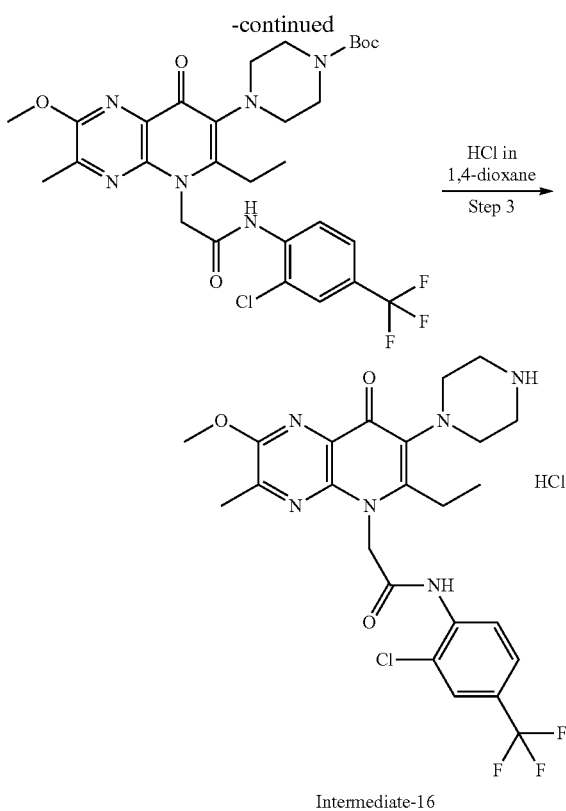

Intermediate-16

Step 1. Synthesis of 2-(7-(4-(tert-butoxycarbonyl) piperazin-1-yl)-6-ethyl-2-methoxy-3-methyl-8-oxopyrido[2,3-b]pyrazin-5 (8H)-yl)acetic Acid To a mixture of MeOH (38 mg, 1.2 mmol, 3.5 eq) in THF (6 mL) was added NaH (48 mg, 1.2 mmol, 60% in mineral oil, 3.5 eq) at 0° C. and then it was stirred at 0° C. for 0.5 h. A solution of tert-butyl 4-(1-(6-bromo-3-((2-(tert-butoxy)-2-oxoethyl)amino)-5-methylpyrazin-2-yl)-1,3-dioxopentan-2-yl)piperazine-1-carboxylate (Intermediate-15) (200 mg, 342 mol, 1.0 eq) in THF (4 mL) was added to the reaction at 0° C. and the resulting mixture was stirred at room temperature for 0.5 h. The mixture was quenched by H₂O (30 mL), the pH was adjusted to 4 by aqueous HCl solution (1N), and extracted with EtOAc (30 mL*2). The combined organic layers were dried over anhydrous Na₂SO₄, filtered and the filtrate was concentrated under reduced pressure to afford title compound, which was used directly in the next step without further purification.

LCMS: 462.1 [M+H]⁺.

Step 2. Synthesis of tert-butyl 4-(5-(2-((2-chloro-4-(trifluoromethyl)phenyl)amino)-2-oxoethyl)-6-ethyl-2-methoxy-3-methyl-8-oxo-5,8-dihydropyrido[2,3-b]pyrazin-7-yl)piperazine-1-carboxylate To a solution of 2-(7-(4-(tert-butoxycarbonyl)piperazin-1-yl)-6-ethyl-2-methoxy-3-methyl-8-oxopyrido[2,3-b]pyrazin-5 (8H)-yl)acetic acid (100 mg, 217 mol, 1.0 eq) and 2-chloro-4-(trifluoromethyl)aniline (47 mg, 0.24 mmol, 1.1 eq) in pyridine (1 mL) and DCM (1 mL) was added POCl₃ (50 mg, 0.33 mmol, 1.5 eq) dropwise at −10° C., and the resulting mixture was stirred at −10° C. for 10 mins. The reaction mixture was quenched by H₂O (30 mL) and extracted with EtOAc (30 mL*2). The combined organic layers were washed with saturated citric acid aqueous solution (30 mL), then dried over anhydrous Na₂SO₄, filtered and the filtrate was concentrated under reduced pressure. The residue was purified by flash silica gel chromatography (Eluent of EtOAc/PE) to afford the title compound.

LCMS: 639.3 [M+H]⁺.

Step 3. Synthesis of N-(2-chloro-4-(trifluoromethyl) phenyl)-2-(6-ethyl-2-methoxy-3-methyl-8-oxo-7-(piperazin-1-yl)pyrido[2,3-b]pyrazin-5 (8H)-yl)acetamide Hydrochloride To tert-butyl 4-(5-(2-((2-chloro-4-(trifluoromethyl)phenyl)amino)-2-oxoethyl)-6-ethyl-2-methoxy-3-methyl-8-oxo-5,8-dihydropyrido[2,3-b]pyrazin-7-yl)piperazine-1-carboxylate (32 mg, 50 mol, 1.0 eq) was added a solution of HCl in 1,4-dioxane (2 mL, 4 M) and it was stirred at room temperature for 0.2 h. The mixture was concentrated to afford the title compound, which was used directly in the next step without further purification.

LCMS: 539.1 [M+H]⁺.

Intermediate-17: tert-butyl (E)-4-(5-(2-((2-chloro-4-(trifluoromethyl)phenyl)amino)-2-oxoethyl)-2-(2-ethoxyvinyl)-6-ethyl-8-oxo-5,8-dihydropyrido[2,3-b]pyrazin-7-yl)piperazine-1-carboxylate Intermediate-18: tert-butyl 4-(5-(2-((2-chloro-4-(trifluoromethyl)phenyl)amino)-2-oxoethyl)-6-ethyl-2-formyl-8-oxo-5,8-dihydropyrido[2,3-b]pyrazin-7-yl)piperazine-1-carboxylate Intermediate-19: N-(2-chloro-4-(trifluoromethyl) phenyl)-2-(2-(difluoromethyl)-6-ethyl-8-oxo-7-(piperazin-1-yl)pyrido[2,3-b]pyrazin-5 (8H)-yl)acetamide Hydrochloride

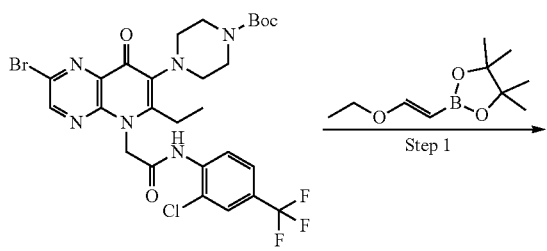

Intermediate-17

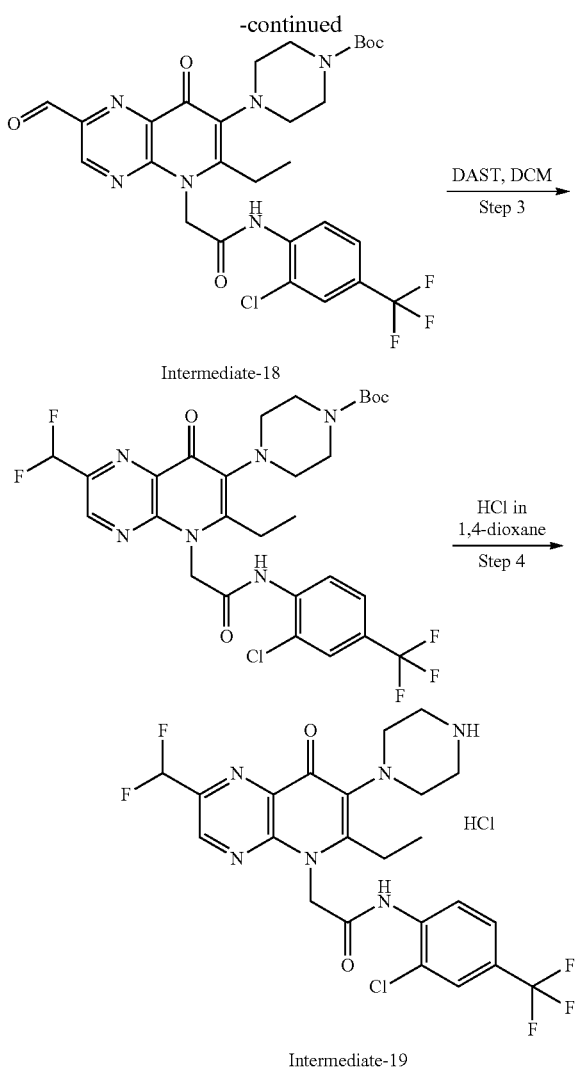

Intermediate-18

Intermediate-19

Step 1. Synthesis of tert-butyl (E)-4-(5-(2-((2-chloro-4-(trifluoromethyl)phenyl)amino)-2-oxoethyl)-2-(2-ethoxyvinyl)-6-ethyl-8-oxo-5,8-dihydropyrido[2,3-b]pyrazin-7-yl)piperazine-1-carboxylate to a solution of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (Intermediate-4) (200 mg, 296 mol, 1.0 eq) and (E)-2-(2-ethoxyvinyl)-4,4,5,5-tetramethyl-1,3,2-dioxaborolane (59 mg, 296 mol, 1.0 eq) in 1,4-dioxane (5 mL) and H$_2$O (1 mL) was added Pd(dppf)Cl$_2$ (22 mg, 29 mol, 0.1 eq) and K$_3$PO$_4$ (126 mg, 593 mol, 2.0 eq). The mixture was stirred at 80° C. for 1 h under N$_2$ atmosphere. The reaction mixture was concentrated under reduced pressure and then purified by silica gel chromatography (EtOAc/PE) to afford the title compound.

LCMS: 665.2 [M+H]$^+$.

Step 2. Synthesis of tert-butyl 4-(5-(2-((2-chloro-4-(trifluoromethyl)phenyl)amino)-2-oxoethyl)-6-ethyl-2-formyl-8-oxo-5,8-dihydropyrido[2,3-b]pyrazin-7-yl)piperazine-1-carboxylate To a solution of tert-butyl (E)-4-(5-(2-((2-chloro-4-(trifluoromethyl)phenyl)amino)-2-oxoethyl)-2-(2-ethoxyvinyl)-6-ethyl-8-oxo-5,8-dihydropyrido[2,3-b]pyrazin-7-yl)piperazine-1-carboxylate (Intermediate-17) (100 mg, 150 mol, 1.0 eq) in 1,4-dioxane (2 mL) and H$_2$O (0.4 mL) was added K$_2$OsO$_4$·2H$_2$O (11 mg, 30 mol, 0.2 eq) and NaIO$_4$ (64 mg, 0.30 mmol, 2.0 eq), and then the mixture was stirred at room temperature for 2 h. The reaction mixture was quenched with H$_2$O (10 mL), extracted with EtOAc (10 mL*2). The combined organic layers were washed with brine (10 mL), dried over anhydrous Na$_2$SO$_4$, filtered and the filtrate was concentrated under reduced pressure. The residue was purified by silica gel chromatography (EtOAc/PE) to afford the title compound.

LCMS: 623.2 [M+H]$^+$.

Step 3. Synthesis of tert-butyl 4-(5-(2-((2-chloro-4-(trifluoromethyl)phenyl)amino)-2-oxoethyl)-2-(difluoromethyl)-6-ethyl-8-oxo-5,8-dihydropyrido[2,3-b]pyrazin-7-yl)piperazine-1-carboxylate To a solution of tert-butyl 4-(5-(2-((2-chloro-4-(trifluoromethyl)phenyl)amino)-2-oxoethyl)-6-ethyl-2-formyl-8-oxo-5,8-dihydropyrido[2,3-b]pyrazin-7-yl)piperazine-1-carboxylate (Intermediate-18) (20 mg, 32 mol, 1.0 eq) in DCM (2 mL) was added DAST (16 mg, 96 mol, 3.0 eq) at 0° C. and it was stirred at 0° C. for 3 h under N$_2$ atmosphere. The reaction mixture was poured into saturated NaHCO$_3$ aqueous solution (10 mL), extracted with DCM (10 mL*2). The organic layers were washed with brine (10 mL), dried over anhydrous Na$_2$SO$_4$, filtered and the filtrate was concentrated under reduced pressure to afford the title compound, which was used directly in the next step without further purification.

LCMS: 645.2 [M+H]$^+$.

Step 4. Synthesis of N-(2-chloro-4-(trifluoromethyl)phenyl)-2-(2-(difluoromethyl)-6-ethyl-8-oxo-7-(piperazin-1-yl)pyrido[2,3-b]pyrazin-5 (8H)-yl)acetamide Hydrochloride To tert-butyl 4-(5-(2-((2-chloro-4-(trifluoromethyl)phenyl)amino)-2-oxoethyl)-2-(difluoromethyl)-6-ethyl-8-oxo-5,8-dihydropyrido[2,3-b]pyrazin-7-yl)piperazine-1-carboxylate (15 mg, 23 mol, 1.0 eq) was added a solution of HCl in 1,4-dioxane (0.5 mL, 4 M) and it was stirred at room temperature for 0.5 h. The mixture was concentrated under reduced pressure to afford the title compound, which was used directly in the next step without further purification.

LCMS: 545.2 [M+H]$^+$.

Intermediate-20: N-(2-chloro-4-(trifluoromethyl)phenyl)-2-(6-ethyl-8-oxo-7-(piperazin-1-yl)-2-(prop-1-yn-1-yl)pyrido[2,3-b]pyrazin-5 (8H)-yl)acetamide Trifluoroacetate

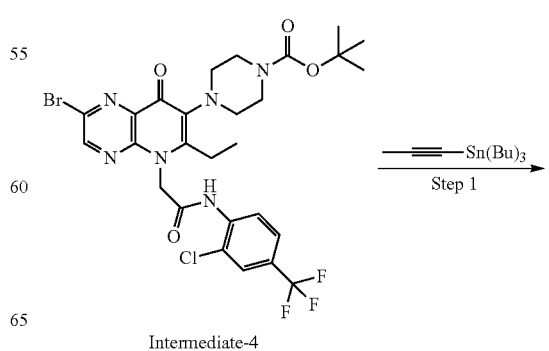

Intermediate-4

-continued

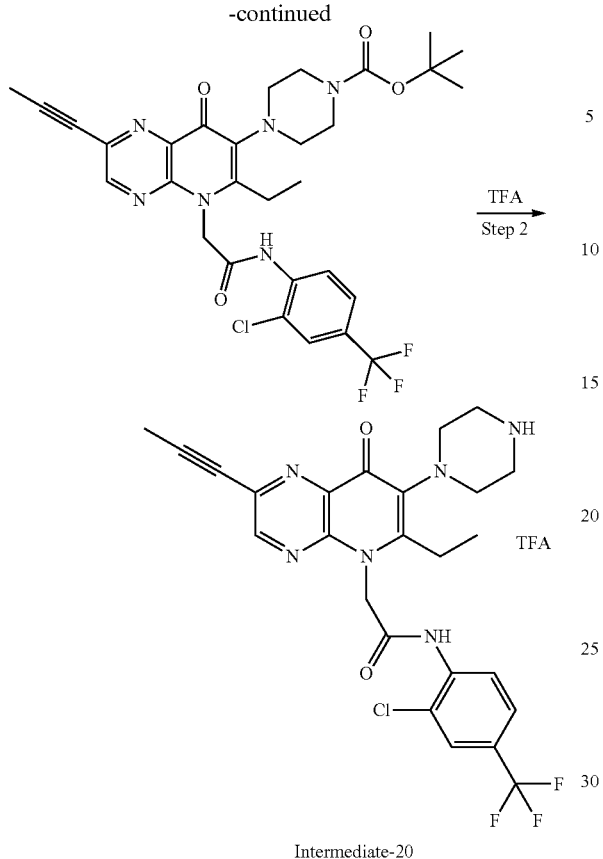

Intermediate-20

Step 1: Synthesis of tert-butyl 4-(5-(2-((2-chloro-4-(trifluoromethyl)phenyl)amino)-2-oxoethyl)-6-ethyl-8-oxo-2-(prop-1-yn-1-yl)-5,8-dihydropyrido[2,3-b]pyrazin-7-yl)piperazine-1-carboxylate To a solution of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (Intermediate-4) (80 mg, 0.12 mmol, 1.0 eq) and tributyl(prop-1-yn-1-yl)stannane (59 mg, 0.18 mmol, 1.5 eq) in toluene (1 mL) was added CuI (5 mg, 23 mol, 0.2 eq) and Pd(PPh$_3$)$_2$Cl$_2$ (8 mg, 12 µmol, 0.1 eq). Then the mixture was stirred at 60° C. for 15 h under N$_2$ atmosphere. The reaction mixture was poured into ice-water (10 mL) and extracted with EtOAc (10 mL*3). The combined organic layers were washed with brine (20 mL), dried over anhydrous Na$_2$SO$_4$, and concentrated under reduced pressure. The residue was purified by silica gel chromatography (EtOAc/PE) to afford the title compound.

LCMS: 633.4[M+H]$^+$.

Step 2: Synthesis of N-(2-chloro-4-(trifluoromethyl)phenyl)-2-(6-ethyl-8-oxo-7-(piperazin-1-yl)-2-(prop-1-yn-1-yl)pyrido[2,3-b]pyrazin-5 (8H)-yl)acetamide Trifluoroacetate To a solution of tert-butyl 4-(5-(2-((2-chloro-4-(trifluoromethyl)phenyl)amino)-2-oxoethyl)-6-ethyl-8-oxo-2-(prop-1-yn-1-yl)-5,8-dihydropyrido[2,3-b]pyrazin-7-yl)piperazine-1-carboxylate (40 mg, 63 mol, 1.0 eq) in DCM (1 mL) was added TFA (0.4 mL) and the resulting mixture was stirred at room temperature for 1 h. The reaction mixture was concentrated under reduced pressure to afford the title compound, which was used directly in the next step without further purification.

LCMS: 533.4[M+H]$^+$.

Intermediate-21: 2-(2-bromo-6-ethyl-7-(4-(5-hydroxy-6-methylpyrimidine-4-carbonyl)piperazin-1-yl)-8-oxopyrido[2,3-b]pyrazin-5 (8H)-yl)-N-(2-chloro-4-(trifluoromethyl)phenyl)acetamide

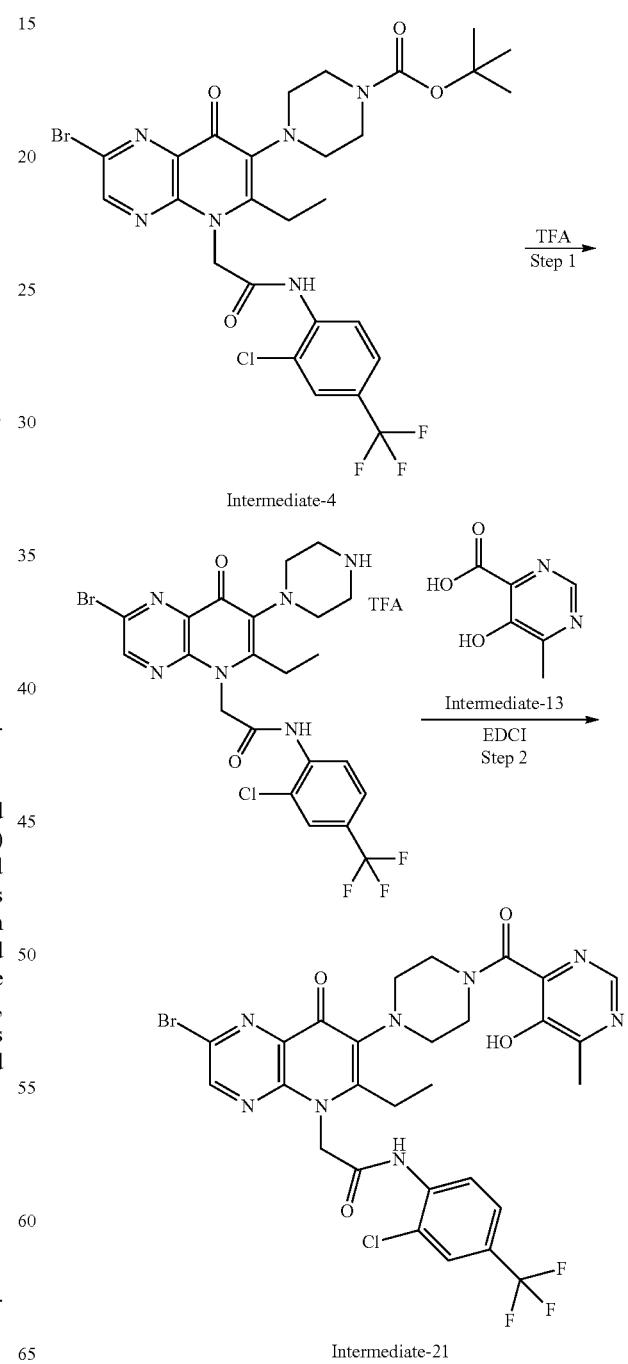

Intermediate-21

Step 1. Synthesis of 2-(2-bromo-6-ethyl-8-oxo-7-(piperazin-1-yl)pyrido[2,3-b]pyrazin-5 (8H)-yl)-N-(2-chloro-4-(trifluoromethyl)phenyl)acetamide Trifluoroacetate To a solution of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (Intermediate-4) (70 mg, 0.10 mmol, 1.0 eq) in DCM (1.2 mL) was added TFA (0.3 mL), and the resulting mixture was stirred at room temperature for 0.5 h. The reaction mixture was concentrated under reduced pressure to afford the title compound, which was used directly in the next step without further purification.

LCMS: 575.2 [M+H]$^+$.

Step 2. Synthesis of 2-[2-bromo-6-ethyl-7-[4-(5-hydroxy-6-methyl-pyrimidine-4-carbonyl)piperazin-1-yl]-8-oxo-pyrido[2,3-b]pyrazin-5-yl]-N-[2-chloro-4-(trifluoromethyl)phenyl]acetamide To a solution of 5-hydroxy-6-methylpyrimidine-4-carboxylic acid (Intermediate-13) (64 mg, 0.42 mmol, 4.0 eq) in pyridine (1 mL) was added EDCI (80 mg, 0.42 mmol, 4.0 eq) and 2-(2-bromo-6-ethyl-8-oxo-7-(piperazin-1-yl)pyrido[2,3-b]pyrazin-5 (8H)-yl)-N-(2-chloro-4-(trifluoromethyl)phenyl)acetamide trifluoroacetate (60 mg, 0.10 mmol, 1.0 eq), the resulting mixture was stirred at 40° C. for 1 h. The reaction mixture was concentrated under reduced pressure to give a residue. The residue was purified by reverse phase HPLC (C18 column, H$_2$O (10 mmol/L NH$_4$HCO$_3$-ACN) to afford the title compound.

LCMS: 711.2 [M+H]$^+$.

$^1$H NMR (400 MHz, CDCl$_3$) δ 11.80 (br s, 1H), 8.68 (s, 1H), 8.59 (s, 2H), 8.46 (br d, 1H), 7.66 (s, 1H), 7.56-7.49 (m, 1H), 5.69-5.54 (m, 1H), 5.53-5.30 (m, 2H), 4.87-4.69 (m, 1H), 4.05-3.90 (m, 2H), 3.60-3.40 (m, 1H), 3.35-3.20 (m, 2H), 3.17-3.00 (m, 1H), 2.90-2.69 (m, 2H), 2.57 (s, 3H), 1.36 (br t, 3H).

Intermediate-26: (E)-N-(2-chloro-4-(trifluoromethyl)phenyl)-2-(2-(2-ethoxyvinyl)-6-ethyl-8-oxo-7-(piperazin-1-yl)pyrido[2,3-b]pyrazin-5 (8H)-yl)acetamide Trifluoroacetate

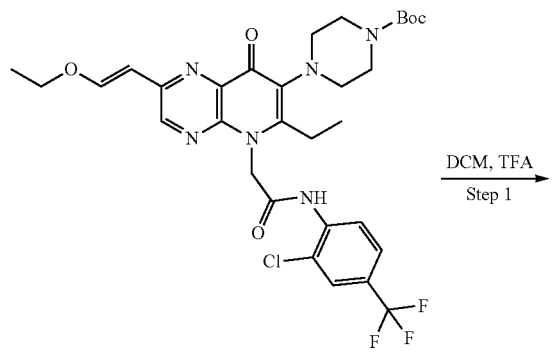

Intermediate-17

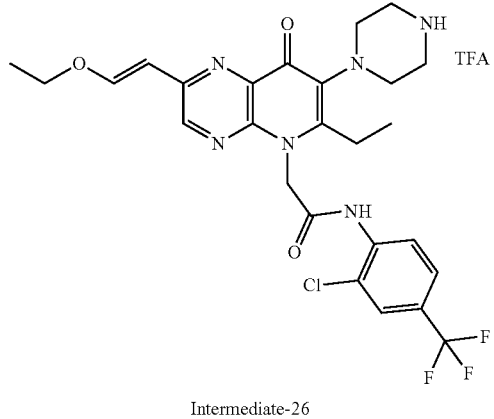

Intermediate-26

Step 1. Synthesis of (E)-N-(2-chloro-4-(trifluoromethyl)phenyl)-2-(2-(2-ethoxyvinyl)-6-ethyl-8-oxo-7-(piperazin-1-yl)pyrido[2,3-b]pyrazin-5 (8H)-yl)acetamide Trifluoroacetate To a solution of tert-butyl (E)-4-(5-(2-((2-chloro-4-(trifluoromethyl)phenyl)amino)-2-oxoethyl)-2-(2-ethoxyvinyl)-6-ethyl-8-oxo-5,8-dihydropyrido[2,3-b]pyrazin-7-yl)piperazine-1-carboxylate (Intermediate-17) (30 mg, 45 mol, 1 eq) in DCM (0.8 mL) was added TFA (0.2 mL) and the resulting mixture was stirred at room temperature for 0.5 h. The reaction mixture was concentrated under reduced pressure to afford the title compound, which was used in the next step without further purification.

LCMS: 565.2 [M+H]$^+$.

Intermediate-24: tert-butyl (5-bromo-3-(2-bromo-3-oxopentanoyl)-6-methylpyrazin-2-yl)glycinate Intermediate-28: rac-2-(7-(−5-(tert-butoxycarbonyl)-2,5-diazabicyclo[4.2.0]octan-2-yl)-6-ethyl-2-methoxy-3-methyl-8-oxopyrido[2,3-b]pyrazin-5 (8H)-yl)acetic Acid (Racemic Mixture, Trans)

Intermediate-29: rac-2-(7-(2,5-diazabicyclo[4.2.0]octan-2-yl)-6-ethyl-2-methoxy-3-methyl-8-oxopyrido[2,3-b]pyrazin-5 (8H)-yl)-N-(2-chloro-4-(trifluoromethyl)phenyl)acetamide Hydrochloride (Racemic Mixture, Trans)

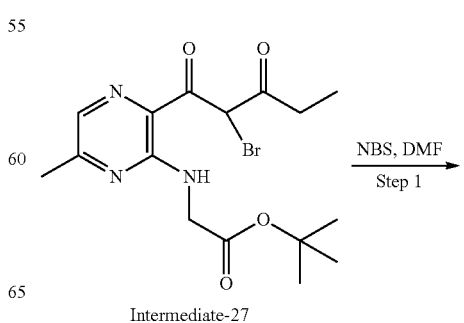

Intermediate-27

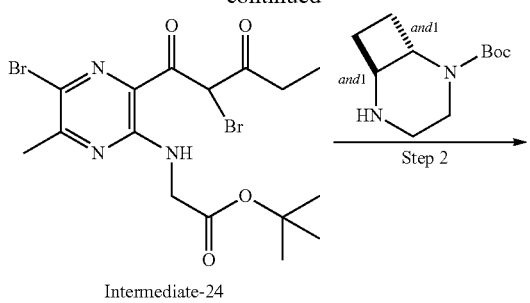

Intermediate-24

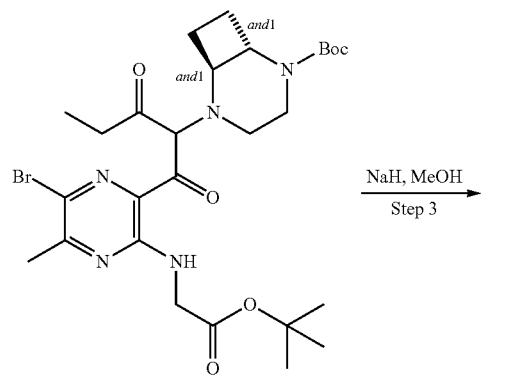

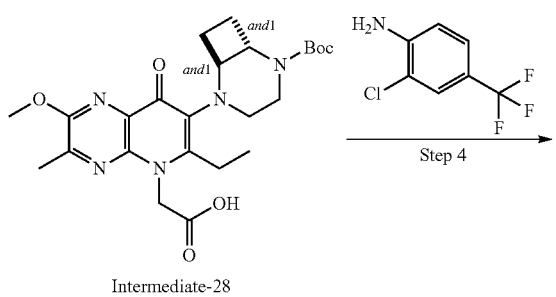

Intermediate-28

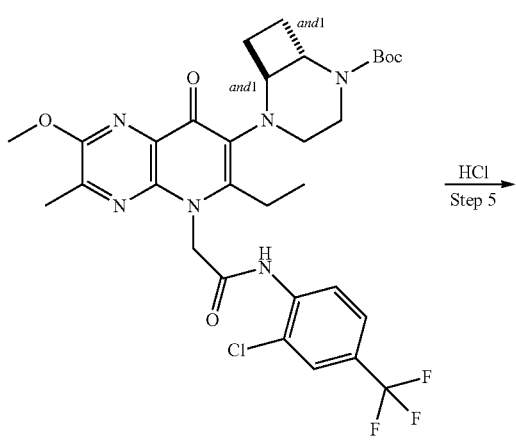

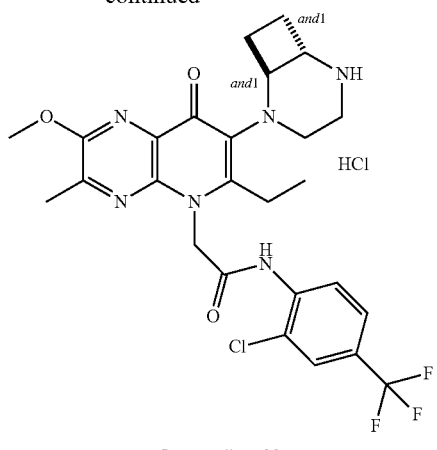

Intermediate-29

Step 1. Synthesis of tert-butyl (5-bromo-3-(2-bromo-3-oxopentanoyl)-6-methylpyrazin-2-yl)glycinate To a solution of tert-butyl (3-(2-bromo-3-oxopentanoyl)-6-methylpyrazin-2-yl)glycinate (Intermediate-27) (11.00 g, 27.48 mmol, 1.0 eq) in DMF (110 mL) was added NBS (2.45 g, 13.74 mmol, 0.5 eq) and the resulting mixture was stirred at room temperature for 1 h. Second batch of NBS (978 mg, 5.50 mmol, 0.2 eq) was added and the reaction was stirred for another 0.3 h at room temperature. The reaction mixture was diluted with H$_2$O (50 mL), extracted with EtOAc (50 mL). The organic phase was dried over anhydrous Na$_2$SO$_4$, filtered and concentrated under reduced pressure to afford title compound, which was used directly in the next step without further purification.

Step 2. Synthesis of rac-tert-butyl-5-(1-(6-bromo-3-((2-(tert-butoxy)-2-oxoethyl)amino)-5-methylpyrazin-2-yl)-1,3-dioxopentan-2-yl)-2,5-diazabicyclo[4.2.0]octane-2-carboxylate (Racemic Mixture, Trans)

To a solution of tert-butyl (5-bromo-3-(2-bromo-3-oxopentanoyl)-6-methylpyrazin-2-yl)glycinate (Intermediate-24) (1.70 g, 3.55 mmol, 1.0 eq) and re-tert-butyl (1R,6R)-2,5-diazabicyclo[4.2.0]octane-2-carboxylate (CAS: 2648861-36-1, racemic mixture, trans, 753 mg, 3.55 mmol, 1.0 eq) in DMF (20 mL) was added DIEA (917 mg, 7.10 mmol, 2.0 eq) and the resulting mixture was stirred at room temperature for 1 h. The reaction mixture was quenched by H$_2$O (100 mL) and extracted with EtOAc (50 mL*3). The combined organic layers were washed with brine (30 mL), dried over anhydrous Na$_2$SO$_4$, filtered and the filtrate was concentrated to afford the title compound, which was used into the next step without further purification.

LCMS: 609.4 [M+H]$^+$.

Step 3. Synthesis of rac-2-(7-(5-(tert-butoxycarbonyl)-2,5-diazabicyclo[4.2.0]octan-2-yl)-6-ethyl-2-methoxy-3-methyl-8-oxopyrido[2,3-b]pyrazin-5(8H)-yl)acetic Acid (Racemic Mixture, Trans)

To a mixture of MeOH (312 mg, 9.75 mmol, 3.5 eq) in THF (45 mL) was added NaH (390 mg, 9.75 mmol, 60% in mineral oil, 3.5 eq) at 0° C. and the mixture was stirred at 0° C. for 0.5 h. To the resulting mixture was added a solution of rac-tert-butyl-5-(1-(6-bromo-3-((2-(tert-butoxy)-2-oxo-ethyl)amino)-5-methylpyrazin-2-yl)-1,3-dioxopentan-2-yl)-2,5-diazabicyclo[4.2.0]octane-2-carboxylate (racemic mixture, trans) (1.70 g, 2.78 mmol, 1.0 eq) in THF (30 mL) at room temperature and the mixture was stirred at room temperature for 0.5 h. The reaction mixture was quenched by saturated NH₄Cl aqueous solution (100 mL) and extracted with EtOAc (50 mL*3). The combined organic layers were washed with brine (30 mL), dried over Na₂SO₄, filtered and the filtrate was concentrated under reduced pressure. The residue was purified by reverse phase HPLC (C18 column, water (0.1% FA)-ACN) to afford the title compound.

LCMS: 488.3 [M+H]⁺.

Step 4. Synthesis of rac-tert-butyl-5-(5-(2-((2-chloro-4-(trifluoromethyl)phenyl)amino)-2-oxo-ethyl)-6-ethyl-2-methoxy-3-methyl-8-oxo-5,8-dihydropyrido[2,3-b]pyrazin-7-yl)-2,5-diazabicyclo[4.2.0]octane-2-carboxylate (Racemic Mixture, Trans)

To a solution of rac-2-(7-(5-(tert-butoxycarbonyl)-2,5-diazabicyclo[4.2.0]octan-2-yl)-6-ethyl-2-methoxy-3-methyl-8-oxopyrido[2,3-b]pyrazin-5 (8H)-yl)acetic acid (racemic mixture, trans) (intermediate-28) (70 mg, 0.14 mmol, 1.0 eq) and 2-chloro-4-(trifluoromethyl)aniline (31 mg, 0.16 mmol, 1.1 eq) in DCM (1 mL) was added POCl₃ (33 mg, 0.22 mmol, 1.5 eq) at −10° C. and the mixture was stirred at −10° C. for 5 mins. The reaction mixture was poured into water (10 mL), adjusted to pH 8 by saturated NaHCO₃ aqueous solution. The resulting aqueous solution was extracted with EtOAc (10 mL*3). The combined organic layers were dried with anhydrous Na₂SO₄, filtered and the filtrate was concentrated under reduced pressure. The residue was purified by flash silica gel chromatography (Eluent of EtOAc/PE) to afford the title compound.

LCMS: 665.2 [M+H]⁺.

Step 5. Synthesis of rac-2-(7-(2,5-diazabicyclo[4.2.0]octan-2-yl)-6-ethyl-2-methoxy-3-methyl-8-oxopyrido[2,3-b]pyrazin-5 (8H)-yl)-N-(2-chloro-4-(trifluoromethyl)phenyl)acetamide Hydrochloride (Racemic Mixture, Trans)

To rac-tert-butyl-5-(5-(2-((2-chloro-4-(trifluoromethyl)phenyl)amino)-2-oxoethyl)-6-ethyl-2-methoxy-3-methyl-8-oxo-5,8-dihydropyrido[2,3-b]pyrazin-7-yl)-2,5-diazabicyclo[4.2.0]octane-2-carboxylate (racemic mixture, trans) (30 mg, 45 mol, 1.0 eq) was added a 4 M of solution of HCl in 1,4-dioxane (1 mL) and the resulting mixture was stirred at room temperature for 1 h. The reaction mixture was concentrated under reduced pressure to afford the title compound, which was used directly in the next step without further purification.

LCMS: 565.2 [M+H]⁺.

Intermediate-30: N-[2-chloro-4-(trifluoromethyl)phenyl]-2-(2-cyclopropyl-6-ethyl-3-methyl-8-oxo-7-piperazin-1-yl-pyrido[2,3-b]pyrazin-5-yl)acetamide Hydrochloride

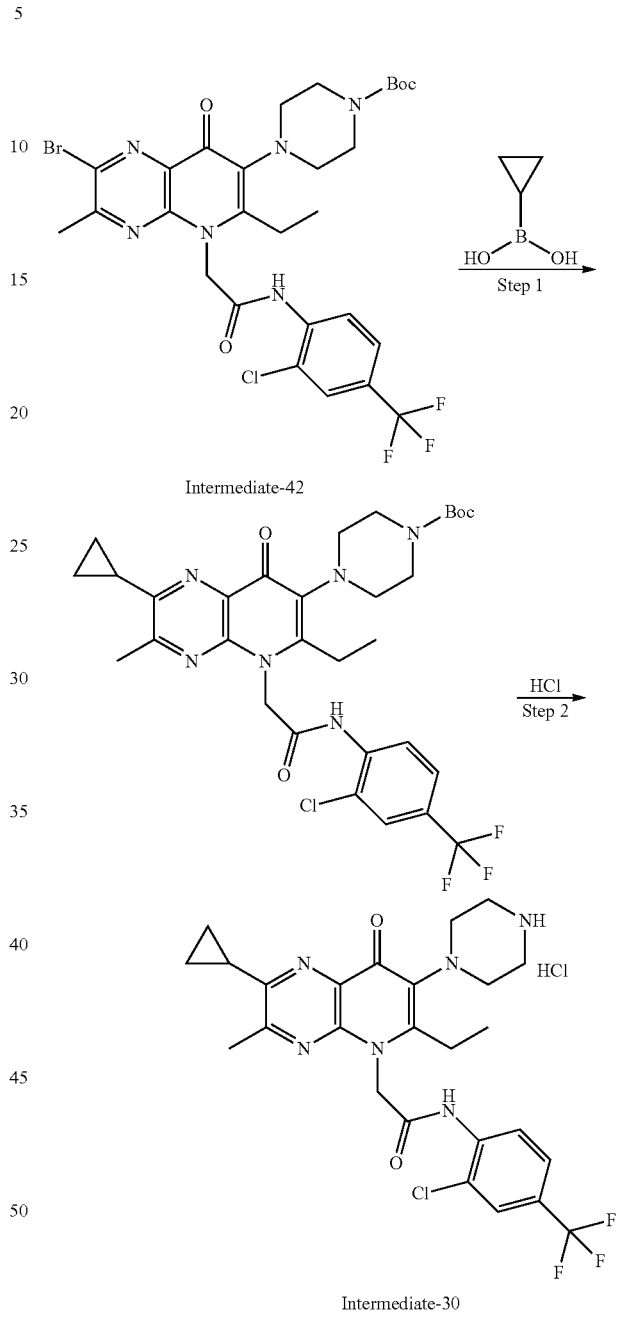

Step 1. Synthesis of tert-butyl 4-(5-(2-((2-chloro-4-(trifluoromethyl)phenyl)amino)-2-oxoethyl)-2-cyclopropyl-6-ethyl-3-methyl-8-oxo-5,8-dihydropyrido[2,3-b]pyrazin-7-yl)piperazine-1-carboxylate To a solution of tert-butyl 4-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)piperazine-1-carboxylate (Intermediate-42) (110 mg, 160 mol, 1.0 eq) and cyclopropylboronic acid (27 mg, 0.32 mmol, 2.0 eq) in 1,4-dioxane (2 mL) was added K₂CO₃ (44 mg, 0.32 mmol, 2.0 eq) and Pd(PPh₃)₄ (18 mg, 16 mol, 0.1 eq), the resulting mixture was stirred at 110° C. under N₂ atmosphere for 12 h. The reaction mixture was quenched by H₂O (100 mL) and extracted with EtOAc (50 mL*3). The combined organic layers were washed with brine (30 mL), dried over anhydrous Na₂SO₄, filtered and concentrated under reduced pressure to afford the title compound, which was used into the next step without further purification.

LCMS: 649.2 [M+H]⁺.

Step 2. Synthesis of N-[2-chloro-4-(trifluoromethyl) phenyl]-2-(2-cyclopropyl-6-ethyl-3-methyl-8-oxo-7-piperazin-1-yl-pyrido[2,3-b]pyrazin-5-yl)acetamide Hydrochloride To a solution of HCl in 1,4-dioxane (1 mL, 4 M) was added tert-butyl 4-(5-(2-((2-chloro-4-(trifluoromethyl)phenyl)amino)-2-oxoethyl)-2-cyclopropyl-6-ethyl-3-methyl-8-oxo-5,8-dihydropyrido[2,3-b]pyrazin-7-yl)piperazine-1-carboxylate (100 mg, 154 mol, 1.0 eq), and it was stirred at room temperature for 1 h. The reaction mixture was concentrated under reduced pressure to afford the title compound, which was used into the next step without further purification.

LCMS: 549.2 [M+H]⁺.

Intermediate-31: N-(2-chloro-4-(trifluoromethyl) phenyl)-2-(2-chloro-6-ethyl-8-oxo-7-(piperazin-1-yl) pyrido[2,3-b]pyrazin-5 (8H)-yl)acetamide Hydrochloride

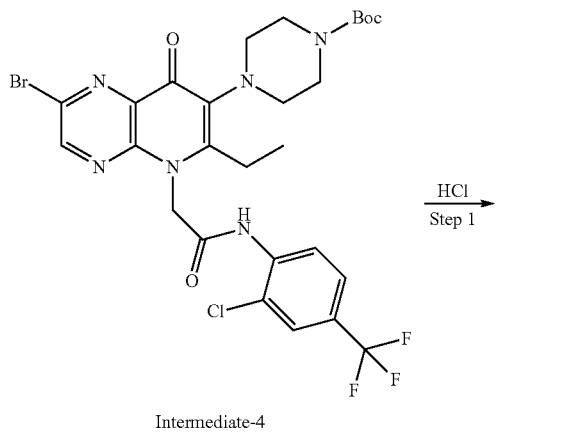

Intermediate-4

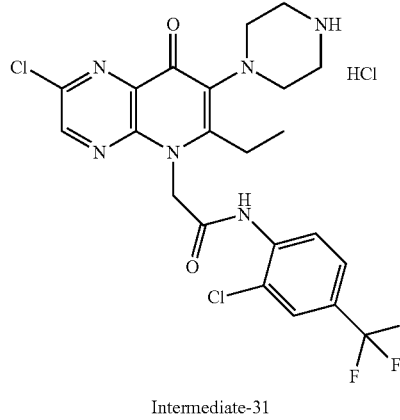

Intermediate-31

Step 1: Synthesis of N-(2-chloro-4-(trifluoromethyl) phenyl)-2-(2-chloro-6-ethyl-8-oxo-7-(piperazin-1-yl) pyrido[2,3-b]pyrazin-5 (8H)-yl)acetamide Hydrochloride To tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (Intermediate-4) (500 mg, 742 mol, 1.0 eq) was added a solution of HCl in 1,4-dioxane (6 mL, 4 M), and it was stirred at room temperature for 1 h. The reaction mixture was concentrated under reduced pressure to afford the title compound, which was used in the next step without further purification.

LCMS: 529.4 [M+H]⁺.

Intermediate-32: N-(2-chloro-4-(trifluoromethyl) phenyl)-2-(6-ethyl-7-(4-(5-hydroxy-6-methylpyrimidine-4-carbonyl)piperazin-1-yl)-2-((4-methoxybenzyl)(methyl)amino)-8-oxopyrido[2,3-b]pyrazin-5 (8H)-yl)acetamide

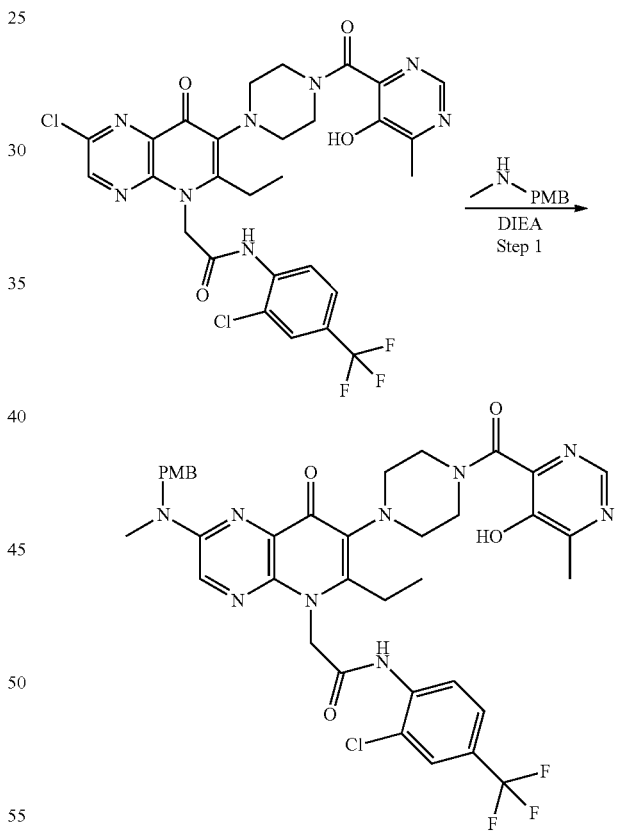

Intermediate-32

Step 1: Synthesis of N-(2-chloro-4-(trifluoromethyl) phenyl)-2-(6-ethyl-7-(4-(5-hydroxy-6-methylpyrimidine-4-carbonyl)piperazin-1-yl)-2-((4-methoxybenzyl)(methyl)amino)-8-oxopyrido[2,3-b]pyrazin-5 (8H)-yl)acetamide To a solution of N-(2-chloro-4-(trifluoromethyl)phenyl)-2-(2-chloro-6-ethyl-7-(4-(5-hydroxy-6-methylpyrimidine- 4-carbonyl)piperazin-1-yl)-8-oxopyrido[2,3-b]pyrazin-5 (8H)-yl)acetamide (100 mg, 150 mol, 1.0 eq) and 1-(4-methoxyphenyl)-N-methylmethanamine (45 mg, 0.31 mmol, 2.0 eq) in 1,4-dioxane (2 mL) was added DIEA (58 mg, 0.45 mmol, 3.0 eq). The mixture was stirred at 100° C. for 15 h and then concentrated under reduced pressure. The residue was purified by flash silica gel chromatography (Eluent of EtOAc/PE) to afford the title compound.

LCMS: 780.4 [M+H]+.

Intermediate-33: tert-butyl 4-(5-(2-((2-chloro-4-(trifluoromethyl)phenyl)amino)-2-oxoethyl)-6-ethyl-2-hydroxy-8-oxo-5,8-dihydropyrido[2,3-b]pyrazin-7-yl)piperazine-1-carboxylate Intermediate-34: N-(2-chloro-4-(trifluoromethyl)phenyl)-2-(6-ethyl-2-hydroxy-8-oxo-7-(piperazin-1-yl)pyrido[2,3-b]pyrazin-5 (8H)-yl)acetamide Hydrochloride Step 1. Synthesis of tert-butyl 4-(5-(2-((2-chloro-4-(trifluoromethyl)phenyl)amino)-2-oxoethyl)-6-ethyl-2-hydroxy-8-oxo-5,8-dihydropyrido[2,3-b]pyrazin-7-yl)piperazine-1-carboxylate To a solution of tert-butyl 4-[2-bromo-5-[2-[2-chloro-4-(trifluoromethyl)anilino]-2-oxo-ethyl]-6-ethyl-8-oxo-pyrido [2,3-b]pyrazin-7-yl]piperazine-1-carboxylate (Intermediate-4) (400 mg, 593 mol, 1.0 eq) in in DMA (4 mL) and H₂O (0.8 mL) was added CuCN (53 mg, 0.60 mmol, 1.0 eq), and then the mixture was stirred at 100° C. for 4 h. After being cooled to room temperature, the reaction mixture was poured into H₂O (50 mL) and extracted with EtOAc (20 mL*3). The combined organic layers were washed with brine (20 mL), dried over anhydrous Na₂SO₄, filtered and the filtrate was concentrated under reduced pressure. The residue was purified by reverse phase HPLC (C18 column, water (0.1% FA-ACN) to afford the title compound.

LCMS: 611.4 [M+H]+.

Step 2. Synthesis of N-(2-chloro-4-(trifluoromethyl) phenyl)-2-(6-ethyl-2-hydroxy-8-oxo-7-(piperazin-1-yl)pyrido[2,3-b]pyrazin-5 (8H)-yl)acetamide Hydrochloride Tert-butyl 4-(5-(2-((2-chloro-4-(trifluoromethyl)phenyl) amino)-2-oxoethyl)-6-ethyl-2-hydroxy-8-oxo-5,8-dihydropyrido[2,3-b]pyrazin-7-yl)piperazine-1-carboxylate (Intermediate-33) (25 mg, 41 mol, 1.0 eq) was dissolved into a solution of HCl in 1,4-dioxane (0.4 mL, 4 M), and the mixture was stirred at room temperature for 1 h. The reaction mixture was concentrated under reduced pressure to afford the title compound, which was used in the next step without further purification.

LCMS: 511.2 [M+H]+.

Intermediate-35: N-(2-chloro-4-(trifluoromethyl) phenyl)-2-(6-ethyl-2-(hydroxymethyl)-8-oxo-7-(piperazin-1-yl)pyrido[2,3-b]pyrazin-5 (8H)-yl)acetamide Trifluoroacetate

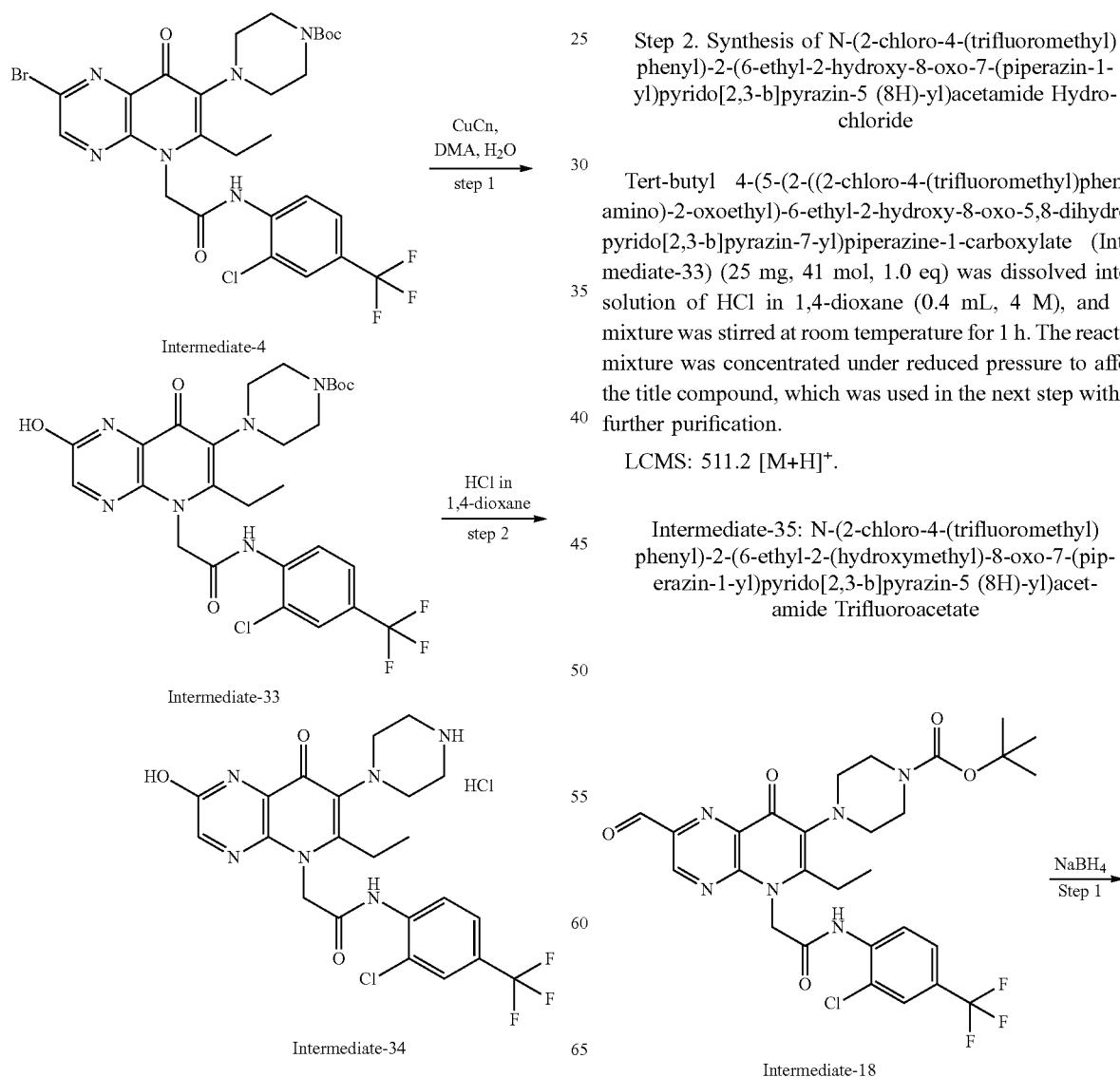

283

-continued

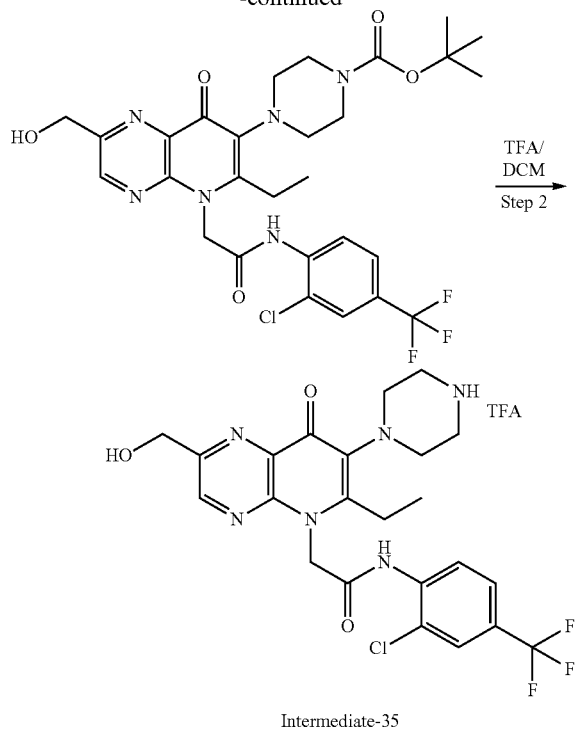

Intermediate-35

Step 1. Synthesis of tert-butyl 4-(5-(2-((2-chloro-4-(trifluoromethyl)phenyl)amino)-2-oxoethyl)-6-ethyl-2-(hydroxymethyl)-8-oxo-5,8-dihydropyrido[2,3-b]pyrazin-7-yl)piperazine-1-carboxylate To a solution of tert-butyl 4-(5-(2-((2-chloro-4-(trifluoromethyl)phenyl)amino)-2-oxoethyl)-6-ethyl-2-formyl-8-oxo-5,8-dihydropyrido[2,3-b]pyrazin-7-yl)piperazine-1-carboxylate (Intermediate-18) (60 mg, 96 mol, 1.0 eq) in THF (3 mL) and $H_2O$ (0.6 mL) was added $NaBH_4$ (5 mg, 0.14 mmol, 1.5 eq), the mixture was stirred at 0° C. for 2 h. The reaction mixture was quenched by saturated $NH_4Cl$ aqueous solution (5 mL) at 0° C., then diluted with $H_2O$ (10 mL) and extracted with EtOAc (10 mL*2). The combined organic layers were washed with brine (7.5 mL*2), dried over anhydrous $Na_2SO_4$, filtered and the filtrate was concentrated under reduced pressure. The residue was purified by flash silica gel chromatography (Eluent of EtOAc/PE) to afford the title compound.

LCMS: 625.4 $[M+H]^+$.

Step 2. Synthesis of N-(2-chloro-4-(trifluoromethyl)phenyl)-2-(6-ethyl-2-(hydroxymethyl)-8-oxo-7-(piperazin-1-yl)pyrido[2,3-b]pyrazin-5 (8H)-yl)acetamide Trifluoroacetate To a solution of tert-butyl 4-(5-(2-((2-chloro-4-(trifluoromethyl)phenyl)amino)-2-oxoethyl)-6-ethyl-2-(hydroxymethyl)-8-oxo-5,8-dihydropyrido[2,3-b]pyrazin-7-yl)piperazine-1-carboxylate (50 mg, 80 mol, 1.0 eq) in DCM (4 mL) was added TFA (1 mL) and the resulting mixture was stirred at room temperature for 0.5 h. The mixture was concentrated under reduced pressure to afford the title compound, which was used in the next step without further purification.

LCMS: 525.1 $[M+H]^+$.

284

Intermediate-36: N-(2-chloro-4-(trifluoromethyl)phenyl)-2-(2-(difluoromethoxy)-6-ethyl-8-oxo-7-(piperazin-1-yl)pyrido[2,3-b]pyrazin-5 (8H)-yl)acetamide Hydrochloride

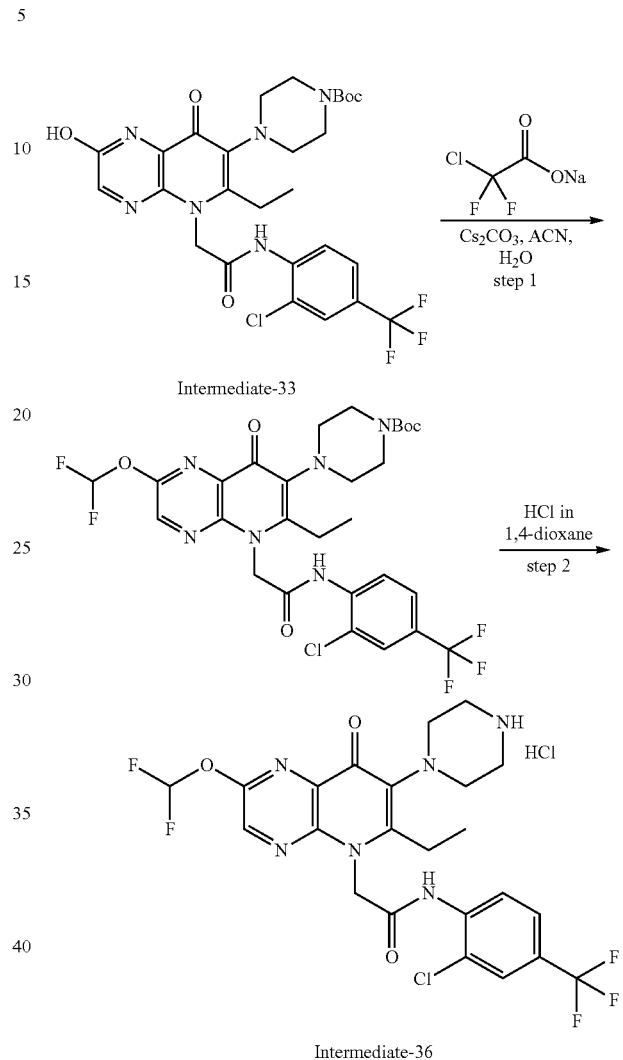

Intermediate-36

Step 1. Synthesis of tert-butyl 4-(5-(2-((2-chloro-4-(trifluoromethyl)phenyl)amino)-2-oxoethyl)-2-(difluoromethoxy)-6-ethyl-8-oxo-5,8-dihydropyrido[2,3-b]pyrazin-7-yl)piperazine-1-carboxylate To a solution of tert-butyl 4-(5-(2-((2-chloro-4-(trifluoromethyl)phenyl)amino)-2-oxoethyl)-6-ethyl-2-hydroxy-8-oxo-5,8-dihydropyrido[2,3-b]pyrazin-7-yl)piperazine-1-carboxylate (Intermediate-33) (37 mg, 60 mol, 1.0 eq) and sodium 2-chloro-2,2-difluoroacetate (21 mg, 0.14 mmol, 2.3 eq) in ACN (2 mL) and $H_2O$ (0.2 mL) was added $Cs_2CO_3$ (26 mg, 78 mol, 1.3 eq), and the mixture was stirred at 80° C. for 48 h under $N_2$ atmosphere. After being cooled to room temperature, the reaction mixture was diluted with $H_2O$ (10 mL) and extracted with EtOAc (10 mL*3). The combined organic layers were washed with brine (20 mL), dried over anhydrous $Na_2SO_4$, filtered and the filtrate was concentrated under reduced pressure. The residue was purified by silica gel chromatography (PE/EtOAc) to afford the title compound.

LCMS: 661.2 $[M+H]^+$.

Step 2. Synthesis of N-(2-chloro-4-(trifluoromethyl)phenyl)-2-(2-(difluoromethoxy)-6-ethyl-8-oxo-7-(piperazin-1-yl)pyrido[2,3-b]pyrazin-5 (8H)-yl)acetamide Hydrochloride To tert-butyl 4-(5-(2-((2-chloro-4-(trifluoromethyl)phenyl)amino)-2-oxoethyl)-2-(difluoromethoxy)-6-ethyl-8-oxo-5,8-dihydropyrido[2,3-b]pyrazin-7-yl)piperazine-1-carboxylate (17 mg, 25 mol, 1.0 eq) was added a solution of HCl in 1,4-dioxane (0.5 mL, 4 M), and the mixture was stirred at room temperature for 1 h. The reaction mixture was concentrated under reduced pressure to afford the title compound, which was used directly in the next step without further purification.

LCMS: 561.2 [M+H]+.

Intermediate-37: N-(2-chloro-4-(trifluoromethyl)phenyl)-2-(6-ethyl-8-oxo-2-(2-oxopyrrolidin-1-yl)-7-(piperazin-1-yl)pyrido[2,3-b]pyrazin-5 (8H)-yl)acetamide Hydrochloride

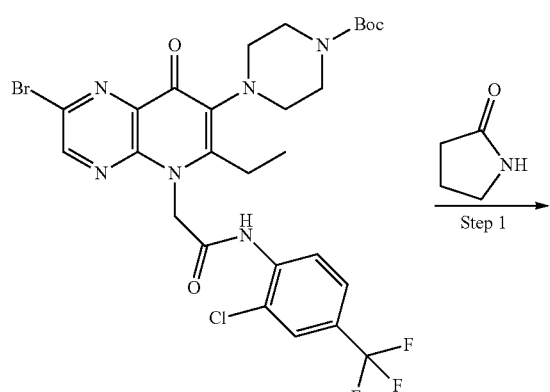

Intermediate-4

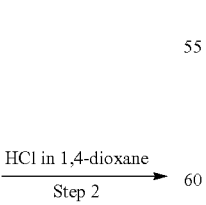

Step 1

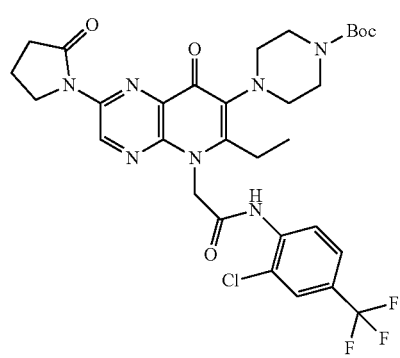

HCl in 1,4-dioxane
Step 2

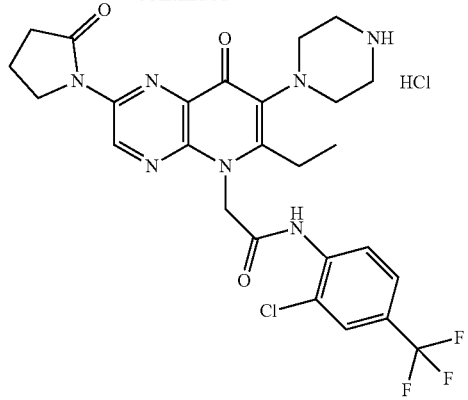

Intermediate-37

Step 1. Synthesis of tert-butyl 4-(5-(2-((2-chloro-4-(trifluoromethyl)phenyl)amino)-2-oxoethyl)-6-ethyl-8-oxo-2-(2-oxopyrrolidin-1I-yl)-5,8-dihydropyrido[2,3-b]pyrazin-7-yl)piperazine-1-carboxylate To a solution of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (Intermediate-4) (50 mg, 74 μmol, 1.0 eq) in 1,4-dioxane (2 mL) was added CuI (1 mg, 7 mol, 0.1 eq), pyrrolidin-2-one (13 mg, 0.15 mmol, 2.0 eq), $K_3PO_4$ (32 mg, 0.15 mmol, 2.0 eq) and N,N'-dimethylethane-1,2-diamine (1 mg, 15 mol, 0.2 eq) at room temperature. The mixture was stirred at 80° C. for 12 h under $N_2$ atmosphere and then concentrated under reduced pressure. The residue was purified by silica gel chromatography (EtOAc/PE) to afford the title compound.

LCMS: 678.2 [M+H]+.

Step 2. Synthesis of N-(2-chloro-4-(trifluoromethyl)phenyl)-2-(6-ethyl-8-oxo-2-(2-oxopyrrolidin-1-yl)-7-(piperazin-1-yl)pyrido[2,3-b]pyrazin-5 (8H)-yl)acetamide Hydrochloride To tert-butyl 4-(5-(2-((2-chloro-4-(trifluoromethyl)phenyl)amino)-2-oxoethyl)-6-ethyl-8-oxo-2-(2-oxopyrrolidin-1-yl)-5,8-dihydropyrido[2,3-b]pyrazin-7-yl)piperazine-1-carboxylate (30 mg, 44 mol, 1.0 eq) was added a solution of HCl in 1,4-dioxane (1 mL, 4 M) and it was stirred at room temperature for 0.5 h. The mixture was concentrated under reduced pressure to afford the title compound, which was used into the next step without further purification.

LCMS: 578.2 [M+H]+.

287

Intermediate-38: 2-(7-(4-(tert-butoxycarbonyl)piperazin-1-yl)-2-(difluoromethyl)-6-ethyl-3-methyl-8-oxopyrido[2,3-b]pyrazin-5 (8H)-yl)acetic Acid Intermediate-39: N-(2-chloro-4-(trifluoromethyl)phenyl)-2-(2-(difluoromethyl)-6-ethyl-3-methyl-8-oxo-7-(piperazin-1-yl)pyrido[2,3-b]pyrazin-5 (8H)-yl)acetamide Hydrochloride

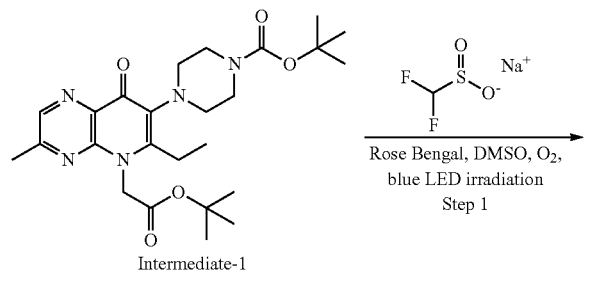

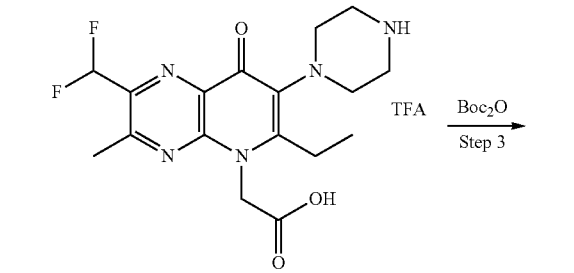

288

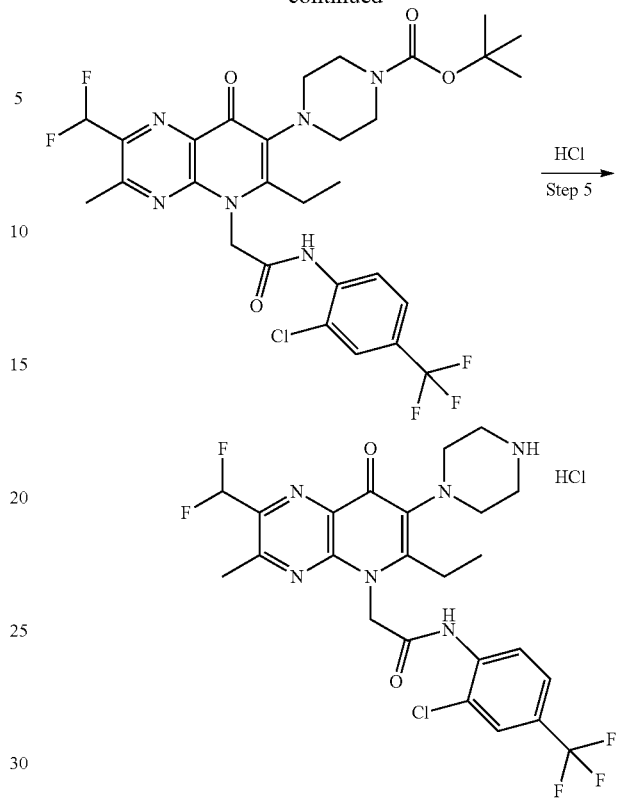

Step 1. Synthesis of tert-butyl 4-(5-(2-(tert-butoxy)-2-oxoethyl)-2-(difluoromethyl)-6-ethyl-3-methyl-8-oxo-5,8-dihydropyrido[2,3-b]pyrazin-7-yl)piperazine-1-carboxylate To a solution of tert-butyl 4-(5-(2-(tert-butoxy)-2-oxoethyl)-6-ethyl-3-methyl-8-oxo-5,8-dihydropyrido[2,3-b]pyrazin-7-yl)piperazine-1-carboxylate (Intermediate-1) (500 mg, 1.03 mmol, 1.0 eq) and sodium difluoromethanesulfinate (283 mg, 2.05 mmol, 2 eq) in DMSO (10 mL) was added rose bengal (21 mg, 21 mol, 0.02 eq). The resulting mixture was irradiated with a 525 nm green LED and stirred at room temperature for 48 h under $O_2$ atmosphere. The reaction mixture was poured into $H_2O$ (50 mL) and extracted with EtOAc (50 mL*2). The combined organic layers were washed with $H_2O$ (50 mL*3), dried over anhydrous $Na_2SO_4$, filtered and the filtrate was concentrated under reduced pressure. The residue was purified by flash silica gel chromatography (Eluent of EtOAc/PE) to afford the title compound.

LCMS: 538.2 [M+H]$^+$.

Step 2. Synthesis of 2-(7-(4-(tert-butoxycarbonyl)piperazin-1-yl)-2-(difluoromethyl)-6-ethyl-3-methyl-8-oxopyrido[2,3-b]pyrazin-5 (8H)-yl)acetic Acid Trifluoroacetate To a solution of tert-butyl 4-(5-(2-(tert-butoxy)-2-oxoethyl)-2-(difluoromethyl)-6-ethyl-3-methyl-8-oxo-5,8-dihydropyrido[2,3-b]pyrazin-7-yl)piperazine-1-carboxylate (140 mg, 260 mol, 1.0 eq) in DCM (0.5 mL) was added TFA (2 mL), and it was stirred at 30° C. for 10 mins. The resulting mixture was concentrated to dryness to afford the title compound, which was used into the next step without further purification.

LCMS: 382.2 [M+H]$^+$.

Step 3. Synthesis of 2-(7-(4-(tert-butoxycarbonyl) piperazin-1-yl)-2-(difluoromethyl)-6-ethyl-3-methyl-8-oxopyrido[2,3-b]pyrazin-5 (8H)-yl)acetic Acid To a mixture of 2-(7-(4-(tert-butoxycarbonyl)piperazin-1-yl)-2-(difluoromethyl)-6-ethyl-3-methyl-8-oxopyrido[2,3-b]pyrazin-5 (8H)-yl)acetic acid trifluoroacetate (99 mg, 0.26 mmol, 1.0 eq) in DCM (2 mL) was added DIEA (134 mg, 1.04 mmol, 181 μL, 4.0 eq) and (Boc)$_2$O (62 mg, 0.29 mmol, 1.1 eq) at 0° C. The mixture was stirred at room temperature for 0.5 h. The reaction mixture was diluted with H$_2$O (50 mL), extracted with EtOAc (30 mL*2). The combined organic layers were dried over anhydrous Na$_2$SO$_4$, filtered, the filtrate was concentrated to dryness. The residue was purified by reverse phase HPLC (C18 column, water (0.1% FA-ACN) to afford the title compound.

LCMS: 482.2 [M+H]$^+$.

Step 4. Synthesis of tert-butyl 4-(5-(2-((2-chloro-4-(trifluoromethyl)phenyl)amino)-2-oxoethyl)-2-(difluoromethyl)-6-ethyl-3-methyl-8-oxo-5,8-dihydropyrido[2,3-b]pyrazin-7-yl)piperazine-1-carboxylate To a solution of 2-(7-(4-(tert-butoxycarbonyl)piperazin-1-yl)-2-(difluoromethyl)-6-ethyl-3-methyl-8-oxopyrido[2,3-b]pyrazin-5 (8H)-yl)acetic acid (Intermediate-38) (84 mg, 0.17 mmol, 1.0 eq) and 2-chloro-4-(trifluoromethyl)aniline (38 mg, 0.19 mmol, 1.1 eq) in DCM (1 mL) and pyridine (1 mL) was added POCl$_3$ (40 mg, 0.26 mmol, 1.5 eq) at −10° C., and the resulting mixture was stirred at −10° C. for 5 mins. The reaction mixture was poured into water (10 mL) and extracted with EtOAc (5 mL*3). The organic layer was discarded, the aqueous phase was adjusted to pH 8 by saturated NaHCO$_3$ aqueous solution. The resulting aqueous solution was extracted with EtOAc (10 mL*3). The combined organic layers were dried over anhydrous Na$_2$SO$_4$, filtered and the filtrate was concentrated under reduced pressure. The residue was purified by flash silica gel chromatography (Eluent of EtOAc/PE) to afford the title compound.

LCMS: 659.2 [M+H]$^+$.

Step 5. Synthesis of N-(2-chloro-4-(trifluoromethyl) phenyl)-2-(2-(difluoromethyl)-6-ethyl-3-methyl-8-oxo-7-(piperazin-1-yl)pyrido[2,3-b]pyrazin-5 (8H)-yl)acetamide Hydrochloride To tert-butyl 4-(5-(2-((2-chloro-4-(trifluoromethyl)phenyl)amino)-2-oxoethyl)-2-(difluoromethyl)-6-ethyl-3-methyl-8-oxo-5,8-dihydropyrido[2,3-b]pyrazin-7-yl)piperazine-1-carboxylate (74 mg, 0.11 mmol, 1.0 eq) was added a 4 M solution of HCl in 1,4-dioxane (1 mL). The mixture was stirred at room temperature for 1 h and then concentrated under reduced pressure to afford the title compound, which was used into the next step without further purification.

LCMS: 559.3 [M+H]$^+$.

Intermediate-43: rac-tert-butyl-5-(2-bromo-6-ethyl-8-oxo-5,8-dihydropyrido[2,3-b]pyrazin-7-yl)-2,5-diazabicyclo[4.2.0]octane-2-carboxylate (Racemic Mixture, Trans)

Intermediate-44: rac-tert-butyl-5-(2-bromo-5-(2-((2-chloro-4-(trifluoromethyl)phenyl)amino)-2-oxoethyl)-6-ethyl-8-oxo-5,8-dihydropyrido[2,3-b] pyrazin-7-yl)-2,5-diazabicyclo[4.2.0]octane-2-carboxylate (Racemic Mixture, Trans)

Intermediate-45: rac-2-(7-(2,5-diazabicyclo[4.2.0] octan-2-yl)-2-(dimethylamino)-6-ethyl-8-oxopyrido [2,3-b]pyrazin-5 (8H)-yl)-N-(2-chloro-4-(trifluoromethyl)phenyl)acetamide Trifluoroacetate (Racemic Mixture, Trans)

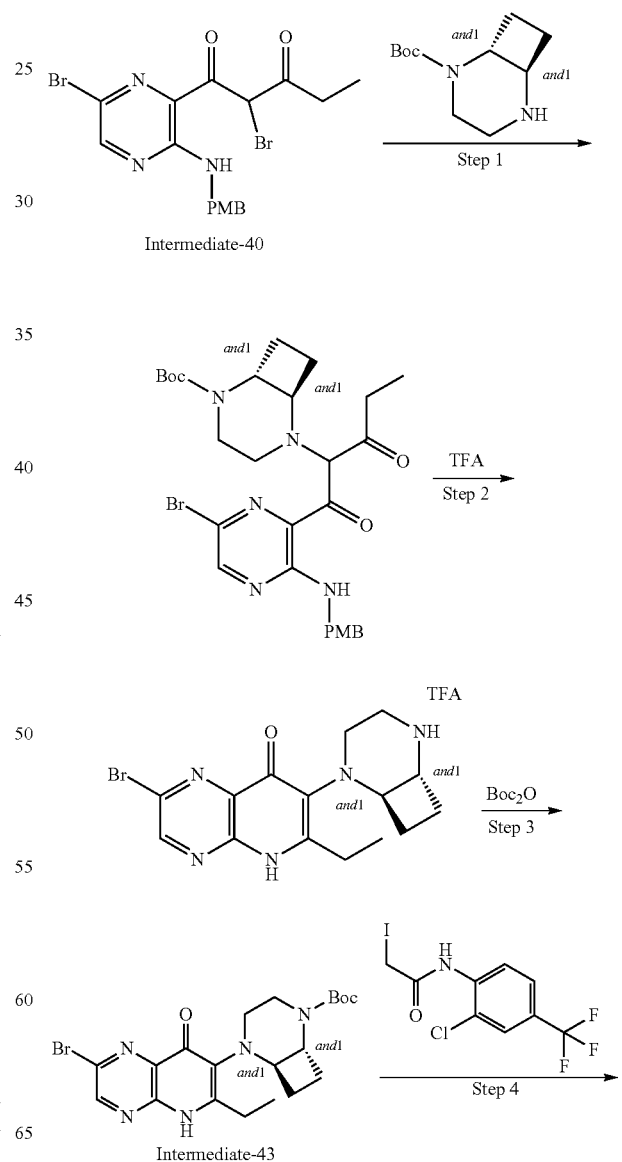

291

-continued

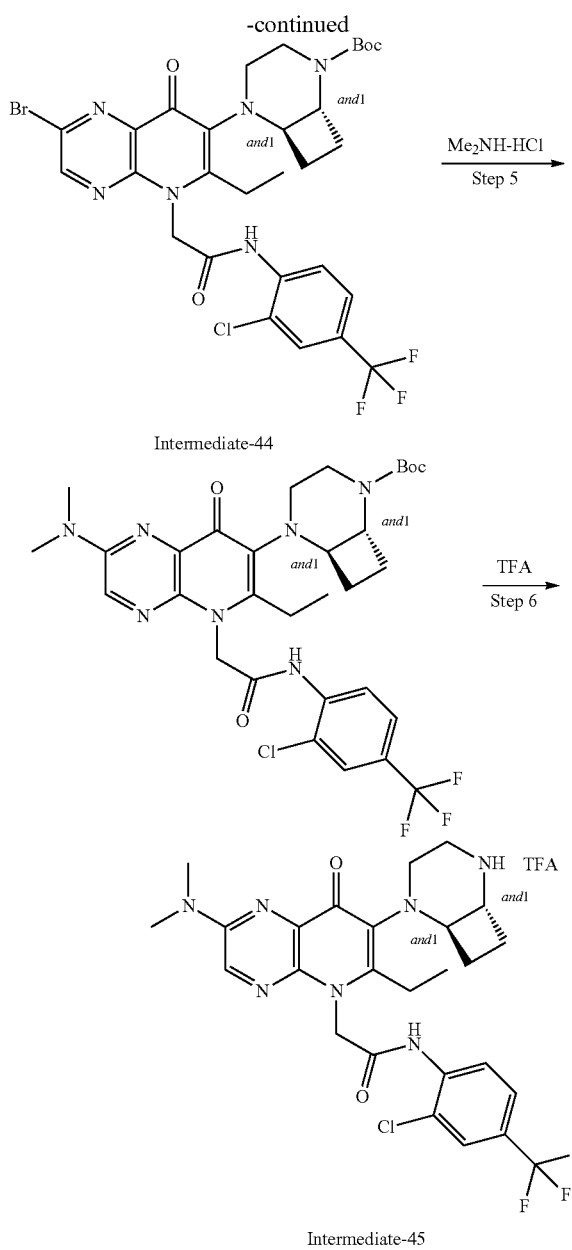

Intermediate-44

Intermediate-45

Step1: Synthesis of rac-tert-butyl-5-(1-(6-bromo-3-((4-methoxybenzyl)amino)pyrazin-2-yl)-1,3-dioxopentan-2-yl)-2,5-diazabicyclo[4.2.0]octane-2-carboxylate (Racemic Mixture, Trans)

To a solution of 2-bromo-1-(6-bromo-3-((4-methoxybenzyl)amino)pyrazin-2-yl)pentane-1,3-dione (Intermediate-40) (5.00 g, 5.31 mmol, 1.0 eq) in THF (10 mL) was added DIEA (1.37 g, 10.6 mmol, 2.0 eq) and rel-tert-butyl (1R,6R)-2,5-diazabicyclo[4.2.0]octane-2-carboxylate (CAS: 2648861-36-1, racemic mixture, trans, 1.69 g, 7.96 mmol, 1.5 eq). The mixture was stirred at room temperature for 0.5 h and then quenched with $H_2O$ (100 mL). The resulting mixture was extracted with EtOAc (50 mL*3). The combined organic layers were washed with brine (30 mL), dried over $Na_2SO_4$, filtered and the filtrate was concentrated in vacuo. The residue was purified by silica gel chromatography (EtOAc/PE) to afford the title compound.
LCMS: 602.1 $[M+H]^+$.

292

Step 2: Synthesis of rac-7-(2,5-diazabicyclo[4.2.0]octan-2-yl)-2-bromo-6-ethylpyrido[2,3-b]pyrazin-8 (5H)-one trifluoroacetate (Racemic Mixture, Trans)

A solution of rac-tert-butyl-5-(1-(6-bromo-3-((4-methoxybenzyl)amino)pyrazin-2-yl)-1,3-dioxopentan-2-yl)-2,5-diazabicyclo[4.2.0]octane-2-carboxylate (racemic mixture, trans) (700 mg, 1.16 mmol, 1.0 eq) in TFA (3.5 mL) was stirred at 50° C. for 3 h and then concentrated under reduced pressure to afford the title compound, which was used in the next step without further purification.
LCMS: 364.1 $[M+H]^+$.

Step 3: Synthesis of rac-tert-butyl-5-(2-bromo-6-ethyl-8-oxo-5,8-dihydropyrido[2,3-b]pyrazin-7-yl)-2,5-diazabicyclo[4.2.0]octane-2-carboxylate (Racemic Mixture, Trans)

To a solution of rac-7-(2,5-diazabicyclo[4.2.0]octan-2-yl)-2-bromo-6-ethylpyrido[2,3-b]pyrazin-8 (5H)-one trifluoroacetate (racemic mixture, trans) (400 mg, 1.10 mmol, 1.0 eq) in DCM (8 mL) was added DIEA (710 mg, 5.49 mmol, 5.0 eq) and $Boc_2O$ (264 mg, 1.21 mmol, 1.1 eq). The mixture was stirred at room temperature for 0.5 h. The reaction mixture was diluted with $H_2O$ (20 mL) and extracted with DCM (10 mL*2). The combined organic layers were washed with brine (10 mL*2), dried over $Na_2SO_4$, filtered and the filtrate was concentrated under reduced pressure. The residue was purified by silica gel chromatography (EtOAc/PE) to afford the title compound.
LCMS: 466.1 $[M+H]^+$.

Step 4: Synthesis of rac-tert-butyl-5-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)-2,5-diazabicyclo[4.2.0]octane-2-carboxylate (Racemic Mixture, Trans)

To a solution of rac-tert-butyl-5-(2-bromo-6-ethyl-8-oxo-5,8-dihydropyrido[2,3-b]pyrazin-7-yl)-2,5-diazabicyclo[4.2.0]octane-2-carboxylate (racemic mixture, trans) (Intermediate-43) (250 mg, 431 mol, 1.0 eq) in DMF (3 mL) was added $K_2CO_3$ (60 mg, 0.43 mmol, 1.0 eq) and N-(2-chloro-4-(trifluoromethyl)phenyl)-2-iodoacetamide (157 mg, 431 mol, 1.0 eq). The reaction mixture was stirred at room temperature for 2 h and then quenched with saturated $NH_4Cl$ aqueous solution (100 mL). The resulting solution was extracted with EtOAc (50 mL*3). The combined organic layers were washed with brine (30 mL), dried over $Na_2SO_4$, filtered and the filtrate was concentrated in vacuo. The residue was purified by silica gel chromatography (EtOAc/PE) to afford the title compound.
LCMS: 701.1 $[M+H]^+$.

Step 5: Synthesis of rac-tert-butyl-5-(5-(2-((2-chloro-4-(trifluoromethyl)phenyl)amino)-2-oxoethyl)-2-(dimethylamino)-6-ethyl-8-oxo-5,8-dihydropyrido[2,3-b]pyrazin-7-yl)-2,5-diazabicyclo[4.2.0]octane-2-carboxylate (Racemic Mixture, Trans)

To a solution of rac-tert-butyl-5-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)-2,5-diazabicyclo[4.2.0]octane-2-carboxylate (racemic mixture, trans) (Intermediate-44) (90 mg, 0.13 mmol, 1.0 eq) in 1,4-dioxane (2 mL) was added dimethylamine hydrochloride (52 mg, 0.64 mmol, 5.0 eq) and DIEA (100 mg, 771 mol, 6.0 eq). The mixture was stirred at 100° C. for 1 h and then quenched by H₂O (100 mL). The resulting solution was extracted with EtOAc (50 mL*3). The combined organic layers were washed with brine (30 mL), dried over Na₂SO₄, filtered and the filtrate was concentrated in vacuo to afford the title compound, which was used in the next step without further purification.

LCMS: 664.2 [M+H]⁺.

Step 6: Synthesis of rac-2-(7-(2,5-diazabicyclo [4.2.0]octan-2-yl)-2-(dimethylamino)-6-ethyl-8-oxopyrido[2,3-b]pyrazin-5 (8H)-yl)-N-(2-chloro-4-(trifluoromethyl)phenyl)acetamide Trifluoroacetate (Racemic Mixture, Trans)

To a solution of rac-tert-butyl-5-(5-(2-((2-chloro-4-(trifluoromethyl)phenyl)amino)-2-oxoethyl)-2-(dimethylamino)-6-ethyl-8-oxo-5,8-dihydropyrido[2,3-b]pyrazin-7-yl)-2,5-diazabicyclo[4.2.0]octane-2-carboxylate (racemic mixture, trans) (85 mg, 0.13 mmol, 1.0 eq) in DCM (1 mL) was added TFA (5 mL) and the resulting mixture was stirred at 30° C. for 1 h. The reaction mixture was concentrated in vacuo to afford the title compound, which was used into the next step without further purification.

LCMS: 564.3 [M+H]⁺.

Intermediate-46: 2-bromo-1-(3-((4-methoxybenzyl) amino)-6-methylthieno[2,3-b]pyrazin-2-yl)pentane-1,3-dione

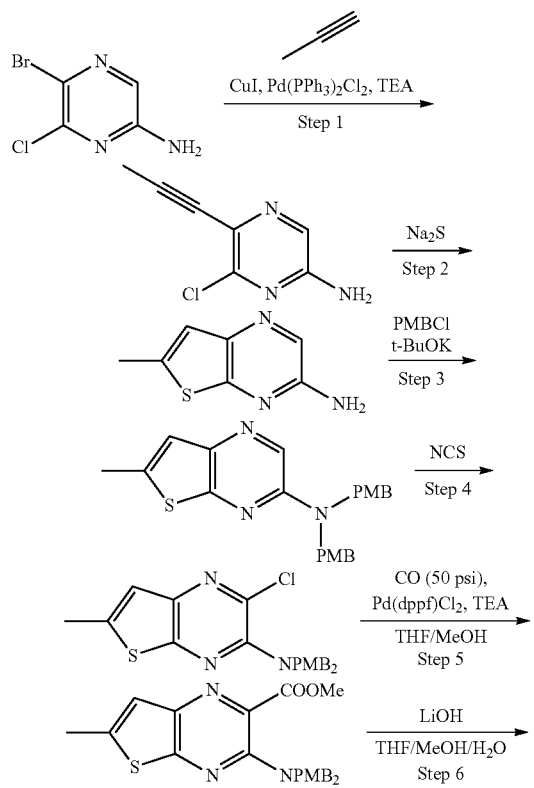

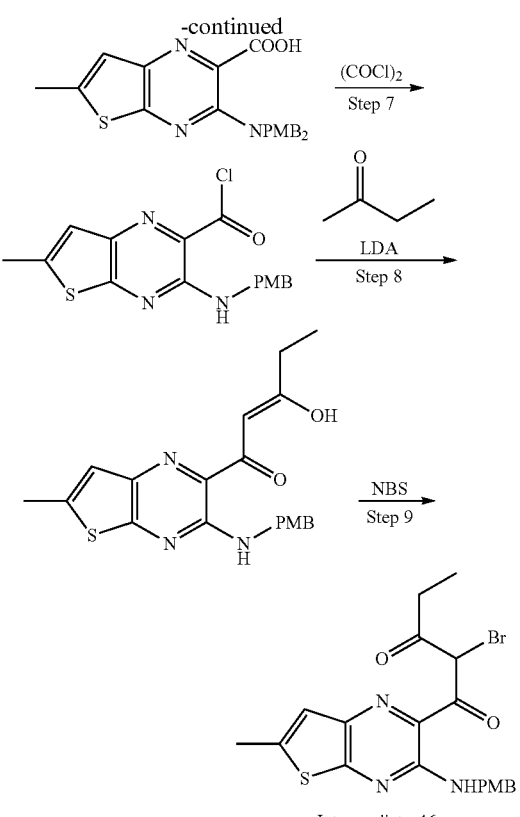

Intermediate-46

Step 1. Synthesis of 6-chloro-5-(prop-1-yn-1-yl) pyrazin-2-amine

To a solution of methyl 5-bromo-6-chloro-pyrazin-2-amine (20.00 g, 95.95 mmol, 1 eq) in THF (20 mL) was added Et₃N (33.98 g, 335.8 mmol, 46.74 mL, 3.5 eq), Pd(PPh₃)₂Cl₂ (6.73 g, 9.59 mmol, 0.1 eq), CuI (914 mg, 4.80 mmol, 0.05 eq) and prop-1-yne (1 M in THF, 191.90 mL, 2 eq). The mixture was stirred at 50° C. for 2 h. The reaction solution was filtered and the filtrate was concentrated under reduced pressure to give the residue. The residue was purified by flash silica gel chromatography (Eluent of EtOAc/PE) to afford the title compound.

¹H NMR (400 MHz, DMSO-d₆) δ ppm 7.76 (s, 1H), 7.18 (s, 2H), 2.07 (s, 3H).

LCMS: 168.0 [M+H]⁺.

Step 2. Synthesis of 6-methylthieno[2,3-b]pyrazin-3-amine

To a solution of 6-chloro-5-prop-1-ynyl-pyrazin-2-amine (10.00 g, 59.67 mmol, 1 eq) in DMF (100 mL) and H₂O (15 mL) was added Na₂S (13.97 g, 179.0 mmol, 3 eq). The mixture was stirred at 90° C. for 3 h. The reaction mixture was diluted with H₂O (150 mL) and extracted with EtOAc (80 mL*3). The combined organic layers were washed with brine (100 mL*2), dried over anhydrous Na₂SO₄, filtered and concentrated under reduced pressure to give a residue. The residue was purified by flash silica gel chromatography (Eluent of EtOAc/PE) to afford the title compound.

¹H NMR (400 MHz, CDCl3) δ ppm 7.98 (s, 1H), 6.97 (s, 1H), 4.58 (br s, 2H), 2.57 (s, 3H).

LCMS: 166.0 [M+H]⁺.

Step 3. Synthesis of N,N-bis(4-methoxybenzyl)-6-methylthieno[2,3-b]pyrazin-3-amine To a solution of 6-methylthieno[2,3-b]pyrazin-3-amine (3.60 g, 21.79 mmol, 1 eq) in THE (80 mL) was added t-BuOK (7.34 g, 65.4 mmol, 3 eq) and 1-(chloromethyl)-4-methoxy-benzene (8.19 g, 52.3 mmol, 7.10 mL, 2.4 eq). The mixture was stirred at 60° C. for 1 h. The reaction mixture was diluted by water (80 mL) and extracted with EtOAc (50 mL*3). The combined organic layers were washed with brine (60 mL*2), dried over anhydrous $Na_2SO_4$, filtered and concentrated under reduced pressure to give a residue. The residue was purified by flash silica gel chromatography (Eluent of EtOAc/PE) to afford the title compound.

$^1$H NMR (400 MHz, DMSO-$d_6$) δ ppm 8.06 (s, 1H), 7.21-7.19 (m, 4H), 7.00 (s, 1H), 6.90-6.83 (m, 4H), 4.77 (s, 4H), 3.72-3.69 (s, 6H), 2.49 (s, 3H).

LCMS: 406.2 [M+H]$^+$.

Step 4. Synthesis of 2-chloro-N,N-bis(4-methoxybenzyl)-6-methylthieno[2,3-b]pyrazin-3-amine To a solution of N,N-bis[(4-methoxyphenyl)methyl]-6-methyl-thieno[2,3-b]pyrazin-3-amine (6.50 g, 12.0 mmol, 1 eq) in DMF (65 mL) was added NCS (1.77 g, 13.2 mmol, 1.1 eq). The mixture was stirred at 80° C. for 0.5 h. The reaction mixture was diluted by $H_2O$ (80 mL) and extracted with EtOAc (50 mL*3). The combined organic layers were washed with brine (60 mL*2), dried over anhydrous $Na_2SO_4$, filtered and concentrated under reduced pressure to give a residue. The residue was purified by flash silica gel chromatography (Eluent of EtOAc/PE) to afford the title compound.

$^1$H NMR (400 MHz, DMSO-$d_6$) δ ppm 7.23-7.21 (m, 4H), 7.17 (s, 1H), 6.89-6.82 (m, 4H), 4.43 (s, 4H), 3.69 (s, 6H), 2.57 (s, 3H).

LCMS: 440.1 [M+H]$^+$.

Step 5. Synthesis of methyl 3-(bis(4-methoxybenzyl)amino)-6-methylthieno[2,3-b]pyrazine-2-carboxylate To a solution of 2-chloro-N,N-bis[(4-methoxyphenyl)methyl]-6-methyl-thieno[2,3-b]pyrazin-3-amine (2.30 g, 5.23 mmol, 1 eq) and Pd(dppf)Cl$_2$ (382 mg, 523 mol, 0.1 eq) in MeOH (50 mL) was added Et$_3$N (1.59 g, 15.7 mmol, 2.18 mL, 3 eq) under N$_2$ atmosphere. The suspension was degassed under vacuum and purged with CO three times. The mixture was stirred at 50° C. for 12 h under CO (50 Psi). The reaction solution was filtered and the filtrate was concentrated under reduced pressure to give a residue. The residue was purified by flash silica gel chromatography (Eluent of EtOAc/PE) to afford the title compound.

$^1$H NMR (400 MHz, DMSO-$d_6$) δ ppm 7.14 (s, 1H), 7.14-7.12 (m, 4H), 6.87-6.85 (m, 4H), 4.51 (s, 4H), 3.82 (s, 3H), 3.70 (s, 6H), 2.57 (s, 3H).

LCMS: 464.3 [M+H]$^+$.

Step 6. Synthesis of 3-(bis(4-methoxybenzyl)amino)-6-methylthieno[2,3-b]pyrazine-2-carboxylic Acid To a solution of methyl 3-[bis[(4-methoxyphenyl)methyl]amino]-6-methyl-thieno[2,3-b]pyrazine-2-carboxylate (1.80 g, 3.88 mmol, 1 eq) in THF (12 mL), MeOH (4 mL) and $H_2O$ (4 mL) was added LiOH—$H_2O$ (1.63 g, 38.83 mmol, 10 eq). The mixture was stirred at 25° C. for 16 h. The reaction mixture was concentrated in vacuum, the resulting residue was diluted with $H_2O$ (150 mL), saturated critic acid aqueous solution was added until the pH of mixture was acidified to 4-5. Then the mixture was extracted with EtOAc (100 mL*3). The combined organic layer was washed with brine (200 mL), dried over anhydrous $Na_2SO_4$, filtered and concentrated under reduced pressure to afford the title compound.

$^1$H NMR (400 MHz, CDCl$_3$) δ ppm 7.18 (s, 1H), 7.12-7.10 (m, 4H), 6.78-6.76 (m, 4H), 4.41 (s, 4H), 3.75 (s, 6H), 2.69 (s, 3H).

Step 7. Synthesis of 3-((4-methoxybenzyl)amino)-6-methylthieno[2,3-b]pyrazine-2-carbonyl Chloride To a solution of 3-[bis[(4-methoxyphenyl)methyl]amino]-6-methyl-thieno[2,3-b]pyrazine-2-carboxylic acid (1.60 g, 3.56 mmol, 1 eq) in DCM (20 mL) was added (COCl)$_2$ (678 mg, 5.34 mmol, 467 µL, 1.5 eq) and DMF (5 mg, 71 mol, 5 µL, 0.02 eq) at 0° C., The mixture was stirred at 25° C. for 1 h. The reaction mixture was concentrated in vacuum, the resulting residue was diluted with THF (8 mL) and concentrated under reduced pressure, this process was repeated three times to obtain the title compound, which was used in the next step directly without further purification.

Step 8. Synthesis of 3-hydroxy-1-(3-((4-methoxybenzyl)amino)-6-methylthieno[2,3-b]pyrazin-2-yl)pent-2-en-1-one To a solution of butan-2-one (407 mg, 5.65 mmol, 505 µL, 1.5 eq) in THF (8 mL) was added LDA (2 M, 2.82 mL, 1.5 eq) at −78° C. under N$_2$ atmosphere, then the mixture was stirred at −78° C. for 0.5 h. A solution of 3-[(4-methoxyphenyl)methylamino]-6-methyl-thieno[2,3-b]pyrazine-2-carbonyl chloride (1.31 g, 3.77 mmol, 1 eq) in THF (8 mL) was added dropwise into the butan-3-one solution. The mixture was stirred at 25° C. for another 1 h. The reaction mixture was poured into saturated NH$_4$Cl aqueous solution (100 mL) and extracted with EtOAc (50 mL*3). The combined organic layer was washed with brine (150 mL), dried over anhydrous Na$_2$SO$_4$, filtered and concentrated under reduced pressure to give a residue. The residue was purified by flash silica gel chromatography (Eluent of EtOAc/PE) to afford the title compound.

LCMS: 384.1 [M+H]$^+$.

Step 9. Synthesis of 2-bromo-1-(3-((4-methoxybenzyl)amino)-6-methylthieno[2,3-b]pyrazin-2-yl)pentane-1,3-dione To a solution of (Z)-3-hydroxy-1-[3-[(4-methoxyphenyl)methylamino]-6-methyl-thieno[2,3-b]pyrazin-2-yl]pent-2-en-1-one (230 mg, 600 mol, 1 eq) in DCM (4 mL) was added NBS (107 mg, 600 µmol, 1 eq). The mixture was stirred at −10° C. for 1 h. The reaction mixture was quenched with saturated Na$_2$SO$_3$ aqueous solution (10 mL) and extracted with DCM (5 mL*3). The combined organic layer was washed with brine (10 mL), dried over anhydrous Na$_2$SO$_4$, filtered and concentrated under reduced pressure to give a residue. The residue was purified by flash silica gel chromatography (Eluent of EtOAc/PE) to afford the title compound.

$^1$H NMR (400 MHz, CDCl$_3$) δ ppm 8.71-8.69 (m, 1H), 7.32-7.30 (m, 2H), 6.91-6.87 (m, 2H), 6.82 (s, 1H), 6.31 (s, 1H), 4.77-4.64 (m, 2H), 3.81 (s, 3H), 2.95 (q, 2H), 2.57 (s, 3H), 1.18 (t, 3H).

LCMS: 464.0 [M+H]$^+$.

Intermediate-47: tert-butyl 4-(7-ethyl-2-methyl-5-oxo-5,8-dihydropyrido[2,3-b]thieno[3,2-e]pyrazin-6-yl)piperazine-1-carboxylate Intermediate-48: N-(2-chloro-4-(trifluoromethyl)phenyl)-2-(7-ethyl-2-methyl-5-oxo-6-(piperazin-1-yl)pyrido[2,3-b]thieno[3,2-e]pyrazin-8 (5H)-yl)acetamide hydrochloride

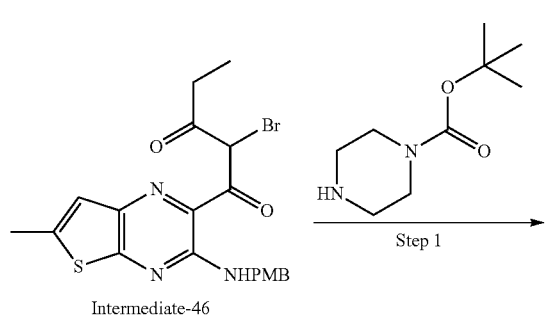

Intermediate-46

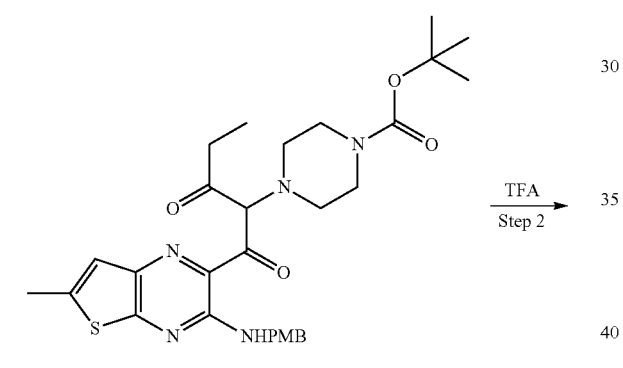

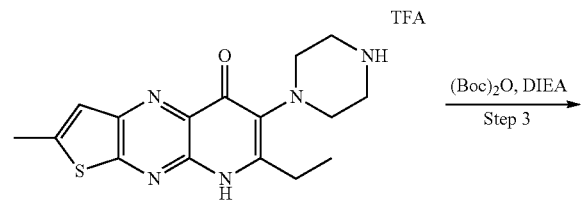

Intermediate-47

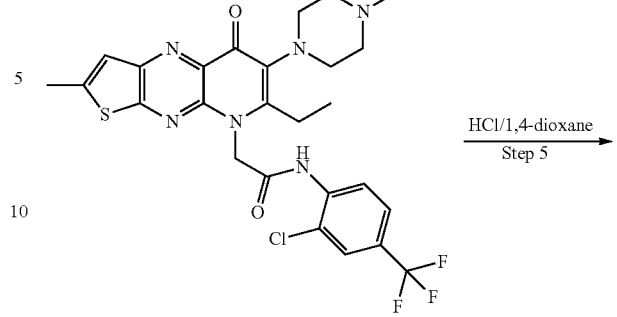

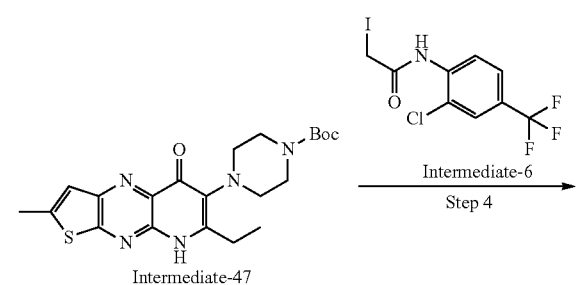

Intermediate-48

Step 1. Synthesis of tert-butyl 4-(1-(3-((4-methoxybenzyl)amino)-6-methylthieno[2,3-b]pyrazin-2-yl)-1,3-dioxopentan-2-yl)piperazine-1-carboxylate To a solution of 2-bromo-1-[3-[(4-methoxyphenyl)methylamino]-6-methyl-thieno[2,3-b]pyrazin-2-yl]pentane-1,3-dione (Intermediate-46) (180 mg, 389 mol, 1 eq) and tert-butyl piperazine-1-carboxylate (80 mg, 0.43 mmol, 1.1 eq) in THF (2 mL) was added DIEA (101 mg, 779 mol, 136 μL, 2 eq). The mixture was stirred at 25° C. for 2 h. The reaction mixture was concentrated in vacuum to give a residue. The residue was purified by flash silica gel chromatography (Eluent of EtOAc/PE) to afford the title compound.

$^1$H NMR (400 MHz, CDCl$_3$) δ ppm 8.87-8.85 (m, 1H), 7.32-7.30 (m, 2H), 6.89-6.87 (m, 2H), 6.81 (s, 1H), 5.56 (s, 1H), 4.76-4.62 (m, 2H), 3.81 (s, 3H), 3.52-3.39 (m, 4H), 2.93-2.81 (m, 3H), 2.74-2.59 (m, 3H), 2.56 (s, 3H), 1.45 (s, 9H), 1.12 (t, 3H).

LCMS: 568.3 [M+H]$^+$.

Step 2. Synthesis of 7-ethyl-2-methyl-6-(piperazin-1-yl)pyrido[2,3-b]thieno[3,2-e]pyrazin-5 (8H)-one Trifluoroacetate A mixture of tert-butyl 4-[1-[3-[(4-methoxyphenyl)methylamino]-6-methyl-thieno[2,3-b]pyrazine-2-carbonyl]-2-oxobutyl]piperazine-1-carboxylate (200 mg, 352 mol, 1 eq) in TFA (4 mL) was stirred at 50° C. for 1 h. The reaction mixture was concentrated in vacuum to obtained the title compound, which was used into the next step directly without further purification.

LCMS: 330.1 [M+H]$^+$.

Step 3. Synthesis of tert-butyl 4-(7-ethyl-2-methyl-5-oxo-5,8-dihydropyrido[2,3-b]thieno[3,2-e]pyrazin-6-yl)piperazine-1-carboxylate To a solution of 7-ethyl-2-methyl-6-(piperazin-1-yl)pyrido[2,3-b]thieno[3,2-e]pyrazin-5 (8H)-one trifluoroacetate (160 mg, 361 mol, 1 eq) in DCM (4 mL) was added DIEA (140 mg, 1.08 mmol, 189 μL, 3.0 eq) and Boc$_2$O (94 mg, 0.43 mmol, 99 μL, 1.2 eq). The mixture was stirred at 25° C. for 1 h. The reaction mixture was concentrated in vacuum to give a residue. The residue was purified by flash silica gel chromatography (Eluent of EtOAc/PE) to afford the title compound.

$^1$H NMR (400 MHz, CDCl$_3$) δ ppm 8.52-8.50 (brs, 1H), 7.30 (s, 1H), 4.14-3.98 (m, 2H), 3.97-3.79 (m, 2H), 3.10-2.84 (m, 4H), 2.70 (s, 3H), 2.68-2.53 (m, 2H), 1.50 (s, 9H), 1.37 (t, 3H).

LCMS: 430.2 [M+H]$^+$.

Step 4. Synthesis of tert-butyl 4-(8-(2-((2-chloro-4-(trifluoromethyl)phenyl)amino)-2-oxoethyl)-7-ethyl-2-methyl-5-oxo-5,8-dihydropyrido[2,3-b]thieno[3,2-e]pyrazin-6-yl)piperazine-1-carboxylate To a solution of tert-butyl 4-(7-ethyl-2-methyl-5-oxo-5,8-dihydropyrido[2,3-b]thieno[3,2-e]pyrazin-6-yl)piperazine-1-carboxylate (Intermediate-47) (80 mg, 0.19 mmol, 1 eq) and N-[2-chloro-4-(trifluoromethyl)phenyl]-2-iodo-acetamide (Intermediate-6) (102 mg, 279 mol, 1.5) in 1,4-dioxane (4 mL) was added DIEA (72 mg, 0.56 mmol, 97 μL, 3 eq). The mixture was stirred at 80° C. for 2 h. The reaction mixture was cooled at room temperature and concentrated in vacuum to give a residue. The residue was triturated with EtOAc (5 mL) and purified by Prep-TLC (SiO$_2$, Eluent of MeOH/DCM) to afford the title compound.

$^1$H NMR (400 MHz, DMSO-d$_6$) δ ppm 10.43 (s, 1H), 8.14-7.83 (m, 2H), 7.78-7.60 (m, 1H), 7.46 (s, 1H), 5.53 (s, 2H), 3.96-3.93 (m, 2H), 3.66 (q, 2H), 3.17-3.15 (m, 2H), 3.03-2.83 (m, 2H), 2.71 (s, 3H), 2.64-2.62 (m, 2H), 1.45 (s, 9H), 1.25 (t, 3H).

LCMS: 665.2 [M+H]$^+$.

Step 5. Synthesis of N-(2-chloro-4-(trifluoromethyl)phenyl)-2-(7-ethyl-2-methyl-5-oxo-6-(piperazin-1-yl)pyrido[2,3-b]thieno[3,2-e]pyrazin-8 (5H)-yl)acetamide Hydrochloride A mixture of tert-butyl 4-(8-(2-((2-chloro-4-(trifluoromethyl)phenyl)amino)-2-oxoethyl)-7-ethyl-2-methyl-5-oxo-5,8-dihydropyrido[2,3-b]thieno[3,2-e]pyrazin-6-yl)piperazine-1-carboxylate (30 mg, 45 mol, 1 eq) in HCl/1,4-dioxane (2 M, 2.57 mL, 114 eq) was stirred at 25° C. for 1 h. The reaction mixture was concentrated in vacuum to obtained the title compound, which was used into the next step directly without further purification.

LCMS: 565.2 [M+H]$^+$.

Intermediate-49: N-(2-chloro-4-(trifluoromethyl)phenyl)-2-(6-ethyl-2-(morpholinomethyl)-8-oxo-7-(piperazin-1-yl)pyrido[2,3-b]pyrazin-5 (8H)-yl)acetamide Hydrochloride

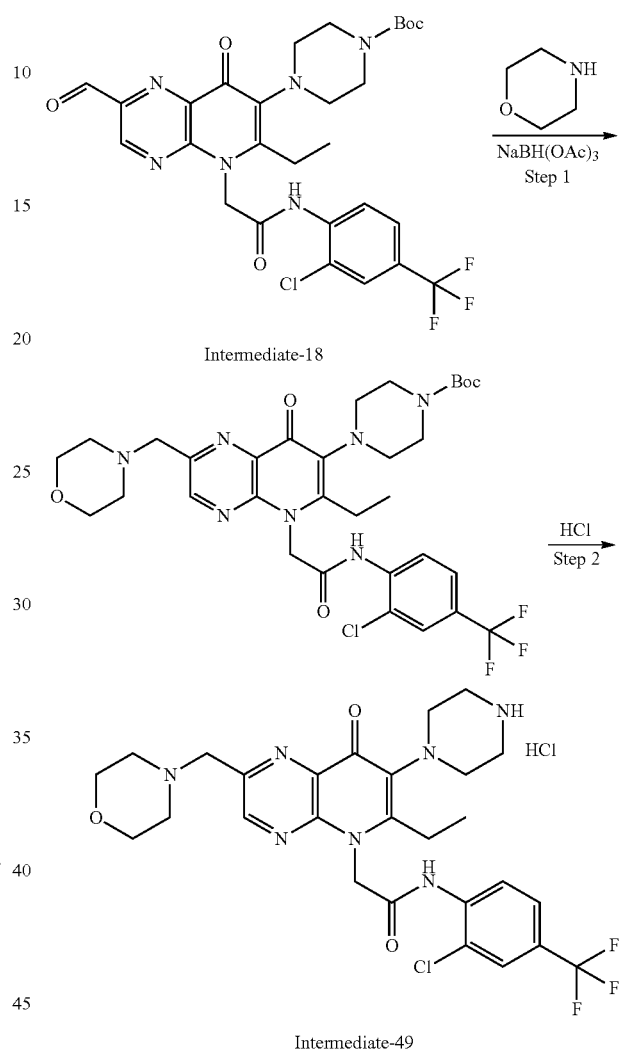

Step 1. Synthesis of tert-butyl 4-(5-(2-((2-chloro-4-(trifluoromethyl)phenyl)amino)-2-oxoethyl)-6-ethyl-2-(morpholinomethyl)-8-oxo-5,8-dihydropyrido[2,3-b]pyrazin-7-yl)piperazine-1-carboxylate To a solution of tert-butyl 4-(5-(2-((2-chloro-4-(trifluoromethyl)phenyl)amino)-2-oxoethyl)-6-ethyl-2-formyl-8-oxo-5,8-dihydropyrido[2,3-b]pyrazin-7-yl)piperazine-1-carboxylate (Intermediate-18) (80 mg, 0.13 mmol, 1.0 eq) and morpholine (56 mg, 0.64 mmol, 5.0 eq) in DCM (2 mL) was added NaBH(OAc)$_3$ (136 mg, 0.64 mmol, 5.0 eq). The mixture was stirred at room temperature for 1 h and then concentrated under reduced pressure. The residue was purified by reverse phase HPLC (C18 column, water (0.1% FA)-ACN) to afford the title compound.

LCMS: 694.4 [M+H]$^+$.

Step 2. Synthesis of N-(2-chloro-4-(trifluoromethyl)phenyl)-2-(6-ethyl-2-(morpholinomethyl)-8-oxo-7-(piperazin-1-yl)pyrido[2,3-b]pyrazin-5 (8H)-yl)acetamide Hydrochloride To a solution of HCl in 1,4-dioxane (2 M, 2 mL) was added tert-butyl 4-(5-(2-((2-chloro-4-(trifluoromethyl)phenyl)amino)-2-oxoethyl)-6-ethyl-2-(morpholinomethyl)-8-oxo-5,8-dihydropyrido[2,3-b]pyrazin-7-yl)piperazine-1-carboxylate (60 mg, 86 mol, 1.0 eq), and then the resulting mixture was stirred at room temperature for 0.5 h. The reaction mixture was concentrated under reduced pressure to afford the title compound, which was used into the next step without further purification.
LCMS: 594.4 [M+H]$^+$.

Intermediate-50: 5-(2-((2-chloro-4-(trifluoromethyl)phenyl)amino)-2-oxoethyl)-6-ethyl-N,N-dimethyl-8-oxo-7-(piperazin-1-yl)-5,8-dihydropyrido[2,3-b]pyrazine-2-carboxamide Hydrochloride

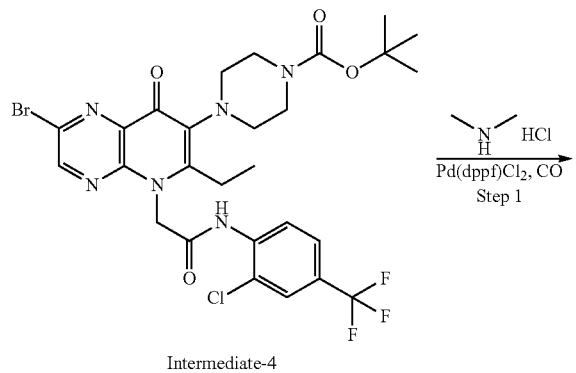

Intermediate-4

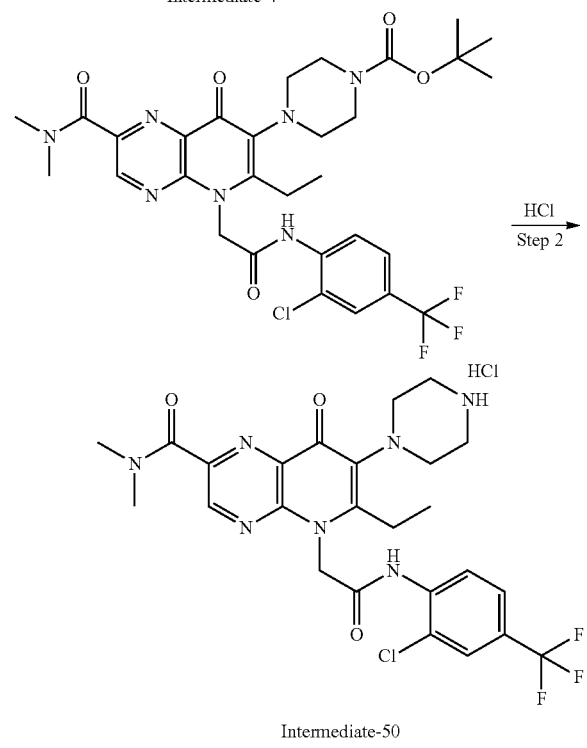

Intermediate-50

Step 1. Synthesis of tert-butyl 4-(5-(2-((2-chloro-4-(trifluoromethyl)phenyl)amino)-2-oxoethyl)-2-(dimethylcarbamoyl)-6-ethyl-8-oxo-5,8-dihydropyrido[2,3-b]pyrazin-7-yl)piperazine-1-carboxylate To a solution of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (Intermediate-4) (100 mg, 148 mol, 1.0 eq) in DMF (3 mL) was added Pd(dppf)Cl$_2$ (11 mg, 15 mol, 0.1 eq), DIEA (96 mg, 0.74 mol, 5.0 eq) and dimethylamine hydrochloride (36 mg, 0.45 mmol, 3.0 eq). The resulting mixture was purged with CO gas and then stirred at 80° C. overnight. The reaction was diluted with H$_2$O (10 mL) and extracted with EtOAc (5 mL*3). The combined organic layers were washed with brine (5 mL*3), dried over anhydrous Na$_2$SO$_4$, filtered and the filtrate was concentrated under reduced pressure. The residue was purified by reverse phase HPLC (C18 column, water (0.1% FA)-ACN) to afford the title compound.
LCMS: 666.4 [M+H]$^+$.

Step 2. 5-(2-((2-chloro-4-(trifluoromethyl)phenyl)amino)-2-oxoethyl)-6-ethyl-N,N-dimethyl-8-oxo-7-(piperazin-1-yl)-5,8-dihydropyrido[2,3-b]pyrazine-2-carboxamide Hydrochloride To a solution of HCl in 1,4-dioxane (2 M, 2 mL) was added tert-butyl 4-(5-(2-((2-chloro-4-(trifluoromethyl)phenyl)amino)-2-oxoethyl)-2-(dimethylcarbamoyl)-6-ethyl-8-oxo-5,8-dihydropyrido[2,3-b]pyrazin-7-yl)piperazine-1-carboxylate (44 mg, 66 mol, 1.0 eq), and the resulting mixture was stirred at room temperature for 0.5 h. The reaction mixture was concentrated under reduced pressure to afford the title compound, which was used into the next step without further purification.
LCMS: 566.3 [M+H]$^+$.

Intermediate-51: 2-(2-acetamido-6-ethyl-8-oxo-7-(piperazin-1-yl)pyrido[2,3-b]pyrazin-5 (8H)-yl)-N-(2-chloro-4-(trifluoromethyl)phenyl)acetamide Trifluoroacetate

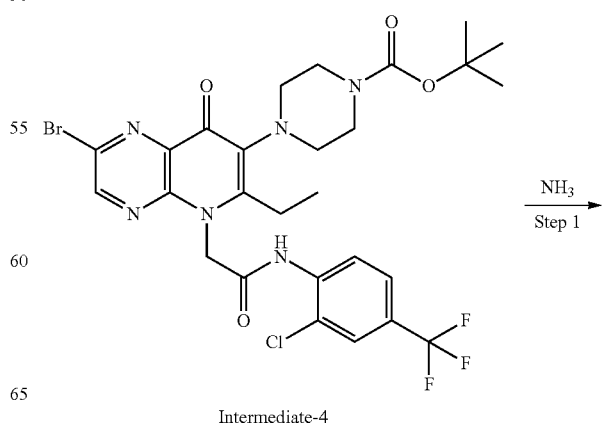

Intermediate-4

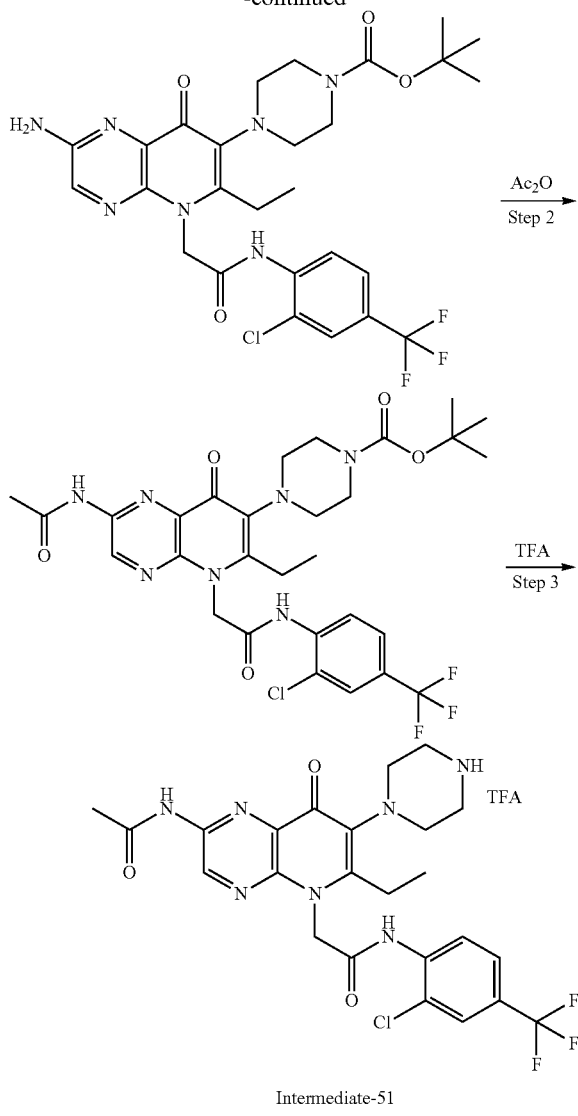

Intermediate-51

Step 1. Synthesis of tert-butyl 4-(2-amino-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate To a solution of $NH_3$ in 1,4-dioxane (4 M, 6 mL) was added tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (Intermediate-4) (300 mg, 445 mol, 1.0 eq). The mixture was stirred at 140° C. overnight in sealed tube. The reaction mixture was cooled to room temperature and concentrated under reduced pressure. The residue was purified by silica gel chromatography (EtOAc/PE) to afford the title compound.
LCMS: 610.4 $[M+H]^+$.

Step 2. Synthesis of tert-butyl 4-(2-acetamido-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate To a solution of tert-butyl 4-(2-amino-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (60 mg, 98 mol, 1.0 eq) in DCM (1 mL) was added $Ac_2O$ (0.5 mL), and then the resulting mixture was stirred at 40° C. overnight. The reaction mixture was diluted with $H_2O$ (10 mL) and extracted with EtOAc (5 mL*3). The combined organic layers were washed with brine (5 mL*3), dried over anhydrous $Na_2SO_4$, filtered and the filtrate was concentrated under reduced pressure. The residue was purified by silica gel chromatography (EtOAc/PE) to afford the title compound.
LCMS: 652.4 $[M+H]^+$.

Step 3. Synthesis of 2-(2-acetamido-6-ethyl-8-oxo-7-(piperazin-1-yl)pyrido[2,3-b]pyrazin-5 (8H)-yl)-N-(2-chloro-4-(trifluoromethyl)phenyl)acetamide Trifluoroacetate To a solution of tert-butyl 4-(2-acetamido-5-(2-((2-chloro-4-(trifluoromethyl)phenyl)amino)-2-oxoethyl)-6-ethyl-8-oxo-5,8-dihydropyrido[2,3-b]pyrazin-7-yl)piperazine-1-carboxylate (40 mg, 61 mol, 1.0 eq) in DCM (0.8 mL) was added TFA (0.2 mL) and the resulting mixture was stirred at room temperature for 0.5 h. The reaction mixture was concentrated under reduced pressure to afford the title compound, which was used into the next step without further purification.
LCMS: 552.3 $[M+H]^+$.

Intermediate-52:2-bromo-1-(6-((4-methoxybenzyl)amino)-2-methylthiazolo[4,5-b]pyrazin-5-yl)pentane-1,3-dione

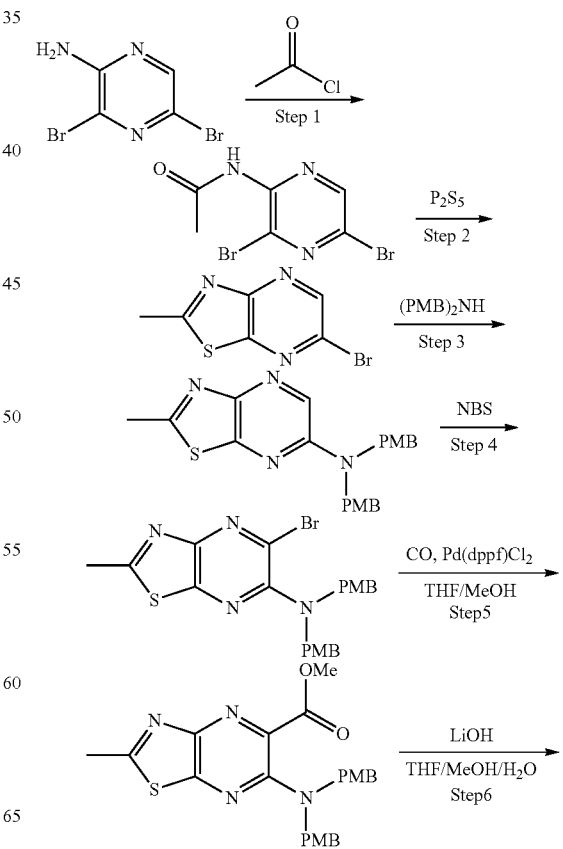

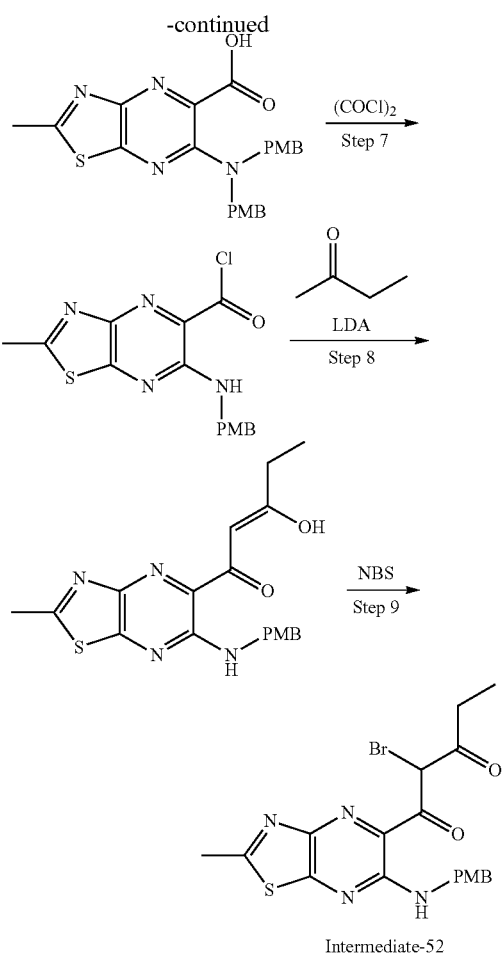

Intermediate-52

Step 1. Synthesis of N-(3,5-dibromopyrazin-2-yl)acetamide

To a solution of 3,5-dibromopyrazin-2-amine (10.00 g, 39.54 mmol, 1 eq) and DMAP (4.83 g, 39.5 mmol, 1 eq) in ACN (100 mL) was added acetyl chloride (9.31 g, 118 mmol, 8.43 mL, 3 eq), then the mixture was stirred at 80° C. for 1.5 h. The mixture was concentrated to give a residue. The residue was purified by silica gel chromatography (Eluent of EtOAc/PE) to afford the title compound.

$^1$H NMR (400 MHz, CDCl$_3$) δ ppm 8.38 (s, 1H), 7.91 (s, 1H), 2.45 (s, 3H).

LCMS: 296.0 [M+H]$^+$.

Step 2. Synthesis of 6-bromo-2-methylthiazolo[4,5-b]pyrazine

To a solution of N-(3,5-dibromopyrazin-2-yl)acetamide (6.80 g, 23.1 mmol, 1 eq) in toluene (136 mL) was added P$_2$S$_5$ (3.07 g, 13.8 mmol, 1.47 mL, 0.6 eq), then the mixture was stirred at 110° C. for 1 h. The mixture was concentrated under reduced pressure and neutralized with saturated NaHCO$_3$ to pH=~7. Then the mixture was extracted with EtOAc (150 mL*3). Then the organic phase was washed with brine (300 mL), dried over anhydrous Na$_2$SO$_4$ and concentrated under reduce pressure to give a residue. The residue was purified by silica gel chromatography (Eluent of EtOAc/PE) to afford the title compound.

$^1$H NMR (400 MHz, CDCl$_3$) δ ppm 8.71 (s, 1H), 2.94 (s, 3H).

LCMS: 232.1 [M+H]$^+$.

Step 3. Synthesis of N,N-bis(4-methoxybenzyl)-2-methylthiazolo[4,5-b]pyrazin-6-amine To a solution of 6-bromo-2-methylthiazolo[4,5-b]pyrazine (10.00 g, 43.46 mmol, 1 eq) and 1-(4-methoxyphenyl)-N-[(4-methoxyphenyl)methyl]methanamine (13.42 g, 52.15 mmol, 1.2 eq) in NMP (100 mL) was added DIEA (8.43 g, 65.2 mmol, 11.4 mL, 1.5 eq), the mixture was stirred at 140° C. for 16 h. The mixture was poured to water (500 mL). Then the mixture was extracted with EtOAc (150 mL*3). The organic phase was washed with brine (500 mL), dried over anhydrous Na$_2$SO$_4$ and concentrated under reduced pressure to give a residue. The residue was purified by flash silica gel chromatography (Eluent of EtOAc/PE) and reversed-phase HPLC (C18 column, water (0.1% FA-ACN) to afford the title compound.

$^1$H NMR (400 MHz, CDCl$_3$) δ ppm 8.01 (s, 1H), 7.17 (d, 4H), 6.86 (d, 4H), 4.77 (s, 4H), 3.80 (s, 6H), 2.81 (s, 3H).

LCMS: 407.3 [M+H]$^+$.

Step 4. Synthesis of 5-bromo-N,N-bis(4-methoxybenzyl)-2-methylthiazolo[4,5-b]pyrazin-6-amine To a solution of N,N-bis(4-methoxybenzyl)-2-methylthiazolo[4,5-b]pyrazin-6-amine (10.00 g, 24.60 mmol, 1 eq) in DMF (100 mL) was added NBS (4.38 g, 24.6 mmol, 1 eq), then the mixture was stirred at 25° C. for 1 h. The mixture was poured into water (500 mL). Then the mixture was extracted with EtOAc (200 mL*3). Then the organic phase was washed with brine (500 mL), dried over anhydrous Na$_2$SO$_4$ and concentrated under reduced pressure to give a residue. The residue was triturated with (EtOH/EtOAc=3/1, 100 mL) to afford the title compound.

$^1$H NMR (400 MHz, CDCl$_3$) δ ppm 7.22 (d, 4H), 6.83 (d, 4H), 4.48 (s, 4H), 3.79 (s, 6H), 2.84 (s, 3H).

LCMS: 487.2 [M+H]$^+$.

Step 5. Synthesis of methyl 6-(bis(4-methoxybenzyl)amino)-2-methylthiazolo[4,5-b]pyrazine-5-carboxylate To a solution of 5-bromo-N,N-bis(4-methoxybenzyl)-2-methylthiazolo[4,5-b]pyrazin-6-amine (1.10 g, 2.27 mmol, 1 eq) and Et$_3$N (688 mg, 6.80 mmol, 946 μL, 3 eq) in MeOH (20 mL) and THF (20 mL) was added Pd(dppf)Cl$_2$ (166 mg, 227 mol, 0.1 eq) under N$_2$. The mixture was degassed and purged with CO several times. The mixture was stirred under CO (50 psi) at 50° C. for 16 h. Then it was concentrated under reduced pressure to give a residue. The residue was purified by flash silica gel chromatography (Eluent of EtOAc/PE) to afford the title compound.

$^1$H NMR (400 MHz, CDCl$_3$) δ ppm 7.09 (d, 4H), 6.83 (d, 4H), 4.54 (s, 4H), 3.91 (s, 3H), 3.79 (s, 6H), 2.84 (s, 3H).

LCMS: 465.3 [M+H]$^+$.

Step 6. Synthesis of 6-(bis(4-methoxybenzyl)amino)-2-methylthiazolo[4,5-b]pyrazine-5-carboxylic Acid To a solution of methyl 6-(bis(4-methoxybenzyl)amino)-2-methylthiazolo[4,5-b]pyrazine-5-carboxylate (920 mg, 1.98 mmol, 1 eq) in THF (9 mL), H$_2$O (3 mL) and MeOH (3 mL) was added LiOH—H$_2$O (415 mg, 9.90 mmol, 5 eq), then the mixture was stirred at 25° C. for 3 h. Acidified the mixture to pH=~3 with saturated citric acid aqueous solution. And the mixture was extracted with EtOAc (100 mL*3). Then the organic phase was washed with brine (200 mL), dried over anhydrous $Na_2SO_4$ and concentrated under reduced pressure to give a residue. The residue was purified by flash silica gel chromatography (Eluent of EtOAc/PE) to afford the title compound.

LCMS: 451.3 $[M+H]^+$.

Step 7. Synthesis of 6-((4-methoxybenzyl)amino)-2-methylthiazolo[4,5-b]pyrazine-5-carbonyl Chloride To a solution of 6-(bis(4-methoxybenzyl)amino)-2-methylthiazolo[4,5-b]pyrazine-5-carboxylic acid (700 mg, 1.55 mmol, 1 eq) in DCM (7 mL) was added $(COCl)_2$ (237 mg, 1.86 mmol, 163 µL, 1.2 eq) and DMF (2 mg, 31 mol, 2 µL, 0.02 eq) at 0° C., the mixture was stirred at 25° C. for 1 h. The mixture was concentrated under reduced pressure to obtain the title compound, which was used into next step directly without further purification.

Step 8. Synthesis of 3-hydroxy-1-(6-((4-methoxybenzyl)amino)-2-methylthiazolo[4,5-b]pyrazin-5-yl)pent-2-en-1-one To a solution of butan-2-one (167 mg, 2.32 mmol, 208 µL, 1.5 eq) in THF (5 mL) was added LDA (2 M in THF, 1.16 mL, 1.5 eq) at −78° C., then the mixture was stirred at −78° C. for 0.5 h. A solution of 6-((4-methoxybenzyl)amino)-2-methylthiazolo[4,5-b]pyrazine-5-carbonyl chloride (540 mg, 1.55 mmol, 1 eq) in THF (5 mL) was added, the mixture was stirred at 25° C. for 1 h. The mixture was poured to a saturated $NH_4Cl$ (20 mL) aqueous solution. Then the mixture was extracted with EtOAc (20 mL*3). Then the organic phase was washed with brine (20 mL), dried over anhydrous $Na_2SO_4$ and concentrated under reduced pressure to give a residue. The residue was purified by flash silica gel chromatography (Eluent of EtOAc/PE) to afford the title compound.

LCMS: 385.3 $[M+H]^+$.

Step 9. Synthesis of 2-bromo-1-(6-((4-methoxybenzyl)amino)-2-methylthiazolo[4,5-b]pyrazin-5-yl)pentane-1,3-dione To a solution of 3-hydroxy-1-(6-((4-methoxybenzyl)amino)-2-methylthiazolo[4,5-b]pyrazin-5-yl)pent-2-en-1-one (380 mg, 988 µmol, 1 eq) in DCM (7 mL) was added NBS (176 mg, 988 µmol, 1 eq), then the mixture was stirred at 25° C. for 1 h. The mixture was concentrated under reduced pressure to give a residue. The residue was purified by flash silica gel chromatography (Eluent of EtOAc/PE) to afford the title compound.

LCMS: 463.1 $[M+H]^+$.

Intermediate-53: tert-butyl 4-(6-ethyl-2-methyl-8-oxo-5,8-dihydropyrido[2,3-b]thiazolo[4,5-e]pyrazin-7-yl)piperazine-1-carboxylate

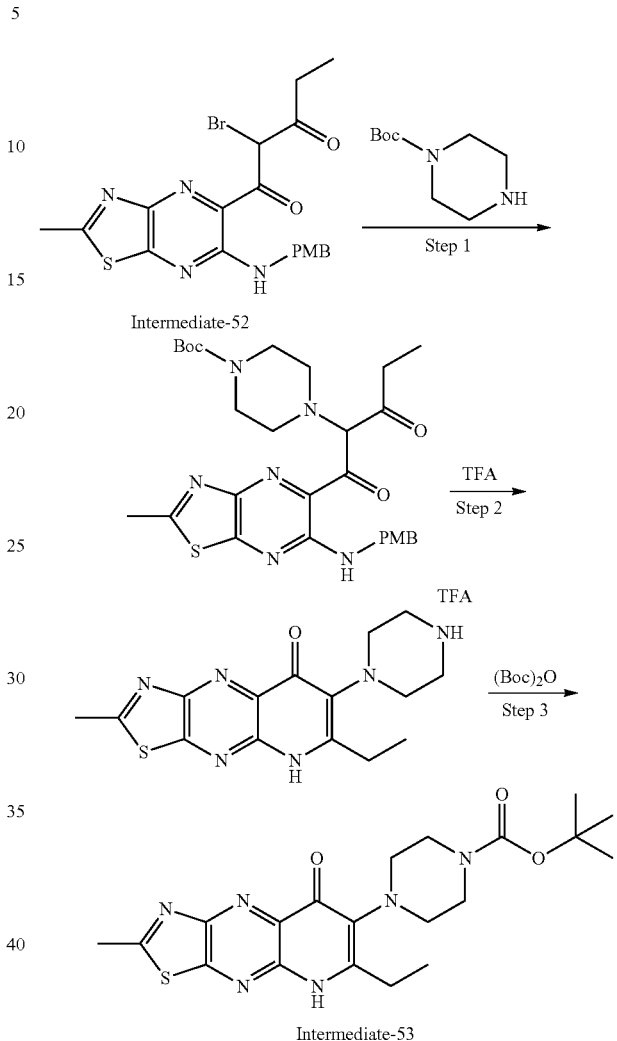

Intermediate-53

Step 1. Synthesis of tert-butyl 4-(1-(6-((4-methoxybenzyl)amino)-2-methylthiazolo[4,5-b]pyrazin-5-yl)-1,3-dioxopentan-2-yl)piperazine-1-carboxylate To a solution of 2-bromo-1-(6-((4-methoxybenzyl)amino)-2-methylthiazolo[4,5-b]pyrazin-5-yl)pentane-1,3-dione (Intermediate-52) (450 mg, 971 mol, 1 eq) and tert-butyl piperazine-1-carboxylate (181 mg, 971 mol, 1 eq) in THF (10 mL) was added DIEA (251 mg, 1.94 mmol, 338 µL, 2 eq), the mixture was stirred at 25° C. for 1 h. The mixture was concentrated under reduced pressure to give a residue. The residue was purified by flash silica gel chromatography (Eluent of EtOAc/PE) to afford the title compound.

LCMS: 569.3 $[M+H]^+$.

Step 2. Synthesis of 6-ethyl-2-methyl-7-(piperazin-1-yl)pyrido[2,3-b]thiazolo[4,5-e]pyrazin-8 (5H)-one Trifluoroacetate To a solution of tert-butyl 4-(1-(6-((4-methoxybenzyl)amino)-2-methylthiazolo[4,5-b]pyrazin-5-yl)-1,3-dioxopentan-2-yl)piperazine-1-carboxylate (130 mg, 229 mol, 1 eq) in TFA (3 mL) was stirred at 50° C. for 1 h. The reaction mixture was concentrated in vacuum to obtain the title compound, which was used into next step directly without further purification.

LCMS: 331.2 [M+H]$^+$.

Step 3. Synthesis of tert-butyl 4-(6-ethyl-2-methyl-8-oxo-5,8-dihydropyrido[2,3-b]thiazolo[4,5-e]pyrazin-7-yl)piperazine-1-carboxylate To a solution of 6-ethyl-2-methyl-7-(piperazin-1-yl)pyrido[2,3-b]thiazolo[4,5-e]pyrazin-8 (5H)-one trifluoroacetate (101 mg, 227 mol, 1 eq) and DIEA (88 mg, 681 mol, 119 μL, 3 eq) in DCM (2 mL) was added (Boc)$_2$O (99 mg, 454 mol, 104 μL, 2 eq), then the mixture was stirred at 25° C. for 1 h. The reaction mixture was concentrated in vacuum to give a residue. The residue was purified by flash silica gel chromatography (Eluent of EtOAc/PE) to afford the title compound.

LCMS: 431.3 [M+H]$^+$.

Intermediate-54: N-(2-chloro-4-(trifluoromethyl)phenyl)-2-(6-ethyl-2-methyl-8-oxo-7-(piperazin-1-yl)pyrido[2,3-b]thiazolo[4,5-e]pyrazin-5 (8H)-yl) acetamide Trifluoroacetate

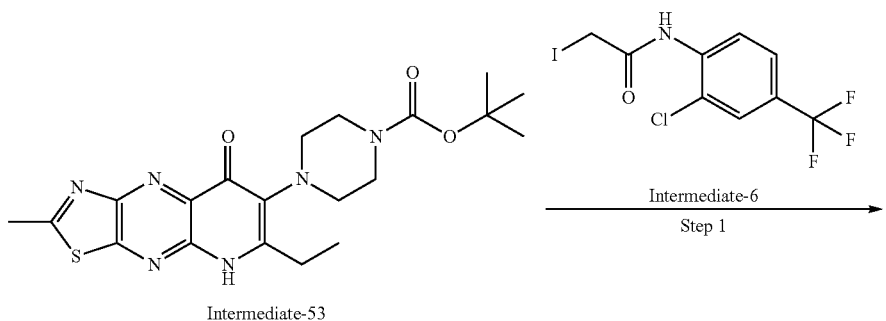

Intermediate-53

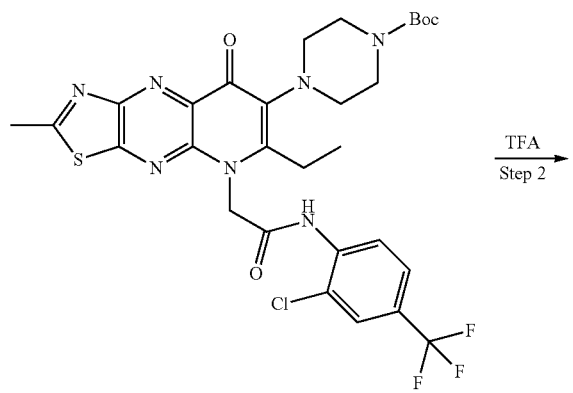

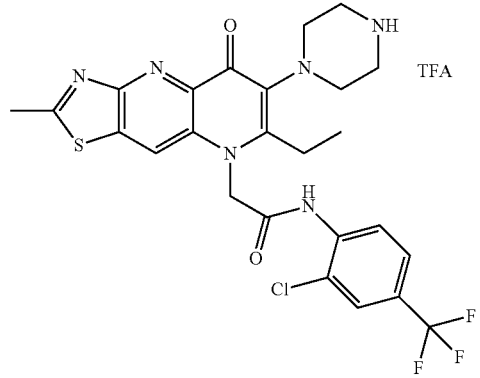

Intermediate-54

Step 1. Synthesis of tert-butyl 4-(5-(2-((2-chloro-4-(trifluoromethyl)phenyl)amino)-2-oxoethyl)-6-ethyl-2-methyl-8-oxo-5,8-dihydropyrido[2,3-b]thiazolo[4,5-e]pyrazin-7-yl)piperazine-1-carboxylate To a solution of tert-butyl 4-(6-ethyl-2-methyl-8-oxo-5,8-dihydropyrido[2,3-b]thiazolo[4,5-e]pyrazin-7-yl)piperazine-1-carboxylate (Intermediate-53) (50 mg, 0.12 mmol, 1 eq) and N-[2-chloro-4-(trifluoromethyl)phenyl]-2-iodo-acetamide (Intermediate-6) (84 mg, 0.23 mmol, 2 eq) in dioxane (1 mL) was added DIEA (45 mg, 0.35 mmol, 61 µL, 3 eq), the mixture was stirred at 80° C. for 3 h. The mixture was concentrated under reduced pressure to give a residue. The residue was purified by flash silica gel chromatography (Eluent of EtOAc/PE) and reversed-phase HPLC (C18 column, water (0.1% FA-ACN) to afford the title compound.

$^1$H NMR (400 MHz, DMSO-d$_6$) δ ppm 10.44 (s, 1H), 8.04-7.96 (m, 2H), 7.74-7.71 (m, 1H), 5.57 (s, 2H), 4.07-3.92 (m, 2H), 3.66 (q, 2H), 3.21-3.19 (m, 2H), 3.05-2.89 (m, 5H), 2.74-2.63 (m, 2H), 1.48 (s, 9H), 1.27 (t, 3H).

LCMS: 666.2 [M+H]$^+$.

Step 2. Synthesis of N-(2-chloro-4-(trifluoromethyl)phenyl)-2-(6-ethyl-2-methyl-8-oxo-7-(piperazin-1-yl)pyrido[2,3-b]thiazolo[4,5-e]pyrazin-5 (8H)-yl) acetamide Trifluoroacetate To a solution of tert-butyl 4-(5-(2-((2-chloro-4-(trifluoromethyl)phenyl)amino)-2-oxoethyl)-6-ethyl-2-methyl-8-oxo-5,8-dihydropyrido[2,3-b]thiazolo[4,5-e]pyrazin-7-yl)piperazine-1-carboxylate (21 mg, 31 mol, 1 eq) in DCM (2.4 mL) was added TFA (1.23 g, 10.8 mmol, 0.80 mL, 342 eq), the mixture was stirred at 25° C. for 1 h. The reaction mixture was concentrated in vacuum to obtain the title compound, which was used into next step directly without further purification.

LCMS: 566.2 [M+H]$^+$.

Intermediate-55: sodium 5-hydroxy-6-methylpyrimidine-4-carboxylate

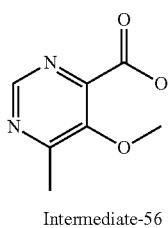

Intermediate-56

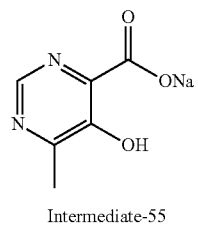

Intermediate-55

Step 1. Synthesis of sodium 5-hydroxy-6-methylpyrimidine-4-carboxylate

To a solution of methyl 5-methoxy-6-methyl-pyrimidine-4-carboxylate (Intermediate-56) (210 g, 1.15 mol, 1 eq) was added 40% aqueous HBr (850 mL) at 20° C. After addition, the mixture was stirred at 50° C. for 16 hr, and then was added 55% aqueous HI (600 mL) at 50° C. The resulting mixture was stirred at 50° C. for 6 hr. The reaction mixture was filtered. The filtrate was adjusted to pH 8-9 with aqueous NaOH solution (30% in water) at 0-5° C. The mixture was filtered, the filter cake was dried under reduced pressure to afford the title compound, which was used into next step directly without further purification.

$^1$H NMR (400 MHz, CD$_3$OD) δ ppm 8.47 (s, 1H), 2.48 (s, 3H).

Intermediate-59: tert-butyl 4-(6-bromo-2-ethyl-7-fluoro-4-oxo-1,4-dihydro-1,5-naphthyridin-3-yl)piperazine-1-carboxylate

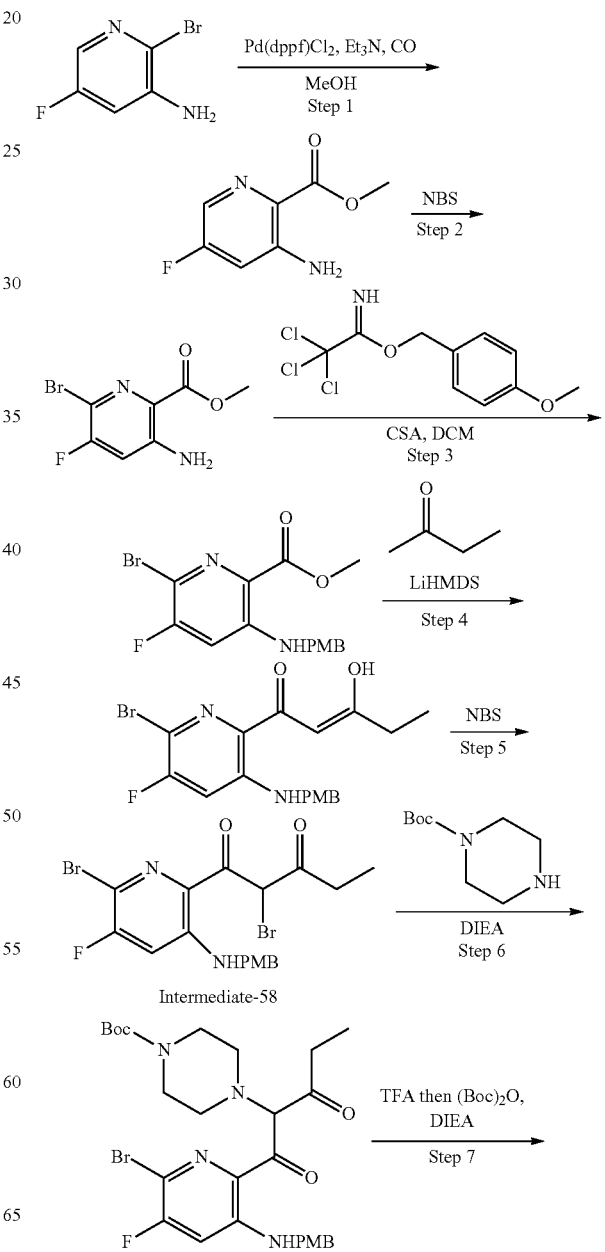

-continued

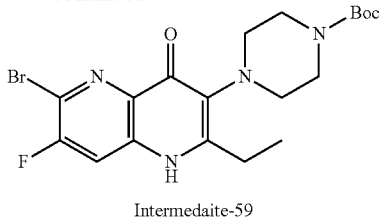

Intermedaite-59

Step 1. Synthesis of methyl 3-amino-5-fluoropicolinate

To a solution of 2-bromo-5-fluoro-pyridin-3-amine (10.00 g, 52.36 mmol, 1 eq) in MeOH (350 mL) was added Et$_3$N (10.60 g, 104.71 mmol, 14.57 mL, 2 eq) and Pd(dppf)Cl$_2$ (1.92 g, 2.62 mmol, 0.05 eq). The mixture was stirred at 80° C. for 16 h under CO (50 psi). 50 mL H$_2$O was added to the mixture and concentrated under reduced pressure to remove MeOH. Then the mixture was diluted with 100 mL H$_2$O and extracted with EtOAc (80 mL*3). The combined organic layers were dried over anhydrous Na$_2$SO$_4$, filtered and the filtrate was concentrated under reduced pressure to give a residue. The residue was purified by silica gel chromatography (Eluent of EtOAc/PE) to afford the title compound.

$^1$H NMR (400 MHz, DMSO-d$_6$) δ ppm 7.81 (s, 1H), 7.03 (d, 1H), 6.94 (br s, 2H), 3.81 (s, 3H).

Step 2. Synthesis of methyl 3-amino-6-bromo-5-fluoropicolinate

To a solution of methyl 3-amino-5-fluoro-pyridine-2-carboxylate (27.00 g, 158.69 mmol, 1 eq) in ACN (500 mL) was added NBS (31.07 g, 174.56 mmol, 1.1 eq). The mixture was stirred at 20° C. for 2.5 h. 200 mL saturated NaHCO$_3$ aqueous solution was added to the reaction solution and the mixture was extracted with EtOAc (300 mL*3). The combined organic layers were washed with brine (200 mL*2), dried over anhydrous Na$_2$SO$_4$, filtered and the filtrate was concentrated under reduced pressure to give a residue. The residue was added dropwise into DCM (80 mL) and stirred for 10 min, filtered and the filter cake was dried under reduced pressure to give the title compound, which was used in next step directly without further purification.

$^1$H NMR (400 MHz, CDCl$_3$) δ ppm 6.81 (d, 1H), 6.00 (br s, 2H), 3.95 (s, 3H).

LCMS: 250.8 [M+H]$^+$.

Step 3. Synthesis of methyl 6-bromo-5-fluoro-3-((4-methoxybenzyl)amino) picolinate To a solution of methyl 3-amino-6-bromo-5-fluoro-pyridine-2-carboxylate (35.00 g, 118.05 mmol, 1 eq) in DCM (350 mL) was added CSA (13.71 g, 59.03 mmol, 0.5 eq) and 4-methoxybenzyl 2,2,2-trichloroacetimidate (50.03 g, 177.08 mmol, 1.5 eq). The mixture was stirred at 20° C. for 1 h. The reaction mixture was quenched by 200 mL saturated NaHCO$_3$ aqueous solution and extracted with DCM (100 mL*3). The combined organic layers were dried over anhydrous Na$_2$SO$_4$, filtered and concentrated under reduced pressure to give a residue. The residue was purified by trituration (MeOH, 30 mL) to afford the title compound.

$^1$H NMR (400 MHz, DMSO-d$_6$) δ ppm 8.21 (br s, 1H), 7.33-7.26 (m, 3H), 6.96-6.85 (m, 2H), 4.41 (d, 2H), 3.83 (s, 3H), 3.72 (s, 3H).

LCMS: 371.0 [M+H]$^+$.

Step 4. Synthesis of 1-(6-bromo-5-fluoro-3-((4-methoxybenzyl)amino) pyridin-2-yl)-3-hydroxy-pent-2-en-1-one To a solution of butan-2-one (10.01 g, 138.82 mmol, 12.42 mL, 2.5 eq) in THF (30 mL) was added LiHMDS (1 M, 138.82 mL, 138.82 mmol, 2.5 eq) at 0° C. under N$_2$ atmosphere. The reaction mixture was stirred at 25° C. for 0.5 h. Then a solution of methyl 6-bromo-5-fluoro-3-[(4-methoxyphenyl)methylamino]pyridine-2-carboxylate (20.50 g, 55.53 mmol, 1 eq) in THF (150 mL) was added to the mixture. Then the reaction mixture was stirred at 60° C. for 1.5 h under N$_2$ atmosphere. The reaction mixture was added into 250 mL saturated NH$_4$Cl aqueous solution and extracted with EtOAc (150 mL*3). The combined organic layers were dried over anhydrous Na$_2$SO$_4$, filtered and concentrated under reduced pressure to give a residue. The residue was purified by silica gel chromatography (Eluent of EtOAc/PE) to afford the title compound.

$^1$H NMR (400 MHz, CDCl$_3$) δ ppm 15.06 (s, 1H), 9.14 (br s, 1H), 7.31-7.28 (m, 1H), 6.98-6.88 (m, 2H), 6.82-6.71 (m, 2H), 4.38 (d, 2H), 3.85 (s, 3H), 2.43 (q, 2H), 1.27 (t, 3H).

LCMS: 409.0 [M+H]$^+$.

Step 5. Synthesis of 2-bromo-1-(6-bromo-5-fluoro-3-((4-methoxybenzyl)amino) pyridin-2-yl) pentane-1,3-dione To a solution of 1-[6-bromo-5-fluoro-3-[(4-methoxyphenyl)methylamino]-2-pyridyl]-3-hydroxy-pent-2-en-1-one (18.20 g, 44.47 mmol, 1 eq) in DCM (360 mL) was added NBS (6.73 g, 37.80 mmol, 0.85 eq). The mixture was stirred at 0° C. for 1 h. The reaction mixture was diluted with H$_2$O (300 mL) and extracted with DCM (100 mL*3). The combined organic layer was washed with brine (100 mL*2), dried over anhydrous Na$_2$SO$_4$, filtered and concentrated under reduced pressure to afford the title compound, which was used in next step directly without further purification.

LCMS: 489.0 [M+H]$^+$.

Step 6. Synthesis of tert-butyl 4-(1-(6-bromo-5-fluoro-3-((4-methoxybenzyl)amino) pyridin-2-yl)-1,3-dioxopentan-2-yl) piperazine-1-carboxylate A mixture of 2-bromo-1-[6-bromo-5-fluoro-3-[(4-methoxyphenyl)methylamino]-2-pyridyl]pentane-1,3-dione (Intermediate-58) (23.90 g, 48.96 mmol, 1 eq), tert-butyl piperazine-1-carboxylate (9.12 g, 48.96 mmol, 1 eq) and DIEA (12.66 g, 97.92 mmol, 17.06 mL, 2 eq) in THF (250 mL) was stirred at 25° C. for 16 h. The reaction mixture was diluted with H$_2$O (300 mL) and extracted with EtOAc (100 mL*3), the combined organic layer was washed with brine (100 mL*2), dried over anhydrous Na$_2$SO$_4$, filtered and concentrated under reduced pressure to give a residue. The residue was triturated with EtOAc (40 mL) and purified by silica gel chromatography (Eluent of EtOAc/PE) to afford the title compound.

$^1$H NMR (400 MHz, CDCl$_3$) δ ppm 8.99 (br s, 1H), 7.22 (d, 2H), 6.89 (d, 2H), 6.74 (d, 1H), 5.32 (s, 1H), 4.33 (d, 2H), 3.81 (s, 3H), 3.56-3.37 (m, 4H), 3.08-2.96 (m, 1H), 2.95-2.86 (m, 2H), 2.76-2.57 (m, 3H), 1.46 (s, 9H), 1.14 (t, 3H).

LCMS: 595.2 [M+H]$^+$.

Step 7. Synthesis of tert-butyl 4-(6-bromo-2-ethyl-7-fluoro-4-oxo-1,4-dihydro-1,5-naphthyridin-3-yl) piperazine-1-carboxylate Tert-butyl 4-[1-[6-bromo-5-fluoro-3-[(4-methoxyphenyl)methylamino]pyridine-2-carbonyl]-2-oxobutyl]piperazine-1-carboxylate (10.00 g, 16.85 mmol, 1 eq) was added to TFA (80 mL) and stirred at 50° C. for 1 h. Then it was cooled to room temperature naturally and concentrated to dryness. Then it was dissolved in DCM (60 mL). DIEA (8.73 g, 67.57 mmol, 11.77 mL, 4 eq) and (Boc)₂O (11.06 g, 50.67 mmol, 11.64 mL, 3 eq) were added to the solution. The reaction mixture was stirred at 20° C. for 16 h and quenched by H₂O (100 mL) then extracted with DCM (30 mL*3). The combined organic layers were dried over anhydrous Na₂SO₄, filtered and concentrated under reduced pressure to give a residue. The residue was and purified by silica gel chromatography (Eluent of DCM/MeOH) and triturated with EtOAc (10 mL) to afford the title compound.

¹H NMR (400 MHz, DMSO-d₆) δ ppm 11.80 (s, 1H), 7.83 (d, 1H), 4.08-3.75 (m, 2H), 3.69-3.39 (m, 2H), 3.07-2.75 (m, 4H), 2.60-2.50 (m, 2H), 1.43 (s, 9H), 1.23 (t, 3H).

LCMS: 455.0 [M+H]⁺.

Intermediate-60: tert-butyl 4-(6-bromo-1-(2-ethoxy-2-oxoethyl)-2-ethyl-7-fluoro-4-oxo-1,4-dihydro-1,5-naphthyridin-3-yl) piperazine-1-carboxylate Intermediate-61: 2-(3-(4-(tert-butoxycarbonyl) piperazin-1-yl)-6-(dimethylamino)-2-ethyl-7-fluoro-4-oxo-1,5-naphthyridin-1 (4H)-yl) acetic Acid

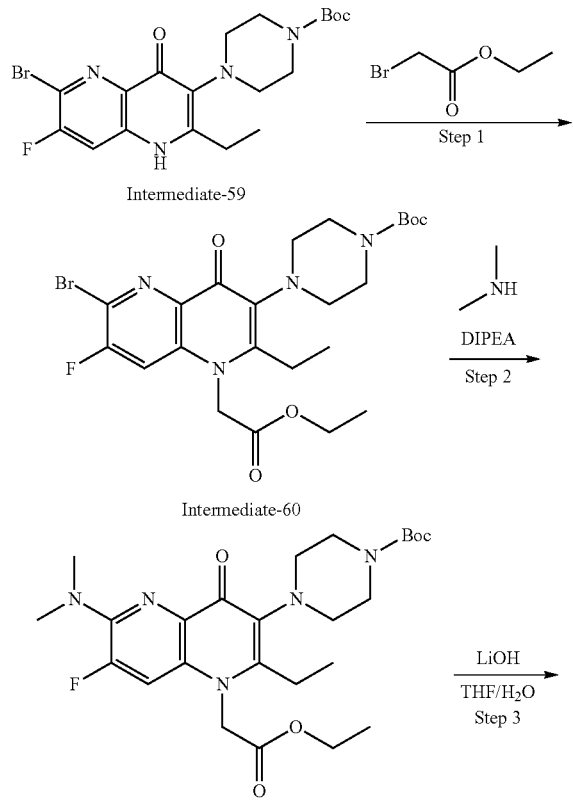

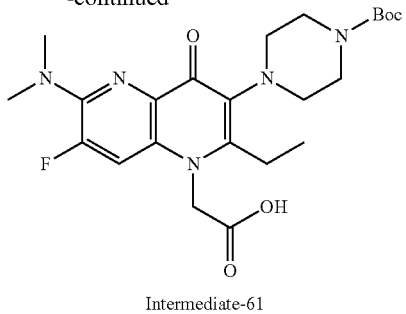

Intermediate-61

Step 1. Synthesis of tert-butyl 4-(6-bromo-1-(2-ethoxy-2-oxoethyl)-2-ethyl-7-fluoro-4-oxo-1,4-dihydro-1,5-naphthyridin-3-yl) piperazine-1-carboxylate To a solution of tert-butyl 4-(6-bromo-2-ethyl-7-fluoro-4-oxo-1H-1,5-naphthyridin-3-yl) piperazine-1-carboxylate (Intermediate-59) (4.00 g, 8.79 mmol, 1 eq) in 1,4-dioxane (120 mL) was added DIEA (6.82 g, 52.72 mmol, 9.18 mL, 6 eq), KI (1.46 g, 8.79 mmol, 1 eq) and ethyl 2-bromoacetate (8.80 g, 52.72 mmol, 5.84 mL, 6 eq). The reaction mixture was stirred at 110° C. for 16 h. The reaction mixture was quenched by brine 100 mL and extracted with EtOAc (100 mL*3). The combined organic layers were dried over anhydrous Na₂SO₄, filtered and concentrated under reduced pressure to give a residue. The residue was purified by silica gel chromatography (Eluent of EtOAc/PE) to afford the title compound.

¹H NMR (400 MHz, CDCl₃) δ ppm 7.36 (d, 1H), 4.86 (s, 2H), 4.74-4.41 (m, 2H), 4.31 (q, 2H), 4.16-4.00 (m, 2H), 3.83 (q, 2H), 3.36-2.80 (m, 2H), 2.61-2.59 (m, 2H), 1.49 (s, 9H), 1.32 (t, 3H), 1.26 (t, 3H).

LCMS: 543.1 [M+H]⁺.

Step 2. Synthesis of tert-butyl 4-(6-(dimethylamino)-1-(2-ethoxy-2-oxoethyl)-2-ethyl-7-fluoro-4-oxo-1,4-dihydro-1,5-naphthyridin-3-yl) piperazine-1-carboxylate To a solution of tert-butyl 4-[6-bromo-1-(2-ethoxy-2-oxo-ethyl)-2-ethyl-7-fluoro-4-oxo-1,5-naphthyridin-3-yl]piperazine-1-carboxylate (Intermediate-60) (1.00 g, 1.85 mmol, 1 eq) and dimethylamine hydrochloride (602 mg, 7.39 mmol, 4 eq) in 1,4-dioxane (6 mL) was added DIEA (1.91 g, 14.78 mmol, 2.57 mL, 8 eq). The mixture was stirred at 100° C. for 16 h. The reaction mixture was quenched by brine (50 mL) and extracted with EtOAc (40 mL*3). The combined organic layers were dried over anhydrous Na₂SO₄, filtered and concentrated under reduced pressure to give a residue. The residue was purified by reversed-phase HPLC (C18 column, water (0.1% FA-ACN) to afford the title compound.

¹H NMR (400 MHz, CDCl₃) δ ppm 7.16 (d, 1H), 4.81 (s, 2H), 4.29 (q, 2H), 4.18-3.96 (m, 2H), 3.94-3.80 (m, 2H), 3.21 (s, 6H), 3.13-2.81 (m, 4H), 2.68-2.50 (m, 2H), 1.49 (s, 9H), 1.30 (t, 3H), 1.24 (t, 3H).

LCMS: 506.3 [M+H]⁺.

Step 3. Synthesis of 2-(3-(4-(tert-butoxycarbonyl) piperazin-1-yl)-6-(dimethylamino)-2-ethyl-7-fluoro-4-oxo-1,5-naphthyridin-1 (4H)-yl) acetic Acid To a solution of tert-butyl 4-[6-(dimethylamino)-1-(2-ethoxy-2-oxo-ethyl)-2-ethyl-7-fluoro-4-oxo-1,5-naphthyridin-3-yl]piperazine-1-carboxylate (80 mg, 158 mol, 1 eq) in H₂O (1 mL) and THF (2 mL) was added LiOH—H₂O (13 mg, 316 mol, 2 eq). The mixture was stirred at 20° C. for 1 h. The reaction mixture was diluted by H₂O (5 mL) and pH was adjusted to about 4 by 0.5 M HCl aqueous solution. Then the mixture was extracted with EtOAc (30 mL*3). The combined organic layers were dried over anhydrous Na₂SO₄, filtered and concentrated under reduced pressure to afford the title compound, which was used in next step directly without further purification.

LCMS: 478.2 [M+H]⁺.

Intermediate-57: N-(2-chloro-4-(trifluoromethyl)phenyl)-2-(6-(dimethylamino)-2-ethyl-7-fluoro-4-oxo-3-(piperazin-1-yl)-1,5-naphthyridin-1 (4H)-yl)acetamide Hydrochloride

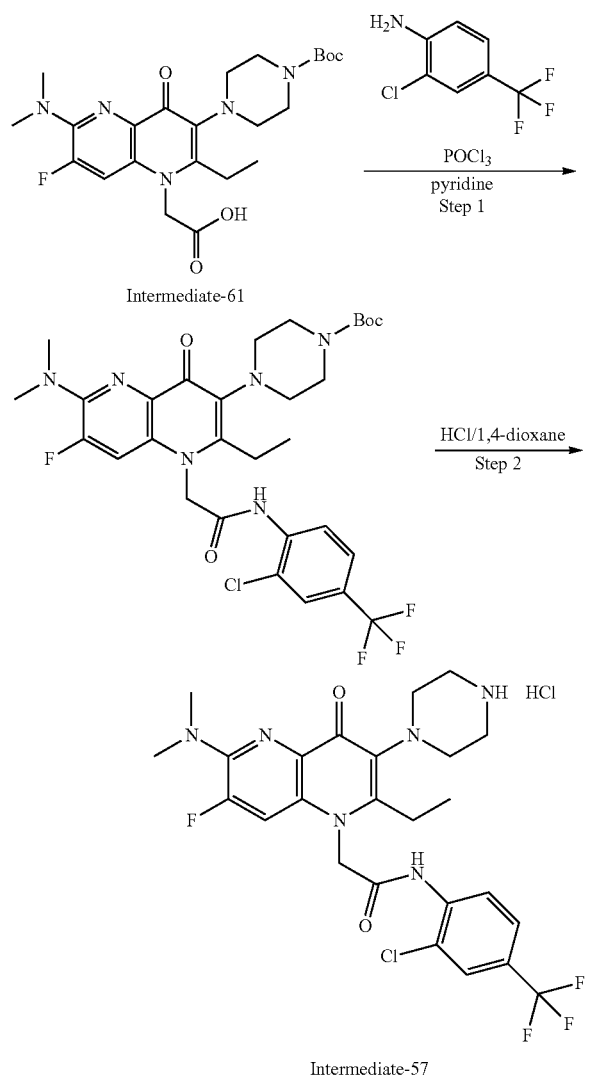

Intermediate-57

Step 1. Synthesis of tert-butyl 4-(1-(2-((2-chloro-4-(trifluoromethyl)phenyl) amino)-2-oxoethyl)-6-(dimethylamino)-2-ethyl-7-fluoro-4-oxo-1,4-dihydro-1,5-naphthyridin-3-yl) piperazine-1-carboxylate To a solution of 2-[3-(4-tert-butoxycarbonylpiperazin-1-yl)-6-(dimethylamino)-2-ethyl-7-fluoro-4-oxo-1,5-naphthyridin-1-yl]acetic acid (Intermediate-61) (70 mg, 147 mol, 1 eq), 2-chloro-4-(trifluoromethyl) aniline (86 mg, 440 mol, 3 eq) in pyridine (1.2 mL) was added POCl₃ (45 mg, 293 mol, 27 μL, 2 eq). The mixture was stirred at 60° C. for 1.5 h. The reaction mixture was diluted with H₂O (30 mL) and extracted with EtOAc (30 mL*3). The combined organic phase was washed with brine (30 mL), dried over anhydrous Na₂SO₄, filtered and concentrated under reduced pressure to give a residue. The residue was purified by silica gel chromatography (Eluent of EtOAc/PE then DCM/MeOH) to afford the title compound.

LCMS: 655.3 [M+H]⁺.

Step 2. Synthesis of N-(2-chloro-4-(trifluoromethyl)phenyl)-2-(6-(dimethylamino)-2-ethyl-7-fluoro-4-oxo-3-(piperazin-1-yl)-1,5-naphthyridin-1 (4H)-yl)acetamide Hydrochloride Tert-butyl 4-[1-[2-[2-chloro-4-(trifluoromethyl) anilino]-2-oxo-ethyl]-6-(dimethylamino)-2-ethyl-7-fluoro-4-oxo-1,5-naphthyridin-3-yl]piperazine-1-carboxylate (15 mg, 23 mol, 1 eq) was dissolved in HCl/1,4-dioxane (2 M, 572 μL, 1.14 mmol, 50 eq). The mixture was stirred at 20° C. for 1 h. Then the mixture was concentrated under reduced pressure to afford the title compound, which was used in next step directly without further purification.

Intermediate-62: 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetic Acid

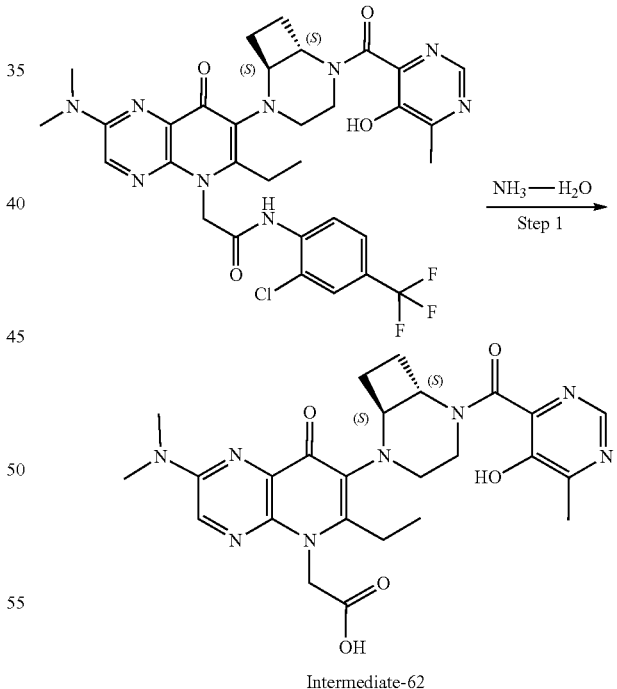

Intermediate-62

Step 1. Synthesis of 2-(2-(dimethylamino)-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)acetic Acid To a pressure tube was added N-(2-chloro-4-(trifluoromethyl)phenyl)-2-(2-(dimethylamino)-6-ethyl-7-((1S,6S)-5-

(5-hydroxy-6-methylpyrimidine-4-carbonyl)-2,5-diazabicyclo[4.2.0]octan-2-yl)-8-oxopyrido[2,3-b]pyrazin-5 (8H)-yl) acetamide single enantiomer (50 mg, 71 μmol, 1.0 eq) and NH₃—H₂O (25% in water, 0.5 mL), the tube was sealed and then heated to 80° C. overnight. The reaction mixture was concentrated under reduced pressure and then purified by reverse phase HPLC (C18 column, water (0.1% FA-ACN) to afford the title compound.

LCMS: 523.2 [M+H]⁺.

Intermediate-66: tert-butyl (1S,6S)-5-(2-bromo-6-ethyl-8-oxo-5,8-dihydropyrido[2,3-b]pyrazin-7-yl)-2,5-diazabicyclo[4.2.0]octane-2-carboxylate Intermediate-65: tert-butyl (1S,6S)-5-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)-2,5-diazabicyclo[4.2.0]octane-2-carboxylate Intermediate-64: 2-(7-((1S,6S)-2,5-diazabicyclo[4.2.0]octan-2-yl)-2-bromo-6-ethyl-8-oxopyrido[2,3-b]pyrazin-5 (8H)-yl)-N-(2-chloro-4-(trifluoromethyl)phenyl)acetamide Trifluoroacetate Intermediate-63: 2-(2-bromo-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b]pyrazin-5 (8H)-yl)-N-(2-chloro-4-(trifluoromethyl)phenyl)acetamide

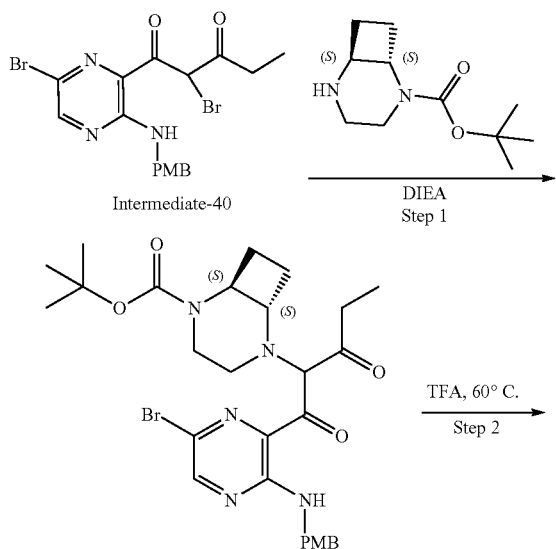

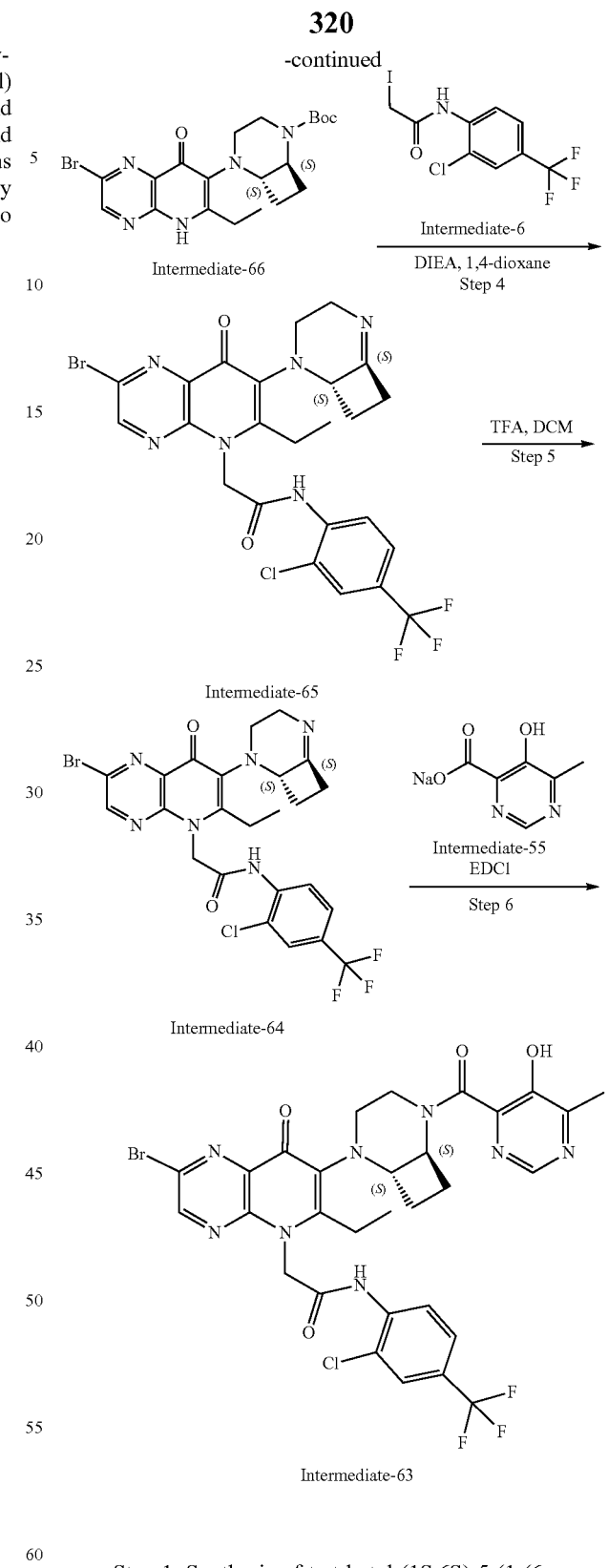

Step 1. Synthesis of tert-butyl (1S,6S)-5-(1-(6-bromo-3-((4-methoxybenzyl)amino)pyrazin-2-yl)-1,3-dioxopentan-2-yl)-2,5-diazabicyclo[4.2.0]octane-2-carboxylate To a solution of 2-bromo-1-(6-bromo-3-((4-methoxybenzyl)amino)pyrazin-2-yl)pentane-1,3-dione (Intermediate- 40) (24.00 g, 50.94 mmol, 1.0 eq) in THF (250 mL) was added DIEA (13.17 g, 101.88 mmol, 2.0 eq) and tert-butyl (1S,6S)-2,5-diazabicyclo[4.2.0]octane-2-carboxylate (CAS: 2920219-11-8) (8.65 g, 40.75 mmol, 0.8 eq), and the resulting mixture was stirred at room temperature for 2 h. The reaction mixture was diluted with H$_2$O (200 mL) and extracted with EtOAc (60 mL*3). The combined organic layers were washed with brine (50 mL*3), dried over anhydrous Na$_2$SO$_4$, filtered and the filtrate was concentrated under reduced pressure. The residue was purified by silica gel chromatography (EtOAc/PE) to afford the title compound.

LCMS: 602.52 [M+H]$^+$.

Step 2. Synthesis of 7-((1S,6S)-2,5-diazabicyclo [4.2.0]octan-2-yl)-2-bromo-6-ethylpyrido[2,3-b] pyrazin-8 (5H)-one Trifluoroacetate tert-butyl (1S,6S)-5-(1-(6-bromo-3-((4-methoxybenzyl) amino)pyrazin-2-yl)-1,3-dioxopentan-2-yl)-2,5-diazabicyclo[4.2.0]octane-2-carboxylate (24.30 g, 40.33 mmol, 1.0 eq) was dissolved into TFA (120 mL) and it was stirred at 60° C. for 2 h. The reaction mixture was concentrated under reduced pressure to afford the title compound, which was used into the next step without further purification.

LCMS: 364.24 [M+H]$^+$.

Step 3. Synthesis of tert-butyl (1S,6S)-5-(2-bromo-6-ethyl-8-oxo-5,8-dihydropyrido[2,3-b]pyrazin-7-yl)-2,5-diazabicyclo[4.2.0]octane-2-carboxylate To a solution of 7-((1S,6S)-2,5-diazabicyclo[4.2.0]octan-2-yl)-2-bromo-6-ethylpyrido[2,3-b]pyrazin-8 (5H)-one trifluoroacetate (14.50 g, 39.81 mmol, 1.0 eq) in DCM (150 mL) was added DIEA (25.73 g, 199.04 mmol, 5.0 eq) and Boc$_2$O (9.56 g, 43.79 mmol, 1.1 eq), and the resulting mixture was stirred at room temperature for 1 h. The reaction mixture was diluted with H$_2$O (100 mL) and extracted with DCM (60 mL*3). The combined organic layers were washed with brine (50 mL), dried over anhydrous Na$_2$SO$_4$, filtered and the filtrate was concentrated in vacuo. The residue was purified by silica gel chromatography (EtOAc/PE) to afford the title compound.

LCMS: 464.36 [M+H]$^+$.

Step 4. Synthesis of tert-butyl (1S,6S)-5-(2-bromo-5-(2-((2-chloro-4-(trifluoromethyl)phenyl)amino)-2-oxoethyl)-6-ethyl-8-oxo-5,8-dihydropyrido[2,3-b] pyrazin-7-yl)-2,5-diazabicyclo[4.2.0]octane-2-carboxylate To a solution of tert-butyl (1S,6S)-5-(2-bromo-6-ethyl-8-oxo-5,8-dihydropyrido[2,3-b]pyrazin-7-yl)-2,5-diazabicyclo[4.2.0]octane-2-carboxylate (Intermediate-66) (12.18 g, 26.23 mmol, 1.0 eq) in 1,4-dioxane (150 mL) was added DIEA (10.17 g, 78.69 mmol, 3.0 eq) and N-(2-chloro-4-(trifluoromethyl)phenyl)-2-iodoacetamide (Intermediate-6) (14.30 g, 39.34 mmol, 1.5 eq), and the resulting mixture was stirred at 80° C. for 2 h. The reaction mixture was diluted with H$_2$O (100 mL) and extracted with EtOAc (50 mL*3). The combined organic layers were washed with brine (50 mL), dried over anhydrous Na$_2$SO$_4$, filtered and the filtrate was concentrated in vacuo. The residue was purified by silica gel chromatography (EtOAc/PE) to afford the title compound.

LCMS: 699.95 [M+H]$^+$.

Step 5. Synthesis of 2-(7-((1S,6S)-2,5-diazabicyclo [4.2.0]octan-2-yl)-2-bromo-6-ethyl-8-oxopyrido[2,3-b]pyrazin-5 (8H)-yl)-N-(2-chloro-4-(trifluoromethyl)phenyl)acetamide Trifluoroacetate To a solution of tert-butyl (1S,6S)-5-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)-2,5-diazabicyclo[4.2.0]octane-2-carboxylate (Intermediate-65) (100 mg, 143 mol, 1.0 eq) in DCM (0.2 mL) was added TFA (1 mL), and the resulting mixture was stirred at room temperature for 1 h. The reaction mixture was concentrated under reduced pressure to afford the title compound, which was used into the next step without further purification.

LCMS: 601.2 [M+H]$^+$.

Step 6. Synthesis of 2-(2-bromo-6-ethyl-7-((1S,6S)-5-(5-hydroxy-6-methylpyrimidine-4-carbonyl)-2,5-diazabicyclo[4.2.0]octan-2-yl)-8-oxopyrido[2,3-b] pyrazin-5 (8H)-yl)-N-(2-chloro-4-(trifluoromethyl) phenyl)acetamide To a mixture of 2-(7-((1S,6S)-2,5-diazabicyclo[4.2.0]octan-2-yl)-2-bromo-6-ethyl-8-oxopyrido[2,3-b]pyrazin-5 (8H)-yl)-N-(2-chloro-4-(trifluoromethyl)phenyl)acetamide trifluoroacetate (Intermediate-64) (100 mg, 167 mol, 1.0 eq) and sodium 5-hydroxy-6-methylpyrimidine-4-carboxylate (Intermediate-55) (77 mg, 500 mol, 3.0 eq) in pyridine (40 mL) was added EDCI (192 mg, 1.00 mmol, 6.0 eq), and the resulting mixture was stirred at 40° C. for 1 h. The reaction mixture was diluted with H$_2$O (10 mL) and extracted with EtOAc (5 mL*3). The combined organic layers were washed with brine (30 mL), dried over anhydrous Na$_2$SO$_4$, filtered and the filtrate was concentrated under reduced pressure. The residue was purified by reverse phase HPLC (C18 column, water (0.1% FA-ACN) to afford the title compound.

LCMS: 737.3 [M+H]$^+$.

Intermediate-66a: 1-(6-(bis(4-methoxybenzyl) amino)-3-(methylthio)-1,2,4-triazin-5-yl)-2-bromopentane-1,3-dione Intermediate-67: tert-butyl (1S,6S)-5-(7-ethyl-3-(methylthio)-5-oxo-5,8-dihydropyrido[3,2-e][1,2,4] triazin-6-yl)-2,5-diazabicyclo[4.2.0]octane-2-carboxylate Intermediate-68: tert-butyl(1S,6S)-5-(8-(2-((2-chloro-4-(trifluoromethyl)phenyl)amino)-2-oxoethyl)-7-ethyl-3-(methylthio)-5-oxo-5,8-dihydropyrido[3,2-e][1,2,4]triazin-6-yl)-2,5-diazabicyclo [4.2.0]octane-2-carboxylate Intermediate-69: 2-(6-((1S,6S)-2,5-diazabicyclo [4.2.0]octan-2-yl)-7-ethyl-3-(2-methylprop-1-en-1-yl)-5-oxopyrido[3,2-e][1,2,4]triazin-8 (5H)-yl)-N-(2-chloro-4-(trifluoromethyl)phenyl)acetamide Trifluoroacetate

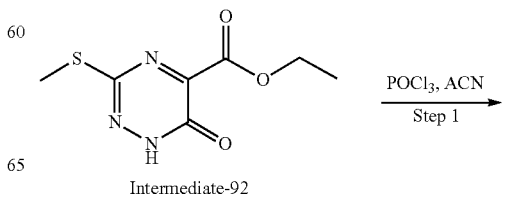

Intermediate-92

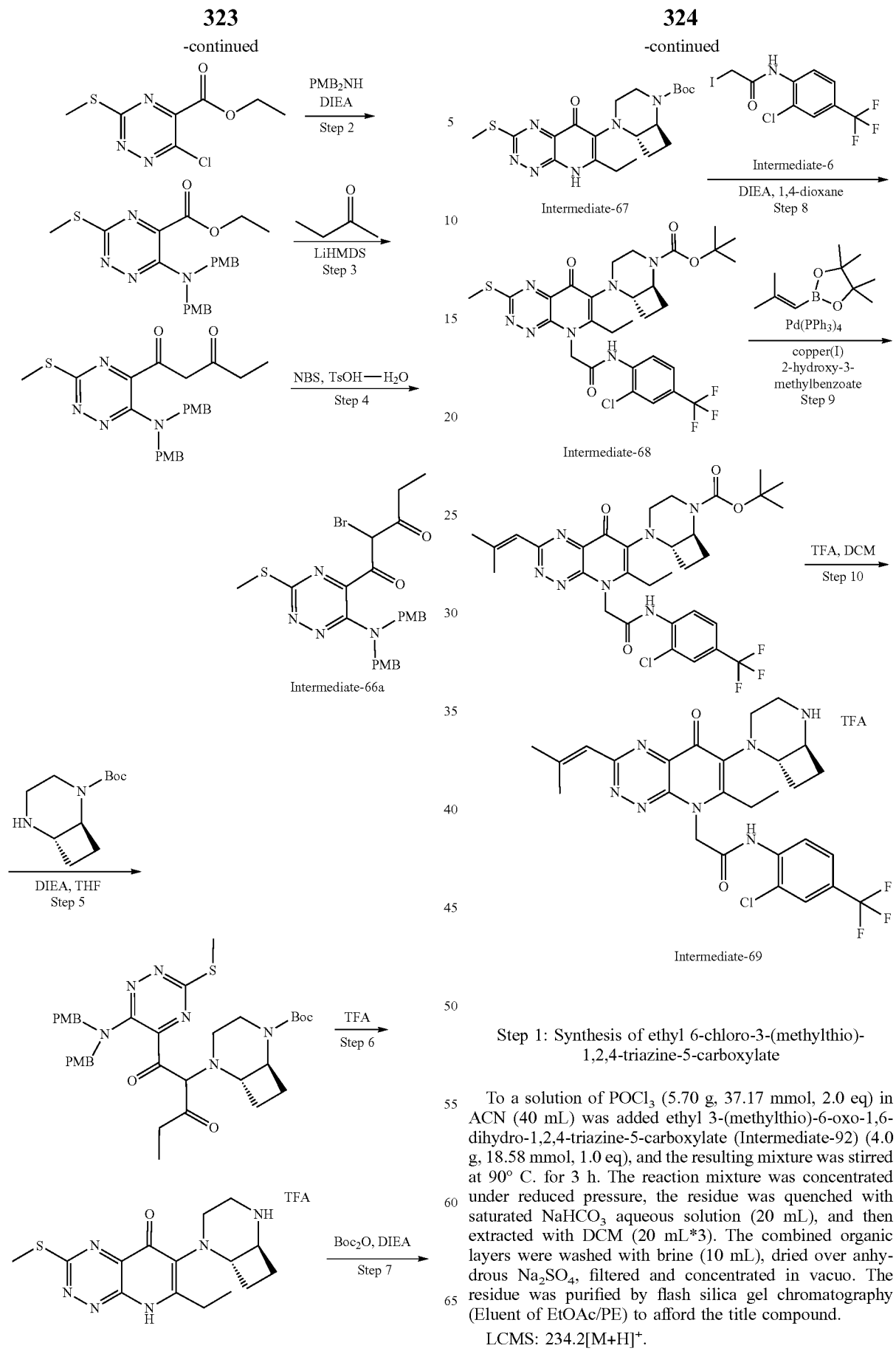

Step 1: Synthesis of ethyl 6-chloro-3-(methylthio)-1,2,4-triazine-5-carboxylate

To a solution of POCl$_3$ (5.70 g, 37.17 mmol, 2.0 eq) in ACN (40 mL) was added ethyl 3-(methylthio)-6-oxo-1,6-dihydro-1,2,4-triazine-5-carboxylate (Intermediate-92) (4.0 g, 18.58 mmol, 1.0 eq), and the resulting mixture was stirred at 90° C. for 3 h. The reaction mixture was concentrated under reduced pressure, the residue was quenched with saturated NaHCO$_3$ aqueous solution (20 mL), and then extracted with DCM (20 mL*3). The combined organic layers were washed with brine (10 mL), dried over anhydrous Na$_2$SO$_4$, filtered and concentrated in vacuo. The residue was purified by flash silica gel chromatography (Eluent of EtOAc/PE) to afford the title compound.

LCMS: 234.2[M+H]$^+$.

Step 2: Synthesis of ethyl 6-(bis(4-methoxybenzyl) amino)-3-(methylthio)-1,2,4-triazine-5-carboxylate To a solution of ethyl 6-chloro-3-(methylthio)-1,2,4-triazine-5-carboxylate (2.9 g, 12.41 mmol, 1.0 eq) and bis(4-methoxybenzyl)amine (3.83 g, 14.89 mmol, 1.2 eq) in 1,4-dioxane (15 mL) was added DIEA (4.81 g, 37.23 mmol, 3.0 eq), and the resulting mixture was stirred at 110° C. for 32 h. The reaction mixture was concentrated under reduced pressure and then purified by flash silica gel chromatography (Eluent of EtOAc/PE) to afford the title compound.
LCMS: 455.2[M+H]$^+$.
$^1$H NMR (400 MHz, CDCl$_3$) δ=7.02 (d, 4H), 6.79-6.70 (m, 4H), 4.50 (s, 4H), 4.23 (q, 2H), 3.72 (s, 6H), 2.59 (s, 3H), 1.23 (t, 3H).

Step 3: Synthesis of 1-(6-(bis(4-methoxybenzyl) amino)-3-(methylthio)-1,2,4-triazin-5-yl)pentane-1, 3-dione To a solution of butan-2-one (1.43 g, 19.80 mmol, 3.0 eq) and ethyl 6-(bis(4-methoxybenzyl)amino)-3-(methylthio)-1, 2,4-triazine-5-carboxylate (3.00 g, 6.60 mmol, 1.0 eq) in 2-methylfuran (30 mL) was added a solution of LiHMDS (1 M in THF, 19.80 mL, 3.0 eq), and the resulting mixture was stirred at 80° C. for 2 h. The reaction mixture was quenched with saturated NH$_4$Cl aqueous solution (100 mL), and then extracted with EtOAc (50 mL*3). The combined organic layers were washed with brine (20 mL), dried over anhydrous Na$_2$SO$_4$, filtered and concentrated under reduced pressure. The residue was purified by flash silica gel chromatography (Eluent of EtOAc/PE) to afford the title compound.
LCMS: 481.2[M+H]$^+$.

Step 4: Synthesis of 1-(6-(bis(4-methoxybenzyl) amino)-3-(methylthio)-1,2,4-triazin-5-yl)-2-bromopentane-1,3-dione To a solution of 1-(6-(bis(4-methoxybenzyl)amino)-3-(methylthio)-1,2,4-triazin-5-yl)pentane-1,3-dione (2.3 g, 4.79 mmol, 1.0 eq) and TsOH·H$_2$O (165 mg, 957 mol, 0.2 eq) in DCM (20 mL) was added NBS (767 mg, 4.31 mmol, 0.9 eq) at 0° C., and the resulting mixture was stirred at 0° C. for 1 h. The reaction mixture was poured into ice-water (20 mL) and extracted with DCM (20 mL*3). The combined organic layers were washed with brine (30 mL), dried over anhydrous Na$_2$SO$_4$, filtered and concentrated in vacuo to afford the title compound, which was used in the next step without further purification.
LCMS: 559.2[M+H]$^+$.

Step 5: Synthesis of tert-butyl (1S,6S)-5-(1-(6-(bis (4-methoxybenzyl)amino)-3-(methylthio)-1,2,4-triazin-5-yl)-1,3-dioxopentan-2-yl)-2,5-diazabicyclo [4.2.0]octane-2-carboxylate To a solution of 1-(6-(bis(4-methoxybenzyl)amino)-3-(methylthio)-1,2,4-triazin-5-yl)-2-bromopentane-1,3-dione (Intermediate-66) (2.60 g, 4.65 mmol, 1.0 eq) and tert-butyl (1S,6S)-2,5-diazabicyclo[4.2.0]octane-2-carboxylate (CAS: 2920219-11-8) (987 mg, 4.65 mmol, 1.0 eq) in THF (26 mL) was added DIEA (1.20 g, 9.29 mmol, 2.0 eq), and the resulting mixture was stirred at 50° C. for 1.5 h. The reaction mixture was poured into water (20 mL) and extracted with EtOAc (20 mL*3). The combined organic layers were washed with brine (30 mL), dried over anhydrous Na$_2$SO$_4$, filtered and concentrated in vacuo. The residue was purified by flash silica gel chromatography (Eluent of EtOAc/PE) to afford the title compound.
LCMS: 691.2 [M+H]$^+$.

Step 6: Synthesis of 6-((1S,6S)-2,5-diazabicyclo [4.2.0]octan-2-yl)-7-ethyl-3-(methylthio)pyrido[3,2-e][1,2,4]triazin-5 (8H)-one Trifluoroacetate A solution of tert-butyl (1S,6S)-5-(1-(6-(bis(4-methoxybenzyl)amino)-3-(methylthio)-1,2,4-triazin-5-yl)-1,3-dioxopentan-2-yl)-2,5-diazabicyclo[4.2.0]octane-2-carboxylate (1.89 g, 2.74 mmol, 1.0 eq) in TFA (20 mL) was stirred at 50° C. for 1 h, and then it was concentrated in vacuo to afford the title compound, which was used into the next step without further purification.
LCMS: 333.2[M+H]$^+$.

Step 7: Synthesis of tert-butyl (1S,6S)-5-(7-ethyl-3-(methylthio)-5-oxo-5,8-dihydropyrido[3,2-e][1,2,4] triazin-6-yl)-2,5-diazabicyclo[4.2.0]octane-2-carboxylate To a solution of 6-((1S,6S)-2,5-diazabicyclo[4.2.0]octan-2-yl)-7-ethyl-3-(methylthio)pyrido[3,2-e][1,2,4]triazin-5 (8H)-one trifluoroacetate (914 mg, 2.75 mmol, 1.0 eq) and DIEA (1.78 g, 13.75 mmol, 5.0 eq) in DCM (10 mL) was added Boc$_2$O (600 mg, 2.75 mmol, 1.0 eq), and the resulting mixture was stirred at room temperature for 1 h. The reaction mixture was poured into H$_2$O (20 mL), extracted with EtOAc (20 mL*3). The combined organic layers were washed with brine (10 mL), dried over Na$_2$SO$_4$, filtered and concentrated under reduced pressure. The residue was triturated with a mixed solvent of PE and DCM (PE/DCM=4/1, 5 mL) to afford the title compound.
LCMS: 433.2 [M+H]$^+$.

Step 8: Synthesis of tert-butyl (1S,6S)-5-(8-(2-((2-chloro-4-(trifluoromethyl)phenyl)amino)-2-oxoethyl)-7-ethyl-3-(methylthio)-5-oxo-5,8-dihydropyrido[3,2-e][1,2,4]triazin-6-yl)-2,5-diazabicyclo [4.2.0]octane-2-carboxylate To a solution of tert-butyl (1S,6S)-5-(7-ethyl-3-(methylthio)-5-oxo-5,8-dihydropyrido[3,2-e][1,2,4]triazin-6-yl)-2, 5-diazabicyclo[4.2.0]octane-2-carboxylate (Intermediate-67) (500 mg, 1.16 mmol, 1.0 eq) and N-(2-chloro-4-(trifluoromethyl)phenyl)-2-iodoacetamide (Intermediate-6) (462 mg, 1.27 mmol, 1.1 eq) in 1,4-dioxane (5 mL) was added DIEA (448 mg, 3.47 mmol, 3.0 eq), and the resulting mixture was stirred at 80° C. overnight. The mixture was concentrated in vacuo and then purified by reverse phase HPLC (C18 column, water (0.1% FA-ACN) to afford the title compound.
LCMS: 668.2 [M+H]$^+$.

Step 9: Synthesis of tert-butyl (1S,6S)-5-(8-(2-((2-chloro-4-(trifluoromethyl)phenyl)amino)-2-oxoethyl)-7-ethyl-3-(2-methylprop-1-en-1-yl)-5-oxo-5, 8-dihydropyrido[3,2-e][1,2,4]triazin-6-yl)-2,5-diazabicyclo[4.2.0]octane-2-carboxylate To a solution of tert-butyl (1S,6S)-5-(8-(2-((2-chloro-4-(trifluoromethyl)phenyl)amino)-2-oxoethyl)-7-ethyl-3-(methylthio)-5-oxo-5,8-dihydropyrido[3,2-e][1,2,4]triazin-6-yl)-2,5-diazabicyclo[4.2.0]octane-2-carboxylate (Intermediate-68) (400 mg, 599 mol, 1.0 eq) and 4,4,5,5- tetramethyl-2-(2-methylprop-1-en-1-yl)-1,3,2-dioxaborolane (150 mg, 1.50 mmol, 2.5 eq) in THF (4 mL) was added Pd(PPh$_3$)$_4$ (69 mg, 60 mol, 0.1 eq) and copper(I) 2-hydroxy-3-methylbenzoate (321 mg, 1.50 mmol, 2.5 eq) under N$_2$ atmosphere, and then the resulting mixture was stirred at 60° C. overnight. The reaction mixture was concentrated in vacuo and then purified by reverse phase HPLC (C18 column, water (0.1% FA-ACN) to afford the title compound.

LCMS: 676.2 [M+H]$^+$.

Step 10: Synthesis of 2-(6-(((1S,6S)-2,5-diazabicyclo[4.2.0]octan-2-yl)-7-ethyl-3-(2-methylprop-1-en-1-yl)-5-oxopyrido[3,2-e][1,2,4]triazin-8 (5H)-yl)-N-(2-chloro-4-(trifluoromethyl)phenyl)acetamide Trifluoroacetate To a solution of tert-butyl (1S,6S)-5-(8-(2-((2-chloro-4-(trifluoromethyl)phenyl)amino)-2-oxoethyl)-7-ethyl-3-(2-methylprop-1-en-1-yl)-5-oxo-5,8-dihydropyrido[3,2-e][1,2,4]triazin-6-yl)-2,5-diazabicyclo[4.2.0]octane-2-carboxylate (220 mg, 325 mol, 1.0 eq) in DCM (0.3 mL) was added TFA (3.30 mL), and it was stirred at room temperature for 1 h. The reaction mixture was concentrated in vacuo to afford the title compound, which was used into the next step without further purification.

LCMS: 576.2 [M+H]$^+$.

Intermediate-70: 2-bromo-1-(3-((4-methoxybenzyl)amino)-6-methylfuro[2,3-b]pyrazin-2-yl)pentane-1,3-dione Intermediate-71: tert-butyl 4-(7-ethyl-2-methyl-5-oxo-5,8-dihydrofuro[2,3-b]pyrido[3,2-e]pyrazin-6-yl)piperazine-1-carboxylate Intermediate-72: N-(2-chloro-4-(trifluoromethyl)phenyl)-2-(7-ethyl-2-methyl-5-oxo-6-(piperazin-1-yl)furo[2,3-b]pyrido[3,2-e]pyrazin-8 (5H)-yl)acetamide Hydrochloride

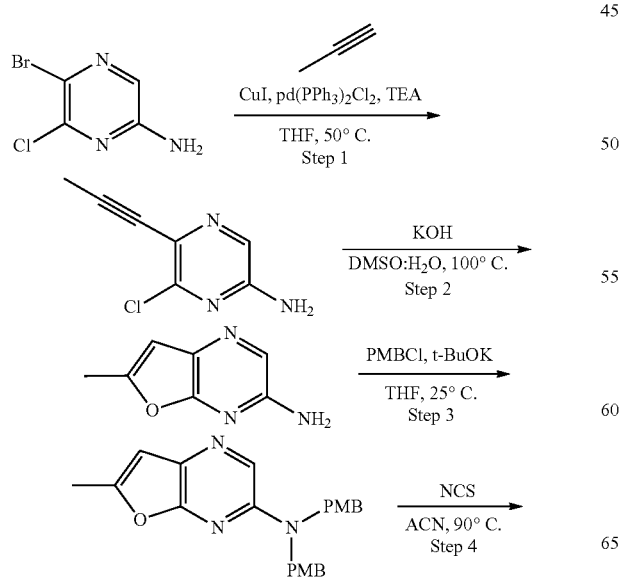

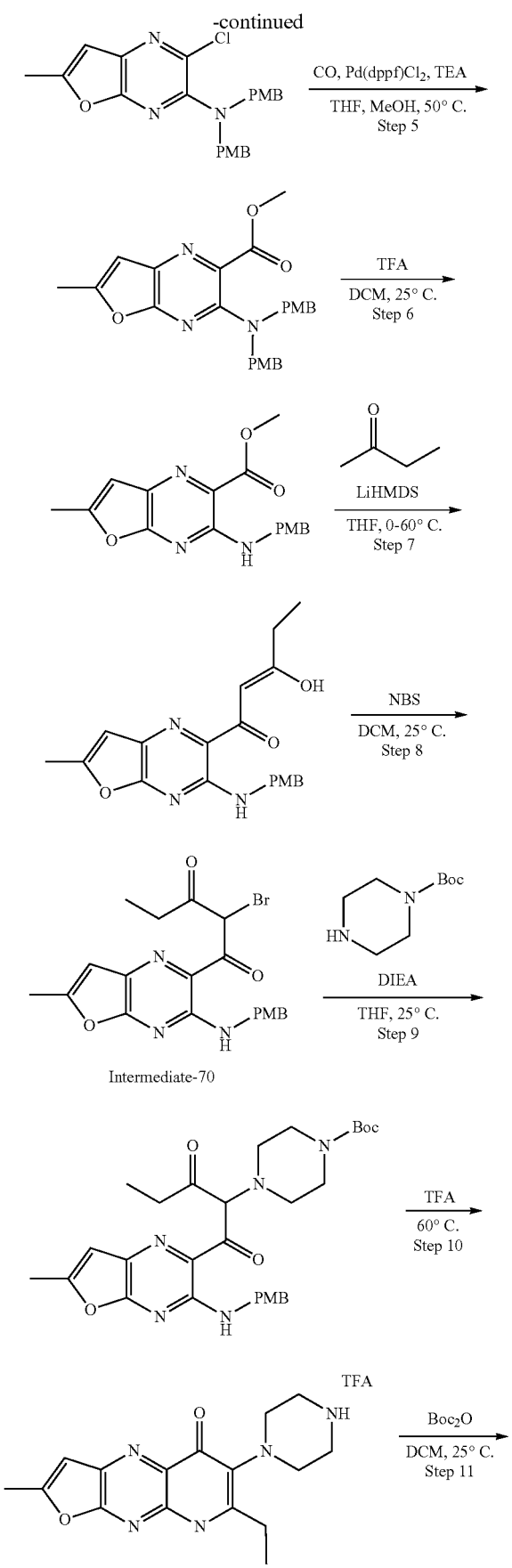

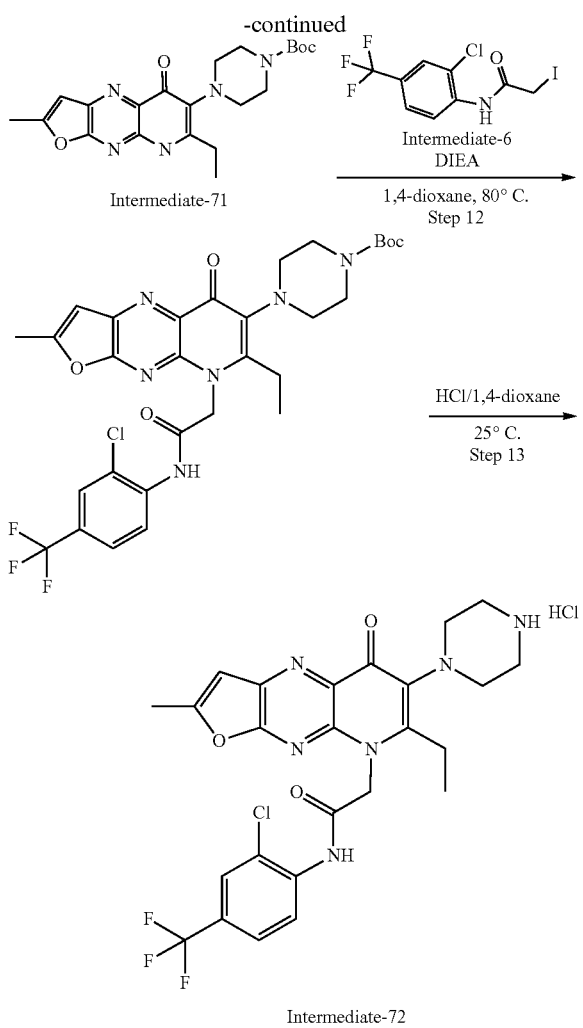

Step 1. Synthesis of 6-chloro-5-(prop-1-yn-1-yl)pyrazin-2-amine

To a solution of methyl 5-bromo-6-chloro-pyrazin-2-amine (10.00 g, 47.97 mmol, 1 eq) in THF (10 mL) was added Et$_3$N (16.99 g, 167.91 mmol, 23.37 mL, 3.5 eq), Pd(PPh$_3$)$_2$Cl$_2$ (3.37 g, 4.80 mmol, 0.1 eq), CuI (457 mg, 2.40 mmol, 0.05 eq) and prop-1-yne (1 M, 95.95 mL, 2 eq). The mixture was stirred at 50° C. for 12 h. The resulting mixture was filtered to remove the insoluble and concentrated in vacuum to give a residue. The residue was purified by silica gel chromatography (Eluent of EtOAc/PE) to afford the title compound.
$^1$H NMR (400 MHz, CDCl$_3$) δ ppm 7.83 (s, 1H), 4.89 (s, 2H), 2.13 (s, 3H).
LCMS: 168.0 [M+H]$^+$.

Step 2. Synthesis of 6-methylfuro[2,3-b]pyrazin-3-amine

To a solution of 6-chloro-5-prop-1-ynyl-pyrazin-2-amine (6.50 g, 38.78 mmol, 1 eq) in DMSO (65 mL) and H$_2$O (65 mL) was added KOH (4.35 g, 77.57 mmol, 2 eq). The mixture was stirred at 100° C. for 16 h. The reaction mixture was poured into saturated NH$_4$Cl aqueous solution (400 mL) and extracted with EtOAc (200 mL*3). The combined organic layer was washed with brine (100 mL*2), dried over anhydrous Na$_2$SO$_4$, filtered and concentrated in vacuum to give a residue. The residue was purified by silica gel chromatography (Eluent of EtOAc/PE) to afford the title compound.
$^1$H NMR (400 MHz, DMSO-d$_6$) δ ppm 7.76 (s, 1H), 6.54 (s, 1H), 6.42 (s, 2H), 2.38 (s, 3H).
LCMS: 150.2 [M+H]$^+$.

Step 3. Synthesis of N,N-bis(4-methoxybenzyl)-6-methylfuro[2,3-b]pyrazin-3-amine To a solution of 6-methylfuro[2,3-b]pyrazin-3-amine (1.50 g, 10.06 mmol, 1 eq) in THF (30 mL) was added t-BuOK (4.51 g, 40.24 mmol, 2.01 mL, 4 eq) and 1-(chloromethyl)-4-methoxy-benzene (5.36 g, 34.19 mmol, 4.64 mL, 3.4 eq). The mixture was stirred at 25° C. for 1 h. The mixture was poured into H$_2$O (80 mL). Then the mixture was extracted with EtOAc (30 mL*3). Then the combined organic phase was washed with brine (40 mL), dried over Na$_2$SO$_4$, filtered and concentrated in vacuum to give a residue. The residue was purified by silica gel chromatography (Eluent of EtOAc/PE) to afford the title compound.
$^1$H NMR (400 MHz, CDCl$_3$) δ ppm 7.87 (s, 1H), 7.17 (d, 4H), 6.84 (d, 4H), 6.44 (s, 1H), 4.75 (s, 4H), 3.80 (s, 6H), 2.47 (s, 3H).
LCMS: 390.2 [M+H]$^+$.

Step 4. Synthesis of 2-chloro-N,N-bis(4-methoxybenzyl)-6-methylfuro[2,3-b]pyrazin-3-amine To a solution of N,N-bis[(4-methoxyphenyl)methyl]-6-methyl-furo[2,3-b]pyrazin-3-amine (2.10 g, 5.39 mmol, 1 eq) in ACN (25 mL) was added NCS (720 mg, 5.39 mmol, 1 eq). The mixture was stirred at 90° C. for 3 h. Then it was poured into H$_2$O (20 mL). The mixture was extracted with EtOAc (30 mL*3) and the combined organic phase was washed with brine (50 mL), dried over anhydrous Na$_2$SO$_4$ and concentrated under reduced pressure to give a residue. The residue was purified by silica gel chromatography (Eluent of EtOAc/PE) to afford the title compound.
LCMS: 424.2 [M+H]$^+$.

Step 5. Synthesis of methyl 3-(bis(4-methoxybenzyl)amino)-6-methylfuro[2,3-b]pyrazine-2-carboxylate To a solution of 2-chloro-N,N-bis[(4-methoxyphenyl)methyl]-6-methyl-furo[2,3-b]pyrazin-3-amine (1.00 g, 2.36 mmol, 1 eq) in THF (10 mL) and MeOH (10 mL) was added Et$_3$N (716 mg, 7.08 mmol, 985 µL, 3 eq) and Pd(dppf)Cl$_2$ (173 mg, 236 mol, 0.1 eq). The mixture was degassed and purged with N$_2$ for 3 times then degassed and purged with CO for 3 times. The reaction was stirred under CO (50 psi) atmosphere at 50° C. for 16 h. The reaction mixture was filtered and concentrated under reduced pressure to give a residue. The residue was purified by silica gel chromatography (Eluent of EtOAc/PE) to afford the title compound.
LCMS: 448.2 [M+H]$^+$.

Step 6. Synthesis of methyl 3-((4-methoxybenzyl)amino)-6-methylfuro[2,3-b]pyrazine-2-carboxylate To a solution of methyl 3-[bis[(4-methoxyphenyl)methyl]amino]-6-methyl-furo[2,3-b]pyrazine-2-carboxylate (950 mg, 2.12 mmol, 1 eq) in DCM (10 mL) was added TFA (726 mg, 6.37 mmol, 473 µL, 3 eq). The mixture was stirred at 25° C. for 0.5 h. The mixture was adjusted pH to 7 by saturated NaHCO₃ aqueous solution (20 mL), then extracted with DCM (15 mL*3). The combined organic layer was dried over anhydrous Na₂SO₄, filtered and concentrated in vacuum to give the title compound, which was used into next step without further purification.

LCMS: 328.0 [M+H]⁺.

Step 7. Synthesis of 3-hydroxy-1-(3-((4-methoxybenzyl)amino)-6-methylfuro[2,3-b]pyrazin-2-yl)pent-2-en-1-one To a solution of butan-2-one (611 mg, 8.48 mmol, 758 µL, 3 eq) in THF (5 mL) was added LiHMDS (1 M, 8.48 mL, 3 eq) at 0° C. The mixture was stirred at 0° C. for 0.5 h. Then to the mixture was added a solution of methyl 3-((4-methoxybenzyl)amino)-6-methylfuro[2,3-b]pyrazine-2-carboxylate (925 mg, 2.83 mmol, 1 eq) in THF (5 mL) dropwise at 0° C. The reaction mixture was stirred at 60° C. for 1 h. Then it was quenched by saturated NH₄Cl aqueous solution (20 mL) and extracted with EtOAc (20 mL*3). The combined organic layer was dried over anhydrous Na₂SO₄, filtered and concentrated in vacuum to give a residue. The residue was purified by silica gel chromatography (Eluent of EtOAc/PE) to afford the title compound.

LCMS: 368.2 [M+H]⁺.

Step 8. Synthesis of 2-bromo-1-(3-((4-methoxybenzyl)amino)-6-methylfuro[2,3-b]pyrazin-2-yl)pentane-1,3-dione To a solution of 3-hydroxy-1-(3-((4-methoxybenzyl)amino)-6-methylfuro[2,3-b]pyrazin-2-yl)pent-2-en-1-one (330 mg, 898 mol, 1 eq) in DCM (5 mL) was added NBS (160 mg, 898 mol, 1 eq). The mixture was stirred at 25° C. for 1 h. The reaction was poured into H₂O (20 mL) and extracted with DCM (10 mL*3). The combined organic layer was dried over anhydrous Na₂SO₄, filtered and concentrated under vacuum to give a residue. The residue was purified by silica gel chromatography (Eluent of EtOAc/PE) to afford the title compound.

LCMS: 446.1 [M+H]⁺.

Step 9. Synthesis of tert-butyl 4-(1-(3-((4-methoxybenzyl)amino)-6-methylfuro[2,3-b]pyrazin-2-yl)-1,3-dioxopentan-2-yl)piperazine-1-carboxylate To a solution of 2-bromo-1-(3-((4-methoxybenzyl)amino)-6-methylfuro[2,3-b]pyrazin-2-yl)pentane-1,3-dione (Intermediate-70) (350 mg, 784 mol, 1 eq) and tert-butyl piperazine-1-carboxylate (190 mg, 1.02 mmol, 1.3 eq) in THF (5 mL) was added DIEA (152 mg, 1.18 mmol, 205 µL, 1.5 eq). The mixture was stirred at 25° C. for 2 h. The reaction was poured into H₂O (20 mL) and extracted with DCM (10 mL*3). The combined organic layer was concentrated in vacuum to give a residue. The residue was purified by silica gel chromatography (Eluent of EtOAc/PE) to afford the title compound.

LCMS: 552.3 [M+H]⁺.

Step 10. Synthesis of 7-ethyl-2-methyl-6-(piperazin-1-yl)furo[2,3-b]pyrido[3,2-e]pyrazin-5 (8H)-one trifluoroacetate A solution of tert-butyl 4-(1-(3-((4-methoxybenzyl)amino)-6-methylfuro[2,3-b]pyrazin-2-yl)-1,3-dioxopentan-2-yl)piperazine-1-carboxylate (360 mg, 653 mol, 1 eq) in TFA (5 mL) was stirred at 60° C. for 1 h. The mixture was concentrated in vacuum directly to afford the title compound, which was used into next step without further purification.

LCMS: 314.1 [M+H]⁺.

Step 11. Synthesis of tert-butyl 4-(7-ethyl-2-methyl-5-oxo-5,8-dihydrofuro[2,3-b]pyrido[3,2-e]pyrazin-6-yl)piperazine-1-carboxylate To a solution of 7-ethyl-2-methyl-6-(piperazin-1-yl)furo[2,3-b]pyrido[3,2-e]pyrazin-5 (8H)-one trifluoroacetate (350 mg, 1.12 mmol, 1 eq) in DCM (5 mL) was added Boc₂O (366 mg, 1.68 mmol, 385 µL, 1.5 eq) and DIEA (433 mg, 3.35 mmol, 584 µL, 3 eq). The mixture was stirred at 25° C. for 1 h. The reaction was poured into H₂O (20 mL) and extracted with DCM (10 mL*3), the combined organic layer was dried over anhydrous Na₂SO₄, filtered and concentrated in vacuum to give a residue. The residue was purified by silica gel chromatography (Eluent of EtOAc/PE) to afford the title compound.

LCMS: 414.2 [M+H]⁺.

Step 12. Synthesis of tert-butyl 4-(8-(2-((2-chloro-4-(trifluoromethyl)phenyl)amino)-2-oxoethyl)-7-ethyl-2-methyl-5-oxo-5,8-dihydrofuro[2,3-b]pyrido[3,2-e]pyrazin-6-yl)piperazine-1-carboxylate To a solution of tert-butyl 4-(7-ethyl-2-methyl-5-oxo-5,8-dihydrofuro[2,3-b]pyrido[3,2-e]pyrazin-6-yl)piperazine-1-carboxylate (Intermediate-71) (100 mg, 242 mol, 1 eq) in 1,4-dioxane (3 mL) was added DIEA (94 mg, 726 mol, 126 µL, 3 eq) and N-[2-chloro-4-(trifluoromethyl)phenyl]-2-iodo-acetamide (Intermediate-6) (132 mg, 363 mol, 1.5 eq). The mixture was stirred at 80° C. for 1 h. The reaction mixture was poured into H₂O (10 mL) and extracted with DCM (10 mL*3). The combined organic layer was concentrated in vacuum to give a residue. The residue was purified by silica gel chromatography (Eluent of EtOAc/PE) to afford the title compound.

¹H NMR (400 MHz, CD₃OD) δ ppm 8.12 (d, 1H), 7.81 (s, 1H), 7.59 (d, 1H), 6.89 (s, 1H), 5.64 (s, 2H), 4.05-4.03 (m, 2H), 3.86-3.65 (m, 3H), 3.15-3.09 (m, 3H), 2.73-2.70 (m, 2H), 2.62 (s, 3H), 1.49 (s, 9H), 1.34 (t, 3H).

LCMS: 649.2 [M+H]⁺.

Step 13. Synthesis of N-(2-chloro-4-(trifluoromethyl)phenyl)-2-(7-ethyl-2-methyl-5-oxo-6-(piperazin-1-yl)furo[2,3-b]pyrido[3,2-e]pyrazin-8 (5H)-yl)acetamide Hydrochloride To a solution of tert-butyl 4-(8-(2-((2-chloro-4-(trifluoromethyl)phenyl)amino)-2-oxoethyl)-7-ethyl-2-methyl-5-oxo-5,8-dihydrofuro[2,3-b]pyrido[3,2-e]pyrazin-6-yl)piperazine-1-carboxylate (80 mg, 123 mol, 1 eq) in DCM (0.5 mL) was added HCl/1,4-dioxane (2 M, 1.60 mL, 26 eq). The mixture was stirred at 25° C. for 20 min. The solution was concentrated in vacuum directly to give the title compound, which was used into next step without further purification.

LCMS: 549.2 [M+H]⁺.

Intermediate-73: 2-bromo-1-(2-((4-methoxybenzyl)amino)-6-methylthieno[2,3-b]pyrazin-3-yl) pentane-1,3-dione Intermediate-74: tert-butyl 4-(6-ethyl-2-methyl-8-oxo-5,8-dihydropyrido[2,3-b]thieno[2,3-e]pyrazin-7-yl)piperazine-1-carboxylate Intermediate-75: N-(2-chloro-4-(trifluoromethyl)phenyl)-2-(6-ethyl-2-methyl-8-oxo-7-(piperazin-1-yl)pyrido[2,3-b]thieno[2,3-e]pyrazin-5 (8H)-yl)acetamide Hydrochloride

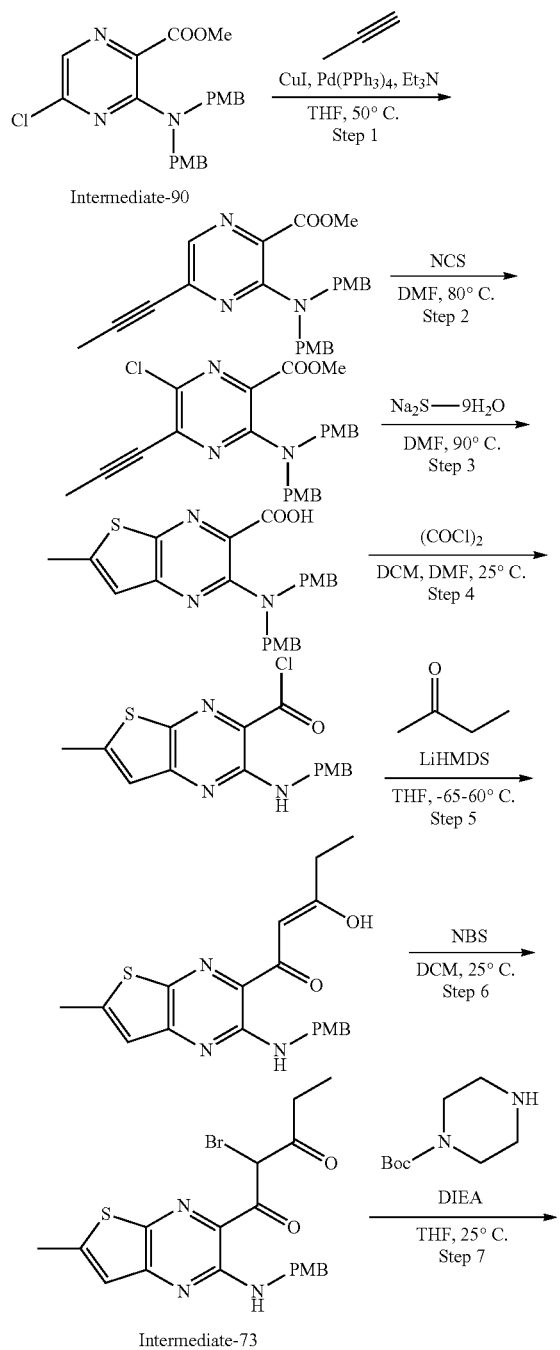

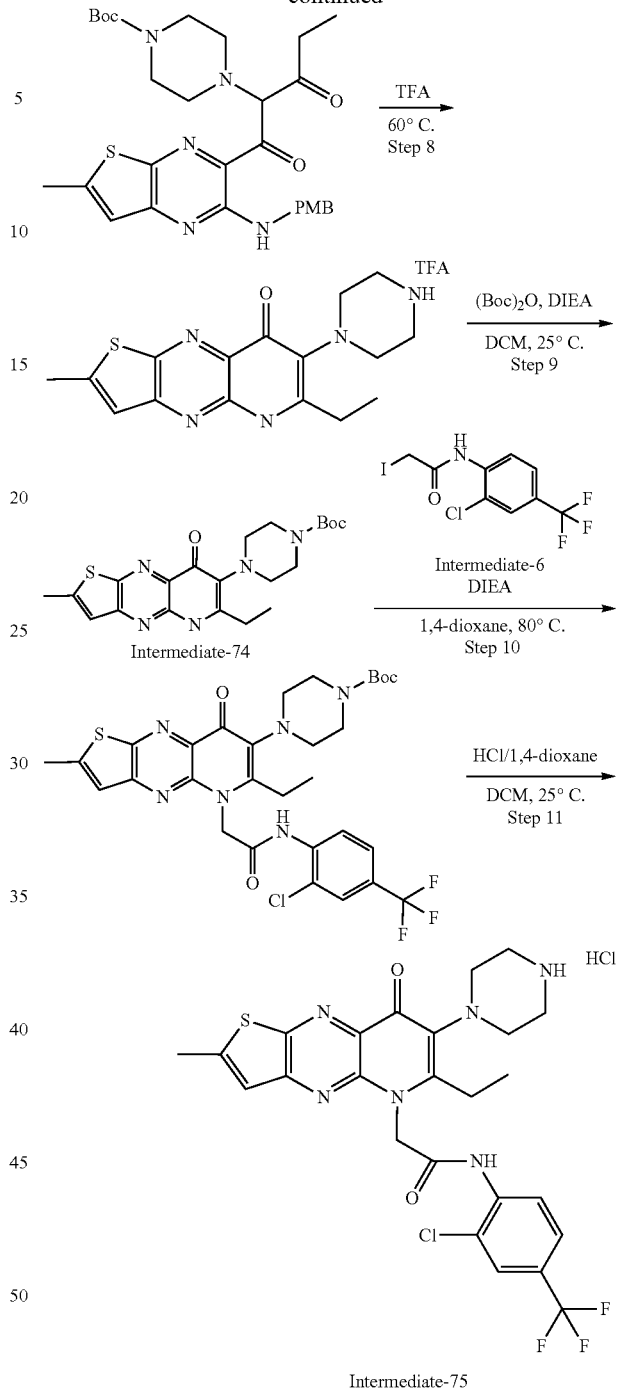

Step 1. Synthesis of methyl 3-(bis(4-methoxybenzyl)amino)-5-(prop-1-yn-1-yl) pyrazine-2-carboxylate To a solution of methyl 3-(bis(4-methoxybenzyl)amino)-5-chloropyrazine-2-carboxylate (Intermediate-90) (5.00 g, 11.69 mmol, 1 eq) in THF (50 mL) was added prop-1-yne (1 M THF solution, 35.06 mL, 3 eq), Pd(PPh$_3$)$_4$ (2.70 g, 2.34 mmol, 0.2 eq), CuI (445 mg, 2.34 mmol, 0.2 eq) and Et$_3$N (5.91 g, 58.43 mmol, 8.13 mL, 5 eq). The mixture was stirred at 50° C. for 5 h. The resulting mixture was filtered to remove the insoluble and concentrated in vacuum to give a residue. The residue was purified by silica gel chromatography (Eluent of EtOAc/PE) to afford the title compound.

LCMS: 432.2 [M+H]$^+$.

Step 2. Synthesis of methyl 3-(bis(4-methoxybenzyl)amino)-6-chloro-5-(prop-1-yn-1-yl) pyrazine-2-carboxylate To a solution of methyl 3-(bis(4-methoxybenzyl)amino)-5-(prop-1-yn-1-yl) pyrazine-2-carboxylate (5.00 g, 11.59 mmol, 1 eq) in DMF (100 mL) was added NCS (1.55 g, 11.59 mmol, 1.0 eq). The mixture was stirred at 80° C. for 1 h. Then it was diluted with H$_2$O (50 mL) and extracted with EtOAc (50 mL*2). The combined organic phase was washed with brine (50 mL), dried over anhydrous Na$_2$SO$_4$, filtered and concentrated in vacuum to give a residue. The residue was purified by silica gel chromatography (Eluent of EtOAc/PE) to afford the title compound.

$^1$H NMR (400 MHz, CDCl$_3$) δ ppm 7.03 (d, 4H), 6.82 (d, 4H), 4.52 (s, 4H), 3.85 (s, 3H), 3.79 (s, 6H), 2.19 (s, 3H).

LCMS: 466.2 [M+H]$^+$.

Step 3. Synthesis of 2-(bis(4-methoxybenzyl)amino)-6-methylthieno[2,3-b]pyrazine-3-carboxylic Acid To a solution of methyl 3-(bis(4-methoxybenzyl)amino)-6-chloro-5-(prop-1-yn-1-yl) pyrazine-2-carboxylate (4.50 g, 9.66 mmol, 1 eq) in DMF (45 mL) was added Na$_2$S·9H$_2$O (11.60 g, 48.29 mmol, 5 eq). The mixture was stirred at 90° C. for 0.5 h. Then it was diluted with H$_2$O (100 mL) and filtered to remove the insoluble. The filtrate was extracted with DCM (100 mL*2). The combined organic phase was washed with brine (100 mL), dried over anhydrous Na$_2$SO$_4$, filtered and concentrated in vacuum to give the title compound, which was used into the next step directly without further purification.

LCMS: 450.2 [M+H]$^+$.

Step 4. Synthesis of 2-((4-methoxybenzyl)amino)-6-methylthieno[2,3-b]pyrazine-3-carbonyl Chloride To a solution of 2-(bis(4-methoxybenzyl)amino)-6-methylthieno[2,3-b]pyrazine-3-carboxylic acid (2.40 g, 5.34 mmol, 1 eq) in DCM (48 mL) was added (COCl)$_2$ (814 mg, 6.41 mmol, 561 µL, 1.2 eq) and DMF (39 mg, 534 mol, 41 µL, 0.1 eq). The mixture was stirred at 25° C. for 20 min. Then the mixture was concentrated in vacuum to give the title compound, which was used into the next step directly without further purification.

Step 5. Synthesis of 3-hydroxy-1-(2-((4-methoxybenzyl)amino)-6-methylthieno[2,3-b]pyrazin-3-yl) pent-2-en-1-one To a solution of butan-2-one (622 mg, 8.63 mmol, 772 µL, 3 eq) in THF (16 mL) was added LiHMDS (1 M, 8.63 mL, 3 eq) at –65° C. and stirred for 20 min. Then the solution of 2-((4-methoxybenzyl)amino)-6-methylthieno[2,3-b]pyrazine-3-carbonyl chloride (1.00 g, 2.88 mmol, 1 eq) in THF (8 mL) was added into the solution at –65° C. dropwise and the mixture was stirred at 60° C. for 1 h. The mixture was quenched by saturated NH$_4$Cl aqueous solution (50 mL) and extracted with EtOAc (50 mL*2). The combined organic phase was washed with brine (40 mL), dried over anhydrous Na$_2$SO$_4$, filtered and concentrated in vacuum to give a residue. The residue was purified by silica gel chromatography (Eluent of EtOAc/PE) to afford the title compound.

LCMS: 384.1 [M+H]$^+$.

Step 6. Synthesis of 2-bromo-1-(2-((4-methoxybenzyl)amino)-6-methylthieno[2,3-b]pyrazin-3-yl) pentane-1,3-dione To a solution of 3-hydroxy-1-(2-((4-methoxybenzyl)amino)-6-methylthieno[2,3-b]pyrazin-3-yl) pent-2-en-1-one (340 mg, 887 mol, 1 eq) in DCM (6 mL) was added the solution of NBS (142 mg, 798 µmol, 0.9 eq) in DCM (1 mL) dropwise at 0° C. The mixture was stirred at 25° C. for 0.5 h. The residue was diluted with H$_2$O (20 mL) and extracted with DCM (25 mL*2). The combined organic phase was washed with brine (10 mL), dried over anhydrous Na$_2$SO$_4$, filtered and concentrated in vacuum to give a residue. The residue was purified by silica gel chromatography (Eluent of EtOAc/PE) to afford the title compound.

$^1$H NMR (400 MHz, CDCl$_3$) δ ppm 7.32 (d, 2H), 6.93 (s, 1H), 6.88 (d, 2H), 6.32 (s, 1H), 4.71-4.67 (m, 2H), 3.81 (s, 3H), 2.94 (q, 2H), 2.66 (s, 3H), 1.18 (t, 3H).

LCMS: 464.0 [M+H]$^+$.

Step 7. Synthesis of tert-butyl 4-(1-(2-((4-methoxybenzyl)amino)-6-methylthieno[2,3-b]pyrazin-3-yl)-1,3-dioxopentan-2-yl) piperazine-1-carboxylate To a solution of 2-bromo-1-(2-((4-methoxybenzyl)amino)-6-methylthieno[2,3-b]pyrazin-3-yl) pentane-1,3-dione (Intermediate-73) (270 mg, 584 µmol, 1 eq) and tert-butyl piperazine-1-carboxylate (163 mg, 876 µmol, 1.5 eq) in THF (4 mL) was added DIEA (226 mg, 1.75 mmol, 305 µL, 3 eq). The mixture was stirred at 25° C. for 1 h. The mixture was diluted with H$_2$O (20 mL) and was extracted with EtOAc (25 mL*2). The combined organic phase was washed with brine (10 mL), dried over anhydrous Na$_2$SO$_4$, filtered and concentrated in vacuum to give a residue. The residue was and purified by silica gel chromatography (Eluent of EtOAc/PE) to afford the title compound.

LCMS: 568.3 [M+H]$^+$.

Step 8. Synthesis of 6-ethyl-2-methyl-7-(piperazin-1-yl)pyrido[2,3-b]thieno[2,3-e]pyrazin-8 (5H)-one Trifluoroacetate A mixture of tert-butyl 4-(1-(2-((4-methoxybenzyl)amino)-6-methylthieno[2,3-b]pyrazin-3-yl)-1,3-dioxopentan-2-yl) piperazine-1-carboxylate (270 mg, 476 mol, 1 eq) in TFA (2 mL) was stirred at 60° C. for 0.5 h. The mixture was concentrated in vacuum directly to afford the title compound, which was used into next step directly without further purification.

LCMS: 330.2 [M+H]$^+$.

Step 9. Synthesis of tert-butyl 4-(6-ethyl-2-methyl-8-oxo-5,8-dihydropyrido[2,3-b]thieno[2,3-e]pyrazin-7-yl)piperazine-1-carboxylate To a solution of 6-ethyl-2-methyl-7-(piperazin-1-yl)pyrido[2,3-b]thieno[2,3-e]pyrazin-8 (5H)-one trifluoroacetate (145 mg, 440 mol, 1 eq) in DCM (4 mL) was added DIEA (228 mg, 176 mol, 307 µL, 4 eq) and Boc$_2$O (192 mg, 880 mol, 202 µL, 2 eq). The mixture was stirred at 25° C. for 0.5 h. The mixture was diluted with H$_2$O (20 mL) and was extracted with DCM (25 mL*2). The combined organic phase was washed with brine (10 mL), dried over anhydrous Na$_2$SO$_4$, filtered and concentrated in vacuum to give a residue. The residue was and purified by silica gel chromatography (Eluent of EtOAc/PE) to afford the title compound.

$^1$H NMR (400 MHz, CDCl$_3$) δ ppm 8.45 (s, 1H), 7.01 (s, 1H), 4.08-4.02 (m, 2H), 3.79-3.78 (m, 2H), 2.93 (q, 2H), 2.91-2.75 (m, 2H), 2.67 (s, 3H), 2.59-2.55 (m, 2H), 1.42 (s, 9H), 1.29 (t, 3H).

LCMS: 430.3 [M+H]$^+$.

Step 10. Synthesis of tert-butyl 4-(5-(2-((2-chloro-4-(trifluoromethyl)phenyl)amino)-2-oxoethyl)-6-ethyl-2-methyl-8-oxo-5,8-dihydropyrido[2,3-b]thieno[2,3-e]pyrazin-7-yl)piperazine-1-carboxylate To a solution of tert-butyl 4-(6-ethyl-2-methyl-8-oxo-5,8-dihydropyrido[2,3-b]thieno[2,3-e]pyrazin-7-yl)piperazine-1-carboxylate (Intermediate-74) (65 mg, 151 mol, 1 eq) and N-[2-chloro-4-(trifluoromethyl)phenyl]-2-iodo-acetamide (Intermediate-6) (72 mg, 197 mol, 1.3 eq) in 1,4-dioxane (1.3 mL) was added DIEA (59 mg, 454 mol, 79 µL, 3 eq). The mixture was stirred at 80° C. for 0.5 h. The mixture was diluted with H$_2$O (20 mL) and was extracted with EtOAc (25 mL*2). The combined organic phase was washed with brine (10 mL), dried over anhydrous Na$_2$SO$_4$, filtered and concentrated in vacuum to give a residue. The residue was purified by silica gel chromatography (Eluent of EtOAc/PE) to afford the title compound.

$^1$H NMR (400 MHz, CDCl$_3$) δ ppm 8.70 (s, 1H), 8.52 (d, 1H), 7.59 (s, 1H), 7.53 (d, 1H), 7.17 (d, 1H), 5.40 (s, 2H), 4.20-4.02 (m, 2H), 3.92-3.86 (m, 2H), 3.32-3.30 (m, 2H), 2.99 (q, 2H), 2.77 (s, 3H), 2.67-2.64 (m, 2H), 1.50 (s, 9H), 1.35 (t, 3H).

LCMS: 665.2 [M+H]$^+$.

Step 11. Synthesis of N-(2-chloro-4-(trifluoromethyl)phenyl)-2-(6-ethyl-2-methyl-8-oxo-7-(piperazin-1-yl)pyrido[2,3-b]thieno[2,3-e]pyrazin-5 (8H)-yl)acetamide Hydrochloride To a solution of tert-butyl 4-(5-(2-((2-chloro-4-(trifluoromethyl)phenyl)amino)-2-oxoethyl)-6-ethyl-2-methyl-8-oxo-5,8-dihydropyrido[2,3-b]thieno[2,3-e]pyrazin-7-yl)piperazine-1-carboxylate (30 mg, 45 mol, 1 eq) in DCM (0.5 mL) was added HCl/1,4-dioxane (2 M, 1 mL). The mixture was stirred at 25° C. for 0.5 h. The reaction mixture was concentrated under vacuum to afford the title compound, which was used into the next step without further purification.

LCMS: 565.3 [M+H]$^+$.

Intermediate-76: tert-butyl (1S,6S)-5-(6-ethyl-2-methyl-8-oxo-5,8-dihydropyrido[2,3-b]thiazolo[4,5-e]pyrazin-7-yl)-2,5-diazabicyclo[4.2.0]octane-2-carboxylate Intermediate-77: 2-(7-((1S,6S)-2,5-diazabicyclo[4.2.0]octan-2-yl)-6-ethyl-2-methyl-8-oxopyrido[2,3-b]thiazolo[4,5-e]pyrazin-5 (8H)-yl)-N-(2-chloro-4-(trifluoromethyl)phenyl)acetamide Trifluoroacetate

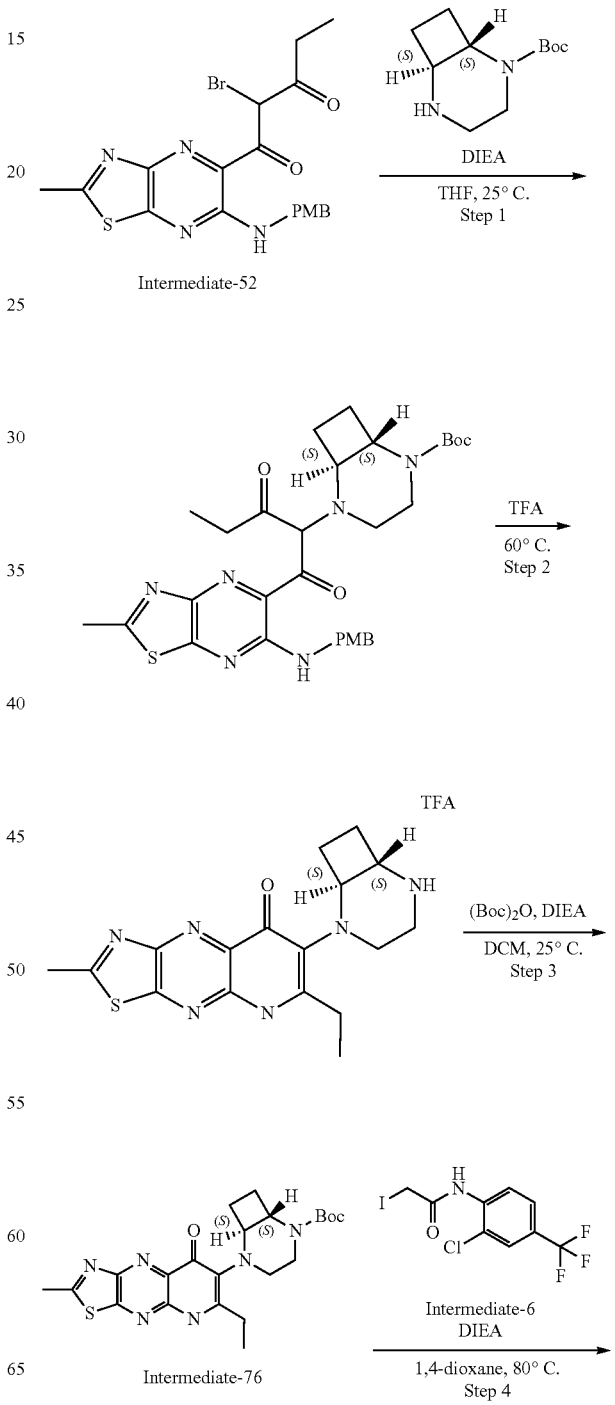

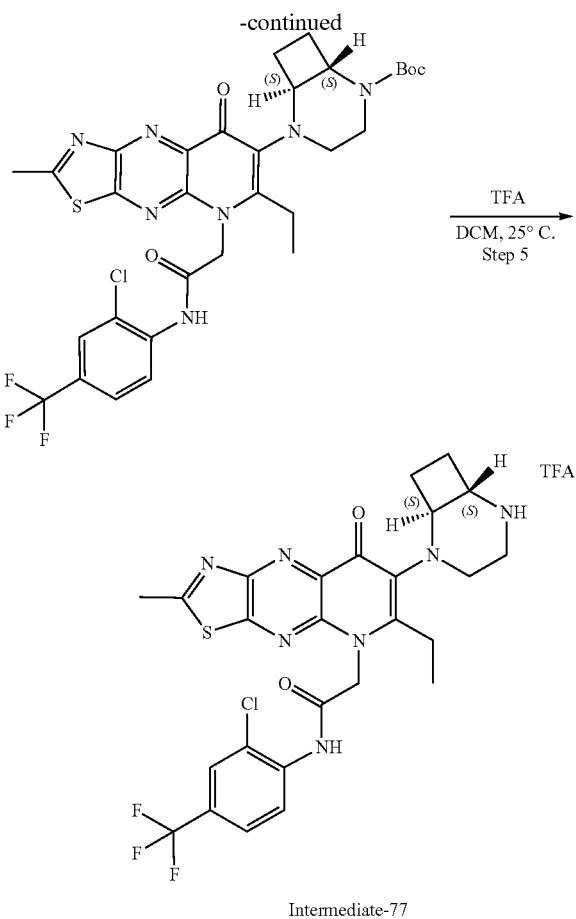

Intermediate-77

Step 1. Synthesis of tert-butyl (1S,6S)-5-(1-(6-((4-methoxybenzyl)amino)-2-methylthiazolo[4,5-b]pyrazin-5-yl)-1,3-dioxopentan-2-yl)-2,5-diazabicyclo[4.2.0]octane-2-carboxylate To a solution of 2-bromo-1-(6-((4-methoxybenzyl)amino)-2-methylthiazolo[4,5-b]pyrazin-5-yl) pentane-1,3-dione (Intermediate-52) (830 mg, 1.79 mmol, 1 eq) and tert-butyl (1S,6S)-2,5-diazabicyclo[4.2.0]octane-2-carboxylate (399 mg, 1.88 mmol, 1.05 eq) in THF (16 mL) was added DIEA (463 mg, 3.58 mmol, 624 μL, 2 eq). The mixture was stirred at 25° C. for 1 h. The reaction mixture was poured into H₂O (20 mL) and extracted with DCM (30 mL*3). The combined organic layer was dried over anhydrous Na₂SO₄, filtered and concentrated under vacuum to give a residue. The residue was purified by silica gel chromatography (Eluent of EtOAc/PE) to afford the title compound.

LCMS: 595.3 [M+H]⁺.

Step 2. Synthesis of 7-((1S,6S)-2,5-diazabicyclo[4.2.0]octan-2-yl)-6-ethyl-2-methylpyrido[2,3-b]thiazolo[4,5-e]pyrazin-8 (5H)-one Trifluoroacetate A solution of tert-butyl (1S,6S)-5-(1-(6-((4-methoxybenzyl)amino)-2-methylthiazolo[4,5-b]pyrazin-5-yl)-1,3-dioxopentan-2-yl)-2,5-diazabicyclo[4.2.0]octane-2-carboxylate (750 mg, 1.26 mmol, 1 eq) in TFA (8 mL) was stirred at 60° C. for 4 h. The mixture was concentrated in vacuum directly to afford the title compound.

LCMS: 357.1 [M+H]⁺.

Step 3. Synthesis of tert-butyl (1S,6S)-5-(6-ethyl-2-methyl-8-oxo-5,8-dihydropyrido[2,3-b]thiazolo[4,5-e]pyrazin-7-yl)-2,5-diazabicyclo[4.2.0]octane-2-carboxylate To a solution of 7-((1S,6S)-2,5-diazabicyclo[4.2.0]octan-2-yl)-6-ethyl-2-methylpyrido[2,3-b]thiazolo[4,5-e]pyrazin-8 (5H)-one trifluoroacetate (700 mg, 1.96 mmol, 1 eq) in DCM (7 mL) was added (Boc)₂O (471 mg, 2.16 mmol, 496 μL, 1.1 eq) and DIEA (1.27 g, 9.82 mmol, 1.71 mL, 5 eq). The mixture was stirred at 25° C. for 1 h. Then it was poured into H₂O (20 mL) and extracted with DCM (30 mL*3). The combined organic layer was dried over anhydrous Na₂SO₄, filtered and concentrated under vacuum to give a residue. The residue was purified by flash silica gel chromatography (Eluent of EtOAc/PE) to afford the title compound.

LCMS: 457.1 [M+H]⁺.

Step 4. Synthesis of tert-butyl (1S,6S)-5-(5-(2-((2-chloro-4-(trifluoromethyl)phenyl) amino)-2-oxoethyl)-6-ethyl-2-methyl-8-oxo-5,8-dihydropyrido[2,3-b]thiazolo[4,5-e]pyrazin-7-yl)-2,5-diazabicyclo[4.2.0]octane-2-carboxylate To a solution of tert-butyl (1S,6S)-5-(6-ethyl-2-methyl-8-oxo-5,8-dihydropyrido[2,3-b]thiazolo[4,5-e]pyrazin-7-yl)-2,5-diazabicyclo[4.2.0]octane-2-carboxylate (Intermediate-76) (150 mg, 328 mol, 1 eq) and N-[2-chloro-4-(trifluoromethyl)phenyl]-2-iodo-acetamide (Intermediate-6) (179 mg, 492 μmol, 1.5 eq) in 1,4-dioxane (3 mL) was added DIEA (64 mg, 492 μmol, 85 μL, 1.5 eq). The mixture was stirred at 80° C. for 1 h. The reaction was diluted with H₂O (20 mL) and extracted with DCM (30 mL*3). The combined organic layer was dried over anhydrous Na₂SO₄, filtered and concentrated in vacuum to give a residue. The residue was purified by flash silica gel chromatography (Eluent of MeOH/DCM) to afford the title compound.

¹H NMR (400 MHz, CD₃OD) δ ppm 8.08 (d, 1H), 7.81 (s, 1H), 7.59 (d, 1H), 5.66 (s, 2H), 4.17-4.06 (m, 1H), 3.98-3.97 (m, 1H), 3.71-3.61 (m, 1H), 3.47-3.37 (m, 1H), 3.32-3.28 (m, 2H), 3.15 (q, 2H), 2.96 (s, 3H), 2.33-2.20 (m, 1H), 2.06-1.93 (m, 1H), 1.86-1.71 (m, 1H), 1.57-1.52 (m, 1H), 1.48 (s, 9H), 1.38 (t, 3H).

LCMS: 692.3 [M+H]⁺.

Step 5. Synthesis of 2-(7-((1S,6S)-2,5-diazabicyclo[4.2.0]octan-2-yl)-6-ethyl-2-methyl-8-oxopyrido[2,3-b]thiazolo[4,5-e]pyrazin-5 (8H)-yl)-N-(2-chloro-4-(trifluoromethyl)phenyl)acetamide Trifluoroacetate To a solution of tert-butyl (1S,6S)-5-(5-(2-((2-chloro-4-(trifluoromethyl)phenyl) amino)-2-oxoethyl)-6-ethyl-2-methyl-8-oxo-5,8-dihydropyrido[2,3-b]thiazolo[4,5-e]pyrazin-7-yl)-2,5-diazabicyclo[4.2.0]octane-2-carboxylate (80 mg, 116 mol, 1 eq) in DCM (1 mL) was added TFA (0.25 mL). The mixture was stirred at 25° C. for 0.5 h. Then it was concentrated in vacuum directly to afford the title compound.

LCMS: 592.3 [M+H]⁺.

341

Intermediate-78: 1-(6-bromo-3-((4-methoxybenzyl) amino)pyrazin-2-yl)-3-hydroxypent-2-en-1-one

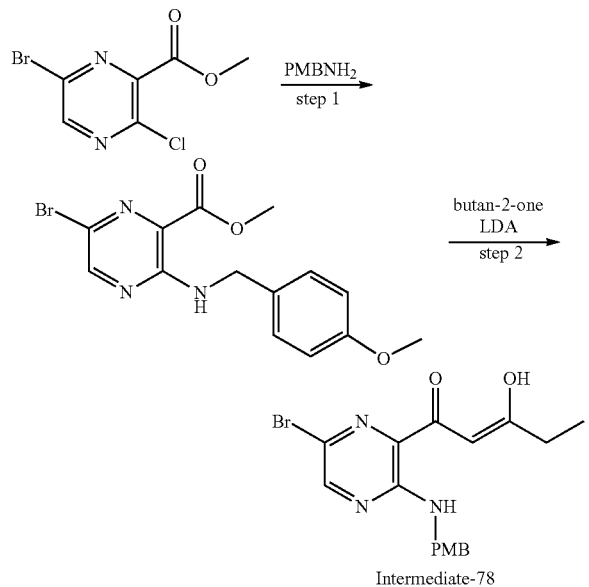

Intermediate-78

Step 1: Synthesis of methyl 6-bromo-3-((4-methoxybenzyl)amino)pyrazine-2-carboxylate To a solution of methyl 6-bromo-3-chloropyrazine-2-carboxylate (52.00 g, 206.79 mmol, 1.0 eq) in 1,4-dioxane (500 mL) was added DIEA (40.09 g, 310.18 mmol, 1.5 eq) and (4-methoxybenzyl)amine (31.20 g, 227.47 mmol, 1.1 eq), the resulting mixture was stirred at 100° C. overnight. The reaction mixture was concentrated under reduced pressure to remove solvent. The residue was diluted with $H_2O$ (1500 mL) and extracted with EtOAc (1000 mL*2). The combined organic layers were washed with brine (1000 mL), dried over anhydrous $Na_2SO_4$, filtered and concentrated under reduced pressure. The crude product was triturated with (PE:EtOAc=10:1, 440 mL) to afford the title compound.

LCMS: 352.0 $[M+H]^+$.
$^1$H NMR (400 MHz, $CDCl_3$) δ ppm 8.35 (s, 1H), 8.31 (br s, 1H), 7.29 (d, 2H), 6.90 (d, 2H), 4.65 (d, 2H), 3.97 (s, 3H), 3.82 (s, 3H).

Step 2: Synthesis of 1-(6-bromo-3-((4-methoxybenzyl)amino)pyrazin-2-yl)-3-hydroxypent-2-en-1-one To a solution of methyl 6-bromo-3-((4-methoxybenzyl) amino)pyrazine-2-carboxylate (61.50 g, 166.94 mmol, 1.0 eq) and butan-2-one (26.48 g, 367.27 mmol, 2.2 eq) in toluene (1500 mL) was added LDA (2 M in THF, 183.6 mL, 2.2 eq) dropwise at 0° C. After addition, the mixture was stirred at 60° C. for 2 h. The reaction mixture was slowly poured into aqueous HCl solution (0.5 M, 1500 mL), and then extracted with EtOAc (1000 mL*3). The combined organic layers were washed with brine (500 mL), dried over anhydrous $Na_2SO_4$, filtered and concentrated under reduced pressure. The residue was purified by silica gel chromatography (EtOAc/PE) to afford the title compound.

LCMS: 392.0 $[M+H]^+$.

342

Intermediate-82: 2-(6-(4-(tert-butoxycarbonyl)piperazin-1-yl)-7-ethyl-2-methyl-5-oxopyrido[2,3-b]thieno[3,2-e]pyrazin-8 (5H)-yl)acetic Acid Intermediate-83: 2-(7-ethyl-2-methyl-5-oxo-6-(piperazin-1-yl)pyrido[2,3-b]thieno[3,2-e]pyrazin-8 (5H)-yl)-N-(3-(trifluoromethyl)bicyclo[1.1.1]pentan-1-yl)acetamide Trifluoroacetate

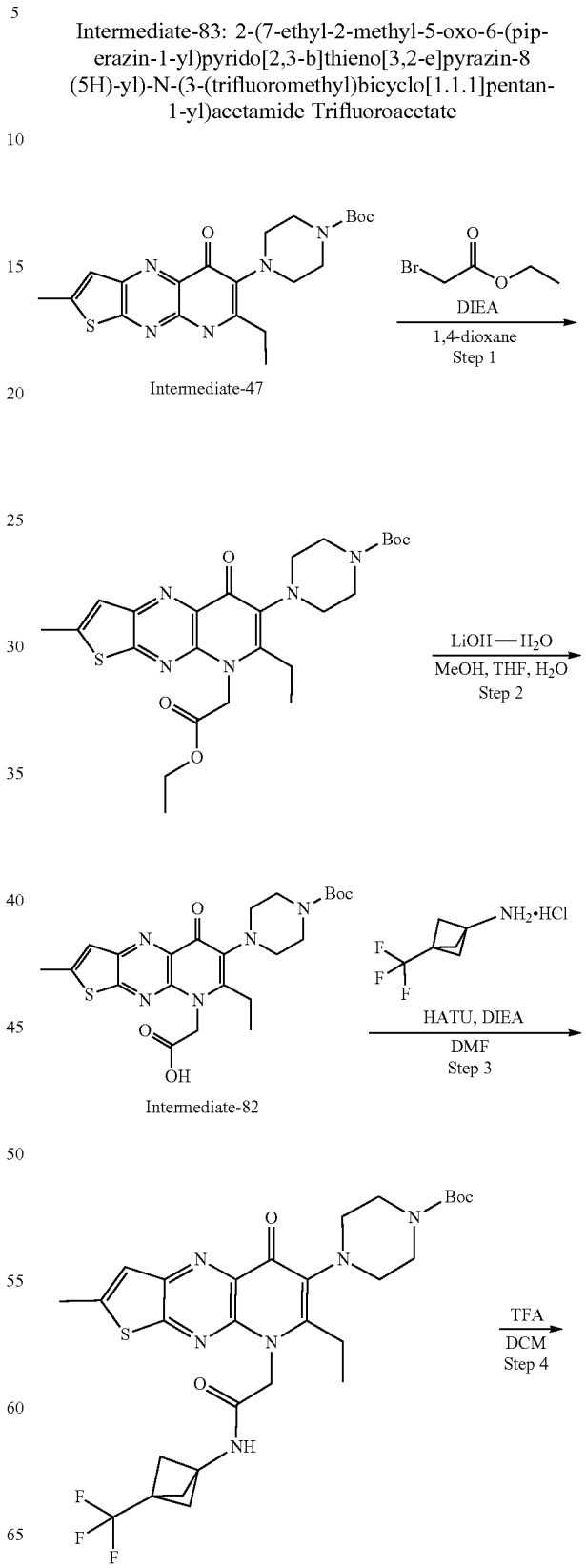

-continued

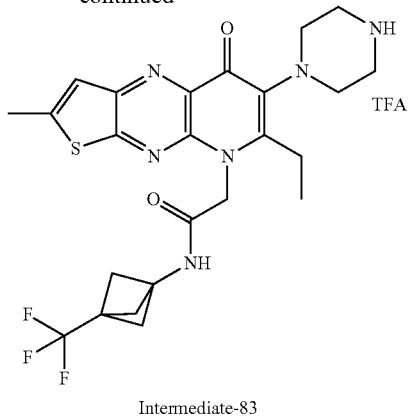

Intermediate-83

Step 1. Synthesis of tert-butyl 4-(8-(2-ethoxy-2-oxoethyl)-7-ethyl-2-methyl-5-oxo-5,8-dihydropyrido[2,3-b]thieno[3,2-e]pyrazin-6-yl)piperazine-1-carboxylate To a solution of tert-butyl 4-(7-ethyl-2-methyl-5-oxo-5,8-dihydropyrido[2,3-b]thieno[3,2-e]pyrazin-6-yl)piperazine-1-carboxylate (Intermediate-47) (350 mg, 815 mol, 1 eq) and ethyl 2-bromoacetate (272 mg, 1.63 mmol, 180 μL, 2 eq) in 1,4-dioxane (7 mL) was added DIEA (316 mg, 2.44 mmol, 426 μL, 3 eq). The mixture was stirred at 80° C. for 16 h. Then the second batch of ethyl 2-bromoacetate (272 mg, 1.63 mmol, 180 μL, 2 eq) was added into the mixture and stirred at 80° C. for another 16 h. The mixture was concentrated under reduced pressure to give a residue. The residue was purified by silica gel chromatography (Eluent of EtOAc/PE) to afford the title compound.

$^1$H NMR (400 MHz, DMSO-$d_6$) δ ppm 7.51 (s, 1H), 5.35 (s, 2H), 4.22 (q, 2H), 4.03-3.92 (m, 2H), 3.70-3.61 (m, 2H), 3.18 (q, 2H), 3.07-2.85 (m, 2H), 2.75 (s, 3H), 2.66-2.64 (m, 2H), 1.48 (s, 9H), 1.26-1.20 (m, 6H).

LCMS: 516.4 [M+H]$^+$.

Step 2. Synthesis of 2-(6-(4-(tert-butoxycarbonyl)piperazin-1-yl)-7-ethyl-2-methyl-5-oxopyrido[2,3-b]thieno[3,2-e]pyrazin-8 (5H)-yl)acetic Acid To a solution of tert-butyl 4-(8-(2-ethoxy-2-oxoethyl)-7-ethyl-2-methyl-5-oxo-5,8-dihydropyrido[2,3-b]thieno[3,2-e]pyrazin-6-yl)piperazine-1-carboxylate (292 mg, 566 mol, 1 eq) in THF (3 mL), MeOH (1 mL) and H$_2$O (1 mL) was added LiOH—H$_2$O (238 mg, 5.66 mmol, 10 eq). Then the mixture was stirred at 25° C. for 1 h. To the reaction mixture was added saturated citric acid until pH achieved was around 3. Then it was extracted with EtOAc (10 mL*3) and the combined organic phase was washed with brine (40 mL), dried over anhydrous Na$_2$SO$_4$ and concentrated under reduced pressure to afford the title compound, which was used into next step directly without further purification.

LCMS: 488.1 [M+H]$^+$.

Step 3. Synthesis of tert-butyl 4-(7-ethyl-2-methyl-5-oxo-8-(2-oxo-2-((3-(trifluoromethyl)bicyclo[1.1.1]pentan-1-yl)amino)ethyl)-5,8-dihydropyrido[2,3-b]thieno[3,2-e]pyrazin-6-yl)piperazine-1-carboxylate To a solution of 2-(6-(4-(tert-butoxycarbonyl)piperazin-1-yl)-7-ethyl-2-methyl-5-oxopyrido[2,3-b]thieno[3,2-e]pyrazin-8 (5H)-yl)acetic acid (Intermediate-82) (276 mg, 566 mol, 1 eq) and 3-(trifluoromethyl)bicyclo[1.1.1]pentan-1-amine hydrochloride salt (212 mg, 1.13 mmol, 2 eq) in DMF (5 mL) was added HATU (430 mg, 1.13 mmol, 2 eq) and DIEA (219 mg, 1.70 mmol, 296 μL, 3 eq). The mixture was stirred at 25° C. for 1 h. 30 mL brine was added into the mixture and extracted with EtOAc (30 mL). Then the organic layer was washed with brine (20 mL*3), dried over anhydrous Na$_2$SO$_4$ and concentrated under reduced pressure to give a residue. The residue was purified by silica gel chromatography (Eluent of EtOAc/PE) to afford the title compound.

$^1$H NMR (400 MHz, DMSO-$d_6$) δ ppm 7.95 (s, 1H), 7.46 (s, 1H), 3.93 (s, 2H), 3.68-3.54 (m, 2H), 3.05-3.03 (m, 2H), 2.89 (s, 3H), 2.73 (q, 2H), 2.72-2.71 (m, 2H), 2.62-2.59 (m, 2H), 2.22 (s, 6H), 1.44 (s, 9H), 1.16 (t, 3H).

LCMS: 621.2 [M+H]$^+$.

Step 4. Synthesis of 2-(7-ethyl-2-methyl-5-oxo-6-(piperazin-1-yl)pyrido[2,3-b]thieno[3,2-e]pyrazin-8 (5H)-yl)-N-(3-(trifluoromethyl)bicyclo[1.1.1]pentan-1-yl)acetamide Trifluoroacetate To a solution of tert-butyl 4-(7-ethyl-2-methyl-5-oxo-8-(2-oxo-2-((3-(trifluoromethyl)bicyclo[1.1.1]pentan-1-yl)amino)ethyl)-5,8-dihydropyrido[2,3-b]thieno[3,2-e]pyrazin-6-yl)piperazine-1-carboxylate (100 mg, 161 mol, 1 eq) in DCM (3 mL) was added TFA (1 mL). The mixture was stirred at 25° C. for 1 h. Then the mixture was concentrated in vacuum to afford the title compound, which was used into next step directly without further purification.

LCMS: 521.2 [M+H]$^+$.

Intermediate-84:
5-hydroxy-6-methylpyrimidine-4-carbonyl Chloride

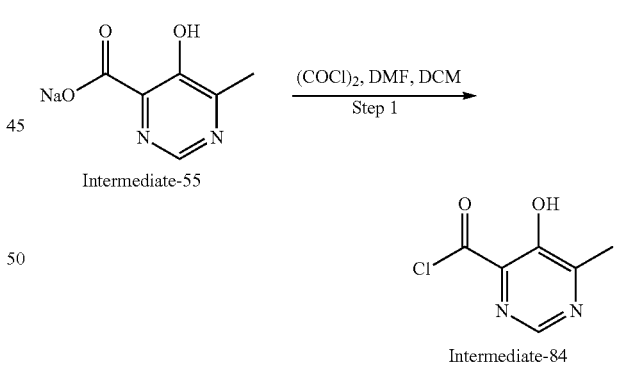

Step 1. Synthesis of
5-hydroxy-6-methylpyrimidine-4-carbonyl Chloride

To a solution of sodium 5-hydroxy-6-methylpyrimidine-4-carboxylate (Intermediate-55) (90 mg, 584 mol, 1.0 eq) in DCM (1 mL) was added oxalyl dichloride (148 mg, 1.17 mmol, 2.0 eq) and one drop of DMF. The resulting mixture was stirred at room temperature for 30 min and then concentrated in vacuo to afford the title compound, which was used into the next step without further purification.

345
Intermediate-94: benzyl (2-(3-bromo-5-(2-bromo-3-oxopentanoyl)-6-((4-methoxybenzyl)amino)pyrazin-2-yl)ethyl)(methyl)carbamate
Intermediate-85: tert-butyl 4-(11-ethyl-4-methyl-13-oxo-2,4,8,10-tetrazatricyclo[7.4.0.03,7]trideca-1(9),2,7,11-tetraen-12-yl)piperazine-1-carboxylate
Intermediate-86: N-[2-chloro-4-(trifluoromethyl)phenyl]-2-(11-ethyl-4-methyl-13-oxo-12-piperazin-1-yl-2,4,8,10-tetrazatricyclo[7.4.0.03,7]trideca-1(9),2,7,11-tetraen-10-yl)acetamide Trifluoroacetate
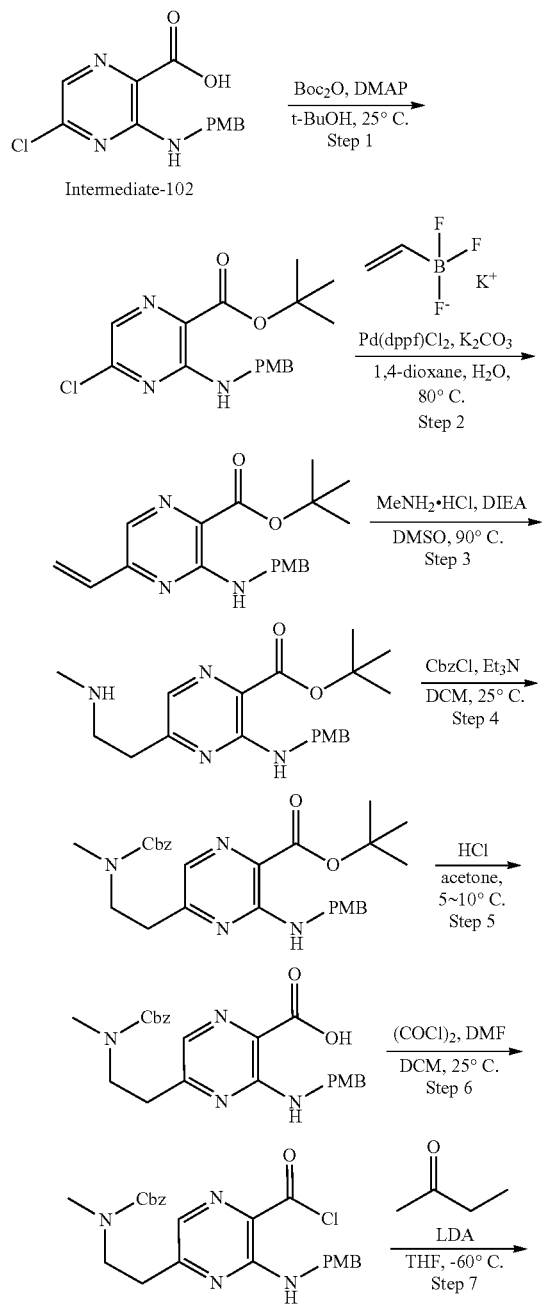
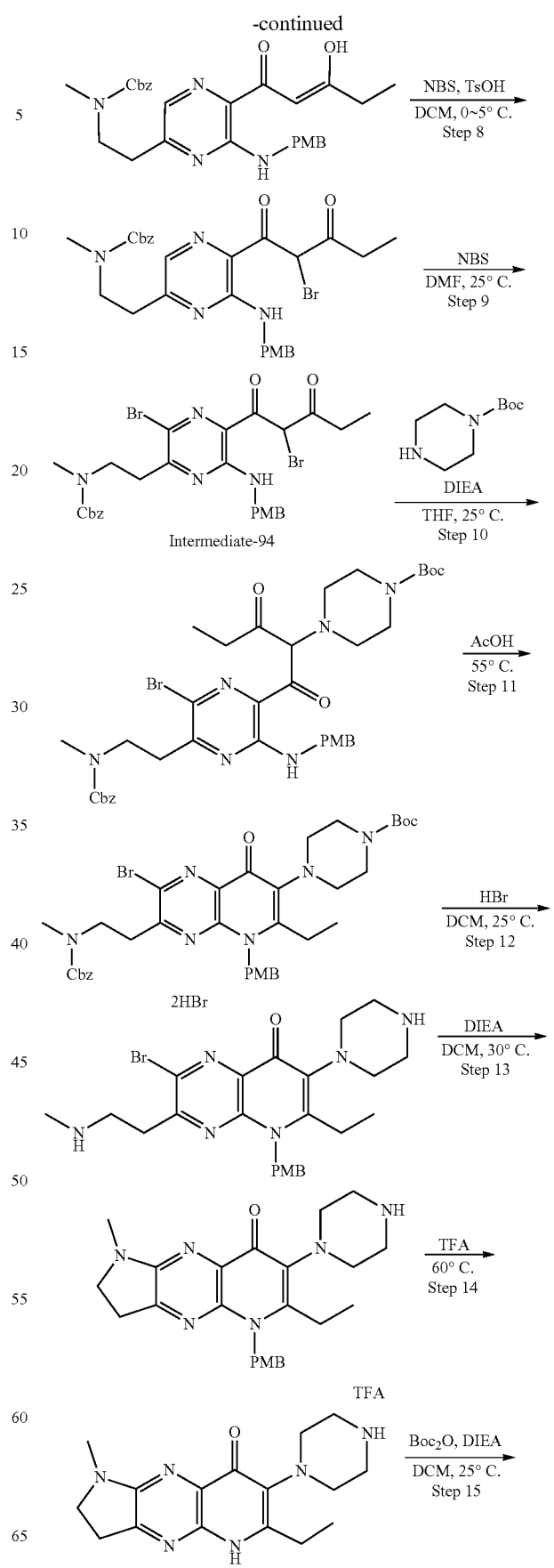

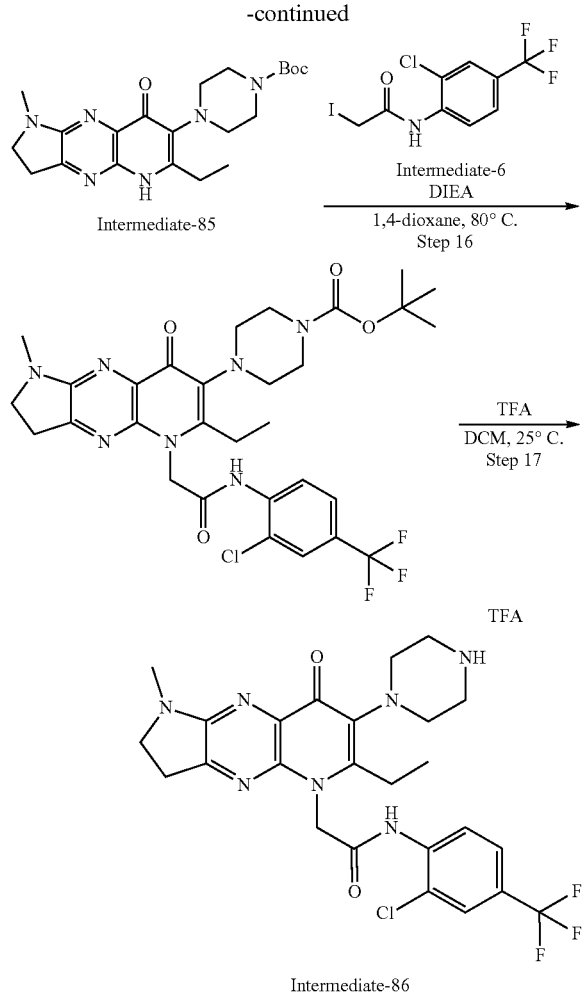

Step 1: Synthesis of tert-butyl 5-chloro-3-((4-methoxybenzyl)amino)pyrazine-2-carboxylate To a solution of 5-chloro-3-((4-methoxybenzyl)amino)pyrazine-2-carboxylic acid (Intermediate-102) (10.00 g, 34.05 mmol, 1 eq) in t-BuOH (100 mL) was added DMAP (5.41 g, 44.26 mmol, 1.3 eq), then Boc$_2$O (14.86 g, 68.10 mmol, 2.0 eq) was added to the mixture dropwise at room temperature, and the reaction was stirred at room temperature for 2 h. The reaction mixture was diluted with H$_2$O (100 mL), extracted with EtOAc (100 mL*2), the organic phase was washed with brine (100 mL), dried over anhydrous Na$_2$SO$_4$, concentrated under reduced pressure to give a residue. The residue was purified by flash silica gel chromatography (Eluent of EtOAc/PE), then triturated with PE (40 mL) to afford the title compound.
LCMS: 350.1[M+H]$^+$.

Step 2: Synthesis of tert-butyl 3-((4-methoxybenzyl)amino)-5-vinylpyrazine-2-carboxylate To a solution of tert-butyl 5-chloro-3-((4-methoxybenzyl)amino)pyrazine-2-carboxylate (5.50 g, 15.72 mmol, 1.0 eq), potassium vinyltrifluoroborate (3.16 g, 23.58 mmol, 1.5 eq) in 1,4-dioxane (50 mL) and H$_2$O (10 mL) was added Pd(dppf)Cl$_2$ (575 mg, 786 mol, 0.05 eq), K$_2$CO$_3$ (4.35 g, 31.45 mmol, 2.0 eq), and the reaction was stirred at 80° C. overnight under N$_2$ atmosphere. The reaction mixture was concentrated under reduced pressure and then purified by flash silica gel chromatography (Eluent of EtOAc/PE) to afford the title compound.
LCMS: 342.2 [M+H]$^+$.

Step 3: Synthesis of tert-butyl 3-((4-methoxybenzyl)amino)-5-(2-(methylamino)ethyl)pyrazine-2-carboxylate To a solution of tert-butyl 3-((4-methoxybenzyl)amino)-5-vinylpyrazine-2-carboxylate (1.00 g, 2.93 mmol, 1.0 eq) in DMSO (20 mL) was added methylamine hydrochloride (989 mg, 14.65 mmol, 5.0 eq) and DIEA (3.79 g, 29.29 mmol, 10.0 eq), the resulting mixture was stirred at 90° C. for 0.5 h. The reaction mixture was diluted with H$_2$O (200 mL), extracted with EtOAc (100 mL*2), the organic phase was washed with brine (100 mL), dried over anhydrous Na$_2$SO$_4$, filtered and concentrated under reduced pressure to afford the title compound, which was used into the next step without further purification.
LCMS: 373.2[M+H]$^+$.

Step 4: Synthesis of tert-butyl 5-(2-(((benzyloxy)carbonyl)(methyl)amino)ethyl)-3-((4-methoxybenzyl)amino)pyrazine-2-carboxylate To a solution of tert-butyl 3-((4-methoxybenzyl)amino)-5-(2-(methylamino)ethyl)pyrazine-2-carboxylate (5.00 g, 13.42 mmol, 1.0 eq) in DCM (50 mL) was added Et$_3$N (2.72 g, 26.85 mmol, 2.0 eq) and CbzCl (2.75 g, 16.11 mmol, 1.2 eq), and the resulting mixture was stirred at room temperature for 0.5 h. The reaction mixture was diluted with H$_2$O (30 mL), extracted with DCM (50 mL*2), the organic phase was washed with brine (50 mL), dried over anhydrous Na$_2$SO$_4$, filtered and concentrated under reduced pressure. The residue was purified by flash silica gel chromatography (Eluent of EtOAc/PE) to afford the title compound.
LCMS: 507.4[M+H]$^+$.

Step 5: Synthesis of 5-(2-(((benzyloxy)carbonyl)(methyl)amino)ethyl)-3-((4-methoxybenzyl)amino)pyrazine-2-carboxylic Acid To a solution of tert-butyl 5-(2-(((benzyloxy)carbonyl)(methyl)amino)ethyl)-3-((4-methoxybenzyl)amino)pyrazine-2-carboxylate (5.60 g, 11.05 mmol, 1.0 eq) in acetone (30 mL) was added aqueous HCl solution (6 M, 36.85 mL, 20.0 eq) dropwise at 5-10° C., and the resulting mixture was stirred at room temperature overnight. The reaction mixture was concentrated under reduced pressure to give a residue. The residue was diluted with H$_2$O (50 mL), extracted with DCM (50 mL*2), and the organic phase was washed with brine (50 mL), dried over anhydrous Na$_2$SO$_4$, filtered and concentrated under reduced pressure to afford the title compound, which was used into the next step without further purification.
LCMS: 451.3[M+H]$^+$.

Step 6: Synthesis of benzyl (2-(5-(chlorocarbonyl)-6-((4-methoxybenzyl)amino)pyrazin-2-yl)ethyl)(methyl)carbamate To a solution of 5-(2-(((benzyloxy)carbonyl)(methyl)amino)ethyl)-3-((4-methoxybenzyl)amino)pyrazine-2-carboxylic acid (4.60 g, 10.21 mmol, 1.0 eq) in DCM (50 mL)

was added two drops of DMF and (COCl)$_2$ (1.94 g, 15.32 mmol, 1.5 eq), and the resulting mixture was stirred at room temperature for 1 h. The reaction mixture was concentrated under reduced pressure to afford the title compound, which was used into the next step without further purification.

Step 7: Synthesis of benzyl (2-(5-(3-hydroxypent-2-enoyl)-6-((4-methoxybenzyl)amino)pyrazin-2-yl)ethyl)(methyl)carbamate To a solution of butan-2-one (1.41 g, 19.62 mmol, 2.0 eq) in THF (46 mL) was added LDA (2 M in THF, 9.81 mL, 2.0 eq) at −60° C., and the mixture was stirred at −60° C. for 0.5 h under N$_2$ atmosphere. Then benzyl (2-(5-(chlorocarbonyl)-6-((4-methoxybenzyl)amino)pyrazin-2-yl)ethyl)(methyl)carbamate (4.60 g, 9.81 mmol, 1.0 eq) was added to the mixture, and the reaction was stirred at −60° C. for another 0.5 h under N$_2$ atmosphere. The reaction mixture was quenched with aqueous HCl solution (1N, 100 mL), extracted with EtOAc (50 mL*2), the organic phase was washed with brine (50 mL), dried over anhydrous Na$_2$SO$_4$, filtered and concentrated under reduced pressure. The residue was purified by flash silica gel chromatography (Eluent of EtOAc/PE) to afford the title compound.

LCMS: 505.4[M+H]$^+$.

Step 8: Synthesis of benzyl (2-(5-(2-bromo-3-oxopentanoyl)-6-((4-methoxybenzyl)amino)pyrazin-2-yl)ethyl)(methyl)carbamate To a solution of benzyl (2-(5-(3-hydroxypent-2-enoyl)-6-((4-methoxybenzyl)amino)pyrazin-2-yl)ethyl)(methyl)carbamate (1.80 g, 3.57 mmol, 1.0 eq) in DCM (20 mL) was added TsOH·H$_2$O (123 mg, 713 mol, 0.2 eq) and NBS (762 mg, 4.28 mmol, 1.2 eq) at 0° C., then the reaction was stirred at 0° C. for 0.5 h. The reaction mixture was quenched with H$_2$O (20 mL), extracted with DCM (20 mL*2), the organic phase was washed with brine (10 mL), dried over anhydrous Na$_2$SO$_4$, filtered and concentrated under reduced pressure to afford the title compound, which was used into the next step without further purification.

LCMS: 583.3[M+H]$^+$.

Step 9: Synthesis of benzyl (2-(3-bromo-5-(2-bromo-3-oxopentanoyl)-6-((4-methoxybenzyl)amino)pyrazin-2-yl)ethyl)(methyl)carbamate (Intermediate-94)

To a solution of benzyl (2-(5-(2-bromo-3-oxopentanoyl)-6-((4-methoxybenzyl)amino)pyrazin-2-yl)ethyl)(methyl)carbamate (2.08 g, 3.56 mmol, 1 eq) in DMF (20 mL) was added NBS (634 mg, 3.56 mmol, 1.0 eq), and the reaction was stirred at room temperature for 2 h. The reaction mixture was quenched with H$_2$O (30 mL), extracted with EtOAc (20 mL*2), the organic phase was washed with brine (10 mL), dried over anhydrous Na$_2$SO$_4$, filtered and concentrated under reduced pressure. The residue was purified by flash silica gel chromatography (Eluent of EtOAc/PE) to afford the title compound.

LCMS: 663.0[M+H]$^+$.

Step 10: Synthesis of tert-butyl 4-(1-(5-(2-(((benzyloxy)carbonyl)(methyl)amino)ethyl)-6-bromo-3-((4-methoxybenzyl)amino)pyrazin-2-yl)-1,3-dioxopentan-2-yl)piperazine-1-carboxylate To a solution of benzyl (2-(3-bromo-5-(2-bromo-3-oxopentanoyl)-6-((4-methoxybenzyl)amino)pyrazin-2-yl)ethyl)(methyl)carbamate (Intermediate-94) (1.50 g, 2.26 mmol, 1.0 eq) in THF (15 mL) was added DIEA (585 mg, 4.53 mmol, 2.0 eq) and tert-butyl piperazine-1-carboxylate (506 mg, 2.72 mmol, 1.2 eq), and the resulting mixture was stirred at room temperature overnight. The reaction mixture was diluted with H$_2$O (10 mL), extracted with EtOAc (10 mL*2), the organic phase was washed with brine (10 mL), dried over anhydrous Na$_2$SO$_4$, filtered and concentrated under reduced pressure. The residue was purified by flash silica gel chromatography (Eluent of EtOAc/PE) to afford the title compound.

LCMS: 767.4[M+H]$^+$.

Step 11: Synthesis of tert-butyl 4-[3-[2-[benzyloxycarbonyl(methyl)amino]ethyl]-2-bromo-6-ethyl-5-[(4-methoxyphenyl)methyl]-8-oxopyrido[2,3-b]pyrazin-7-yl]piperazine-1-carboxylate A solution of tert-butyl 4-(1-(5-(2-(((benzyloxy)carbonyl)(methyl)amino)ethyl)-6-bromo-3-((4-methoxybenzyl)amino)pyrazin-2-yl)-1,3-dioxopentan-2-yl)piperazine-1-carboxylate (1.00 g, 1.30 mmol, 1.0 eq) in AcOH (8 mL) was stirred at 55° C. for 6 h. The reaction mixture was concentrated under reduced pressure to give a residue. The residue was diluted with H$_2$O (20 mL), then the pH was adjusted to 7-8 with saturated NaHCO$_3$ aqueous solution. The resulting mixture was extracted with DCM (20 mL*2) and the organic phase was washed with brine (10 mL), dried over anhydrous Na$_2$SO$_4$, filtered and concentrated under reduced pressure. The residue was purified by flash silica gel chromatography (Eluent of EtOAc/PE) to afford the title compound.

LCMS: 749.2[M+H]$^+$.

Step 12: Synthesis of 2-bromo-6-ethyl-5-[(4-methoxyphenyl)methyl]-3-[2-(methylamino)ethyl]-7-piperazin-1-yl-pyrido[2,3-b]pyrazin-8-one Dihydrobromide To a solution of tert-butyl 4-[3-[2-[benzyloxycarbonyl(methyl)amino]ethyl]-2-bromo-6-ethyl-5-[(4-methoxyphenyl)methyl]-8-oxo-pyrido[2,3-b]pyrazin-7-yl]piperazine-1-carboxylate (700 mg, 934 mol, 1.0 eq) in DCM (5 mL) was added HBr solution (768 µL, 33% in water), and the resulting mixture was stirred at room temperature for 0.5 h. The reaction mixture was concentrated under reduced pressure to afford the title compound, which was used into the next step without further purification.

LCMS: 515.2[M+H]$^+$.

Step 13: Synthesis of 11-ethyl-10-[(4-methoxyphenyl)methyl]-4-methyl-12-piperazin-1-yl-2,4,8,10-tetrazatricyclo[7.4.0.03,7]trideca-1 (9),2,7,11-tetraen-13-one To a solution of 2-bromo-6-ethyl-5-[(4-methoxyphenyl)methyl]-3-[2-(methylamino)ethyl]-7-piperazin-1-ylpyrido[2,3-b]pyrazin-8-one dihydrobromide (500 mg, 970 mol, 1.0 eq) in DCM (5 mL) was added DIEA (627 mg, 4.85 mmol, 5.0 eq), and the resulting mixture was stirred at room temperature overnight. The reaction mixture was concentrated under reduced pressure and then purified by reverse phase HPLC (C18 column, water (0.1% FA-ACN) to afford the title compound.

LCMS: 435.3[M+H]$^+$.

Step 14: Synthesis of 11-ethyl-4-methyl-12-piperazin-1-yl-2,4,8,10-tetrazatricyclo[7.4.0.03,7]trideca-1 (9),2,7,11-tetraen-13-one Trifluoroacetate A solution of 11-ethyl-10-[(4-methoxyphenyl)methyl]-4-methyl-12-piperazin-1-yl-2,4,8,10-tetrazatricyclo[7.4.0.03,7]trideca-1 (9),2,7,11-tetraen-13-one (60 mg, 138 mol, 1.0 eq) in TFA (0.5 mL) was stirred at 60° C. for 2.5 h. The reaction mixture was concentrated under reduced pressure to afford the title compound, which was used into the next step without further purification.
LCMS: 315.2[M+H]+.

Step 15: Synthesis of tert-butyl 4-(11-ethyl-4-methyl-13-oxo-2,4,8,10-tetrazatricyclo[7.4.0.03,7]trideca-1 (9),2,7,11-tetraen-12-yl)piperazine-1-carboxylate To a solution of 11-ethyl-4-methyl-12-piperazin-1-yl-2,4,8,10-tetrazatricyclo[7.4.0.03,7]trideca-1 (9),2,7,11-tetraen-13-one trifluoroacetate (43 mg, 137 mol, 1.0 eq) in DCM (0.5 mL) was added DIEA (53 mg, 410 mol, 3.0 eq) and Boc2O (45 mg, 205 mol, 1.5 eq), and the resulting mixture was stirred at room temperature for 20 min. The reaction mixture was diluted with H2O (10 mL), extracted with DCM (10 mL*2), the organic phase was washed with brine (10 mL), dried over anhydrous Na2SO4, filtered and concentrated under reduced pressure to give a residue. The residue was purified by pre-TLC (SiO2, DCM:MeOH=10:1) to afford the title compound.
LCMS: 415.3[M+H]+.

Step 16: Synthesis of tert-butyl 4-[10-[2-[2-chloro-4-(trifluoromethyl)anilino]-2-oxo-ethyl]-11-ethyl-4-methyl-13-oxo-2,4,8,10-tetrazatricyclo[7.4.0.03,7]trideca-1 (9),2,7,11-tetraen-12-yl]piperazine-1-carboxylate To a solution of tert-butyl 4-(11-ethyl-4-methyl-13-oxo-2,4,8,10-tetrazatricyclo[7.4.0.03,7]trideca-1 (9),2,7,11-tetraen-12-yl)piperazine-1-carboxylate (Intermediate-85) (20 mg, 48 mol, 1.0 eq) and N-[2-chloro-4-(trifluoromethyl)phenyl]-2-iodoacetamide (Intermediate-6) (21 mg, 58 mol, 1.2 eq) in 1,4-dioxane (0.5 mL) was added DIEA (12 mg, 96 mol, 2.0 eq), and the resulting mixture was stirred at 80° C. for 3 h under N2 atmosphere. The reaction mixture was concentrated under reduced pressure and then purified by reverse phase HPLC (C18 column, water (0.1% NH3H2O-ACN) to afford the title compound.
LCMS: 650.3[M+H]+.

Step 17: Synthesis of N-[2-chloro-4-(trifluoromethyl)phenyl]-2-(11-ethyl-4-methyl-13-oxo-12-piperazin-1-yl-2,4,8,10-tetrazatricyclo[7.4.0.03,7]trideca-1 (9),2,7,11-tetraen-10-yl)acetamide Trifluoroacetate To a solution of tert-butyl 4-[10-[2-[2-chloro-4-(trifluoromethyl)anilino]-2-oxo-ethyl]-11-ethyl-4-methyl-13-oxo-2,4,8,10-tetrazatricyclo[7.4.0.03,7]trideca-1 (9),2,7,11-tetraen-12-yl]piperazine-1-carboxylate (9 mg, 14 mol, 1.0 eq) in DCM (0.3 mL) was added TFA (0.6 mL), and the reaction was stirred at room temperature for 10 min. The reaction mixture was concentrated under reduced pressure to afford the title compound, which was used into the next step without further purification.
LCMS: 550.2[M+H]+.

Intermediate-87: tert-butyl 4-(2-bromo-6-ethyl-8-oxo-5,8-dihydropyrido[2,3-b]pyrazin-7-yl)-3-methylpiperazine-1-carboxylate Intermediate-88: N-(2-chloro-4-(trifluoromethyl)phenyl)-2-(2-(dimethylamino)-6-ethyl-7-(2-methylpiperazin-1-yl)-8-oxopyrido[2,3-b]pyrazin-5 (8H)-yl)acetamide Trifluoroacetate

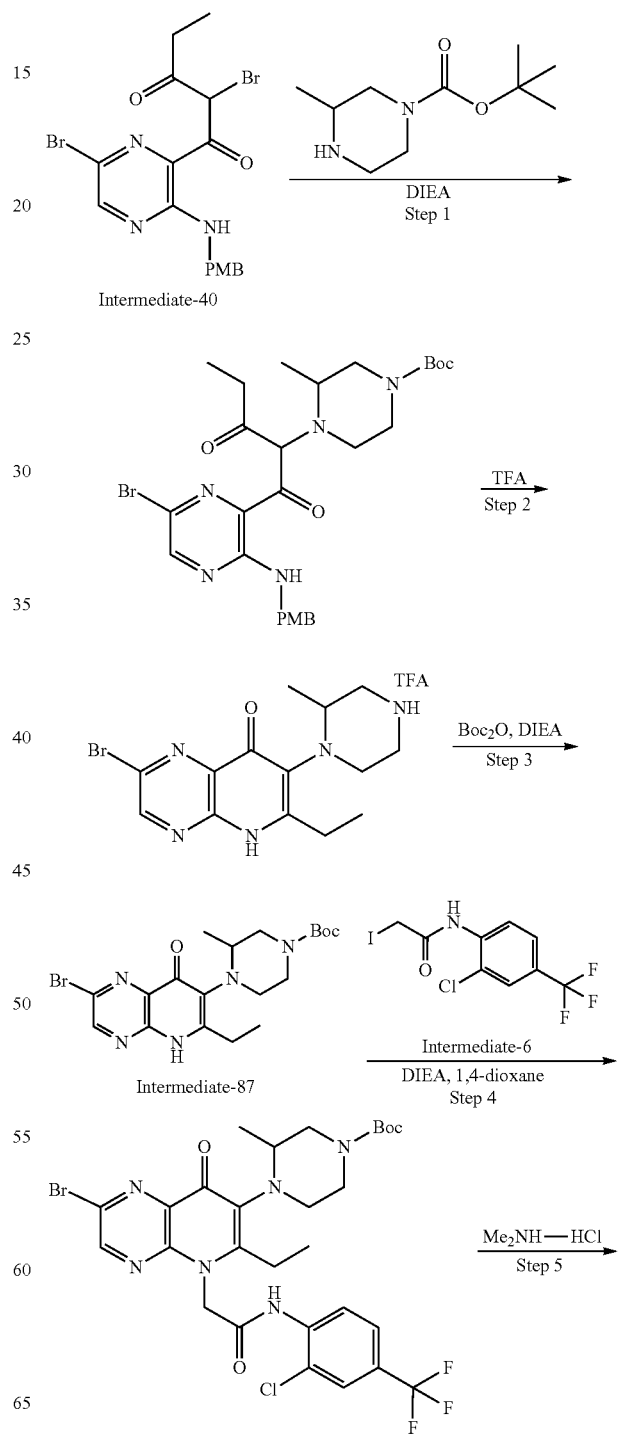

353

-continued

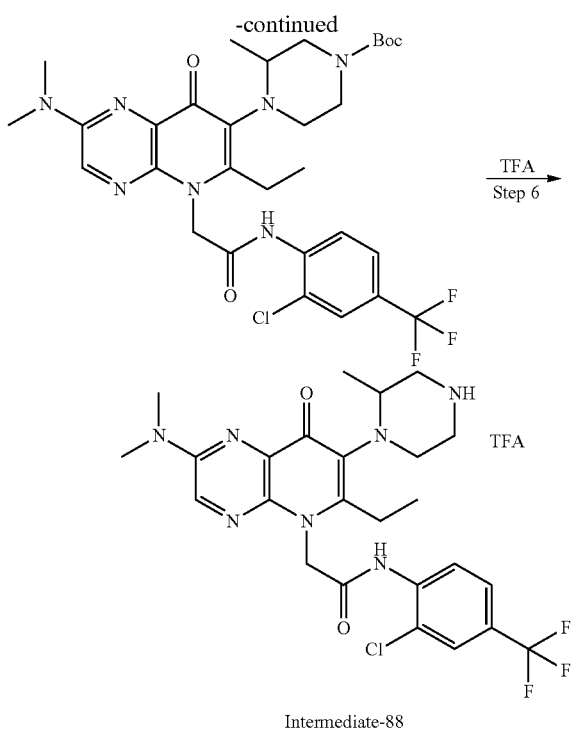

Intermediate-88

Step 1. Synthesis of tert-butyl 4-(1-(6-bromo-3-((4-methoxybenzyl)amino)pyrazin-2-yl)-1,3-dioxopentan-2-yl)-3-methylpiperazine-1-carboxylate To a solution of 2-bromo-1-(6-bromo-3-((4-methoxybenzyl)amino)pyrazin-2-yl)pentane-1,3-dione (Intermediate-40) (3.8 g, 8.07 mmol, 1.0 eq) in THF (40 mL) was added DIEA (2.08 g, 16.13 mmol, 2.0 eq) and tert-butyl 3-methylpiperazine-1-carboxylate (1.62 g, 8.07 mmol, 1.0 eq), and the resulting mixture was stirred at room temperature overnight. The reaction mixture was diluted with H₂O (100 mL) and then extracted with EtOAc (50 mL*3). The combined organic layers were washed with brine (40 mL*2), dried over anhydrous Na₂SO₄, filtered and concentrated under reduced pressure. The residue was purified by silica gel chromatography (EtOAc/PE) to afford the title compound.
LCMS: 592.2 [M+H]⁺.

Step 2. Synthesis of 2-bromo-6-ethyl-7-(2-methylpiperazin-1-yl)pyrido[2,3-b]pyrazin-8 (5H)-one Trifluoroacetate To a TFA (10 mL) solution was added tert-butyl 4-(1-(6-bromo-3-((4-methoxybenzyl)amino)pyrazin-2-yl)-1,3-dioxopentan-2-yl)-3-methylpiperazine-1-carboxylate (1.4 g, 2.37 mmol, 1.0 eq) and it was stirred at 55° C. for 0.5 h. The reaction mixture was concentrated under reduced pressure to afford the title compound, which was used into the next step without further purification.
LCMS: 354.1 [M+H]⁺.

Step 3. Synthesis of tert-butyl 4-(2-bromo-6-ethyl-8-oxo-5,8-dihydropyrido[2,3-b]pyrazin-7-yl)-3-methylpiperazine-1-carboxylate To a solution of 2-bromo-6-ethyl-7-(2-methylpiperazin-1-yl)pyrido[2,3-b]pyrazin-8 (5H)-one trifluoroacetate (800 mg, 2.27 mmol, 1.0 eq) and DIEA (1.47 g, 11.36 mmol, 5.0 eq) in DCM (15 mL) was added (Boc)₂O (496 mg, 2.27 mmol, 1.0 eq), and the resulting mixture was stirred at room temperature for 1 h. The reaction mixture was diluted with H₂O (20 mL) and then extracted with DCM (15 mL*3). The combined organic layers were washed with brine (20 mL), dried over anhydrous Na₂SO₄, filtered and the filtrate was concentrated under reduced pressure. The residue was purified by silica gel chromatography (EtOAc/PE) to afford the title compound.
LCMS: 454.1 [M+H]⁺.

Step 4. Synthesis of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)-3-methylpiperazine-1-carboxylate To a solution of tert-butyl 4-(2-bromo-6-ethyl-8-oxo-5,8-dihydropyrido[2,3-b]pyrazin-7-yl)-3-methylpiperazine-1-carboxylate (Intermediate-87) (300 mg, 663 mol, 1.0 eq) in 1,4-dioxane (3 mL) was added DIEA (257 mg, 1.99 mmol, 3.0 eq) and N-(2-chloro-4-(trifluoromethyl)phenyl)-2-iodoacetamide (Intermediate-6) (241 mg, 663 mol, 1.0 eq), and the resulting mixture was stirred at 80° C. overnight. The reaction mixture was concentrated under reduced pressure and then purified by reverse phase HPLC (water (0.1% FA-ACN) to afford the title compound.
LCMS: 689.1 [M+H]⁺.

Step 5. Synthesis of tert-butyl 4-(5-(2-((2-chloro-4-(trifluoromethyl)phenyl)amino)-2-oxoethyl)-2-(dimethylamino)-6-ethyl-8-oxo-5,8-dihydropyrido[2,3-b]pyrazin-7-yl)-3-methylpiperazine-1-carboxylate To a solution of tert-butyl 4-(2-bromo-5-(2-((2-chloro-4-(trifluoromethyl)phenyl)amino)-2-oxoethyl)-6-ethyl-8-oxo-5,8-dihydropyrido[2,3-b]pyrazin-7-yl)-3-methylpiperazine-1-carboxylate (230 mg, 334 mol, 1.0 eq) in 1,4-dioxane (2.5 mL) was added dimethylamine hydrochloride (82 mg, 1.00 mmol, 3.0 eq) and DIEA (216 mg, 1.67 mmol, 5.0 eq), and the resulting mixture was stirred at 100° C. for 4 h. The reaction mixture was diluted with H₂O (50 mL) and extracted with EtOAc (30 mL*2). The combined organic layers were washed with brine (50 mL), dried over anhydrous Na₂SO₄, filtered and concentrated under reduced pressure to afford the title compound, which was used into next step without further purification.
LCMS: 652.2 [M+H]⁺.

Step 6. Synthesis of N-(2-chloro-4-(trifluoromethyl) phenyl)-2-(2-(dimethylamino)-6-ethyl-7-(2-methylpiperazin-1-yl)-8-oxopyrido[2,3-b]pyrazin-5 (8H)-yl)acetamide Trifluoroacetate To a solution of tert-butyl 4-(5-(2-((2-chloro-4-(trifluoromethyl)phenyl)amino)-2-oxoethyl)-2-(dimethylamino)-6-ethyl-8-oxo-5,8-dihydropyrido[2,3-b]pyrazin-7-yl)-3-methylpiperazine-1-carboxylate (210 mg, 322 mol, 1.0 eq) in DCM (12 mL) was added TFA (3 mL), and it was stirred at room temperature for 0.5 h. The reaction mixture was concentrated under reduced pressure to afford the title compound, which was used into next step without further purification.
LCMS: 552.4 [M+H]⁺.

Intermediate-89: 2-((3-methoxycyclobutylidene)methyl)-4,4,5,5-tetramethyl-1,3,2-dioxaborolane

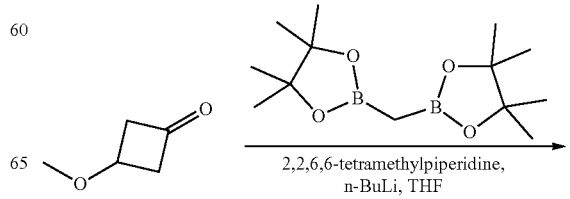

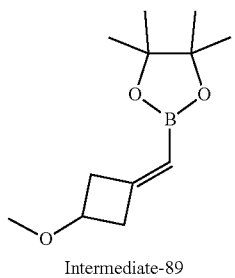

Intermediate-89

Step 1. Synthesis of 2-((3-methoxycyclobutylidene)methyl)-4,4,5,5-tetramethyl-1,3,2-dioxaborolane To a solution of 2,2,6,6-tetramethylpiperidine (508 mg, 3.60 mmol, 1.2 eq) in THF (2 mL) was added n-BuLi (2.5 M in THF, 1.32 mL, 1.1 eq) at −30° C. under $N_2$ atmosphere. After stirring at −30° C. for 0.5 h, the mixture was cooled to −78° C., and then a solution of bis(4,4,5,5-tetramethyl-1,3,2-dioxaborolan-2-yl)methane (803 mg, 3.00 mmol, 1.0 eq) in THF (2 mL) was added dropwise, and it was stirred at −78° C. for 0.5 h after addition. Then, a solution of 3-methoxycyclobutan-1-one (300 mg, 3.00 mmol, 1.0 eq) in THF (0.2 mL) was added dropwise at −78° C., and the resulting mixture was slowly warmed to room temperature and stirred at room temperature overnight. The reaction mixture was poured into saturated $NH_4Cl$ aqueous solution (80 mL) and extracted with EtOAc (70 mL*3). The combined organic layers were washed with brine (80 mL), dried over anhydrous $Na_2SO_4$, filtered and the filtrate was concentrated in vacuo. The residue was purified by silica gel chromatography (EtOAc/PE) to afford the title compound.

LCMS: 225.2 $[M+H]^+$.

Intermediate-90: methyl 3-(bis(4-methoxybenzyl)amino)-5-chloropyrazine-2-carboxylate

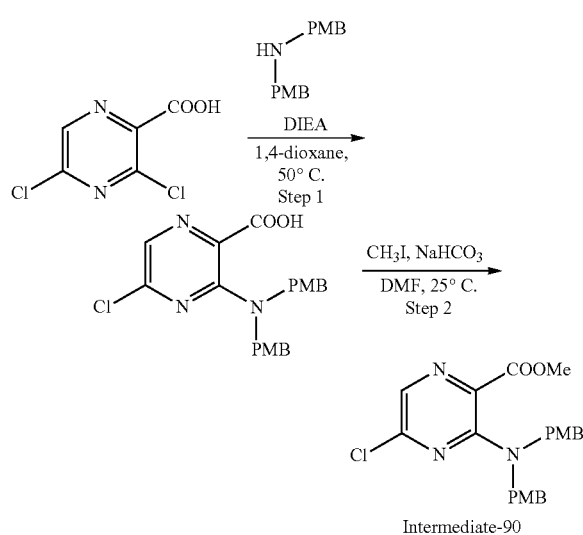

Step 1. Synthesis of 3-(bis(4-methoxybenzyl)amino)-5-chloropyrazine-2-carboxylic Acid To a solution of 3,5-dichloropyrazine-2-carboxylic acid (50.00 g, 259.08 mmol, 1 eq), 1-(4-methoxyphenyl)-N-[(4-methoxyphenyl)methyl]methanamine (66.67 g, 259.08 mmol, 1 eq) in 1,4-dioxane (1000 mL) was added DIEA (83.71 g, 647.71 mmol, 113 mL, 2.5 eq). The mixture was stirred at 50° C. for 16 h. The reaction mixture was concentrated under reduced pressure to give a residue. The residue was suspended into DCM:EtOAc=1:5 (500 mL) and stirred for 30 min. Then filtered, the filtrate was collected and concentrated under reduced pressure to give the title compound, which was used into the next step without further purification.

LCMS: 412.1 $[M+H]^+$.

Step 2. Synthesis of methyl 3-(bis(4-methoxybenzyl)amino)-5-chloropyrazine-2-carboxylate To a solution of 3-(bis(4-methoxybenzyl)amino)-5-chloropyrazine-2-carboxylic acid (90.00 g, 217.47 mmol, 1 eq) in DMF (900 mL) was added $CH_3I$ (92.60 g, 652.40 mmol, 40 mL, 3 eq) and $NaHCO_3$ (21.92 g, 260.96 mmol, 1.2 eq). Then the mixture was stirred at 25° C. for 5 h. It was poured into saturated $NH_4Cl$ aqueous solution (2.00 L) and extracted with EtOAc (800 mL*3). The combined organic layer was washed with brine (100 mL*2), dried over anhydrous $Na_2SO_4$, filtered and concentrated under vacuum to give a residue. The residue was purified by silica gel chromatography (Eluent of EtOAc/PE) to afford the title compound.

$^1$H NMR (400 MHz, $CDCl_3$) δ ppm 7.91 (s, 1H), 7.05 (d, 4H), 6.83 (d, 4H), 4.56 (s, 4H), 3.84 (s, 3H), 3.78 (s, 6H).

LCMS: 428.1 $[M+H]^+$.

Intermediate-91: 2-(2-(dimethylamino)-6-ethyl-7-(4-(5-hydroxy-6-methylpyrimidine-4-carbonyl)piperazin-1-yl)-8-oxopyrido[2,3-b]pyrazin-5 (8H)-yl) acetic Acid

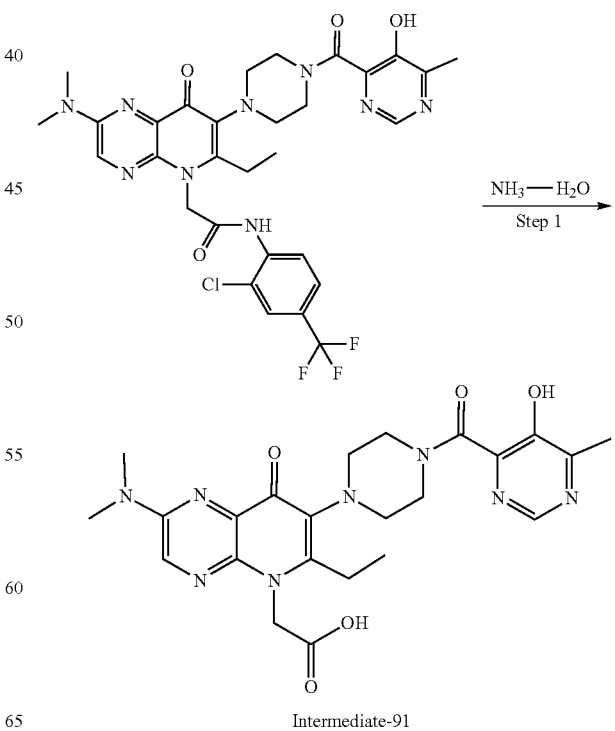

Step 1. Synthesis of 2-(2-(dimethylamino)-6-ethyl-7-(4-(5-hydroxy-6-methylpyrimidine-4-carbonyl)piperazin-1-yl)-8-oxopyrido[2,3-b]pyrazin-5 (8H)-yl)acetic Acid A solution of N-(2-chloro-4-(trifluoromethyl)phenyl)-2-(2-(dimethylamino)-6-ethyl-7-(4-(5-hydroxy-6-methylpyrimidine-4-carbonyl)piperazin-1-yl)-8-oxopyrido[2,3-b]pyrazin-5 (8H)-yl)acetamide (I-14) (100 mg, 148 mol, 1.0 eq) in NH$_3$—H$_2$O (2 mL) was stirred at 80° C. overnight. The reaction mixture was concentrated in vacuo and then purified by reverse phase HPLC (C18 column, water (0.1% FA)-ACN) to afford the title compound.

LCMS: 497.3 [M+H]$^+$.

Intermediate-92: ethyl 3-(methylthio)-6-oxo-1,6-dihydro-1,2,4-triazine-5-carboxylate Intermediate-93: ethyl 3-(methylthio)-5-oxo-4,5-dihydro-1,2,4-triazine-6-carboxylate Step 1: Synthesis of ethyl 3-(methylthio)-6-oxo-1,6-dihydro-1,2,4-triazine-5-carboxylate and ethyl 3-(methylthio)-5-oxo-4,5-dihydro-1,2,4-triazine-6-carboxylate To a solution of methyl hydrazinecarbimidothioate hydroiodide (35.13 g, 150.73 mmol, 1.05 eq) and TEA (15.25 g, 150.73 mmol, 1.05 eq) in THF (400 mL) was added dropwise a solution of diethyl 2-oxomalonate (25 g, 143.55 mmol, 1.0 eq) at 0° C. under N$_2$. The resulting mixture was stirred at 45° C. under N$_2$ atmosphere for 15 h. The reaction mixture was filtered, the filtrate was concentrated under reduced pressure. The residue was purified by flash silica gel chromatography (Eluent of EtOAc/PE) to afford the title compounds.

Analytical data of ethyl 3-(methylthio)-6-oxo-1,6-dihydro-1,2,4-triazine-5-carboxylate (Intermediate-92)

LCMS: 216.2 [M+H]$^+$.
$^1$H NMR (400 MHz, CDCl$_3$) δ 4.41 (q, 2H), 2.41 (s, 3H), 1.35 (t, 3H).

Analytical data of ethyl 3-(methylthio)-5-oxo-4,5-dihydro-1,2,4-triazine-6-carboxylate (Intermediate-93)

LCMS: 216.1 [M+H]$^+$.
$^1$H NMR (400 MHz, CDCl$_3$) δ 4.48 (q, 2H), 2.63 (s, 3H), 1.45-1.40 (m, 3H).

Intermediate-96: tert-butyl (3S)-4-(8-(2-((2-chloro-4-(trifluoromethyl)phenyl)amino)-2-oxoethyl)-7-ethyl-3-(methylsulfinyl)-5-oxo-5,8-dihydropyrido[3,2-e][1,2,4]triazin-6-yl)-3-methylpiperazine-1-carboxylate Intermediate-97: tert-butyl (S)-4-(7-ethyl-3-(methylthio)-5-oxo-5,8-dihydropyrido[3,2-e][1,2,4]triazin-6-yl)-3-methylpiperazine-1-carboxylate Intermediate-95: (S)—N-(2-chloro-4-(trifluoromethyl)phenyl)-2-(3-(dimethylamino)-7-ethyl-6-(2-methylpiperazin-1-yl)-5-oxopyrido[3,2-e][1,2,4]triazin-8 (5H)-yl)acetamide Trifluoroacetate

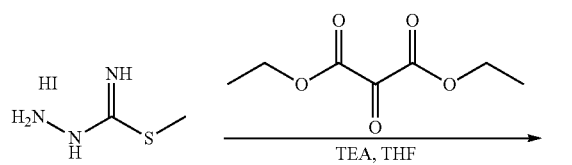

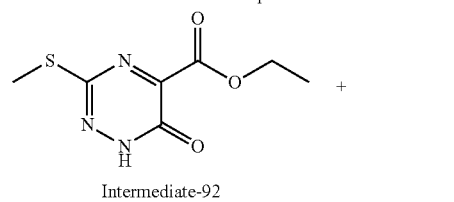

Intermediate-92

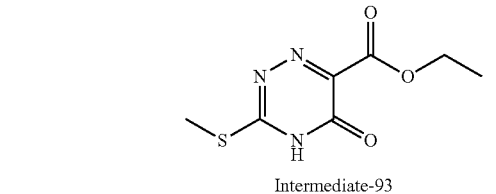

Intermediate-93

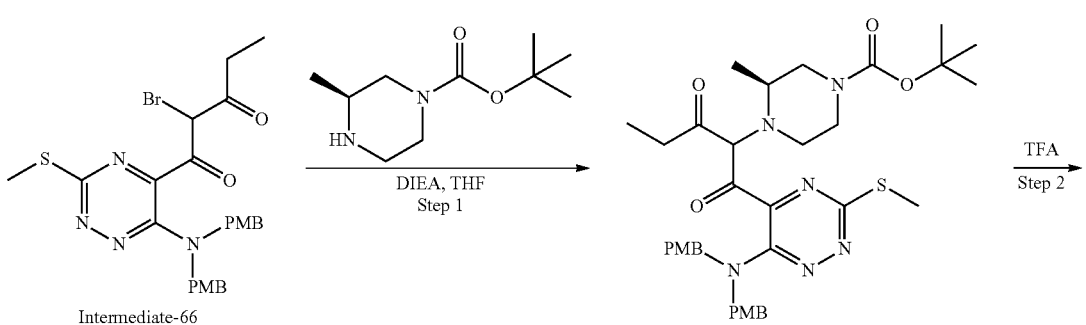

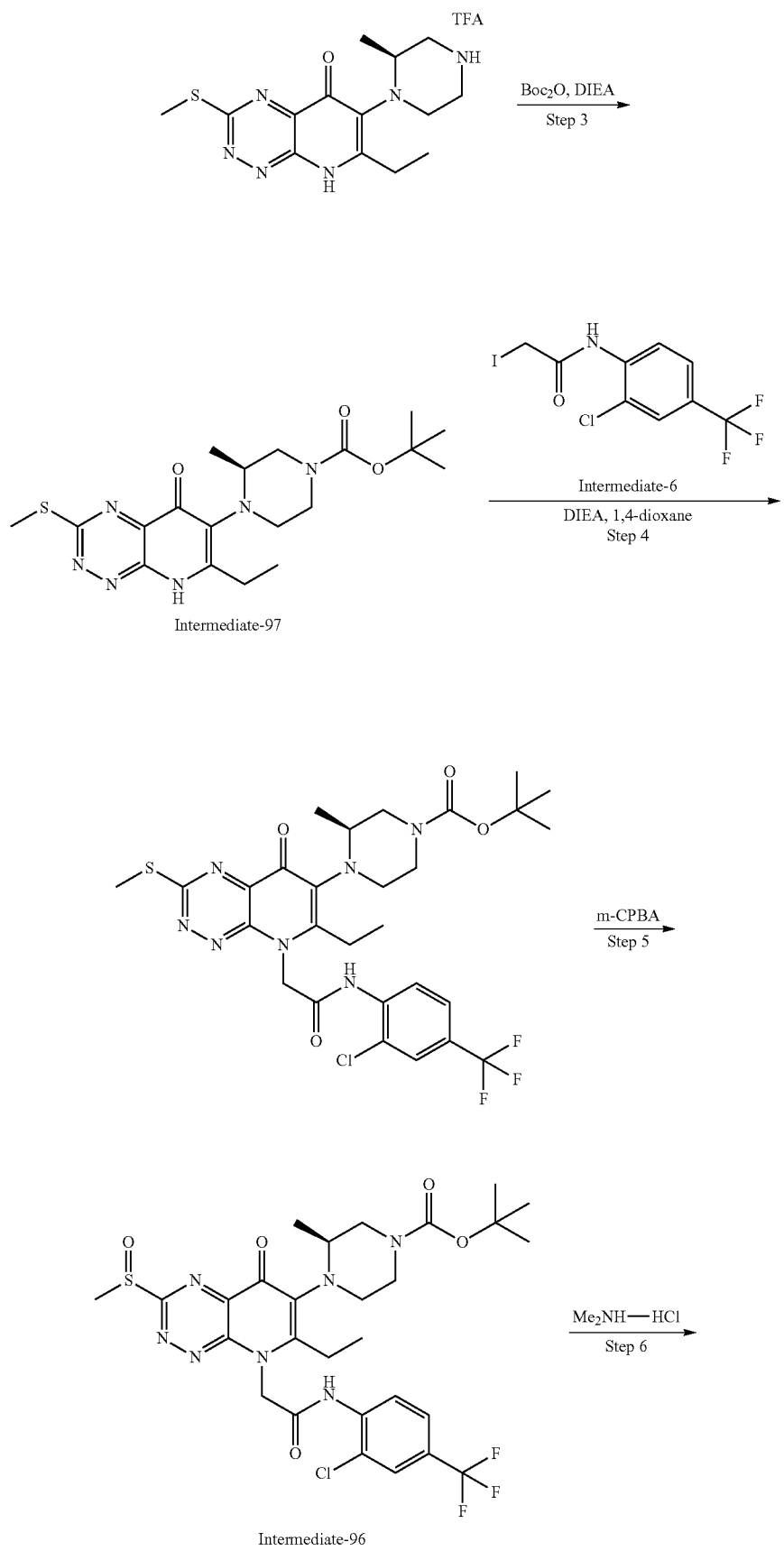

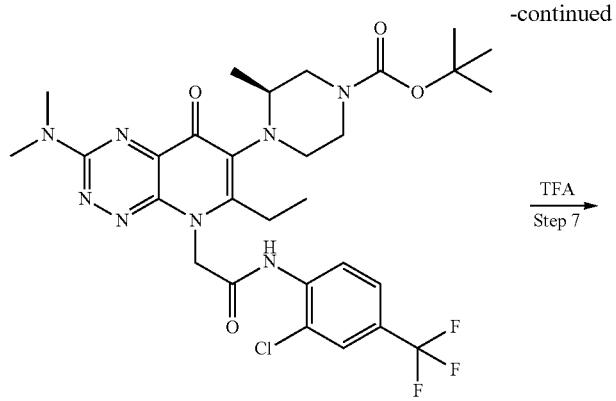

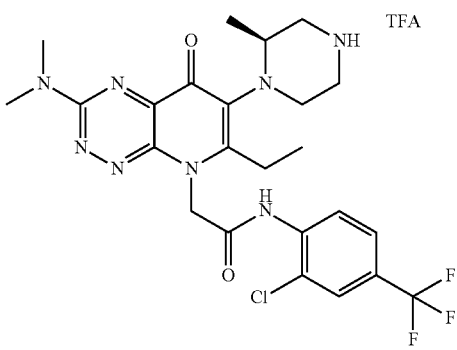

Intermediate-95

Step 1: Synthesis of tert-butyl (3S)-4-(1-(6-(bis(4-methoxybenzyl)amino)-3-(methylthio)-1,2,4-triazin-5-yl)-1,3-dioxopentan-2-yl)-3-methylpiperazine-1-carboxylate To a solution of 1-(6-(bis(4-methoxybenzyl)amino)-3-(methylthio)-1,2,4-triazin-5-yl)-2-bromopentane-1,3-dione (Intermediate-66) (1.8 g, 3.22 mmol, 1.0 eq) and tert-butyl (S)-3-methylpiperazine-1-carboxylate (709 mg, 3.54 mmol, 1.1 eq) in THF (20 mL) was added DIEA (832 mg, 6.43 mmol, 2.0 eq), and the resulting mixture was stirred at 50° C. overnight. The reaction mixture was poured into ice-water (20 mL) and extracted with DCM (20 mL*3). The combined organic layers were washed with brine (30 mL), dried over anhydrous $Na_2SO_4$, filtered and concentrated in vacuo. The residue was purified by flash silica gel chromatography (Eluent of EtOAc/PE) to afford the title compound.

LCMS: 679.2 [M+H]$^+$.

Step 2: Synthesis of (S)-7-ethyl-6-(2-methylpiperazin-1-yl)-3-(methylthio)pyrido[3,2-e][1,2,4]triazin-5 (8H)-one Trifluoroacetate A solution of tert-butyl (3S)-4-(1-(6-(bis(4-methoxybenzyl)amino)-3-(methylthio)-1,2,4-triazin-5-yl)-1,3-dioxopentan-2-yl)-3-methylpiperazine-1-carboxylate (650 mg, 958 mol, 1.0 eq) in TFA (7 mL) was stirred at 50° C. for 1 h and then concentrated under reduced pressure to afford the title compound, which was used into the next step without further purification.

LCMS: 321.2[M+H]$^+$.

Step 3: Synthesis of tert-butyl (S)-4-(7-ethyl-3-(methylthio)-5-oxo-5,8-dihydropyrido[3,2-e][1,2,4]triazin-6-yl)-3-methylpiperazine-1-carboxylate (Intermediate-97)

To a solution of (S)-7-ethyl-6-(2-methylpiperazin-1-yl)-3-(methylthio)pyrido[3,2-e][1,2,4]triazin-5 (8H)-one trifluoroacetate (305 mg, 952 mol, 1.0 eq) and DIEA (369 mg, 2.86 mmol, 3.0 eq) in DCM (4 mL) was added $Boc_2O$ (208 mg, 952 mol, 1.0 eq), and the resulting mixture was stirred at room temperature for 1 h. The reaction mixture was poured into $H_2O$ (10 mL), and then extracted with DCM (10 mL*3). The combined organic layers were washed with brine (10 mL), dried over anhydrous $Na_2SO_4$, filtered and concentrated under reduced pressure. The filtrate was purified by flash silica gel chromatography (Eluent of EtOAc/PE) to afford the title compound.

LCMS: 421.2 [M+H]$^+$.

Step 4: Synthesis of tert-butyl (S)-4-(8-(2-((2-chloro-4-(trifluoromethyl)phenyl)amino)-2-oxoethyl)-7-ethyl-3-(methylthio)-5-oxo-5,8-dihydropyrido[3,2-e][1,2,4]triazin-6-yl)-3-methylpiperazine-1-carboxylate To a solution of tert-butyl (S)-4-(7-ethyl-3-(methylthio)-5-oxo-5,8-dihydropyrido[3,2-e][1,2,4]triazin-6-yl)-3-methylpiperazine-1-carboxylate (Intermediate-97) (100 mg, 238 mol, 1.0 eq) and N-(2-chloro-4-(trifluoromethyl)phenyl)-2-iodoacetamide (Intermediate-6) (95 mg, 262 mol, 1.1 eq) in 1,4-dioxane (2 mL) was added DIEA (77 mg, 594 mol, 2.5 eq), and the resulting mixture was stirred at 80° C. overnight. The reaction mixture was poured into $H_2O$ (10 mL), and then extracted with DCM (10 mL*3). The combined organic layers were washed with brine (10 mL), dried over anhydrous $Na_2SO_4$, filtered and concentrated under reduced pressure. The residue was purified by reverse phase HPLC (C18 column, water (0.1% FA-ACN) to afford the title compound.

LCMS: 656.2 [M+H]$^+$.

$^1$H NMR (400 MHz, $CDCl_3$) δ 8.65 (s, 1H), 8.43 (d, 1H), 7.67 (d, 1H), 7.51 (br d, 1H), 5.85-5.42 (m, 2H), 4.23-3.96 (m, 2H), 3.96-3.85 (m, 1H), 3.70 (dt, 1H), 3.63-3.50 (m, 1H), 3.15-2.89 (m, 2H), 2.75 (s, 3H), 2.66 (br d, 1H), 2.60-2.49 (m, 1H), 1.50 (s, 9H), 1.36 (t, 3H), 0.86 (d, 3H).

Step 5: Synthesis of tert-butyl (3S)-4-(8-(2-((2-chloro-4-(trifluoromethyl)phenyl)amino)-2-oxoethyl)-7-ethyl-3-(methylsulfinyl)-5-oxo-5,8-dihydropyrido[3,2-e][1,2,4]triazin-6-yl)-3-methylpiperazine-1-carboxylate (Intermediate-96)

To a solution of tert-butyl (S)-4-(8-(2-((2-chloro-4-(trifluoromethyl)phenyl)amino)-2-oxoethyl)-7-ethyl-3-(methylthio)-5-oxo-5,8-dihydropyrido[3,2-e][1,2,4]triazin-6-yl)-3-methylpiperazine-1-carboxylate (62 mg, 95 mol, 1.0 eq) in DCM (1.5 mL) was added m-CPBA (38 mg, 189 mol, 85%, 2.0 eq) at 0° C. and the resulting mixture was stirred at 0° C. for 1 h. The reaction mixture was poured into saturated $Na_2SO_3$ aqueous solution (5 mL), and then extracted with DCM (5 mL*3). The combined organic layers were washed with brine (5 mL), dried over anhydrous $Na_2SO_4$, filtered and concentrated under reduced pressure to afford the title compound, which was used into the next step without further purification.

LCMS: 672.2 [M+H]$^+$.

Step 6: Synthesis of tert-butyl (S)-4-(8-(2-((2-chloro-4-(trifluoromethyl)phenyl)amino)-2-oxoethyl)-3-(dimethylamino)-7-ethyl-5-oxo-5,8-dihydropyrido[3,2-e][1,2,4]triazin-6-yl)-3-methylpiperazine-1-carboxylate To a solution of tert-butyl (3S)-4-(8-(2-((2-chloro-4-(trifluoromethyl)phenyl)amino)-2-oxoethyl)-7-ethyl-3-(methylsulfinyl)-5-oxo-5,8-dihydropyrido[3,2-e][1,2,4]triazin-6-yl)-3-methylpiperazine-1-carboxylate (Intermediate-96) (64 mg, 95 mol, 1.0 eq) and dimethylamine hydrochloride (16 mg, 190 mol, 2.0 eq) in 1,4-dioxane (2 mL) was added DIEA (37 mg, 286 mol, 3.0 eq), and the resulting mixture was stirred at 80° C. for 1 h. The reaction mixture was poured into ice-water (10 mL) and extracted with EtOAc (5 mL*3). The combined organic layers were washed with brine (10 mL), dried over anhydrous Na$_2$SO$_4$, filtered and concentrated in vacuo. The residue was purified by flash silica gel chromatography (Eluent of EtOAc/PE) to afford the title compound.
LCMS: 653.2 [M+H]$^+$.

Step 7: Synthesis of (S)—N-(2-chloro-4-(trifluoromethyl)phenyl)-2-(3-(dimethylamino)-7-ethyl-6-(2-methylpiperazin-1-yl)-5-oxopyrido[3,2-e][1,2,4]triazin-8 (5H)-yl)acetamide Trifluoroacetate To a solution of tert-butyl (S)-4-(8-(2-((2-chloro-4-(trifluoromethyl)phenyl)amino)-2-oxoethyl)-3-(dimethylamino)-7-ethyl-5-oxo-5,8-dihydropyrido[3,2-e][1,2,4]triazin-6-yl)-3-methylpiperazine-1-carboxylate (39 mg, 60 mol, 1.0 eq) in DCM (0.5 mL) was added TFA (0.5 mL), and the resulting mixture was stirred at room temperature for 0.5 h. The reaction mixture was concentrated under reduced pressure to afford the title compound, which was used into the next step without further purification.
LCMS: 553.2 [M+H]$^+$.

Intermediate-99: methyl 4-hydroxy-2-methoxynicotinate

Intermediate-100: 4-hydroxy-2-methoxy-5-methylnicotinic Acid

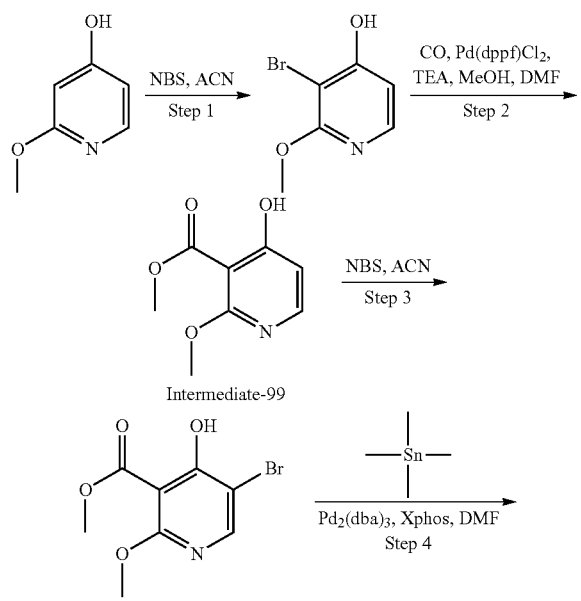

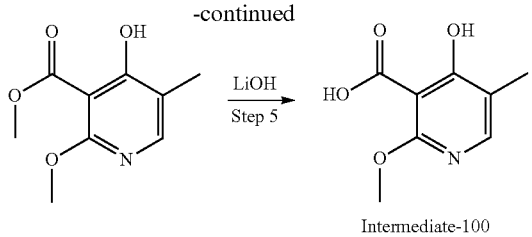

Intermediate-100

Step 1: Synthesis of 3-bromo-2-methoxypyridin-4-ol

To a solution of 2-methoxypyridin-4-ol (5.00 g, 39.96 mmol, 1.0 eq) in ACN (80 mL) was added NBS (7.11 g, 39.96 mmol, 1.0 eq) at 0° C., and the resulting mixture was stirred at room temperature overnight. The reaction mixture was diluted with H$_2$O (100 mL), and then extracted with EtOAc (100 mL*3). The combined organic layers were dried over anhydrous Na$_2$SO$_4$, filtered and concentrated under reduced pressure to give a residue. The residue was purified by flash silica gel chromatography (Eluent of EtOAc/PE) to afford the title compound.
LCMS: 203.9 [M+H]$^+$.
$^1$H NMR (400 MHz, CDCl$_3$) δ 7.92 (d, 1H), 6.63 (d, 1H), 4.03 (s, 3H).

Step 2: Synthesis of methyl 4-hydroxy-2-methoxynicotinate (Intermediate-99)

To a mixture of 3-bromo-2-methoxypyridin-4-ol (3.84 g, 18.82 mmol, 1.0 eq) in MeOH (20 mL) and DMF (20 mL) was added Pd(dppf)Cl$_2$·CH$_2$Cl$_2$ (1.54 g, 1.88 mmol, 0.1 eq) and TEA (5.71 g, 56.46 mmol, 3.0 eq), and the resulting mixture was stirred at 80° C. overnight under CO (50 psi) atmosphere. The reaction mixture was filtered and the filtrate was concentrated under reduced pressure. The residue was dissolved into DCM (100 mL), washed with saturated NH$_4$Cl (70 mL*3), dried over Na$_2$SO$_4$, filtered and concentrated under reduced pressure to give a residue. The residue was purified by flash silica gel chromatography (Eluent of EtOAc/PE) to afford the title compound.
$^1$H NMR (400 MHz, CDCl$_3$) δ 12.26 (s, 1H), 8.05 (d, 1H), 6.57 (d, 1H), 4.01 (d, 6H).

Step 3: Synthesis of methyl 5-bromo-4-hydroxy-2-methoxynicotinate

To a solution of methyl 4-hydroxy-2-methoxynicotinate (Intermediate-99) (1.40 g, 7.64 mmol, 1.0 eq) in ACN (14 mL) was added NBS (1.36 g, 7.64 mmol, 1.0 eq), and the resulting mixture was stirred at room temperature for 3 h. The reaction mixture was filtered, the filter cake was washed with cold ACN (5 mL) and then dried in vacuo to afford the title compound, which was used into the next step without further purification.
LCMS: 262.1 [M+H]$^+$.
$^1$H NMR (400 MHz, CDCl$_3$) δ 12.90 (s, 1H), 8.15 (s, 1H), 3.92 (d, 6H).

Step 4: Synthesis of methyl 4-hydroxy-2-methoxy-5-methylnicotinate

To a mixture of methyl 5-bromo-4-hydroxy-2-methoxynicotinate (300 mg, 1.14 mmol, 1.0 eq) and tetramethylstannane (409 mg, 2.29 mmol, 2.0 eq) in DMF (2 mL) was added Pd$_2$(dba)$_3$ (105 mg, 114 mol, 0.1 eq) and XPhos (109 mg, 229 mol, 0.2 eq), and the resulting mixture was stirred at 120° C. overnight under N$_2$ atmosphere. The reaction mixture was diluted with H$_2$O (20 mL), extracted with EtOAc (10 mL*3). The combined organic layers were washed with brine (5 mL), dried over anhydrous Na$_2$SO$_4$, filtered and concentrated under reduced pressure. The residue was purified by reverse phase HPLC (C18 column, water (0.1% FA-ACN) to afford the title compound.

LCMS: 198.3 [M+H]$^+$.

$^1$H NMR (400 MHz, CDCl$_3$) δ 12.48 (s, 1H), 7.91 (s, 1H), 3.99 (d, 6H), 2.14 (s, 3H).

Step 5: Synthesis of 4-hydroxy-2-methoxy-5-methylnicotinic Acid

To a solution of methyl 4-hydroxy-2-methoxy-5-methylnicotinate (30 mg, 152 mol, 1.0 eq) in H$_2$O (0.2 mL), THF (0.2 mL) and MeOH (0.2 mL) was added aqueous LiOH solution (1 M, 608 µL, 4.0 eq) and it was stirred at 40° C. overnight. The reaction mixture was acidified by addition of aqueous HCl solution (1 M) to pH 5-6, and then extracted with EtOAc (5 mL*10). The combined organic layers were dried over anhydrous Na$_2$SO$_4$, filtered and concentrated under reduced pressure to afford the title compound, which was used into the next step without further purification.

LCMS: 184.1 [M+H]$^+$.

Intermediate-101: 4-hydroxy-2-methoxy-pyridine-3-carboxylic Acid

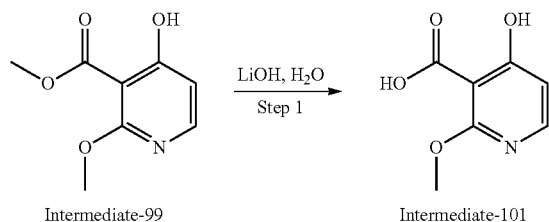

Step 1: Synthesis of 4-hydroxy-2-methoxy-pyridine-3-carboxylic Acid

To a solution of methyl 4-hydroxy-2-methoxy-pyridine-3-carboxylate (Intermediate-99) (1.00 g, 5.46 mmol, 1.0 eq) in THF (5 mL), H$_2$O (5 mL) and MeOH (10 mL) was added LiOH—H$_2$O (1.37 g, 32.76 mmol, 6.0 eq) and the reaction mixture was stirred overnight at room temperature. The reaction mixture was diluted with H$_2$O (3 mL) and then separated. The aqueous phase was washed with EtOAc 6 mL (3 mL*2) and then adjusted to pH=6 with aqueous HCl solution (2 M). The resulting mixture was concentrated under reduced pressure and then purified by reverse phase HPLC (C18 column, water (0.1% FA)-ACN) to afford the title compound.

LCMS: 170.1 [M+H]$^+$.

$^1$H NMR (400 MHz, CDCl$_3$) δ ppm 12.60 (s, 1H), 11.28-10.86 (m, 1H), 8.08 (d, 1H), 6.68 (d, 1H), 4.19 (s, 3H).

Intermediate-102: Synthesis of 5-chloro-3-((4-methoxybenzyl)amino)pyrazine-2-carboxylic Acid

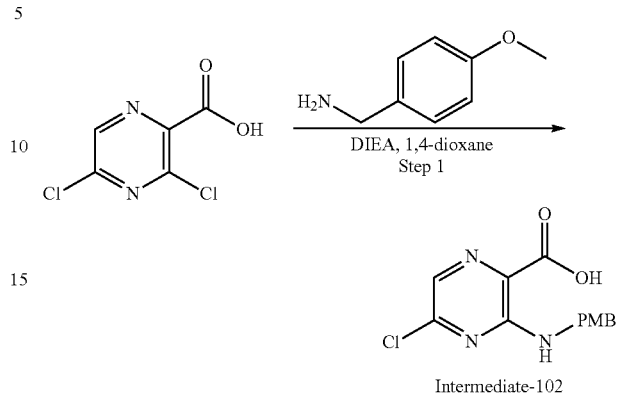

Step 1. Synthesis of 5-chloro-3-((4-methoxybenzyl)amino)pyrazine-2-carboxylic Acid To a solution of 3,5-dichloropyrazine-2-carboxylic acid (200 mg, 1.04 mmol, 1.0 eq) and (4-methoxyphenyl)methanamine (142 mg, 1.04 mmol, 1.0 eq) in 1,4-dioxane (2 mL) was added DIEA (335 mg, 2.59 mmol, 2.5 eq), and the resulting mixture was stirred at 100° C. for 2 h. The reaction mixture was acidized to pH 2 with aqueous HCl solution (1 M), and then extracted with EtOAc (30 mL*2). The combined organic layers were dried over anhydrous Na$_2$SO$_4$, filtered and concentrated in vacuo. The residue was purified by flash silica gel chromatography (Eluent of EtOAc/PE) to afford the title compound.

LCMS: 294.1[M+H]$^+$.

$^1$H NMR (400 MHz, CDCl$_3$) δ ppm 8.37 (br s, 1H), 7.72 (s, 1H), 7.32-7.27 (m, 2H), 6.91-6.86 (m, 2H), 4.66 (d, 2H), 3.81 (s, 3H).

Intermediate-104: 2-bromo-1-(6-bromo-3-((4-methoxybenzyl)amino)-5-methylpyrazin-2-yl)pentane-1,3-dione Intermediate-105: tert-butyl (1S,6S)-5-(2-bromo-6-ethyl-3-methyl-8-oxo-5,8-dihydropyrido[2,3-b]pyrazin-7-yl)-2,5-diazabicyclo[4.2.0]octane-2-carboxylate

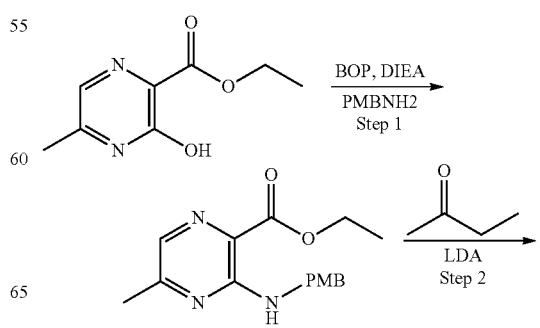

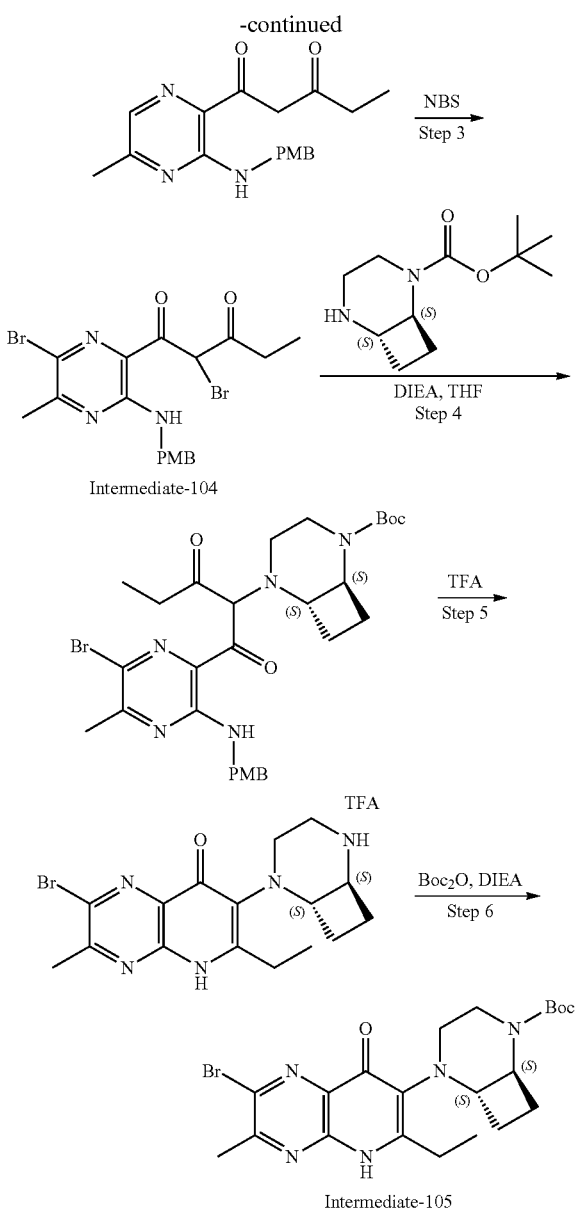

Intermediate-104

Intermediate-105

Step 1: Synthesis of ethyl 3-((4-methoxybenzyl) amino)-5-methylpyrazine-2-carboxylate To a solution of ethyl 3-hydroxy-5-methylpyrazine-2-carboxylate (10.00 g, 54.89 mmol, 1.0 eq) in DMF (100 mL) was added DIEA (10.64 g, 82.34 mmol, 1.5 eq) and BOP (26.71 g, 60.38 mmol, 1.1 eq), and the resulting mixture was stirred at 45° C. for 0.5 h. Then PMBNH$_2$ (9.04 g, 65.87 mmol, 1.2 eq) was added and the mixture was stirred at 45° C. overnight. The reaction mixture was diluted with H$_2$O (1000 mL) and extracted with EtOAc (300 mL*3). The combined organic layers were washed with brine (300 mL*2), dried over anhydrous Na$_2$SO$_4$, filtered and concentrated under reduced pressure. The residue was purified by silica gel chromatography (Eluent of EtOAc/PE) to afford the title compound.

LCMS: 302.2 [M+H]$^+$.

Step 2: Synthesis of 1-(3-((4-methoxybenzyl) amino)-5-methylpyrazin-2-yl)pentane-1,3-dione To a solution of ethyl 3-((4-methoxybenzyl)amino)-5-methylpyrazine-2-carboxylate (10.50 g, 34.84 mmol, 1.0 eq) and butan-2-one (7.54 g, 104.53 mmol, 3.0 eq) in toluene (105 mL) was added LDA (2 M in hexane, 52.27 mL, 3.0 eq) at 0° C. under N$_2$ atmosphere, and the resulting mixture was stirred at 60° C. for 0.5 h. The reaction mixture was quenched by saturated NH$_4$Cl solution (300 mL), extracted with EtOAc (300 mL*3). The combined organic layers were dried over anhydrous Na$_2$SO$_4$, filtered and concentrated in vacuo. The residue was purified by silica gel chromatography (Eluent of EtOAc/PE) to afford the title compound.

LCMS: 328.2 [M+H]$^+$.

Step 3: Synthesis of 2-bromo-1-(6-bromo-3-((4-methoxybenzyl)amino)-5-methylpyrazin-2-yl)pentane-1,3-dione (Intermediate-104)

To a solution of 1-(3-((4-methoxybenzyl)amino)-5-methylpyrazin-2-yl)pentane-1,3-dione (2.00 g, 6.11 mmol, 1.0 eq) in DCM (20 mL) was added NBS (1.09 g, 6.11 mmol, 1.0 eq) and TsOH-H$_2$O (316 mg, 1.83 mmol, 0.3 eq), and the resulting mixture was stirred at 0° C. for 1 h. The reaction mixture was diluted with H$_2$O (30 mL) and extracted with DCM (20 mL*3). The combined organic layers were washed with brine (30 mL), dried over anhydrous Na$_2$SO$_4$, filtered and concentrated under reduced pressure. The obtained material was treated with DMF (20 mL) and NBS (1.16 g, 6.50 mmol, 1.1 eq) and the resulting mixture was stirred at room temperature for 2 h. The reaction mixture was diluted with H$_2$O (50 mL) and extracted with MTBE (50 mL*3). The combined organic layers were washed with brine (20 mL), dried over anhydrous Na$_2$SO$_4$, filtered and concentrated under reduced pressure to afford the title compound, which was used into the next step without further purification.

LCMS: 486.0 [M+H]$^+$.

Step 4: Synthesis of tert-butyl (1S,6S)-5-(1-(6-bromo-3-((4-methoxybenzyl)amino)-5-methylpyrazin-2-yl)-1,3-dioxopentan-2-yl)-2,5-diazabicyclo[4.2.0]octane-2-carboxylate To a solution of 2-bromo-1-(6-bromo-3-((4-methoxybenzyl)amino)-5-methylpyrazin-2-yl)pentane-1,3-dione (Intermediate-104) (2.87 g, 5.92 mmol, 1.0 eq) in THF (30 mL) was added tert-butyl (1S,6S)-2,5-diazabicyclo[4.2.0]octane-2-carboxylate (CAS: 2920219-11-8) (1.38 g, 6.51 mmol, 1.1 eq) and DIEA (1.53 g, 11.83 mmol, 2.0 eq), and the resulting mixture was stirred at room temperature for 1 h. The reaction mixture was diluted with H$_2$O (50 mL) and extracted with EtOAc (50 mL*3). The combined organic layers were dried over anhydrous Na$_2$SO$_4$, filtered and concentrated under reduced pressure. The residue was purified by silica gel chromatography (Eluent of EtOAc/PE) to afford the title compound.

LCMS: 618.3 [M+H]$^+$.

Step 5: Synthesis of 7-((1S,6S)-2,5-diazabicyclo [4.2.0]octan-2-yl)-2-bromo-6-ethyl-3-methylpyrido [2,3-b]pyrazin-8 (5H)-one Trifluoroacetate A solution of tert-butyl (1S,6S)-5-(1-(6-bromo-3-((4-methoxybenzyl)amino)-5-methylpyrazin-2-yl)-1,3-dioxopentan-2-yl)-2,5-diazabicyclo[4.2.0]octane-2-carboxylate (2.80 g, 4.54 mmol, 1.0 eq) in TFA (30 mL) was stirred at room temperature for 2 h, and heated to 50° C. for another 2 h. The reaction mixture was concentrated under reduced pressure to afford the title compound, which was used into the next step without further purification.
LCMS: 378.1 [M+H]$^+$.

Step 6: Synthesis of tert-butyl (1S,6S)-5-(2-bromo-6-ethyl-3-methyl-8-oxo-5,8-dihydropyrido[2,3-b]pyrazin-7-yl)-2,5-diazabicyclo[4.2.0]octane-2-carboxylate To a solution of 7-((1S,6S)-2,5-diazabicyclo[4.2.0]octan-2-yl)-2-bromo-6-ethyl-3-methylpyrido[2,3-b]pyrazin-8 (5H)-one trifluoroacetate (1.70 g, 4.49 mmol, 1.0 eq) in DCM (20 mL) was added Boc$_2$O (1.08 g, 4.94 mmol, 1.1 eq) and DIEA (2.90 g, 22.47 mmol, 5.0 eq), and the resulting mixture was stirred at room temperature for 0.5 h. The reaction mixture was diluted with H$_2$O (50 mL) and extracted with MTBE (50 mL*3). The combined organic layers were washed with brine (30 mL), dried over Na$_2$SO$_4$, filtered and concentrated under reduced pressure. The residue was purified by silica gel chromatography (Eluent of EtOAc/PE) to afford the title compound.
LCMS: 480.2 [M+H]$^+$.

Intermediate-106: tert-butyl (1S,6S)-5-(2-bromo-6-ethyl-5-(2-((2-fluoro-4-(trifluoromethyl)phenyl)amino)-2-oxoethyl)-3-methyl-8-oxo-5,8-dihydropyrido[2,3-b]pyrazin-7-yl)-2,5-diazabicyclo[4.2.0]octane-2-carboxylate Intermediate-107: 2-(7-((1S,6S)-2,5-diazabicyclo[4.2.0]octan-2-yl)-2-bromo-6-ethyl-3-methyl-8-oxopyrido[2,3-b]pyrazin-5 (8H)-yl)-N-(2-fluoro-4-(trifluoromethyl)phenyl)acetamide Trifluoroacetate Intermediate-108: 2-(2-bromo-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5 (8H)-yl)-N-(2-fluoro-4-(trifluoromethyl)phenyl)acetamide

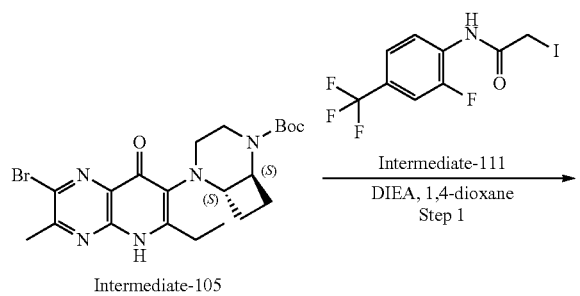

Intermediate-105

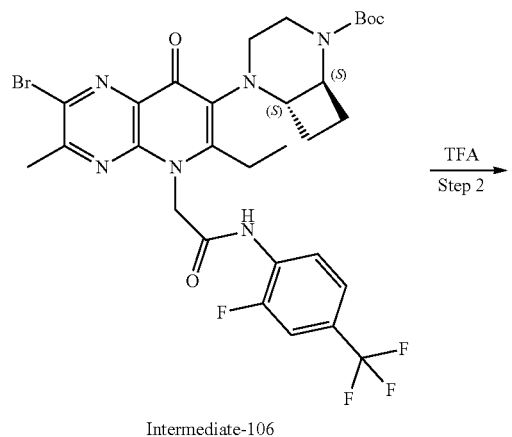

Intermediate-106

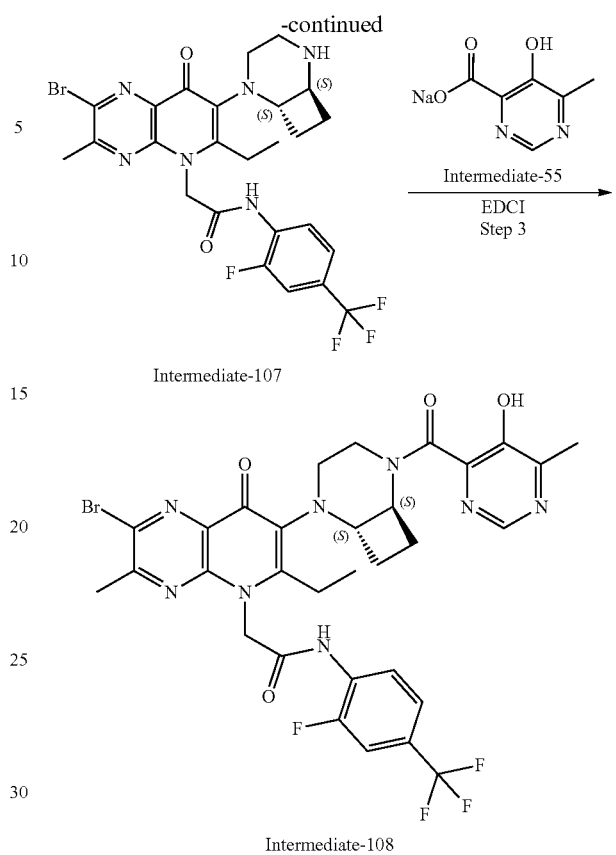

Intermediate-107

Intermediate-108

Step 1: Synthesis of tert-butyl (1S,6S)-5-(2-bromo-6-ethyl-5-(2-((2-fluoro-4-(trifluoromethyl)phenyl)amino)-2-oxoethyl)-3-methyl-8-oxo-5,8-dihydropyrido[2,3-b]pyrazin-7-yl)-2,5-diazabicyclo[4.2.0]octane-2-carboxylate (Intermediate-106)

To a solution of tert-butyl (1S,6S)-5-(2-bromo-6-ethyl-3-methyl-8-oxo-5,8-dihydropyrido[2,3-b]pyrazin-7-yl)-2,5-diazabicyclo[4.2.0]octane-2-carboxylate (Intermediate-105) (500 mg, 1.05 mmol, 1.0 eq) and N-(2-fluoro-4-(trifluoromethyl)phenyl)-2-iodoacetamide (Intermediate-111) (544 mg, 1.57 mmol, 1.5 eq) in 1,4-dioxane (4.5 mL) was added DIEA (405 mg, 3.14 mmol, 3.0 eq), and the resulting mixture was stirred at 80° C. for 3 h. The reaction mixture was concentrated under reduced pressure and then purified by silica gel chromatography (Eluent of EtOAc/PE) to afford the title compound.
LCMS: 697.3 [M+H]$^+$.

Step 2: Synthesis of 2-(7-((1S,6S)-2,5-diazabicyclo[4.2.0]octan-2-yl)-2-bromo-6-ethyl-3-methyl-8-oxopyrido[2,3-b]pyrazin-5 (8H)-yl)-N-(2-fluoro-4-(trifluoromethyl)phenyl)acetamide Trifluoroacetate (Intermediate-107)

To a solution of tert-butyl (1S,6S)-5-(2-bromo-6-ethyl-5-(2-((2-fluoro-4-(trifluoromethyl)phenyl)amino)-2-oxoethyl)-3-methyl-8-oxo-5,8-dihydropyrido[2,3-b]pyrazin-7-yl)-2,5-diazabicyclo[4.2.0]octane-2-carboxylate (Intermediate-106) (700 mg, 1.00 mmol, 1.0 eq) in DCM (18 mL) was added TFA (6 mL), and it was stirred at room temperature for 0.5 h. The reaction mixture was concentrated under reduced pressure to afford the title compound, which was used into the next step without further purification.

LCMS: 599.0 [M+H]$^+$.

Step 3: Synthesis of 2-(2-bromo-6-ethyl-7-((1S,6S)-5-(5-hydroxy-6-methylpyrimidine-4-carbonyl)-2,5-diazabicyclo[4.2.0]octan-2-yl)-3-methyl-8-oxopyrido[2,3-b]pyrazin-5 (8H)-yl)-N-(2-fluoro-4-(trifluoromethyl)phenyl)acetamide To a solution of 2-(7-((1S,6S)-2,5-diazabicyclo[4.2.0]octan-2-yl)-2-bromo-6-ethyl-3-methyl-8-oxopyrido[2,3-b]pyrazin-5 (8H)-yl)-N-(2-fluoro-4-(trifluoromethyl)phenyl)acetamide trifluoroacetate (Intermediate-107) (549 mg, 919 mol, 1.0 eq) and sodium 5-hydroxy-6-methylpyrimidine-4-carboxylate (Intermediate-55) (425 mg, 2.76 mmol, 3.0 eq) in pyridine (5.5 mL) was added EDCI (3.52 g, 18.38 mmol, 20.0 eq), and the resulting mixture was stirred at 45° C. for 15 min. To the reaction mixture was added aqueous NaOH solution (1 M, 5.5 mL) and the mixture was stirred for 15 min at room temperature. Then the resulting mixture was adjusted to pH=6 with aqueous HCl solution (1 M) and extracted with EtOAc (20 mL*2). The combined organic layers were washed with brine (10 mL), dried over anhydrous Na$_2$SO$_4$, filtered and concentrated under reduced pressure. The residue was purified by reverse phase HPLC (C18 column, water (0.1% FA)-ACN) to afford the title compound.

LCMS: 735.3 [M+H]$^+$.

Intermediate-109: tert-butyl (1S,6S)-5-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)-2,5-diazabicyclo[4.2.0]octane-2-carboxylate Intermediate-110: 2-(7-((1S,6S)-2,5-diazabicyclo[4.2.0]octan-2-yl)-6-ethyl-2,3-dimethyl-8-oxopyrido[2,3-b]pyrazin-5 (8H)-yl)-N-(2-chloro-4-(trifluoromethyl)phenyl)acetamide Hydrochloride

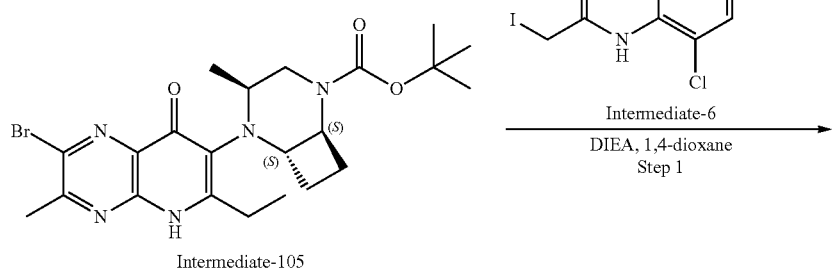

Intermediate-105

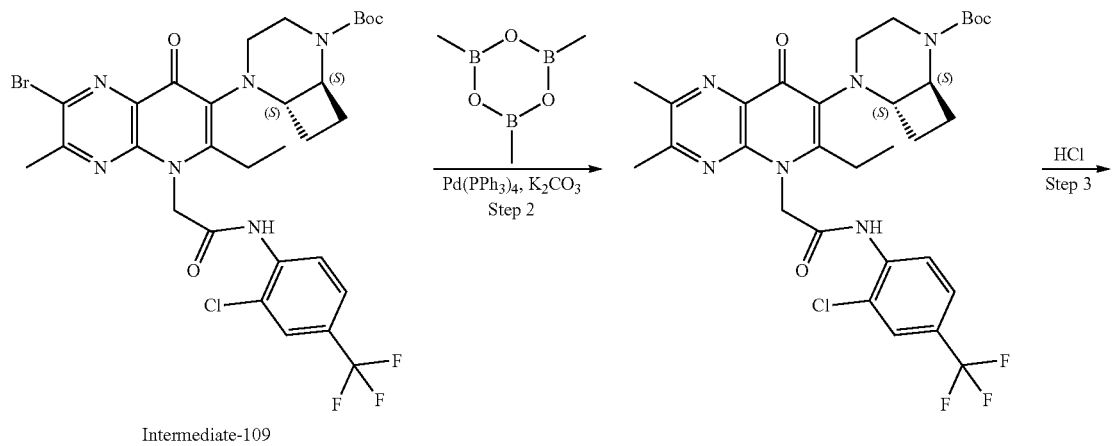

Intermediate-109

-continued

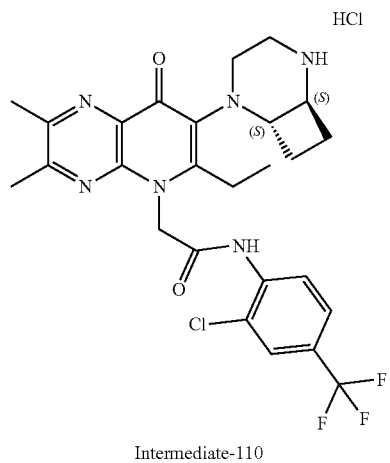

Intermediate-110

Step 1: Synthesis of tert-butyl (1S,6S)-5-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)-2,5-diazabicyclo[4.2.0]octane-2-carboxylate (Intermediate-109)

To a solution of tert-butyl (1S,6S)-5-(2-bromo-6-ethyl-3-methyl-8-oxo-5,8-dihydropyrido[2,3-b]pyrazin-7-yl)-2,5-diazabicyclo[4.2.0]octane-2-carboxylate (Intermediate-105) (500 mg, 1.05 mmol, 1.0 eq) in 1,4-dioxane (5.0 mL) was added DIEA (405 mg, 3.14 mmol, 3.0 eq) and N-(2-chloro-4-(trifluoromethyl)phenyl)-2-iodoacetamide (Intermediate-6) (570 mg, 1.57 mmol, 1.5 eq), and the resulting mixture was stirred at 80° C. for 3 h. The mixture was concentrated under reduced pressure and then purified by silica gel chromatography (Eluent of EtOAc/PE) to afford the title compound.

LCMS: 715.3 [M+H]+.

Step 2: Synthesis of tert-butyl (1S,6S)-5-(5-(2-((2-chloro-4-(trifluoromethyl)phenyl)amino)-2-oxoethyl)-6-ethyl-2,3-dimethyl-8-oxo-5,8-dihydropyrido[2,3-b]pyrazin-7-yl)-2,5-diazabicyclo[4.2.0]octane-2-carboxylate To a solution of tert-butyl (1S,6S)-5-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)-2,5-diazabicyclo[4.2.0]octane-2-carboxylate (Intermediate-109) (200 mg, 280 mol, 1.0 eq) and 2,4,6-trimethyl-1,3,5,2,4,6-trioxatriborinane (70 mg, 560 mol, 2.0 eq) in 1,4-dioxane (5 mL) was added K2CO3 (116 mg, 840 mol, 3.0 eq) and Pd(PPh3)4 (65 mg, 56 mol, 0.2 eq), the resulting mixture was degassed and purged with N2 for 3 times, and then stirred at 110° C. overnight under N2 atmosphere. The reaction mixture was diluted with H2O (10 mL) and extracted with DCM (10 mL*3). The combined organic layers were washed with brine (10 mL), dried over anhydrous Na2SO4, filtered and concentrated under reduced pressure. The residue was purified by silica gel chromatography (Eluent of EtOAc/PE) to afford the title compound.

LCMS: 649.5 [M+H]+.

Step 3: Synthesis of 2-(7-((1S,6S)-2,5-diazabicyclo[4.2.0]octan-2-yl)-6-ethyl-2,3-dimethyl-8-oxopyrido[2,3-b]pyrazin-5 (8H)-yl)-N-(2-chloro-4-(trifluoromethyl)phenyl)acetamide Hydrochloride To a solution of HCl in 1,4-dioxane (2 M, 2 mL) was added tert-butyl (1S,6S)-5-(5-(2-((2-chloro-4-(trifluoromethyl)phenyl)amino)-2-oxoethyl)-6-ethyl-2,3-dimethyl-8-oxo-5,8-dihydropyrido[2,3-b]pyrazin-7-yl)-2,5-diazabicyclo[4.2.0]octane-2-carboxylate (170 mg, 262 mol, 1.0 eq), and it was stirred at room temperature for 1 h. The reaction mixture was concentrated under reduced pressure to afford the title compound, which was used into the next step without further purification.

LCMS: 549.3 [M+H]+.

Intermediate-111: N-(2-fluoro-4-(trifluoromethyl)phenyl)-2-iodoacetamide

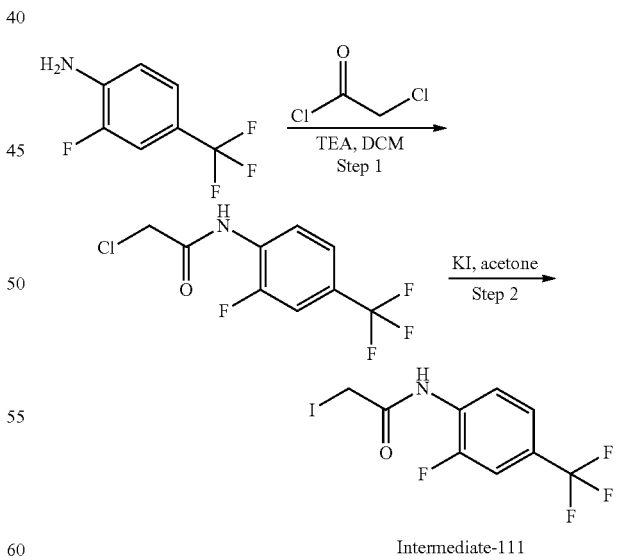

Intermediate-111

Step 1. Synthesis of 2-chloro-N-(2-fluoro-4-(trifluoromethyl)phenyl)acetamide

To a solution of 2-fluoro-4-(trifluoromethyl)aniline (1.00 g, 5.58 mmol, 1.0 eq) in DCM (10 mL) was added TEA (2.26 g, 22.33 mmol, 4.0 eq) and 2-chloroacetyl chloride (1.58 g, 13.96 mmol, 2.5 eq) in DCM (7.5 mL) at 0° C. After addition, the resulting mixture was stirred at room temperature overnight. The reaction mixture was diluted with H₂O (20 mL) and extracted with DCM (20 mL*2). The combined organic layers were washed with brine (10 mL), dried over anhydrous Na₂SO₄, filtered and concentrated under reduced pressure. The residue was purified by silica gel chromatography (EtOAc/PE) to afford the title compound.

LCMS: 255.9 [M+H]⁺.

Step 2. Synthesis of N-(2-fluoro-4-(trifluoromethyl) phenyl)-2-iodoacetamide

To a solution of 2-chloro-N-(2-fluoro-4-(trifluoromethyl) phenyl)acetamide (1.00 g, 3.91 mmol, 1.0 eq) in acetone (10 mL) was added KI (714 mg, 4.30 mmol, 1.1 eq), and the resulting mixture was stirred at 60° C. for 2 hrs. The reaction mixture was filtered and the filtrate was concentrated under reduced pressure to afford the title compound, which was used into the next step without further purification.

LCMS: 347.9 [M+H]⁺.

Intermediate-113: tert-butyl (1S,6S)-5-(2-bromo-6-ethyl-5-(2-((2-fluoro-4-(trifluoromethyl)phenyl) amino)-2-oxoethyl)-8-oxo-5,8-dihydropyrido[2,3-b]pyrazin-7-yl)-2,5-diazabicyclo[4.2.0]octane-2-carboxylate Intermediate-114: 2-(7-((1S,6S)-2,5-diazabicyclo[4.2.0]octan-2-yl)-2-(dimethylamino)-6-ethyl-8-oxopyrido[2,3-b]pyrazin-5 (8H)-yl)-N-(2-fluoro-4-(trifluoromethyl)phenyl)acetamide Trifluoroacetate

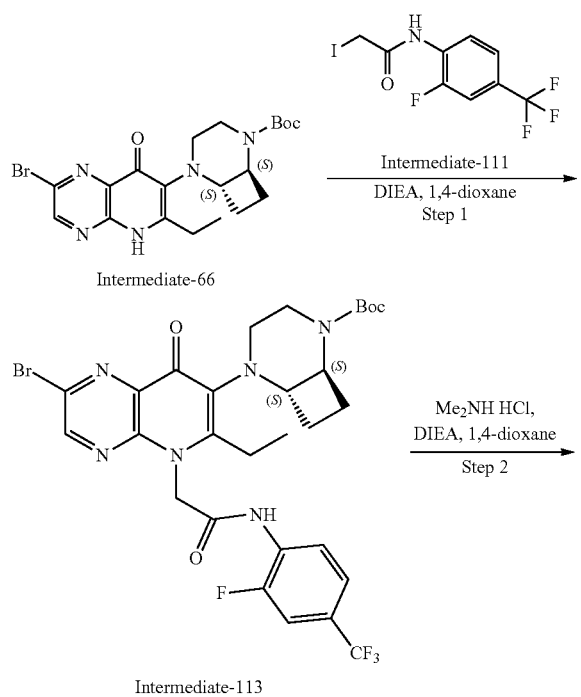

Intermediate-113

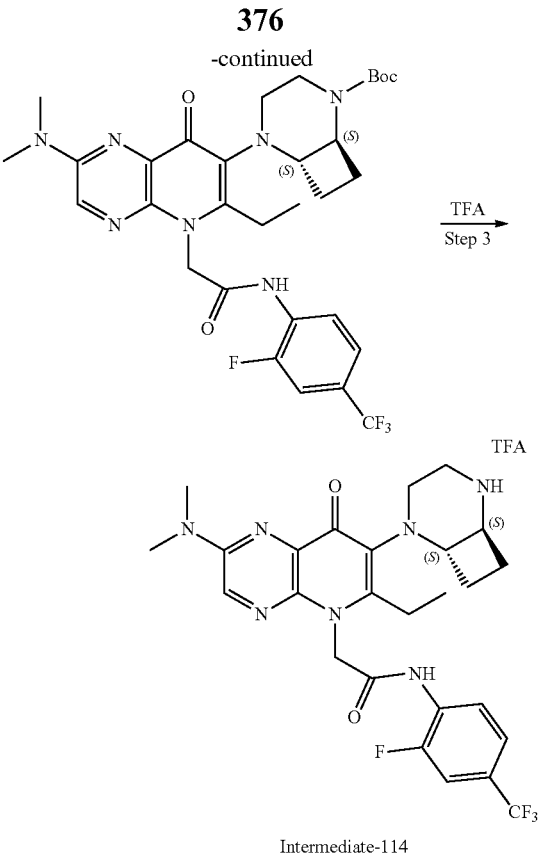

Intermediate-114

Step 1. Synthesis of tert-butyl (1S,6S)-5-(2-bromo-6-ethyl-5-(2-((2-fluoro-4-(trifluoromethyl)phenyl) amino)-2-oxoethyl)-8-oxo-5,8-dihydropyrido[2,3-b]pyrazin-7-yl)-2,5-diazabicyclo[4.2.0]octane-2-carboxylate To a solution of tert-butyl (1S,6S)-5-(2-bromo-6-ethyl-8-oxo-5,8-dihydropyrido[2,3-b]pyrazin-7-yl)-2,5-diazabicyclo[4.2.0]octane-2-carboxylate (Intermediate-66) (100 mg, 215 mol, 1.0 eq) in 1,4-dioxane (1 mL) was added DIEA (84 mg, 646 mol, 3.0 eq) and N-(2-fluoro-4-(trifluoromethyl) phenyl)-2-iodoacetamide (Intermediate-111) (90 mg, 258 mol, 1.2 eq), and the resulting mixture was stirred at 80° C. for 2 h. The reaction mixture was concentrated under reduced pressure to give a residue. The residue was purified by silica gel chromatography (EtOAc/PE) to afford the title compound.

LCMS: 683.1 [M+H]⁺.

Step 2. Synthesis of tert-butyl (1S,6S)-5-(2-(dimethylamino)-6-ethyl-5-(2-((2-fluoro-4-(trifluoromethyl)phenyl)amino)-2-oxoethyl)-8-oxo-5,8-dihydropyrido[2,3-b]pyrazin-7-yl)-2,5-diazabicyclo[4.2.0]octane-2-carboxylate To a solution of tert-butyl (1S,6S)-5-(2-bromo-6-ethyl-5-(2-((2-fluoro-4-(trifluoromethyl)phenyl)amino)-2-oxoethyl)-8-oxo-5,8-dihydropyrido[2,3-b]pyrazin-7-yl)-2,5-diazabicyclo[4.2.0]octane-2-carboxylate (Intermediate-113) (75 mg, 110 mol, 1.0 eq) in 1,4-dioxane (1 mL) was added dimethylamine hydrochloride (27 mg, 329 mol, 3.0 eq) and DIEA (71 mg, 549 mol, 5.0 eq), the resulting mixture was stirred at 100° C. for 2 h. The reaction mixture was diluted with H₂O (5 mL) and extracted with EtOAc (5 mL*3). The combined organic layers were washed with brine (5 mL), dried over anhydrous Na₂SO₄, filtered and concentrated under reduced pressure to afford the title compound, which was used into next step without further purification.

LCMS: 648.3 [M+H]⁺.

Step 3. Synthesis of 2-(7-((1S,6S)-2,5-diazabicyclo [4.2.0]octan-2-yl)-2-(dimethylamino)-6-ethyl-8-oxopyrido[2,3-b]pyrazin-5 (8H)-yl)-N-(2-fluoro-4-(trifluoromethyl)phenyl)acetamide Trifluoroacetate To a solution of tert-butyl (1S,6S)-5-(2-(dimethylamino)-6-ethyl-5-(2-((2-fluoro-4-(trifluoromethyl)phenyl)amino)-2-oxoethyl)-8-oxo-5,8-dihydropyrido[2,3-b]pyrazin-7-yl)-2,5-diazabicyclo[4.2.0]octane-2-carboxylate (75 mg, 116 mol, 1.0 eq) in DCM (1.5 mL) was added TFA (0.7 mL), and the resulting mixture was stirred at room temperature for 1 h. The reaction mixture was concentrated under reduced pressure to afford the title compound, which was used into the next step without further purification.

LCMS: 548.3 [M+H]⁺.

Intermediate-115: 2-(7-((1S,6S)-2,5-diazabicyclo [4.2.0]octan-2-yl)-2-cyclopropyl-6-ethyl-8-oxopyrido[2,3-b]pyrazin-5 (8H)-yl)-N-(2-fluoro-4-(trifluoromethyl)phenyl)acetamide Trifluoroacetate

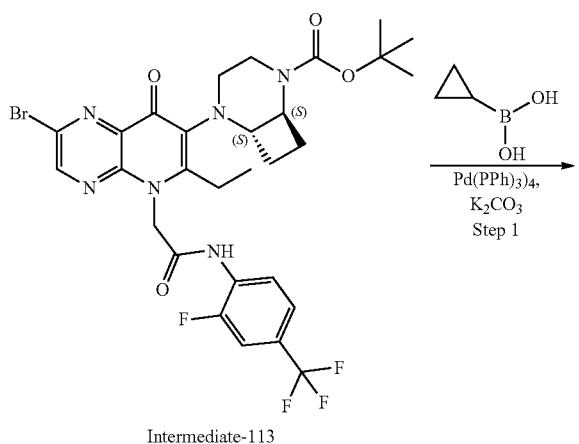

Intermediate-113

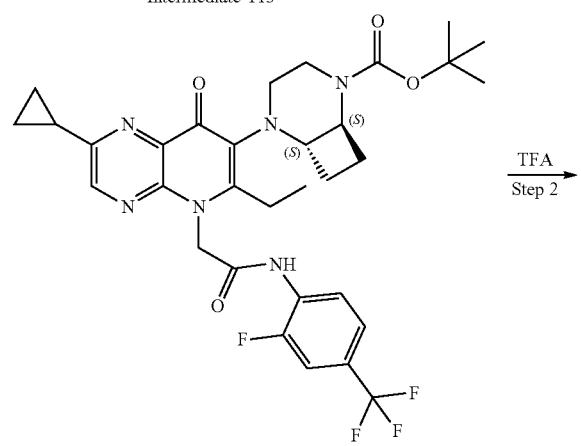

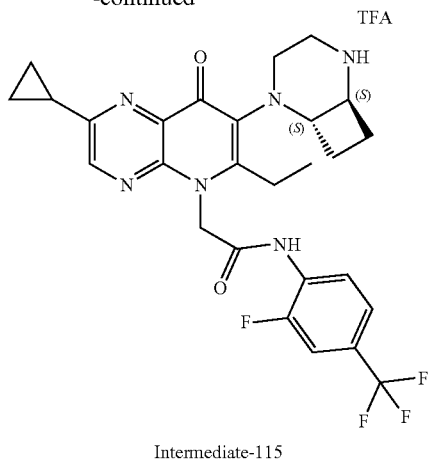

Intermediate-115

Step 1: Synthesis of tert-butyl (1S,6S)-5-(2-cyclopropyl-6-ethyl-5-(2-((2-fluoro-4-(trifluoromethyl) phenyl)amino)-2-oxoethyl)-8-oxo-5,8-dihydropyrido [2,3-b]pyrazin-7-yl)-2,5-diazabicyclo[4.2.0]octane-2-carboxylate To a solution of tert-butyl (1S,6S)-5-(2-bromo-6-ethyl-5-(2-((2-fluoro-4-(trifluoromethyl)phenyl)amino)-2-oxo-ethyl)-8-oxo-5,8-dihydropyrido[2,3-b]pyrazin-7-yl)-2,5-diazabicyclo[4.2.0]octane-2-carboxylate (Intermediate-113) (300 mg, 439 mol, 1.0 eq) and cyclopropylboronic acid (75 mg, 878 mol, 2.0 eq) in 1,4-dioxane (5 mL) was added Pd(PPh₃)₄ (76 mg, 66 mol, 0.15 eq) and K₂CO₃ (182 mg, 1.32 mmol, 3.0 eq), the resulting mixture was degassed and then stirred at 110° C. for 4 h under N₂ atmosphere. The reaction mixture was poured into H₂O (50 mL) and extracted with EtOAc (50 mL*2). The combined organic layers were washed with brine (50 mL*2), dried over anhydrous Na₂SO₄, filtered, and concentrated under reduced pressure. The residue was purified by silica gel chromatography (Eluent of EtOAc/PE) to afford the title compound.

LCMS: 645.3 [M+H]⁺.

Step 2: Synthesis of 2-(7-((1S,6S)-2,5-diazabicyclo [4.2.0]octan-2-yl)-2-cyclopropyl-6-ethyl-8-oxopyrido[2,3-b]pyrazin-5 (8H)-yl)-N-(2-fluoro-4-(trifluoromethyl)phenyl)acetamide Trifluoroacetate To a solution of tert-butyl (1S,6S)-5-(2-cyclopropyl-6-ethyl-5-(2-((2-fluoro-4-(trifluoromethyl)phenyl)amino)-2-oxoethyl)-8-oxo-5,8-dihydropyrido[2,3-b]pyrazin-7-yl)-2, 5-diazabicyclo[4.2.0]octane-2-carboxylate (180 mg, 279 mol, 1.0 eq) in DCM (2 mL) was added TFA (2 mL), and it was stirred at room temperature for 0.5 h. The reaction mixture was concentrated under reduced pressure to afford the title compound, which was used into the next step without further purification.

LCMS: 545.3 [M+H]⁺.

Alternative procedure for Intermediate-109: tert-butyl (1S,6S)-5-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)-2,5-diazabicyclo[4.2.0]octane-2-carboxylate Intermediate-116: 2-(2-bromo-7-((1S,6S)-5-(tert-butoxycarbonyl)-2,5-diazabicyclo[4.2.0]octan-2-yl)-6-ethyl-3-methyl-8-oxopyrido[2,3-b]pyrazin-5 (8H)-yl)acetic Acid

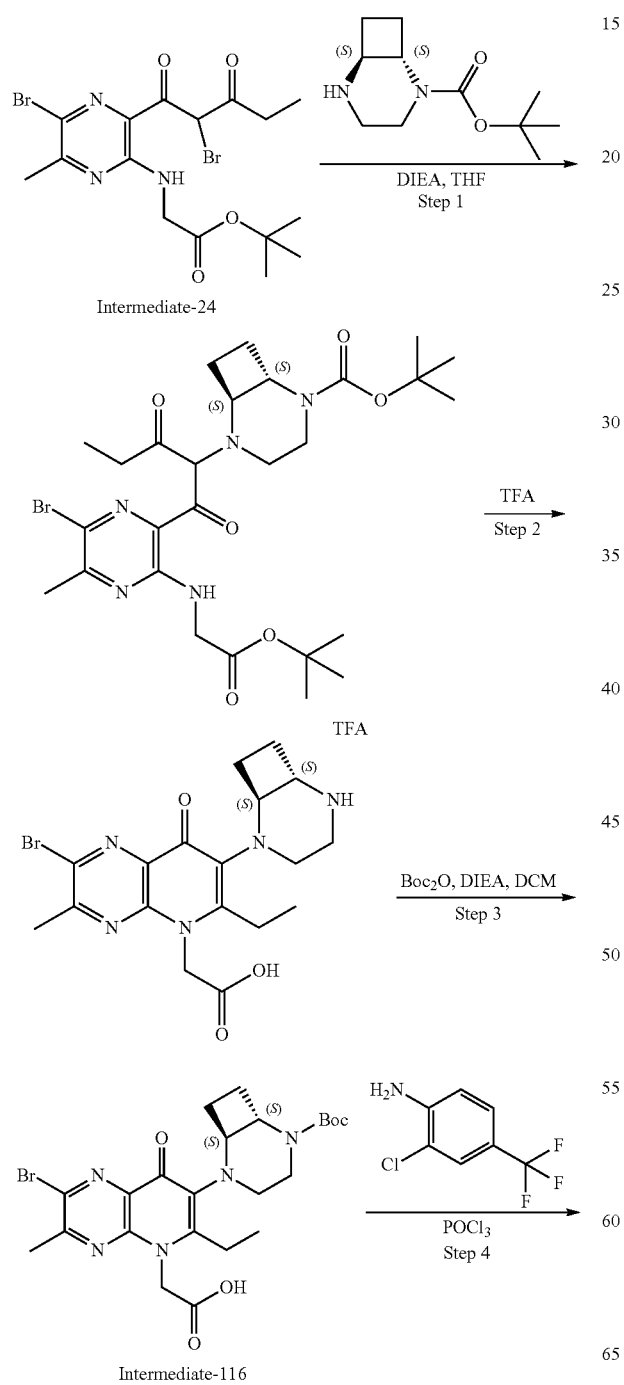

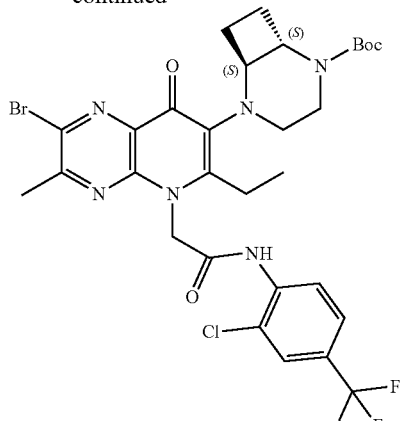

Intermediate-109

Step 1: Synthesis of tert-butyl (1S,6S)-5-(1-(6-bromo-3-((2-(tert-butoxy)-2-oxoethyl)amino)-5-methylpyrazin-2-yl)-1,3-dioxopentan-2-yl)-2,5-diazabicyclo[4.2.0]octane-2-carboxylate To a solution of tert-butyl (5-bromo-3-(2-bromo-3-oxopentanoyl)-6-methylpyrazin-2-yl)glycinate (Intermediate-24) (1.99 g, 4.15 mmol, 1.0 eq) in THF (10 mL) was added DIEA (1.61 g, 12.46 mmol, 3.0 eq) and tert-butyl (1S,6S)-2,5-diazabicyclo[4.2.0]octane-2-carboxylate (882 mg, 4.15 mmol, 1.0 eq), and the resulting mixture was stirred at room temperature overnight. The reaction mixture was quenched by water (50 mL) and extracted with EtOAc (50 mL*3). The combined organic layers were washed with brine (30 mL), dried over anhydrous $Na_2SO_4$, filtered and concentrated in vacuo. The residue was purified by silica gel chromatography (EtOAc/PE) to afford the title compound.
LCMS: 612.3 [M+H]$^+$.

Step 2: Synthesis of 2-(7-((1S,6S)-2,5-diazabicyclo[4.2.0]octan-2-yl)-2-bromo-6-ethyl-3-methyl-8-oxopyrido[2,3-b]pyrazin-5 (8H)-yl)acetic Acid Trifluoroacetate A solution of tert-butyl (1S,6S)-5-(1-(6-bromo-3-((2-(tert-butoxy)-2-oxoethyl)amino)-5-methylpyrazin-2-yl)-1,3-dioxopentan-2-yl)-2,5-diazabicyclo[4.2.0]octane-2-carboxylate (500 mg, 819 mol, 1.0 eq) in TFA (10 mL) was stirred at 60° C. for 8 h. The reaction mixture concentrated in vacuo to afford the title compound, which was used into the next step without further purification.
LCMS: 436.1 [M+H]$^+$.

Step 3: Synthesis of 2-(2-bromo-7-((1S,6S)-5-(tert-butoxycarbonyl)-2,5-diazabicyclo[4.2.0]octan-2-yl)-6-ethyl-3-methyl-8-oxopyrido[2,3-b]pyrazin-5 (8H)-yl)acetic Acid To a solution of 2-(7-((1S,6S)-2,5-diazabicyclo[4.2.0]octan-2-yl)-2-bromo-6-ethyl-3-methyl-8-oxopyrido[2,3-b]pyrazin-5 (8H)-yl)acetic acid trifluoroacetate (400 mg, 917 mol, 1.0 eq) in DCM (10 mL) was added DIEA (355 mg, 2.75 mmol, 3.0 eq) and Boc$_2$O (300 mg, 1.38 mmol, 1.5 eq), and the resulting mixture was stirred at room temperature for 2 h. The reaction mixture was poured into water (30 mL), and extracted with EtOAc (2*30 mL). The combined organic layers were washed with brine (30 mL), dried over anhydrous Na₂SO₄, filtered and concentrated in vacuo. The residue was purified by reverse phase HPLC (C18 column, water (0.1% FA)-ACN) to afford the title compound.

LCMS: 538.3 [M+H]⁺.

Step 4: Synthesis of tert-butyl (1S,6S)-5-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)-2,5-diazabicyclo[4.2.0]octane-2-carboxylate To a solution of 2-[2-bromo-7-[(1S,6S)-5-tert-butoxycarbonyl-2,5-diazabicyclo[4.2.0]octan-2-yl]-6-ethyl-3-methyl-8-oxo-pyrido[2,3-b]pyrazin-5-yl]acetic acid (Intermediate-116) (240 mg, 447 mol, 1.0 eq) and 2-chloro-4-(trifluoromethyl)aniline (105 mg, 537 μmol, 1.2 eq) in DCM (3 mL) and pyridine (3 mL) was added POCl₃ (103 mg, 671 mol, 1.5 eq) at −10° C., and the resulting mixture was stirred at −10° C. for 10 min. The reaction mixture was quenched by H₂O (20 mL) and extracted with EtOAc (25 mL*3). The combined organic layers were washed with brine (10 mL), dried over anhydrous Na₂SO₄, filtered and concentrated in vacuo. The residue was purified by flash silica gel chromatography (Eluent of EtOAc/PE) to afford the title compound.

LCMS: 715.2 [M+H]⁺.

Intermediate-117: 2-(7-((1S,6S)-2,5-diazabicyclo[4.2.0]octan-2-yl)-2-(dimethylamino)-6-ethyl-3-methyl-8-oxopyrido[2,3-b]pyrazin-5 (8H)-yl)-N-(2-chloro-4-(trifluoromethyl)phenyl)acetamide Trifluoroacetate

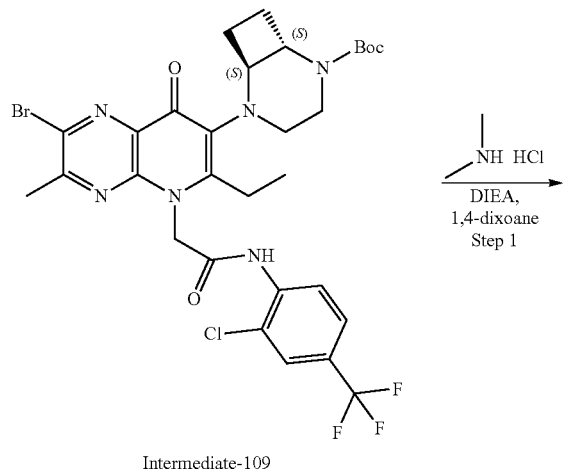

Intermediate-109

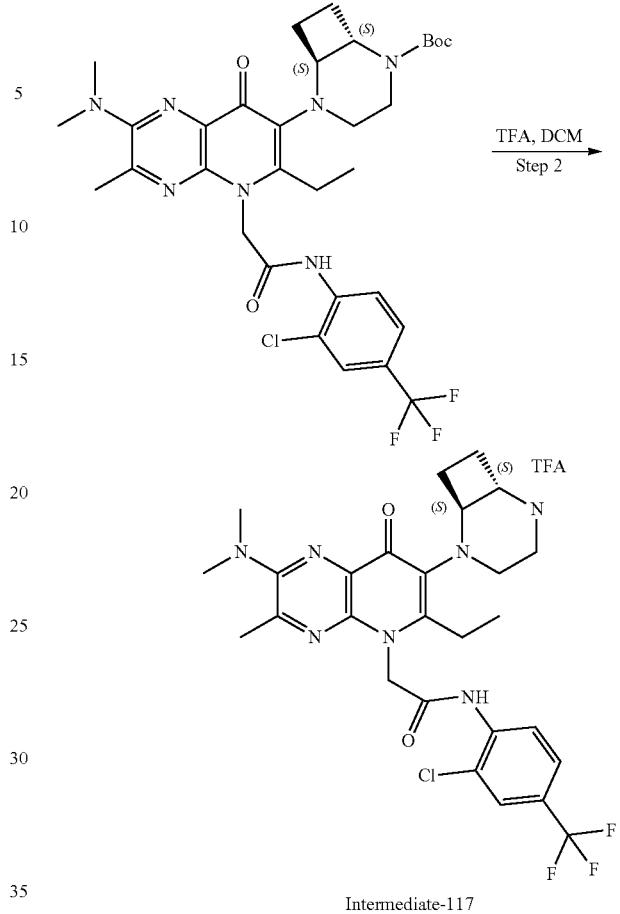

Intermediate-117

Step 1: Synthesis of tert-butyl (1S,6S)-5-(5-(2-((2-chloro-4-(trifluoromethyl)phenyl)amino)-2-oxoethyl)-2-(dimethylamino)-6-ethyl-3-methyl-8-oxo-5,8-dihydropyrido[2,3-b]pyrazin-7-yl)-2,5-diazabicyclo[4.2.0]octane-2-carboxylate To a solution of tert-butyl (1S,6S)-5-(2-bromo-5-(2-((2-chloro-4-(trifluoromethyl)phenyl)amino)-2-oxoethyl)-6-ethyl-3-methyl-8-oxo-5,8-dihydropyrido[2,3-b]pyrazin-7-yl)-2,5-diazabicyclo[4.2.0]octane-2-carboxylate (Intermediate-109) (180 mg, 252 mol, 1.0 eq) in 1,4-dioxane (2 mL) was added dimethylamine hydrochloride (103 mg, 1.26 mmol, 5.0 eq) and DIEA (163 mg, 1.26 mmol, 5.0 eq), the resulting mixture was stirred at 100° C. overnight. The reaction mixture was poured into water (20 mL), extracted with EtOAc (30 mL*3). The combined organic layers were washed with brine (20 mL), dried with anhydrous Na₂SO₄, filtered and concentrated in vacuo to afford the title compound, which was used into the next step without further purification.

LCMS: 678.5 [M+H]⁺.

Step 2: Synthesis of 2-(7-((1S,6S)-2,5-diazabicyclo[4.2.0]octan-2-yl)-2-(dimethylamino)-6-ethyl-3-methyl-8-oxopyrido[2,3-b]pyrazin-5 (8H)-yl)-N-(2-chloro-4-(trifluoromethyl)phenyl)acetamide Trifluoroacetate To a solution of tert-butyl (1S,6S)-5-(5-(2-((2-chloro-4-(trifluoromethyl)phenyl)amino)-2-oxoethyl)-2-(dimethylamino)-6-ethyl-3-methyl-8-oxo-5,8-dihydropyrido[2,3-b]pyrazin-7-yl)-2,5-diazabicyclo[4.2.0]octane-2-carboxylate (120 mg, 177 mol, 1.0 eq) in DCM (2 mL) was added TFA (2 mL), and the resulting mixture was stirred at room temperature for 1 h. The reaction mixture was concentrated in vacuo to afford the title compound, which was used into the next step without further purification.

LCMS: 578.3 [M+H]$^+$.

Intermediate-118: 3-(trifluoromethoxy)bicyclo[1.1.1]pentan-1-amine Trifluoroacetate

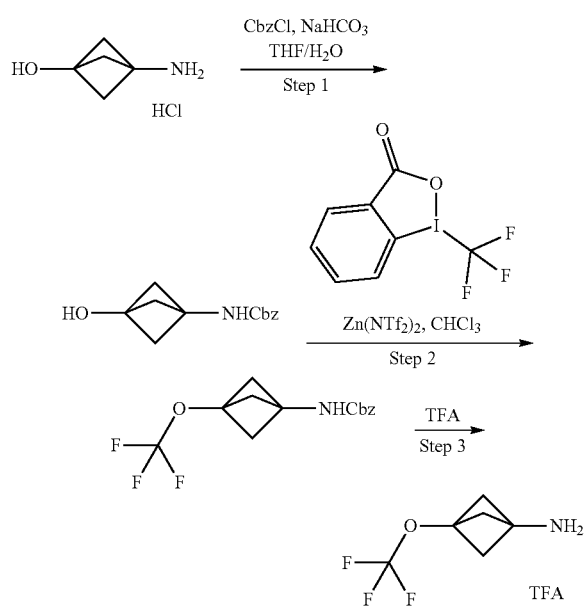

Step 1. Synthesis of benzyl (3-hydroxybicyclo[1.1.1]pentan-1-yl)carbamate

To a suspension of 3-aminobicyclo[1.1.1]pentan-1-ol hydrochloride (530 mg, 3.91 mmol, 1 eq) in THF (5.4 mL) and H$_2$O (2.7 mL) was added NaHCO$_3$ (985 mg, 11.73 mmol, 3 eq) at 20° C. The mixture was cooled to 0° C., then CbzCl (733 mg, 4.30 mmol, 613 μL, 1.1 eq) was added dropwise at 0° C. under N$_2$ atmosphere. The resulting mixture was stirred at 0° C. for 15 min, then warmed to 20° C. and stirred at 20° C. for 16 h under N$_2$ atmosphere. The mixture was diluted with brine (10 mL) and then extracted with EtOAc (3×10 ml). The combined organic layers were dried over anhydrous Na$_2$SO$_4$, filtered and concentrated under reduced pressure to give a residue. The residue was purified by flash silica gel chromatography (Eluent of EtOAc/PE) to afford the title compound.

LCMS: 234.0 [M+H]$^+$.

Step 2. Synthesis of benzyl (3-(trifluoromethoxy)bicyclo[1.1.1]pentan-1-yl)carbamate To a solution of benzyl N-(3-hydroxy-1-bicyclo[1.1.1]pentanyl)carbamate (610 mg, 2.62 mmol, 1 eq) and Zn(NTf$_2$)$_2$ (1.96 g, 3.14 mmol, 1.2 eq) in CHCl$_3$ (5 mL) was added 1-(trifluoromethyl)-1,2-benziodoxol-3-one (992 mg, 3.14 mmol, 1.2 eq). The mixture was stirred at 25° C. for 16 h. The mixture was filtered and the filter cake was washed with DCM (2×5 mL). The combined filtrate was concentrated under reduced pressure to give a residue. The residue was purified by flash silica gel chromatography (Eluent of EtOAc/PE) to afford the title compound.

LCMS: 324.0 [M+Na]$^+$.

Step 3. Synthesis of 3-(trifluoromethoxy)bicyclo[1.1.1]pentan-1-amine Trifluoroacetate A solution of benzyl N-[3-(trifluoromethoxy)-1-bicyclo[1.1.1]pentanyl]carbamate (100 mg, 330 μmol, 1 eq) in TFA (3 mL) was stirred at 70° C. for 5 h. The mixture was concentrated under reduced pressure to afford the title compound, which was used directly in the next step without further purification.

LCMS: 168.0 [M+H]$^+$.

Alternative procedure for Intermediate-55: sodium 5-hydroxy-6-methylpyrimidine-4-carboxylate

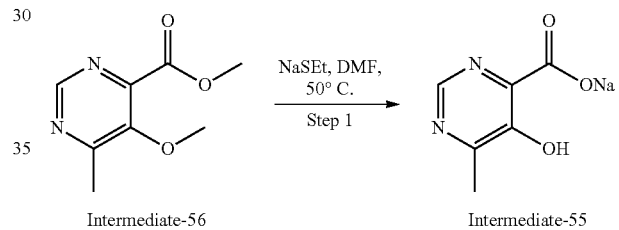

Step 1. Synthesis of sodium 5-hydroxy-6-methylpyrimidine-4-carboxylate

To a solution of methyl 5-methoxy-6-methylpyrimidine-4-carboxylate (Intermediate-56) (10.0 g, 41.1 mmol, 1.00 eq) (can be obtained as described in step 1 and step 2 of Intermediate-6 synthesis) in DMF (100 mL) was added NaSEt (17.3 g, 205 mmol, 5.00 eq) under N$_2$ atmosphere. The reaction mixture was stirred at 50° C. for 3 hours, then cooled to 20° C., diluted with water (30 mL) and stirred for 1 hour. Then MTBE (200 mL) was added and the resulting mixture was stirred for 30 min. The aqueous layer was separated and adjusted to pH=7.0-8.0 with 12 M HCl (aq.) at 0° C. The resulting mixture was stirred for 1 hour at 0° C. and filtered to give the crude product. The crude product was triturated with EtOH (70 mL) at 20° C. for 4 hours, filtered and dried under reduced pressure to afford the title compound.

LCMS: 155.1 [M-Na+2H]$^+$.

The compounds of the disclosure are shown below in Table 2 along with the LCMS method (see below table for method conditions), mass observed, and retention time of compound.

TABLE 2

| No. | | Method | (Mass Observed) [g/mol] | (Retention time) [min] |
|---|---|---|---|---|
| I-1 | | LCMS 1 | 645.4 | 0.578 |
| I-2 | | LCMS 1 | 617.2 | 0.548 |
| I-3 | | LCMS 1 | 630.2 | 0.537 |

TABLE 2-continued
| No. | | Method | (Mass Observed) [g/mol] | (Retention time) [min] |
|---|---|---|---|---|
| I-4 | 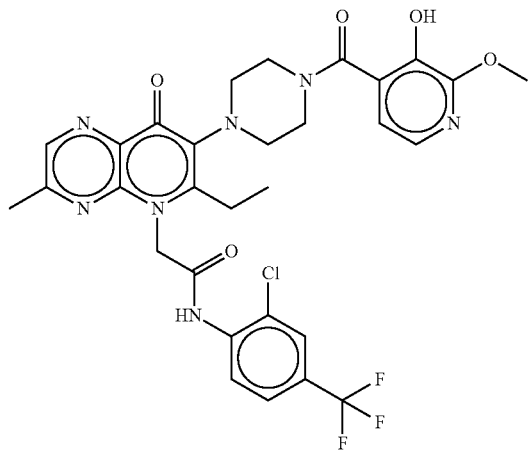 | LCMS 1 | 660.4 | 0.585 |
| I-5 | 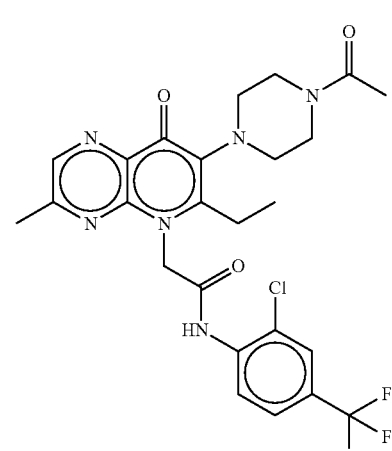 | LCMS 1 | 551.2 | 0.553 |
| I-6 | 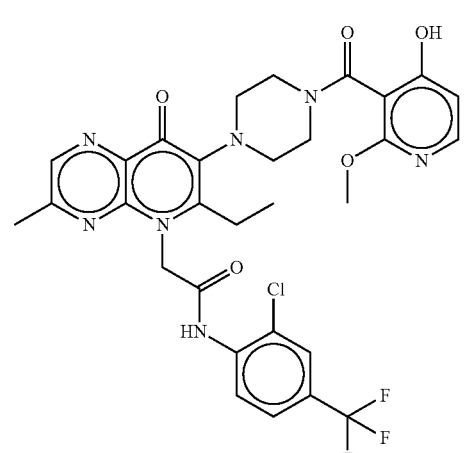 | LCMS 1 | 660.2 | 0.533 |

TABLE 2-continued

| No. | | Method | (Mass Observed) [g/mol] | (Retention time) [min] |
|---|---|---|---|---|
| I-7 | | LCMS 1 | 738.2 | 0.576 |
| I-8 | | LCMS 1 | 671.4 | 0.611 |
| I-9 | | LCMS 1 | 671.2 | 0.576 |

TABLE 2-continued
| No. | | Method | (Mass Observed) [g/mol] | (Retention time) [min] |
|---|---|---|---|---|
| I-10 | 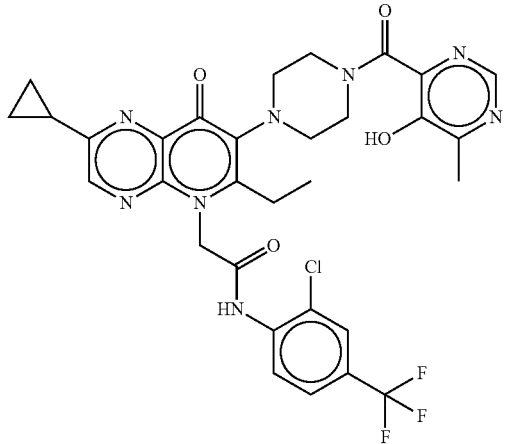 | LCMS 1 | 671.4 | 0.594 |
| I-11 | 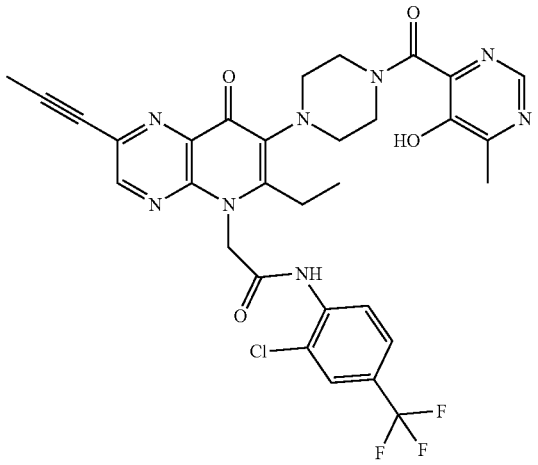 [SMILES: CC#Cc1cnc2c(n1)c(=O)c(N1CCN(C(=O)c3ncnc(C)c3O)CC1)c(CC)n2CC(=O)Nc1ccc(C(F)(F)F)cc1Cl] | LCMS 1 | 669.4 | 0.598 |
| I-12 | 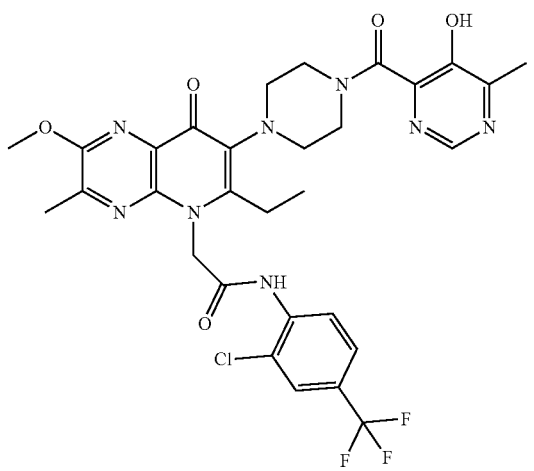 | LCMS 1 | 675.0 | 0.889 |

TABLE 2-continued
| No. | | Method | (Mass Observed) [g/mol] | (Retention time) [min] |
|---|---|---|---|---|
| I-13 | 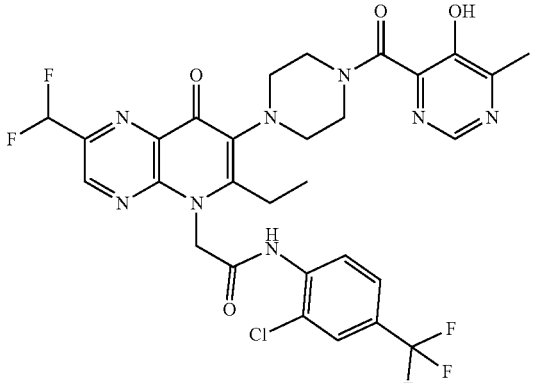 | LCMS 1 | 681.2 | 0.566 |
| I-14 | 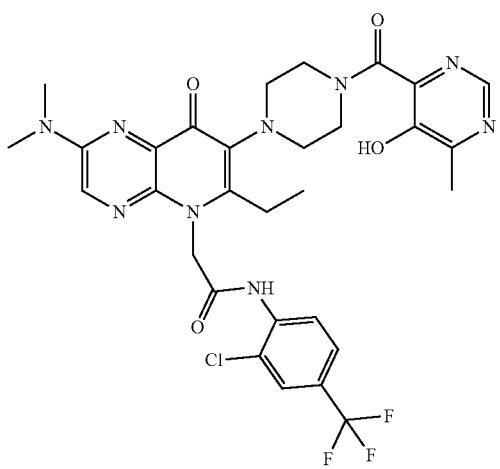 [SMILES: CCc1c(N2CCN(C(=O)c3ncnc(C)c3O)CC2)c(=O)c2nc(N(C)C)cnc2n1CC(=O)Nc1ccc(C(F)(F)F)cc1Cl] | LCMS 1 | 674.4 | 0.568 |
| I-15 | 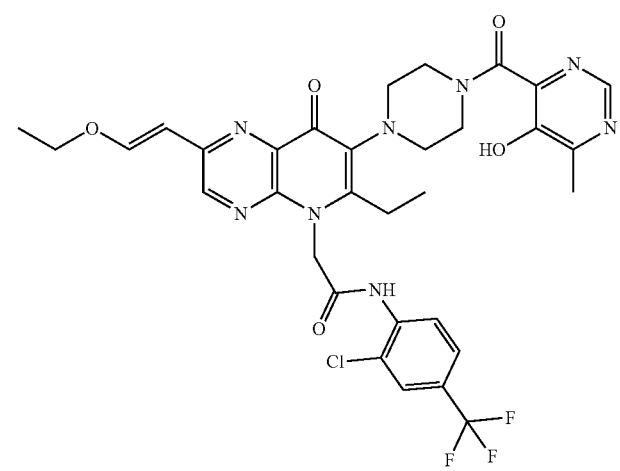 [SMILES: CCO/C=C/c1cnc2c(n1)c(=O)c(N1CCN(C(=O)c3ncnc(C)c3O)CC1)c(CC)n2CC(=O)Nc1ccc(C(F)(F)F)cc1Cl] | LCMS 1 | 701.4 | 0.611 |

TABLE 2-continued
| No. | | Method | (Mass Observed) [g/mol] | (Retention time) [min] |
|---|---|---|---|---|
| I-16 | 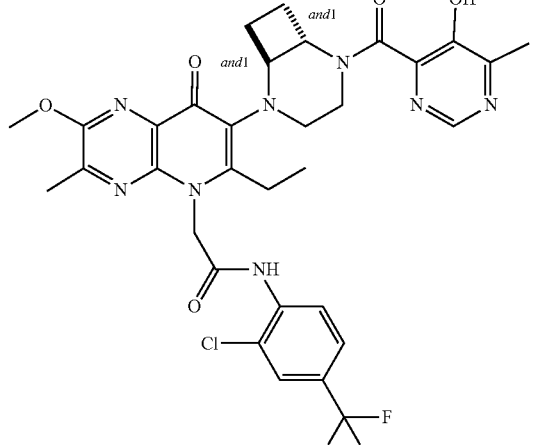 | LCMS 1 | 701.2 | 0.600 |
| I-17 | 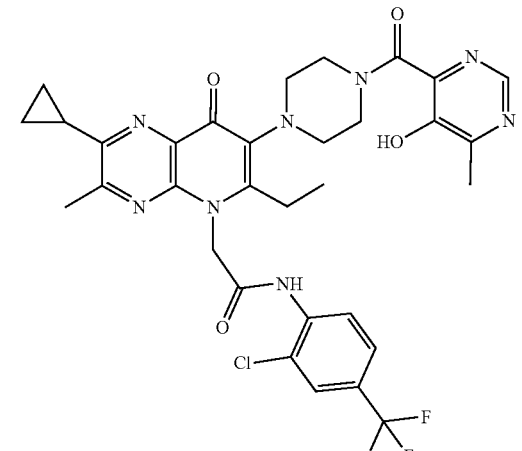 | LCMS 1 | 685.2 | 0.583 |
| I-18 | 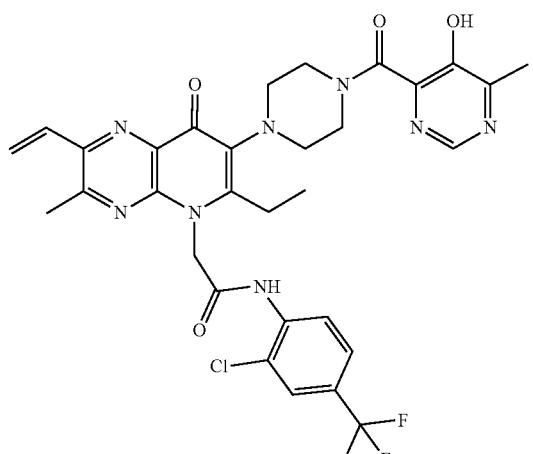 | LCMS 1 | 671.2 | 0.859 |

TABLE 2-continued

| No. | Method | (Mass Observed) [g/mol] | (Retention time) [min] |
|---|---|---|---|
| I-19 | LCMS 1 | 669.4 | 0.598 |
| I-20 | LCMS 1 | 660.4 | 0.549 |
| I-21 | LCMS 1 | 685.2 | 0.594 |

TABLE 2-continued
| No. | | Method | (Mass Observed) [g/mol] | (Retention time) [min] |
|---|---|---|---|---|
| I-22 | 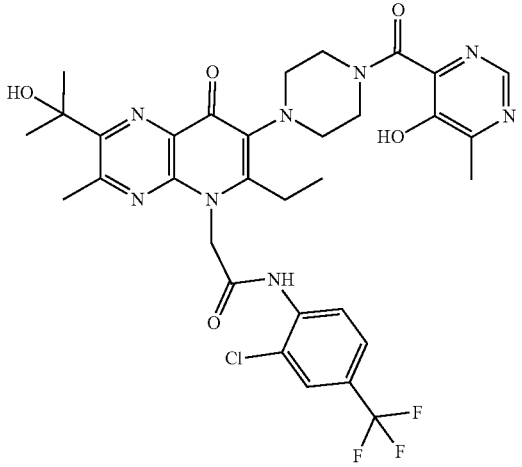 [SMILES: CCc1c(N2CCN(C(=O)c3ncnc(C)c3O)CC2)c(=O)c2nc(C(C)(C)O)c(C)nc2n1CC(=O)Nc1ccc(C(F)(F)F)cc1Cl] | LCMS 1 | 703.4 | 0.597 |
| I-23 | 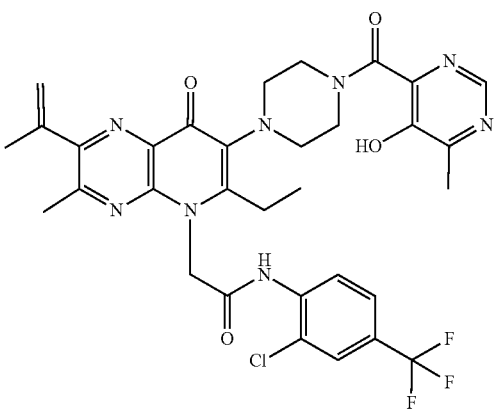 [SMILES: C=C(C)c1nc2c(=O)c(N3CCN(C(=O)c4ncnc(C)c4O)CC3)c(CC)n(CC(=O)Nc3ccc(C(F)(F)F)cc3Cl)c2nc1C] | LCMS 1 | 685.4 | 0.612 |
| I-24 | 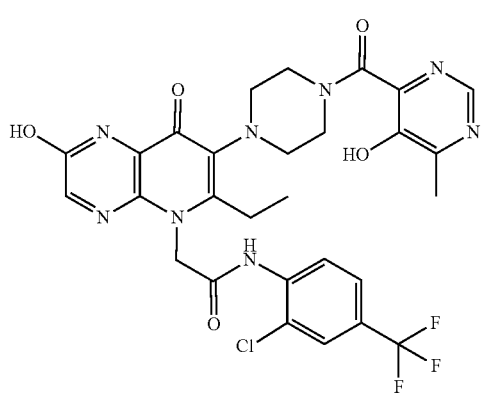 [SMILES: CCc1c(N2CCN(C(=O)c3ncnc(C)c3O)CC2)c(=O)c2nc(O)cnc2n1CC(=O)Nc1ccc(C(F)(F)F)cc1Cl] | LCMS 1 | 647.1 | 0.799 |

TABLE 2-continued
| No. | | Method | (Mass Observed) [g/mol] | (Retention time) [min] |
| --- | --- | --- | --- | --- |
| I-25 | 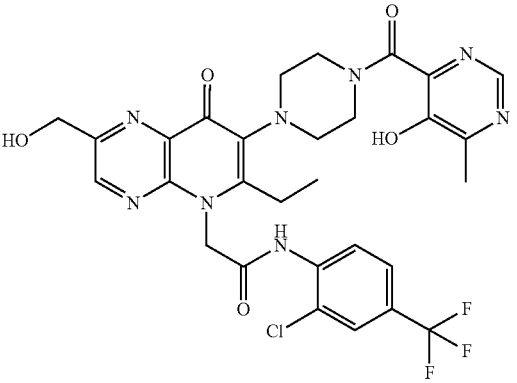 [SMILES: CCc1c(N2CCN(C(=O)c3ncnc(C)c3O)CC2)c(=O)c2nc(CO)cnc2n1CC(=O)Nc1ccc(C(F)(F)F)cc1Cl] | LCMS 1 | 661.1 | 0.809 |
| I-26 | 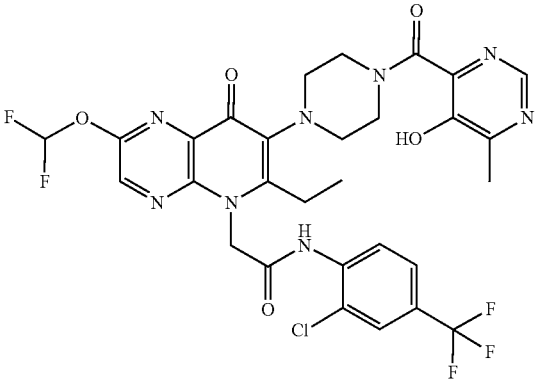 [SMILES: CCc1c(N2CCN(C(=O)c3ncnc(C)c3O)CC2)c(=O)c2nc(OC(F)F)cnc2n1CC(=O)Nc1ccc(C(F)(F)F)cc1Cl] | LCMS 1 | 697.1 | 0.866 |
| I-27 | 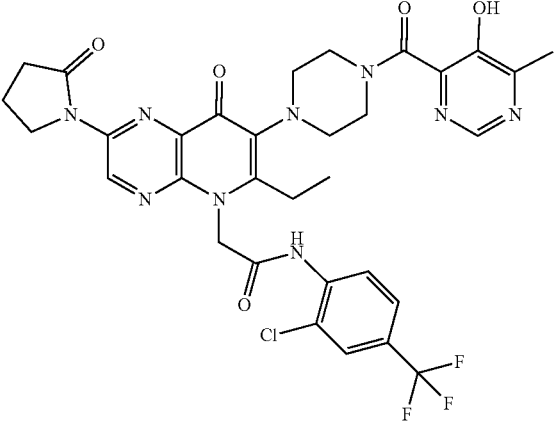 [SMILES: CCc1c(N2CCN(C(=O)c3ncnc(C)c3O)CC2)c(=O)c2nc(N3CCCC3=O)cnc2n1CC(=O)Nc1ccc(C(F)(F)F)cc1Cl] | LCMS 1 | 714.2 | 0.560 |

TABLE 2-continued

| No. | | Method | (Mass Observed) [g/mol] | (Retention time) [min] |
|---|---|---|---|---|
| I-28 | | LCMS 1 | 695.1 | 0.574 |
| I-29 | | LCMS 1 | 688.2 | 0.599 |
| I-30 | | LCMS 1 | 702.4 | 0.558 |

TABLE 2-continued
| No. | | Method | (Mass Observed) [g/mol] | (Retention time) [min] |
|---|---|---|---|---|
| I-31 | 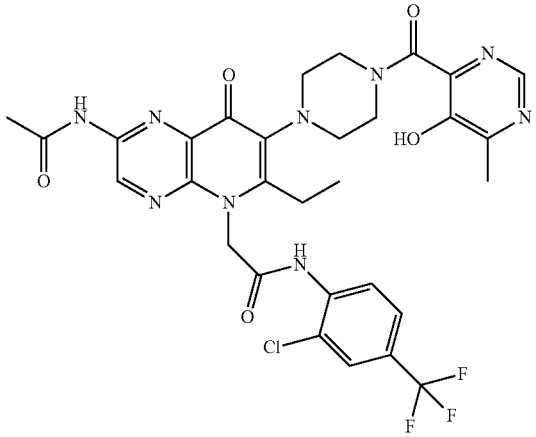 [SMILES: CCc1c(N2CCN(C(=O)c3ncnc(C)c3O)CC2)c(=O)c2nc(NC(C)=O)cnc2n1CC(=O)Nc1ccc(C(F)(F)F)cc1Cl] | LCMS 1 | 688.3 | 0.572 |
| I-32 | 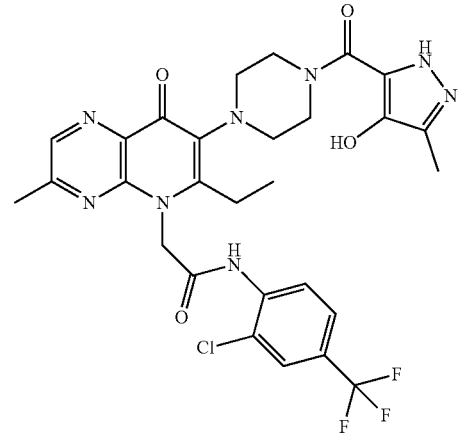 [SMILES: CCc1c(N2CCN(C(=O)c3[nH]nc(C)c3O)CC2)c(=O)c2ncc(C)nc2n1CC(=O)Nc1ccc(C(F)(F)F)cc1Cl] | LCMS 1 | 633.2 | 0.579 |
| I-33 | 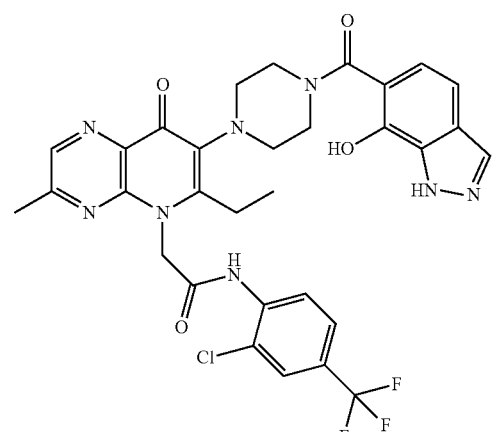 | LCMS 1 | 669.2 | 0.561 |

TABLE 2-continued
| No. | | Method | (Mass Observed) [g/mol] | (Retention time) [min] |
|---|---|---|---|---|
| I-34 | 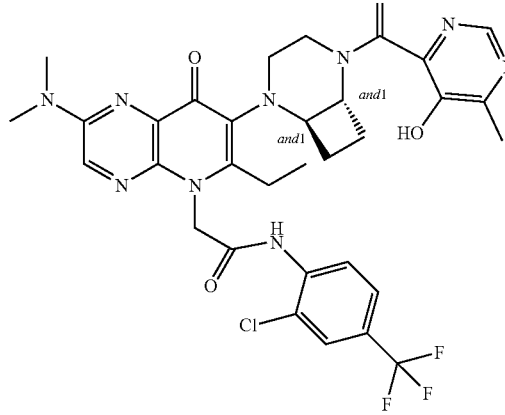 | LCMS 1 | 700.4 | 0.559 |
| I-35 | 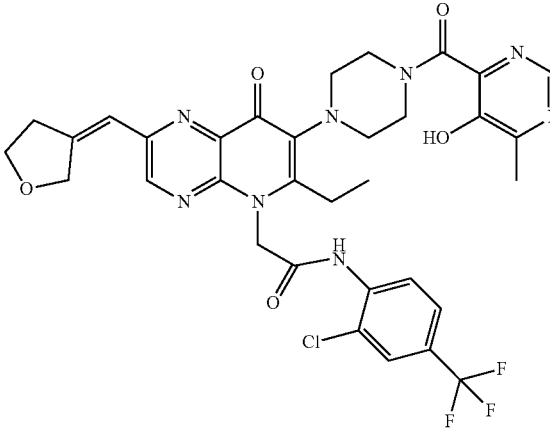<br>(A)<br>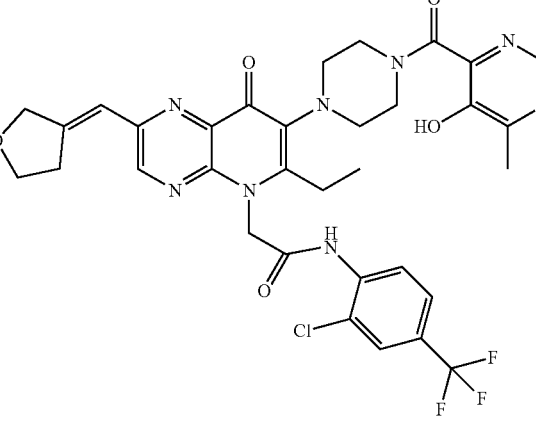<br>(B) | LCMS 1 | 713.2 | 0.568 |

TABLE 2-continued
| No. | | Method | (Mass Observed) [g/mol] | (Retention time) [min] |
|---|---|---|---|---|
| I-36 | 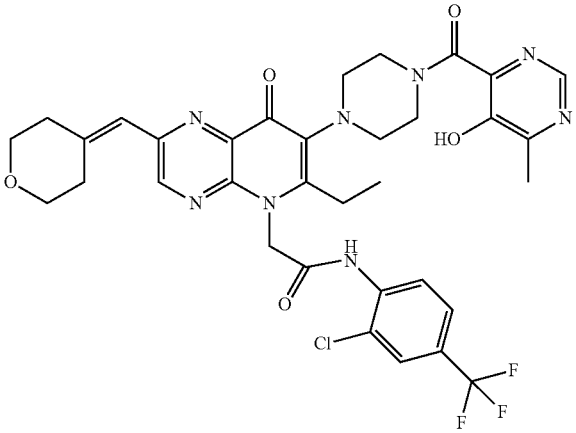 [SMILES: CCc1c(N2CCN(C(=O)c3ncnc(C)c3O)CC2)c(=O)c2nc(C=C3CCOCC3)cnc2n1CC(=O)Nc1ccc(C(F)(F)F)cc1Cl] | LCMS 1 | 727.3 | 0.956 |
| I-37 | 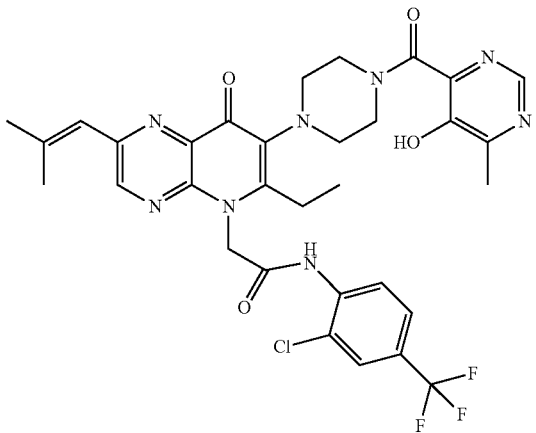 [SMILES: CCc1c(N2CCN(C(=O)c3ncnc(C)c3O)CC2)c(=O)c2nc(C=C(C)C)cnc2n1CC(=O)Nc1ccc(C(F)(F)F)cc1Cl] | LCMS 1 | 685.2 | 0.597 |
| I-38 | 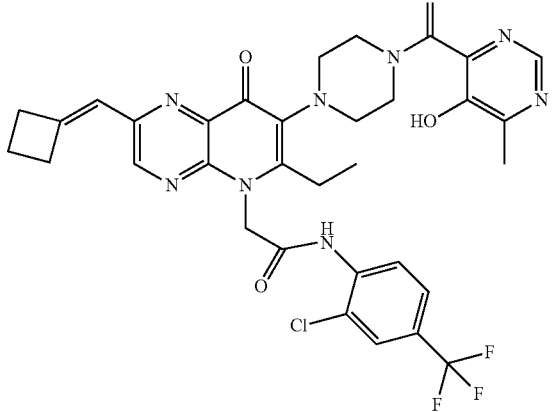 | LCMS 1 | 697.2 | 0.607 |

TABLE 2-continued
| No. | | Method | (Mass Observed) [g/mol] | (Retention time) [min] |
|---|---|---|---|---|
| I-39 | 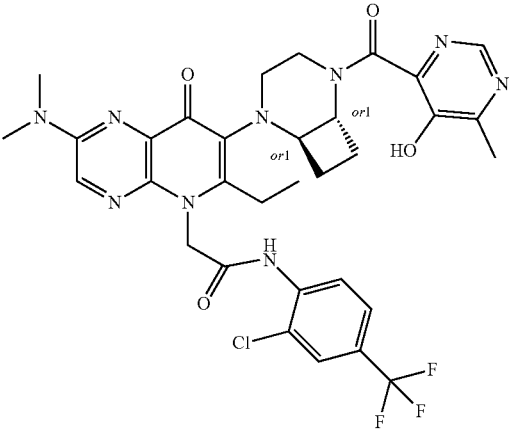 [SMILES: CCc1c(N2CCN(C(=O)c3ncnc(C)c3O)[C@@H]3CC[C@H]32)c(=O)c2nc(N(C)C)cnc2n1CC(=O)Nc1ccc(C(F)(F)F)cc1Cl] | LCMS 1 | 700.4 | 0.593 |
| I-40 | 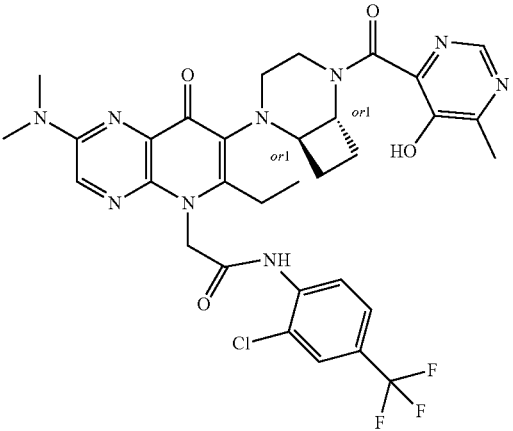 [SMILES: CCc1c(N2CCN(C(=O)c3ncnc(C)c3O)[C@@H]3CC[C@H]32)c(=O)c2nc(N(C)C)cnc2n1CC(=O)Nc1ccc(C(F)(F)F)cc1Cl] | LCMS 1 | 700.4 | 0.59 |
| I-41 | 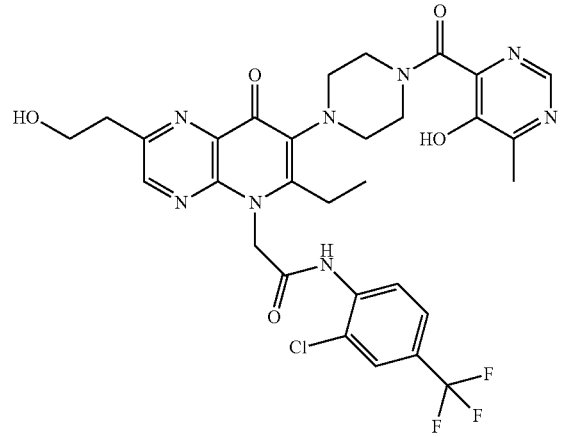 [SMILES: CCc1c(N2CCN(C(=O)c3ncnc(C)c3O)CC2)c(=O)c2nc(CCO)cnc2n1CC(=O)Nc1ccc(C(F)(F)F)cc1Cl] | LCMS 1 | 675.2 | 0.532 |

TABLE 2-continued
| No. | | Method | (Mass Observed) [g/mol] | (Retention time) [min] |
|---|---|---|---|---|
| I-42 | 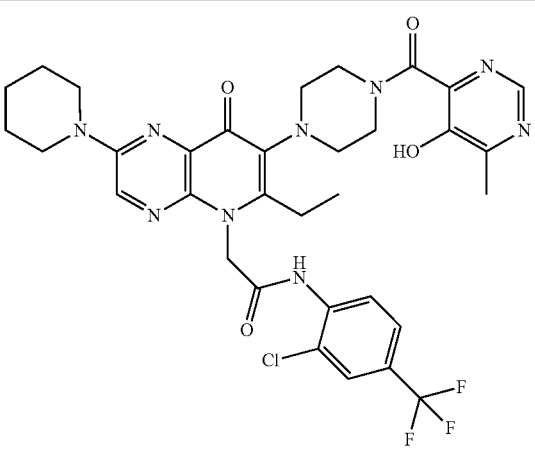 [SMILES: CCc1c(N2CCN(C(=O)c3ncnc(C)c3O)CC2)c(=O)c2nc(N3CCCCC3)cnc2n1CC(=O)Nc1ccc(C(F)(F)F)cc1Cl] | LCMS 1 | 714.3 | 0.610 |
| I-43 | 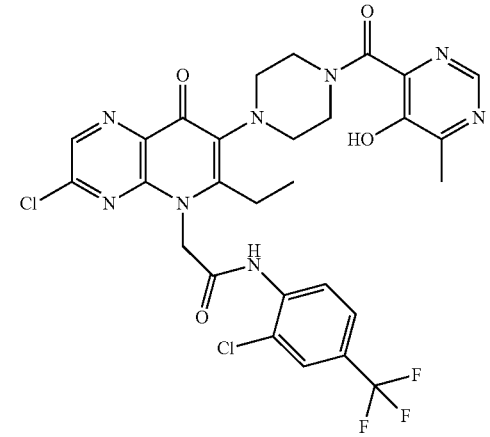 [SMILES: CCc1c(N2CCN(C(=O)c3ncnc(C)c3O)CC2)c(=O)c2ncc(Cl)nc2n1CC(=O)Nc1ccc(C(F)(F)F)cc1Cl] | LCMS 1 | 665.1 | 0.562 |
| I-44 | 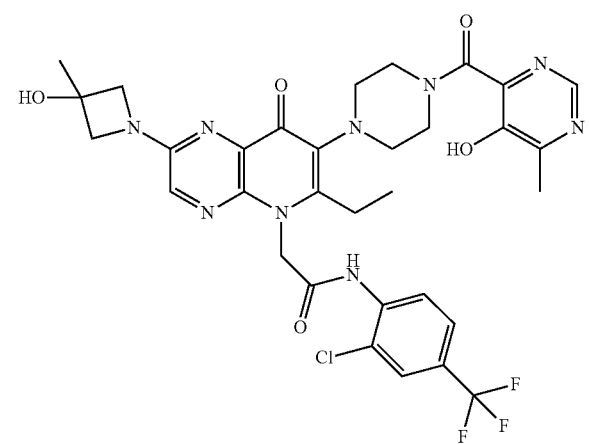 [SMILES: CCc1c(N2CCN(C(=O)c3ncnc(C)c3O)CC2)c(=O)c2nc(N3CC(C)(O)C3)cnc2n1CC(=O)Nc1ccc(C(F)(F)F)cc1Cl] | LCMS 1 | 716.2 | 0.537 |

TABLE 2-continued

| No. | | Method | (Mass Observed) [g/mol] | (Retention time) [min] |
|---|---|---|---|---|
| I-45 | | LCMS 1 | 702.2 | 0.530 |
| I-46 | | LCMS 1 | 631.1 | 0.537 |
| I-47 | | LCMS 1 | 730.2 | 0.538 |

TABLE 2-continued
| No. | Method | (Mass Observed) [g/mol] | (Retention time) [min] |
|---|---|---|---|
| I-48 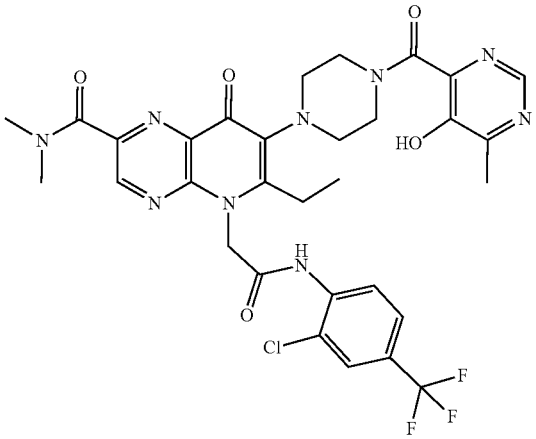 [SMILES: CCc1c(N2CCN(C(=O)c3ncnc(C)c3O)CC2)c(=O)c2nc(C(=O)N(C)C)cnc2n1CC(=O)Nc1ccc(C(F)(F)F)cc1Cl] | LCMS 1 | 702.2 | 0.538 |
| I-49 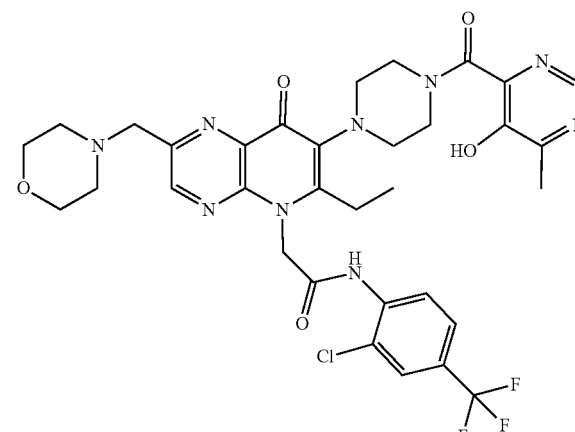 | LCMS 1 | 730.2 | 0.509 |
| I-50 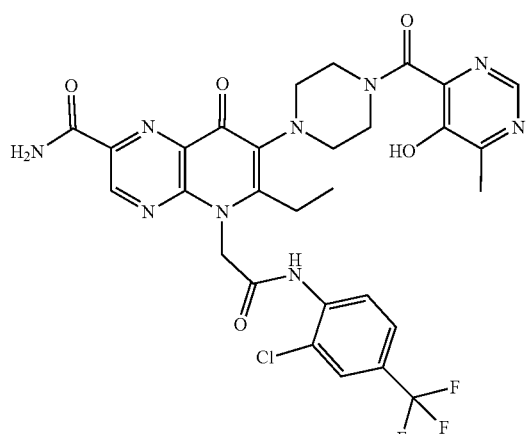 | LCMS 1 | 674.2 | 0.536 |

TABLE 2-continued
| No. | | Method | (Mass Observed) [g/mol] | (Retention time) [min] |
|---|---|---|---|---|
| I-51 | 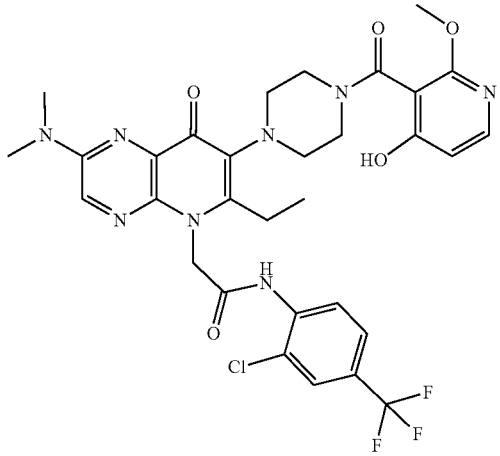 [SMILES: CCc1c(N2CCN(C(=O)c3c(O)ccnc3OC)CC2)c(=O)c2nc(N(C)C)cnc2n1CC(=O)Nc1ccc(C(F)(F)F)cc1Cl] | LCMS 1 | 689.2 | 0.536 |
| I-52 | 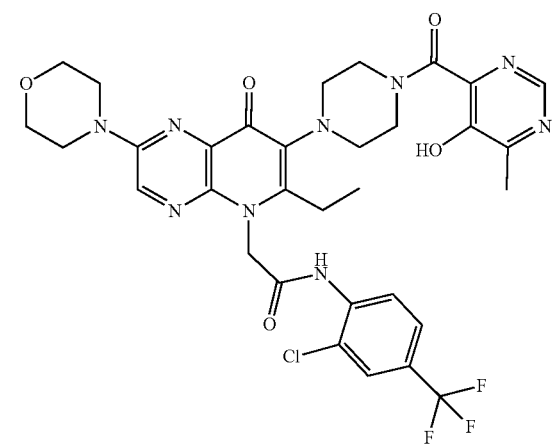 [SMILES: CCc1c(N2CCN(C(=O)c3ncnc(C)c3O)CC2)c(=O)c2nc(N3CCOCC3)cnc2n1CC(=O)Nc1ccc(C(F)(F)F)cc1Cl] | LCMS 1 | 716.2 | 0.554 |
| I-53 | 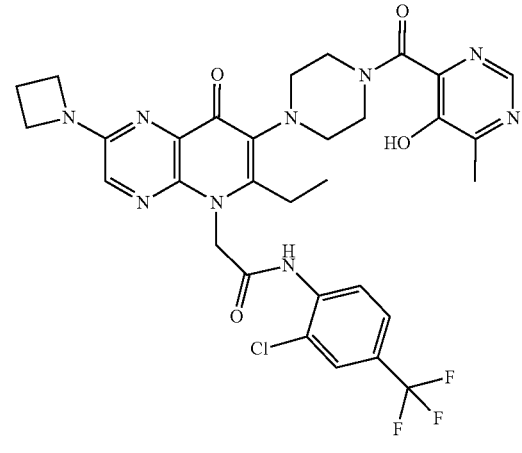 [SMILES: CCc1c(N2CCN(C(=O)c3ncnc(C)c3O)CC2)c(=O)c2nc(N3CCC3)cnc2n1CC(=O)Nc1ccc(C(F)(F)F)cc1Cl] | LCMS 1 | 686.2 | 0.561 |

TABLE 2-continued

| No. | | Method | (Mass Observed) [g/mol] | (Retention time) [min] |
|---|---|---|---|---|
| I-54 | | LCMS 1 | 688.2 | 0.547 |
| I-55 | | LCMS 1 | 701.2 | 0.573 |
| I-56 | | LCMS 1 | 716.2 | 0.526 |

TABLE 2-continued

| No. | | Method | (Mass Observed) [g/mol] | (Retention time) [min] |
|---|---|---|---|---|
| I-57 | (structure) | LCMS 1 | 688.2 | 0.559 |
| I-58 | (structure) | LCMS 1 | 700.3 | 0.575 |
| I-59 | (structure) | LCMS 1 | 744.4 | 0.561 |

TABLE 2-continued
| No. | | Method | (Mass Observed) [g/mol] | (Retention time) [min] |
|---|---|---|---|---|
| I-60 | 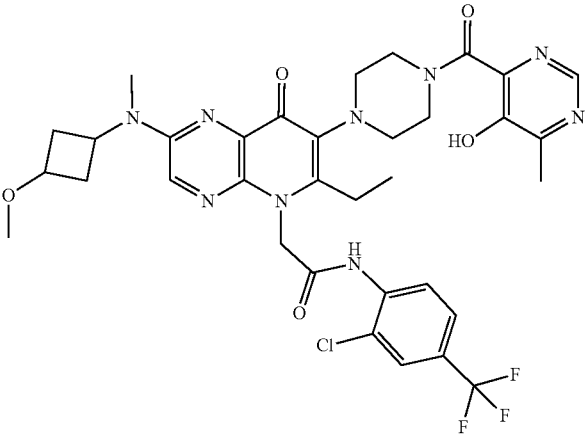 [SMILES: CCc1c(N2CCN(C(=O)c3ncnc(C)c3O)CC2)c(=O)c2nc(N(C)C3CC(OC)C3)cnc2n1CC(=O)Nc1ccc(C(F)(F)F)cc1Cl] | LCMS 1 | 744.5 | 0.581 |
| I-61 | 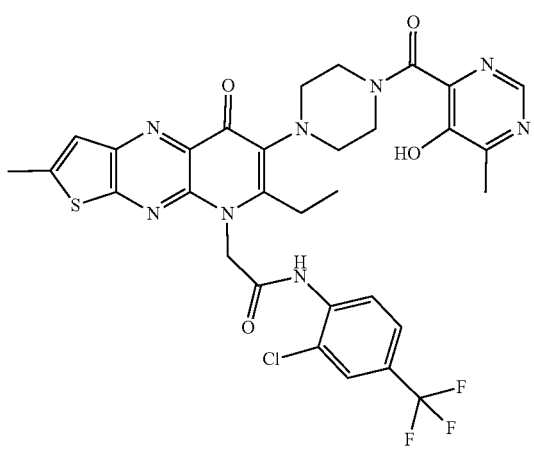 [SMILES: CCc1c(N2CCN(C(=O)c3ncnc(C)c3O)CC2)c(=O)c2nc3cc(C)sc3nc2n1CC(=O)Nc1ccc(C(F)(F)F)cc1Cl] | LCMS 4 | 701.2 | 0.432 |
| I-62 | 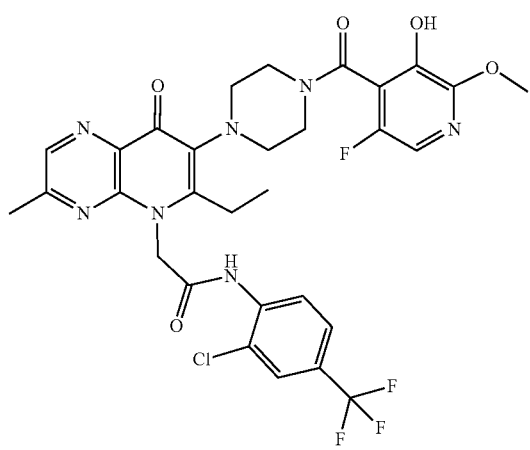 | LCMS 1 | 678.4 | 0.589 |

TABLE 2-continued
| No. | | Method | (Mass Observed) [g/mol] | (Retention time) [min] |
|---|---|---|---|---|
| I-63 | 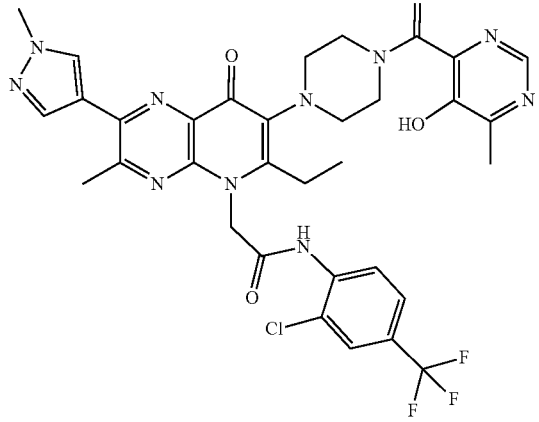 | LCMS 1 | 725.4 | 0.590 |
| I-64 | 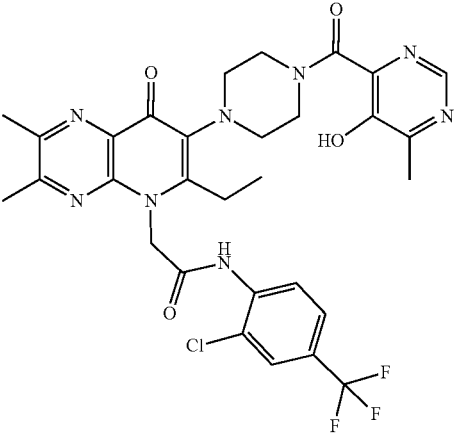 [SMILES: CCc1c(N2CCN(C(=O)c3ncnc(C)c3O)CC2)c(=O)c2nc(C)c(C)nc2n1CC(=O)Nc1ccc(C(F)(F)F)cc1Cl] | LCMS 1 | 659.2 | 0.559 |
| I-65 | 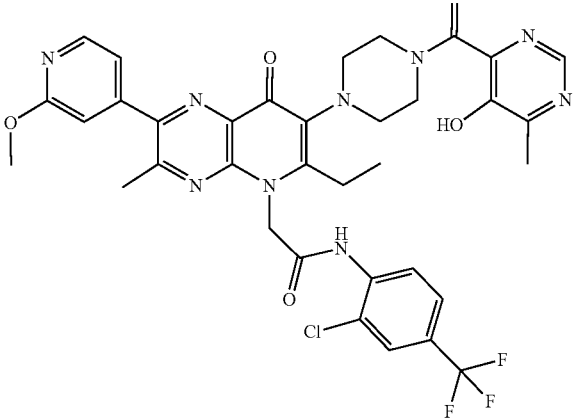 | LCMS 1 | 752.2 | 0.871 |

TABLE 2-continued
| No. | | Method | (Mass Observed) [g/mol] | (Retention time) [min] |
|---|---|---|---|---|
| I-66 | 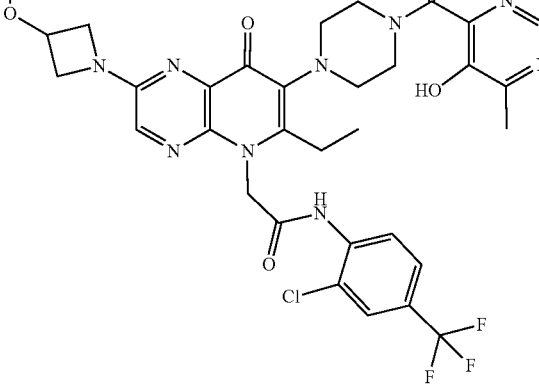 | LCMS 1 | 716.3 | 0.577 |
| I-67 | 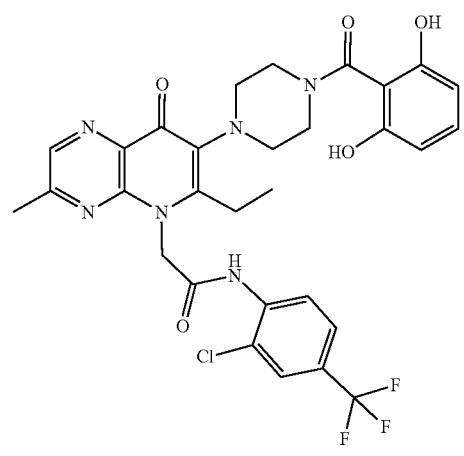 [SMILES: CCc1c(N2CCN(C(=O)c3c(O)cccc3O)CC2)c(=O)c2ncc(C)nc2n1CC(=O)Nc1ccc(C(F)(F)F)cc1Cl] | LCMS 1 | 645.4 | 0.563 |
| I-68 | 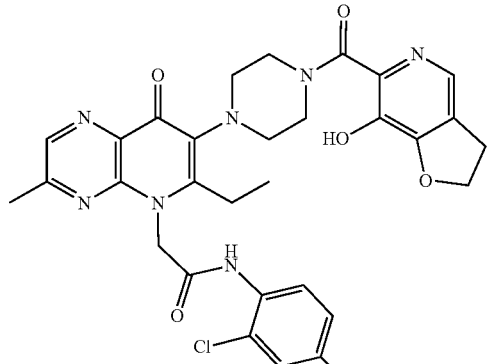 | LCMS 3 | 672.25 | 1.310 |

| No. | | Method | (Mass Observed) [g/mol] | (Retention time) [min] |
|---|---|---|---|---|
| I-69 | 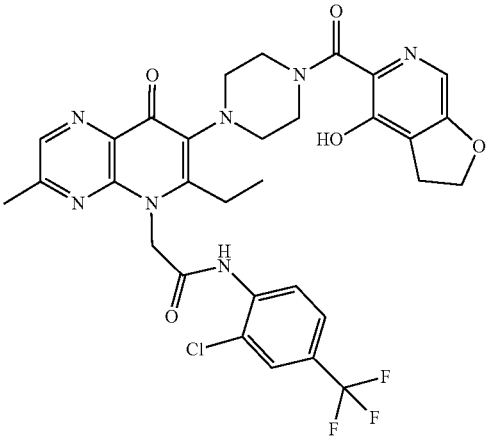 [SMILES: CCc1c(N2CCN(C(=O)c3ncc4c(c3O)CCO4)CC2)c(=O)c2ncc(C)nc2n1CC(=O)Nc1ccc(C(F)(F)F)cc1Cl] | LCMS 2 | 672.25 | 0.840 |
| I-70 | 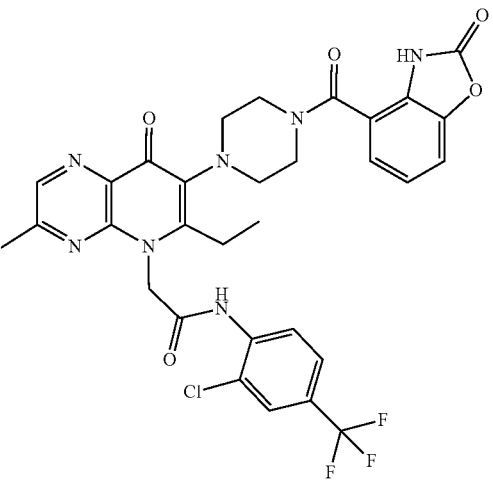 [SMILES: CCc1c(N2CCN(C(=O)c3cccc4oc(=O)[nH]c34)CC2)c(=O)c2ncc(C)nc2n1CC(=O)Nc1ccc(C(F)(F)F)cc1Cl] | LCMS 1 | 670.3 | 0.600 |
| I-71 | 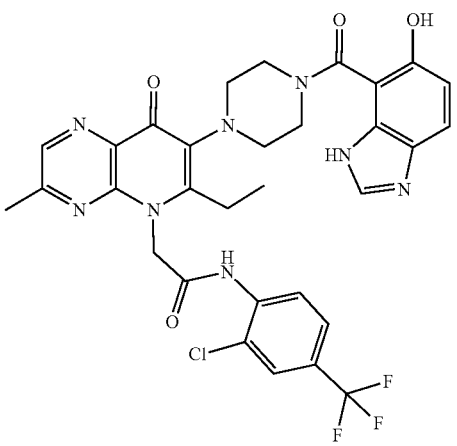 [SMILES: CCc1c(N2CCN(C(=O)c3c(O)ccc4nc[nH]c34)CC2)c(=O)c2ncc(C)nc2n1CC(=O)Nc1ccc(C(F)(F)F)cc1Cl] | LCMS 1 | 669.3 | 0.536 |

TABLE 2-continued
| No. | | Method | (Mass Observed) [g/mol] | (Retention time) [min] |
|---|---|---|---|---|
| I-72 | 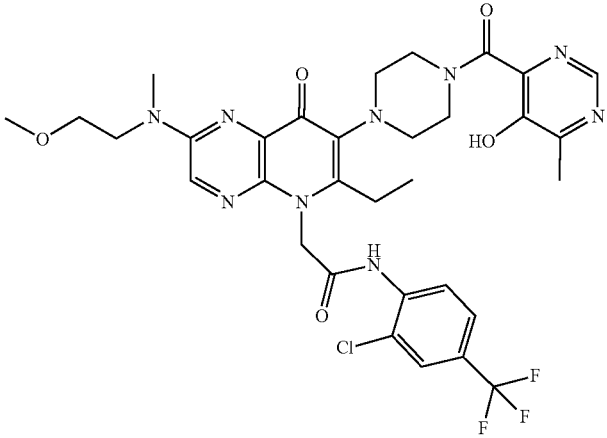 [SMILES: CCc1c(N2CCN(C(=O)c3ncnc(C)c3O)CC2)c(=O)c2nc(N(C)CCOC)cnc2n1CC(=O)Nc1ccc(C(F)(F)F)cc1Cl] | LCMS 1 | 718.2 | 0.858 |
| I-73 | 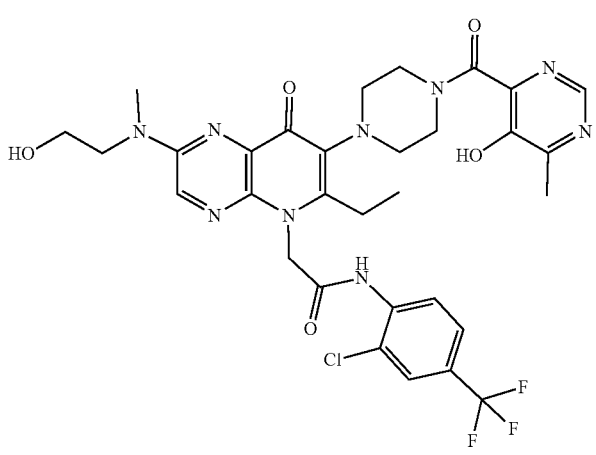 [SMILES: CCc1c(N2CCN(C(=O)c3ncnc(C)c3O)CC2)c(=O)c2nc(N(C)CCO)cnc2n1CC(=O)Nc1ccc(C(F)(F)F)cc1Cl] | LCMS 1 | 704.2 | 0.828 |
| I-74 | 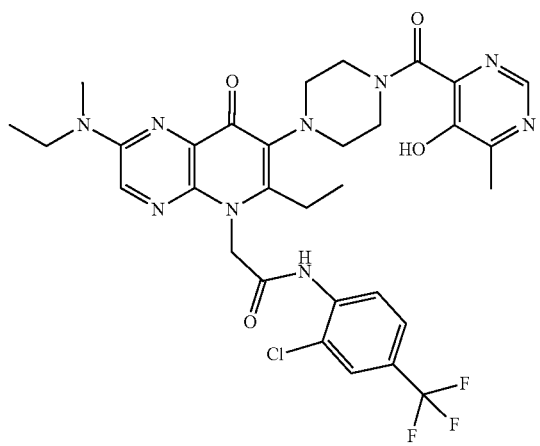 [SMILES: CCc1c(N2CCN(C(=O)c3ncnc(C)c3O)CC2)c(=O)c2nc(N(C)CC)cnc2n1CC(=O)Nc1ccc(C(F)(F)F)cc1Cl] | LCMS 1 | 688.4 | 0.580 |

TABLE 2-continued
| No. | | Method | (Mass Observed) [g/mol] | (Retention time) [min] |
|---|---|---|---|---|
| I-75 | 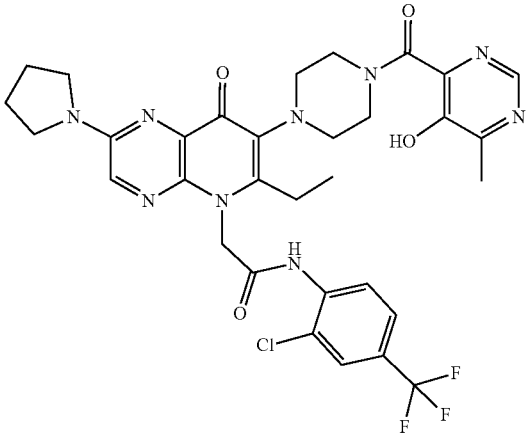 [SMILES: CCc1c(N2CCN(C(=O)c3ncnc(C)c3O)CC2)c(=O)c2nc(N3CCCC3)cnc2n1CC(=O)Nc1ccc(C(F)(F)F)cc1Cl] | LCMS 1 | 700.4 | 0.583 |
| I-76 | 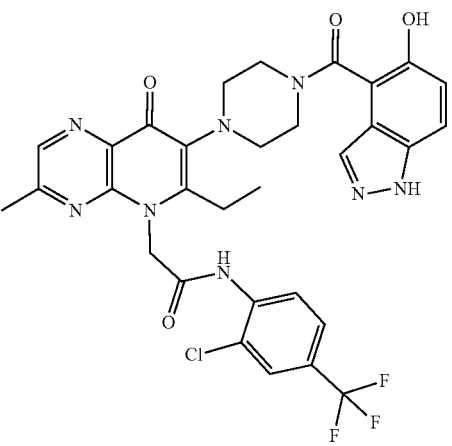 [SMILES: CCc1c(N2CCN(C(=O)c3c(O)ccc4[nH]ncc34)CC2)c(=O)c2ncc(C)nc2n1CC(=O)Nc1ccc(C(F)(F)F)cc1Cl] | LCMS 1 | 669.2 | 0.538 |
| I-77 | 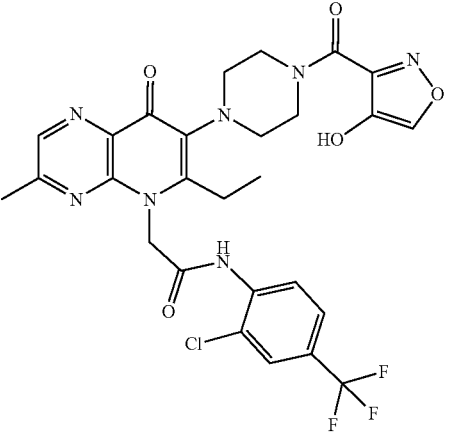 [SMILES: CCc1c(N2CCN(C(=O)c3nocc3O)CC2)c(=O)c2ncc(C)nc2n1CC(=O)Nc1ccc(C(F)(F)F)cc1Cl] | LCMS 1 | 620.1 | 0.550 |

TABLE 2-continued

| No. | | Method | (Mass Observed) [g/mol] | (Retention time) [min] |
|---|---|---|---|---|
| I-79 | | LCMS 1 | 711.2 | 0.837 |
| I-80 | | LCMS 1 | 645.2 | 0.550 |
| I-81 | | LCMS 1 | 661.1 | 0.558 |

TABLE 2-continued
| No. | | Method | (Mass Observed) [g/mol] | (Retention time) [min] |
|---|---|---|---|---|
| I-82 | 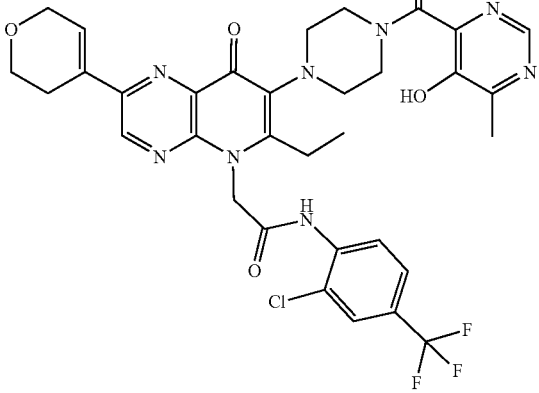 | LCMS 1 | 713 | 0.889 |
| I-83 | 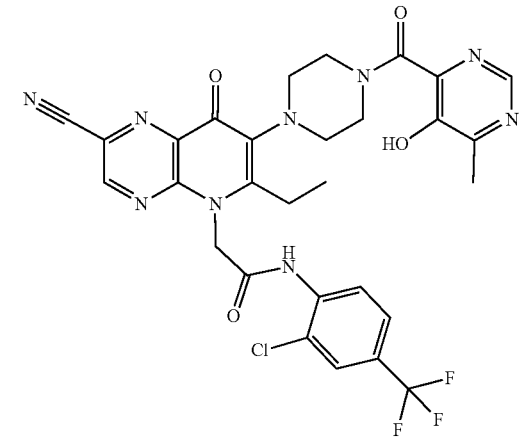 [SMILES: CCc1c(N2CCN(C(=O)c3ncnc(C)c3O)CC2)c(=O)c2nc(C#N)cnc2n1CC(=O)Nc1ccc(C(F)(F)F)cc1Cl] | LCMS 1 | 656.2 | 0.555 |
| I-84 | 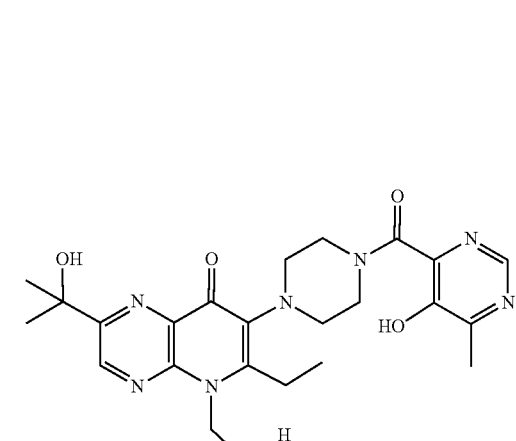 | LCMS 1 | 689.2 | 0.550 |

TABLE 2-continued

| No. | Method | (Mass Observed) [g/mol] | (Retention time) [min] |
|---|---|---|---|
| I-86 | LCMS 1 | 711.2 | 0.598 |
| I-87 | LCMS 1 | 702.5 | 0.590 |
| I-88 | LCMS 1 | 716.3 | 0.527 |

TABLE 2-continued
| No. | | Method | (Mass Observed) [g/mol] | (Retention time) [min] |
|---|---|---|---|---|
| I-89 | 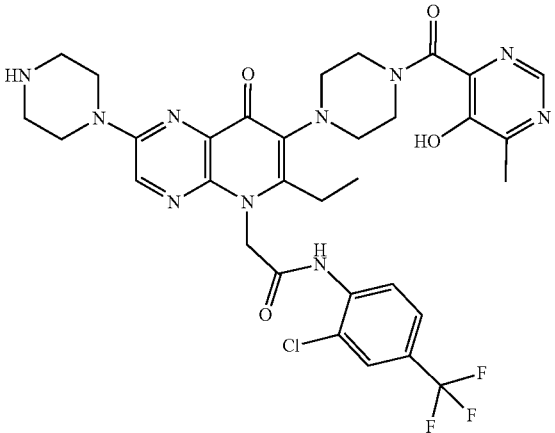 [SMILES: CCc1c(N2CCN(C(=O)c3ncnc(C)c3O)CC2)c(=O)c2nc(N3CCNCC3)cnc2n1CC(=O)Nc1ccc(C(F)(F)F)cc1Cl] | LCMS 1 | 715.3 | 0.498 |
| I-90 | 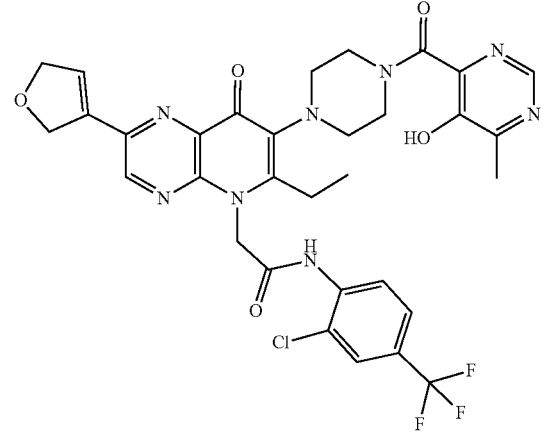 [SMILES: CCc1c(N2CCN(C(=O)c3ncnc(C)c3O)CC2)c(=O)c2nc(C3=CCOC3)cnc2n1CC(=O)Nc1ccc(C(F)(F)F)cc1Cl] | LCMS 1 | 699.2 | 0.551 |
| I-91 | 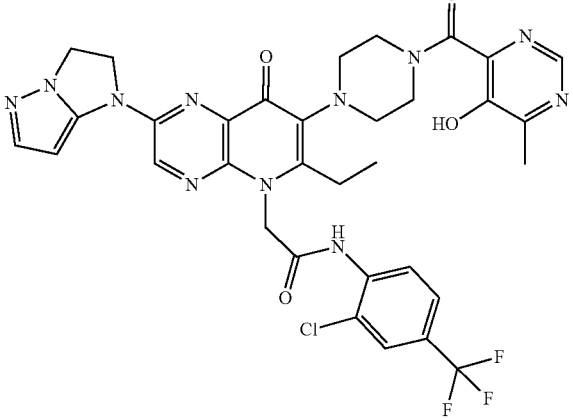 | LCMS 1 | 738.2 | 0.553 |

TABLE 2-continued
| No. | | Method | (Mass Observed) [g/mol] | (Retention time) [min] |
|---|---|---|---|---|
| I-92 | 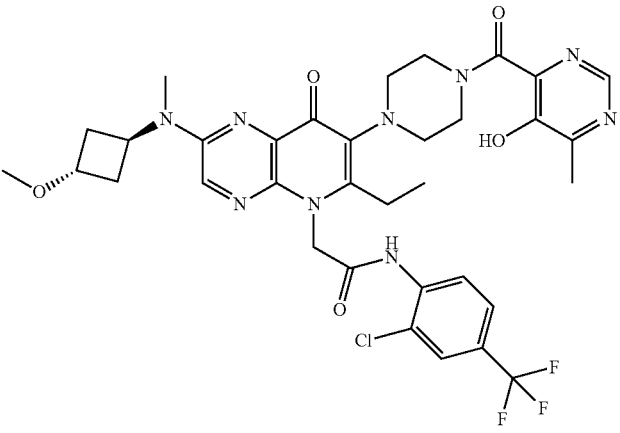 [SMILES: CCc1c(N2CCN(C(=O)c3ncnc(C)c3O)CC2)c(=O)c2nc(N(C)[C@H]3C[C@H](OC)C3)cnc2n1CC(=O)Nc1ccc(C(F)(F)F)cc1Cl] | LCMS 1 | 744.2 | 0.568 |
| I-93 | 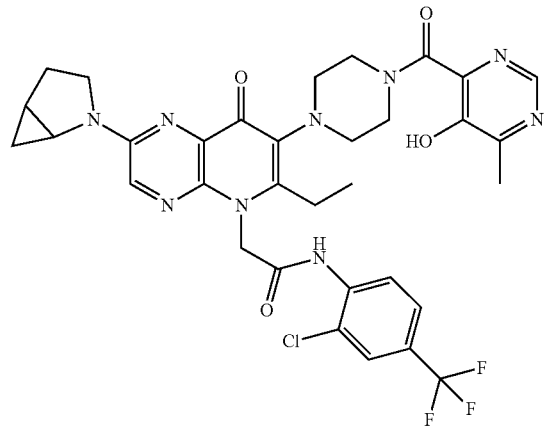 [SMILES: CCc1c(N2CCN(C(=O)c3ncnc(C)c3O)CC2)c(=O)c2nc(N3CCC4CC43)cnc2n1CC(=O)Nc1ccc(C(F)(F)F)cc1Cl] | LCMS 1 | 712.2 | 0.571 |
| I-94 | 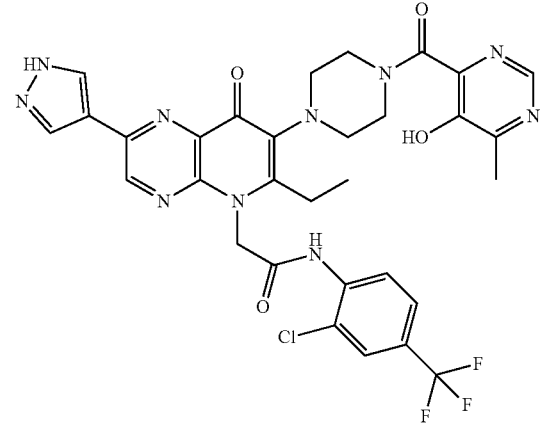 [SMILES: CCc1c(N2CCN(C(=O)c3ncnc(C)c3O)CC2)c(=O)c2nc(-c3cn[nH]c3)cnc2n1CC(=O)Nc1ccc(C(F)(F)F)cc1Cl] | LCMS 1 | 697.2 | 0.539 |

TABLE 2-continued

| No. | | Method | (Mass Observed) [g/mol] | (Retention time) [min] |
|---|---|---|---|---|
| I-95 | | LCMS 1 | 702.3 | 0.542 |
| I-96 | | LCMS 1 | 718.2 | 0.553 |
| I-97 | | LCMS 1 | 686.2 | 0.543 |

TABLE 2-continued

| No. | Method | (Mass Observed) [g/mol] | (Retention time) [min] |
|---|---|---|---|
| I-98 | LCMS 1 | 688.2 | 0.551 |
| I-99 | LCMS 1 | 688.2 | 0.544 |
| I-100 | LCMS 1 | 697.2 | 2.38 |

TABLE 2-continued

| No. | | Method | (Mass Observed) [g/mol] | (Retention time) [min] |
|---|---|---|---|---|
| I-101 | | LCMS 1 | 706.5 | 0.59 |
| I-102 | | LCMS 1 | 713.2 | 2.42 |
| I-103 | | LCMS 1 | 680.3 | 2.17 |

TABLE 2-continued
| No. | | Method | (Mass Observed) [g/mol] | (Retention time) [min] |
|---|---|---|---|---|
| I-104 | 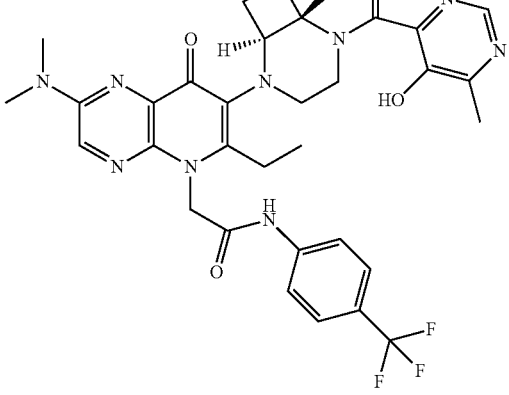 | LCMS 1 | 666.2 | 2.09 |
| I-105 | 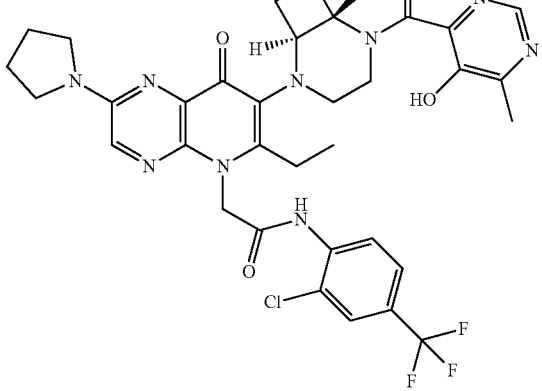 | LCMS 1 | 726.2 | 2.31 |
| I-106 | 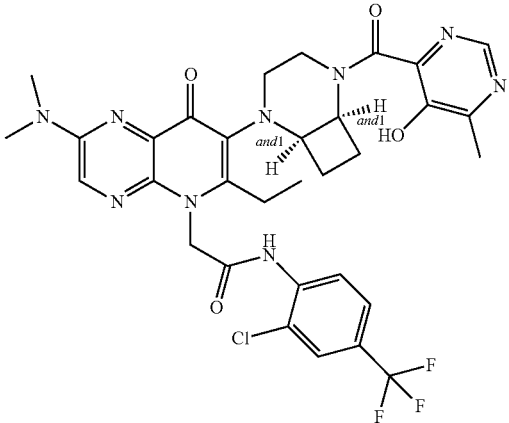 [SMILES: CCc1c(N2CCN(C(=O)c3ncnc(C)c3O)[C@H]3CC[C@H]32)c(=O)c2nc(N(C)C)cnc2n1CC(=O)Nc1ccc(C(F)(F)F)cc1Cl] | LCMS 1 | 700.2 | 2.25 |

TABLE 2-continued
| No. | | Method | (Mass Observed) [g/mol] | (Retention time) [min] |
|---|---|---|---|---|
| I-107 | 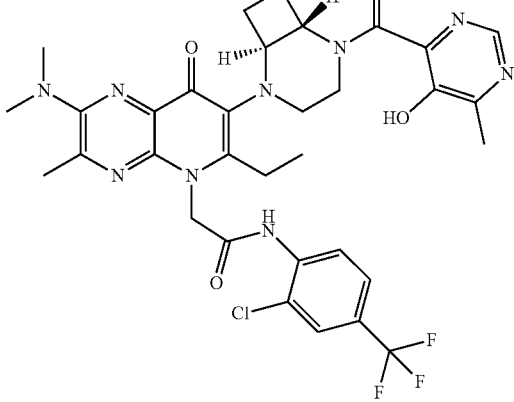 | LCMS 1 | 714.3 | 2.31 |
| I-108 | 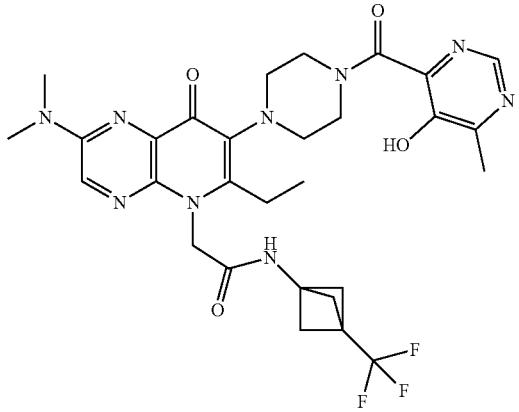 [SMILES: CCc1c(N2CCN(C(=O)c3ncnc(C)c3O)CC2)c(=O)c2nc(N(C)C)cnc2n1CC(=O)NC12CC(C(F)(F)F)(C1)C2] | LCMS 1 | 630.3 | 0.506 |
| I-109 | 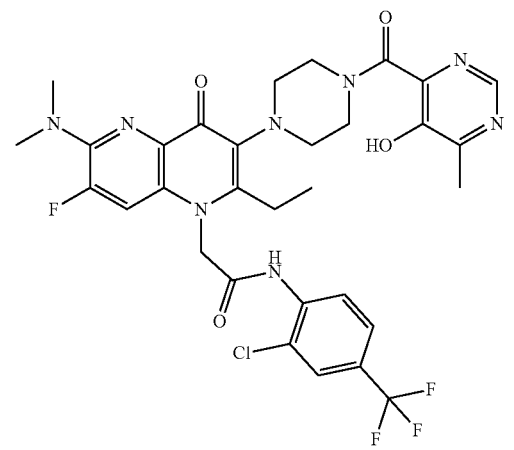 [SMILES: CCc1c(N2CCN(C(=O)c3ncnc(C)c3O)CC2)c(=O)c2nc(N(C)C)c(F)cc2n1CC(=O)Nc1ccc(C(F)(F)F)cc1Cl] | LCMS 1 | 691.3 | 0.53 |

TABLE 2-continued

| No. | Method | (Mass Observed) [g/mol] | (Retention time) [min] |
|---|---|---|---|
| I-110 | LCMS 1 | 656.5 | 0.561 |
| I-111 | LCMS 1 | 712.2 | 2.47 |
| I-112 | LCMS 1 | 685.3 | 0.54 |

TABLE 2-continued
| No. | | Method | (Mass Observed) [g/mol] | (Retention time) [min] |
|---|---|---|---|---|
| I-113 | 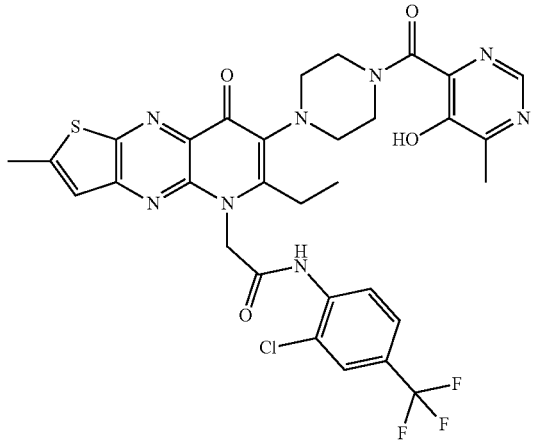 [SMILES: CCc1c(N2CCN(C(=O)c3ncnc(C)c3O)CC2)c(=O)c2nc3sc(C)cc3nc2n1CC(=O)Nc1ccc(C(F)(F)F)cc1Cl] | LCMS 1 | 701.3 | 0.558 |
| I-114 | 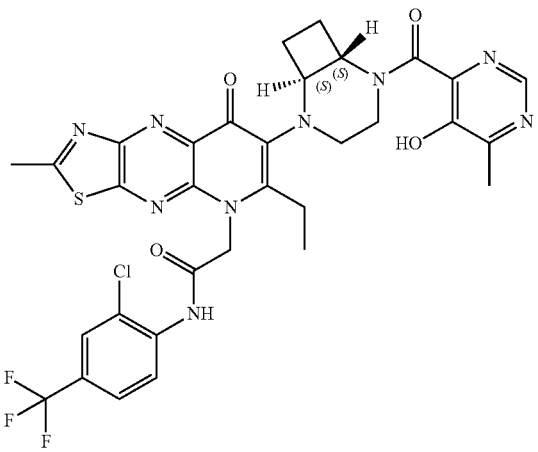 | LCMS 1 | 728.2 | 0.572 |
| I-115 | 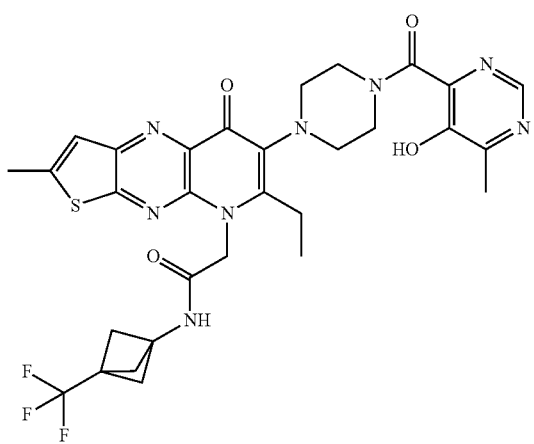 [SMILES: CCc1c(N2CCN(C(=O)c3ncnc(C)c3O)CC2)c(=O)c2nc3cc(C)sc3nc2n1CC(=O)NC12CC(C(F)(F)F)(C1)C2] | LCMS 1 | 657.3 | 0.519 |

TABLE 2-continued

| No. | | Method | (Mass Observed) [g/mol] | (Retention time) [min] |
|---|---|---|---|---|
| I-116 | | LCMS 1 | 686.5 | 0.554 |
| I-117 | | LCMS 1 | 727.2 | 0.585 |
| I-118 | | LCMS 1 | 689.4 | 0.6 |

TABLE 2-continued
| No. | Method | (Mass Observed) [g/mol] | (Retention time) [min] |
|---|---|---|---|
| I-119 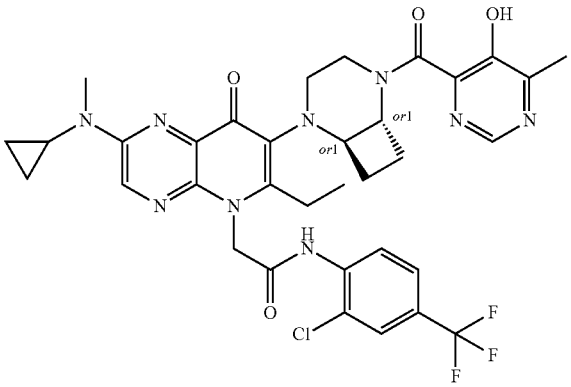 [SMILES: CCc1c(N2CCN(C(=O)c3ncnc(C)c3O)[C@@H]3CC[C@H]32)c(=O)c2nc(N(C)C3CC3)cnc2n1CC(=O)Nc1ccc(C(F)(F)F)cc1Cl] | LCMS 1 | 726.2 | 0.586 |
| I-120 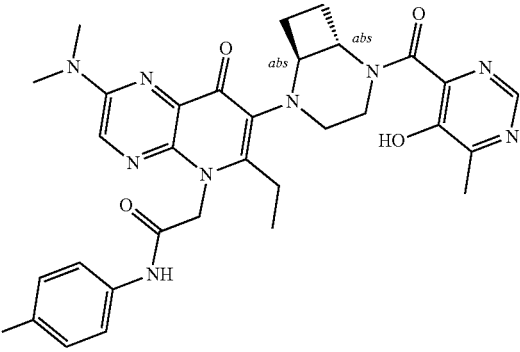 | LCMS 1 | 682.3 | 2.16 |
| I-121 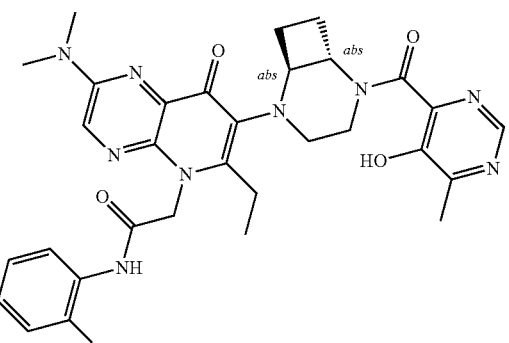 | LCMS 1 | 684.3 | 2.18 |

TABLE 2-continued

| No. | | Method | (Mass Observed) [g/mol] | (Retention time) [min] |
|---|---|---|---|---|
| I-122 | (structure) | LCMS 1 | 722.3 | 2.24 |
| I-123 | (structure) | LCMS 4 | 725.3 | 0.41 |

TABLE 2-continued
| No. | | Method | (Mass Observed) [g/mol] | (Retention time) [min] |
|---|---|---|---|---|
| I-124 | 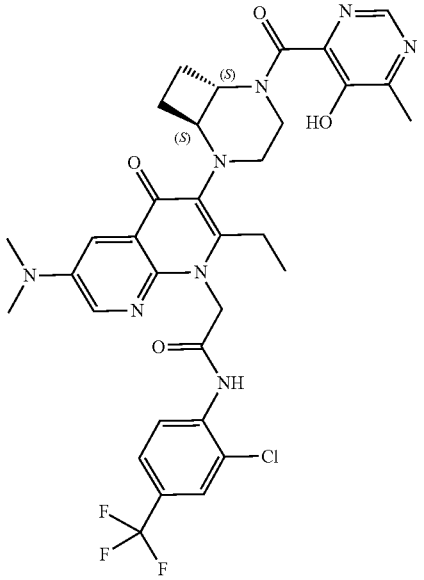 | LCMS 2 | 699.4 | 1.01 |
| I-125 | 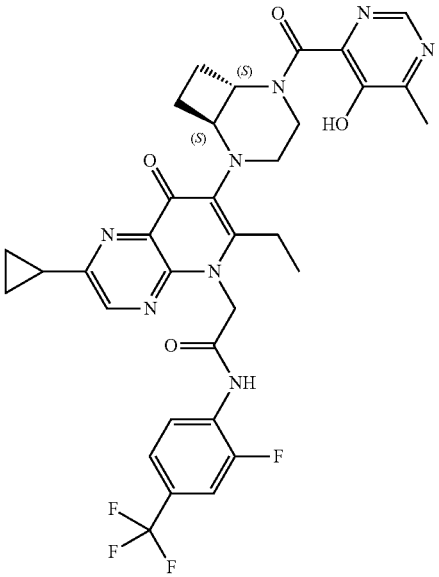 | LCMS 1 | 681.3 | 2.28 |
| I-126 | 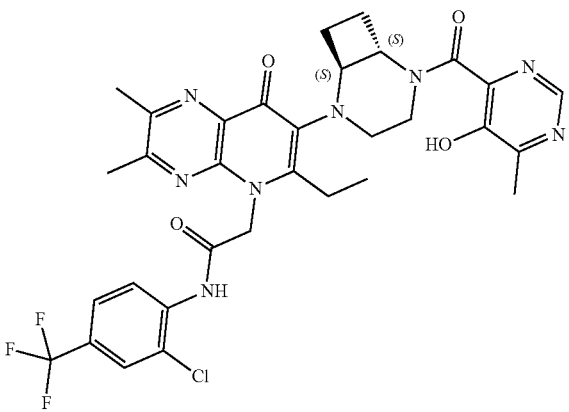 | LCMS 1 | 685.3 | 2.28 |

TABLE 2-continued
| No. | | Method | (Mass Observed) [g/mol] | (Retention time) [min] |
|---|---|---|---|---|
| I-127 | 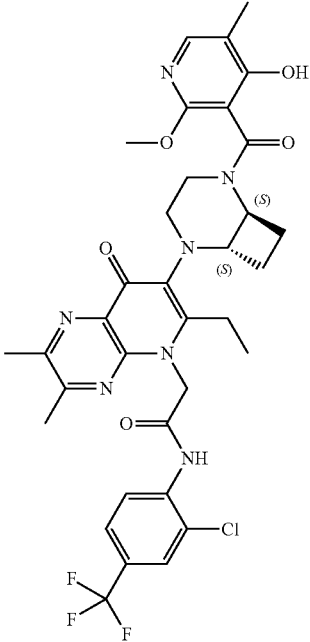 | LCMS 1 | 714.2 | 0.57 |
| I-128 | 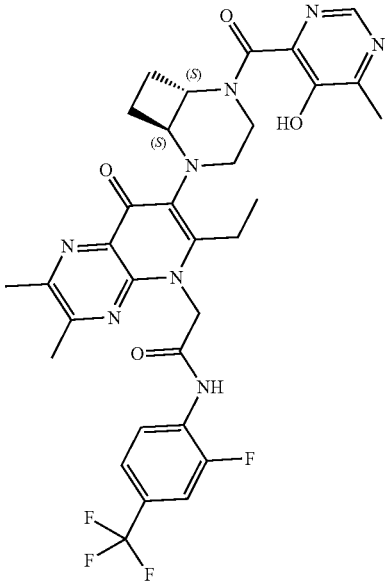 | LCMS 1 | 699.3 | 2.18 |

TABLE 2-continued

| No. | Method | (Mass Observed) [g/mol] | (Retention time) [min] |
|---|---|---|---|
| I-129 | LCMS 1 | 698.3 | 2.21 |
| I-130 | LCMS 4 | 714.3 | 0.43 |

TABLE 2-continued
| No. | | Method | (Mass Observed) [g/mol] | (Retention time) [min] |
|---|---|---|---|---|
| I-131 | 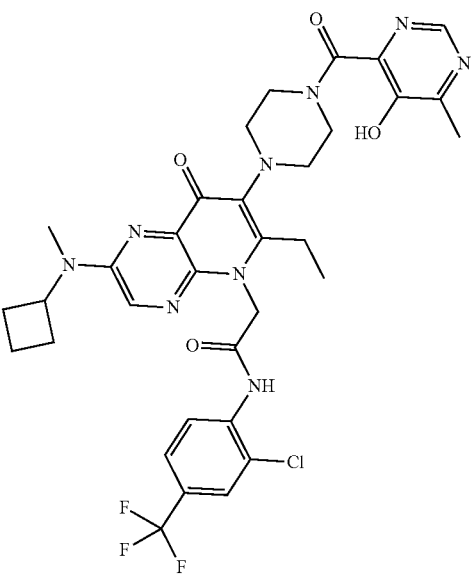 [SMILES: CCc1c(N2CCN(C(=O)c3ncnc(C)c3O)CC2)c(=O)c2nc(N(C)C3CCC3)cnc2n1CC(=O)Nc1ccc(C(F)(F)F)cc1Cl] | LCMS 1 | 714.4 | 0.60 |
| I-132 | 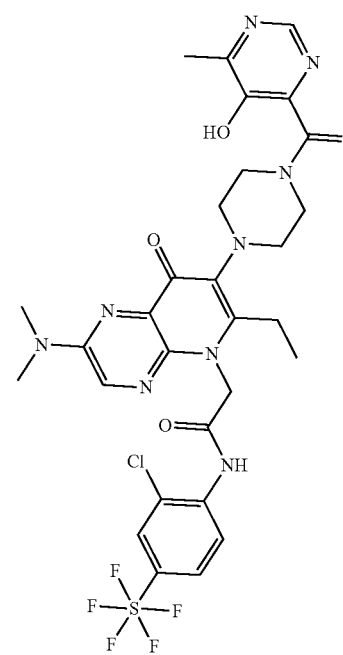 | LCMS 1 | 732.1 | 0.56 |

TABLE 2-continued
| No. | | Method | (Mass Observed) [g/mol] | (Retention time) [min] |
|---|---|---|---|---|
| I-133 | 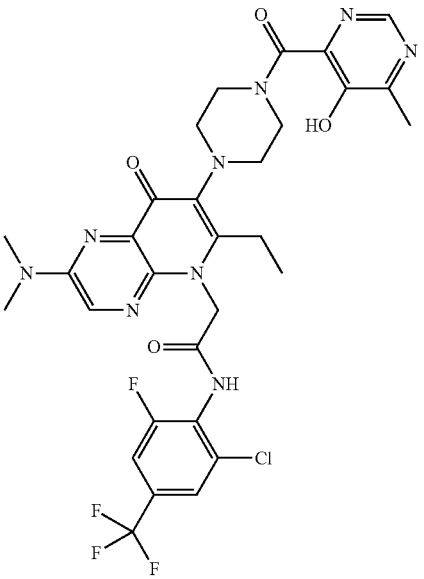 | LCMS 1 | 692.4 | 0.54 |
| I-134 | 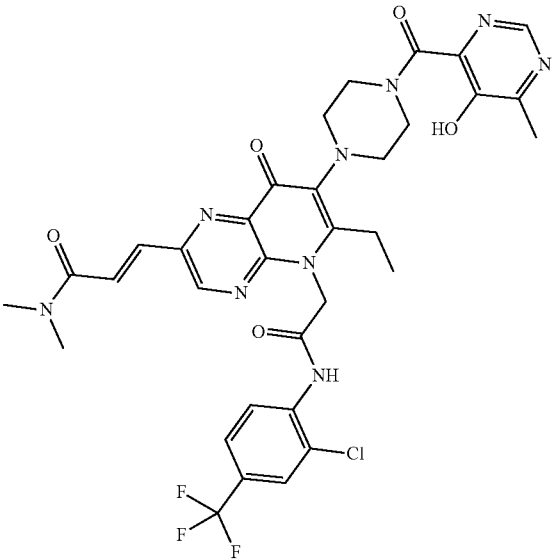 [SMILES: CCc1c(N2CCN(C(=O)c3ncnc(C)c3O)CC2)c(=O)c2nc(/C=C/C(=O)N(C)C)cnc2n1CC(=O)Nc1ccc(C(F)(F)F)cc1Cl] | LCMS 1 | 728.4 | 0.57 |

TABLE 2-continued
| No. | | Method | (Mass Observed) [g/mol] | (Retention time) [min] |
|---|---|---|---|---|
| I-135 | 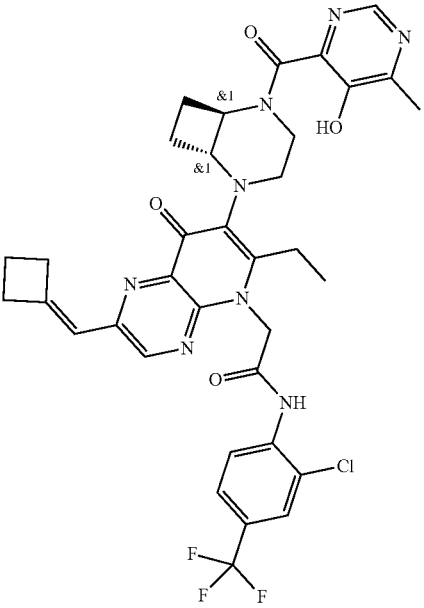 [SMILES: CCc1c(N2CCN(C(=O)c3ncnc(C)c3O)[C@@H]3CC[C@H]32)c(=O)c2nc(C=C3CCC3)cnc2n1CC(=O)Nc1ccc(C(F)(F)F)cc1Cl] | LCMS 1 | 723.2 | 0.63 |
| I-136 | 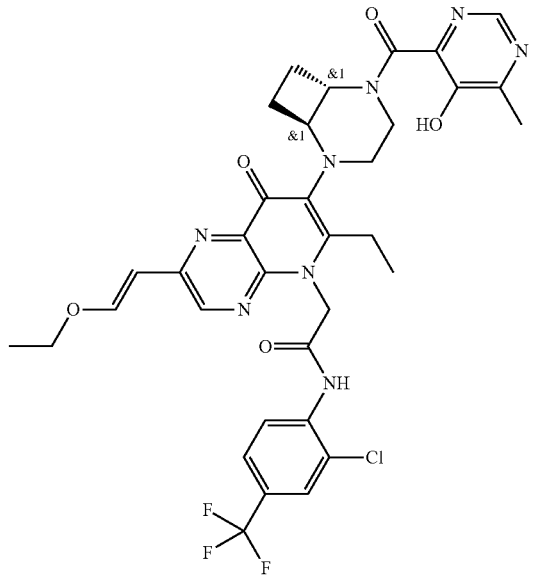 [SMILES: CCO/C=C/c1cnc2c(n1)c(=O)c(N1CCN(C(=O)c3ncnc(C)c3O)[C@H]3CC[C@@H]31)c(CC)n2CC(=O)Nc1ccc(C(F)(F)F)cc1Cl] | LCMS 1 | 727.2 | 0.61 |

TABLE 2-continued

| No. | Method | (Mass Observed) [g/mol] | (Retention time) [min] |
|---|---|---|---|
| I-137 | LCMS 1 | 711.1 | 0.56 |
| I-138 | LCMS 1 | 715.2 | 0.55 |

TABLE 2-continued

| No. | Method | (Mass Observed) [g/mol] | (Retention time) [min] |
|---|---|---|---|
| I-139 | LCMS 1 | 715.4 | 0.57 |
| I-140 | LCMS 1 | 703.1 | 0.55 |

TABLE 2-continued
| No. | | Method | (Mass Observed) [g/mol] | (Retention time) [min] |
|---|---|---|---|---|
| I-141 | 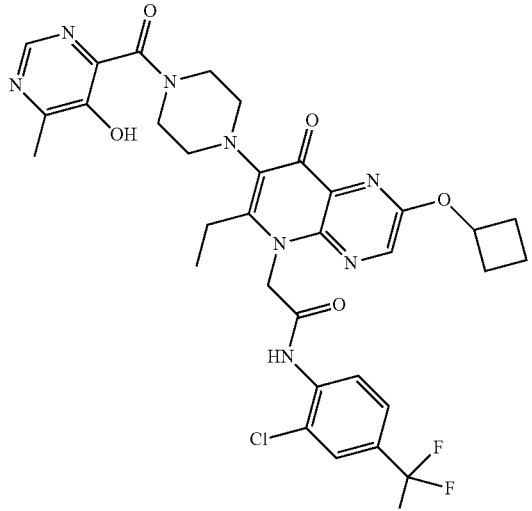 | LCMS 1 | 701.2 | 0.60 |
| I-142 | 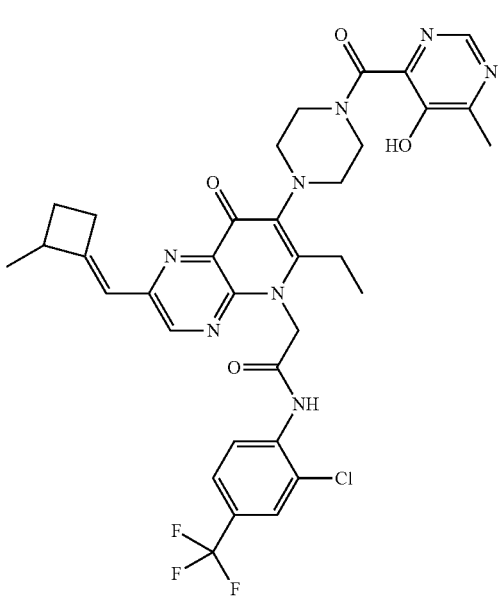 | LCMS 1 | 711.4 | 0.65 |

TABLE 2-continued
| No. | | Method | (Mass Observed) [g/mol] | (Retention time) [min] |
|---|---|---|---|---|
| I-143 | 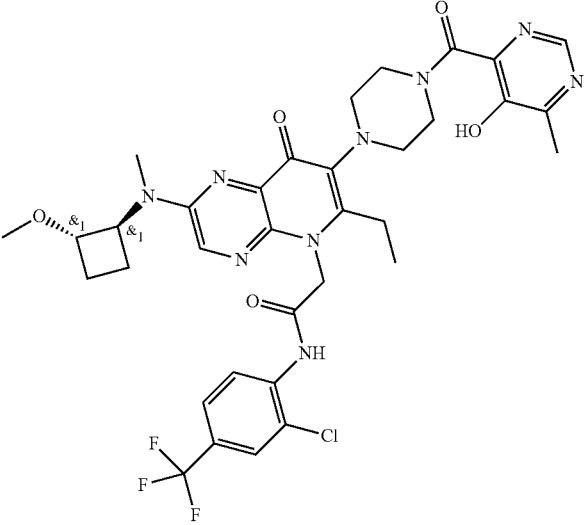 [SMILES: CCc1c(N2CCN(C(=O)c3ncnc(C)c3O)CC2)c(=O)c2nc(N(C)[C@H]3CC[C@@H]3OC)cnc2n1CC(=O)Nc1ccc(C(F)(F)F)cc1Cl] | LCMS 1 | 744.4 | 0.59 |
| I-144 | 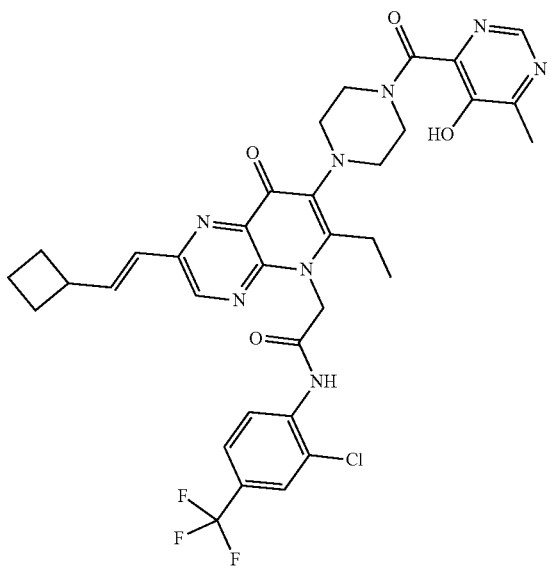 [SMILES: CCc1c(N2CCN(C(=O)c3ncnc(C)c3O)CC2)c(=O)c2nc(/C=C/C3CCC3)cnc2n1CC(=O)Nc1ccc(C(F)(F)F)cc1Cl] | LCMS 1 | 711.2 | 0.62 |
| I-145 | 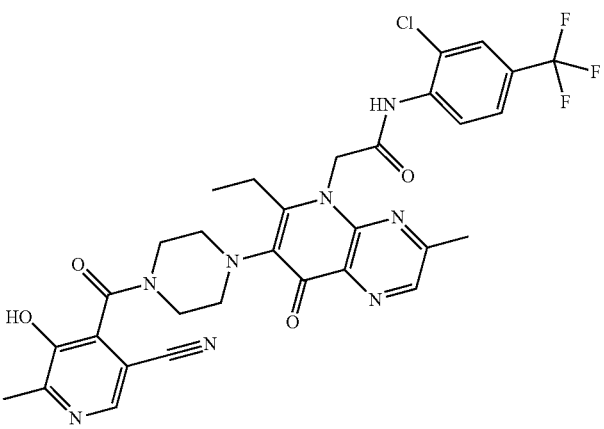 [SMILES: CCc1c(N2CCN(C(=O)c3c(C#N)cnc(C)c3O)CC2)c(=O)c2ncc(C)nc2n1CC(=O)Nc1ccc(C(F)(F)F)cc1Cl] | LCMS 1 | 669.2 | 0.59 |

TABLE 2-continued
| No. | | Method | (Mass Observed) [g/mol] | (Retention time) [min] |
|---|---|---|---|---|
| I-146 | 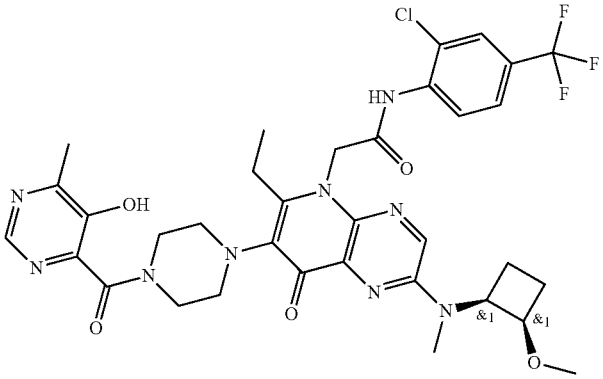 [SMILES: CCc1c(N2CCN(C(=O)c3ncnc(C)c3O)CC2)c(=O)c2nc(N(C)[C@H]3CC[C@H]3OC)cnc2n1CC(=O)Nc1ccc(C(F)(F)F)cc1Cl] | LCMS 1 | 744.2 | 0.61 |
| I-147 | 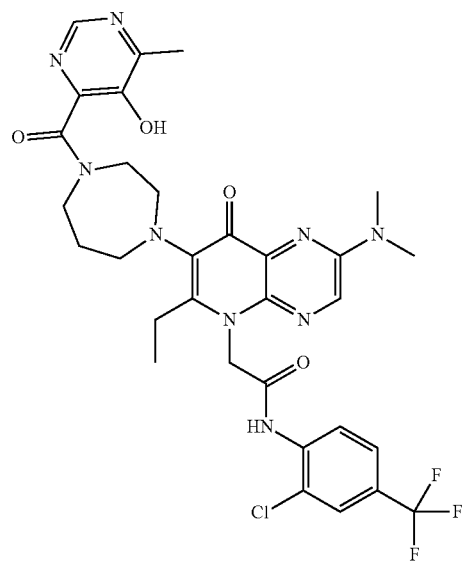 [SMILES: CCc1c(N2CCCN(C(=O)c3ncnc(C)c3O)CC2)c(=O)c2nc(N(C)C)cnc2n1CC(=O)Nc1ccc(C(F)(F)F)cc1Cl] | LCMS 1 | 688.4 | 0.57 |
| I-148 | 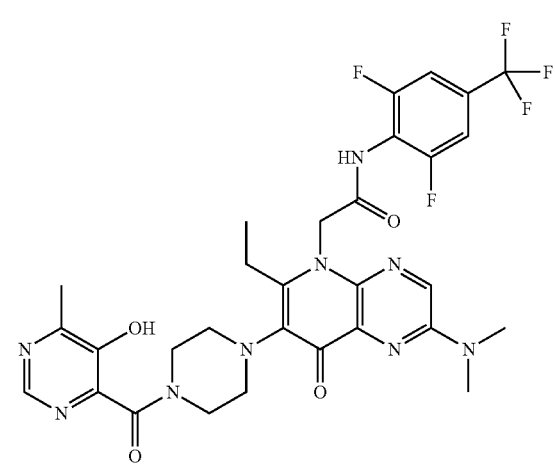 [SMILES: CCc1c(N2CCN(C(=O)c3ncnc(C)c3O)CC2)c(=O)c2nc(N(C)C)cnc2n1CC(=O)Nc1c(F)cc(C(F)(F)F)cc1F] | LCMS 1 | 676.4 | 0.55 |

TABLE 2-continued
| No. | | Method | (Mass Observed) [g/mol] | (Retention time) [min] |
|---|---|---|---|---|
| I-149 | 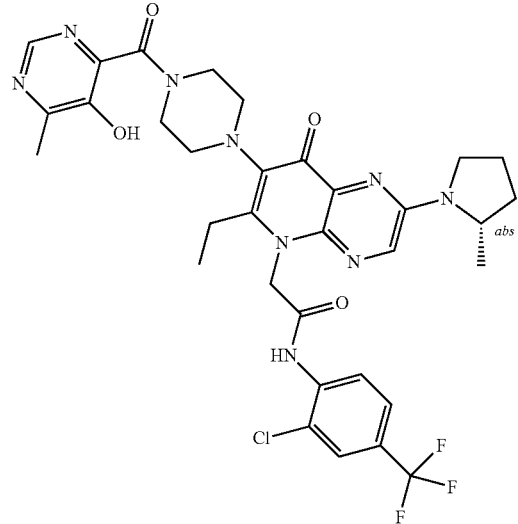 [SMILES: CCc1c(N2CCN(C(=O)c3ncnc(C)c3O)CC2)c(=O)c2nc(N3CCC[C@@H]3C)cnc2n1CC(=O)Nc1ccc(C(F)(F)F)cc1Cl] | LCMS 1 | 714.2 | 0.57 |
| I-150 | 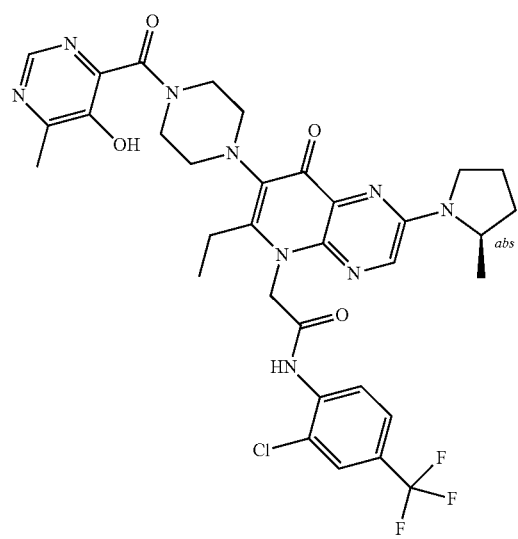 [SMILES: CCc1c(N2CCN(C(=O)c3ncnc(C)c3O)CC2)c(=O)c2nc(N3CCC[C@H]3C)cnc2n1CC(=O)Nc1ccc(C(F)(F)F)cc1Cl] | LCMS 1 | 714.2 | 0.57 |

TABLE 2-continued
| No. | | Method | (Mass Observed) [g/mol] | (Retention time) [min] |
|---|---|---|---|---|
| I-151 | 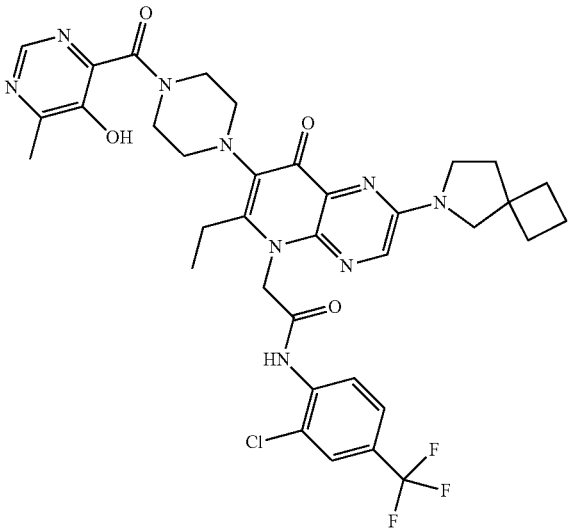 [SMILES: CCc1c(N2CCN(C(=O)c3ncnc(C)c3O)CC2)c(=O)c2nc(N3CCC4(CCC4)C3)cnc2n1CC(=O)Nc1ccc(C(F)(F)F)cc1Cl] | LCMS 1 | 740.2 | 0.59 |
| I-152 | 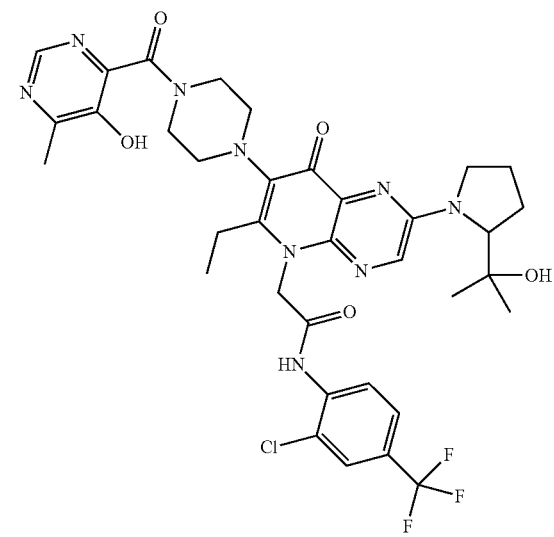 [SMILES: CCc1c(N2CCN(C(=O)c3ncnc(C)c3O)CC2)c(=O)c2nc(N3CCCC3C(C)(C)O)cnc2n1CC(=O)Nc1ccc(C(F)(F)F)cc1Cl] | LCMS 1 | 758.5 | 0.58 |

TABLE 2-continued

| No. | | Method | (Mass Observed) [g/mol] | (Retention time) [min] |
|---|---|---|---|---|
| I-153 | (structure) | LCMS 1 | 758.5 | 0.58 |
| I-154 | (structure) | LCMS 1 | 731.2 | 0.52 |

TABLE 2-continued
| No. | | Method | (Mass Observed) [g/mol] | (Retention time) [min] |
|---|---|---|---|---|
| I-155 | 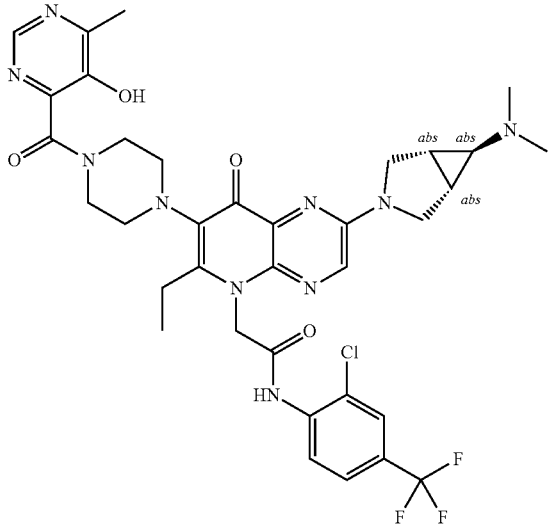 [SMILES: CCc1c(N2CCN(C(=O)c3ncnc(C)c3O)CC2)c(=O)c2nc(N3C[C@@H]4[C@H](C3)[C@H]4N(C)C)cnc2n1CC(=O)Nc1ccc(C(F)(F)F)cc1Cl] | LCMS 1 | 755.2 | 0.50 |
| I-156 | 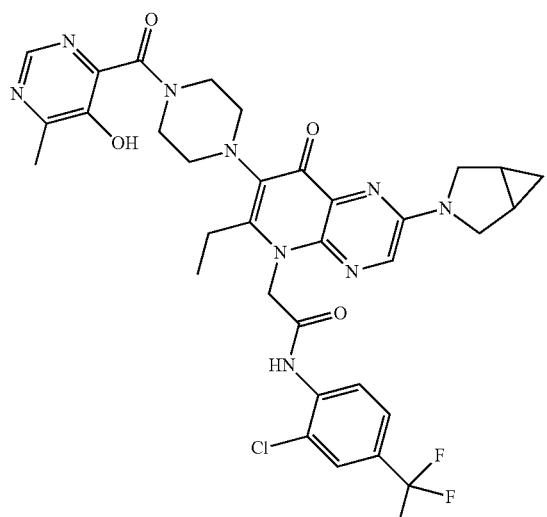 | LCMS 1 | 712.2 | 0.57 |

TABLE 2-continued

| No. | | Method | (Mass Observed) [g/mol] | (Retention time) [min] |
|---|---|---|---|---|
| I-157 | | LCMS 1 | 675.2 | 0.58 |
| I-158 | | LCMS 1 | 669.4 | 0.57 |
| I-159 | | LCMS 1 | 756.4 | 0.59 |

TABLE 2-continued
| No. | | Method | (Mass Observed) [g/mol] | (Retention time) [min] |
|---|---|---|---|---|
| I-160 | 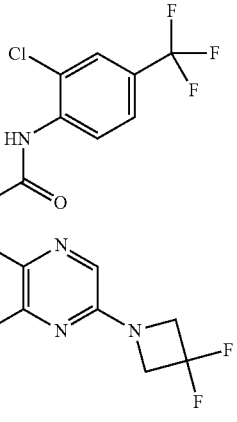 | LCMS 1 | 722.2 | 0.56 |
| I-161 | 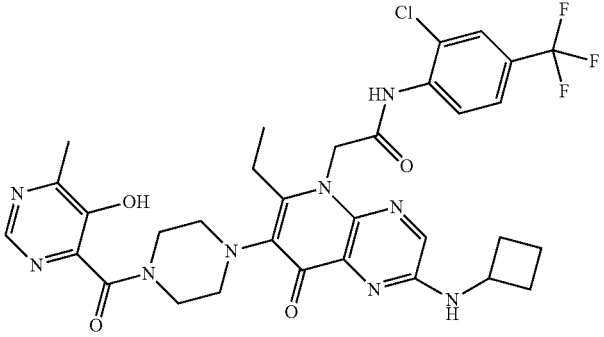 [SMILES: CCc1c(N2CCN(C(=O)c3ncnc(C)c3O)CC2)c(=O)c2nc(NC3CCC3)cnc2n1CC(=O)Nc1ccc(C(F)(F)F)cc1Cl] | LCMS 1 | 700.2 | 0.56 |
| I-162 | 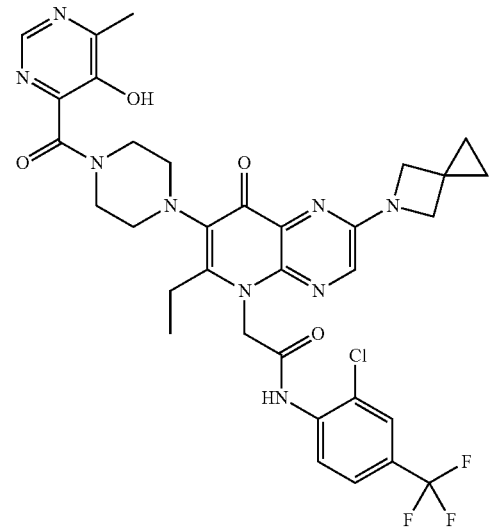 [SMILES: CCc1c(N2CCN(C(=O)c3ncnc(C)c3O)CC2)c(=O)c2nc(N3CC4(CC4)C3)cnc2n1CC(=O)Nc1ccc(C(F)(F)F)cc1Cl] | LCMS 1 | 712.2 | 0.57 |

TABLE 2-continued

| No. | | Method | (Mass Observed) [g/mol] | (Retention time) [min] |
|---|---|---|---|---|
| I-163 | | LCMS 1 | 742.2 | 0.54 |
| I-164 | | LCMS 1 | 704.4 | 0.58 |

TABLE 2-continued
| No. | | Method | (Mass Observed) [g/mol] | (Retention time) [min] |
|---|---|---|---|---|
| I-165 | 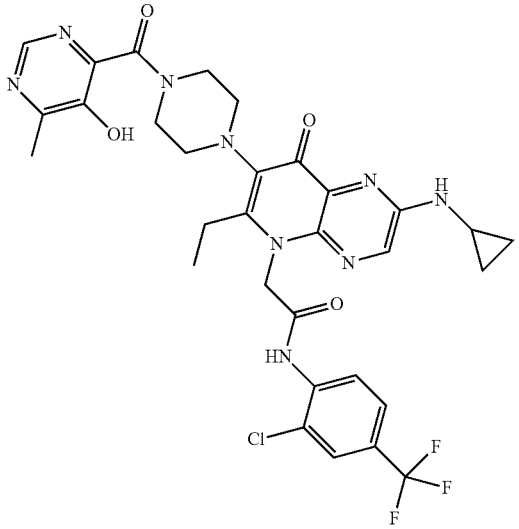 [SMILES: CCc1c(N2CCN(C(=O)c3ncnc(C)c3O)CC2)c(=O)c2nc(NC3CC3)cnc2n1CC(=O)Nc1ccc(C(F)(F)F)cc1Cl] | LCMS 1 | 686.2 | 0.56 |
| I-166 | 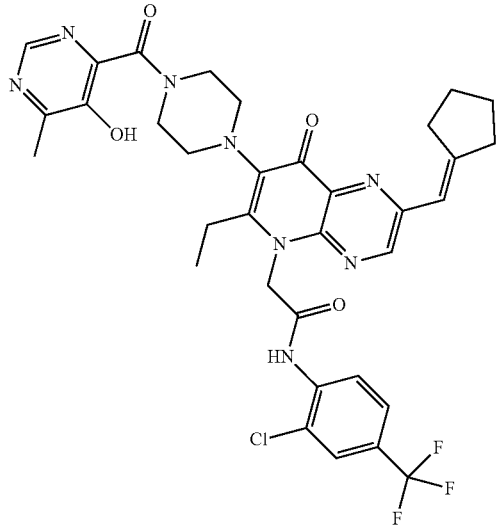 [SMILES: CCc1c(N2CCN(C(=O)c3ncnc(C)c3O)CC2)c(=O)c2nc(C=C3CCCC3)cnc2n1CC(=O)Nc1ccc(C(F)(F)F)cc1Cl] | LCMS 1 | 711.4 | 0.65 |

TABLE 2-continued
| No. | Method | (Mass Observed) [g/mol] | (Retention time) [min] |
|---|---|---|---|
| I-167 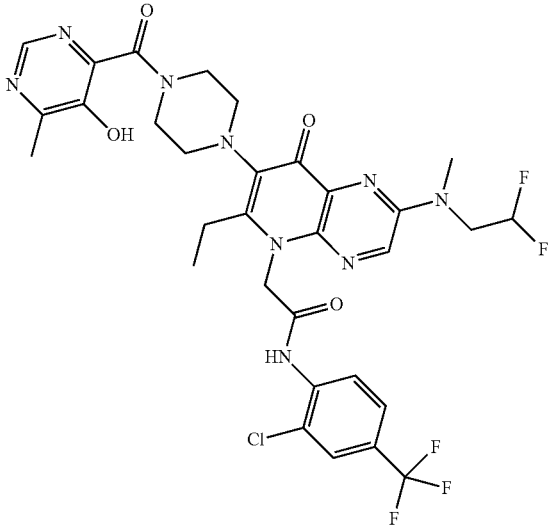 [SMILES: CCc1c(N2CCN(C(=O)c3ncnc(C)c3O)CC2)c(=O)c2nc(N(C)CC(F)F)cnc2n1CC(=O)Nc1ccc(C(F)(F)F)cc1Cl] | LCMS 1 | 724.4 | 0.60 |
| I-168 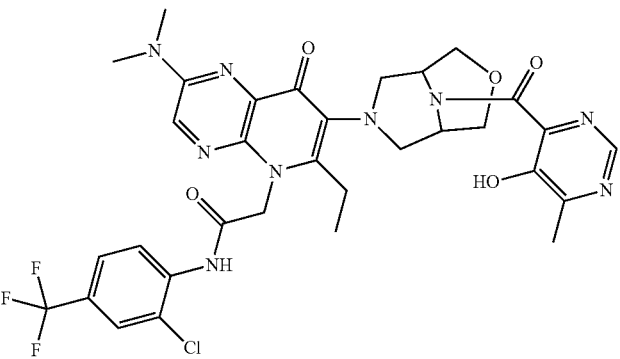 [SMILES: CCc1c(N2CC3COCC(C2)N3C(=O)c2ncnc(C)c2O)c(=O)c2nc(N(C)C)cnc2n1CC(=O)Nc1ccc(C(F)(F)F)cc1Cl] | LCMS 1 | 716.4 | 0.57 |
| I-169 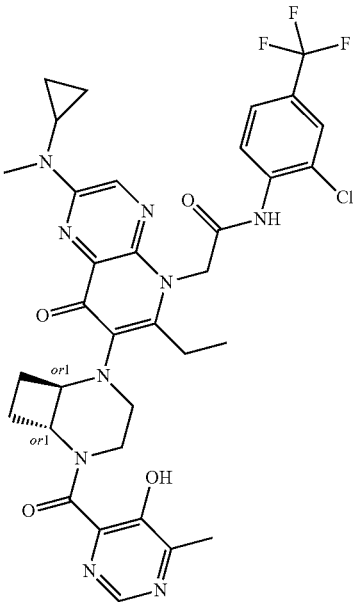 [SMILES: CCc1c(N2CCN(C(=O)c3ncnc(C)c3O)[C@@H]3CC[C@H]32)c(=O)c2nc(N(C)C3CC3)cnc2n1CC(=O)Nc1ccc(C(F)(F)F)cc1Cl] | LCMS 1 | 726.2 | 0.59 |

TABLE 2-continued
| No. | | Method | (Mass Observed) [g/mol] | (Retention time) [min] |
|---|---|---|---|---|
| I-170 | 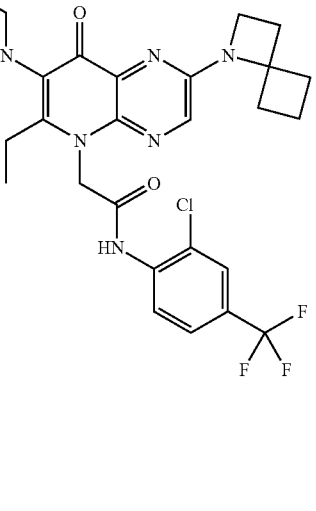 | LCMS 1 | 726.5 | 0.61 |
| I-171 | 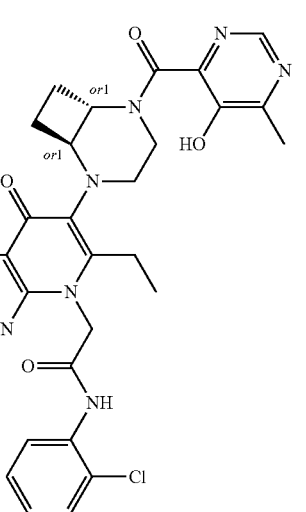 | LCMS 9 | 686.2 | 1.49 |

TABLE 2-continued

| No. | Method | (Mass Observed) [g/mol] | (Retention time) [min] |
|---|---|---|---|
| I-172 | LCMS 9 | 686.2 | 1.49 |
| I-173 | LCMS 2 | 688.4 | 0.81 |

TABLE 2-continued
| No. | | Method | (Mass Observed) [g/mol] | (Retention time) [min] |
|---|---|---|---|---|
| I-174 | 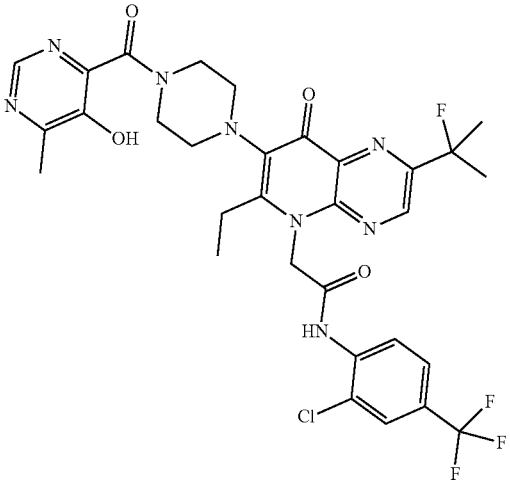 [SMILES: CCc1c(N2CCN(C(=O)c3ncnc(C)c3O)CC2)c(=O)c2nc(C(C)(C)F)cnc2n1CC(=O)Nc1ccc(C(F)(F)F)cc1Cl] | LCMS 1 | 691.1 | 0.88 |
| I-175 | 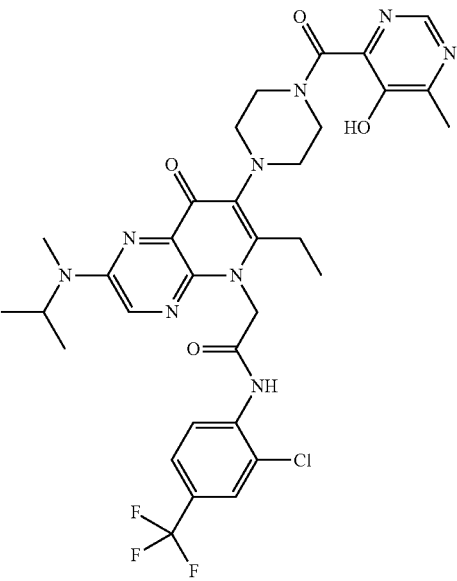 [SMILES: CCc1c(N2CCN(C(=O)c3ncnc(C)c3O)CC2)c(=O)c2nc(N(C)C(C)C)cnc2n1CC(=O)Nc1ccc(C(F)(F)F)cc1Cl] | LCMS 1 | 702.2 | 0.56 |

TABLE 2-continued
| No. | | Method | (Mass Observed) [g/mol] | (Retention time) [min] |
|---|---|---|---|---|
| I-176 | 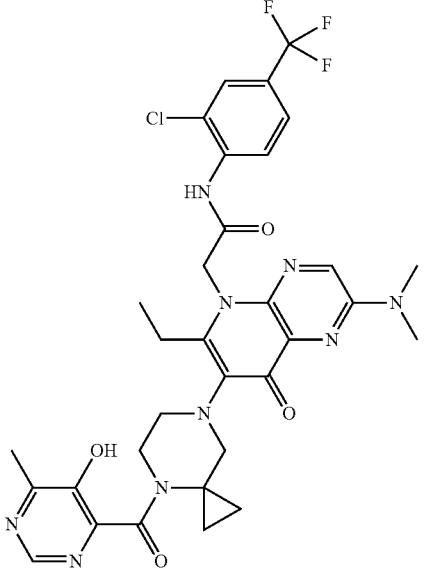 [SMILES: CCc1c(N2CCN(C(=O)c3ncnc(C)c3O)C3(CC3)C2)c(=O)c2nc(N(C)C)cnc2n1CC(=O)Nc1ccc(C(F)(F)F)cc1Cl] | LCMS 1 | 700.5 | 0.58 |
| I-177 | 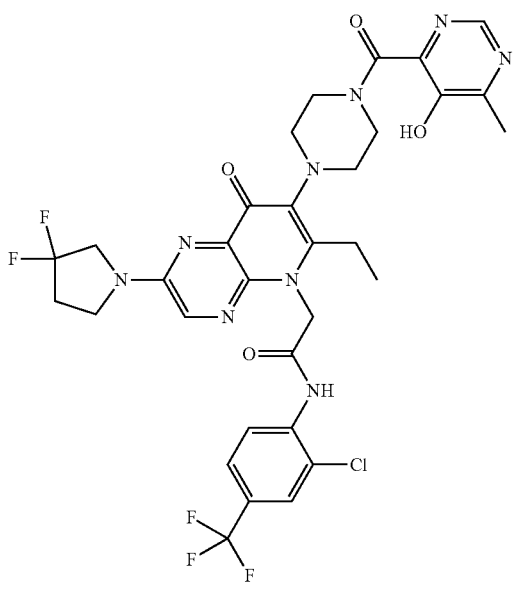 [SMILES: CCc1c(N2CCN(C(=O)c3ncnc(C)c3O)CC2)c(=O)c2nc(N3CCC(F)(F)C3)cnc2n1CC(=O)Nc1ccc(C(F)(F)F)cc1Cl] | LCMS 1 | 736.4 | 0.60 |

TABLE 2-continued
| No. | | Method | (Mass Observed) [g/mol] | (Retention time) [min] |
|---|---|---|---|---|
| I-178 | 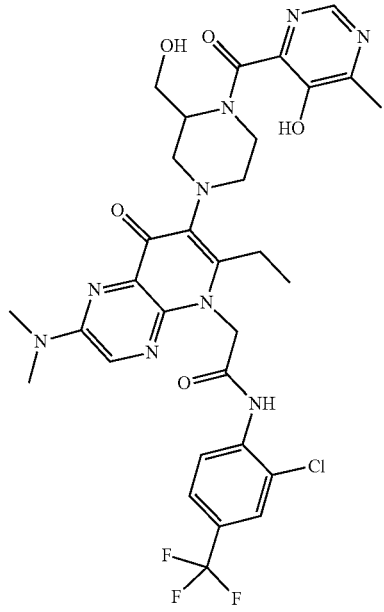 | LCMS 1 | 704.4 | 0.54 |
| I-179 | 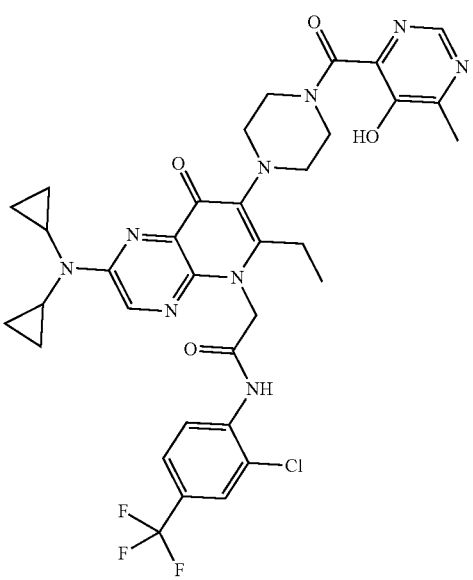 [SMILES: CCc1c(N2CCN(C(=O)c3ncnc(C)c3O)CC2)c(=O)c2nc(N(C3CC3)C3CC3)cnc2n1CC(=O)Nc1ccc(C(F)(F)F)cc1Cl] | LCMS 1 | 726.2 | 0.58 |

TABLE 2-continued
| No. | | Method | (Mass Observed) [g/mol] | (Retention time) [min] |
|---|---|---|---|---|
| I-180 | 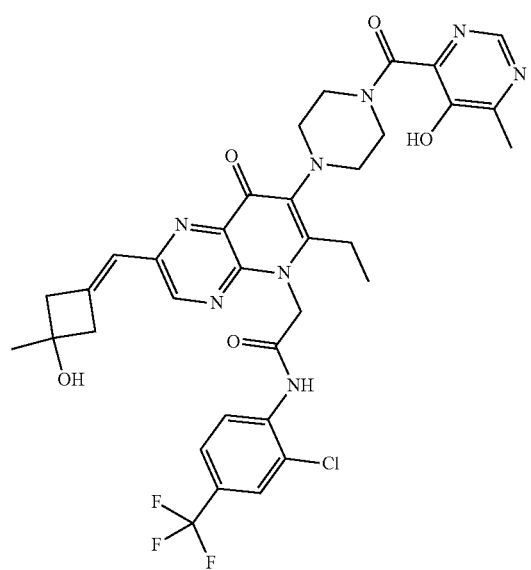 [SMILES: CCc1c(N2CCN(C(=O)c3ncnc(C)c3O)CC2)c(=O)c2nc(C=C3CC(C)(O)C3)cnc2n1CC(=O)Nc1ccc(C(F)(F)F)cc1Cl] | LCMS 1 | 727.2 | 0.55 |
| I-181 | 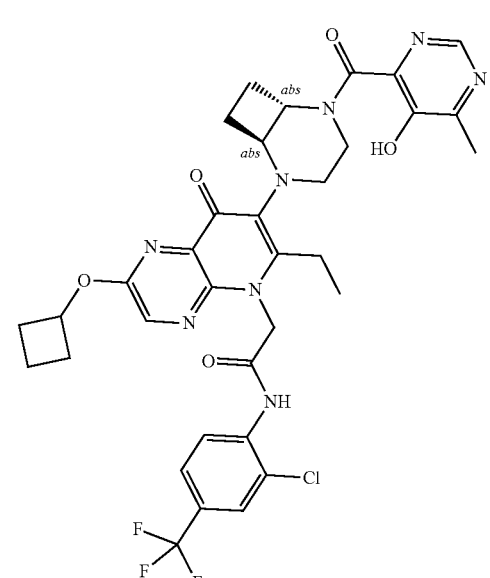 | LCMS 1 | 727.3 | 2.52 |

TABLE 2-continued
| No. | | Method | (Mass Observed) [g/mol] | (Retention time) [min] |
|---|---|---|---|---|
| I-182 | 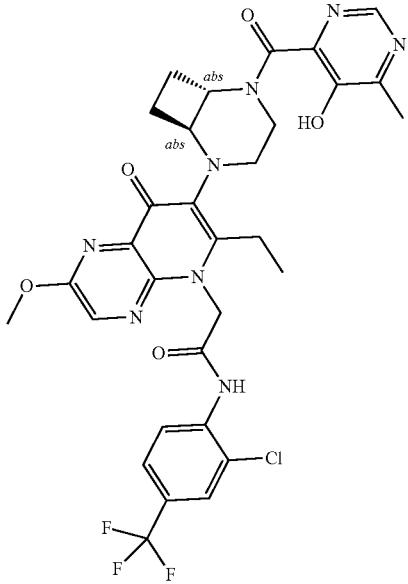 | LCMS 1 | 687.2 | 2.32 |
| I-183 | 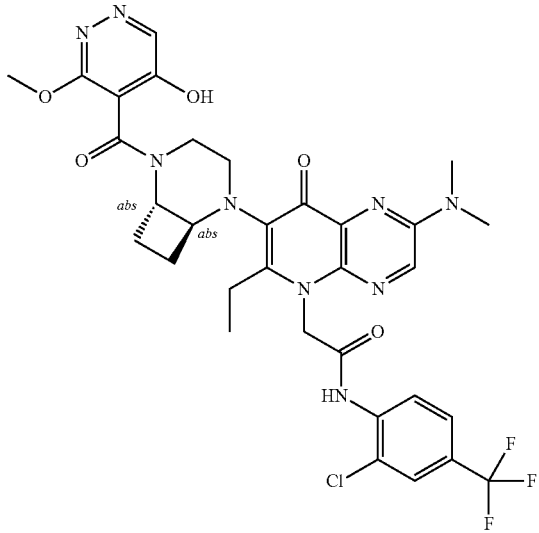 [SMILES: CCc1c(N2CCN(C(=O)c3c(O)cnnc3OC)[C@H]3CC[C@@H]32)c(=O)c2nc(N(C)C)cnc2n1CC(=O)Nc1ccc(C(F)(F)F)cc1Cl] | LCMS 1 | 716.2 | 2.10 |

TABLE 2-continued

| No. | Method | (Mass Observed) [g/mol] | (Retention time) [min] |
|---|---|---|---|
| I-184 | LCMS 1 | 672.2 | 2.10 |
| I-185 | LCMS 1 | 746.2 | 2.25 |

TABLE 2-continued
| No. | | Method | (Mass Observed) [g/mol] | (Retention time) [min] |
|---|---|---|---|---|
| I-186 | 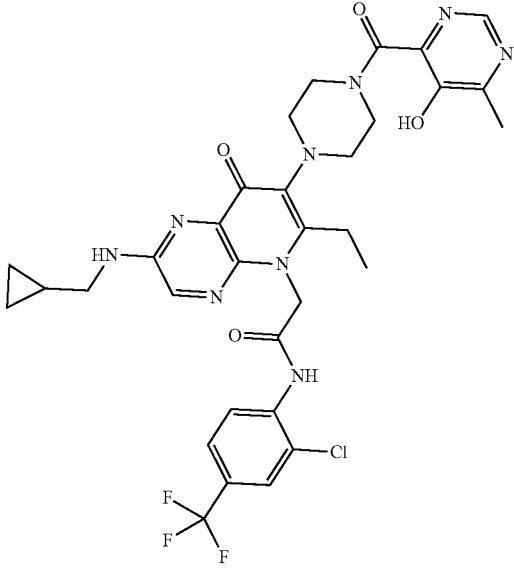 [SMILES: CCc1c(N2CCN(C(=O)c3ncnc(C)c3O)CC2)c(=O)c2nc(NCC3CC3)cnc2n1CC(=O)Nc1ccc(C(F)(F)F)cc1Cl] | LCMS 1 | 700.2 | 0.54 |
| I-187 | 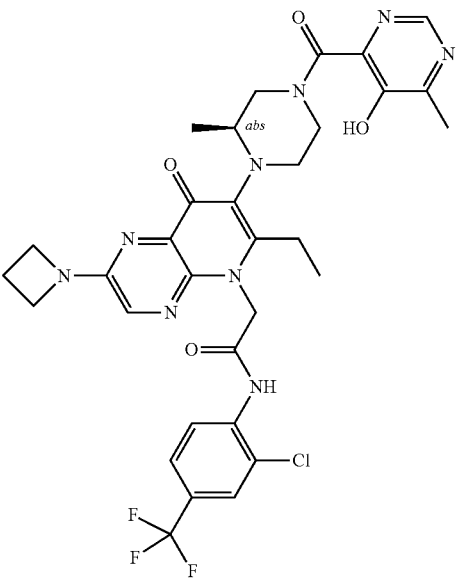 [SMILES: CCc1c(N2CCN(C(=O)c3ncnc(C)c3O)C[C@@H]2C)c(=O)c2nc(N3CCC3)cnc2n1CC(=O)Nc1ccc(C(F)(F)F)cc1Cl] | LCMS 1 | 700.3 | 2.20 |

TABLE 2-continued
| No. | | Method | (Mass Observed) [g/mol] | (Retention time) [min] |
|---|---|---|---|---|
| I-188 | 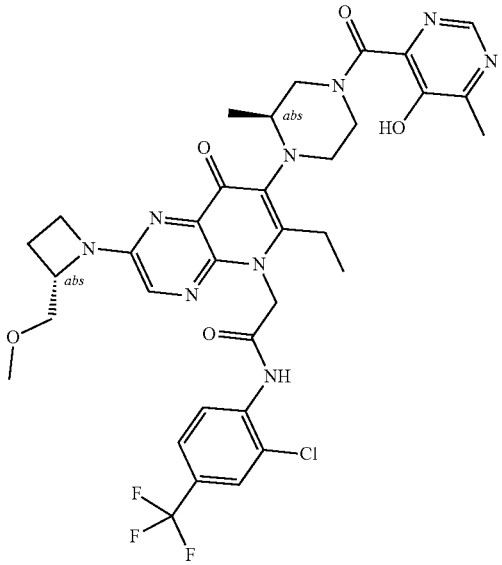 [SMILES: CCc1c(N2CCN(C(=O)c3ncnc(C)c3O)C[C@@H]2C)c(=O)c2nc(N3CC[C@H]3COC)cnc2n1CC(=O)Nc1ccc(C(F)(F)F)cc1Cl] | LCMS 1 | 744.2 | 2.22 |
| I-189 | 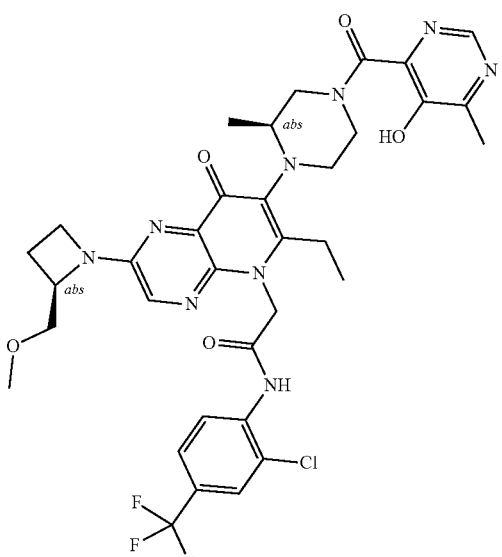 | LCMS 1 | 744.3 | 2.21 |

TABLE 2-continued
| No. | Method | (Mass Observed) [g/mol] | (Retention time) [min] |
|---|---|---|---|
| I-190 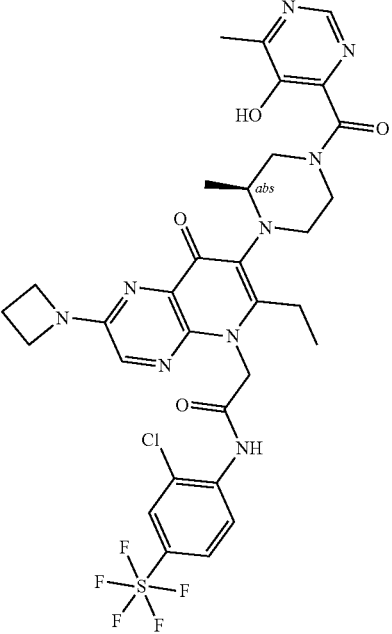 [SMILES: CCc1c(N2CCN(C(=O)c3ncnc(C)c3O)C[C@@H]2C)c(=O)c2nc(N3CCC3)cnc2n1CC(=O)Nc1ccc(S(F)(F)(F)(F)F)cc1Cl] | LCMS 1 | 758.2 | 2.29 |
| I-191 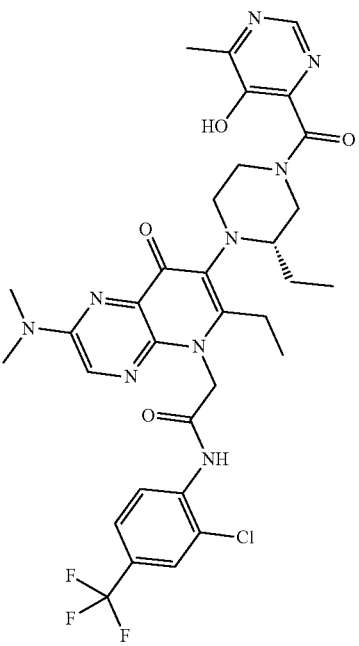 [SMILES: CCc1c(N2CCN(C(=O)c3ncnc(C)c3O)C[C@@H]2CC)c(=O)c2nc(N(C)C)cnc2n1CC(=O)Nc1ccc(C(F)(F)F)cc1Cl] | LCMS 1 | 702.2 | 0.56 |

TABLE 2-continued
| No. | | Method | (Mass Observed) [g/mol] | (Retention time) [min] |
|---|---|---|---|---|
| I-192 | 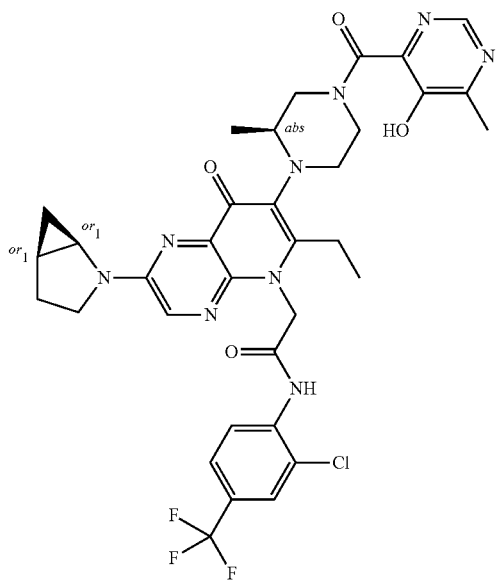 [SMILES: CCc1c(N2CCN(C(=O)c3ncnc(C)c3O)C[C@@H]2C)c(=O)c2nc(N3CC[C@H]4C[C@H]43)cnc2n1CC(=O)Nc1ccc(C(F)(F)F)cc1Cl] | LCMS 1 | 726.2 | 0.86 |
| I-193 | 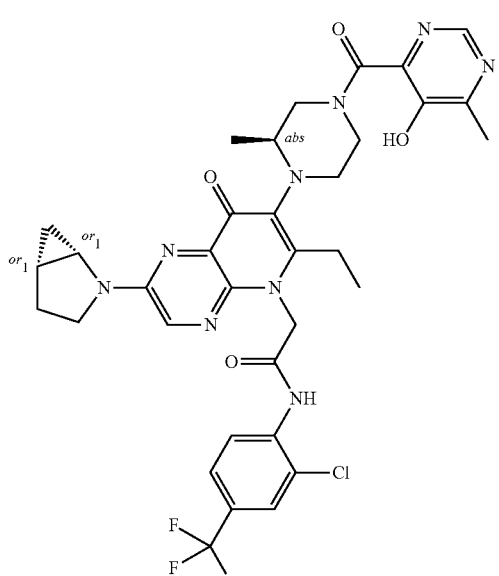 | LCMS 1 | 726.2 | 0.87 |

TABLE 2-continued
| No. | | Method | (Mass Observed) [g/mol] | (Retention time) [min] |
|---|---|---|---|---|
| I-194 | 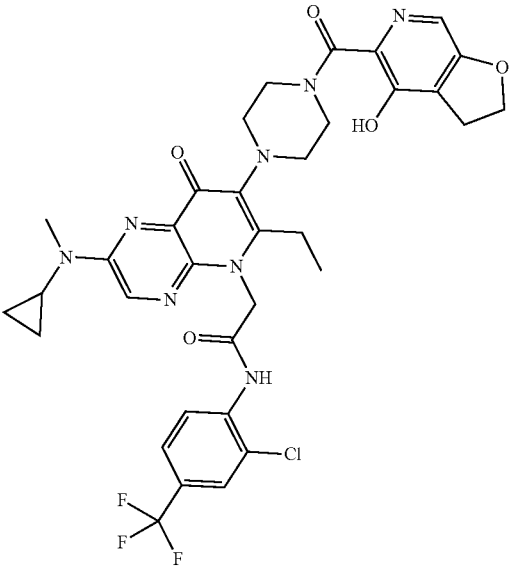 [SMILES: CCc1c(N2CCN(C(=O)c3ncc4c(c3O)CCO4)CC2)c(=O)c2nc(N(C)C3CC3)cnc2n1CC(=O)Nc1ccc(C(F)(F)F)cc1Cl] | LCMS 1 | 727.4 | 0.60 |
| I-195 | 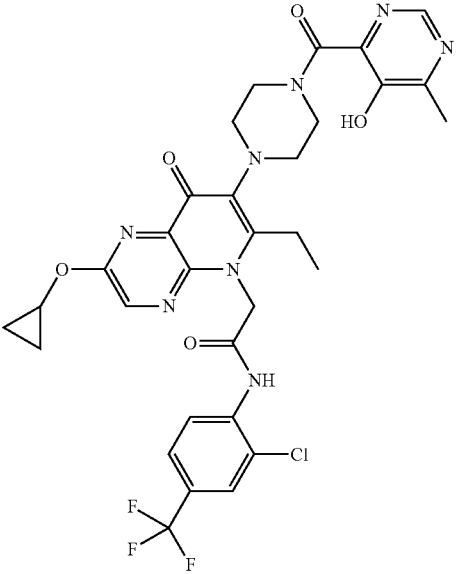 [SMILES: CCc1c(N2CCN(C(=O)c3ncnc(C)c3O)CC2)c(=O)c2nc(OC3CC3)cnc2n1CC(=O)Nc1ccc(C(F)(F)F)cc1Cl] | LCMS 1 | 687.2 | 0.58 |
| I-196 | 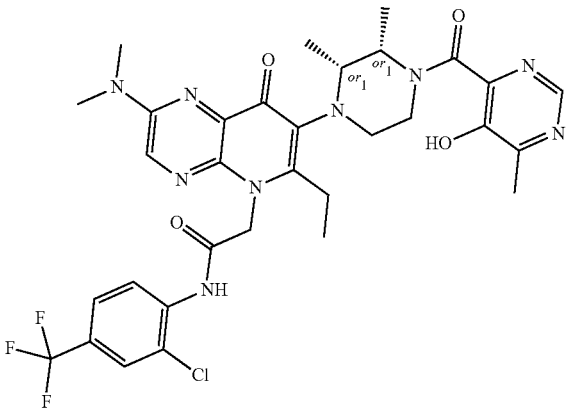 [SMILES: CCc1c(N2CCN(C(=O)c3ncnc(C)c3O)[C@@H](C)[C@H]2C)c(=O)c2nc(N(C)C)cnc2n1CC(=O)Nc1ccc(C(F)(F)F)cc1Cl] | LCMS 1 | 702.3 | 0.92 |

TABLE 2-continued
| No. | | Method | (Mass Observed) [g/mol] | (Retention time) [min] |
|---|---|---|---|---|
| I-197 | 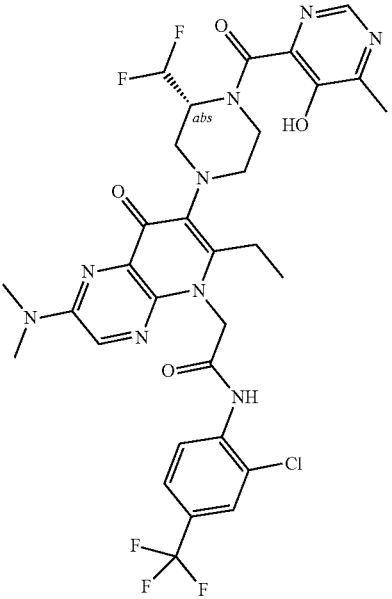 | LCMS 1 | 724.2 | 0.57 |
| I-198 | 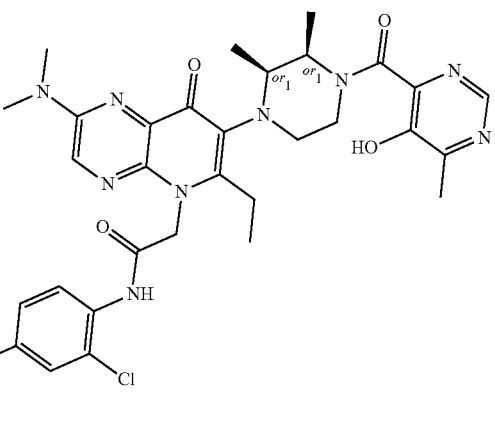 | LCMS 1 | 702.3 | 0.92 |

TABLE 2-continued
| No. | | Method | (Mass Observed) [g/mol] | (Retention time) [min] |
|---|---|---|---|---|
| I-199 | 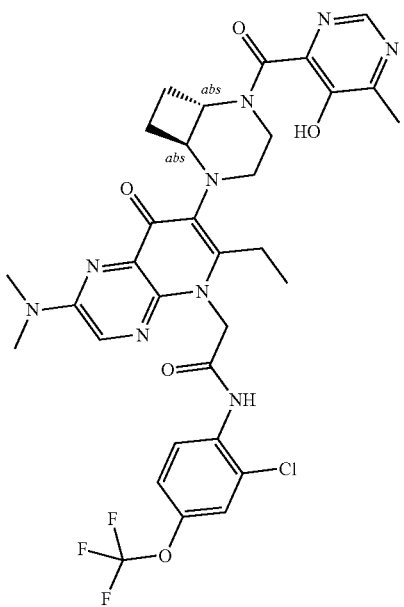 | LCMS 1 | 716.3 | 2.23 |
| I-200 | 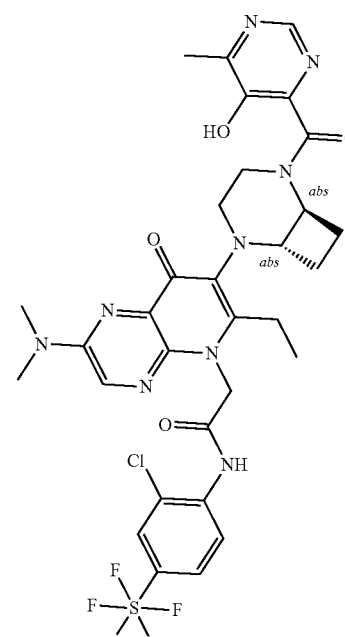 | LCMS 1 | 758.2 | 2.29 |

TABLE 2-continued
| No. | Method | (Mass Observed) [g/mol] | (Retention time) [min] |
|---|---|---|---|
| I-201 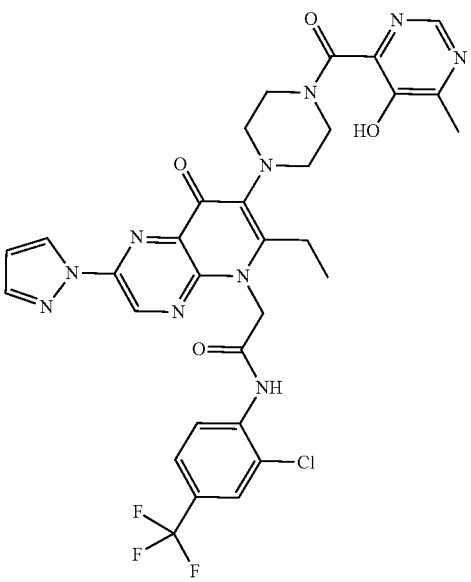 [SMILES: CCc1c(N2CCN(C(=O)c3ncnc(C)c3O)CC2)c(=O)c2nc(-n3cccn3)cnc2n1CC(=O)Nc1ccc(C(F)(F)F)cc1Cl] | LCMS 11 | 697.3 | 0.57 |
| I-203 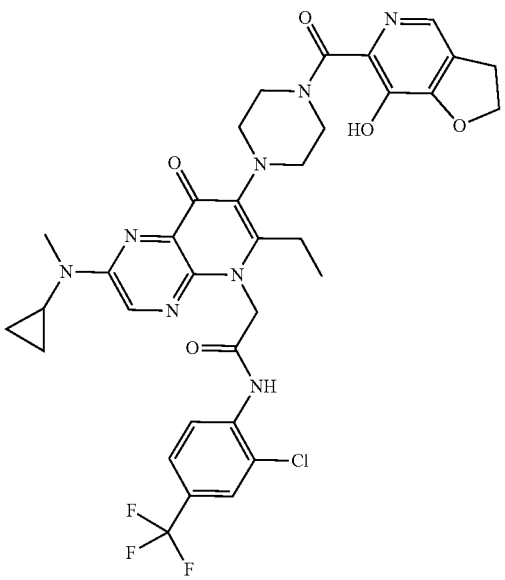 [SMILES: CCc1c(N2CCN(C(=O)c3ncc4c(c3O)OCC4)CC2)c(=O)c2nc(N(C)C3CC3)cnc2n1CC(=O)Nc1ccc(C(F)(F)F)cc1Cl] | LCMS 1 | 727.4 | 0.56 |

TABLE 2-continued

| No. | Method | (Mass Observed) [g/mol] | (Retention time) [min] |
|---|---|---|---|
| I-204 | LCMS 1 | 703.2 | 0.53 |
| I-205 | LCMS 1 | 714.2 | 0.58 |

TABLE 2-continued
| No. | | Method | (Mass Observed) [g/mol] | (Retention time) [min] |
|---|---|---|---|---|
| I-206 | 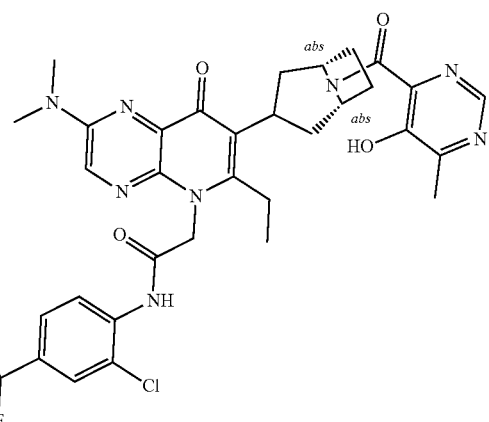 | LCMS 1 | 700.3 | 0.58 |
| I-207 | 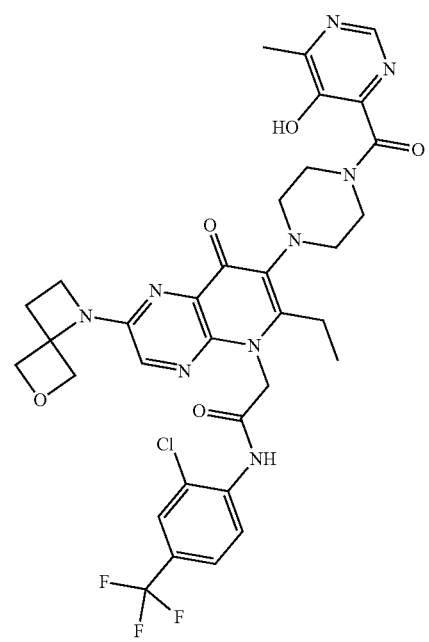 [SMILES: CCc1c(N2CCN(C(=O)c3ncnc(C)c3O)CC2)c(=O)c2nc(N3CCC34COC4)cnc2n1CC(=O)Nc1ccc(C(F)(F)F)cc1Cl] | LCMS 1 | 728.3 | 0.50 |

TABLE 2-continued

| No. | | Method | (Mass Observed) [g/mol] | (Retention time) [min] |
|---|---|---|---|---|
| I-208 | | LCMS 1 | 714.3 | 0.55 |
| I-209 | | LCMS 1 | 714.3 | 0.56 |

TABLE 2-continued
| No. | Method | (Mass Observed) [g/mol] | (Retention time) [min] |
|---|---|---|---|
| I-210 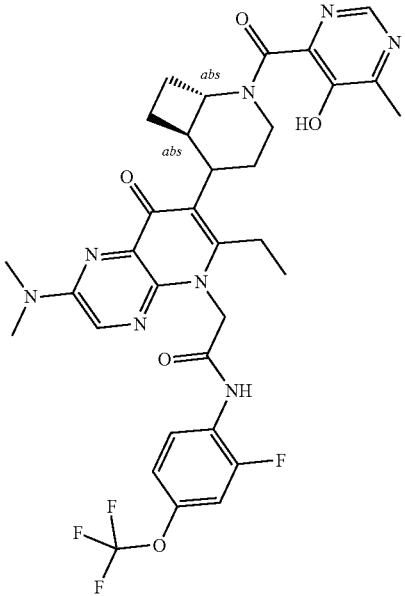 | LCMS 1 | 700.3 | 2.15 |
| I-211 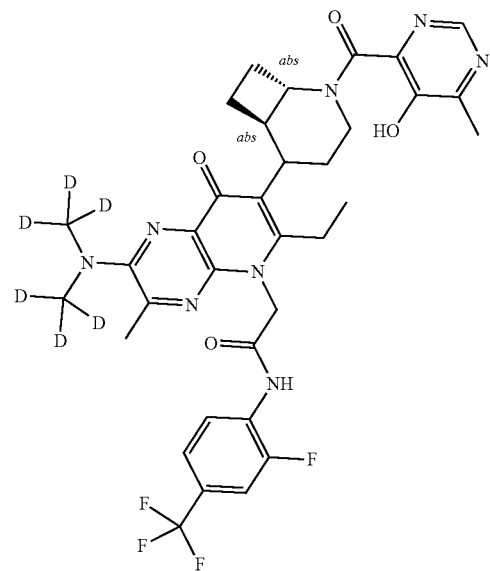 [SMILES: [2H]C([2H])([2H])N(c1nc2c(=O)c(C3CCN(C(=O)c4ncnc(C)c4O)[C@H]4CC[C@H]34)c(CC)n(CC(=O)Nc3ccc(C(F)(F)F)cc3F)c2nc1C)C([2H])([2H])[2H]] | LCMS 1 | 704.3 | 2.21 |

TABLE 2-continued
| No. | | Method | (Mass Observed) [g/mol] | (Retention time) [min] |
|---|---|---|---|---|
| I-212 | 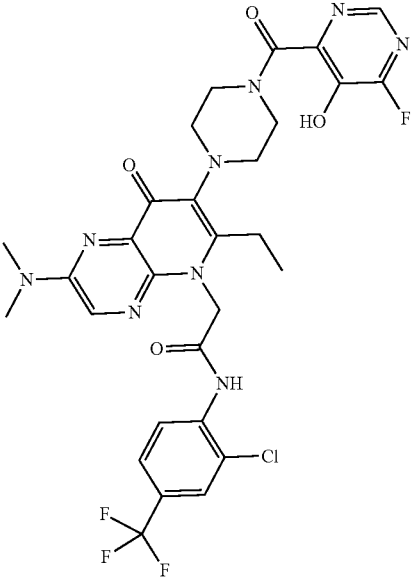 [SMILES: CCc1c(N2CCN(C(=O)c3ncnc(F)c3O)CC2)c(=O)c2nc(N(C)C)cnc2n1CC(=O)Nc1ccc(C(F)(F)F)cc1Cl] | LCMS 1 | 677.4 | 0.52 |
| I-213 | 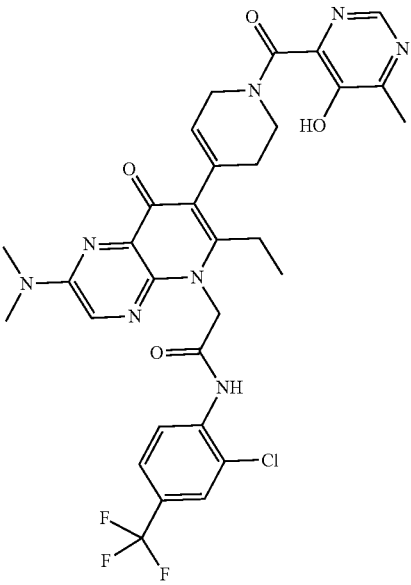 | LCMS 1 | 671.2 | 2.07 |

TABLE 2-continued
| No. | | Method | (Mass Observed) [g/mol] | (Retention time) [min] |
|---|---|---|---|---|
| I-214 | 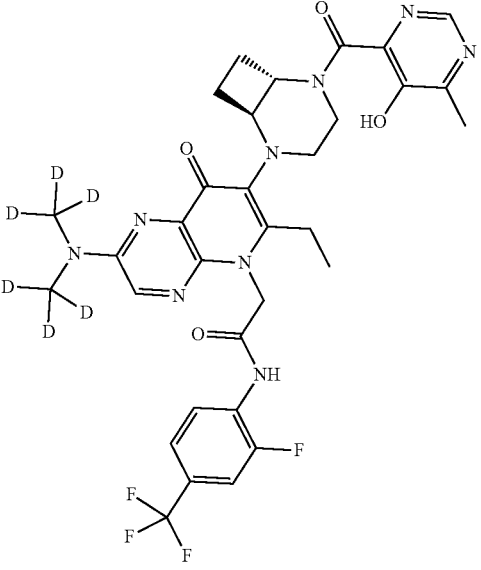 [SMILES: [2H]C([2H])([2H])N(c1cnc2c(n1)c(=O)c(N1CCN(C(=O)c3ncnc(C)c3O)[C@H]3CC[C@@H]31)c(CC)n2CC(=O)Nc1ccc(C(F)(F)F)cc1F)C([2H])([2H])[2H]] | LCMS 1 | 690.3 | 0.55 |
| I-215 | 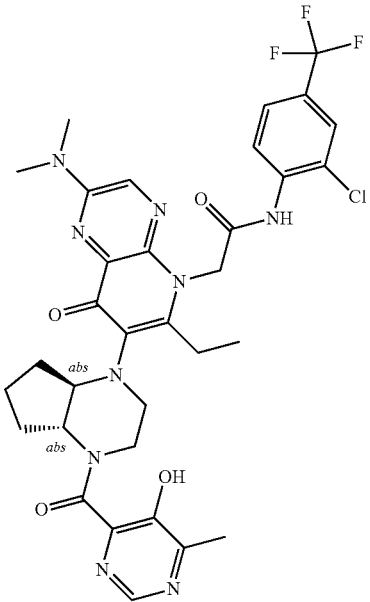 [SMILES: CCc1c(N2CCN(C(=O)c3ncnc(C)c3O)[C@@H]3CCC[C@H]32)c(=O)c2nc(N(C)C)cnc2n1CC(=O)Nc1ccc(C(F)(F)F)cc1Cl] | LCMS 4 | 714.3 | 0.43 |

TABLE 2-continued
| No. | | Method | (Mass Observed) [g/mol] | (Retention time) [min] |
|---|---|---|---|---|
| I-216 | 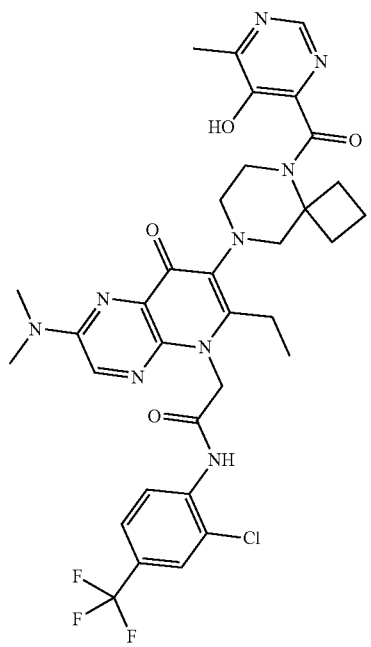 [SMILES: CCc1c(N2CCN(C(=O)c3ncnc(C)c3O)C3(CCC3)C2)c(=O)c2nc(N(C)C)cnc2n1CC(=O)Nc1ccc(C(F)(F)F)cc1Cl] | LCMS 10 | 714.4 | 1.76 |
| I-217 | 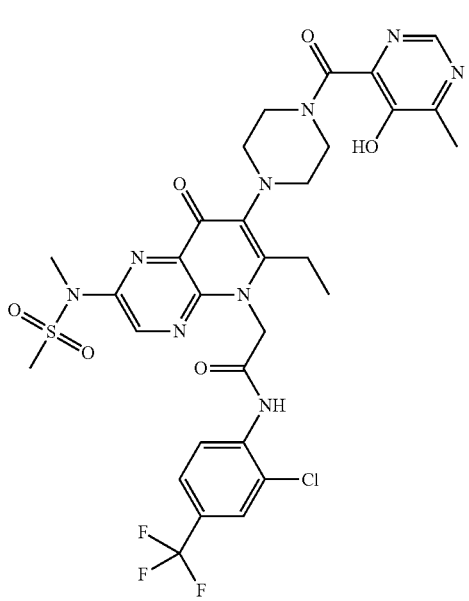 [SMILES: CCc1c(N2CCN(C(=O)c3ncnc(C)c3O)CC2)c(=O)c2nc(N(C)S(C)(=O)=O)cnc2n1CC(=O)Nc1ccc(C(F)(F)F)cc1Cl] | LCMS 1 | 738.1 | 0.55 |

TABLE 2-continued
| No. | | Method | (Mass Observed) [g/mol] | (Retention time) [min] |
|---|---|---|---|---|
| I-218 | 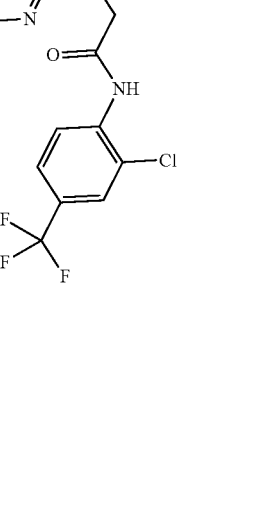 | LCMS 1 | 693.2 | 2.16 |
| I-219 |  | LCMS 1 | 738.4 | 0.62 |

TABLE 2-continued
| No. | | Method | (Mass Observed) [g/mol] | (Retention time) [min] |
|---|---|---|---|---|
| I-220 | 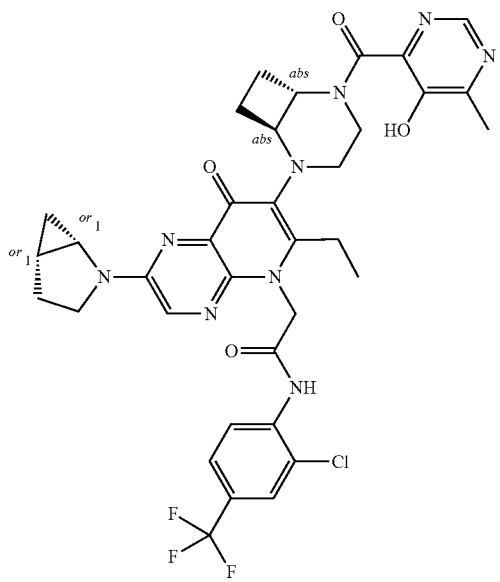 [SMILES: CCc1c(N2CCN(C(=O)c3ncnc(C)c3O)[C@H]3CC[C@@H]32)c(=O)c2nc(N3CC[C@@H]4C[C@@H]43)cnc2n1CC(=O)Nc1ccc(C(F)(F)F)cc1Cl] | LCMS 1 | 738.4 | 0.62 |
| I-221 | 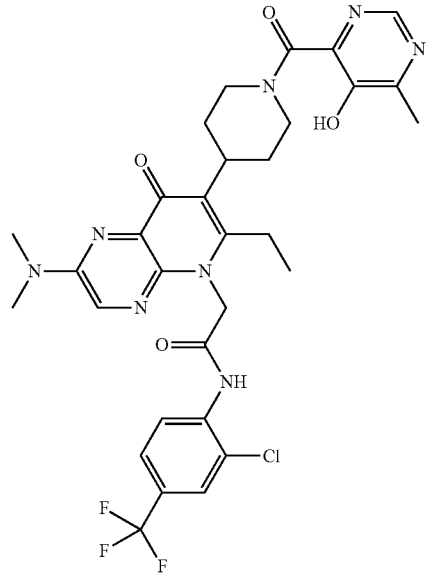 | LCMS 1 | 673.2 | 0.53 |

TABLE 2-continued
| No. | | Method | (Mass Observed) [g/mol] | (Retention time) [min] |
|---|---|---|---|---|
| I-222 | 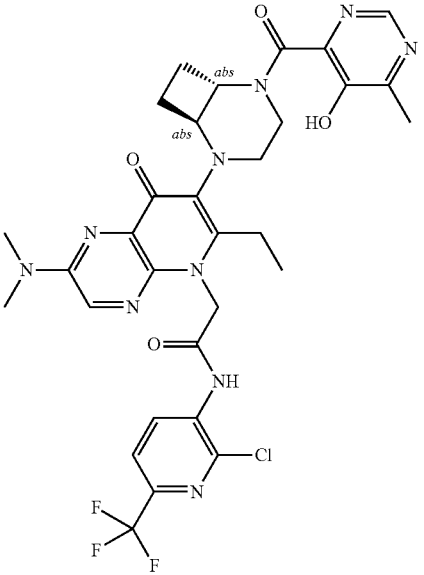 | LCMS 1 | 701.4 | 0.52 |
| I-223 | 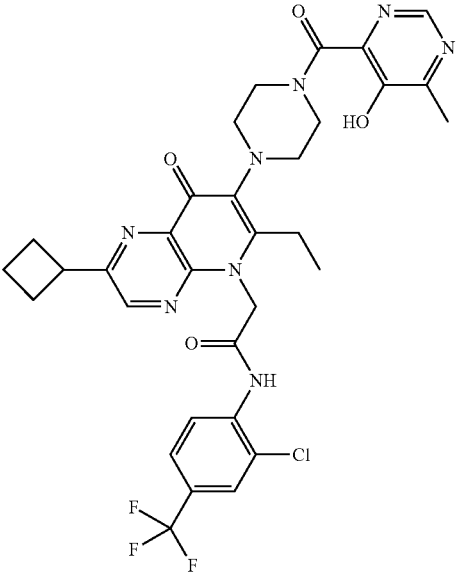 [SMILES: CCc1c(N2CCN(C(=O)c3ncnc(C)c3O)CC2)c(=O)c2nc(C3CCC3)cnc2n1CC(=O)Nc1ccc(C(F)(F)F)cc1Cl] | LCMS 1 | 685.4 | 0.62 |

TABLE 2-continued
| No. | | Method | (Mass Observed) [g/mol] | (Retention time) [min] |
|---|---|---|---|---|
| I-224 | 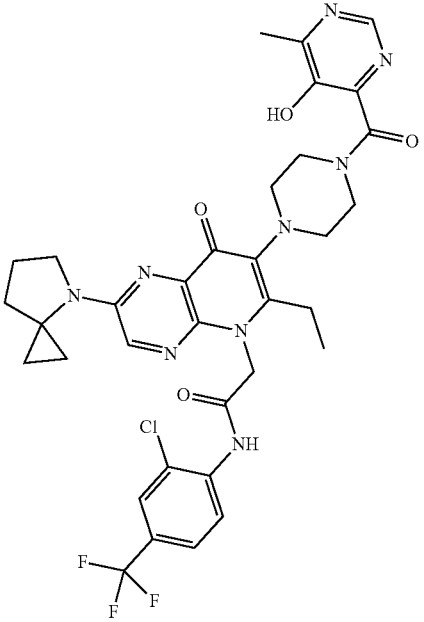 [SMILES: CCc1c(N2CCN(C(=O)c3ncnc(C)c3O)CC2)c(=O)c2nc(N3CCCC34CC4)cnc2n1CC(=O)Nc1ccc(C(F)(F)F)cc1Cl] | LCMS 1 | 726.2 | 0.60 |
| I-225 | 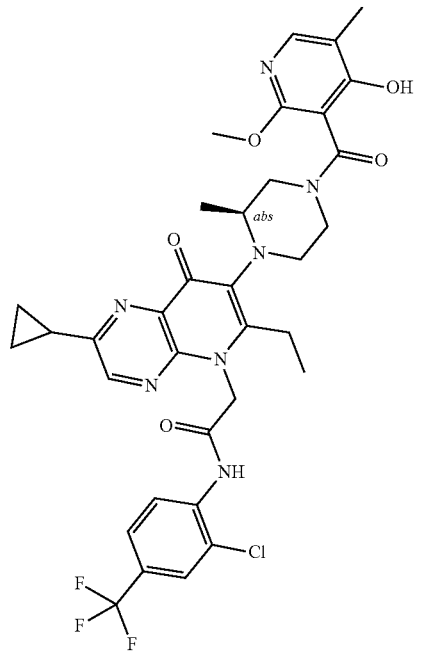 [SMILES: CCc1c(N2CCN(C(=O)c3c(OC)ncc(C)c3O)C[C@@H]2C)c(=O)c2nc(C3CC3)cnc2n1CC(=O)Nc1ccc(C(F)(F)F)cc1Cl] | LCMS 1 | 714.2 | 0.57 |

| No. | | Method | (Mass Observed) [g/mol] | (Retention time) [min] |
|---|---|---|---|---|
| I-226 | 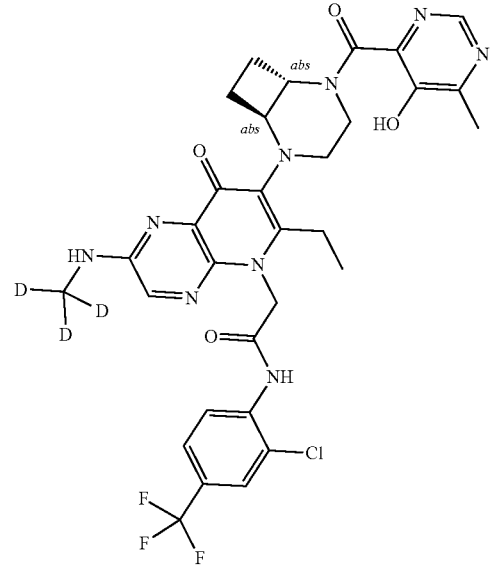 [SMILES: [2H]C([2H])([2H])Nc1cnc2c(n1)c(=O)c(N1CCN(C(=O)c3ncnc(C)c3O)[C@H]3CC[C@@H]31)c(CC)n2CC(=O)Nc1ccc(C(F)(F)F)cc1Cl] | LCMS 1 | 689.3 | 2.15 |
| I-227 | 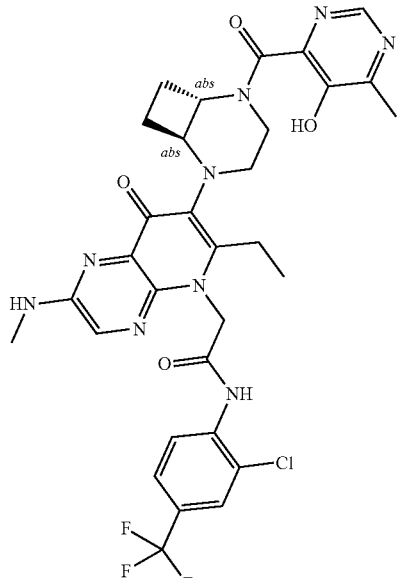 | LCMS 1 | 686.2 | 2.09 |

TABLE 2-continued
| No. | Method | (Mass Observed) [g/mol] | (Retention time) [min] |
|---|---|---|---|
| I-228 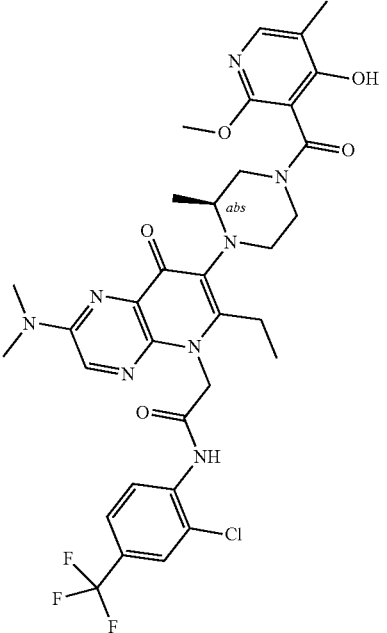 [SMILES: CCc1c(N2CCN(C(=O)c3c(OC)ncc(C)c3O)C[C@@H]2C)c(=O)c2nc(N(C)C)cnc2n1CC(=O)Nc1ccc(C(F)(F)F)cc1Cl] | LCMS 1 | 717.5 | 0.57 |
| I-229 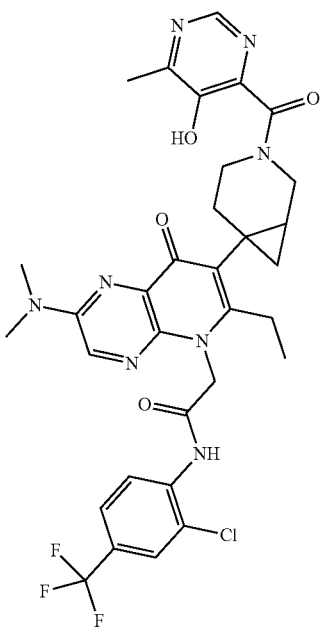 [SMILES: CCc1c(C23CCN(C(=O)c4ncnc(C)c4O)CC2C3)c(=O)c2nc(N(C)C)cnc2n1CC(=O)Nc1ccc(C(F)(F)F)cc1Cl] | LCMS 1 | 685.4 | 0.56 |

TABLE 2-continued
| No. | | Method | (Mass Observed) [g/mol] | (Retention time) [min] |
|---|---|---|---|---|
| I-230 | 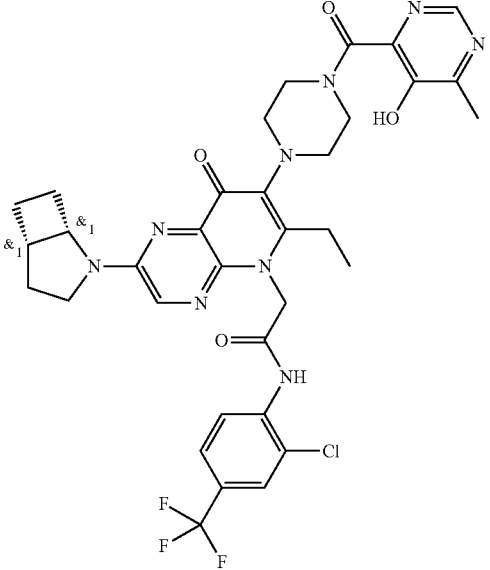 [SMILES: CCc1c(N2CCN(C(=O)c3ncnc(C)c3O)CC2)c(=O)c2nc(N3CC[C@@H]4CC[C@@H]43)cnc2n1CC(=O)Nc1ccc(C(F)(F)F)cc1Cl] | LCMS 4 | 726.4 | 0.45 |
| I-231 | 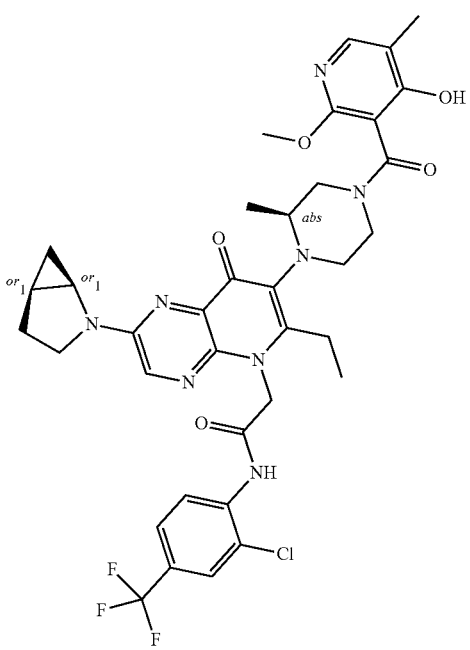 [SMILES: CCc1c(N2CCN(C(=O)c3c(OC)ncc(C)c3O)C[C@@H]2C)c(=O)c2nc(N3CC[C@H]4C[C@H]43)cnc2n1CC(=O)Nc1ccc(C(F)(F)F)cc1Cl] | LCMS 1 | 755.5 | 0.60 |

TABLE 2-continued

| No. | Method | (Mass Observed) [g/mol] | (Retention time) [min] |
|---|---|---|---|
| I-232 | LCMS 1 | 755.5 | 0.59 |
| I-233 | LCMS 1 | 702.3 | 2.15 |
| I-234 | LCMS 1 | 702.3 | 2.14 |

TABLE 2-continued
| No. | | Method | (Mass Observed) [g/mol] | (Retention time) [min] |
|---|---|---|---|---|
| I-236 | 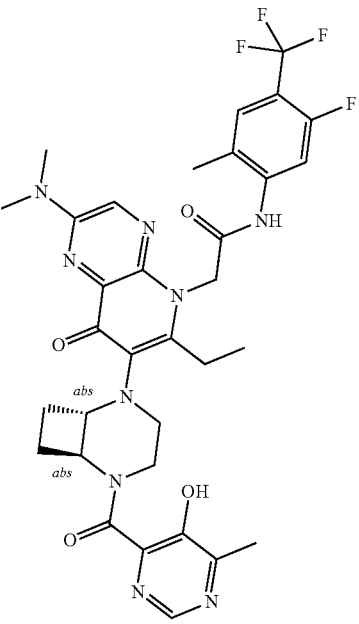 [SMILES: CCc1c(N2CCN(C(=O)c3ncnc(C)c3O)[C@H]3CC[C@@H]32)c(=O)c2nc(N(C)C)cnc2n1CC(=O)Nc1cc(F)c(C(F)(F)F)cc1C] | LCMS 1 | 698.4 | 0.54 |
| I-237 | 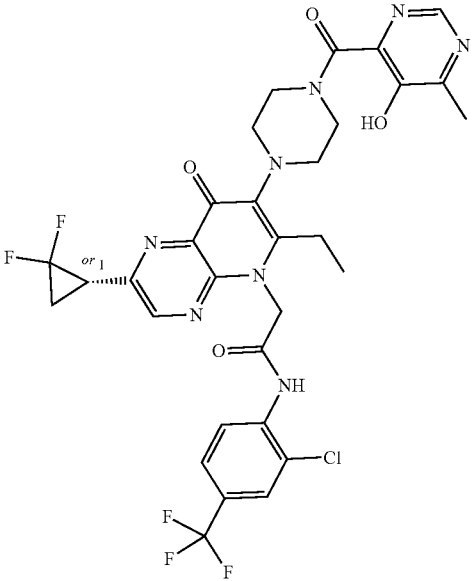 [SMILES: CCc1c(N2CCN(C(=O)c3ncnc(C)c3O)CC2)c(=O)c2nc([C@@H]3CC3(F)F)cnc2n1CC(=O)Nc1ccc(C(F)(F)F)cc1Cl] | LCMS 11 | 707.2 | 0.57 |

TABLE 2-continued
| No. | | Method | (Mass Observed) [g/mol] | (Retention time) [min] |
|---|---|---|---|---|
| I-238 | 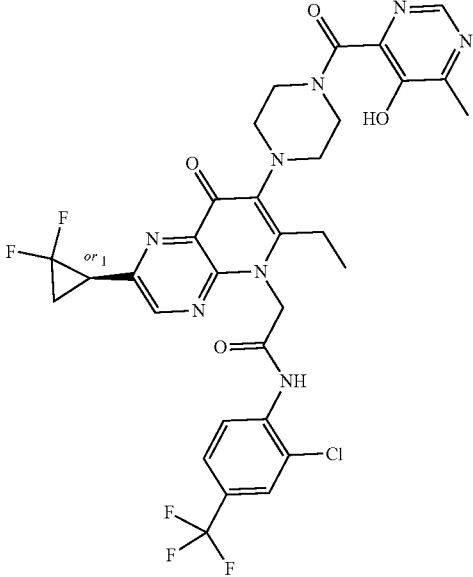 [SMILES: CCc1c(N2CCN(C(=O)c3ncnc(C)c3O)CC2)c(=O)c2nc([C@H]3CC3(F)F)cnc2n1CC(=O)Nc1ccc(C(F)(F)F)cc1Cl] | LCMS 11 | 707.3 | 0.57 |
| I-239 | 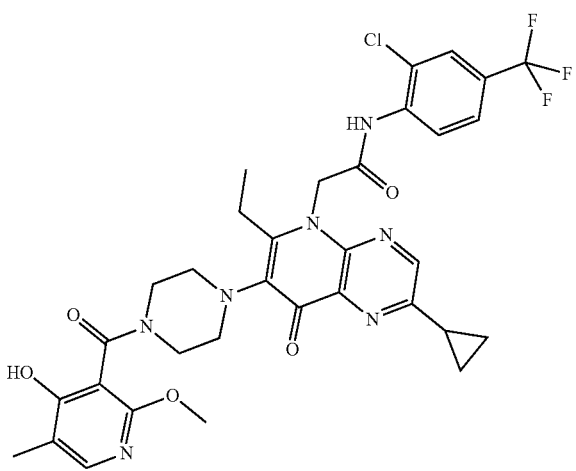 [SMILES: CCc1c(N2CCN(C(=O)c3c(OC)ncc(C)c3O)CC2)c(=O)c2nc(C3CC3)cnc2n1CC(=O)Nc1ccc(C(F)(F)F)cc1Cl] | LCMS 1 | 700.3 | 0.55 |

TABLE 2-continued
| No. | | Method | (Mass Observed) [g/mol] | (Retention time) [min] |
|---|---|---|---|---|
| I-240 | 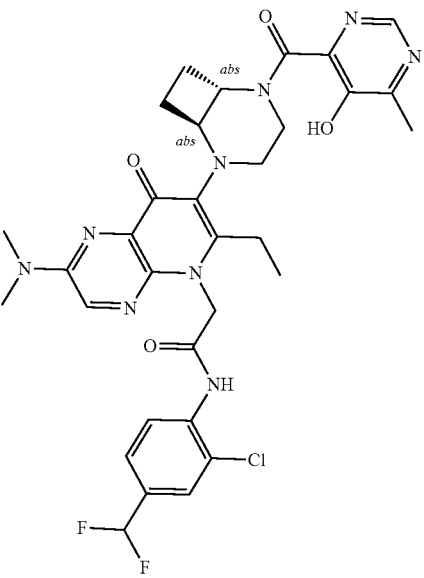 [SMILES: CCc1c(N2CCN(C(=O)c3ncnc(C)c3O)[C@H]3CC[C@@H]32)c(=O)c2nc(N(C)C)cnc2n1CC(=O)Nc1ccc(C(F)F)cc1Cl] | LCMS 1 | 682.2 | 0.51 |
| I-241 | 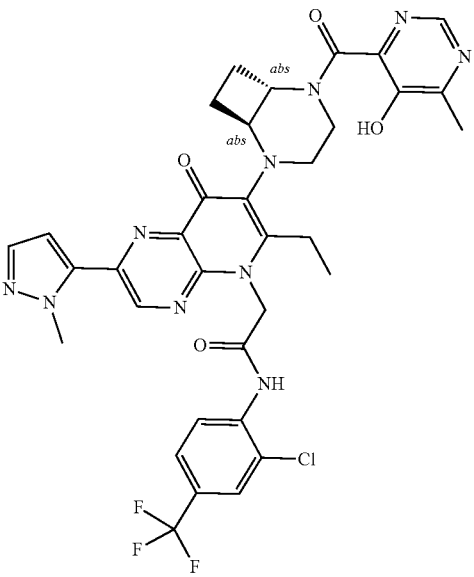 [SMILES: CCc1c(N2CCN(C(=O)c3ncnc(C)c3O)[C@H]3CC[C@@H]32)c(=O)c2nc(-c3ccnn3C)cnc2n1CC(=O)Nc1ccc(C(F)(F)F)cc1Cl] | LCMS 1 | 737.3 | 2.31 |

TABLE 2-continued
| No. | | Method | (Mass Observed) [g/mol] | (Retention time) [min] |
|---|---|---|---|---|
| I-242 | 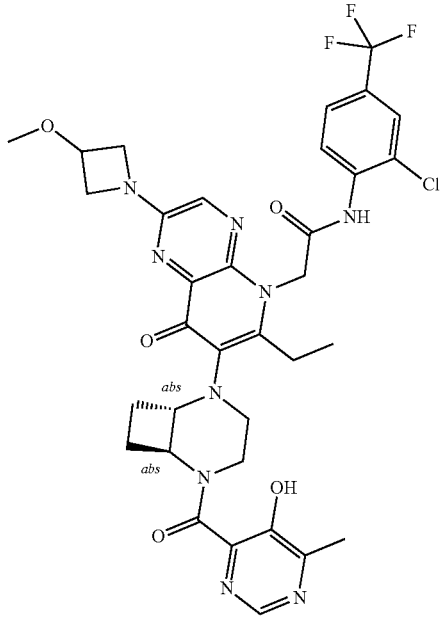 [SMILES: CCc1c(N2CCN(C(=O)c3ncnc(C)c3O)[C@H]3CC[C@@H]32)c(=O)c2nc(N3CC(OC)C3)cnc2n1CC(=O)Nc1ccc(C(F)(F)F)cc1Cl] | LCMS 1 | 742.3 | 2.22 |
| I-243 | 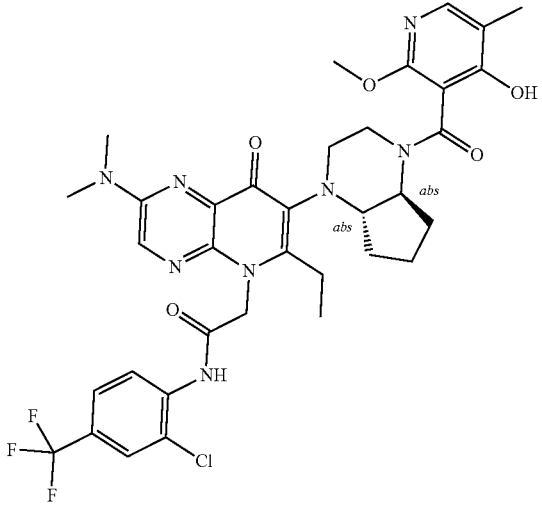 [SMILES: CCc1c(N2CCN(C(=O)c3c(OC)ncc(C)c3O)[C@H]3CCC[C@@H]32)c(=O)c2nc(N(C)C)cnc2n1CC(=O)Nc1ccc(C(F)(F)F)cc1Cl] | LCMS 4 | 743.3 | 0.46 |

TABLE 2-continued

| No. | Method | (Mass Observed) [g/mol] | (Retention time) [min] |
|---|---|---|---|
| I-244 | LCMS 1 | 704.3 | 0.51 |
| I-245 | LCMS 1 | 748.2 | 2.29 |

TABLE 2-continued
| No. | | Method | (Mass Observed) [g/mol] | (Retention time) [min] |
|---|---|---|---|---|
| I-246 | 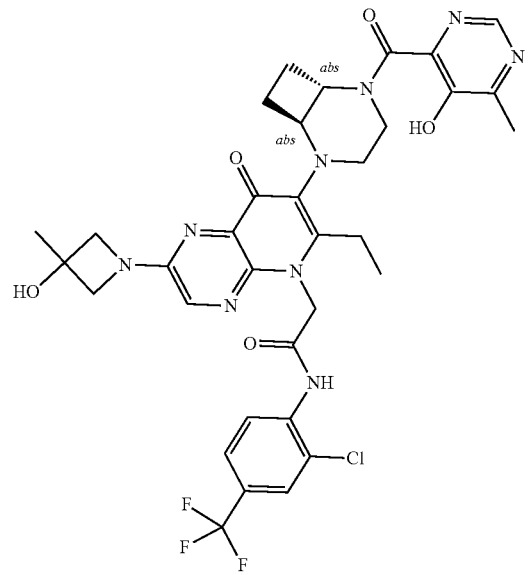 [SMILES: CCc1c(N2CCN(C(=O)c3ncnc(C)c3O)[C@H]3CC[C@@H]32)c(=O)c2nc(N3CC(C)(O)C3)cnc2n1CC(=O)Nc1ccc(C(F)(F)F)cc1Cl] | LCMS 1 | 742.2 | 2.15 |
| I-247 | 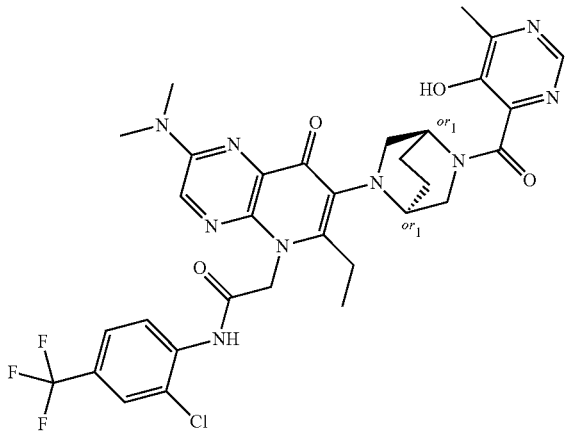 [SMILES: CCc1c(N2C[C@@H]3CC[C@H]2CN3C(=O)c2ncnc(C)c2O)c(=O)c2nc(N(C)C)cnc2n1CC(=O)Nc1ccc(C(F)(F)F)cc1Cl] | LCMS 1 | 700.2 | 0.57 |
| I-248 | 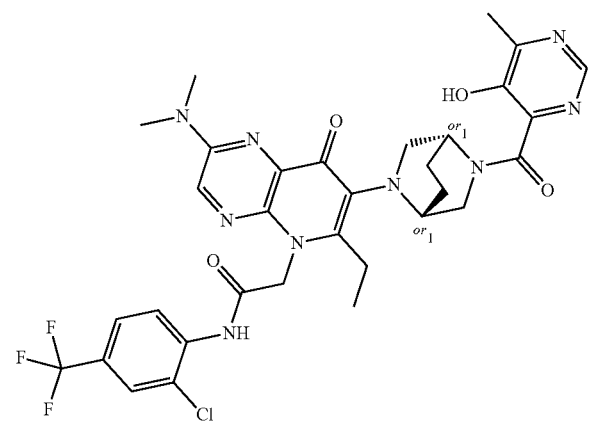 [SMILES: CCc1c(N2C[C@H]3CC[C@@H]2CN3C(=O)c2ncnc(C)c2O)c(=O)c2nc(N(C)C)cnc2n1CC(=O)Nc1ccc(C(F)(F)F)cc1Cl] | LCMS 1 | 700.2 | 0.57 |

TABLE 2-continued

| No. | | Method | (Mass Observed) [g/mol] | (Retention time) [min] |
|---|---|---|---|---|
| I-249 | | LCMS 1 | 702.5 | 0.58 |
| I-250 | | LCMS 1 | 742.2 | 2.21 |

TABLE 2-continued
| No. | | Method | (Mass Observed) [g/mol] | (Retention time) [min] |
|---|---|---|---|---|
| I-251 | 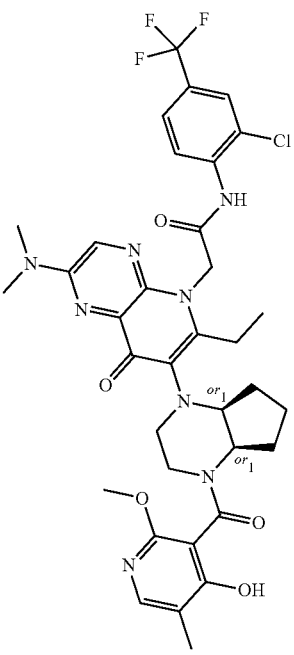 [SMILES: CCc1c(N2CCN(C(=O)c3c(OC)ncc(C)c3O)[C@@H]3CCC[C@@H]32)c(=O)c2nc(N(C)C)cnc2n1CC(=O)Nc1ccc(C(F)(F)F)cc1Cl] | LCMS 4 | 743.4 | 0.46 |
| I-252 | 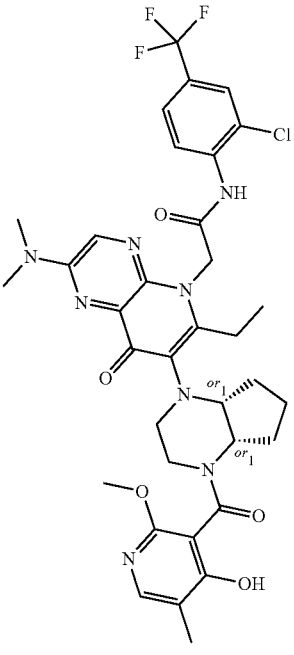 [SMILES: CCc1c(N2CCN(C(=O)c3c(OC)ncc(C)c3O)[C@H]3CCC[C@H]32)c(=O)c2nc(N(C)C)cnc2n1CC(=O)Nc1ccc(C(F)(F)F)cc1Cl] | LCMS 4 | 743.4 | 0.46 |

TABLE 2-continued
| No. | | Method | (Mass Observed) [g/mol] | (Retention time) [min] |
|---|---|---|---|---|
| I-253 | 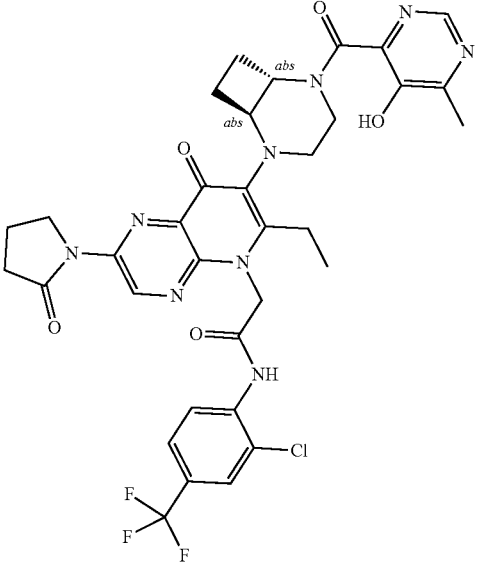 [SMILES: CCc1c(N2CCN(C(=O)c3ncnc(C)c3O)[C@H]3CC[C@@H]32)c(=O)c2nc(N3CCCC3=O)cnc2n1CC(=O)Nc1ccc(C(F)(F)F)cc1Cl] | LCMS 1 | 740.3 | 2.28 |
| I-254 | 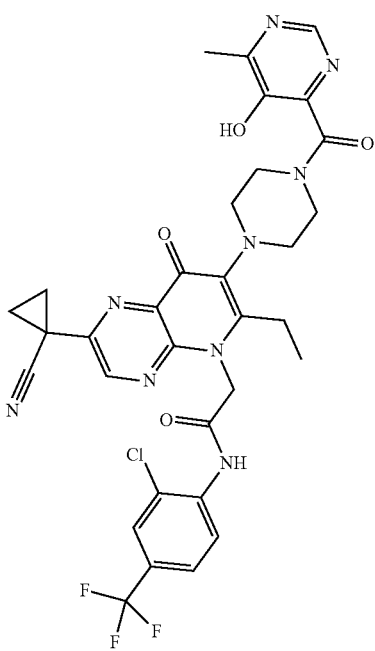 [SMILES: CCc1c(N2CCN(C(=O)c3ncnc(C)c3O)CC2)c(=O)c2nc(C3(C#N)CC3)cnc2n1CC(=O)Nc1ccc(C(F)(F)F)cc1Cl] | LCMS 1 | 696.3 | 0.54 |

TABLE 2-continued
| No. | | Method | (Mass Observed) [g/mol] | (Retention time) [min] |
|---|---|---|---|---|
| I-255 | 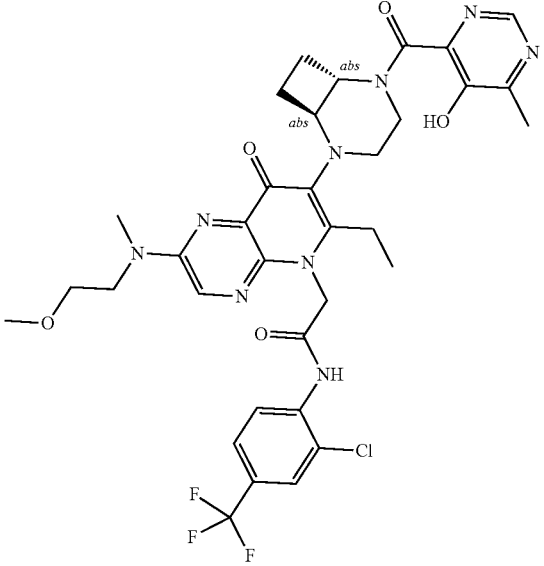 [SMILES: CCc1c(N2CCN(C(=O)c3ncnc(C)c3O)[C@H]3CC[C@@H]32)c(=O)c2nc(N(C)CCOC)cnc2n1CC(=O)Nc1ccc(C(F)(F)F)cc1Cl] | LCMS 1 | 744.3 | 0.57 |
| I-256 | 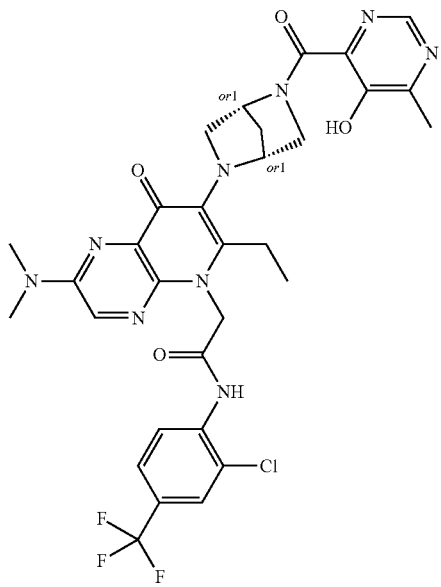 | LCMS 1 | 686.2 | 0.55 |

TABLE 2-continued
| No. | | Method | (Mass Observed) [g/mol] | (Retention time) [min] |
|---|---|---|---|---|
| I-257 | 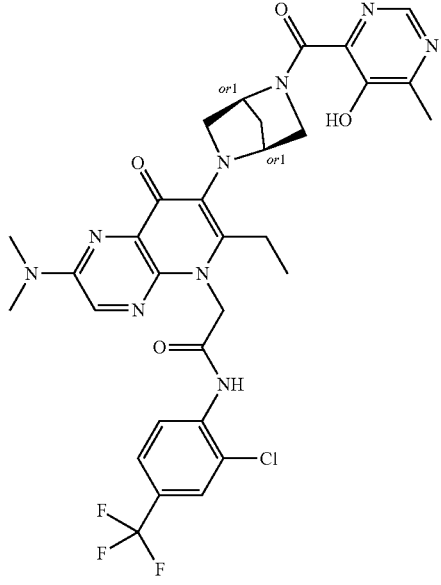 | LCMS 1 | 686.2 | 0.55 |
| I-258 | 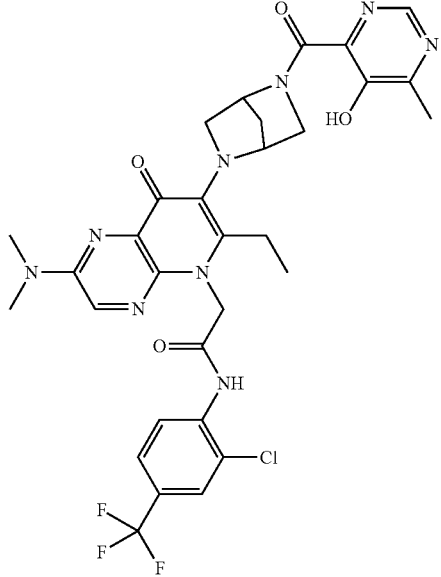 | LCMS 1 | 686.3 | 0.56 |

TABLE 2-continued
| No. | | Method | (Mass Observed) [g/mol] | (Retention time) [min] |
|---|---|---|---|---|
| I-259 | 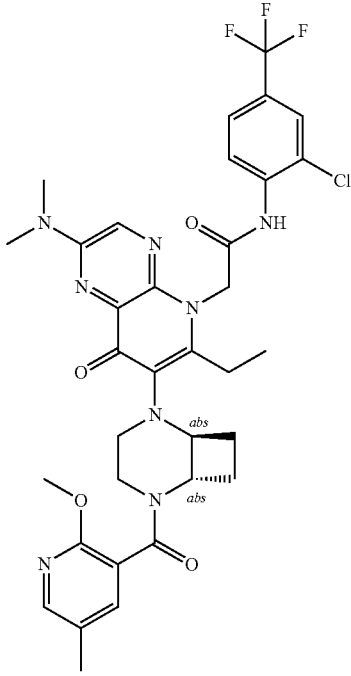 [SMILES: CCc1c(N2CCN(C(=O)c3cc(C)cnc3OC)[C@H]3CC[C@@H]32)c(=O)c2nc(N(C)C)cnc2n1CC(=O)Nc1ccc(C(F)(F)F)cc1Cl] | LCMS 1 | 713.2 | 0.55 |
| I-260 | 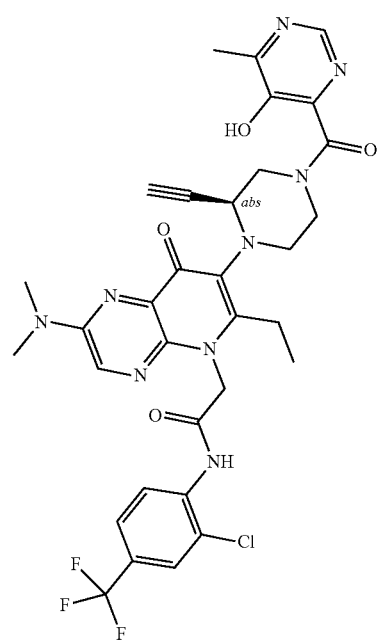 [SMILES: C#C[C@H]1CN(C(=O)c2ncnc(C)c2O)CCN1c1c(CC)n(CC(=O)Nc2ccc(C(F)(F)F)cc2Cl)c2ncc(N(C)C)nc2c1=O] | LCMS 1 | 698.3 | 0.53 |

TABLE 2-continued
| No. | | Method | (Mass Observed) [g/mol] | (Retention time) [min] |
|---|---|---|---|---|
| I-261 | 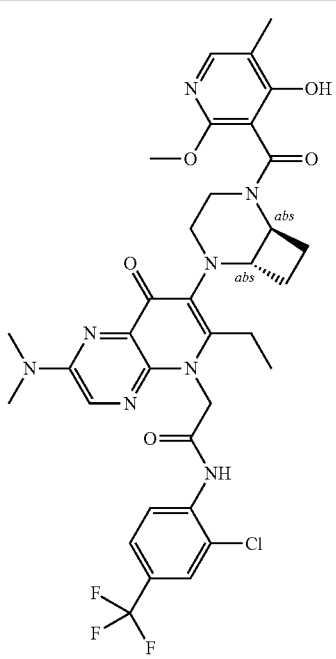 [SMILES: CCc1c(N2CCN(C(=O)c3c(OC)ncc(C)c3O)[C@H]3CC[C@@H]32)c(=O)c2nc(N(C)C)cnc2n1CC(=O)Nc1ccc(C(F)(F)F)cc1Cl] | LCMS 1 | 729.2 | 2.05 |
| I-262 | 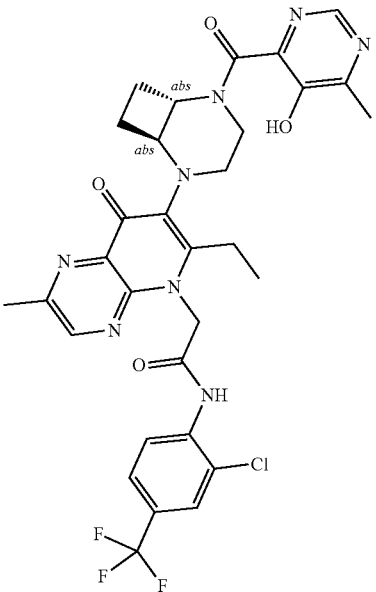 | LCMS 1 | 671.3 | 1.28 |

TABLE 2-continued
| No. | | Method | (Mass Observed) [g/mol] | (Retention time) [min] |
|---|---|---|---|---|
| I-263 | 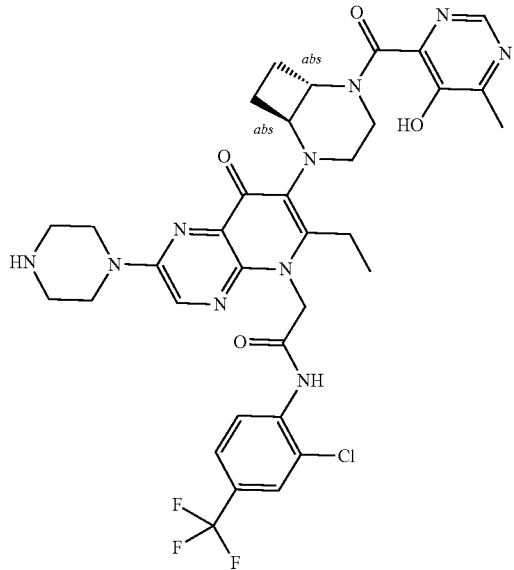 [SMILES: CCc1c(N2CCN(C(=O)c3ncnc(C)c3O)[C@H]3CC[C@@H]32)c(=O)c2nc(N3CCNCC3)cnc2n1CC(=O)Nc1ccc(C(F)(F)F)cc1Cl] | LCMS 1 | 741.3 | 1.93 |
| I-264 | 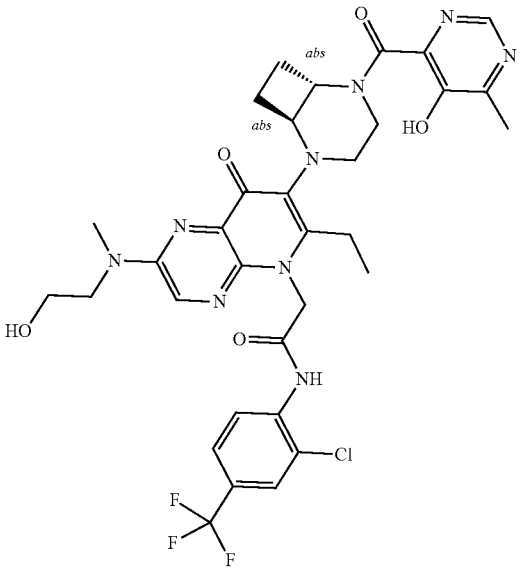 [SMILES: CCc1c(N2CCN(C(=O)c3ncnc(C)c3O)[C@H]3CC[C@@H]32)c(=O)c2nc(N(C)CCO)cnc2n1CC(=O)Nc1ccc(C(F)(F)F)cc1Cl] | LCMS 1 | 730.3 | 2.13 |
| I-265 | 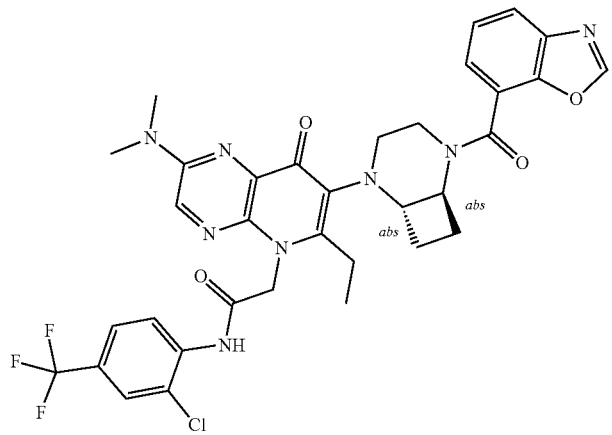 [SMILES: CCc1c(N2CCN(C(=O)c3cccc4ncoc34)[C@H]3CC[C@@H]32)c(=O)c2nc(N(C)C)cnc2n1CC(=O)Nc1ccc(C(F)(F)F)cc1Cl] | LCMS 4 | 709.3 | 0.67 |

TABLE 2-continued
| No. | | Method | (Mass Observed) [g/mol] | (Retention time) [min] |
|---|---|---|---|---|
| I-266 | 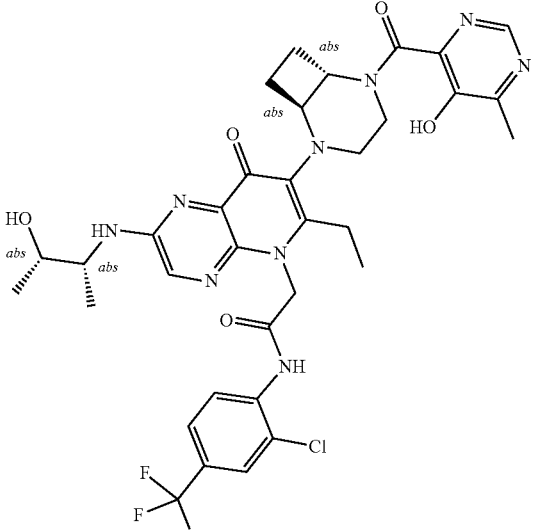 | LCMS 1 | 744.4 | 0.52 |
| I-267 | 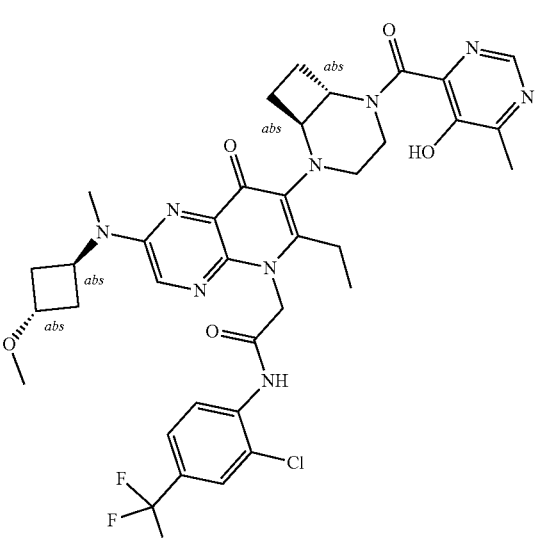 | LCMS 1 | 770.5 | 0.56 |
| I-268 | 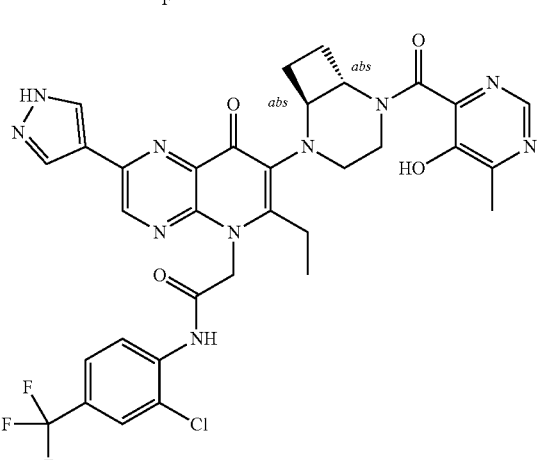 | LCMS 4 | 723.3 | 0.41 |

TABLE 2-continued
| No. | | Method | (Mass Observed) [g/mol] | (Retention time) [min] |
|---|---|---|---|---|
| I-269 | 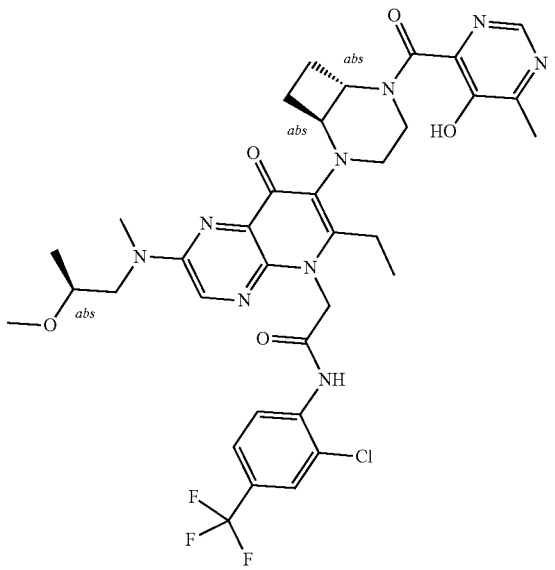 [SMILES: CCc1c(N2CCN(C(=O)c3ncnc(C)c3O)[C@H]3CC[C@@H]32)c(=O)c2nc(N(C)C[C@H](C)OC)cnc2n1CC(=O)Nc1ccc(C(F)(F)F)cc1Cl] | LCMS 1 | 758.4 | 0.57 |
| I-270 | 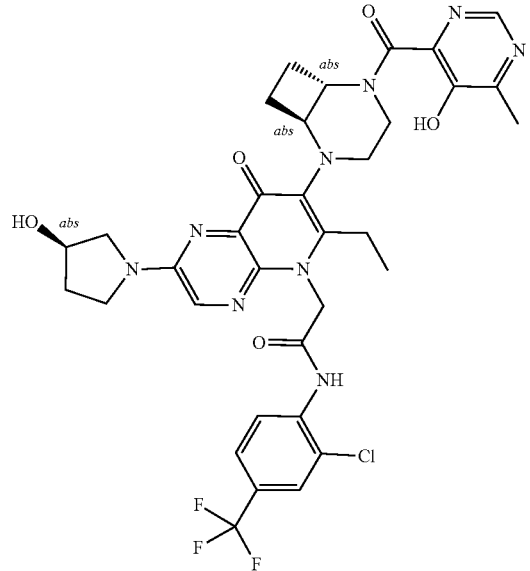 [SMILES: CCc1c(N2CCN(C(=O)c3ncnc(C)c3O)[C@H]3CC[C@@H]32)c(=O)c2nc(N3CC[C@@H](O)C3)cnc2n1CC(=O)Nc1ccc(C(F)(F)F)cc1Cl] | LCMS 1 | 742.3 | 2.10 |

TABLE 2-continued

| No. | | Method | (Mass Observed) [g/mol] | (Retention time) [min] |
|---|---|---|---|---|
| I-271 | | LCMS 1 | 742.3 | 2.12 |
| I-272 | | LCMS 1 | 740.3 | 0.56 |

TABLE 2-continued
| No. | | Method | (Mass Observed) [g/mol] | (Retention time) [min] |
|---|---|---|---|---|
| I-273 | 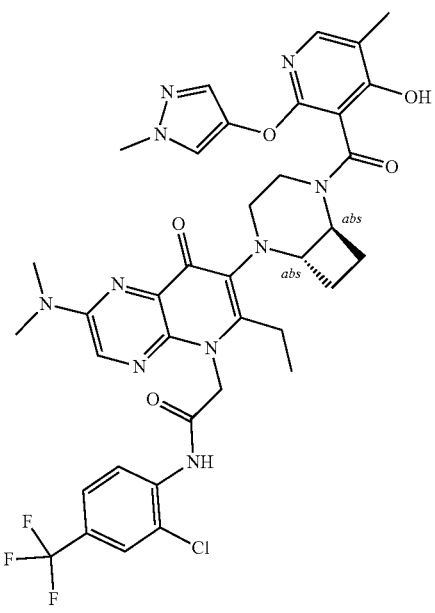 [SMILES: CCc1c(N2CCN(C(=O)c3c(Oc4cnn(C)c4)ncc(C)c3O)[C@H]3CC[C@@H]32)c(=O)c2nc(N(C)C)cnc2n1CC(=O)Nc1ccc(C(F)(F)F)cc1Cl] | LCMS 1 | 795.3 | 0.54 |
| I-274 | 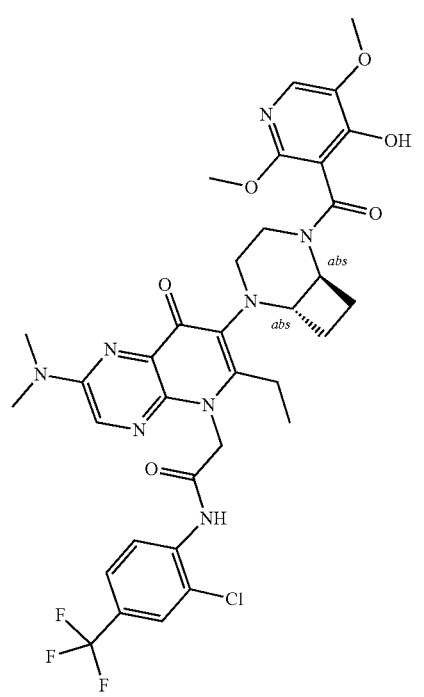 [SMILES: CCc1c(N2CCN(C(=O)c3c(OC)ncc(OC)c3O)[C@H]3CC[C@@H]32)c(=O)c2nc(N(C)C)cnc2n1CC(=O)Nc1ccc(C(F)(F)F)cc1Cl] | LCMS 1 | 745.3 | 2.12 |

TABLE 2-continued

| No. | Method | (Mass Observed) [g/mol] | (Retention time) [min] |
|---|---|---|---|
| I-275 | LCMS 1 | 743.3 | 2.16 |
| I-276 | LCMS 1 | 685.3 | 0.88 |

TABLE 2-continued
| No. | Method | (Mass Observed) [g/mol] | (Retention time) [min] |
|---|---|---|---|
| I-277 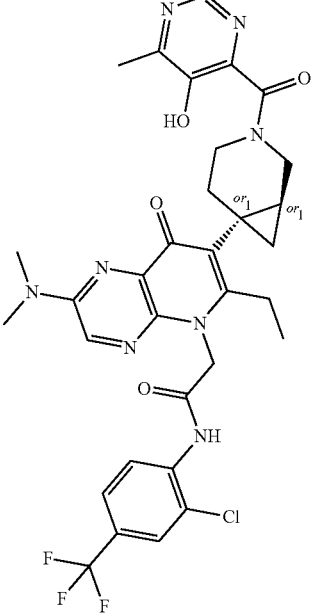 | LCMS 1 | 685.3 | 0.88 |
| I-278 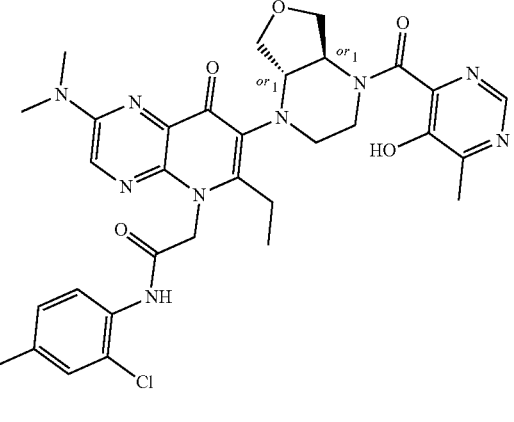 | LCMS 1 | 716.3 | 2.09 |
| I-279 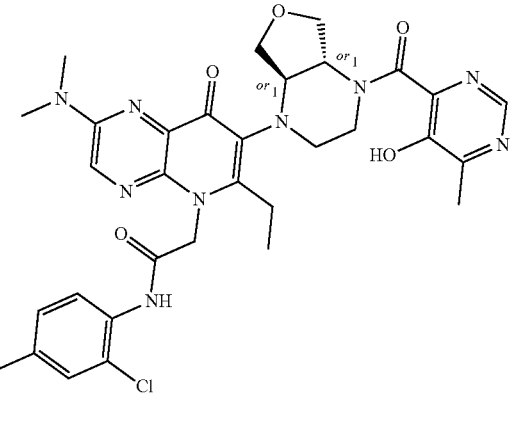 | LCMS 1 | 716.3 | 2.09 |

TABLE 2-continued
| No. | | Method | (Mass Observed) [g/mol] | (Retention time) [min] |
|---|---|---|---|---|
| I-280 | 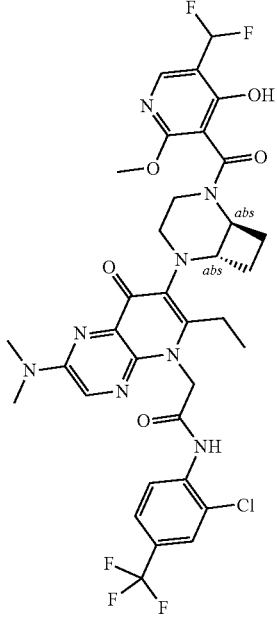 [SMILES: CCc1c(N2CCN(C(=O)c3c(OC)ncc(C(F)F)c3O)[C@H]3CC[C@@H]32)c(=O)c2nc(N(C)C)cnc2n1CC(=O)Nc1ccc(C(F)(F)F)cc1Cl] | LCMS 1 | 765.2 | 2.24 |
| I-281 | 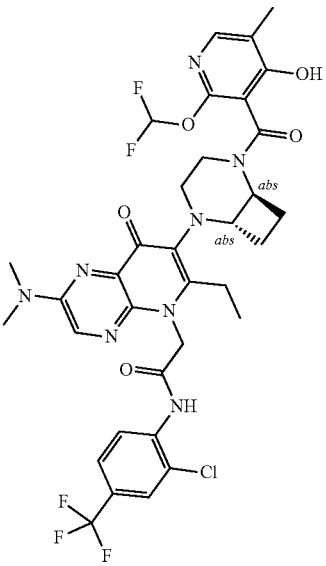 [SMILES: CCc1c(N2CCN(C(=O)c3c(OC(F)F)ncc(C)c3O)[C@H]3CC[C@@H]32)c(=O)c2nc(N(C)C)cnc2n1CC(=O)Nc1ccc(C(F)(F)F)cc1Cl] | LCMS 1 | 765.3 | 2.30 |

TABLE 2-continued
| No. | | Method | (Mass Observed) [g/mol] | (Retention time) [min] |
|---|---|---|---|---|
| I-282 | 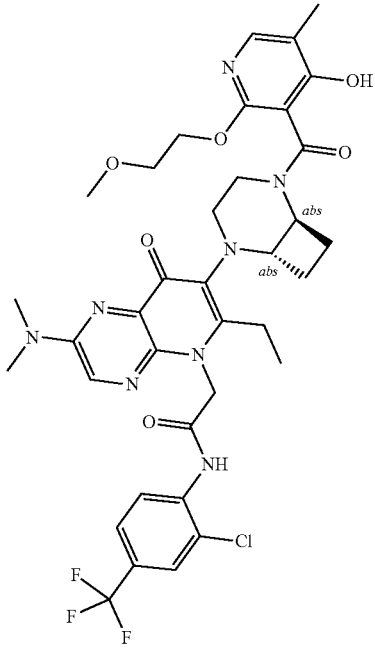 [SMILES: CCc1c(N2CCN(C(=O)c3c(OCCOC)ncc(C)c3O)[C@H]3CC[C@@H]32)c(=O)c2nc(N(C)C)cnc2n1CC(=O)Nc1ccc(C(F)(F)F)cc1Cl] | LCMS 1 | 773.3 | 0.54 |
| I-283 | 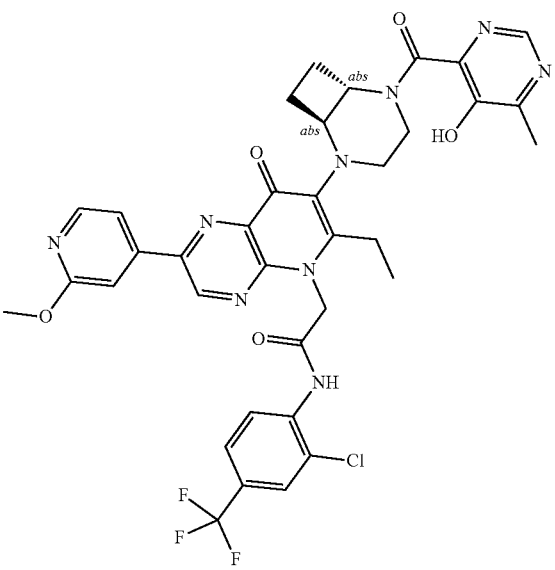 [SMILES: CCc1c(N2CCN(C(=O)c3ncnc(C)c3O)[C@H]3CC[C@@H]32)c(=O)c2nc(-c3ccnc(OC)c3)cnc2n1CC(=O)Nc1ccc(C(F)(F)F)cc1Cl] | LCMS 1 | 764.3 | 2.42 |

TABLE 2-continued
| No. | | Method | (Mass Observed) [g/mol] | (Retention time) [min] |
|---|---|---|---|---|
| I-284 | 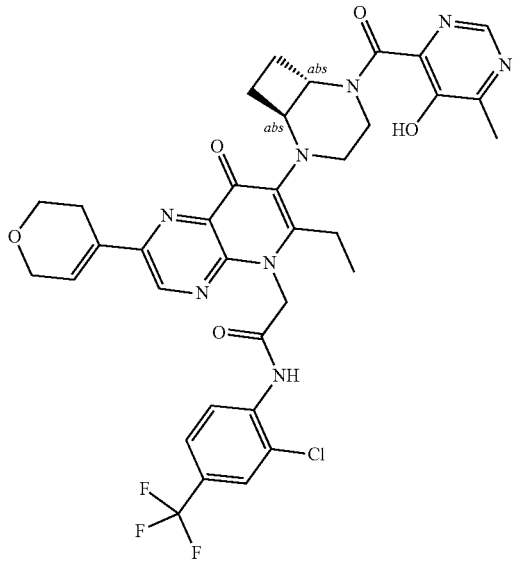 [SMILES: CCc1c(N2CCN(C(=O)c3ncnc(C)c3O)[C@H]3CC[C@@H]32)c(=O)c2nc(C3=CCOCC3)cnc2n1CC(=O)Nc1ccc(C(F)(F)F)cc1Cl] | LCMS 1 | 739.3 | 2.37 |
| I-285 | 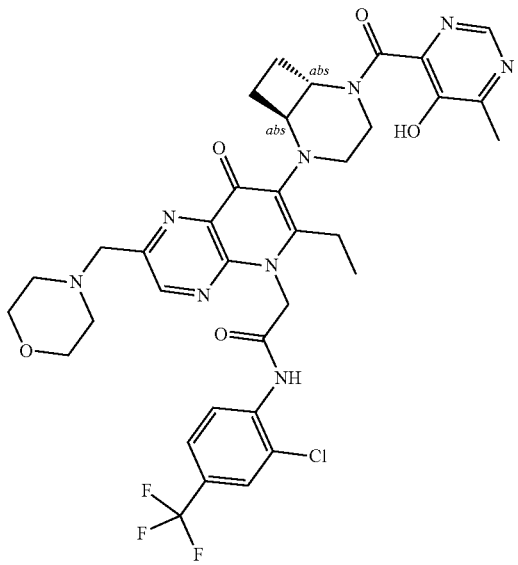 [SMILES: CCc1c(N2CCN(C(=O)c3ncnc(C)c3O)[C@H]3CC[C@@H]32)c(=O)c2nc(CN3CCOCC3)cnc2n1CC(=O)Nc1ccc(C(F)(F)F)cc1Cl] | LCMS 1 | 756.3 | 1.94 |

TABLE 2-continued
| No. | Method | (Mass Observed) [g/mol] | (Retention time) [min] |
|---|---|---|---|
| I-286 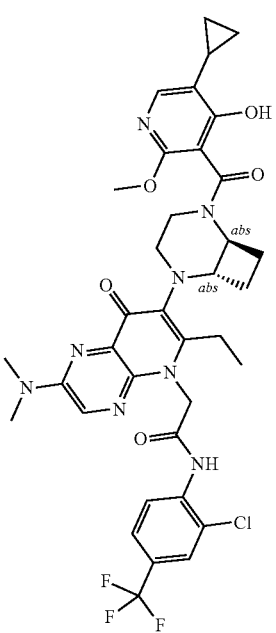 [SMILES: CCc1c(N2CCN(C(=O)c3c(OC)ncc(C4CC4)c3O)[C@H]3CC[C@@H]32)c(=O)c2nc(N(C)C)cnc2n1CC(=O)Nc1ccc(C(F)(F)F)cc1Cl] | LCMS 1 | 755.3 | 2.23 |
| I-287 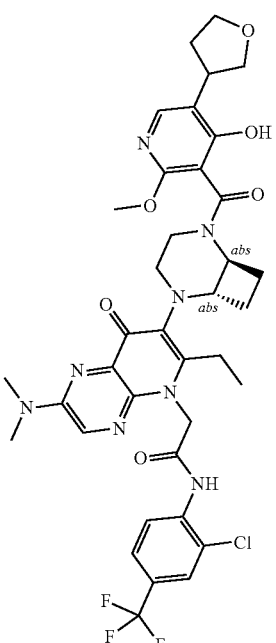 | LCMS 1 | 785.3 | 2.15 |

TABLE 2-continued
| No. | | Method | (Mass Observed) [g/mol] | (Retention time) [min] |
|---|---|---|---|---|
| I-288 | 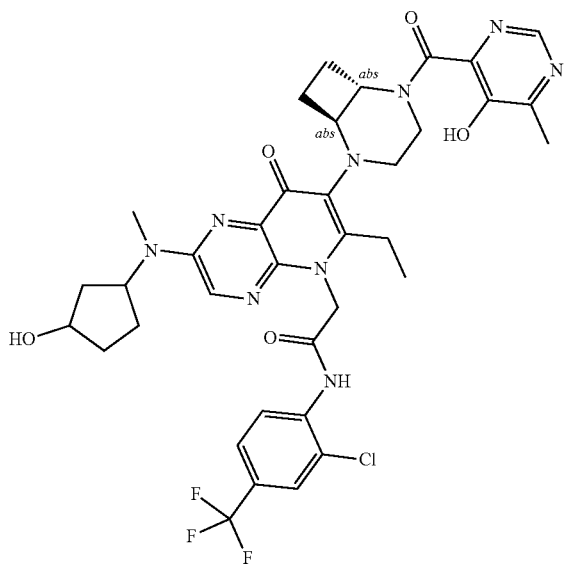 [SMILES: CCc1c(N2CCN(C(=O)c3ncnc(C)c3O)[C@H]3CC[C@@H]32)c(=O)c2nc(N(C)C3CCC(O)C3)cnc2n1CC(=O)Nc1ccc(C(F)(F)F)cc1Cl] | LCMS 1 | 770.3 | 2.19 |
| I-289 | 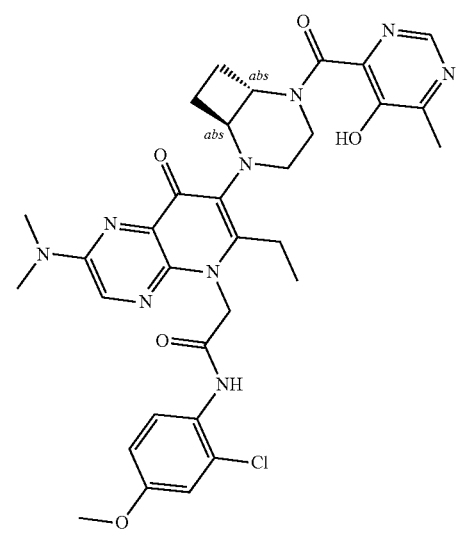 [SMILES: CCc1c(N2CCN(C(=O)c3ncnc(C)c3O)[C@H]3CC[C@@H]32)c(=O)c2nc(N(C)C)cnc2n1CC(=O)Nc1ccc(OC)cc1Cl] | LCMS 1 | 662.3 | 1.96 |

TABLE 2-continued
| No. | Method | (Mass Observed) [g/mol] | (Retention time) [min] |
|---|---|---|---|
| I-290 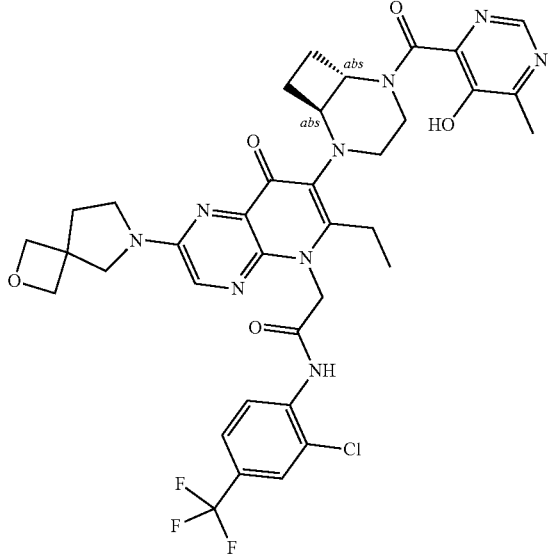 [SMILES: CCc1c(N2CCN(C(=O)c3ncnc(C)c3O)[C@H]3CC[C@@H]32)c(=O)c2nc(N3CCC4(COC4)C3)cnc2n1CC(=O)Nc1ccc(C(F)(F)F)cc1Cl] | LCMS 1 | 768.3 | 2.19 |
| I-291 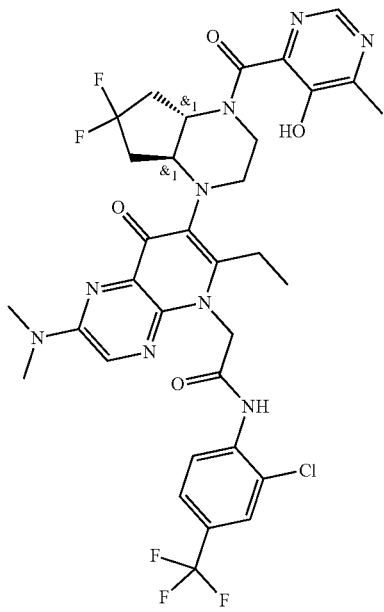 | LCMS 1 | 750.3 | 2.47 |

TABLE 2-continued
| No. | | Method | (Mass Observed) [g/mol] | (Retention time) [min] |
|---|---|---|---|---|
| I-292 | 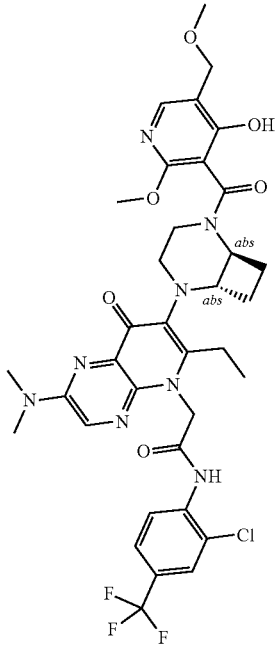 [SMILES: CCc1c(N2CCN(C(=O)c3c(OC)ncc(COC)c3O)[C@H]3CC[C@@H]32)c(=O)c2nc(N(C)C)cnc2n1CC(=O)Nc1ccc(C(F)(F)F)cc1Cl] | LCMS 1 | 759.4 | 0.57 |
| I-293 | 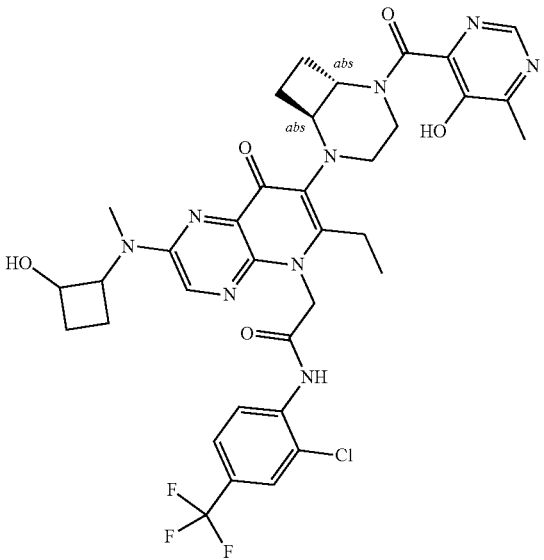 [SMILES: CCc1c(N2CCN(C(=O)c3ncnc(C)c3O)[C@H]3CC[C@@H]32)c(=O)c2nc(N(C)C3CCC3O)cnc2n1CC(=O)Nc1ccc(C(F)(F)F)cc1Cl] | LCMS 1 | 756.3 | 2.55 |

TABLE 2-continued

| No. | Method | (Mass Observed) [g/mol] | (Retention time) [min] |
|---|---|---|---|
| I-294 | LCMS 8 | 716.2 | 4.04 |
| I-295 | LCMS 8 | 716.2 | 4.05 |
| I-296 | LCMS 1 | 750.3 | 2.44 |

TABLE 2-continued

| No. | | Method | (Mass Observed) [g/mol] | (Retention time) [min] |
|---|---|---|---|---|
| I-297 | | LCMS 1 | 750.3 | 2.44 |
| I-299 | | LCMS 1 | 770.3 | 0.56 |

TABLE 2-continued
| No. | | Method | (Mass Observed) [g/mol] | (Retention time) [min] |
|---|---|---|---|---|
| I-300 | 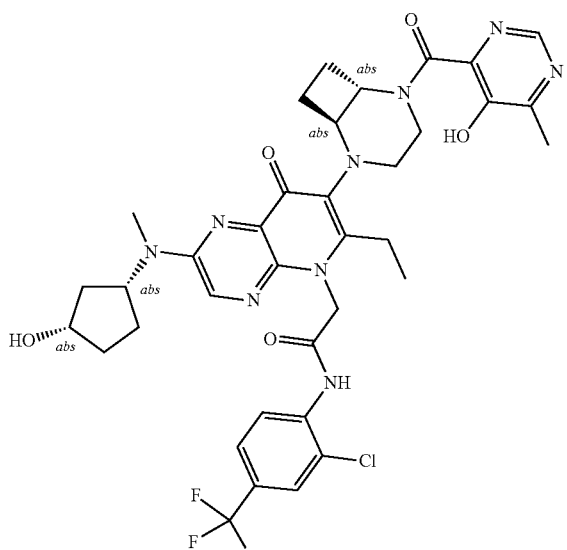 | LCMS 1 | 770.3 | 2.34 |
| I-301 | 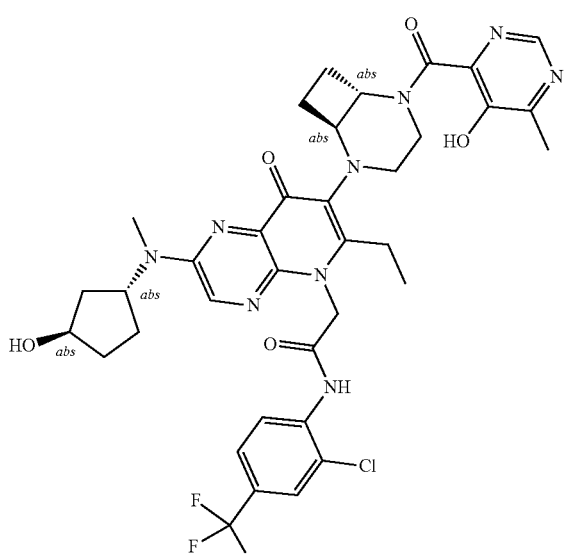 | LCMS 1 | 770.3 | 2.35 |

TABLE 2-continued
| No. | | Method | (Mass Observed) [g/mol] | (Retention time) [min] |
|---|---|---|---|---|
| I-302 | 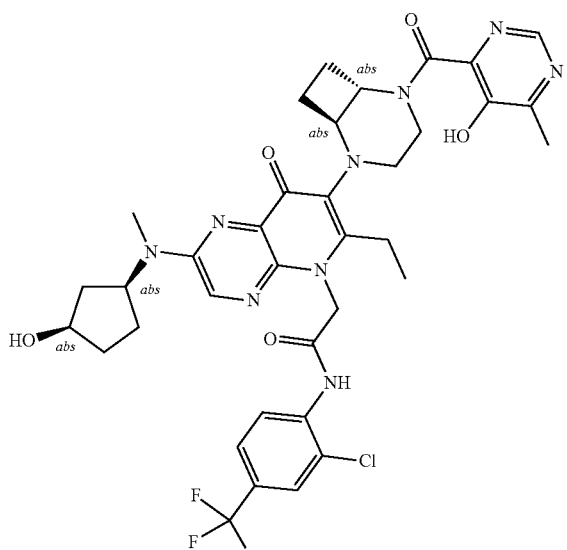 | LCMS 1 | 770.3 | 2.33 |
| I-303 | 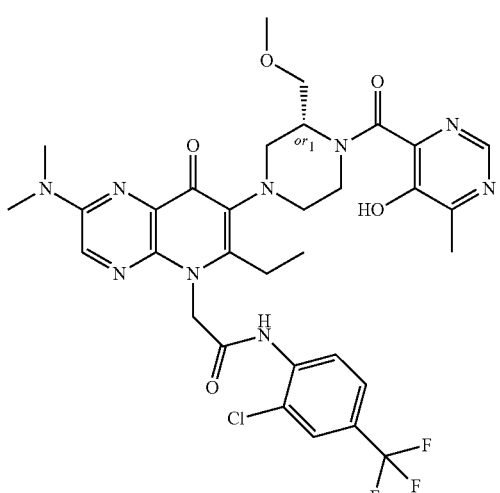 | LCMS 1 | 718.2 | 0.55 |

Further compounds of the disclosure are shown below in Table 2a.
TABLE 2a
Compound No.
I-3a
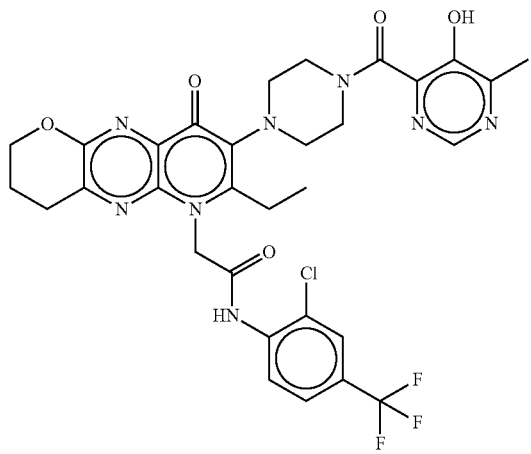
I-4a
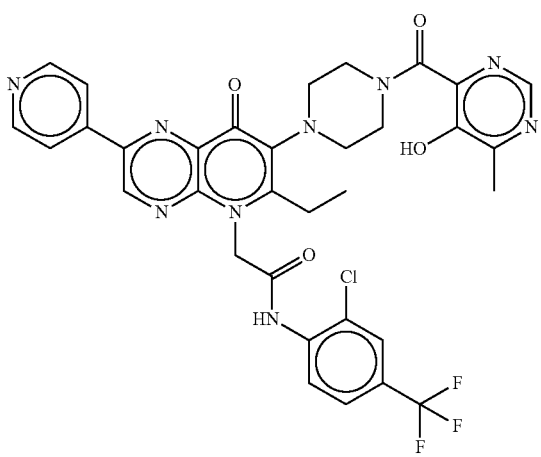
I-5a
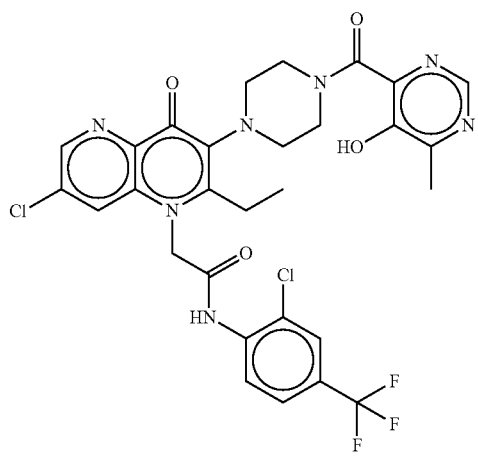

TABLE 2a-continued
Compound No.
I-14a
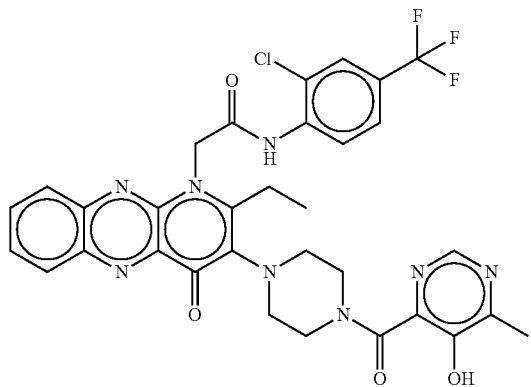
I-15a
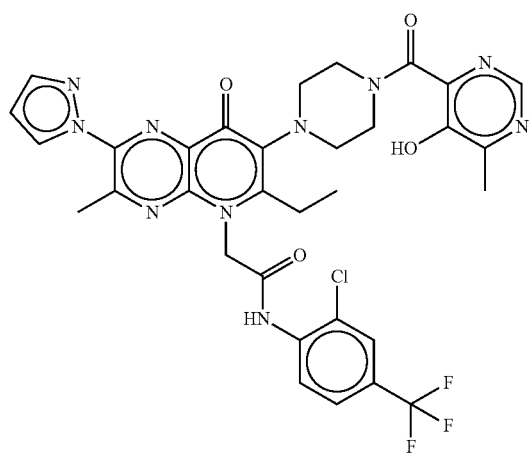
I-16a
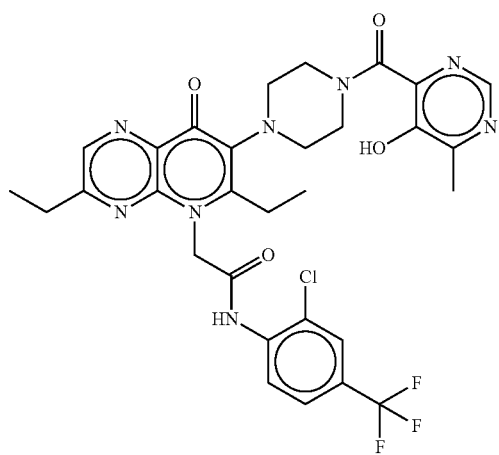

TABLE 2a-continued
Compound No.
I-17a
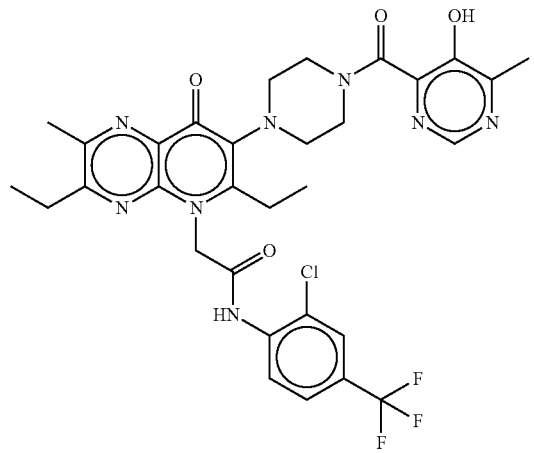
I-18a
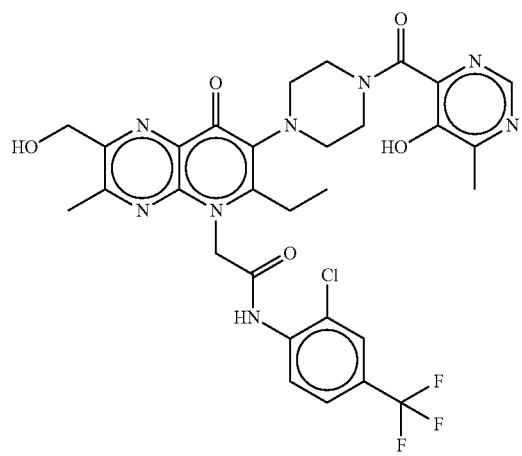
I-23a
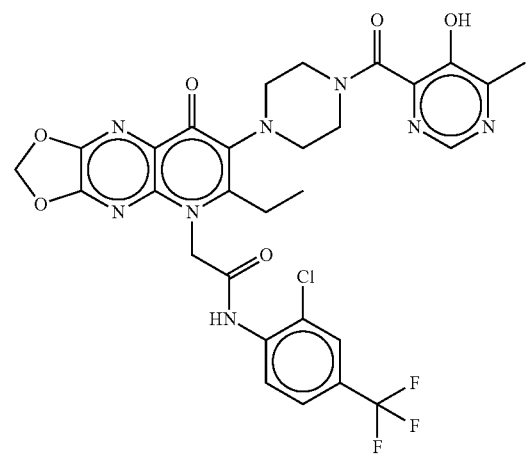

TABLE 2a-continued
Compound No.
I-24a
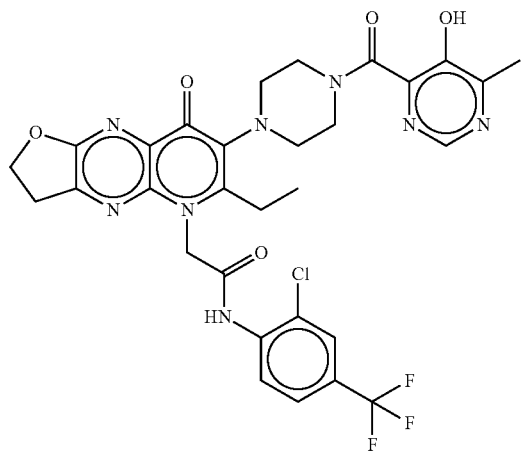
I-25a
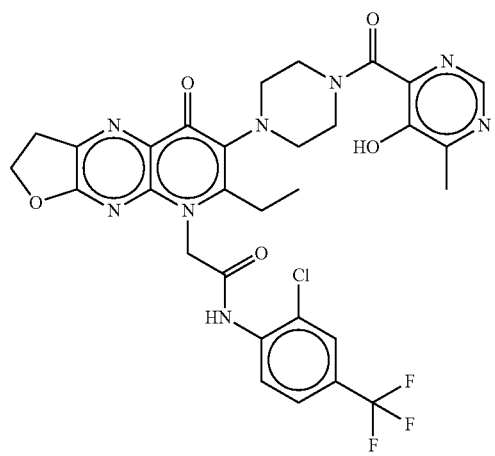
I-28a
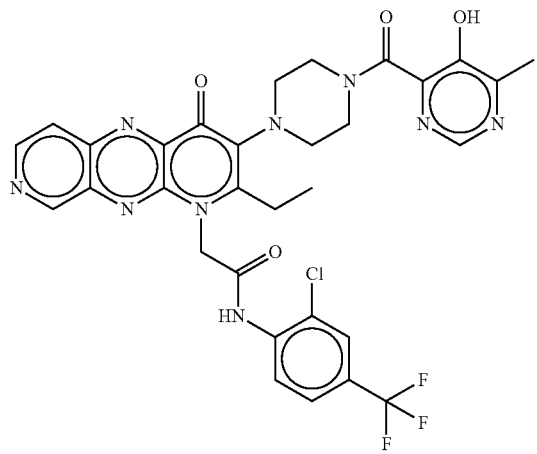

TABLE 2a-continued
Compound No.
I-29a
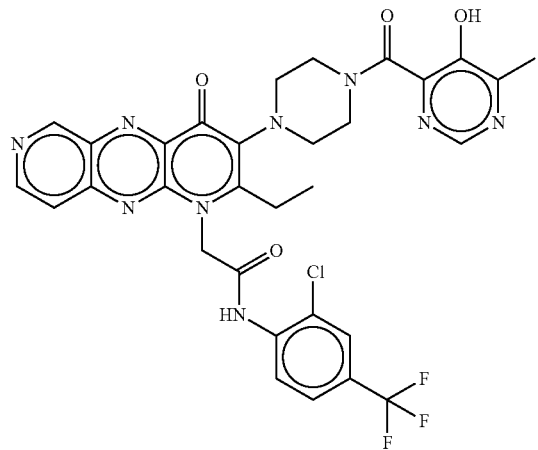
I-31a
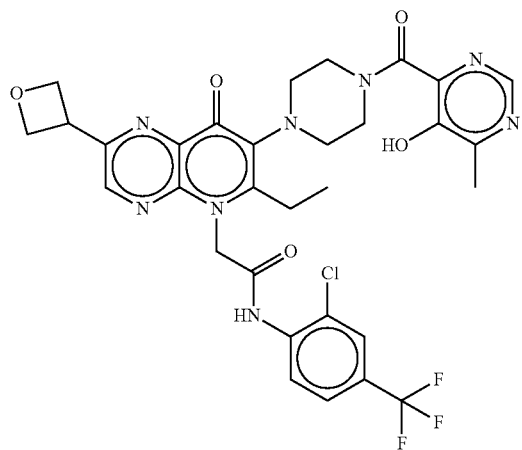
I-32a
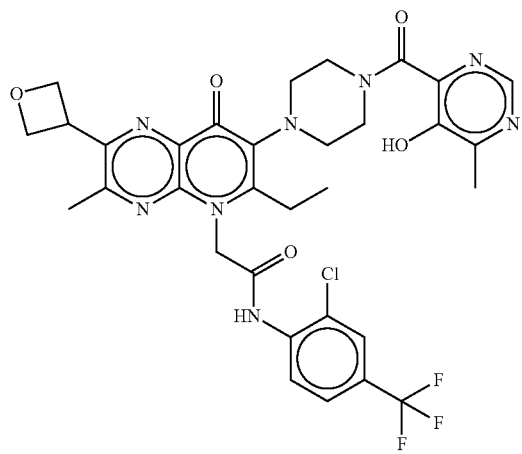

TABLE 2a-continued
Compound No.
I-33a
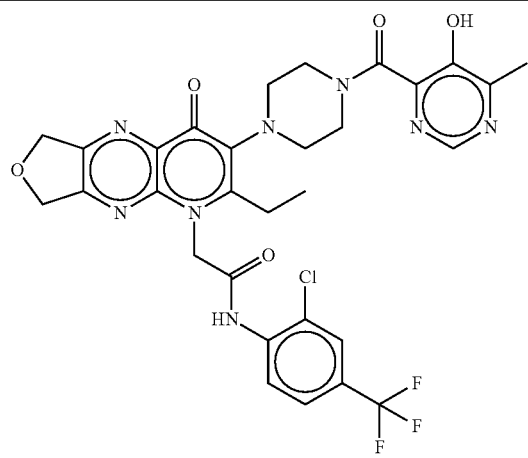
I-34a
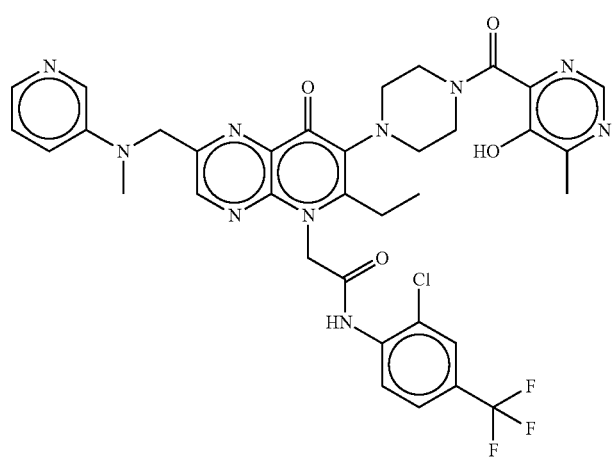
I-35a
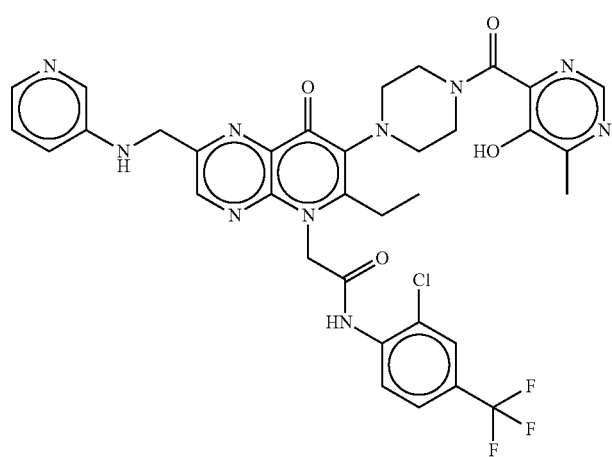

TABLE 2a-continued
Compound No.
I-36a
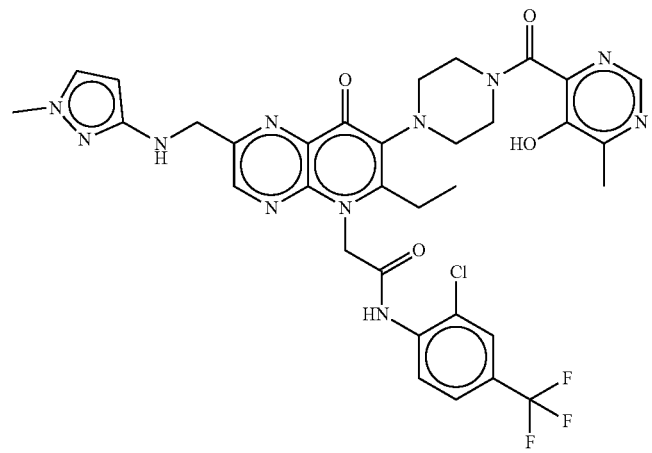
I-37a
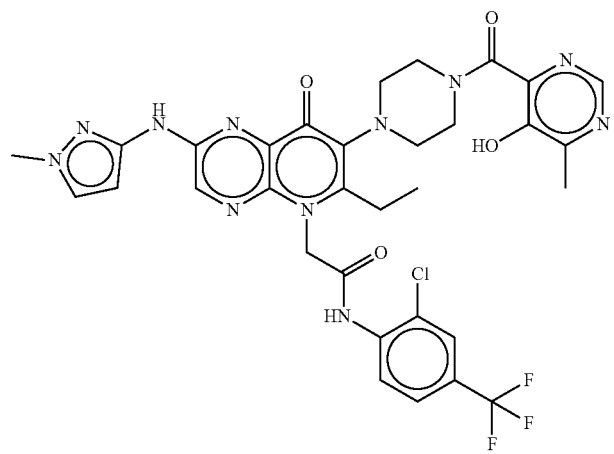
I-38a
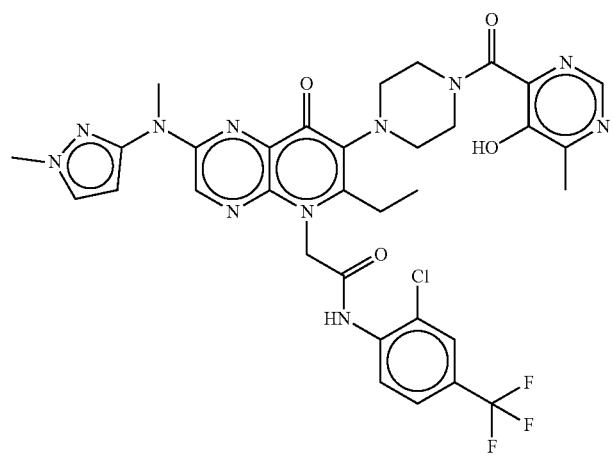

TABLE 2a-continued
Compound No.
I-39a
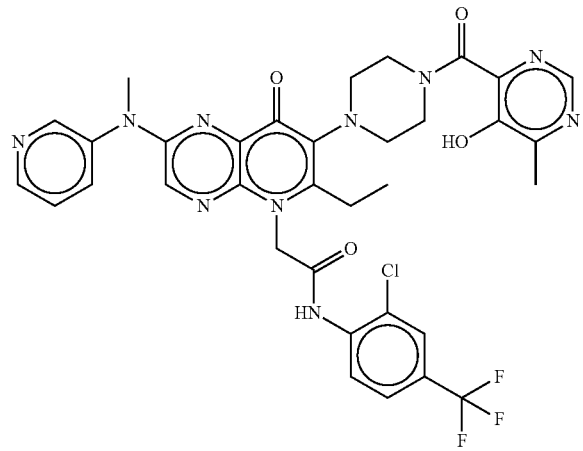
I-40a
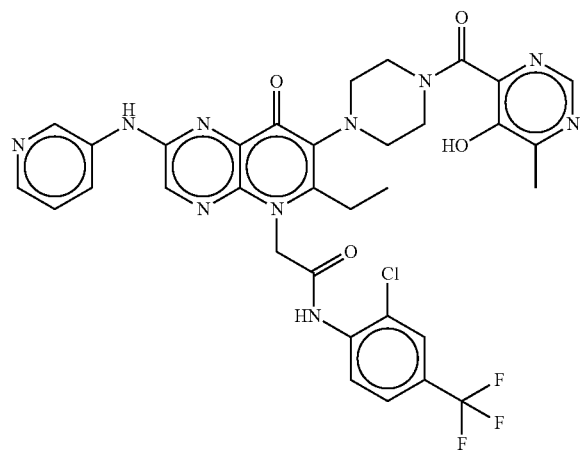
I-41a
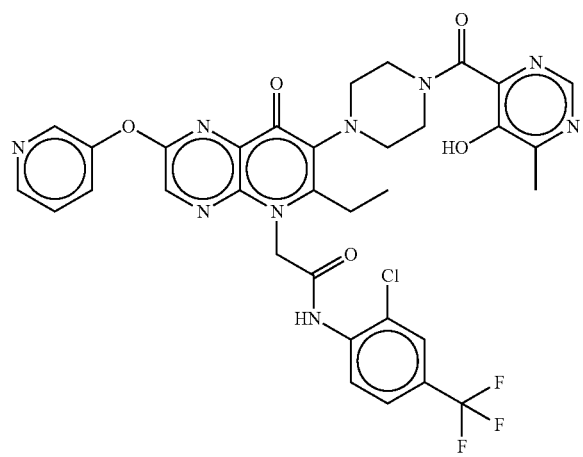

TABLE 2a-continued
Compound No.
I-42a
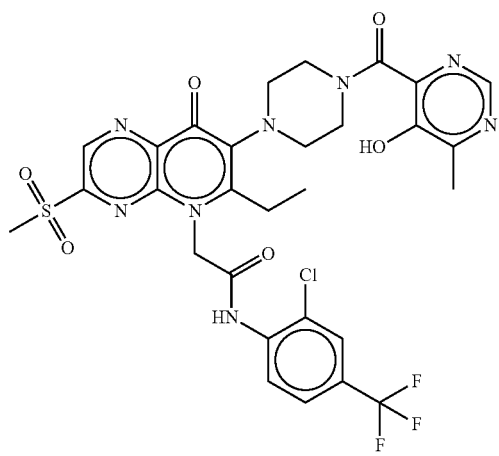
I-43a
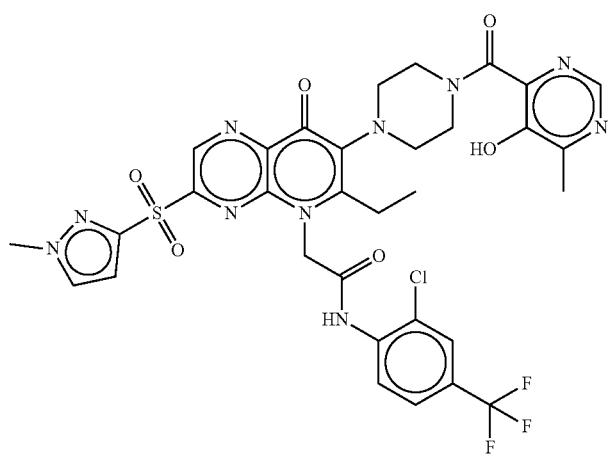
I-44a
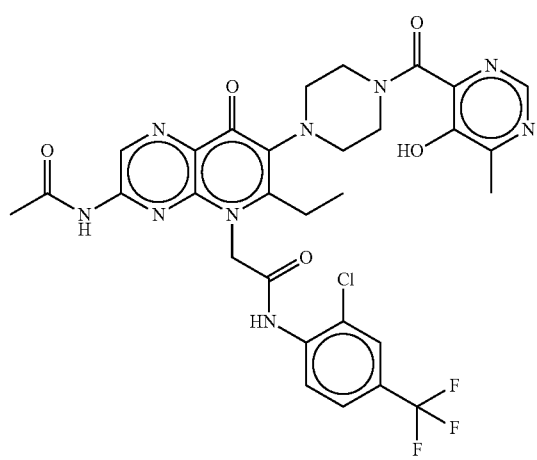

TABLE 2a-continued
Compound No.
I-45a
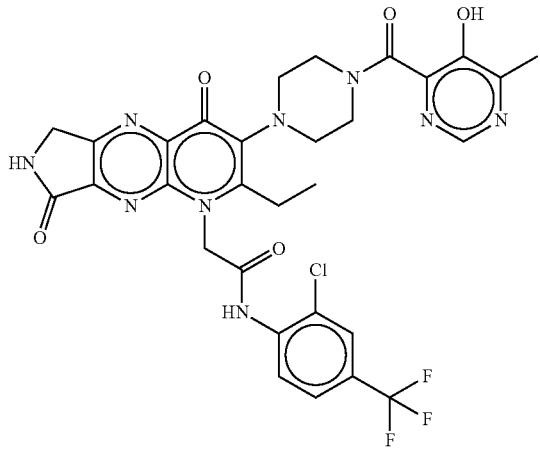
I-46a
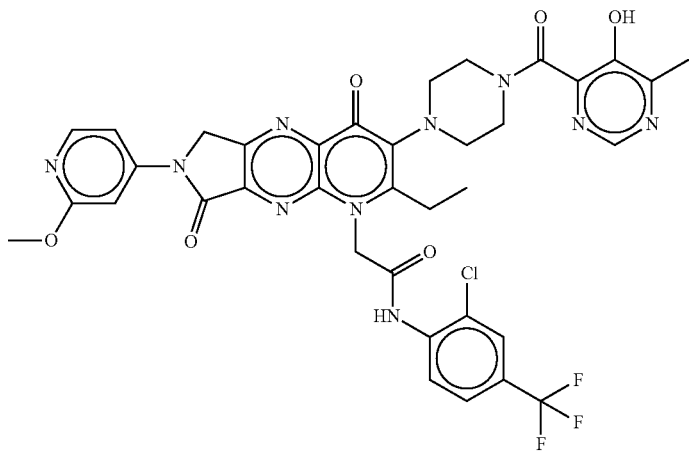
I-47a
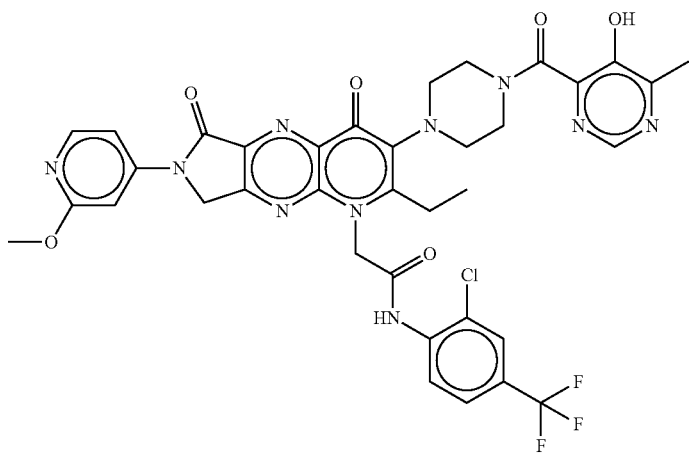

TABLE 2a-continued
Compound No.
I-48a
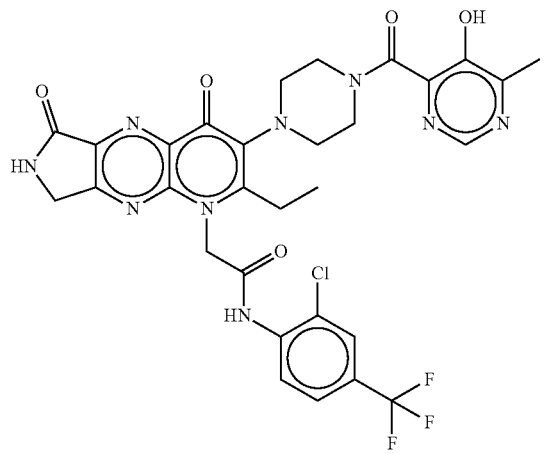
I-49a
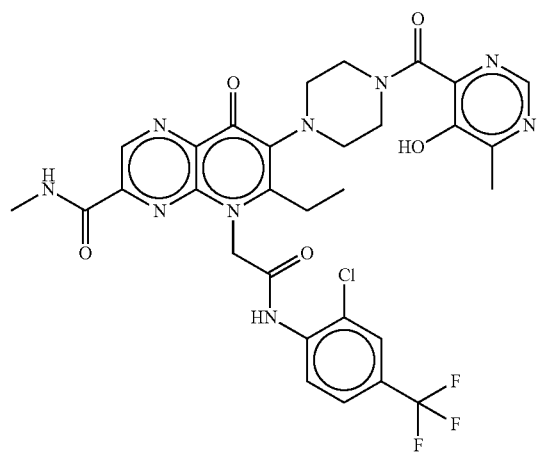
I-50a
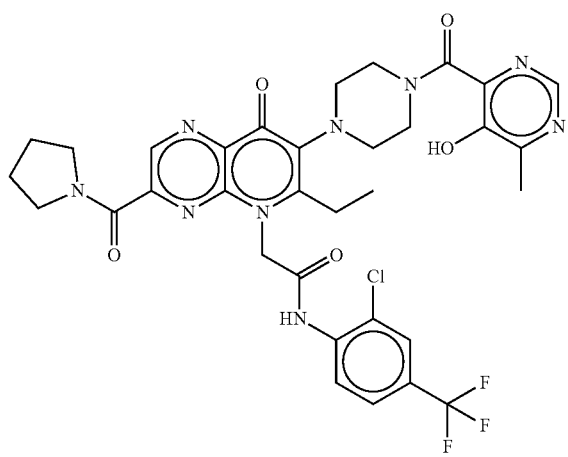

TABLE 2a-continued
Compound No.
I-55a
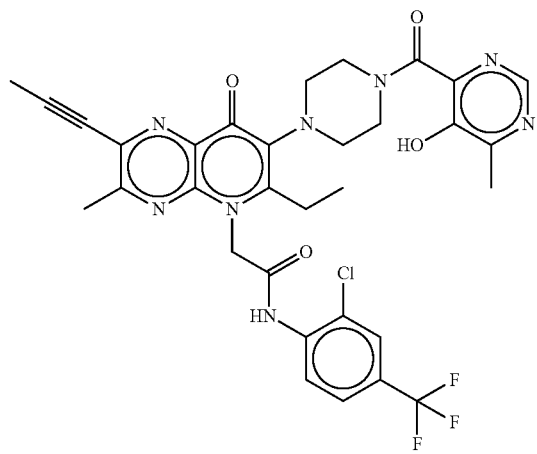
I-56a
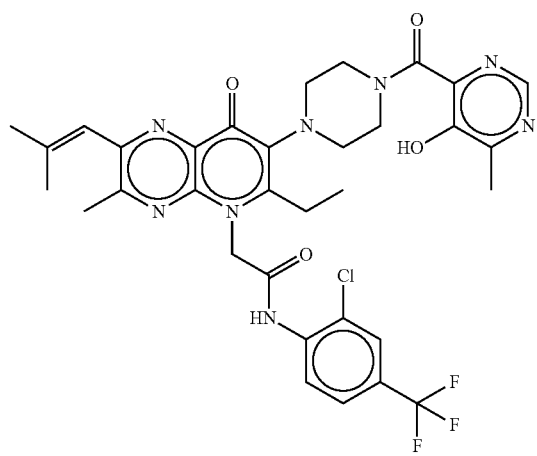
I-58a
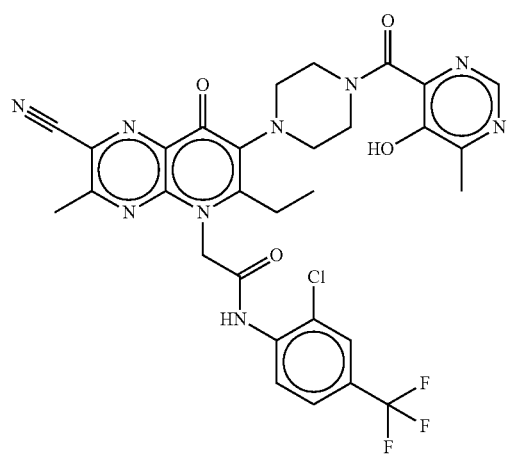

TABLE 2a-continued
Compound No.
I-59a
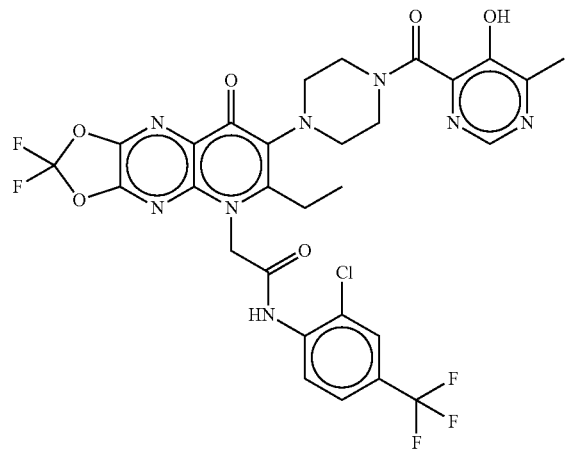
I-60a
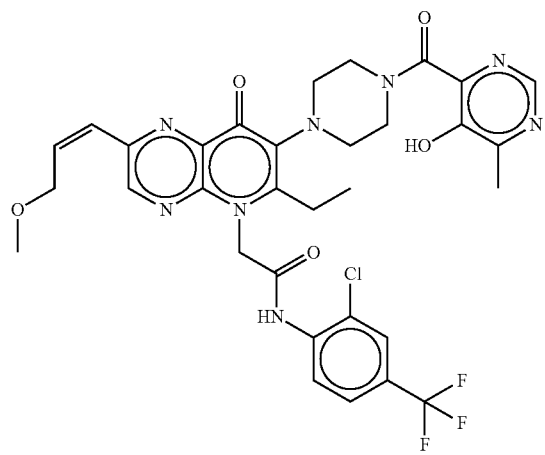
I-61a
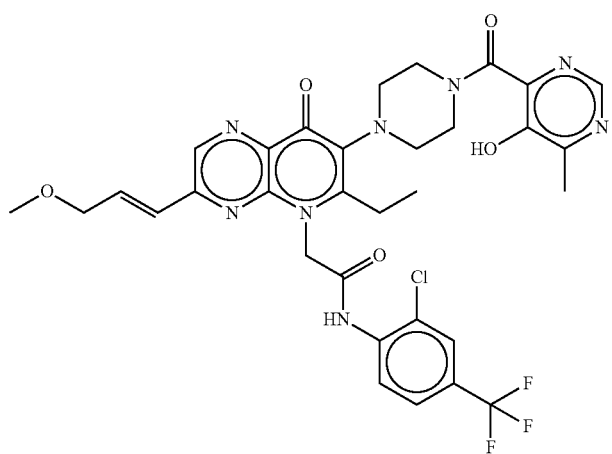

TABLE 2a-continued
Compound No.
I-62a
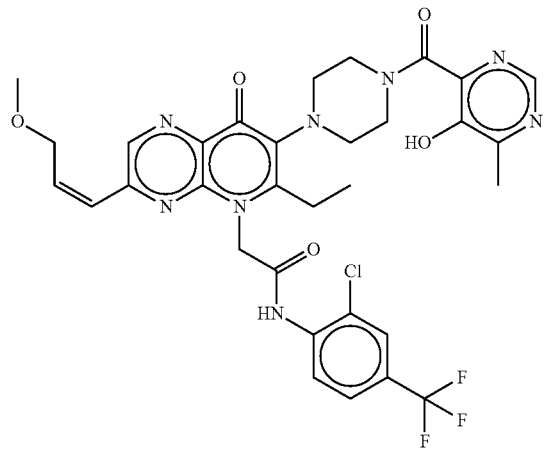
I-64a
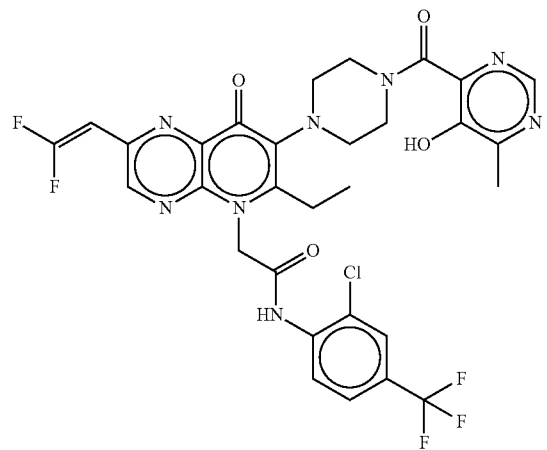
I-65a
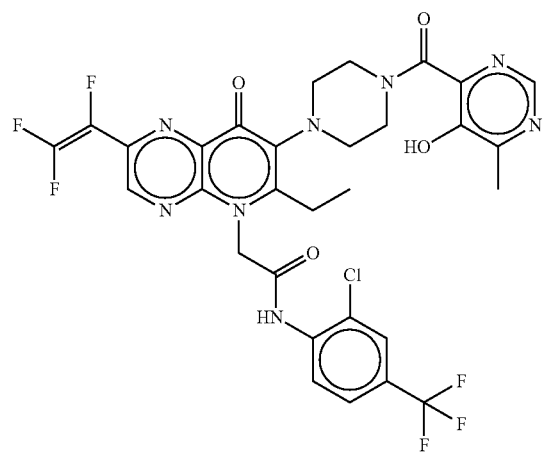

TABLE 2a-continued
Compound No.
I-66a
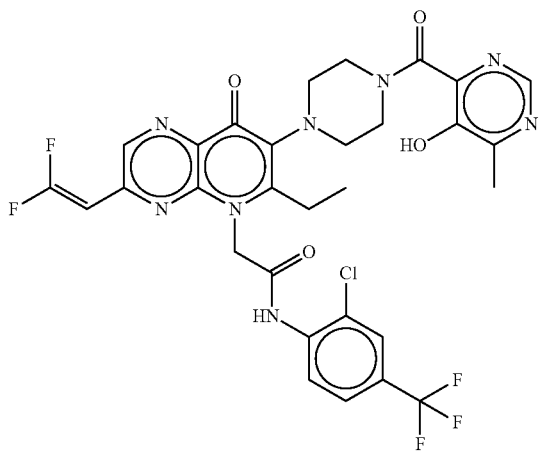
I-67a
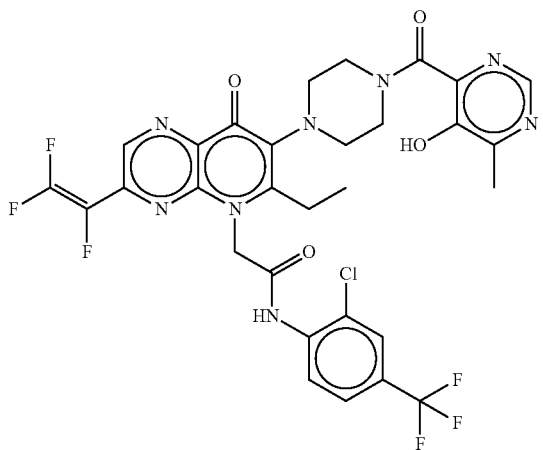
I-68a
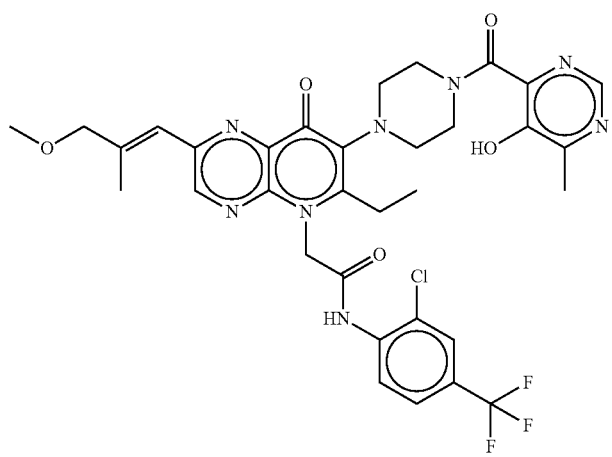

TABLE 2a-continued
Compound No.
I-69a
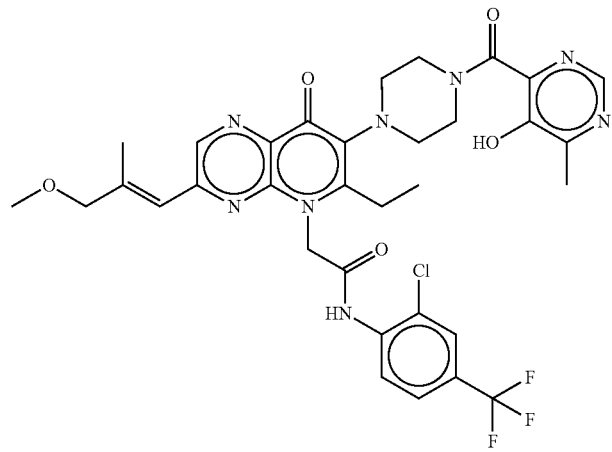
I-70a
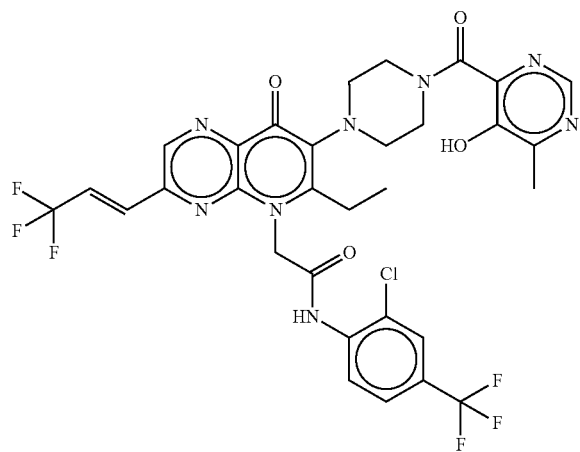
I-71a
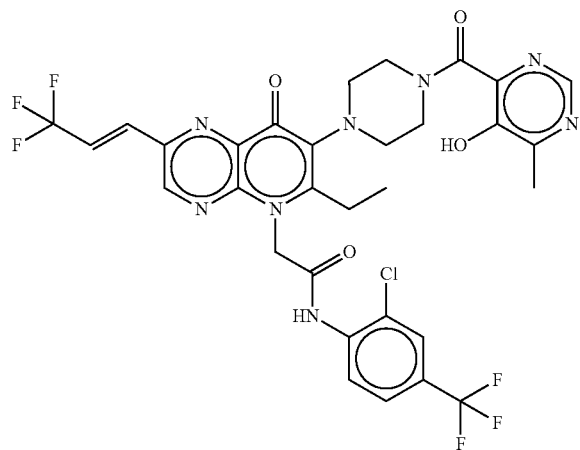

TABLE 2a-continued
Compound No.
I-72a
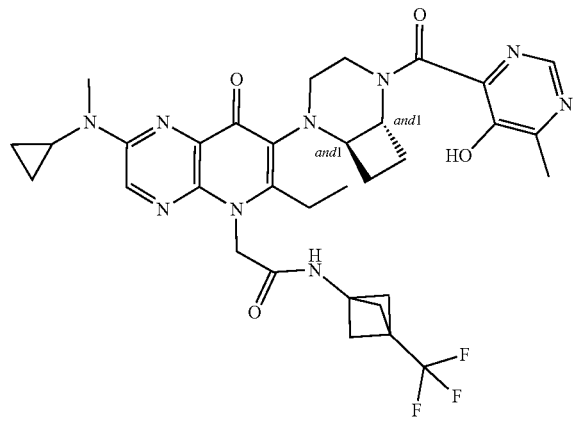 [SMILES: CCc1c(N2CCN(C(=O)c3ncnc(C)c3O)[C@@H]3CC[C@H]32)c(=O)c2nc(N(C)C3CC3)cnc2n1CC(=O)NC12CC(C(F)(F)F)(C1)C2]
I-73a
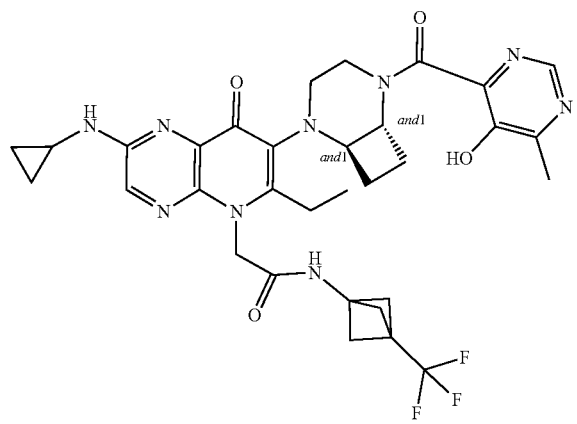 [SMILES: CCc1c(N2CCN(C(=O)c3ncnc(C)c3O)[C@@H]3CC[C@H]32)c(=O)c2nc(NC3CC3)cnc2n1CC(=O)NC12CC(C(F)(F)F)(C1)C2]
I-74a
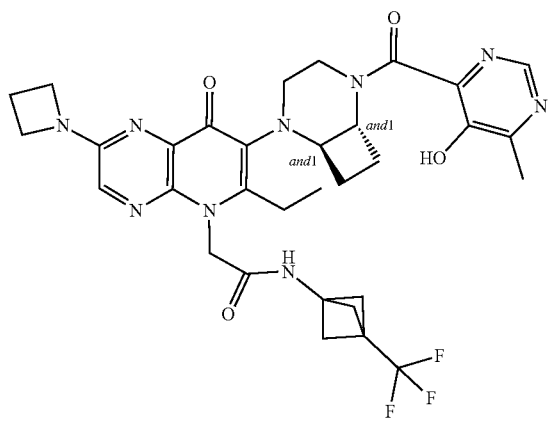 [SMILES: CCc1c(N2CCN(C(=O)c3ncnc(C)c3O)[C@@H]3CC[C@H]32)c(=O)c2nc(N3CCC3)cnc2n1CC(=O)NC12CC(C(F)(F)F)(C1)C2]

TABLE 2a-continued
Compound No.
I-75a
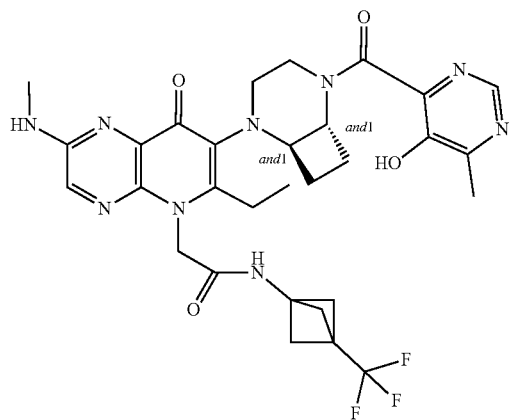 [SMILES: CCc1c(N2CCN(C(=O)c3ncnc(C)c3O)[C@@H]3CC[C@H]32)c(=O)c2nc(NC)cnc2n1CC(=O)NC12CC(C(F)(F)F)(C1)C2]
I-76a
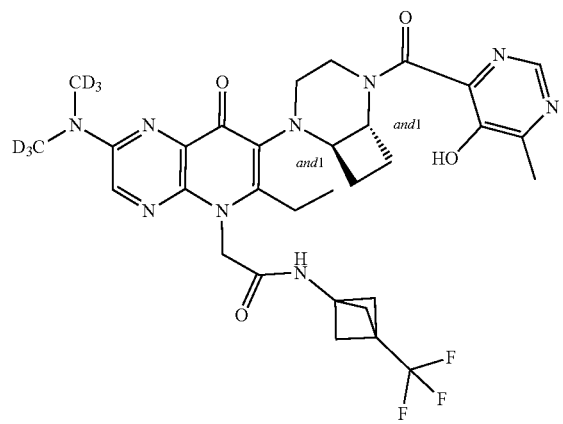 [SMILES: [2H]C([2H])([2H])N(c1cnc2c(n1)c(=O)c(N1CCN(C(=O)c3ncnc(C)c3O)[C@@H]3CC[C@H]31)c(CC)n2CC(=O)NC12CC(C(F)(F)F)(C1)C2)C([2H])([2H])[2H]]
I-77a
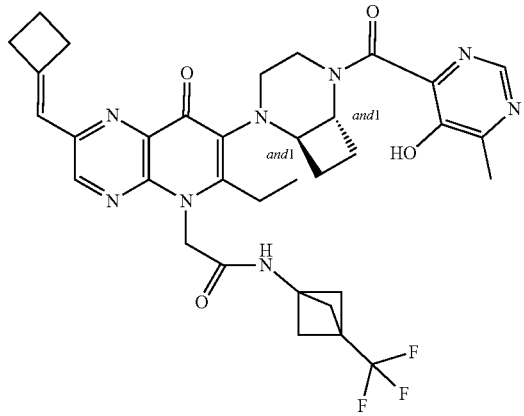 [SMILES: CCc1c(N2CCN(C(=O)c3ncnc(C)c3O)[C@@H]3CC[C@H]32)c(=O)c2nc(C=C3CCC3)cnc2n1CC(=O)NC12CC(C(F)(F)F)(C1)C2]

TABLE 2a-continued
Compound No.
I-78a
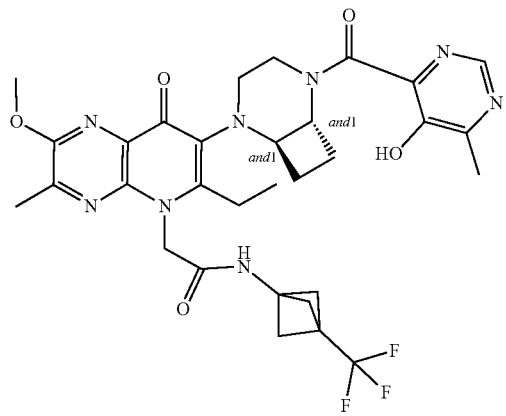 [SMILES: CCc1c(N2CCN(C(=O)c3ncnc(C)c3O)[C@@H]3CC[C@H]32)c(=O)c2nc(OC)c(C)nc2n1CC(=O)NC12CC(C(F)(F)F)(C1)C2]
I-79a
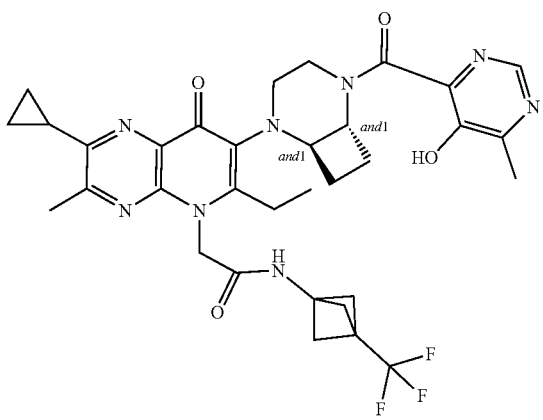 [SMILES: CCc1c(N2CCN(C(=O)c3ncnc(C)c3O)[C@@H]3CC[C@H]32)c(=O)c2nc(C3CC3)c(C)nc2n1CC(=O)NC12CC(C(F)(F)F)(C1)C2]
I-80a
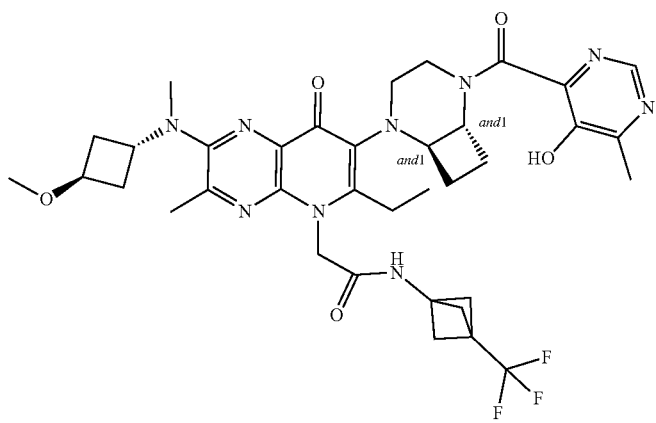 [SMILES: CCc1c(N2CCN(C(=O)c3ncnc(C)c3O)[C@@H]3CC[C@H]32)c(=O)c2nc(N(C)[C@H]3C[C@H](OC)C3)c(C)nc2n1CC(=O)NC12CC(C(F)(F)F)(C1)C2]

TABLE 2a-continued
Compound No.
I-81a
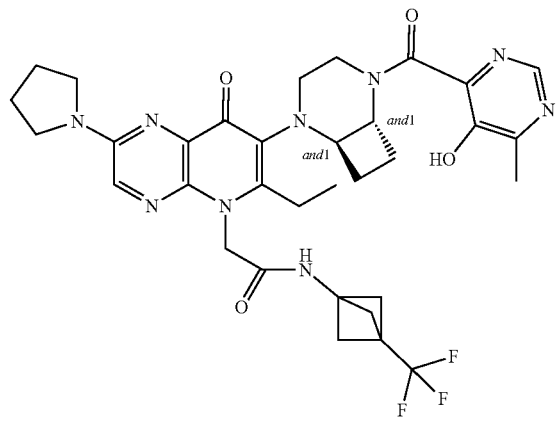 [SMILES: CCc1c(N2CCN(C(=O)c3ncnc(C)c3O)[C@@H]3CC[C@H]32)c(=O)c2nc(N3CCCC3)cnc2n1CC(=O)NC12CC(C(F)(F)F)(C1)C2]
I-82a
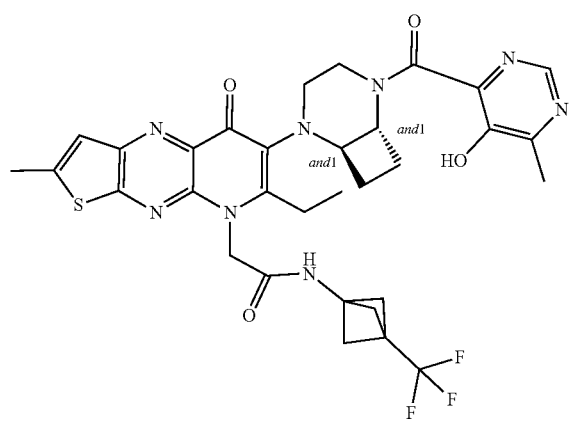 [SMILES: CCc1c(N2CCN(C(=O)c3ncnc(C)c3O)[C@@H]3CC[C@H]32)c(=O)c2nc3cc(C)sc3nc2n1CC(=O)NC12CC(C(F)(F)F)(C1)C2]
I-83a
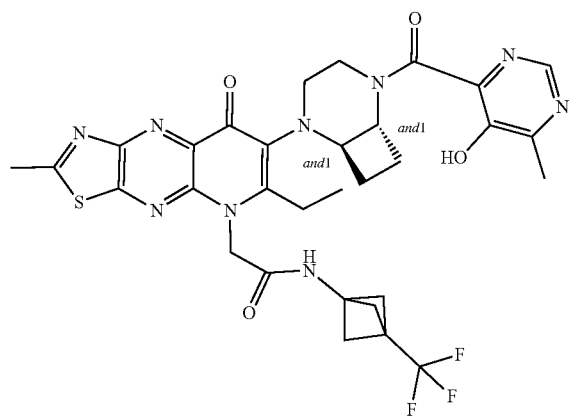 [SMILES: CCc1c(N2CCN(C(=O)c3ncnc(C)c3O)[C@@H]3CC[C@H]32)c(=O)c2nc3nc(C)sc3nc2n1CC(=O)NC12CC(C(F)(F)F)(C1)C2]

TABLE 2a-continued
Compound No.
I-84a
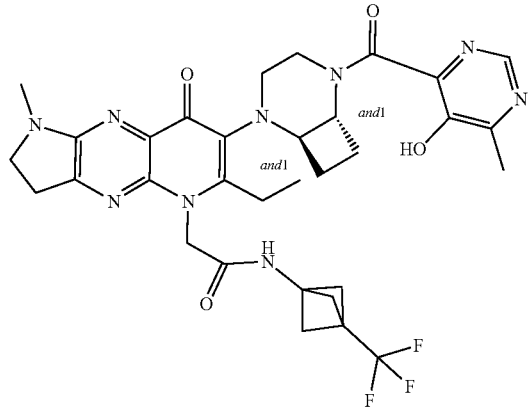 [SMILES: CCc1c(N2CCN(C(=O)c3ncnc(C)c3O)[C@@H]3CC[C@H]32)c(=O)c2nc3c(nc2n1CC(=O)NC12CC(C(F)(F)F)(C1)C2)CCN3C]
I-85a
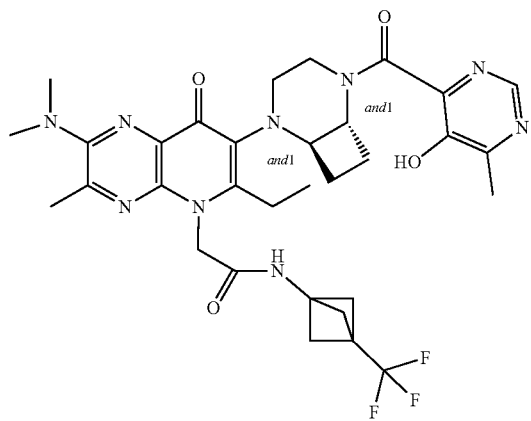 [SMILES: CCc1c(N2CCN(C(=O)c3ncnc(C)c3O)[C@@H]3CC[C@H]32)c(=O)c2nc(N(C)C)c(C)nc2n1CC(=O)NC12CC(C(F)(F)F)(C1)C2]
I-86a
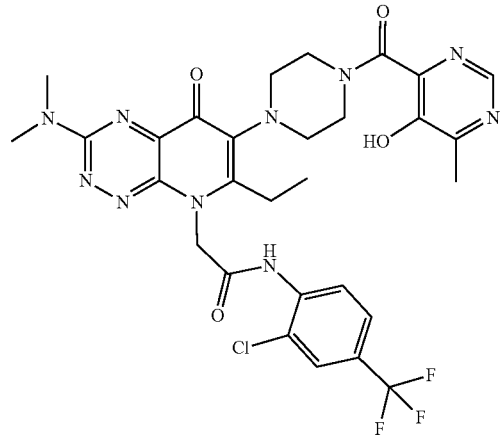 [SMILES: CCc1c(N2CCN(C(=O)c3ncnc(C)c3O)CC2)c(=O)c2nc(N(C)C)nnc2n1CC(=O)Nc1ccc(C(F)(F)F)cc1Cl]

TABLE 2a-continued
Compound No.
I-87a
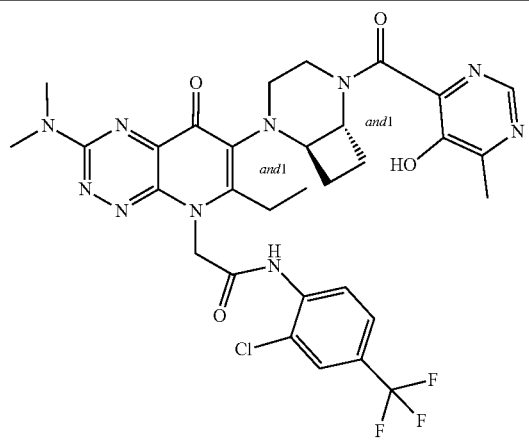
I-89a
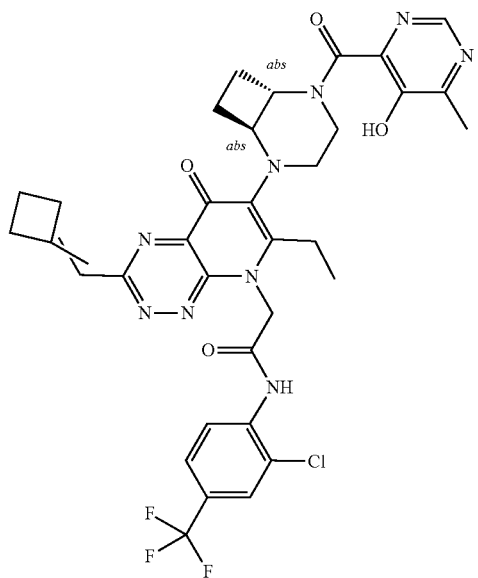
I-91a
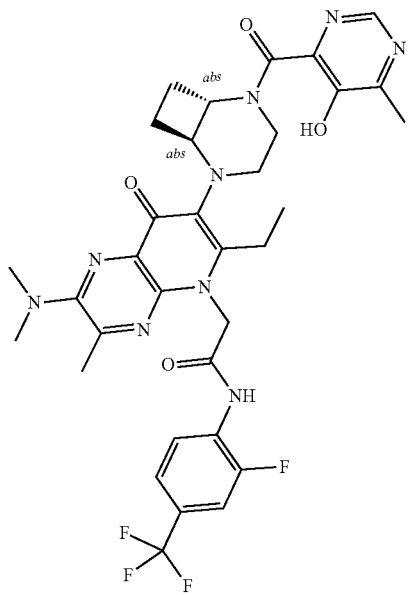

TABLE 2a-continued

Compound No.

I-95a

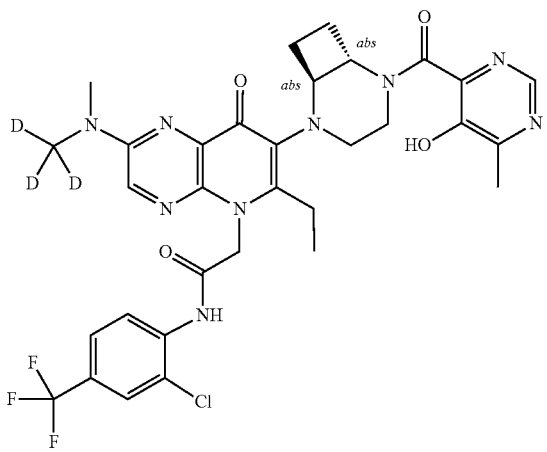 [SMILES: [2H]C([2H])([2H])N(C)c1cnc2c(n1)c(=O)c(N1CCN(C(=O)c3ncnc(C)c3O)[C@H]3CC[C@@H]31)c(CC)n2CC(=O)Nc1ccc(C(F)(F)F)cc1Cl]

LCMS Methods
LCMS 1
 Instrument Shimadzu LCMS-2020
 Stationary Phase HALO C18 3.0×30 mm, 5.0 μm
 Mode Binary Gradient
 Mobile Phase A 0.037500 TFA in water (v/v)
 Mobile Phase B 0.01875% TFA in Acetonitrile (v/v)
 Gradient 5 to 95% B in 0.5 min, 95% B for 0.3 min, 95 to 5% B in 0.25 min
 Flow Rate 1.5 mL/min
 Column Temperature 50° C.
 Column 3.0×30 mm, 5.0 μm
LCMS 2
 Instrument Shimadzu LCMS-2020
 Stationary Phase HALO C18
 Mode Binary Gradient
 Mobile Phase A water/0.05% TFA
 Mobile Phase B ACN/0.05% TFA
 Gradient 5% to 100% B in 1.2 min, hold 100% B in 0.6 min
 Flow Rate (mL/min) 1.5
 Column Temperature (° C.) 40
 Column Dimensions 30×3.0 mm, 2.0 μm
LCMS 3
 Instrument Shimadzu LCMS-2020
 Stationary Phase HALO C18
 Mode Binary Gradient
 Mobile Phase A water/0.05% TFA
 Mobile Phase B ACN/0.05% TFA
 Gradient 5% to 60% B in 1.7 min, 60% to 100% B in 0.6 min, hold 100% B in 0.5 min
 Flow Rate (mL/min) 1.5
 Column Temperature (° C.) 40
 Column Dimensions 30×3.0 mm, 2.0 μm
LCMS 4
 Instrument Shimadzu LCMS-2020
 Mode Binary Gradient
 Stationary Phase Kinetex EVO C18 2.1×30 mm, 5 μm
 Mobile Phase A 0.025% $NH_3·H_2O$ in water (v/v.)
 Mobile Phase B Acetonitrile
 Column Dimensions 2.1×30 mm, 5 μm
 Flow Rate (mL/min) 1.5
 Column Temperature (° C.) 40
 Gradient 5% to 95% B in 0.8 min, hold 95% B for 0.4 min, 95% to 5% B in 0.01 min, hold 5% B for 0.34 min LCMS 8
 Instrument Shimadzu LCMS-2020
 Mode Binary gradient
 Stationary Phase CORTECS C18
 Mobile Phase A water/0.1% FA
 Mobile Phase B ACN/0.07% FA
 Column Dimensions 30×2.1 mm, 2.7 μm
 Flow Rate (mL/min) 1.2
 Column Temperature (° C.) 40
 Gradient 5% to 100% B in 1.2 min, hold 100% B in 0.6 min
LCMS 9
 Instrument Shimadzu LCMS-2020
 Mode Binary gradient
 Stationary Phase Luna Omega PS C18
 Mobile Phase A water/0.1% FA
 Mobile Phase B ACN/0.07% FA
 Column Dimensions 30×2.1 mm, 3.0 μm
 Flow Rate (mL/min) 1.2
 Column Temperature (° C.) 40
 Gradient 5% to 60% B in 1.7 min, 60% to 100% B in 0.6 min, hold 100% B in 0.5 min
LCMS 10
 Instrument Shimadzu LCMS-2020
 Mode Binary gradient
 Stationary Phase HALO C18
 Mobile Phase A water/0.05% TFA
 Mobile Phase B ACN/0.05% TFA
 Column Dimensions 30×3.0 mm, 2.0 um
 Flow Rate (mL/min) 1.5
 Column Temperature (° C.) 40
 Gradient 20% to 50% B in 1.7 min, 50% to 95% B in 0.6 min, hold 100% B in 0.5 min
LCMS 11
 Instrument Shimadzu LCMS-2020
 Mode Binary Gradient
 Stationary Phase Kinetex EVO C18 2.1×30 mm, 5 μm
 Mobile Phase A 0.025% $NH_3·H_2O$ in water (v/v)
 Mobile Phase B Acetonitrile
 Column Dimensions 2.1×30 mm, 5 μm
 Flow Rate (mL/min) 1.5
 Column Temperature (° C.) 40
 Gradient 0% to 60% B in 0.8 min, hold 60% B for 0.4 min, 60% to 0% B in 0.01 min, hold 0% B for 0.34 min Example 2: WRN (BV08) ADP-Glo Assay Protocol Bovine skin gelatin (BSG), dimethyl sulfoxide (DMSO), Pluronic F-127 and tris(2-carboxyethyl)phosphine hydrochloride solution (TCEP) were purchased from Sigma-Aldrich (St. Louis, MO) at the highest level of purity possible. Bicine buffer solution was purchased from Alfa Aesar (Tewksbury, MA) and compound NSC-617145 was purchased from Tocris (Minneapolis, MN). DNA duplex was synthesized at BGI (Shenzhen, China) and was composed of strand 1 with the sequence 5'-GCACTGGCCGTCGTTTTACGGTCG-3' (SEQ ID NO.: 1) and strand 2 with the sequence 5'-TCCAAGTAAAACGACGGCCAGTGC-3' (SEQ ID NO.: 2). DNA strands were annealed by heating to 95° C. for 5 minutes followed by slow cooling to room temperature. Compounds in 100% DMSO (0.1 µl) were spotted into a 384-well white polystyrene Optiplate-384 (Perkin Elmer; Waltham, MA) assay plate using a LabCyte Echo 550 (Agilent; Santa Clara, CA). DMSO (0.1 µl) was added to columns 12, rows A-H and column 24, rows I-P for the maximum signal control. Compound NSC-617145 (0.1 µl) was added to columns 12, rows I-P and 24, rows A-H for the minimum signal control (100% inhibition). Compounds/DMSO were preincubated for 15 minutes at 25° C. with 5 µl 2×WRN (BV08), prepared as described below, in assay buffer containing 20 mM Bicine (pH=7.5), 1 mM $MgCl_2$, 10 mM KCl, 0.1% Pluronic F-127, 0.005% BSG, 1 mM TCEP. The reaction was initiated by the addition of 5 µl 2× substrate mixture in assay buffer and incubated for 60 minutes at 25° C. The final concentrations of the assay components were 0.15 nM WRN, 5 µM ATP, and 0.1 nM DNA duplex. The final DMSO concentration was 1% and the reference compound concentration (NSC-617145) used for the minimal signal control was 20 µM. The reaction was stopped by the addition of the ADP-Glo Kit components (Promega; Madison, WI) as directed and the relative luminescence units (RLU) were read on an Envision 2104 (Perkin Elmer; Waltham, MA).

% INH=(RLU MAX−RLU sample)/(RLU MAX−RLU MIN))×100     % Inhibition Calculation

Where RLU=relative luminescence units, sample=signal in sample well, and MIN and MAX are the respective minimum and maximum signal controls.

Y=Bottom+(Top−Bottom)/(1+(IC50/X)^Hill Slope)     Four-Parameter $IC_{50}$ Fit Equation Where top and bottom are normally allowed to float but may be fixed at 100 or 0 respectively in a 3-parameter fit. Y is the % inhibition and X is the compound concentration.

WRN Protein Production

Molecular Biology and virus production. The DNA encoding human Werner helicase (Uniprot Q14191, amino acids 517-1235 with L1074F point mutation) was generated with codon-optimization for *E. coli* expression and subcloned into the pFastBac vector with a TEV cleavable 8×His tag (WRN—BV08). The baculovirus from the expression plasmid WRN—BV08 was generated from transfection and amplification following the manufacturer's instructions.

Gene Sequence of WRN—BV08 [pFastBac1-WRN-(517-1235 L1074F)-TEV-8His]

(SEQ ID NO.: 3)
ATGAACGAGGGCGAAGAAGACGACGACAAGGACTTCCTGTGGCCTGCCC

CTAACGAAGAACAAGTGACATGCCTGAAGATGTACTTCGGACACAGTAG

CTTCAAGCCTGTGCAATGGAAGGTCATCCACTCCGTGCTGGAAGAAAGA

AGGGACAACGTGGCTGTGATGGCTACCGGATACGGTAAGTCCCTGTGCT

TCCAGTACCCTCCCGTGTACGTGGGCAAGATCGGTCTGGTGATCTCCCC

TCTGATCTCTCTGATGGAGGACCAGGTGCTGCAATTGAAGATGTCCAAC

ATCCCCGCTTGCTTCCTGGGTTCCGCTCAAAGTGAGAACGTGCTGACAG

ACATCAAGCTGGGCAAGTACCGCATCGTGTACGTGACCCCTGAGTACTG

CTCCGGTAACATGGGTCTGCTGCAACAGCTGGAGGCTGACATCGGAATC

ACCCTGATCGCTGTGGACGAGGCTCACTGCATCTCCGAGTGGGGACACG

ACTTCCGCGACTCCTTCCGTAAGCTGGGATCCTTGAAGACCGCTCTCCC

TATGGTGCCTATCGTGGCCCTGACCGCCACTGCTTCCTCCTCCATCCGC

GAGGACATCGTGCGTTGCCTGAACCTGCGCAACCCTCAGATCACTTGCA

CCGGTTTCGACCGCCCTAACTTGTACCTCGAGGTGCGTCGCAAGACCGG

TAACATCCTCCAGGACCTGCAGCCTTTCCTGGTCAAGACCTCCTCCCAC

TGGGAATTTGAGGGCCCTACCATCATCTACTGCCCTTCCCGCAAGATGA

CCCAGCAAGTCACCGGCGAGCTGCGCAAGCTCAACCTCTCCTGCGGTAC

CTACCACGCTGGTATGTCCTTCTCCACCCGCAAGGACATCCACCACCGC

TTCGTCCGTGACGAAATCCAATGCGTCATCGCTACCATCGCTTTCGGAA

TGGGCATCAACAAGGCTGACATCCGCCAGGTGATCCACTACGGCGCCCC

CAAGGACATGGAATCCTACTACCAGGAAATCGGTCGCGCCGGTCGCGAC

GGTCTGCAGTCTTCCTGTCACGTGCTGTGGGCCCCCGCTGACATCAACC

TGAACCGCCACCTGCTGACCGAAATCCGCAACGAGAAGTTCCGCCTGTA

CAAGCTCAAGATGATGGCTAAGATGGAGAAGTACCTGCACTCCTCCCGC

TGTCGCCGTCAGATCATCCTCTCCCACTTCGAGGACAAGCAAGTGCAAA

AGGCTAGCCTGGGTATCATGGGCACCGAAAAGTGTTGTGACAACTGCCG

CTCCCGCCTCGACCACTGCTACTCCATGGACGACAGCGAGGACACCTCC

TGGGACTTCGGTCCTCAAGCTTTCAAGCTCTTGTCCGCTGTGGACATCC

TGGGCGAGAAGTTCGGTATCGGTCTCCCCATCCTCTTCCTGCGTGGTAG

CAACTCCCAACGCCTGGCTGACCAGTACCGCCGCCACTCCCTCTTCGGT

ACCGGTAAGGACCAGACCGAGTCCTGGTGGAAGGCTTTCTCTCGCCAAC

TGATCACCGAAGGTTTCCTGGTGGAGGTGTCCCGCTACAACAAGTTCAT

GAAGATCTGCGCTCTCACTAAGAAGGGAAGGAACTGGCTGCACAAGGCT

AACACTGAGTCCCAATCCCTCATCCTGCAGGCTAACGAGGAGCTGTGCC

CTAAGAAGTTCCTGCTGCCTTCCTCCAAGACCGTGTCCTCCGGAACAAA

GGAACACTGCTACAACCAAGTCCCTGTGGAGCTCTCCACCGAGAAGAAG

TCCAACCTGGAGAAGCTGTACAGCTACAAGCCTTGCGACAAGATCAGCT

CCGGTTCCAACATCAGCAAGAAGTCCATCATGGTGCAATCCCCTGAAAA

GGCCTACTCCAGCTCCCAACCTGTCATCTCCGCTCAAGAGCAAGAGACC

CAGATCGTGCTGTACGGTAAGCTGGTCGAAGCCCGCCAAAAGCACGCTA

ACAAGATGGACGTCCCTCCCGCTATCCTCGCCACCAACAAGATCCTCGT

GGATATGGCTAAGATGCGCCCCACCACCGTCGAGAACGTGAAGCGCATC

GACGGTGTCTCCGAGGGTAAGGCCGCTATGCTGGCTCCTCTGCTGGAAG

TGATCAAGCACTTCTGCCAGACCAACTCCGTGCAGACCGACCTGTTCAG

TAGTGAGAACCTGTACTTCCAAGGCCACCATCATCATCATCATCACCAC

TAA

Protein Sequence of WRN—BV08 [pFastBac1-WRN-(517-1235 L1074F)-TEV-8His] SEQ ID NO.: 4)

(SEQ ID NO.: 4)
MNEGEEDDDKDFLWPAPNEEQVTCLKMYFGHSSFKPVQWKVIHSVLEER

RDNVAVMATGYGKSLCFQYPPVYVGKIGLVISPLISLMEDQVLQLKMSN

IPACFLGSAQSENVLTDIKLGKYRIVYVTPEYCSGNMGLLQQLEADIGI

TLIAVDEAHCISEWGHDFRDSFRKLGSLKTALPMVPIVALTATASSSIR

EDIVRCLNLRNPQITCTGFDRPNLYLEVRRKTGNILQDLQPFLVKTSSH

WEFEGPTIIYCPSRKMTQQVTGELRKLNLSCGTYHAGMSFSTRKDIHHR

FVRDEIQCVIATIAFGMGINKADIRQVIHYGAPKDMESYYQEIGRAGRD

GLQSSCHVLWAPADINLNRHLLTEIRNEKFRLYKLKMMAKMEKYLHSSR

CRRQIILSHFEDKQVQKASLGIMGTEKCCDNCRSRLDHCYSMDDSEDTS

WDFGPQAFKLLSAVDILGEKFGIGLPILFLRGSNSQRLADQYRRHSLFG

TGKDQTESWWKAFSRQLITEGFLVEVSRYNKFMKICALTKKGRNWLHKA

NTESQSLILQANEELCPKKFLLPSSKTVSSGTKEHCYNQVPVELSTEKK

SNLEKLYSYKPCDKISSGSNISKKSIMVQSPEKAYSSSQPVISAQEQET

QIVLYGKLVEARQKHANKMDVPPAILATNKILVDMAKMRPTTVENVKRI

DGVSEGKAAMLAPLLEVIKHFCQTNSVQTDLFSSENLYFQGHHHHHHHH

Sf9 cells grown in SF900II media were infected with 1:200 WRN—BV08 P2 virus and incubated for protein expression for 72 h at 27° C. The WRN protein was purified using the following protocol. The cell pellets were thawed and resuspended in buffer A (50 mM Tris, pH 7.5, 500 mM NaCl, 1 mM TCEP, 10% Glycerol) supplemented with 0.5% CHAPS, 1 mM PMSF, 1 µg/ml Leupeptin, 1 µg/ml Pepstatin, and the Pierce Universal Nuclease and cocktail tablet. Cleared lysates were loaded onto a Ni Sepharose™ excel column and washed with buffer A and bound protein was eluted with buffer A supplemented with 300 mM imidazole. The eluted protein was dialyzed against buffer A and digested by His-tagged TEV (1:5 ratio) overnight at 4° C. $ZnCl_2$ was added into the sample at final 15 µM before loading onto a second Ni Sepharose™ excel column. Untagged WRN protein was eluted from the column with buffer A supplemented with 20 mM imidazole, dialyzed overnight into buffer B (50 mM Tris, pH 7.5, 1 mM TCEP, 10% Glycerol) supplemented with 150 mM NaCl and loaded onto a Heparin column. Proteins were eluted with a step gradient of buffer B supplemented with 150 mM, 200 mM, 300 mM and 500 mM NaCl. WRN containing fractions were pooled and concentrated prior to loading on to size exclusion chromatography using a HiLoad 16/600 Superdex™ 200 pg column (GE Healthcare) in buffer C (20 mM HEPES, pH 7.5, 250 mM NaCl, 0.25 mM TCEP, 2.500 Glycerol).

The resultant $IC_{50}$ results obtained for the tested compounds are shown below in Table 3. Compounds with an $IC_{50}$ less than or equal to 0.005 µM are designated as "A." Compounds with an $IC_{50}$ greater than 0.005 µM and less than or equal to 0.05 µM are designated as "B." Compounds with an $IC_{50}$ greater than 0.05 µM and less than or equal to 0.1 µM are designated as "C." Compounds with an $IC_{50}$ greater than 0.1 µM or equal to 0.5 µM are designated as "D." Compounds with an $IC_{50}$ greater than 0.5 µM are designated as "E."

TABLE 3

| Compound No. | ADP-Glo_hWRN_IC50 [mM] |
| --- | --- |
| I-1 | B |
| I-2 | C |
| I-3 | B |
| I-4 | B |
| I-5 | D |
| I-6 | B |
| I-7 | B |
| I-8 | B |
| I-9 | B |
| I-10 | B |
| I-11 | B |
| I-12 | B |
| I-13 | C |
| I-14 | B |
| I-15 | B |
| I-16 | B |
| I-17 | B |
| I-18 | B |
| I-19 | B |
| I-20 | B |
| I-21 | B |
| I-22 | C |
| I-23 | B |
| I-24 | B |
| I-25 | C |
| I-26 | D |
| I-27 | B |
| I-28 | B |
| I-29 | B |
| I-30 | C |
| I-31 | B |
| I-32 | C |
| I-33 | B |
| I-34 | B |
| I-35 | B |
| I-36 | B |
| I-37 | A |
| I-38 | A |
| I-39 | C |
| I-40 | B |
| I-41 | D |
| I-42 | B |
| I-43 | D |
| I-44 | B |
| I-45 | B |
| I-46 | B |
| I-47 | B |
| I-48 | D |
| I-49 | C |
| I-50 | C |
| I-51 | B |
| I-52 | B |
| I-53 | B |
| I-54 | D |
| I-55 | B |
| I-56 | B |
| I-57 | B |
| I-58 | B |
| I-59 | B |
| I-60 | B |
| I-61 | B |
| I-62 | B |
| I-63 | B |
| I-64 | B |
| I-65 | B |
| I-66 | B |
| I-67 | B |
| I-68 | B |
| I-69 | B |
| I-70 | B |
| I-71 | B |
| I-72 | B |
| I-73 | B |
| I-74 | B |
| I-75 | B |
| I-76 | B |
| I-77 | B |
| I-79 | B |

TABLE 3-continued

| Compound No. | ADP-Glo_hWRN_IC50 [mM] |
|---|---|
| I-80 | B |
| I-81 | C |
| I-82 | B |
| I-83 | B |
| I-84 | C |
| I-86 | B |
| I-87 | B |
| I-88 | B |
| I-89 | D |
| I-90 | B |
| I-91 | B |
| I-92 | B |
| I-93 | B |
| I-94 | B |
| I-95 | B |
| I-96 | B |
| I-97 | B |
| I-98 | B |
| I-99 | B |
| I-100 | A |
| I-101 | B |
| I-102 | A |
| I-103 | B |
| I-104 | B |
| I-105 | B |
| I-106 | B |
| I-107 | A |
| I-108 | D |
| I-109 | B |
| I-110 | D |
| I-111 | A |
| I-112 | B |
| I-113 | A |
| I-114 | B |
| I-115 | B |
| I-116 | B |
| I-117 | B |
| I-118 | B |
| I-119 | B |
| I-120 | B |
| I-121 | B |
| I-122 | A |
| I-123 | B |
| I-124 | B |
| I-125 | A |
| I-126 | B |
| I-127 | B |
| I-128 | B |
| I-129 | B |
| I-130 | B |
| I-131 | B |
| I-132 | B |
| I-133 | B |
| I-134 | C |
| I-135 | B |
| I-136 | B |
| I-137 | B |
| I-138 | B |
| I-139 | B |
| I-140 | E |
| I-141 | B |
| I-142 | A |
| I-143 | B |
| I-144 | A |
| I-145 | B |
| I-146 | B |
| I-147 | B |
| I-148 | B |
| I-149 | B |
| I-150 | B |
| I-151 | B |
| I-152 | B |
| I-153 | B |
| I-154 | E |
| I-155 | C |
| I-156 | B |
| I-157 | B |
| I-158 | B |

TABLE 3-continued

| Compound No. | ADP-Glo_hWRN_IC50 [mM] |
|---|---|
| I-159 | B |
| I-160 | B |
| I-161 | B |
| I-162 | B |
| I-163 | B |
| I-164 | B |
| I-165 | B |
| I-166 | A |
| I-167 | B |
| I-168 | D |
| I-169 | B |
| I-170 | B |
| I-171 | C |
| I-172 | A |
| I-173 | B |
| I-174 | B |
| I-175 | B |
| I-176 | C |
| I-177 | B |
| I-178 | B |
| I-179 | B |
| I-180 | B |
| I-181 | B |
| I-182 | A |
| I-183 | B |
| I-184 | B |
| I-185 | B |
| I-186 | B |
| I-187 | B |
| I-188 | B |
| I-189 | B |
| I-190 | B |
| I-191 | B |
| I-192 | A |
| I-193 | A |
| I-194 | A |
| I-195 | B |
| I-196 | B |
| I-197 | C |
| I-198 | B |
| I-199 | B |
| I-200 | B |
| I-201 | B |
| I-203 | A |
| I-204 | B |
| I-205 | B |
| I-206 | B |
| I-207 | B |
| I-208 | D |
| I-209 | B |
| I-210 | B |
| I-211 | B |
| I-212 | B |
| I-213 | B |
| I-214 | B |
| I-215 | D |
| I-216 | C |
| I-217 | D |
| I-218 | A |
| I-219 | A |
| I-220 | A |
| I-221 | B |
| I-222 | B |
| I-223 | B |
| I-224 | B |
| I-225 | B |
| I-226 | A |
| I-227 | A |
| I-228 | B |
| I-229 | B |
| I-230 | B |
| I-231 | B |
| I-232 | B |
| I-233 | B |
| I-234 | B |
| I-236 | B |
| I-237 | B |
| I-238 | B |

TABLE 3-continued

| Compound No. | ADP-Glo_hWRN_IC50 [mM] |
|---|---|
| I-239 | B |
| I-240 | B |
| I-241 | A |
| I-242 | B |
| I-243 | B |
| I-244 | B |
| I-245 | B |
| I-246 | B |
| I-247 | D |
| I-248 | C |
| I-249 | B |
| I-250 | B |
| I-251 | B |
| I-252 | D |
| I-253 | B |
| I-254 | B |
| I-255 | B |
| I-256 | D |
| I-257 | E |
| I-258 | D |
| I-259 | B |
| I-260 | B |
| I-261 | B |
| I-262 | B |
| I-263 | B |
| I-264 | B |
| I-265 | B |
| I-266 | B |
| I-267 | B |
| I-268 | A |
| I-269 | B |
| I-270 | B |
| I-271 | B |
| I-272 | B |
| I-273 | B |
| I-274 | B |
| I-275 | B |
| I-276 | B |
| I-277 | B |
| I-278 | B |
| I-279 | D |
| I-280 | B |
| I-281 | B |
| I-282 | B |
| I-283 | A |
| I-284 | B |
| I-285 | B |

| Compound No. | ADP-Glo_hWRN_IC50 [mM] |
|---|---|
| I-286 | B |
| I-287 | B |
| I-288 | B |
| I-289 | B |
| I-290 | B |
| I-291 | B |
| I-292 | B |
| I-293 | B |
| I-294 | E |
| I-295 | B |
| I-296 | B |
| I-297 | D |
| I-299 | B |
| I-300 | B |
| I-301 | B |
| I-302 | B |
| I-303 | C |

Example 3: Method for Determining Effect on p21 Induction in Cells

The colon carcinoma cell line HCT116 was obtained from ATCC and cultured in growth medium consisting of Mccoy's 5A Medium (Gibco 16600108) supplemented with 10% FBS (Transgene FS201-02) and 100 units/mL penicillin-streptomycin (Gibco 15140122) and maintained at 37° C. under 5% $CO_2$. On the day of seeding, 2,000 cells in 30 μL of culture media were plated per well to Poly-D-Lysine 384 Well Black Clear Plates (Biocoat 356663) and incubated overnight at 37° C. under 5% $CO_2$. The following day, compounds were serially diluted in DMSO for a total of 11 test concentrations. The typical starting concentration of compounds was 10 μM with 2-fold dilutions. Next, 150 nL of diluted compound was added in duplicate to the assay plate, using an Echo 655 (Labcyte). The plate was centrifuged at 500 RPM for 1 min and then incubated at 37° C. under 5% $CO_2$ for 24 h. After 24 h, medium was removed, and cells were fixed by adding 40 μL of 4% paraformaldehyde solution to each well and incubated for 20 min at room temperature. The plate was then washed 4 times with 100 μL per well of wash buffer (PBS with 0.1% Tween-20) using a microplate washer. Next, 30 μL of ice-cold methanol was added to each well and the plate was incubated at −20° C. for 10 min. The plate was washed 4 times with 100 μL per well of wash buffer by a microplate washer, then 30 μL per well of blocking buffer (Intercept PBS blocking buffer (LI-COR 927-70001) with 0.05% Tween-20) was added and the plate was incubated at room temperature with shaking for 2 h. Next, to each test well, 20 μL of primary antibody solution (p21 Waf1/CIP (12D1) RabbitmAb (Cell Signaling Technologies 2947) diluted 1:1000 and GAPDH (D4C6R) Mouse mAb (Cell Signaling Technologies 97166) diluted 1:2000 in blocking buffer) was added and the plate was placed at 4° C., overnight. The following day, the plate was washed 5 times with 100 μL per well of wash buffer using a microplate washer for 5 min. 20 μL per well of secondary antibody (IRDye 680CW Goat anti-Mouse IgG (H+L) (LI-COR 926-68070) diluted 1:2000 in Blocking Buffer and IRDye 800CW Goat anti-Rabbit IgG (H+L) (LI-COR 926-32211) diluted 1:2000 in Blocking Buffer) was then added and the plate was stored for 2 h in the dark at room temperature with shaking. The plate was then washed 4 times with 100 μL per well of wash buffer again using a microplate washer. Finally, the p21 signal and the GAPDH signal were quantified using a LI-COR Odyssey CLx Imager machine reading at 800 nm and 700 nm, respectively. Each plate contained DMSO control (low control) and an internal reference WRN inhibitor (high control) respectively. For quantitation, the 800 nm/700 nm ratio was calculated for each well to give fold p21 induction and then percent activation for each compound well was calculated as follows (100×(ratio cpd well−ratio low control)/(ratio high control−ratio low control)). EC50 values for each compound were generated after non-linear regression curve fitting using commercially available software. The resultant $EC_{50}$ results obtained for the tested compounds are shown below in Table 4. Compounds with an $EC_{50}$ less than or equal to 0.50 μM are designated as "A." Compounds with an $EC_{50}$ greater than 0.50 μM and less than or equal to 2.00 μM are designated as "B." Compounds with an $EC_{50}$ greater than 2.00 μM and less than or equal to 5.00 μM are designated as "C." Compounds with an $EC_{50}$ greater than 5.00 μM are designated as "D."

TABLE 4

| Compound No. | P21_$EC_{50}$ [mM] |
|---|---|
| I-1 | C |
| I-2 | D |

TABLE 4-continued

| Compound No. | P21_EC$_{50}$ [mM] |
|---|---|
| I-3 | D |
| I-4 | D |
| I-5 | D |
| I-6 | C |
| I-7 | D |
| I-8 | B |
| I-9 | B |
| I-10 | C |
| I-11 | C |
| I-12 | D |
| I-13 | D |
| I-14 | B |
| I-15 | A |
| I-16 | B |
| I-17 | B |
| I-18 | B |
| I-19 | D |
| I-20 | D |
| I-21 | B |
| I-22 | D |
| I-23 | B |
| I-24 | D |
| I-25 | D |
| I-26 | D |
| I-27 | D |
| I-28 | D |
| I-29 | B |
| I-30 | D |
| I-31 | D |
| I-32 | D |
| I-33 | D |
| I-34 | A |
| I-35 | C |
| I-36 | C |
| I-37 | A |
| I-38 | A |
| I-39 | C |
| I-40 | A |
| I-41 | D |
| I-42 | C |
| I-43 | D |
| I-44 | D |
| I-45 | D |
| I-46 | D |
| I-47 | D |
| I-48 | D |
| I-49 | D |
| I-50 | D |
| I-51 | A |
| I-52 | D |
| I-53 | B |
| I-54 | D |
| I-55 | B |
| I-56 | D |
| I-57 | B |
| I-58 | A |
| I-59 | C |
| I-60 | B |
| I-61 | A |
| I-62 | D |
| I-63 | D |
| I-64 | B |
| I-65 | D |
| I-66 | C |
| I-67 | D |
| I-68 | D |
| I-69 | D |
| I-70 | D |
| I-71 | D |
| I-72 | D |
| I-73 | D |
| I-74 | B |
| I-75 | B |
| I-76 | D |
| I-77 | D |
| I-79 | D |
| I-80 | D |
| I-81 | D |
| I-82 | D |
| I-83 | D |
| I-84 | D |
| I-86 | C |
| I-87 | B |
| I-88 | D |
| I-89 | D |
| I-90 | D |
| I-91 | D |
| I-92 | B |
| I-93 | B |
| I-94 | D |
| I-95 | B |
| I-96 | D |
| I-97 | A |
| I-98 | A |
| I-99 | D |
| I-100 | A |
| I-101 | A |
| I-102 | A |
| I-103 | A |
| I-104 | A |
| I-105 | A |
| I-106 | B |
| I-107 | A |
| I-108 | D |
| I-109 | B |
| I-110 | D |
| I-111 | A |
| I-112 | A |
| I-113 | A |
| I-114 | A |
| I-115 | D |
| I-116 | B |
| I-117 | A |
| I-118 | B |
| I-119 | A |
| I-120 | A |
| I-121 | A |
| I-122 | A |
| I-123 | A |
| I-124 | A |
| I-125 | A |
| I-126 | A |
| I-127 | A |
| I-128 | A |
| I-129 | A |
| I-130 | A |
| I-131 | B |
| I-132 | A |
| I-133 | D |
| I-134 | D |
| I-135 | A |
| I-136 | A |
| I-137 | D |
| I-138 | D |
| I-139 | B |
| I-140 | D |
| I-141 | D |
| I-142 | B |
| I-143 | C |
| I-144 | B |
| I-145 | D |
| I-146 | C |
| I-147 | D |
| I-148 | D |
| I-149 | B |
| I-150 | B |
| I-151 | C |
| I-152 | D |
| I-153 | C |
| I-154 | D |
| I-155 | D |
| I-156 | B |
| I-157 | B |
| I-158 | D |
| I-159 | D |
| I-160 | D |

TABLE 4-continued

| Compound No. | P21_EC$_{50}$ [mM] |
|---|---|
| I-161 | C |
| I-162 | B |
| I-163 | D |
| I-164 | C |
| I-165 | B |
| I-166 | B |
| I-167 | C |
| I-168 | D |
| I-169 | B |
| I-170 | A |
| I-171 | D |
| I-172 | A |
| I-173 | NA* |
| I-174 | C |
| I-175 | C |
| I-176 | D |
| I-177 | D |
| I-178 | D |
| I-179 | C |
| I-180 | B |
| I-181 | A |
| I-182 | A |
| I-183 | D |
| I-184 | C |
| I-185 | A |
| I-186 | C |
| I-187 | B |
| I-188 | B |
| I-189 | B |
| I-190 | A |
| I-191 | B |
| I-192 | A |
| I-193 | NA* |
| I-194 | A |
| I-195 | C |
| I-196 | B |
| I-197 | D |
| I-198 | NA* |
| I-199 | A |
| I-200 | A |
| I-201 | C |
| I-203 | B |
| I-204 | A |
| I-205 | A |
| I-206 | D |
| I-207 | C |
| I-208 | D |
| I-209 | A |
| I-210 | A |
| I-211 | A |
| I-212 | B |
| I-213 | B |
| I-214 | A |
| I-215 | D |
| I-216 | D |
| I-217 | D |
| I-218 | B |
| I-219 | A |
| I-220 | A |
| I-221 | D |
| I-222 | A |
| I-223 | B |
| I-224 | C |
| I-225 | A |
| I-226 | A |
| I-227 | A |
| I-228 | A |
| I-229 | B |
| I-230 | A |
| I-231 | A |
| I-232 | A |
| I-233 | D |
| I-234 | B |
| I-236 | A |
| I-237 | D |
| I-238 | D |
| I-239 | A |
| I-240 | A |
| I-241 | A |
| I-242 | A |
| I-243 | A |
| I-244 | D |
| I-245 | A |
| I-246 | B |
| I-247 | D |
| I-248 | NA* |
| I-249 | A |
| I-250 | A |
| I-251 | A |
| I-252 | C |
| I-253 | A |
| I-254 | B |
| I-255 | A |
| I-256 | D |
| I-257 | D |
| I-258 | D |
| I-259 | B |
| I-260 | NA* |
| I-261 | A |
| I-262 | A |
| I-263 | D |
| I-264 | A |
| I-265 | C |
| I-266 | B |
| I-267 | A |
| I-268 | A |
| I-269 | A |
| I-270 | B |
| I-271 | B |
| I-272 | A |
| I-273 | A |
| I-274 | A |
| I-275 | A |
| I-276 | B |
| I-277 | B |
| I-278 | C |
| I-279 | D |
| I-280 | D |
| I-281 | A |
| I-282 | A |
| I-283 | A |
| I-284 | A |
| I-285 | B |
| I-286 | A |
| I-287 | A |
| I-288 | A |
| I-289 | B |
| I-290 | A |
| I-291 | C |
| I-292 | D |
| I-293 | A |
| I-294 | D |
| I-295 | NA* |
| I-296 | B |
| I-297 | D |
| I-299 | A |
| I-300 | A |
| I-301 | A |
| I-302 | A |
| I-303 | D |

NA* = not available

NA*=not available

We claim:

1. A compound selected from the group consisting of:

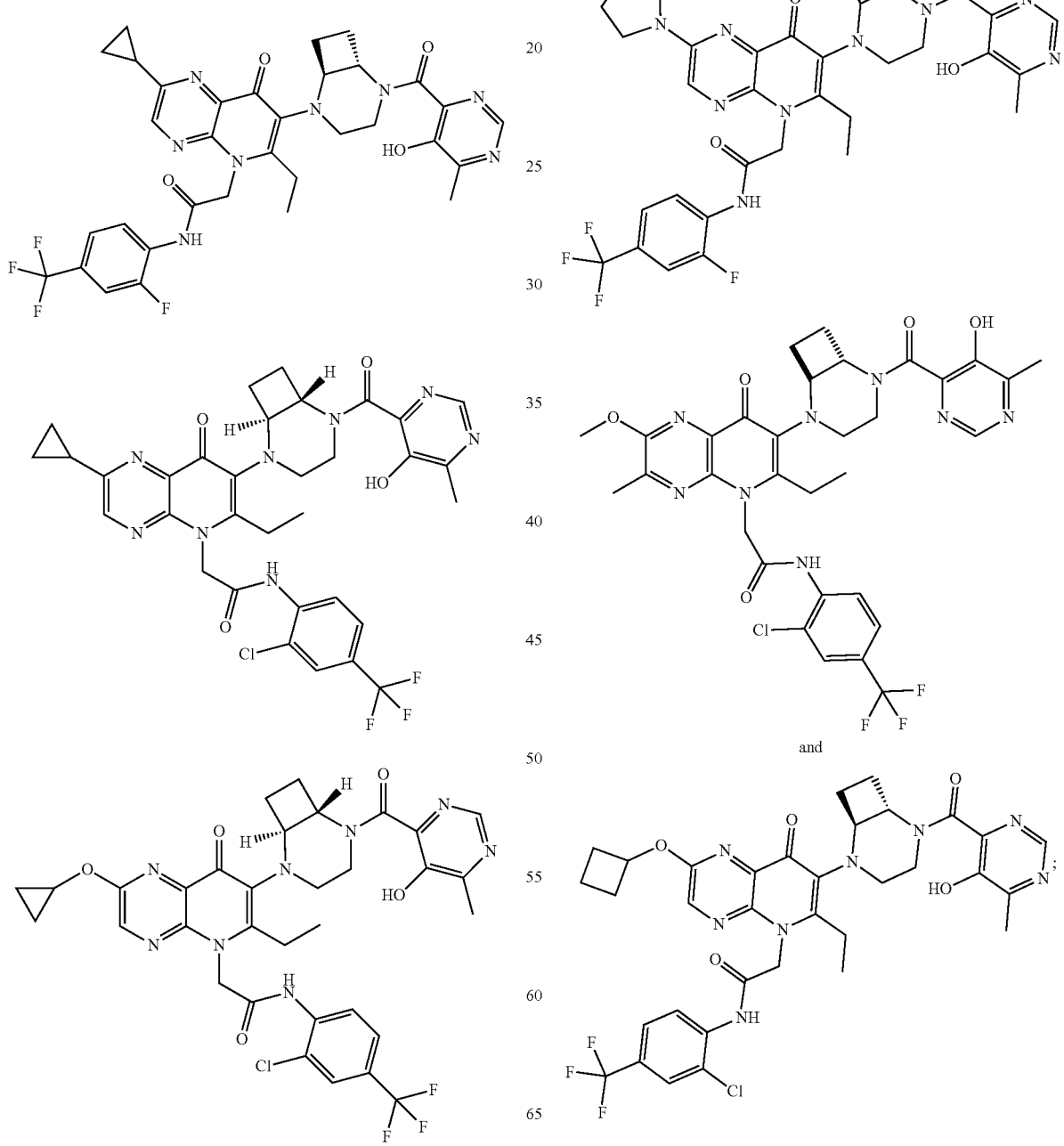

or a pharmaceutically acceptable salt thereof.

2. The compound of claim 1, wherein the compound is:

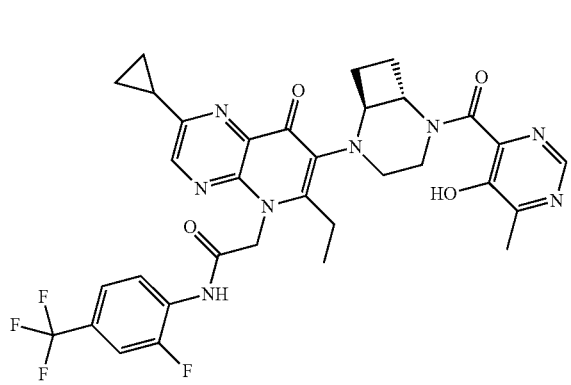 [SMILES: CCc1c(N2CCN(C(=O)c3ncnc(C)c3O)[C@H]3CC[C@@H]32)c(=O)c2nc(C3CC3)cnc2n1CC(=O)Nc1ccc(C(F)(F)F)cc1F]

or a pharmaceutically acceptable salt thereof.

3. The compound of claim 1, wherein the compound is:

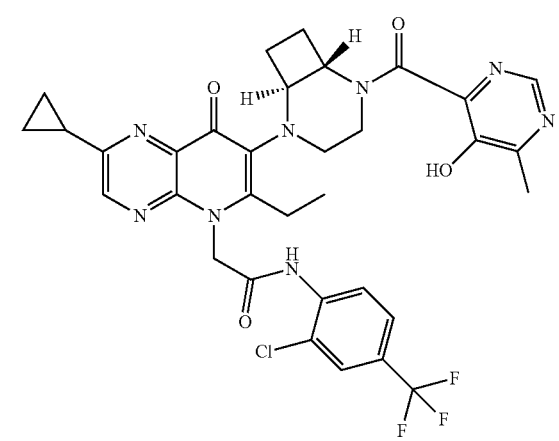 [SMILES: CCc1c(N2CCN(C(=O)c3ncnc(C)c3O)[C@H]3CC[C@@H]32)c(=O)c2nc(C3CC3)cnc2n1CC(=O)Nc1ccc(C(F)(F)F)cc1Cl]

or a pharmaceutically acceptable salt thereof.

4. The compound of claim 1, wherein the compound is:

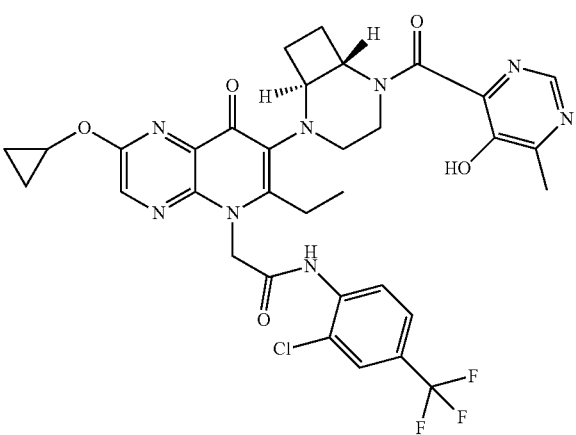 [SMILES: CCc1c(N2CCN(C(=O)c3ncnc(C)c3O)[C@H]3CC[C@@H]32)c(=O)c2nc(OC3CC3)cnc2n1CC(=O)Nc1ccc(C(F)(F)F)cc1Cl]

or a pharmaceutically acceptable salt thereof.

5. The compound of claim 1, wherein the compound is:

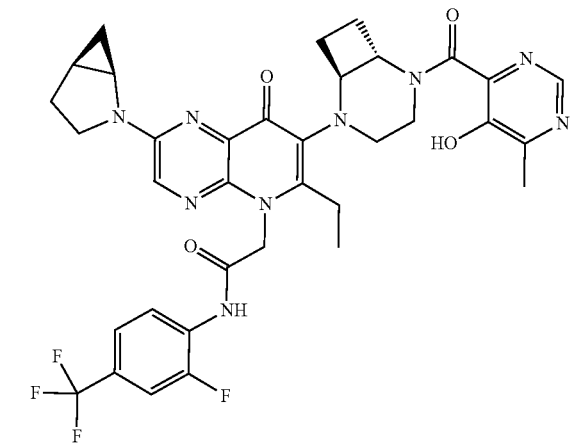 [SMILES: CCc1c(N2CCN(C(=O)c3ncnc(C)c3O)[C@H]3CC[C@@H]32)c(=O)c2nc(N3CC[C@H]4C[C@H]43)cnc2n1CC(=O)Nc1ccc(C(F)(F)F)cc1F]

or a pharmaceutically acceptable salt thereof.

6. The compound of claim 1, wherein the compound is:

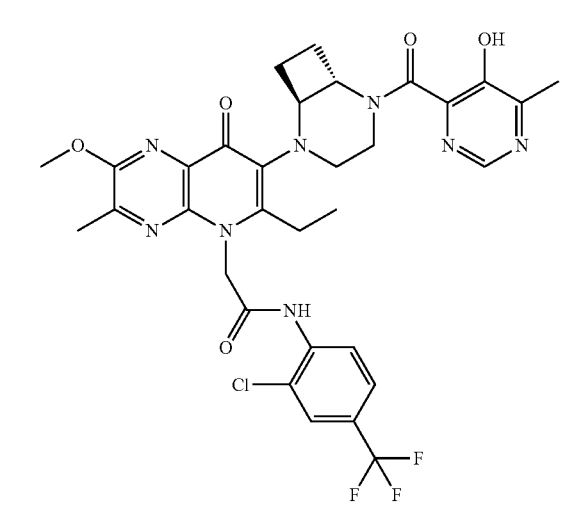

or a pharmaceutically acceptable salt thereof.

7. The compound of claim 1, wherein the compound is:

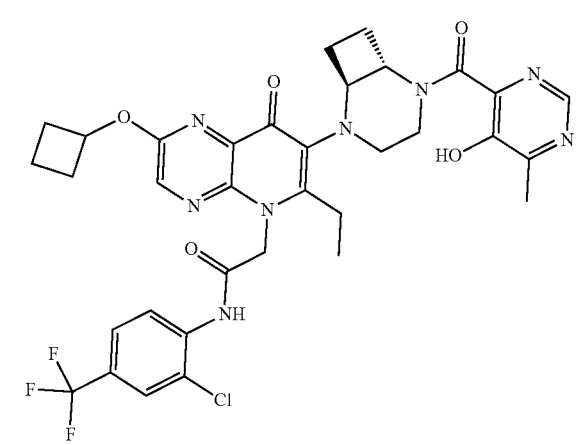 [SMILES: CCc1c(N2CCN(C(=O)c3ncnc(C)c3O)[C@H]3CC[C@@H]32)c(=O)c2nc(OC3CCC3)cnc2n1CC(=O)Nc1ccc(C(F)(F)F)cc1Cl]

or a pharmaceutically acceptable salt thereof.

8. The compound of claim 1, wherein the compound is:
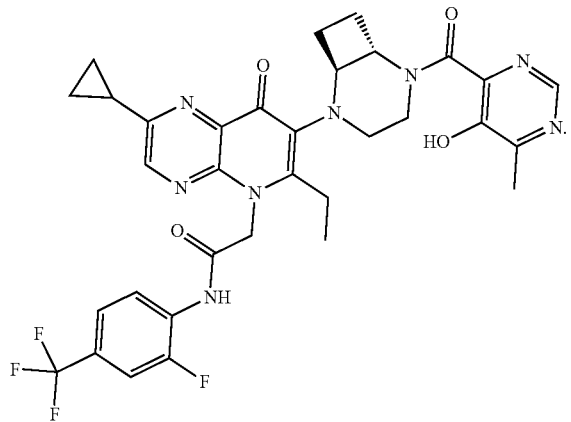 [SMILES: CCc1c(N2CCN(C(=O)c3ncnc(C)c3O)[C@H]3CC[C@@H]32)c(=O)c2nc(C3CC3)cnc2n1CC(=O)Nc1ccc(C(F)(F)F)cc1F]
9. The compound of claim 1, wherein the compound is:
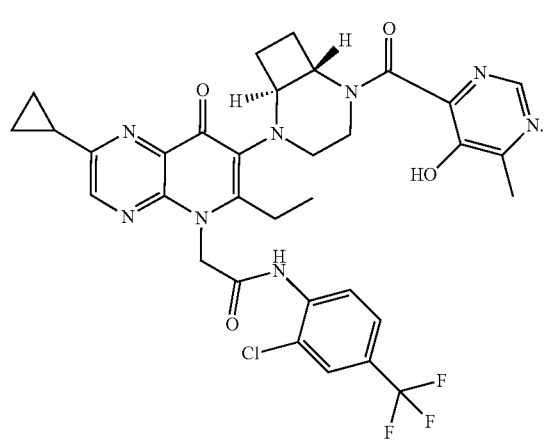 [SMILES: CCc1c(N2CCN(C(=O)c3ncnc(C)c3O)[C@H]3CC[C@@H]32)c(=O)c2nc(C3CC3)cnc2n1CC(=O)Nc1ccc(C(F)(F)F)cc1Cl]
10. The compound of claim 1, wherein the compound is:
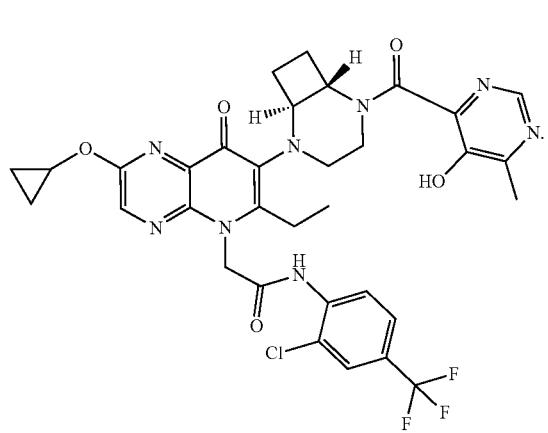 [SMILES: CCc1c(N2CCN(C(=O)c3ncnc(C)c3O)[C@H]3CC[C@@H]32)c(=O)c2nc(OC3CC3)cnc2n1CC(=O)Nc1ccc(C(F)(F)F)cc1Cl]
11. The compound of claim 1, wherein the compound is:
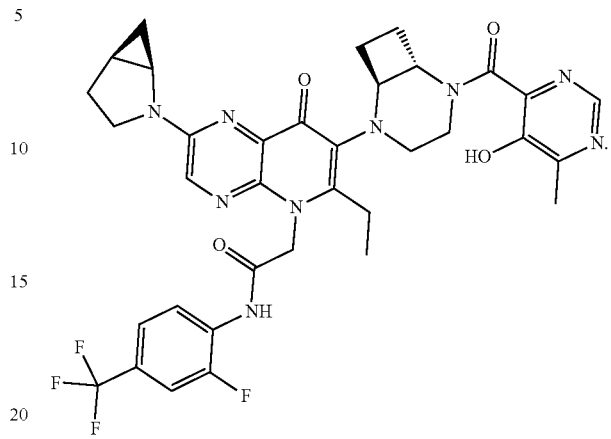
12. The compound of claim 1, wherein the compound is:
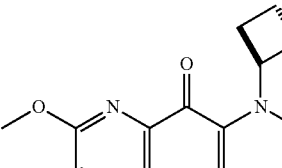
13. The compound of claim 1, wherein the compound is:
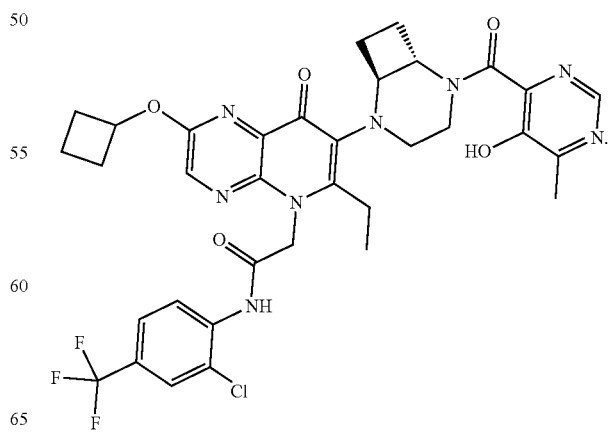

14. A pharmaceutical composition comprising a pharmaceutically acceptable carrier, adjuvant, or vehicle and a compound selected from the group consisting of:
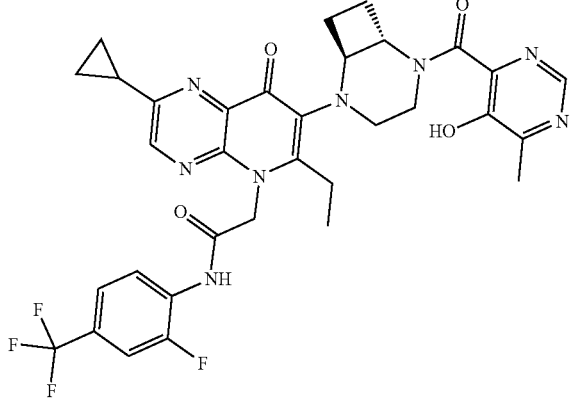
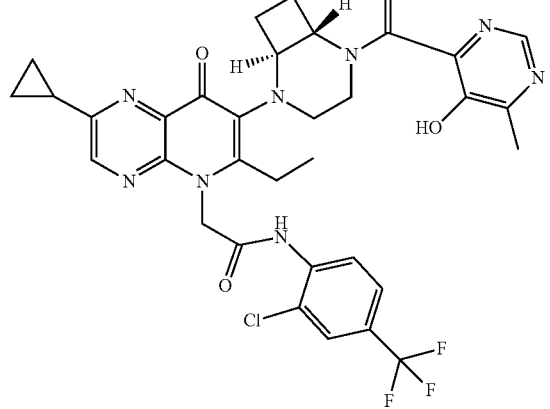
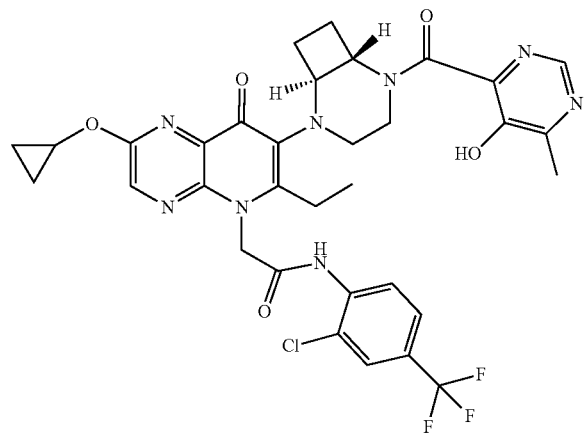
-continued
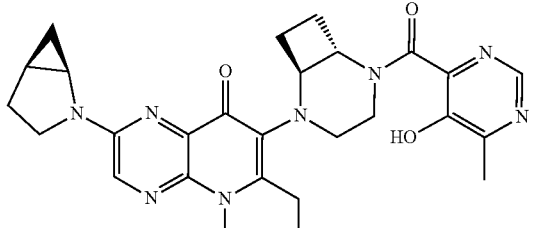
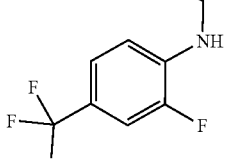
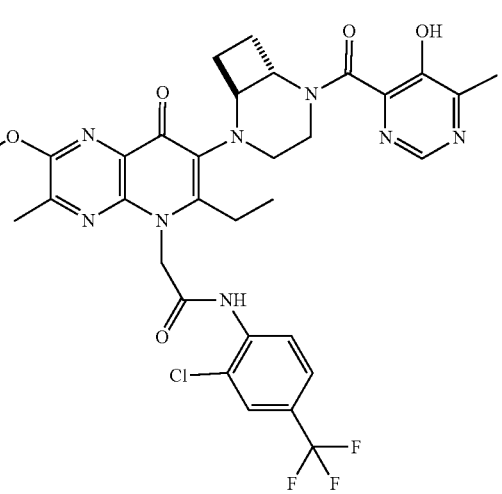
and
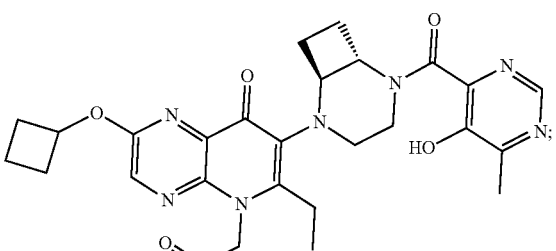
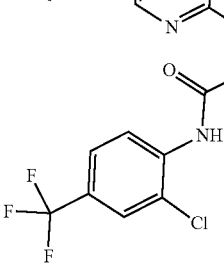
or a pharmaceutically acceptable salt thereof.

15. The pharmaceutical composition of claim 14, wherein the compound is:

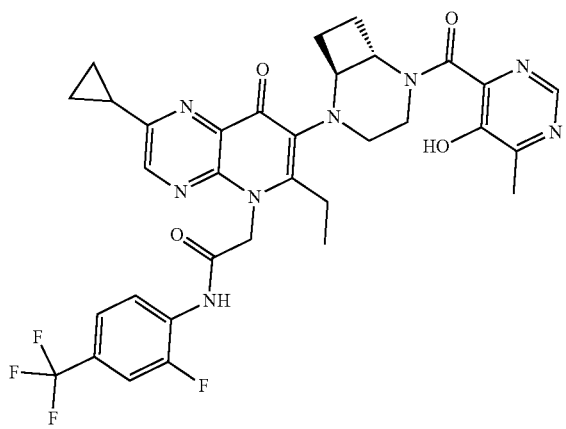 [SMILES: CCc1c(N2CCN(C(=O)c3ncnc(C)c3O)[C@H]3CC[C@@H]32)c(=O)c2nc(C3CC3)cnc2n1CC(=O)Nc1ccc(C(F)(F)F)cc1F]

or a pharmaceutically acceptable salt thereof.

16. The pharmaceutical composition of claim 14, wherein the compound is:

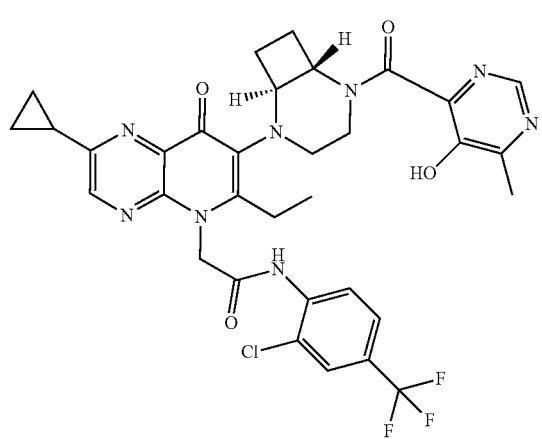 [SMILES: CCc1c(N2CCN(C(=O)c3ncnc(C)c3O)[C@H]3CC[C@@H]32)c(=O)c2nc(C3CC3)cnc2n1CC(=O)Nc1ccc(C(F)(F)F)cc1Cl]

or a pharmaceutically acceptable salt thereof.

17. The pharmaceutical composition of claim 14, wherein the compound is:

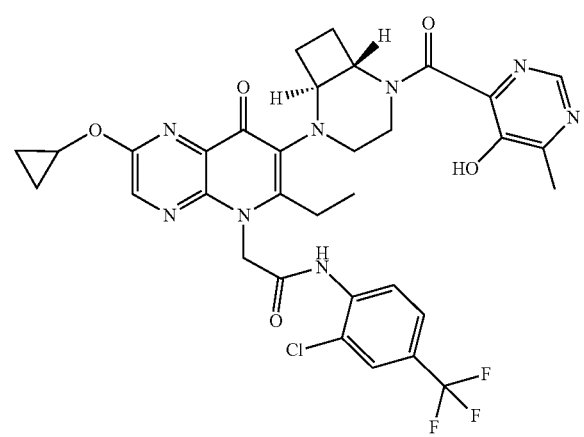 [SMILES: CCc1c(N2CCN(C(=O)c3ncnc(C)c3O)[C@H]3CC[C@@H]32)c(=O)c2nc(OC3CC3)cnc2n1CC(=O)Nc1ccc(C(F)(F)F)cc1Cl]

or a pharmaceutically acceptable salt thereof.

18. The pharmaceutical composition of claim 14, wherein the compound is:

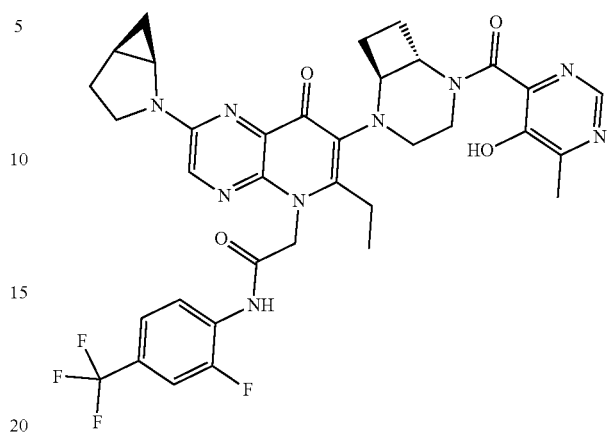

or a pharmaceutically acceptable salt thereof.

19. The pharmaceutical composition of claim 14, wherein the compound is:

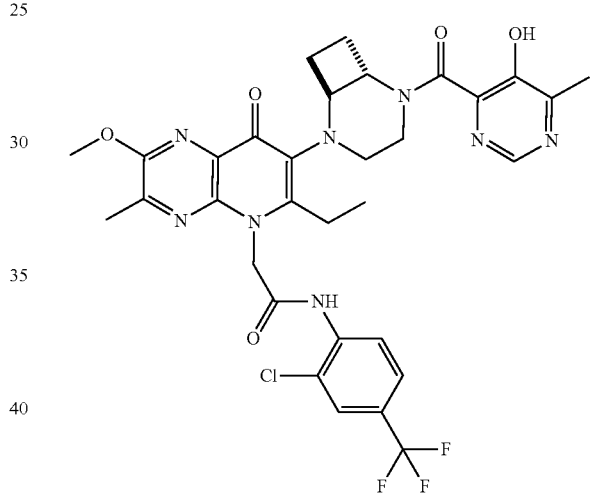

or a pharmaceutically acceptable salt thereof.

20. The pharmaceutical composition of claim 14, wherein the compound is:

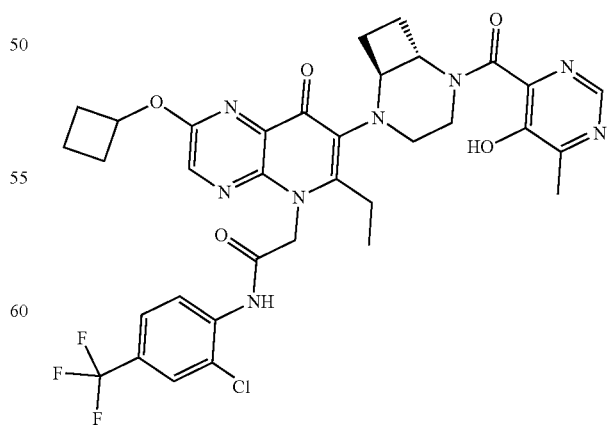

or a pharmaceutically acceptable salt thereof.

* * * * *

SEQUENCE LISTING

```
Sequence total quantity: 4
SEQ ID NO: 1               moltype = DNA   length = 24
FEATURE                    Location/Qualifiers
misc_feature               1..24
                           note = Description of sequence: Component of compound
                           NSC-617145
source                     1..24
                           mol_type = other DNA
                           organism = synthetic construct
SEQUENCE: 1
gcactggccg tcgttttacg gtcg                                                 24

SEQ ID NO: 2               moltype = DNA   length = 23
FEATURE                    Location/Qualifiers
misc_feature               1..23
                           note = Description of sequence: Component of compound
                           NSC-617145
source                     1..23
                           mol_type = other DNA
                           organism = synthetic construct
SEQUENCE: 2
tccaagtaaa acgacggcca gtg                                                  23

SEQ ID NO: 3               moltype = DNA   length = 2208
FEATURE                    Location/Qualifiers
misc_feature               1..2208
                           note = Description of sequence: Gene sequence of WRN-BV08
source                     1..2208
                           mol_type = genomic DNA
                           organism = Homo sapiens
SEQUENCE: 3
atgaacgagg gcgaagaaga cgacgacaag gacttcctgt ggcctgcccc taacgaagaa   60
caagtgacat gcctgaagat gtacttcgga cacagtagct tcaagcctgt gcaatggaag  120
gtcatccact ccgtgctgga agaaagaagg gacaacgtgg ctgtgatggc taccggatac  180
ggtaagtccc tgtgcttcca gtaccctccc gtgtacgtgg caagatcgg tctggtgatc   240
tccctctga tctctctgat ggaggaccag gtgctgcaat tgaagatgtc caacatcccc  300
gcttgcttcc tgggttccgc tcaaagtgag aacgtgctga cagacatcaa gctgggcaag  360
taccgcatcg tgtacgtgac ccctgagtac tgctccggta acatgggtct gctgcaacag  420
ctggaggctg acatcggaat caccctgatc gctgtggacg aggctcactg catctccgag  480
tggggacacg acttccgcga ctccttccgt aagctgggat ccttgaagac cgctctccct  540
atggtgccta tcgtggccct gaccgccact gcttcctcct ccatccgcga ggacatcgtg  600
cgttgcctga acctgcgcaa ccctcagatc acttgcaccg tttcgaccg ccctaacttg   660
tacctcgagg tgcgtcgcaa gaccggtaac atcctccagg acctgcagcc tttcctggtc  720
aagacctcct cccactggga atttgagggc cctaccatca tctactcacc ttcccgccaa  780
atgacccagc aagtcaccgg cgagctgcgc aagctcaacc tctcctgcgg tacctaccac  840
gctggtatgt ccttctccac ccgcaaggac atccaccacc gcttcgtccg tgacgaaatc  900
caatgcgtca tcgctaccat cgcttttcgga atgggcatca acaaggctga catccgccag  960
gtgatccact acggcgcccc caaggacatg gaatcctact accaggaaat cggtcgcgcc  1020
ggtcgcgacg gtctgcagtc ttcctgtcac gtgctgtggg ccccgctga tcatcaacctg  1080
aaccgccacc tgctgaccga aatccgcaac gagaagttcc gcctgtacaa gctcaagatg  1140
atggctaaga tggagaagta cctgcactcc tcccgctgtc gccgtcagat catcctctcc  1200
cacttcgagg acaagcaagt gcaaaaggct agctcgggta tcatgggcac cgaaaagtgt  1260
tgtgacaact gccgctcccg cctcgaccac tgctactcca tggacgacag cgaggacacc  1320
tcctgggact ccggtcctca agctttcaag ctccttgtccg ctgtggacat cctgggcgag  1380
aagttcggta tcggtctccc catcctcttc ctgcgtggta gcaactccca acgcctggct  1440
gaccagtacc gccgccactc cctcttcggt accggtaagg accagaccga gtcctggtgg  1500
aaggcttcct ctcgccaact gatcaccgaa ggtttcctgg tggaggtgtc ccgctacaac  1560
aagttcatga agatctgcgc tctcactaag aagggaagga actgctgca caaggctaac  1620
actgagtccc aatccctcat cctgcaggct aacgaggagc tgtgccctaa gaagttcctg  1680
ctgccttcct ccaagaccgt gtcctccgga caaaaggaac actgctacaa ccaagtccct  1740
gtgggactct ccaccgagaa gaagtccaac ctggagaagc tgtacagcta caagcctgc   1800
gacaagatca gctccggttc caacatcagc aagaagtcca tcatggtgca atcccctgaa  1860
aaggcctact ccagctccca acctgtcatc tccgctcaag agcaagagac ccagatcgtg  1920
ctgtacggta agctggtcga agcccgccaa agcacgctca acaagatgga cgtccctccc  1980
gctatcctcg ccaccaacaa gatcctcgtg gatatgctag agatgcgccc caccaccgtc  2040
gagaacgtga agcgcatcga cggtgtctcc gagggtaagg ccgctatgct ggctcctctg  2100
ctggaagtga tcaagcactt ctgccagacc aactccgtgc agaccgacct gttcagtagt  2160
gagaacctgt acttccaagg ccaccatcat catcatcatc accactaa               2208

SEQ ID NO: 4               moltype = AA    length = 735
FEATURE                    Location/Qualifiers
REGION                     1..735
                           note = Description of sequence: Protein sequence of WRN-BV08
source                     1..735
                           mol_type = protein
                           organism = Homo sapiens
SEQUENCE: 4
MNEGEEDDDK DFLWPAPNEE QVTCLKMYFG HSSFKPVQWK VIHSVLEERR DNVAVMATGY   60
```

```
GKSLCFQYPP VYVGKIGLVI SPLISLMEDQ VLQLKMSNIP ACFLGSAQSE NVLTDIKLGK    120
YRIVYVTPEY CSGNMGLLQQ LEADIGITLI AVDEAHCISE WGHDFRDSFR KLGSLKTALP    180
MVPIVALTAT ASSSIREDIV RCLNLRNPQI TCTGFDRPNL YLEVRRKTGN ILQDLQPFLV    240
KTSSHWEFEG PTIIYCPSRK MTQQVTGELR KLNLSCGTYH AGMSFSTRKD IHHRFVRDEI    300
QCVIATIAFG MGINKADIRQ VIHYGAPKDM ESYYQEIGRA GRDGLQSSCH VLWAPADINL    360
NRHLLTEIRN EKFRLYKLKM MAKMEKYLHS SRCRRQIILS HFEDKQVQKA SLGIMGTEKC    420
CDNCRSRLDH CYSMDDSEDT SWDFGPQAFK LLSAVDILGE KFGIGLPILF LRGSNSQRLA    480
DQYRRHSLFG TGKDQTESWW KAFSRQLITE GFLVEVSRYN KFMKICALTK KGRNWLHKAN    540
TESQSLILQA NEELCPKKFL LPSSKTVSSG TKEHCYNQVP VELSTEKKSN LEKLYSYKPC    600
DKISSGSNIS KKSIMVQSPE KAYSSSQPVI SAQEQETQIV LYGKLVEARQ KHANKMDVPP    660
AILATNKILV DMAKMRPTTV ENVKRIDGVS EGKAAMLAPL LEVIKHFCQT NSVQTDLFSS    720
ENLYFQGHHH HHHHH                                                    735
```